US006613717B1

(12) United States Patent
Langemann et al.

(10) Patent No.: US 6,613,717 B1
(45) Date of Patent: Sep. 2, 2003

(54) PHOSPHORIC BENZOYL DERIVATIVES AND THEIR USE AS HERBICIDES

(75) Inventors: Klaus Langemann, Worms (DE); Thorsten Volk, Mannheim (DE); Ernst Baumann, Dudenhofen (DE); Wolfgang von Deyn, Neustadt (DE); Steffen Kudis, Mannheim (DE); Guido Mayer, Neustadt (DE); Ulf Misslitz, Neustadt (DE); Ulf Neidlein, Mannheim (DE); Matthias Witschel, Ludwigshafen (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/959,510

(22) PCT Filed: Apr. 19, 2000

(86) PCT No.: PCT/EP00/03548

§ 371 (c)(1),
(2), (4) Date: Oct. 29, 2001

(87) PCT Pub. No.: WO00/64912

PCT Pub. Date: Nov. 2, 2000

(30) Foreign Application Priority Data

Apr. 27, 1999 (DE) ........................................ 199 18 914

(51) Int. Cl.$^7$ ........................... A01N 57/26; C07F 9/02

(52) U.S. Cl. ......................................... 504/200; 568/17

(58) Field of Search ............................ 568/17; 504/200

(56) References Cited

U.S. PATENT DOCUMENTS

| | | | | |
|---|---|---|---|---|
| 3,775,057 A | 11/1973 | Redmore | ......................... | 21/2 |
| 3,882,202 A | 5/1975 | Aya et al. | .................... | 260/951 |
| 3,936,433 A | 2/1976 | Satomi et al. | .............. | 260/954 |
| 3,974,243 A | 8/1976 | Kleiner | ....................... | 260/941 |
| 4,780,127 A | 10/1988 | Michaely et al. | ............. | 71/103 |
| 5,834,402 A | 11/1998 | von Deyn et al. | .......... | 504/271 |
| 5,846,907 A | 12/1998 | von Deyn et al. | .......... | 504/221 |
| 6,165,944 A | 12/2000 | von Deyn et al. | .......... | 504/271 |

FOREIGN PATENT DOCUMENTS

| | | |
|---|---|---|
| CA | 2289114 | 11/1998 |
| EP | 203 428 | 12/1986 |
| EP | 315 975 | 5/1989 |
| EP | 418 175 | 3/1991 |
| EP | 609 797 | 8/1994 |
| EP | 625 505 | 11/1994 |
| GB | 1 200 273 | 7/1970 |
| JP | 49 011418 | 3/1974 |
| WO | WO 98/50337 | 11/1998 |

OTHER PUBLICATIONS

Hawkins et al. "An In–depth Study of the Azidobenzophenone–Anthranil–Acridone Transformation"Chem. Soc. Perkins Trans. (1983) pp. 2077–2087.

Kluger et al. "Amide Phosphate Interactions: Acid Catalysts in Amide–Assisted Hydrolysis of Phosphonate Esters" Jour. Am. Chem. Soc. vol. 98, No. 16, (1976) pp. 4913–4917.

Petrakis et al. "Palladium Catalyzed Substitutions of Triflates Derived from Tyrosine–Containing Peptides and Simpler Hydroxyarenes Forming 4–(Diethoxyphosphinyl) pheylzlanines and Diethyl Arylphosphonates" Jour. Am. Chem. SOc. vol. 109 No. 9 (1987) pp. 2831–2833.

El–Deek et al. "Synthesis and reaction of p–(diphenylophosphino)benzoic acid" J. Indian Chem. Soc. vol. 58 No. 2 (1981) pp. 197–199.

Petrovxkii et al. "Amidophosphinylbenzoic acids" Izv. Akad. Nunk. SSSR Ser. Khim. vol. 9 (1974) pp. 2090–2093.

Hall et al. "The Preparation and Diels–Alder Reactivity of Ethyl (Diethoxyphosphinyl) Propynoate" Tetrahedron Letters vol. 23 No. 25 (1982) pp. 2603–2604.

*Primary Examiner*—Joseph K. McKane
*Assistant Examiner*—Golam M. M. Shameem
(74) *Attorney, Agent, or Firm*—Keil & Weinkauf

(57) ABSTRACT

Phosphorus-containing benzoyl derivatives of the formula I

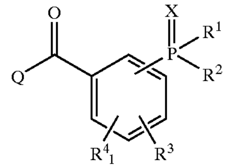

I where:

P(=X)$R^1R^2$X is an organic phosphorus radical;

$R^3$ is hydrogen, nitro, cyano, halogen, unsub. or sub. alkyl, alkylcarbonyl, alkoxycarbonyl, unsub. or sub. alkoxy, unsub. or sub. alkylthio, unsub. or sub. alkylsulfinyl, unsub. or sub. alkylsulfonyl, unsub. or sub. aminosulfonyl, unsub. or sub. amino, P(=X)$R^1R^2$, unsub. or sub. phenyl or unsub. or sub. heterocyclyl;

$R^4$ is nitro, cyano, halogen, alkyl, alkoxy, alkylthio, alkylsulfinyl or alkylsulfonyl;

l is 0, 1 or 2;

Q is unsub. or sub. 1-hydroxy-3-oxocyclohex-1-en-2-yl, unsub. or sub. 5-hydroxypyrazol-4-yl, unsub. or sub. isoxazol-4-yl or unsub. or sub. 2-cyano-1-oxoeth-2-yl;

and their agriculturally useful salts;

processes and intermediates for preparing the phosphorus-containing benzoyl derivatives; compositions comprising them and the use of these derivatives or the compositions comprising them for controlling undesirable plants are described.

13 Claims, No Drawings

PHOSPHORIC BENZOYL DERIVATIVES AND THEIR USE AS HERBICIDES

This application is a 371 of PCT/EP00/03548 Apr. 19, 2000.

The present invention relates to phosphorus-containing benzoyl derivatives of the formula I

I

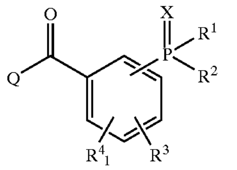

in which:

X is oxygen or sulfur;

$R^1$,$R^2$ are hydrogen, $C_1$–$C_6$-alkyl, $C_2$–$C_6$-alkenyl, $C_2$–$C_6$-alkynyl, hydroxyl, $C_1$–$C_6$-alkoxy, $C_3$–$C_6$-alkenyloxy, $C_3$–$C_6$-alkynyloxy, mercapto, $C_1$–$C_6$-alkylthio, $C_3$–$C_6$-alkenylthio, $C_3$–$C_6$-alkynylthio, amino, $C_1$–$C_6$-alkylamino, di($C_1$–$C_6$-alkyl)amino, ($C_1$–$C_6$-alkoxy)($C_1$–$C_6$-alkyl)amino, ($C_3$–$C_6$-alkenyl)($C_1$–$C_6$-alkyl)amino, ($C_3$–$C_6$-alkynyl)($C_1$–$C_6$-alkyl)amino, di($C_3$–$C_6$-alkenyl)amino or di($C_3$–$C_6$-alkynyl)amino, where the abovementioned alkyl, alkenyl or alkynyl radicals may be partially or fully halogenated and/or may carry one to three of the following groups: nitro, cyano, $C_1$–$C_4$-alkoxy, $C_1$–$C_4$-alkylthio, $C_1$–$C_4$-alkylsulfinyl, $C_1$–$C_4$-alkylsulfonyl, di($C_1$–$C_4$-alkyl)amino, $C_1$–$C_4$-alkylcarbonyl, $C_1$–$C_4$-alkoxycarbonyl, phenyl or heterocyclyl, where the the two last-mentioned radicals for their part may be partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

are phenyl or phenoxy which may be partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl; or $R^1$ and $R^2$ together form an —O—$(CH_2)_m$—O—, —O—$(CH_2)_m$—S—, —S—$(CH_2)_m$—S—, —$NR^5$—$(CH_2)_m$—$NR^5$—, —O—$(CH_2)_m$—$NR^5$—, —S—$(CH_2)_m$—$NR^5$—, —$(CH_2)_n$—O—, —$(CH_2)_n$—S— or —$(CH_2)_n$—$NR^5$ chain which may carry one to three radicals from the following group:

halogen, cyano, $C_1$–$C_4$-alkyl, $C_1$–$C_4$-haloalkyl, $C_1$–$C_4$-alkoxy, $C_1$–$C_4$-alkoxycarbonyl or phenyl which is unsubstituted or partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl; or $R^1$ and $R^2$ together form a —$(CH_2)_p$ chain which may be interrupted by oxygen, sulfur or $NR^5$ and/or may carry one to three radicals from the following group:

halogen, cyano, $C_1$–$C_4$-alkyl, $C_1$–$C_4$-haloalkyl, $C_1$–$C_4$-alkoxy, $C_1$–$C_4$-alkoxycarbonyl or phenyl which is unsubstituted or partially or fully halogenated and/or may carry one to three of the following groups: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^3$ is hydrogen, nitro, cyano, halogen, $C_1$–$C_6$-alkyl, $C_1$–$C_6$-haloalkyl, $C_1$–$C_6$-alkoxy-$C_1$–$C_6$-alkyl, $C_1$–$C_6$-haloalkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylcarbonyl, $C_1$–$C_6$-alkoxycarbonyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, $C_1$–$C_6$-alkylaminosulfonyl, di($C_1$–$C_6$-alkyl)aminosulfonyl, ($C_1$–$C_6$-alkylsulfonyl)amino, ($C_1$–$C_6$-haloalkylsulfonyl)amino, N—($C_1$–$C_6$-alkyl)—N—($C_1$–$C_6$-alkylsulfonyl)amino, N—($C_1$–$C_6$-alkyl)—N—($C_1$–$C_6$-haloalkylsulfonyl)amino, —P(=X)$R^1R^2$, phenyl or heterocyclyl, where the two last-mentioned radicals may be partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^4$ is nitro, cyano, halogen, $C_1$–$C_6$-alkyl, $C_1$–$C_6$-alkoxy, $C_1$–$C_6$-alkylthio, $C_1$–$C_6$-alkylsulfinyl or $C_1$–$C_6$-alkylsulfonyl;

$R^5$ is hydrogen, $C_1$–$C_6$-alkyl, $C_1$–$C_6$-haloalkyl or $C_1$–$C_6$-alkoxy;

l is 0, 1 or 2;

m is 2, 3 or 4;

n is 3, 4 or 5;

p is 4, 5 or 6;

Q is a radical of the formula $Q^1$, $Q^2$, $Q^3$ or $Q^4$ $Q^1$

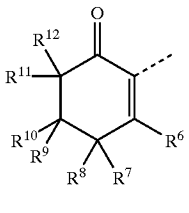

$Q^2$

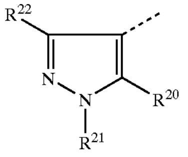

$Q^3$

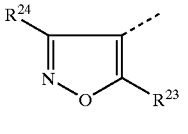

$Q^4$

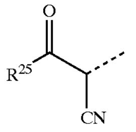

$R^6$ is hydroxyl, mercapto, halogen, $OR^{13}$, $SR^{13}$, $SOR^{14}$, $SO_2R^{14}$, $OSO_2R^{14}$, $POR^{15}R^{16}$, $OPR^{15}R^{16}$, $OPOR^{15}R^{16}$, $OPSR^{15}R^{16}$, $NR^{17}R^{18}$, $ONR^{18}R^{19}$, N-bonded heterocyclyl or O—(N-bonded heterocyclyl), where the heterocyclyl radical of the two last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^7$,$R^9$,$R^{11}$ are hydrogen, nitro, halogen, cyano, $C_1$–$C_6$-alkyl, $C_1$–$C_6$-haloalkyl, di($C_1$–$C_6$-alkoxy)methyl, di($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl;

$R^8$,$R^{10}$,$R^{12}$ are hydrogen, $C_1$–$C_6$-alkyl, $C_1$–$C_6$-alkoxy, $C_1$–$C_6$-alkylthio or $C_1$–$C_6$-alkoxycarbonyl; or $R^7$ and $R^8$ or $R^9$ and $R^{10}$ or $R^{11}$ and $R^{12}$ together form an $—O—(CH_2)_u—O—$, $—O—(CH_2)_u—S—$, $—S—(CH_2)_u—S—$, $—O—(CH_2)_v—$ or $—S—(CH_2)_v$ chain which may be substituted by one to three radicals from the following group:

halogen, cyano, $C_1$–$C_4$-alkyl, $C_1$–$C_4$-haloalkyl or $C_1$–$C_4$-alkoxycarbonyl; or $R^7$ and $R^8$ or $R^9$ and $R^{10}$ or $R^{11}$ and $R^{12}$ together form a $—(CH_2)_w$ chain which may be interrupted by oxygen or sulfur and/or may be substituted by one to four radicals from the following group:

halogen, cyano, $C_1$–$C_4$-alkyl, $C_1$–$C_4$-haloalkyl or $C_1$–$C_4$-alkoxycarbonyl; or $R^7$ and $R^8$ or $R^9$ and $R^{10}$ or $R^{11}$ and $R^{12}$ together form a methylidene group which may be substituted by one to two radicals from the following group:

halogen, hydroxyl, formyl, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl; or $R^7$ and $R^8$ or $R^9$ and $R^{10}$ or $R^{11}$ and $R^{12}$ together with the carbon atom to which they are attached form a carbonyl group; or $R^7$ and $R^9$ or $R^9$ and $R^{11}$ or $R^7$ and $R^{11}$ together form a $—(CH_2)_v$ chain which may be substituted by one to three radicals from the following group:

halogen, $C_1$–$C_6$-alkyl, $C_1$–$C_6$-alkoxy, hydroxyl or $C_1$–$C_6$-alkoxycarbonyl;

$R^{13}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_{20}$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkylaminocarbonyl, $C_1$–$C_6$-alkylcarbonyl-$C_1$–$C_6$-alkyl or $C_1$–$C_6$-alkoxyimino-$C_1$–$C_6$-alkyl, where the abovementioned alkyl and cycloalkyl radicals may be partially or fully halogenated and/or may carry one to three of the following groups:

cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl, heterocyclylcarbonyl, phenylaminocarbonyl or heterocyclylaminocarbonyl, where the phenyl and the heterocyclyl radical of the 8 last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$,$R^{15}$, $R^{16}$ are $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, amino, $C_1$–$C_6$-alkylamino, $C_1$–$C_6$-haloalkylamino, di($C_1$–$C_6$-alkyl)amino or di($C_1$–$C_6$-haloalkyl)amino, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, di($C_1$–$C_4$-alkyl)amino, $C_1$–$C_4$-alkylcarbonyl or $C_1$–$C_4$-alkoxycarbonyl;

are phenyl, heterocyclyl, phenoxy or heterocyclyloxy, where the phenyl and the heterocyclyl radical of the last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{17}$ is $C_1$–$C_6$-alkyl, $C_3$–$C_6$-alkenyl, $C_3$–$C_6$-haloalkenyl, $C_3$–$C_6$-alkynyl, $C_3$–$C_6$-halogenalkynyl, $C_3$–$C_6$-cycloalkyl, hydroxyl, $C_1$–$C_6$-alkoxy, $C_3$–$C_6$-alkenyloxy or $C_3$–$C_6$-alkynyloxy, where the abovementioned alkyl, cycloalkyl and alkoxy radicals may be partially or fully halogenated and/or may carry one to three radicals from the following groups:

cyano, $C_1$–$C_4$-alkoxy, $C_1$–$C_4$-alkylthio or di($C_1$–$C_4$-alkyl)amino;

is phenyl, heterocyclyl, phenyl-$C_1$–$C_6$-alkyl or heterocyclyl-$C_1$–$C_6$-alkyl, where the phenyl or heterocyclyl radical of the four last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{18}$, $R^{19}$ are $C_1$–$C_6$-alkyl, $C_3$–$C_6$-alkenyl, $C_3$–$C_6$-alkynyl or $C_1$–$C_6$-alkylcarbonyl;

u is 2 to 4;

v is 1 to 5;

w is 2 to 5;

$R^{20}$ is a radical as mentioned under $R^6$;

$R^{21}$ is hydrogen, $C_1$–$C_6$-alkyl, $C_1$–$C_6$-haloalkyl, hydroxyl, $C_1$–$C_6$-alkoxy or $C_1$–$C_6$-haloalkoxy;

$R^{22}$ is hydrogen, halogen, $C_1$–$C_6$-alkyl, $C_1$–$C_6$-haloalkyl, hydroxyl, $C_1$–$C_6$-alkoxy, $C_1$–$C_6$-haloalkoxy, $C_1$–$C_6$-alkylthio or $C_1$–$C_6$-haloalkylthio;

$R^{23}$ is hydrogen, $C_1$–$C_6$-alkyl, $C_1$–$C_6$-haloalkyl, $C_3$–$C_6$-cycloalkyl or $C_3$–$C_6$-halocycloalkyl;

$R^{24}$ is hydrogen, $C_1$–$C_6$-alkoxycarbonyl, $C_1$–$C_6$-haloalkoxycarbonyl, hydroxycarbonyl or cyano;

$R^{25}$ is $C_1$–$C_6$-alkyl, $C_1$–$C_6$-haloalkyl, $C_3$–$C_6$-cycloalkyl or $C_3$–$C_6$-halocycloalkyl;

and their agriculturally useful salts.

Moreover, the invention relates to the processes and intermediates for preparing compounds of the formula I, compositions comprising them and to the use of the compounds of the formula I and of the compositions comprising them for controlling pests.

Herbicidally effective phosphorothionoamidates are disclosed in the literature, for example in DE-A 22 60 705 and DE-A 21 66 729. Furtheermore, U.S. Pat. No. 3,775,057 describes pyridinylphosphonates.

Likewise, substituted benzoylisoxazoles or -pyrazoles and substituted 2-phenylcyclohexane-1,3-diones or 1-phenyl-2-cyanoalkane-1,3-diones are disclosed, for example, in EP-A 418 175, EP-A 609 797, WO 96/26 192, WO 96/26 206, EP-A 203 428, U.S. Pat. No. 4,780,127, EP-A 315 075 and EP-A 625 505.

However, the herbicidal properties of the prior art compounds and their compatibility with crop plants are not entirely satisfactory. It is an object of the present invention to provide novel, in particular herbicidally effective compounds having improved properties.

We have found that this object is achieved by the phosphorus-containing benzoyl derivatives of the formula I and their herbicidal action.

Furthermore, we have found herbicidal compositions comprising the compounds I and having very good herbicidal action. Moreover, we have found processes for preparing these compositions and methods for controlling undesirable vegetation using the compounds I.

Depending on the substitution pattern, the compounds of the formula I can contain one or more chiral centers, in which case they exist in the form of enantiomers or diastereomer mixtures.

The invention provides both the pure enantiomers or diastereomers and mixtures thereof.

The compounds of the formula I can also be present in the form of their agriculturally useful salts, the type of salt generally being immaterial. In general, the salts of those cations or the acid addition salts of those acids are suitable whose cations and anions, respectively, do not affect the herbicidal action of the compounds I negatively.

Suitable cations are, in particular, ions of the alkali metals, preferably lithium, sodium and potassium, the alkaline earth metals, preferably calcium and magnesium, and the transition metals, preferably manganese, copper, zinc and iron, and also ammonium, where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$–$C_4$-alkyl)sulfonium and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

The organic molecular moieties mentioned for the substituents $R^1$–$R^{25}$ or as radicals on phenyl and heterocyclyl radicals are collective terms for individual lists of the individual group members. All hydrocarbon chains, i.e. all alkyl, haloalkyl, alkoxy, haloalkoxy, alkylthio, haloalkylthio, alkylsulfinyl, haloalkylsulfinyl, alkylsulfonyl, haloalkylsulfonyl, alkylaminosulfonyl, dialkylaminosulfonyl, alkylamino, dialkylamino, haloalkylamino, di(haloalkyl)amino, N-alkoxy-N-alkylamino, N-alkylsulfonylamino, N-haloalkylsulfonylamino, N-alkyl-N-alkylsulfonylamino, N-alkyl-N-haloalkylsulfonylamino, alkylcarbonyl, haloalkylcarbonyl, alkoxycarbonyl, haloalkoxycarbonyl, alkylaminocarbonyl, dialkylaminocarbonyl, alkoxyalkyl, haloalkoxyalkyl, alkylthioalkyl, alkylsulfinylalkyl, alkylsulfonylalkyl, dialkoxymethyl, dialkylthiomethyl, (alkoxy)(alkylthio)methyl, alkylcarbonylalkyl, alkoxyiminoalkyl, alkoxycarbonyloxy, phenylalkyl, heterocyclylalkyl, dialkylaminoalkoxycarbonyl, alkoxyalkoxycarbonyl, alkenylcarbonyl, N-alkenyl-N-alkylamino, dialkenylamino, alkynylcarbonyl, N-alkynyl-N-alkylamino, dialkynylamino, alkenyl, alkynyl, haloalkenyl, haloalkynyl, alkenyloxy, alkenylthio, alkynyloxy and alkynylthio moieties can be straight-chain or branched. Unless indicated otherwise, halogenated substituents preferably carry one to five identical or different halogen atoms. The term halogen represents in each case fluorine, chlorine, bromine or iodine.

Examples of other meanings are:

$C_1$–$C_4$-alkyl: for example methyl, ethyl, propyl, 1-methylethyl, butyl, 1-methylpropyl, 2-methylpropyl or 1,1-dimethylethyl;

$C_1$–$C_6$-alkyl, and the alkyl moieties of $C_1$–$C_6$-alkylcarbonyl-$C_1$–$C_6$-alkyl, $C_1$–$C_6$-alkoxyimino-$C_1$–$C_6$-alkyl, N—($C_3$–$C_6$-alkenyl)-N—($C_1$–$C_6$-alkyl)amino, N—($C_3$–$C_6$-alkynyl)-N—($C_1$–$C_6$-alkyl)amino, phenyl-$C_1$–$C_6$-alkyl, N—($C_1$–$C_6$-alkyl)-N—($C_1$–$C_6$-alkylsulfonyl)amino, N—($C_1$–$C_6$-alkyl)-N—($C_1$–$C_6$-haloalkylsulfonyl)amino, heterocyclyl-$C_1$–$C_6$-alkyl: $C_1$–$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluorpmethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of $C_1$–$C_6$-haloalkylamino, di($C_1$–$C_6$-haloalkyl)amino: $C_1$–$C_4$-haloalkyl, as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of di($C_1$–$C_6$-alkoxy)methyl, ($C_1$–$C_6$-alkoxy)($C_1$–$C_6$-alkylthio)methyl, $C_1$–$C_6$-alkoxyimino-$C_1$–$C_6$-alkyl and N—($C_1$–$C_6$-alkoxy)-N—($C_1$–$C_6$-alkyl)amino: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy, and the haloalkoxy moieties of $C_1$–$C_6$-haloalkoxy-$C_1$–$C_6$-alkyl: $C_1$–$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio: for example methylthio, ethylthio, propylthio, 1-methylethylthio, butylthio, 1-methylpropylthio, 2-methylpropylthio or 1,1-dimethylethylthio;

$C_1$–$C_6$-alkylthio, and the alkylthio moieties of $C_1$–$C_6$-alkylthio-$C_1$–$C_6$-alkyl, di($C_1$–$C_6$-alkylthio)methyl and ($C_1$–$C_6$-alkoxy)($C_1$–$C_6$-alkylthio)methyl: $C_1$–$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_6$-haloalkylthio: a $C_1$–$C_6$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio, nonafluorobutylthio, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_4$-alkylsulfinyl ($C_1$–$C_4$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl;

$C_1$–$C_6$-alkylsulfinyl and the alkylsulfinyl radicals of $C_1$–$C_6$-alkylsulfinyl-$C_1$–$C_6$-alkyl: $C_1$–$C_4$-alkylsulfinyl, as mentioned above, and also, for example, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethyl propylsulfinyl, 1-ethyl-1-methylpropylsulfinyl or 1-ethyl-2-methylpropylsulfinyl;

$C_1$–$C_6$-haloalkylsulfinyl: a $C_1$–$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chaorohexylsulfinyl, 6-bromohexylsulfinyl, 6-iodohexylsulfinyl or dodecafluorohexylsulfinyl;

$C_1$–$C_4$-alkylsulfonyl ($C_1$–$C_4$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropyl sulfonyl or 1,1-dimethylethylsulfonyl;

$C_1$–$C_6$-alkylsulfonyl, and the alkylsulfonyl radicals of $C_1$–$C_6$-alkylsulfonyl-$C_3$–$C_6$-alkyl, $C_1$–$C_6$-alkylsulfonylamino and N—($C_4$–$C_6$-alkyl)-N—($C_1$–$C_6$-alkylsulfonyl)amino: $C_1$–$C_4$-alkylsulfonyl as mentioned above, and also pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-haloalkylsulfonyl, and the haloalkylsulfonyl radicals of N—($C_1$–$C_6$-haloalkylsulfonyl)amino and N—($C_1$–$C_6$-alkyl)-N—($C_1$–$C_6$-haloalkylsulfonyl) amino: a $C_1$–$_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_1$–$C_6$-alkylamino, and the alkylamino radicals of ($C_1$–$C_6$-alkoxy)($C_1$–$C_6$-alkyl)amino: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

($C_1$–$C_6$-alkylamino)sulfonyl: for example methylaminosulfonyl, ethylaminosulfonyl, propylaminosulfonyl, 1-methylethylaminosulfonyl, butylaminosulfonyl, 1-methylpropylaminosulfonyl, 2-methylpropylaminosulfonyl, 1,1-dimethylethylaminosulfonyl, pentylaminosulfonyl, 1-methylbutylaminosulfonyl, 2-methylbutylaminosulfonyl, 3-methylbutylaminosulfonyl, 2,2-dimethylpropylaminosulfonyl, 1-ethylpropylaminosulfonyl, hexylaminosulfonyl, 1,1-dimethylpropylaminosulfonyl, 1,2-dimethylpropylaminosulfonyl, 1-methylpentylaminosulfonyl, 2-methylpentylaminosulfonyl, 3-methylpentylaminosulfonyl, 4-methylpentylaminosulfonyl, 1,1-dimethylbutylaminosulfonyl, 1,2-dimethylbutylaminosulfonyl, 1,3-dimethylbutylaminosulfonyl, 2,2-dimethylbutylaminosulfonyl, 2,3-dimethylbutylaminosulfonyl, 3,3-dimethylbutylaminosulfonyl, 1-ethylbutylaminosulfonyl, 2-ethylbutylaminosulfonyl, 1,1,2-trimethylpropylaminosulfonyl, 1,2,2-trimethylpropylaminosulfonyl, 1-ethyl-1-methylpropylaminosulfonyl or 1-ethyl-2-methylpropylaminosulfonyl;

di($C_1$–$C_6$-alkyl)aminosulfonyl: for example N,N-dimethylaminosulfonyl, N,N-diethylaminosulfonyl, N,N-di(1-methylethyl)aminosulfonyl, N,N-dipropylaminosulfonyl, N,N-dibutylaminosulfonyl, N,N-di(1-methylpropyl)aminosulfonyl, N,N-di(2-methylpropyl)aminosulfonyl, N,N-di(1,1-dimethylethyl)aminosulfonyl, N-ethyl-N-methylaminosulfonyl, N-methyl-N-propylaminosulfonyl, N-methyl-N-(1-methylethyl) aminosulfonyl, N-butyl-N-methylaminosulfonyl, N-methyl-N-(1-methylpropyl)aminosulfonyl, N-methyl-N-(2-methylpropyl)aminosulfonyl, N-(1,1-dimethylethyl)-N-methylaminosulfonyl, N-ethyl-N-propylaminosulfonyl, N-ethyl-N-(1-methylethyl) aminosulfonyl, N-butyl-N-ethylaminosulfonyl, N-ethyl-N-(1-methylpropyl)aminosulfonyl, N-ethyl-N-(2-methylpropyl)aminosulfonyl, N-ethyl-N-(1,1-dimethylethyl)aminosulfonyl, N-(1-methylethyl)-N-propylaminosulfonyl, N-butyl-N-propylaminosulfonyl, N-(1-methylpropyl)-N-propylaminosulfonyl, N-(2-methylpropyl)-N-propylaminosulfonyl, N-(1,1-dimethylethyl)-N-propylaminosulfonyl, N-butyl-N-(1-methylethyl)aminosulfonyl, N-(1-methylethyl)-N-(1-methylpropyl)aminosulfonyl, N-(1-methylethyl)-N-(2- methylpropyl)aminosulfonyl, N-(1,1-dimethylethyl)-N-(1-methylethyl)aminosulfonyl, N-butyl-N-(1-methylpropyl)aminosulfonyl, N-butyl-N-(2-methylpropyl)aminosulfonyl, N-butyl-N-(1,1-dimethylethyl)aminosulfonyl, N-(1-methylpropyl)-N-(2-methylpropyl)aminosulfonyl, N-(1,1-dimethylethyl)-N-(1-methylpropyl)aminosulfonyl, N-(1,1-dimethylethyl)-N-(2-methylpropyl)aminosulfonyl, N-methyl-N-pentylaminosulfonyl, N-methyl-N-(1-methylbutyl)aminosulfonyl, N-methyl-N-(2-methylbutyl)aminosulfonyl, N-methyl-N-(3-methylbutyl)aminosulfonyl, N-methyl-N-(2,2-dimethylpropyl)aminosulfonyl, N-methyl-N-(1-ethylpropyl)aminosulfonyl, N-methyl-N-hexylaminosulfonyl, N-methyl-N-(1,1-dimethylpropyl)aminosulfonyl, N-methyl-N-(1,2-dimethylpropyl)aminosulfonyl, N-methyl-N-(1-methylpentyl)aminosulfonyl, N-methyl-N-(2-methylpentyl)aminosulfonyl, N-methyl-N-(3-methylpentyl)aminosulfonyl, N-methyl-N-(4-methylpentyl)aminosulfonyl, N-methyl-N-(1,1-dimethylbutyl)aminosulfonyl, N-methyl-N-(1,2-dimethylbutyl)aminosulfonyl, N-methyl-N-(1,3-dimethylbutyl)aminosulfonyl, N-methyl-N-(2,2-dimethylbutyl)aminosulfonyl, N-methyl-N-(2,3-dimethylbutyl)aminosulfonyl, N-methyl-N-(3,3-dimethylbutyl)aminosulfonyl, N-methyl-N-(1-ethylbutyl)aminosulfonyl, N-methyl-N-(2-ethylbutyl)aminosulfonyl, N-methyl-N-(1,1,2-trimethylpropyl)aminosulfonyl, N-methyl-N-(1,2,2-trimethylpropyl)aminosulfonyl, N-methyl-N-(1-ethyl-1-methylpropyl)aminosulfonyl, N-methyl-N-(1-ethyl-2-methylpropyl)aminosulfonyl, N-ethyl-N-pentylaminosulfonyl, N-ethyl-N-(1-methylbutyl)aminosulfonyl, N-ethyl-N-(2-methylbutyl)aminosulfonyl, N-ethyl-N-(3-methylbutyl)aminosulfonyl, N-ethyl-N-(2,2-dimethylpropyl)aminosulfonyl, N-ethyl-N-(1-ethylpropyl)aminosulfonyl, N-ethyl-N-hexylaminosulfonyl, N-ethyl-N-(1,1-dimethylpropyl)aminosulfonyl, N-ethyl-N-(1,2-dimethylpropyl)aminosulfonyl, N-ethyl-N-(1-methylpentyl)aminosulfonyl, N-ethyl-N-(2-methylpentyl)aminosulfonyl, N-ethyl-N-(3-methylpentyl)aminosulfonyl, N-ethyl-N-(4-methylpentyl)aminosulfonyl, N-ethyl-N-(1,1-dimethyl butyl)aminosulfonyl, N-ethyl-N-(1,2-dimethylbutyl)aminosulfonyl, N-ethyl-N-(1,3-dimethylbutyl)aminosulfonyl, N-ethyl-N-(2,2-dimethylbutyl)aminosulfonyl, N-ethyl-N-(2,3-dimethylbutyl)aminosulfonyl, N-ethyl-N-(3,3-dimethylbutyl)aminosulfonyl, N-ethyl-N-(1-ethylbutyl)aminosulfonyl, N-ethyl-N-(2-ethylbutyl)aminosulfonyl, N-ethyl-N-(1,1,2-trimethylpropyl)aminosulfonyl, N-ethyl-N-(1,2,2-trimethylpropyl)aminosulfonyl, N-ethyl-N-(1-ethyl-1-methylpropyl)aminosulfonyl, N-ethyl-N-(1-ethyl-2-methylpropyl)aminosulfonyl, N-propyl-N-pentylaminosulfonyl, N-butyl-N-pentylaminosulfonyl, N,N-dipentylaminosulfonyl, N-propyl-N-hexylaminosulfonyl, N-butyl-N-hexylaminosulfonyl, N-pentyl-N-hexylaminosulfonyl or N,N-dihexylaminosulfonyl;

di($C_1$–$C_4$-alkyl)amino, and the dialkylamino radicals of di($C_1$–$C_4$-alkyl)amino-$C_1$–$C_4$-alkoxycarbonyl: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$–$C_6$-alkyl)amino: di($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of $C_1$–$C_6$-alkylcarbonyl-$C_1$–$C_6$-alkyl: $C_1$–$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_{20}$-alkylcarbonyl: $C_1$–$C_6$-alkylcarbonyl as mentioned above, and also heptylcarbonyl, octylcarbonyl, pentadecylcarbonyl or heptadecylcarbonyl;

$C_1$–$C_6$-haloalkylcarbonyl: a $C_1$–$C_6$-alkylcarbonyl radical as mentioned above which is partially or fully substituted by fluorine, chlorine, bromine and/or iodine, i.e., for example, chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl, nonafluorobutylcarbonyl, 5-fluoropentylcarbonyl, 5-chloropentylcarbonyl, 5-bromopentylcarbonyl, perfluoropentylcarbonyl, 6-fluorohexylcarbonyl, 6-chlorohexylcarbonyl, 6-bromohexylcarbonyl or perfluorohexylcarbonyl;

$C_1$–$C_4$-alkoxycarbonyl, and the alkoxycarbonyl moieties of di($C_1$–$C_4$-alkyl)amino-$C_1$–$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

($C_1$–$C_6$-alkoxy)carbonyl, and the alkoxycarbonyl moieties of $C_1$–$C_6$-alkoxycarbonyloxy: ($C_1$–$C_4$-alkoxy) carbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$–$C_6$-haloalkoxycarbonyl: a $C_1$–$C_6$-alkoxycarbonyl radical as mentioned above which is partially or fully substituted by fluorine, chlorine, bromine and/or iodine, i.e., for example, fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(2fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl, 4-iodobutoxycarbonyl, 5-fluoropentoxycarbonyl, 5-chloropentoxycarbonyl, 5-bromopentoxycarbonyl, 6-fluorohexoxycarbonyl, 6-chlorohexoxycarbonyl or 6-bromohexoxycarbonyl;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino) carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di($C_1$–$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl) aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl) aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl) aminocarbonyl, N-(-methylethyl)-N-(1-methylpropyl) aminocarbonyl, N-(1-methylethyl)-N-(2-methylpropyl)aminocarbonyl, N-(1,1-dimethylethyl)-N-(2-methylethyl)aminocarbonyl, N-butyl-N-(1- methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

$C_1$–$C_6$-alkoxy-$C_1$–$C_6$-alkyl: $C_1$–$C_6$-alkyl which is substituted by $C_1$–$C_6$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl, 4-(1,1-dimethylethoxy)butyl, 5-methoxypentyl, 5-ethoxypentyl, 6-methoxyhexyl or 6-ethoxyhexyl;

the $C_1$–$C_4$-alkoxy-$C_1$–$C_4$-alkoxy radical of $C_1$–$C_4$-alkoxy-$C_1$–$C_4$-alkoxycarbonyl: $C_1$–$C_4$-alkoxy which is substituted by $C_1$–$C_4$-alkoxy as mentioned above, i.e., for example, methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)-butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_3$–$C_6$-alkenyl, and the alkenyl moieties of $C_3$–$C_6$-alkenylcarbonyl, $C_3$–$C_6$-alkenyloxy, $C_3$–$C_6$-alkenylthio, N—($C_3$–$C_6$-alkenyl)-N—($C_1$–$C_6$-alkyl)amino and di($C_3$–$C_6$-alkenyl)amino: for example prop-2-en-1-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl: $C_3$–$C_6$-alkenyl as mentioned above, and also ethenyl;

$C_3$–$C_6$-haloalkenyl: a $C_3$–$C_6$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moieties of $C_3$–$C_6$-alkynylcarbonyl, $C_3$–$C_6$-alkynyloxy, $C_3$–$C_6$-alkynylthio, N—($C_3$–$C_6$-alkynyl)-N—($C_1$–$C_6$-alkyl)amino and di($C_3$–$C_6$-alkynyl)amino: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$-alkynylcarbonyl: $C_3$–$C_6$-alkynyl as mentioned above, and also ethynyl;

$C_3$–$C_6$-haloalkynyl: a $C_3$–$C_6$-alkynyl radical as mentioned above which is partially or fully substituted by fluorine, chlorine, bromine and/or iodine, i.e., for example, 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_3$–$C_6$-cycloalkyl, and the cycloalkyl moieties of $C_3$–$C_6$-cycloalkylcarbonyl: for example cyclopropyl, cyclobutyl, cyclopentyl or cyclohexyl;

$C_3$–$C_6$-halocycloalkyl: a $C_3$–$C_6$-cycloalkyl radical as mentioned above which may be partially or fully substituted by fluorine, chlorine, bromine and/or iodine, i.e., for example, 2,2-dichlorocycloprop-1-yl, 2,2-difluorocycloprop-1-yl, 3-chlorocyclopent-1-yl, 3-fluorocyclopent-1-yl, 3-bromocyclopent-1-yl, 3,3-dichlorocyclopent-1-yl, 3,3-difluorocyclopent-1-yl, 4-chlorocyclohex-1-yl, 4-fluorocyclohex-1-yl, 4-bromocyclohex-1-yl, 4,4-dichlorocyclohex-1-yl or 4,4-difluorocyclohex-1-yl;

heterocyclyl, and the heterocyclyl moieties of heterocyclylcarbonyl, heterocyclyl-$C_1$–$C_6$-alkyl, heterocyclyloxy, heterocyclylaminocarbonyl: a saturated, partially saturated or unsaturated 5- or 6-membered heterocyclic ring which is attached via carbon and contains one to four identical or different heteroatoms selected from the following group: oxygen, sulfur and nitrogen, i.e., for example, 5-membered rings such as:

tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl, pyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-dioxathiolan-4-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl, 6-membered rings such as:

tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,1-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl, pyridin-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

where, if appropriate, the sulfur of the abovementioned heterocycles can oxidized to S=O or $S(=O)_2$;

and where a bicyclic ring system may be formed with a fused-on phenyl ring or a $C_3$–$C_6$-carbocycle or with a further 5- to 6-membered heterocycle.

N-bonded heterocyclyl: a saturated, partially saturated or unsaturated 5- or 6-membered heterocyclic ring which is attached via nitrogen and contains at least one nitrogen and, if appropriate, one to three identical or different heteroatoms selected from the following group: oxygen, sulfur or nitrogen, i.e., for example N-bonded 5-membered rings such as:

tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl, imidazol-1-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazol-1-yl, 1,2,4-triazol-1-yl, tetrazol-1-yl;

and N-bonded 6-membered rings such as:

piperidin-1-yl, 1,2,3,4-tetrahydropyridin-1-yl, 1,2,5,6-tetrahydropyridin-1-yl, 1,4-dihydropyridin-1-yl, 1,2-dihydropyridin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2, 3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl, and N-bonded cyclic imides such as:

phthalimide, tetrahydrophthalimide, succinimide, maleimide or glutarimide, and also 4-oxo-1,4-dihydropyridin-1-yl.

All phenyl rings or heterocyclyl radicals and all phenyl components in phenyl-$C_1$–$C_6$-alkyl, phenoxy, phenylcarbonyl and phenylaminocarbonyl or heterocyclyl components in heterocyclyl-$C_1$–$C_6$-alkyl, heterocyclyloxy, heterocyclylcarbonyl and heterocyclylaminocarbonyl are, unless stated otherwise, preferably unsubstituted or they carry one to three halogen atoms and/or one nitro group, one cyano radical and/or one or two methyl, trifluoromethyl, methoxy or trifluoromethoxy substituents.

Suitable heterocycyl radicals are, in particular, 5-membered aromatic heterocycles, for example 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,4-triazol-3-yl or tetrazol-5-yl;

5-membered partially unsaturated heterocycles, for example 4,5-dihydro-1H-pyrazol-3-yl, 4,5-dihydro-1H-pyrazol-4-yl, 4,5-dihydro-1H-pyrazol-5-yl, 4,5-dihydroisoxazol-3-yl, 4,5-dihydroisoxazol-4-yl, 4,5-dihydroisoxazol-5-yl, 4,5-dihydrooxazol-2-yl, 4,5-dihydrooxazol-2-yl, 4,5-dihydrothiazol-2-yl or 4,5-dihydroimidazol-2-yl;

5-membered saturated heterocycles, for example tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl or 1,3-dithiolan-4-yl;

6-membered aromatic heterocycles, for example pyridin-2-yl, pyridin-3-yl, pyridin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl or 1,2,4-triazin-6-yl;

6-membered partially unsaturated heterocycles, for example 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 4H-5,6-dihydro-1,3-oxazin-2-yl, 4H-5,6-dihydro-1,3-thiazin-2-yl or 3,4,5,6-tetrahydropyrimidin-2-yl;

6-membered saturated heterocycles, for example tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,3-dithian-2-yl, 1,3-dithian-4-yl, 1,3-dithian-5-yl, 1,3-oxathian-2-yl, 1,3-oxathian-4-yl, 1,3-oxathian-5-yl, tetrahydro-1,4-oxazin-2-yl, tetrahydro-1,4-oxazin-3-yl, tetrahydro-1,4-thiazin-2-yl or tetrahydro-1,4-thiazin-3-yl.

The compounds of the formula I according to the invention where $Q=Q^1$ are referred to as compounds of the formula Ia, compounds of the formula I where $Q=Q^2$ are referred to as Ib, compounds of the formula I where $Q=Q^3$ are referred to as Ic and compounds of the formula I where $Q=Q^4$ are referred to as Id.

With respect to the use of the compounds of the formula I according to invention as herbicides, the variables preferably have the following meaning, in each case on their own or in combination:

X is oxygen or sulfur;

in particular oxygen;

$R^1$, $R^2$ are hydrogen, $C_1$–$C_6$-alkyl, hydroxyl, $C_1$–$C_6$-alkoxy, $C_1$–$C_6$-alkylthio, di($C_1$–$C_6$-alkyl)amino, where the alkyl radicals of the five last-mentioned substituents may be partially or fully halogenated and/or may carry one to three of the following groups:

nitro, cyano, $C_1$–$C_4$-alkoxy, $C_1$–$C_4$-alkylsulfonyl or $C_1$–$C_4$-alkoxycarbonyl;

in particular hydrogen, $C_1$–$C_4$-alkyl such as methyl, ethyl, propyl, 1-methylethyl, butyl, 1-methylbutyl or 2-methylbutyl, hydroxyl, $C_1$–$C_4$-alkoxy such as methoxy, ethoxy, propoxy, 1-methylethoxy, butoxy or 2-methylbutoxy, $C_1$–$C_4$-alkylthio such as methylthio, ethylthio, propylthio or 1-methylethylthio, or di($C_1$–$C_4$-alkyl)amino such as dimethylamino, diethylamino, dipropylamino, dibutylamino, N-methyl-N-ethylamino, N-methyl-N-propylamino, N-methyl-N-butylamino, N-ethyl-N-propylamino or N-ethyl-N-butylamino; or $R^1$ and $R^2$ together form a O—O$(CH_2)_m$—O—, —O—$(CH_2)_m$—S—, —S—$(CH_2)_m$—S—, —$NR^5$—$(CH_2)_m$—$NR^5$—, —O—$(CH_2)_m$—$NR^5$—, —S—$(CH_2)_m$—

$NR^5$— or —$(CH_2)_p$ chain which may carry one to three radicals from the following group: halogen, cyano, $C_1$–$C_4$-alkyl or $C_1$–$C_4$-alkoxycarbonyl; in particular, $R^1$ and $R^2$ together form a —O—$(CH_2)_m$—O, —O—$(CH_2)_m$—S—, —S—$(CH_2)_m$—S or —$(CH_2)_p$ chain;

$R^3$ is hydrogen, nitro, cyano, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, —P(=O)($C_1$–$C_4$-alkyl)$_2$ or —P(=O)($C_1$–$C_4$-alkoxy)$_2$; in particular nitro, halogen, $C_1$–$C_4$-alkyl such as methyl or ethyl, $C_1$–$C_4$-haloalkyl such as difluoromethyl or trifluoromethyl, $C_1$–$C_4$-alkoxy such as methoxy or ethoxy, $C_1$–$C_4$-haloalkoxy such as difluoromethoxy, trifluoromethoxy or chlorodifluoromethoxy, $C_1$–$C_4$-alkylthio such as methylthio or ethylthio, $C_1$–$C_4$-alkylsulfonyl such as methylsulfonyl or ethylsulfonyl, $C_1$–$C_4$-haloalkylsulfonyl such as difluoromethylsulfonyl, trifluoromethylsulfonyl or chlorodifluoromethylsulfonyl, —P(=O)$(CH_3)_2$, —P(=O)$(CH_2CH_3)_2$, —P(=O)$(OCH_3)_2$ or —P(=O)$(OCH_2CH_3)_2$;

$R^4$ is halogen, such as chlorine or bromine, or $C_1$–$C_4$-alkyl, such as methyl or ethyl;

$R^5$ is hydrogen or $C_1$–$C_4$-alkyl, such as methyl or ethyl;

l is 0 or 1;

m is 2, 3 or 4;

p is 4 or 5;

Q is a radical of the formula $Q^1$, $Q^2$, $Q^3$ or $Q^4$;

$R^6$ is hydroxyl, mercapto, halogen, $OR^{13}$, $SR^{13}$, $SO_2R^{14}$, $OSO_2R^{14}$, $OPOR^{15}R^{16}$, $OPR^{15}R^{16}$, $OPSR^{15}R^{16}$, $NR^{17}R^{18}$, $ONR^{18}R^{19}$, N-bonded heterocyclyl or O—(N-bonded heterocyclyl), where the heterocyclyl radical of the two last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^7$,$R^9$,$R^{11}$ are hydrogen, halogen, cyano, $C_1$–$C_6$-alkyl, $C_1$–$C_6$-haloalkyl, di($C_1$–$C_6$-alkoxy)methyl, di($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio, $C_1$–$C_6$-haloalkylthio, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl;

$R^8$,$R^{10}$,$R^{12}$ are hydrogen or $C_1$–$C_6$-alkyl;

in particular hydrogen or $C_1$–$C_4$-alkyl, such as methyl or ethyl; or $R^7$ and $R^8$ or $R^9$ and $R^{10}$ or $R^{11}$ and $R^{12}$ together form a —O—$(CH_2)_u$—O—, —O—$(CH_2)_u$—S—, —S—$(CH_2)_u$—S—, —O—$(CH_2)_v$— or —S—$(CH_2)_v$ chain which may be substituted by one to three radicals from the following group:

halogen, cyano, $C_1$–$C_4$-alkyl, $C_1$–$C_4$-haloalkyl or $C_1$–$C_4$-alkoxycarbonyl; or $R^7$ and $R^8$ or $R^9$ and $R^{10}$ or $R^{11}$ and $R^{12}$ together form a —$(CH_2)_w$ chain which may be interrupted by oxygen or sulfur and/or substituted by one to four radicals from the following group:

halogen, cyano, $C_1$–$C_4$-alkyl, $C_1$–$C_4$-haloalkyl or $C_1$–$C_4$-alkoxycarbonyl; or $R^7$ and $R^8$ or $R^9$ and $R^{10}$ or $R^{11}$ and $R^{12}$ together with the carbon atoms to which they are attached form a carbonyl group; or $R^7$ and $R^9$ or $R^9$ and $R^{11}$ or $R^7$ and $R^{11}$ together form a —$(CH_2)_v$ chain which may be substituted by one to three radicals from the following group: halogen, $C_1$–$C_6$-alkyl, $C_1$–$C_6$-alkoxy, hydroxyl or $C_1$–$C_6$-alkoxycarbonyl;

$R^{13}$ is $C_1$–$C_6$-alkyl, $C_3$–$C_6$-alkenyl, $C_3$–$C_6$-haloalkenyl, $C_3$–$C_6$-alkynyl, $C_1$–$C_6$-alkylcarbonyl, $C_2$–$C_6$-alkenylcarbonyl, $C_3$–$C_6$-cycloalkylcarbonyl, $C_1$–$C_6$-alkylaminocarbonyl, $C_1$–$C_6$-alkylcarbonyl-$C_1$–$C_6$-alkyl or $C_1$–$C_6$-alkoxyimino-$C_1$–$C_6$-alkyl, where the abovementioned alkyl and cycloalkyl radicals may be partially or fully halogenated and/or may carry one to three of the following groups:

cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di($C_1$–$C_4$-alkyl)aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl or heterocyclylcarbonyl, where the phenyl and the heterocyclyl radical of the 6 last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$,$R^{15}$, $R^{16}$ are $C_1$–$C_6$-alkyl, $C_3$–$C_6$-alkenyl, $C_3$–$C_6$-haloalkenyl, $C_3$–$C_6$-cycloalkyl, hydroxyl, $C_1$–$C_6$-alkoxy, di($C_1$–$C_6$-alkyl)amino or di($C_1$–$C_6$-haloalkyl)amino, where the abovementioned alkyl, cycloalkyl and alkoxy radicals may be partially or fully halogenated and/or may carry one to three of the following groups: cyano, $C_1$–$C_4$-alkoxy, $C_1$–$C_4$-alkylthio, $C_1$–$C_4$-alkylcarbonyl or $C_1$–$C_4$-alkoxycarbonyl;

are phenyl, heterocyclyl, phenoxy or heterocyclyloxy, where the phenyl and the heterocyclyl radical of the last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{17}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy or $C_3$–$C_6$-alkenyloxy, where the abovementioned alkyl, cycloalkyl and alkoxy radicals may be partially or fully halogenated and/or may carry one to three radicals from the following group:

cyano, $C_1$–$C_4$-alkoxy or $C_1$–$C_4$-alkylthio;

is phenyl, heterocyclyl, phenyl-$C_1$–$C_6$-alkyl or heterocyclyl-$C_1$–$C_6$-alkyl, where the phenyl or heterocyclyl radical of the four last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{18}$, $R^{19}$ are $C_1$–$C_6$-alkyl or $C_3$–$C_6$-alkenyl;

u is from 2 to 4;

v is from 1 to 5;

w is from 2 to 5;

$R^{20}$ is a radical as mentioned under $R^6$;

$R^{21}$ is hydrogen, $C_1$–$C_6$-alkyl or $C_1$–$C_6$-haloalkyl; in particular hydrogen or $C_1$–$C_4$-alkyl such as methyl, ethyl, propyl, 1-methyleth-1-yl or 1,1-dimethyleth-1-yl;

$R^{22}$ is hydrogen or $C_1$–$C_6$-alkyl; in particular hydrogen or $C_1$–$C_4$-alkyl, such as methyl or ethyl;

$R^{23}$ is $C_1$–$C_6$-alkyl, $C_1$–$C_6$-haloalkyl, $C_3$–$C_6$-cycloalkyl or $C_3$–$C_6$-halocycloalkyl; in particular $C_1$–$C_6$-alkyl or $C_3$–$C_6$-cycloalkyl; very preferably cyclopropyl;

$R^{24}$ is hydrogen;

$R^{25}$ is $C_1$–$C_6$-alkyl, $C_1$–$C_6$-haloalkyl, $C_3$–$C_6$-cycloalkyl or $C_3$–$C_6$-halocycloalkyl; in particular $C_1$–$C_6$-alkyl or $C_3$–$C_6$-cycloalkyl.

Particular preference is given to the compounds Ia especially the compounds Ia where the variables have the following meanings, in each case on their own or in combination:

$R^6$ is hydroxyl, mercapto, halogen, $OR^{13}$, $SR^{13}$, $SO_2R^{14}$, $OSO_2R^{14}$, $NR^{17}R^{18}$, $ONR^{18}R^{19}$ or N-bonded heterocyclyl, where the heterocyclyl radical of the last-mentioned substituent may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^7$,$R^9$,$R^{11}$ are hydrogen, halogen, cyano, $C_1$–$C_6$-alkyl, $C_1$–$C_6$-haloalkyl, di($C_1$–$C_6$-alkoxy)methyl, di($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio or $C_1$–$C_6$-haloalkylthio;

$R^8$,$R^{10}$,$R^{12}$ are hydrogen or $C_1$–$C_6$-alkyl;

in particular hydrogen or $C_1$–$C_4$-alkyl, such as methyl or ethyl; or $R^9$ and $R^{10}$ together with the carbon to which they are attached form a carbonyl group; or $R^7$ and $R^{11}$ together form a $-(CH_2)_v$ chain which may be substituted by one to three $C_1$–$C_4$-alkyl radicals;

$R^{13}$ is $C_1$–$C_6$-alkyl, $C_3$–$C_6$-alkenyl, $C_3$–$C_6$-haloalkenyl, $C_3$–$C_6$-alkynyl, $C_1$–$C_6$-alkylcarbonyl, $C_3$–$C_6$-cycloalkylcarbonyl, $C_1$–$C_6$-alkylaminocarbonyl or $C_1$–$C_6$-alkylcarbonyl-$C_1$–$C_6$-alkyl, where the abovementioned alkyl or cycloalkyl radicals may be partially or fully halogenated and/or may carry one to three of the following groups:

cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di($C_1$–$C_4$-alkyl)aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl or heterocyclylcarbonyl, where the phenyl and the heterocyclyl radical of the 6 last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl, $C_3$–$C_6$-alkenyl, $C_3$–$C_6$-haloalkenyl, $C_3$–$C_6$-cycloalkyl, hydroxyl, $C_1$–$C_6$-alkoxy, di($C_1$–$C_6$-alkyl)amino or di($C_1$–$C_6$-haloalkyl)amino, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, $C_1$–$C_4$-alkylcarbonyl or $C_1$–$C_4$-alkoxycarbonyl;

are phenyl, heterocyclyl, phenoxy or heterocyclyloxy, where the phenyl and the heterocyclyl radical of the last-mentioned substituents may be partially or fully halogenated and/or carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{17}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy or $C_3$–$C_6$-alkenyloxy, where the abovementioned alkyl, cycloalkyl and alkoxy radicals may be partially or fully halogenated and/or may carry one to three radicals from the following group:

cyano, $C_1$–$C_4$-alkoxy or $C_1$–$C_4$-alkylthio;

is phenyl, heterocyclyl, phenyl-$C_1$–$C_6$-alkyl or heterocyclyl-$C_1$–$C_6$-alkyl, where the phenyl or heterocyclyl radical of the four last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{18}$, $R^{19}$ are $C_1$–$C_6$-alkyl or $C_3$–$C_6$-alkenyl;

v is 1 or 2;

in particular 2.

Particular preference is also given to compounds of the formula Ia where $R^6$ is hydroxyl, mercapto, phenylcarbonyloxy, $C_1$–$C_6$-alkylthio, phenylthio, N—($C_1$–$C_6$-alkoxy)-N—($C_1$–$C_6$-alkyl)amino, 1-tetrahydropyrrolyl or 2-tetrahydroisoxazolyl, where the phenyl radicals of the abovementioned radicals may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

in particular hydroxyl, phenylcarbonyloxy, $C_1$–$C_4$-alkylthio, phenylthio, N—($C_1$–$C_4$-alkoxy)-N—($C_1$–$C_4$-alkyl)amino, 1-tetrahydropyrrolyl or 2-tetrahydroisoxazolyl;

$R^7$,$R^8$,$R^9$,$R^{10}$,$R^{11}$,$R^{12}$ are hydrogen or $C_1$–$C_4$-alkyl, such as methyl or ethyl;

in particular hydrogen or methyl; or $R^9$ and $R^{10}$ together with the carbon to which they are attached form a carbonyl group; or $R^7$ and $R^{11}$ together form a $-(CH_2)-$ or $-(CH_2)_2-$ chain.

Extraordinary preference is given to the compounds of the formula Ia where $R^6$ is hydroxyl, mercapto, phenylcarbonyloxy, $C_1$–$C_6$-alkylthio, phenylthio, where the phenyl radicals of the abovementioned radicals may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

in particular hydroxyl or phenylthio, where the phenyl radical may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy.

Preference is also given to compounds Ib, especially compounds Ib where the variables have the following meanings:

$R^{20}$ is a radical as mentioned under $R^6$;

$R^{21}$ is hydrogen, $C_1$–$C_6$-alkyl or $C_1$–$C_6$-haloalkyl; in particular $C_1$–$C_4$-alkyl, such as methyl, ethyl, 1-methyleth-1-yl or 1,1-dimethyleth-1-yl, or $C_1$–$C_4$-haloalkyl, such as 2-fluoroethyl or 2,2,2-trifluoroethyl;

$R^{22}$ is hydrogen, $C_1$–$C_6$-alkyl or $C_1$–$C_6$-haloalkyl, in particular hydrogen, $C_1$–$C_4$-alkyl, such as methyl or ethyl, or $C_1$–$C_4$-haloalkyl, such as trifluoromethyl; in particular hydrogen, methyl or trifluoromethyl.

Preference is also given to the compounds Ib where the variables have the following meanings:

$R^{20}$ is hydroxyl, mercapto, halogen, $OR^{13}$, $SR^{13}$, $SO_2R^{14}$, $OSO_2R^{14}$, $NR^{17}R^{18}$, $ONR^{18}R^{19}$ or N-bonded heterocyclyl, where the heterocyclyl radical of the lastmentioned substituent may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_1$–$C_6$-alkyl, $C_3$–$C_6$-alkenyl, $C_3$–$C_6$-haloalkenyl, $C_3$–$C_6$-alkynyl, $C_1$–$C_6$-alkylcarbonyl, $C_3$–$C_6$-cycloalkylcarbonyl, $C_1$–$C_6$-alkylaminocarbonyl, N,N-di-($C_1$–$C_6$-alkyl) or $C_1$–$C_6$-alkylcarbonyl-$C_1$–$C_6$-alkyl, where the alkyl or cycloalkyl radicals mentioned may be partially or fully halogenated and/or may carry one to three of the following groups:

cyano, $C_{1\ 4}$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl or heterocyclylcarbonyl, where the phenyl and the heterocyclyl radical of the 6 lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl, $C_3$–$C_6$-alkenyl, $C_3$–$C_6$-haloalkenyl, $C_3$–$C_6$-cycloalkyl, hydroxyl, $C_1$–$C_6$-alkoxy, di-($C_1$–$C_6$-alkyl)amino or di-($C_1$–$C_6$-haloalkyl)amino, where the alkyl, cycloalkyl and alkoxy radicals mentioned may be partially or fully halogenated and/or may carry one to three of the following groups:

cyano, $C_1$–$C_4$-alkoxy, $C_1$–$C_4$-alkylthio, $C_1$–$C_4$-alkylcarbonyl or $C_1$–$C_4$-alkoxycarbonyl;

is phenyl, heterocyclyl, phenoxy or heterocyclyloxy, where the phenyl and the heterocyclyl radical of the lastmentioned substituents may be partially or fully halogenated and/or may carry one to three of the following radicals:

nitro, cyano, $C_1$–$C_4$-alkyl, $C_1C_4$-haloalkyl, $C_1$–$C_4$-alkoxy or $C_1$–$C_4$-haloalkoxy;

$R^{17}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy or $C_3$–$C_6$-alkenyloxy, where the alkyl, cycloalkyl and alkoxy radicals mentioned may be partially or fully halogenated and/or may carry one to three radicals from the group below:

cyano, $C_1$–$C_4$-alkoxy or $C_1$–$C_4$-alkylthio;

is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{18}$, $R^{19}$ are $C_1$–$C_6$-alkyl or $C_3$–$C_6$-alkenyl;

$R^{21}$ is $C_1$–$C_6$-alkyl, such as methyl, ethyl, 1-methyleth-1-yl, or 1,1-dimethyleth-1-yl;

$R^{22}$ is hydrogen or $C_1$–$C_6$-alkyl such as methyl or ethyl; in particular hydrogen or methyl.

Extraordinary preference is given to the compounds Ib where the variables have the following meaning:

$R^{20}$ is hydroxyl.

Preference is also given to compounds of the formula Ic, especially compounds Ic where the variables have the following meanings:

$R^{23}$ is $C_1$–$C_6$-alkyl or $C_3$–$C_6$-cycloalkyl; in particular cyclopropyl;

$R^{24}$ is hydrogen.

Preference is also given to compounds of the formula Id, especially compounds Id where the variables have the following meanings:

$R^{25}$ is $C_1$–$C_6$-alkyl or $C_3$–$C_6$-cycloalkyl.

Preference is furthermore given to the compounds I1 (≡I where X═O, $R^3$ is attached in the 4-position, $R^4$ is attached in the 5-position and "P(═X)$R^1R^2$" is attached in the 2-position)

I1

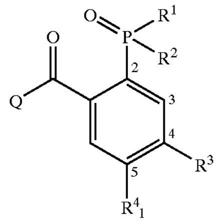

With respect to the variables $R^1$ to $R^4$ and Q, what is said above applies.

Particular preference is given to the compounds I1 where the variables have the following meanings:

$R^3$ is nitro, cyano, halogen, $C_1$–$C_4$-alkyl, $C_1$–$C_4$-haloalkyl, $C_1$–$C_6$-alkoxy, $C_1$–$C_4$-haloalkoxy, $C_1$–$C_4$-alkylsulfonyl or $C_1$–$C_4$-haloalkylsulfonyl;

$R^4$ is halogen, such as chlorine or bromine, or $C_1$–$C_4$-alkyl, such as methyl or ethyl;

l is 0 or 1.

Furthermore, preference is also given to the compounds I2 (≡I where X═O, $R^3$ is attached in the 2-position, $R^4$ is attached in the 5-position and "P(═X)$R^1R^2$" is attached in the 4-position)

I2

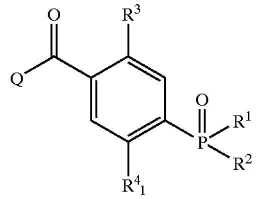

With respect to the variables $R^1$ to $R^4$ and Q, what was said above applies.

Particular preference is given to the compounds I2 where the variables have the following meanings:

$R^3$ is nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl or $C_1$–$C_4$-haloalkylsulfonyl;

$R^4$ is halogen, such as chlorine or bromine, or $C_1$–$C_4$-alkyl, such as methyl or ethyl;

l is 0 or 1.

Preference is furthermore given to the compounds I, in particular the compounds Ia, Ib, I1 or I2, where the variables have the following meanings:

$R^1$,$R^2$ are hydrogen, hydroxyl, $C_1$–$C_6$-alkyl or $C_1$–$C_6$-alkoxy, where the alkyl radicals of the two lastmentioned substituents may be partially or fully halogenated and/or may carry one to three of the following groups: nitro, cyano, $C_1$–$C_4$-alkoxy, $C_1$–$C_4$-alkylsulfonyl or $C_1$–$C_4$-alkoxycarbonyl;

particularly preferably hydrogen, $C_1$–$C_4$-alkyl or $C_1$–$C_4$-alkoxy.

Preference is furthermore given to the compounds I1a (≡I where X═O, $R^3$ is attached in position 4, $R^4_l$ is attached in position 5 and "P(═X)$R^1R^2$" is attached in position 2 and Q=$Q^1$).

Particular preference is given to the compounds I1a (≡I where X═O, $R^3$ is in position 4, $R^4_l$ is in position 5 and "P(═X)$R^1R^2$" is in position 2), where the variables have the following meanings:

$R^1$,$R^2$ are $C_1$–$C_4$-alkyl or $C_1$–$C_4$-alkoxy; in particular $C_1$–$C_4$-alkyl;

$R^3$ is halogen;

l is 0;

$R^6$ is hydroxyl;

$R^7$,$R^8$,$R^9$,$R^{10}$,$R^{11}$,$R^{12}$ are hydrogen or $C_1$–$C_4$-alkyl, or $R^9$ and $R^{10}$ together with the carbon to which they are attached form a carbonyl group.

Preference is furthermore given to the compounds I2a (≡I where X═O, $R^3$ is attached in position 2, $R^4_l$ is attached in position 5 and "P(═X)$R^1R^2$" is attached in position 4 and Q=$Q^1$).

Particular preference is given to the compounds I2a (≡I where X═O, $R^3$ is attached in position 2, $R^4_l$ is attached in position 5 and "P(═X)$R^1R^2$" is attached in position 4 and Q=$Q^1$), where the variables have the following meanings:

$R^1$,$R^2$ are $C_1$–$C_4$-alkyl or $C_1$–$C_4$-alkoxy;

$R^3$ is halogen;

l is 0;

$R^6$ is hydroxyl or phenylthio, where the phenyl radical may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^7$,$R^8$,$R^9$,$R^{10}$,$R^{11}$,$R^{12}$ are hydrogen or $C_1$–$C_4$-alkyl; or $R^9$ and $R^{10}$ together with the carbon to which they are attached form a carbonyl group;

or $R^7$ and $R^{11}$ together form a —$(CH_2)$— or —$(CH_2)_2$— chain, in particular a —$(CH_2)_2$— chain.

Preference is furthermore given to the compounds I2b (≡I where X═O, $R^3$ is in position 2, $R^4_l$ is in position 5 and "P(═X)$R^1R^2$" is in position 4).

Particular preference is given to the compounds I2b (≡I where X═O, $R^3$ is in position 2, $R^4_l$ is in position 5 and "P(═X)$R^1R^2$" is in position 4), where the variables have the following meanings:

$R^1$,$R^2$ are $C_1$–$C_4$-alkyl or $C_1$–$C_4$-alkoxy; in particular $C_1$–$C_4$-alkoxy;

$R^3$ is halogen;

l is 0;

$R^{20}$ is hydroxyl;

$R^{21}$ is $C_1$–$C_4$-alkyl;

$R^{22}$ is hydrogen or $C_1$–$C_4$-alkyl; in particular hydrogen.

Extraordinary preference is given to the compounds I1a1 (≡I where X═O, $R^3$ is attached in the 4-position, $R^4$ is attached in the 5-position and "P(═X)$R^1R^2$" is attached in the 2-position, Q=$Q^1$, $R^7$ to $R^{12}$=hydrogen), in particular to the compounds I1a1.n where the variables $R^1$ to $R^4$ and $R^6$ are as defined in Table 1.

The given radical definitions X, $R^1$ to $R^{12}$, Q and l are preferred for the compounds according to the invention not only in combination with one another, but in each case also on their own.

TABLE 1

I1a1

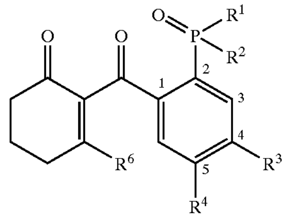

| n | $R^1$ | $R^2$ | $R^3$ | $R^4$ | $R^6$ |
|---|---|---|---|---|---|
| 1 | H | H | H | H(l = O) | OH |
| 2 | $CH_3$ | $CH_3$ | H | H(l = O) | OH |
| 3 | $CH_2CH_3$ | $CH_2CH_3$ | H | H(l = O) | OH |
| 4 | $CH_2CH_2CH_3$ | $CH_2CH_2CH_3$ | H | H(l = O) | OH |
| 5 | $OCH_3$ | $OCH_3$ | H | H(l = O) | OH |
| 6 | $OCH_2CH_3$ | $OCH_2CH_3$ | H | H(l = O) | OH |
| 7 | $OCH_2CH_2CH_3$ | $OCH_2CH_2CH_3$ | H | H(l = O) | OH |
| 8 | $SCH_3$ | $SCH_3$ | H | H(l = O) | OH |
| 9 | $SCH_2CH_3$ | $SCH_2CH_3$ | H | H(l = O) | OH |
| 10 | $N(CH_3)_2$ | $N(CH_3)_2$ | H | H(l = O) | OH |
| 11 | $N(CH_2CH_3)_2$ | $N(CH_2CH_3)_2$ | H | H(l = O) | OH |
| 12 | $N(CH_3)(CH_2CH_3)$ | $N(CH_3)(CH_2CH_3)$ | H | H(l = O) | OH |
| 13 | O—$(CH_2CH_2)$—O | | H | H(l = O) | OH |
| 14 | O—$(CH_2CH_2CH_2)$—O | | H | H(l = O) | OH |
| 15 | S—$(CH_2CH_2)$—S | | H | H(l = O) | OH |
| 16 | S—$(CH_2CH_2CH_2)$—S | | H | H(l = O) | OH |
| 17 | —$(CH_2)_4$— | | H | H(l = O) | OH |
| 18 | —$(CH_2)_5$— | | H | H(l = O) | OH |
| 19 | H | H | $NO_2$ | H(l = O) | OH |

TABLE 1-continued

I1a1

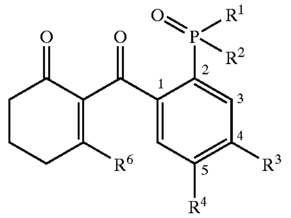

| n | $R^1$ | $R^2$ | $R^3$ | $R^4$ | $R^6$ |
|---|---|---|---|---|---|
| 20 | $CH_3$ | $CH_3$ | $NO_2$ | H(l = O) | OH |
| 21 | $CH_2CH_3$ | $CH_2CH_3$ | $NO_2$ | H(l = O) | OH |
| 22 | $CH_2CH_2CH_3$ | $CH_2CH_2CH_3$ | $NO_2$ | H(l = O) | OH |
| 23 | $OCH_3$ | $OCH_3$ | $NO_2$ | H(l = O) | OH |
| 24 | $OCH_2CH_3$ | $OCH_2CH_3$ | $NO_2$ | H(l = O) | OH |
| 25 | $OCH_2CH_2CH_3$ | $OCH_2CH_2CH_3$ | $NO_2$ | H(l = O) | OH |
| 26 | $SCH_3$ | $SCH_3$ | $NO_2$ | H(l = O) | OH |
| 27 | $SCH_2CH_3$ | $SCH_2CH_3$ | $NO_2$ | H(l = O) | OH |
| 28 | $N(CH_3)_2$ | $N(CH_3)_2$ | $NO_2$ | H(l = O) | OH |
| 29 | $N(CH_2CH_3)_2$ | $N(CH_2CH_3)_2$ | $NO_2$ | H(l = O) | OH |
| 30 | $N(CH_3)(CH_2CH_3)$ | $N(CH_3)(CH_2CH_3)$ | $NO_2$ | H(l = O) | OH |
| 31 | $O—(CH_2CH_2)—O$ | | $NO_2$ | H(l = O) | OH |
| 32 | $O—(CH_2CH_2CH_2)—O$ | | $NO_2$ | H(l = O) | OH |
| 33 | $S—(CH_2CH_2)—S$ | | $NO_2$ | H(l = O) | OH |
| 34 | $S—(CH_2CH_2CH_2)—S$ | | $NO_2$ | H(l = O) | OH |
| 35 | $—(CH_2)_4—$ | | $NO_2$ | H(l = O) | OH |
| 36 | $—(CH_2)_5—$ | | $NO_2$ | H(l = O) | OH |
| 37 | H | H | CN | H(l = O) | OH |
| 38 | $CH_3$ | $CH_3$ | CN | H(l = O) | OH |
| 39 | $CH_2CH_3$ | $CH_2CH_3$ | CN | H(l = O) | OH |
| 40 | $CH_2CH_2CH_3$ | $CH_2CH_2CH_3$ | CN | H(l = O) | OH |
| 41 | $OCH_3$ | $OCH_3$ | CN | H(l = O) | OH |
| 42 | $OCH_2CH_3$ | $OCH_2CH_3$ | CN | H(l = O) | OH |
| 43 | $OCH_2CH_2CH_3$ | $OCH_2CH_2CH_3$ | CN | H(l = O) | OH |
| 44 | $SCH_3$ | $SCH_3$ | CN | H(l = O) | OH |
| 45 | $SCH_2CH_3$ | $SCH_2CH_3$ | CN | H(l = O) | OH |
| 46 | $N(CH_3)_2$ | $N(CH_3)_2$ | CN | H(l = O) | OH |
| 47 | $N(CH_2CH_3)_2$ | $N(CH_2CH_3)_2$ | CN | H(l = O) | OH |
| 48 | $N(CH_3)(CH_2CH_3)$ | $N(CH_3)(CH_2CH_3)$ | CN | H(l = O) | OH |
| 49 | $O—(CH_2CH_2)—O$ | | CN | H(l = O) | OH |
| 50 | $O—(CH_2CH_2CH_2)—O$ | | CN | H(l = O) | OH |
| 51 | $S—(CH_2CH_2)—S$ | | CN | H(l = O) | OH |
| 52 | $S—(CH_2CH_2CH_2)—S$ | | CN | H(l = O) | OH |
| 53 | $—(CH_2)_4—$ | | CN | H(l = O) | OH |
| 54 | $—(CH_2)_5—$ | | CN | H(l = O) | OH |
| 55 | H | H | F | H(l = O) | OH |
| 56 | $CH_3$ | $CH_3$ | F | H(l = O) | OH |
| 57 | $CH_2CH_3$ | $CH_2CH_3$ | F | H(l = O) | OH |
| 58 | $CH_2CH_2CH_3$ | $CH_2CH_2CH_3$ | F | H(l = O) | OH |
| 59 | $OCH_3$ | $OCH_3$ | F | H(l = O) | OH |
| 60 | $OCH_2CH_3$ | $OCH_2CH_3$ | F | H(l = O) | OH |
| 61 | $OCH_2CH_2CH_3$ | $OCH_2CH_2CH_3$ | F | H(l = O) | OH |
| 62 | $SCH_3$ | $SCH_3$ | F | H(l = O) | OH |
| 63 | $SCH_2CH_3$ | $SCH_2CH_3$ | F | H(l = O) | OH |
| 64 | $N(CH_3)_2$ | $N(CH_3)_2$ | F | H(l = O) | OH |
| 65 | $N(CH_2CH_3)_2$ | $N(CH_2CH_3)_2$ | F | H(l = O) | OH |
| 66 | $N(CH_3)(CH_2CH_3)$ | $N(CH_3)(CH_2CH_3)$ | F | H(l = O) | OH |
| 67 | $O—(CH_2CH_2)—O$ | | F | H(l = O) | OH |
| 68 | $O—(CH_2CH_2CH_2)—O$ | | F | H(l = O) | OH |
| 69 | $S—(CH_2CH_2)—S$ | | F | H(l = O) | OH |
| 70 | $S—(CH_2CH_2CH_2)—S$ | | F | H(l = O) | OH |
| 71 | $—(CH_2)_4—$ | | F | H(l = O) | OH |
| 72 | $—(CH_2)_5—$ | | F | H(l = O) | OH |
| 73 | H | H | Cl | H(l = O) | OH |
| 74 | $CH_3$ | $CH_3$ | Cl | H(l = O) | OH |
| 75 | $CH_2CH_3$ | $CH_2CH_3$ | Cl | H(l = O) | OH |
| 76 | $CH_2CH_2CH_3$ | $CH_2CH_2CH_3$ | Cl | H(l = O) | OH |
| 77 | $OCH_3$ | $OCH_3$ | Cl | H(l = O) | OH |
| 78 | $OCH_2CH_3$ | $OCH_2CH_3$ | Cl | H(l = O) | OH |
| 79 | $OCH_2CH_2CH_3$ | $OCH_2CH_2CH_3$ | Cl | H(l = O) | OH |
| 80 | $SCH_3$ | $SCH_3$ | Cl | H(l = O) | OH |
| 81 | $SCH_2CH_3$ | $SCH_2CH_3$ | Cl | H(l = O) | OH |
| 82 | $N(CH_3)_2$ | $N(CH_3)_2$ | Cl | H(l = O) | OH |
| 83 | $N(CH_2CH_3)_2$ | $N(CH_2CH_3)_2$ | Cl | H(l = O) | OH |

TABLE 1-continued

I1a1

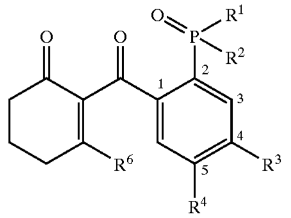

| n | $R^1$ | $R^2$ | $R^3$ | $R^4$ | $R^6$ |
|---|---|---|---|---|---|
| 84 | $N(CH_3)(CH_2CH_3)$ | $N(CH_3)(CH_2CH_3)$ | Cl | H(l = O) | OH |
| 85 | $O—(CH_2CH_2)—O$ | | Cl | H(l = O) | OH |
| 86 | $O—(CH_2CH_2CH_2)—O$ | | Cl | H(l = O) | OH |
| 87 | $S—(CH_2CH_2)—S$ | | Cl | H(l = O) | OH |
| 88 | $S—(CH_2CH_2CH_2)—S$ | | Cl | H(l = O) | OH |
| 89 | $—(CH_2)_4—$ | | Cl | H(l = O) | OH |
| 90 | $—(CH_2)_5—$ | | Cl | H(l = O) | OH |
| 91 | H | H | Br | H(l = O) | OH |
| 92 | $CH_3$ | $CH_3$ | Br | H(l = O) | OH |
| 93 | $CH_2CH_3$ | $CH_2CH_3$ | Br | H(l = O) | OH |
| 94 | $CH_2CH_2CH_3$ | $CH_2CH_2CH_3$ | Br | H(l = O) | OH |
| 95 | $OCH_3$ | $OCH_3$ | Br | H(l = O) | OH |
| 96 | $OCH_2CH_3$ | $OCH_2CH_3$ | Br | H(l = O) | OH |
| 97 | $OCH_2CH_2CH_3$ | $OCH_2CH_2CH_3$ | Br | H(l = O) | OH |
| 98 | $SCH_3$ | $SCH_3$ | Br | H(l = O) | OH |
| 99 | $SCH_2CH_3$ | $SCH_2CH_3$ | Br | H(l = O) | OH |
| 100 | $N(CH_3)_2$ | $N(CH_3)_2$ | Br | H(l = O) | OH |
| 101 | $N(CH_2CH_3)_2$ | $N(CH_2CH_3)_2$ | Br | H(l = O) | OH |
| 102 | $N(CH_3)(CH_2CH_3)$ | $N(CH_3)(CH_2CH_3)$ | Br | H(l = O) | OH |
| 103 | $O—(CH_2CH_2)—O$ | | Br | H(l = O) | OH |
| 104 | $O—(CH_2CH_2CH_2)—O$ | | Br | H(l = O) | OH |
| 105 | $S—(CH_2CH_2)—S$ | | Br | H(l = O) | OH |
| 106 | $S—(CH_2CH_2CH_2)—S$ | | Br | H(l = O) | OH |
| 107 | $—(CH_2)_4—$ | | Br | H(l = O) | OH |
| 108 | $—(CH_2)_5—$ | | Br | H(l = O) | OH |
| 109 | H | H | $CH_3$ | H(l = O) | OH |
| 110 | $CH_3$ | $CH_3$ | $CH_3$ | H(l = O) | OH |
| 111 | $CH_2CH_3$ | $CH_2CH_3$ | $CH_3$ | H(l = O) | OH |
| 112 | $CH_2CH_2CH_3$ | $CH_2CH_2CH_3$ | $CH_3$ | H(l = O) | OH |
| 113 | $OCH_3$ | $OCH_3$ | $CH_3$ | H(l = O) | OH |
| 114 | $OCH_2CH_3$ | $OCH_2CH_3$ | $CH_3$ | H(l = O) | OH |
| 115 | $OCH_2CH_2CH_3$ | $OCH_2CH_2CH_3$ | $CH_3$ | H(l = O) | OH |
| 116 | $SCH_3$ | $SCH_3$ | $CH_3$ | H(l = O) | OH |
| 117 | $SCH_2CH_3$ | $SCH_2CH_3$ | $CH_3$ | H(l = O) | OH |
| 118 | $N(CH_3)_2$ | $N(CH_3)_2$ | $CH_3$ | H(l = O) | OH |
| 119 | $N(CH_2CH_3)_2$ | $N(CH_2CH_3)_2$ | $CH_3$ | H(l = O) | OH |
| 120 | $N(CH_3)(CH_2CH_3)$ | $N(CH_3)(CH_2CH_3)$ | $CH_3$ | H(l = O) | OH |
| 121 | $O—(CH_2CH_2)—O$ | | $CH_3$ | H(l = O) | OH |
| 122 | $O—(CH_2CH_2CH_2)—O$ | | $CH_3$ | H(l = O) | OH |
| 123 | $S—(CH_2CH_2)—S$ | | $CH_3$ | H(l = O) | OH |
| 124 | $S—(CH_2CH_2CH_2)—S$ | | $CH_3$ | H(l = O) | OH |
| 125 | $—(CH_2)_4—$ | | $CH_3$ | H(l = O) | OH |
| 126 | $—(CH_2)_5—$ | | $CH_3$ | H(l = O) | OH |
| 127 | H | H | $CH_2CH_3$ | H(l = O) | OH |
| 128 | $CH_3$ | $CH_3$ | $CH_2CH_3$ | H(l = O) | OH |
| 129 | $CH_2CH_3$ | $CH_2CH_3$ | $CH_2CH_3$ | H(l = O) | OH |
| 130 | $CH_2CH_2CH_3$ | $CH_2CH_2CH_3$ | $CH_2CH_3$ | H(l = O) | OH |
| 131 | $OCH_3$ | $OCH_3$ | $CH_2CH_3$ | H(l = O) | OH |
| 132 | $OCH_2CH_3$ | $OCH_2CH_3$ | $CH_2CH_3$ | H(l = O) | OH |
| 133 | $OCH_2CH_2CH_3$ | $OCH_2CH_2CH_3$ | $CH_2CH_3$ | H(l = O) | OH |
| 134 | $SCH_3$ | $SCH_3$ | $CH_2CH_3$ | H(l = O) | OH |
| 135 | $SCH_2CH_3$ | $SCH_2CH_3$ | $CH_2CH_3$ | H(l = O) | OH |
| 136 | $N(CH_3)_2$ | $N(CH_3)_2$ | $CH_2CH_3$ | H(l = O) | OH |
| 137 | $N(CH_2CH_3)_2$ | $N(CH_2CH_3)_2$ | $CH_2CH_3$ | H(l = O) | OH |
| 138 | $N(CH_3)(CH_2CH_3)$ | $N(CH_3)(CH_2CH_3)$ | $CH_2CH_3$ | H(l = O) | OH |
| 139 | $O—(CH_2CH_2)—O$ | | $CH_2CH_3$ | H(l = O) | OH |
| 140 | $O—(CH_2CH_2CH_2)—O$ | | $CH_2CH_3$ | H(l = O) | OH |
| 141 | $S—(CH_2CH_2)—S$ | | $CH_2CH_3$ | H(l = O) | OH |
| 142 | $S—(CH_2CH_2CH_2)—S$ | | $CH_2CH_3$ | H(l = O) | OH |
| 143 | $—(CH_2)_4—$ | | $CH_2CH_3$ | H(l = O) | OH |
| 144 | $—(CH_2)_5—$ | | $CH_2CH_3$ | H(l = O) | OH |
| 145 | H | H | $CF_3$ | H(l = O) | OH |
| 146 | $CH_3$ | $CH_3$ | $CF_3$ | H(l = O) | OH |
| 147 | $CH_2CH_3$ | $CH_2CH_3$ | $CF_3$ | H(l = O) | OH |

TABLE 1-continued

I1a1

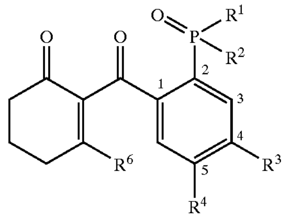

| n | $R^1$ | $R^2$ | $R^3$ | $R^4$ | $R^6$ |
|---|---|---|---|---|---|
| 148 | $CH_2CH_2CH_3$ | $CH_2CH_2CH_3$ | $CF_3$ | H(l = O) | OH |
| 149 | $OCH_3$ | $OCH_3$ | $CF_3$ | H(l = O) | OH |
| 150 | $OCH_2CH_3$ | $OCH_2CH_3$ | $CF_3$ | H(l = O) | OH |
| 151 | $OCH_2CH_2CH_3$ | $OCH_2CH_2CH_3$ | $CF_3$ | H(l = O) | OH |
| 152 | $SCH_3$ | $SCH_3$ | $CF_3$ | H(l = O) | OH |
| 153 | $SCH_2CH_3$ | $SCH_2CH_3$ | $CF_3$ | H(l = O) | OH |
| 154 | $N(CH_3)_2$ | $N(CH_3)_2$ | $CF_3$ | H(l = O) | OH |
| 155 | $N(CH_2CH_3)_2$ | $N(CH_2CH_3)_2$ | $CF_3$ | H(l = O) | OH |
| 156 | $N(CH_3)(CH_2CH_3)$ | $N(CH_3)(CH_2CH_3)$ | $CF_3$ | H(l = O) | OH |
| 157 | $O—(CH_2CH_2)—O$ | | $CF_3$ | H(l = O) | OH |
| 158 | $O—(CH_2CH_2CH_2)—O$ | | $CF_3$ | H(l = O) | OH |
| 159 | $S—(CH_2CH_2)—S$ | | $CF_3$ | H(l = O) | OH |
| 160 | $S—(CH_2CH_2CH_2)—S$ | | $CF_3$ | H(l = O) | OH |
| 161 | $—(CH_2)_4—$ | | $CF_3$ | H(l = O) | OH |
| 162 | $—(CH_2)_5—$ | | $CF_3$ | H(l = O) | OH |
| 163 | H | H | $OCH_3$ | H(l = O) | OH |
| 164 | $CH_3$ | $CH_3$ | $OCH_3$ | H(l = O) | OH |
| 165 | $CH_2CH_3$ | $CH_2CH_3$ | $OCH_3$ | H(l = O) | OH |
| 166 | $CH_2CH_2CH_3$ | $CH_2CH_2CH_3$ | $OCH_3$ | H(l = O) | OH |
| 167 | $OCH_3$ | $OCH_3$ | $OCH_3$ | H(l = O) | OH |
| 168 | $OCH_2CH_3$ | $OCH_2CH_3$ | $OCH_3$ | H(l = O) | OH |
| 169 | $OCH_2CH_2CH_3$ | $OCH_2CH_2CH_3$ | $OCH_3$ | H(l = O) | OH |
| 170 | $SCH_3$ | $SCH_3$ | $OCH_3$ | H(l = O) | OH |
| 171 | $SCH_2CH_3$ | $SCH_2CH_3$ | $OCH_3$ | H(l = O) | OH |
| 172 | $N(CH_3)_2$ | $N(CH_3)_2$ | $OCH_3$ | H(l = O) | OH |
| 173 | $N(CH_2CH_3)_2$ | $N(CH_2CH_3)_2$ | $OCH_3$ | H(l = O) | OH |
| 174 | $N(CH_3)(CH_2CH_3)$ | $N(CH_3)(CH_2CH_3)$ | $OCH_3$ | H(l = O) | OH |
| 175 | $O—(CH_2CH_2)—O$ | | $OCH_3$ | H(l = O) | OH |
| 176 | $O—(CH_2CH_2CH_2)—O$ | | $OCH_3$ | H(l = O) | OH |
| 177 | $S—(CH_2CH_2)—S$ | | $OCH_3$ | H(l = O) | OH |
| 178 | $S—(CH_2CH_2CH_2)—S$ | | $OCH_3$ | H(l = O) | OH |
| 179 | $—(CH_2)_4—$ | | $OCH_3$ | H(l = O) | OH |
| 180 | $—(CH_2)_5—$ | | $OCH_3$ | H(l = O) | OH |
| 181 | H | H | $OCH_2CH_3$ | H(l = O) | OH |
| 182 | $CH_3$ | $CH_3$ | $OCH_2CH_3$ | H(l = O) | OH |
| 183 | $CH_2CH_3$ | $CH_2CH_3$ | $OCH_2CH_3$ | H(l = O) | OH |
| 184 | $CH_2CH_2CH_3$ | $CH_2CH_2CH_3$ | $OCH_2CH_3$ | H(l = O) | OH |
| 185 | $OCH_3$ | $OCH_3$ | $OCH_2CH_3$ | H(l = O) | OH |
| 186 | $OCH_2CH_3$ | $OCH_2CH_3$ | $OCH_2CH_3$ | H(l = O) | OH |
| 187 | $OCH_2CH_2CH_3$ | $OCH_2CH_2CH_3$ | $OCH_2CH_3$ | H(l = O) | OH |
| 188 | $SCH_3$ | $SCH_3$ | $OCH_2CH_3$ | H(l = O) | OH |
| 189 | $SCH_2CH_3$ | $SCH_2CH_3$ | $OCH_2CH_3$ | H(l = O) | OH |
| 190 | $N(CH_3)_2$ | $N(CH_3)_2$ | $OCH_2CH_3$ | H(l = O) | OH |
| 191 | $N(CH_2CH_3)_2$ | $N(CH_2CH_3)_2$ | $OCH_2CH_3$ | H(l = O) | OH |
| 192 | $N(CH_3)(CH_2CH_3)$ | $N(CH_3)(CH_2CH_3)$ | $OCH_2CH_3$ | H(l = O) | OH |
| 193 | $O—(CH_2CH_2)—O$ | | $OCH_2CH_3$ | H(l = O) | OH |
| 194 | $O—(CH_2CH_2CH_2)—O$ | | $OCH_2CH_3$ | H(l = O) | OH |
| 195 | $S—(CH_2CH_2)—S$ | | $OCH_2CH_3$ | H(l = O) | OH |
| 196 | $S—(CH_2CH_2CH_2)—S$ | | $OCH_2CH_3$ | H(l = O) | OH |
| 197 | $—(CH_2)_4—$ | | $OCH_2CH_3$ | H(l = O) | OH |
| 198 | $—(CH_2)_5—$ | | $OCH_2CH_3$ | H(l = O) | OH |
| 199 | H | H | $SCH_3$ | H(l = O) | OH |
| 200 | $CH_3$ | $CH_3$ | $SCH_3$ | H(l = O) | OH |
| 201 | $CH_2CH_3$ | $CH_2CH_3$ | $SCH_3$ | H(l = O) | OH |
| 202 | $CH_2CH_2CH_3$ | $CH_2CH_2CH_3$ | $SCH_3$ | H(l = O) | OH |
| 203 | $OCH_3$ | $OCH_3$ | $SCH_3$ | H(l = O) | OH |
| 204 | $OCH_2CH_3$ | $OCH_2CH_3$ | $SCH_3$ | H(l = O) | OH |
| 205 | $OCH_2CH_2CH_3$ | $OCH_2CH_2CH_3$ | $SCH_3$ | H(l = O) | OH |
| 206 | $SCH_3$ | $SCH_3$ | $SCH_3$ | H(l = O) | OH |
| 207 | $SCH_2CH_3$ | $SCH_2CH_3$ | $SCH_3$ | H(l = O) | OH |
| 208 | $N(CH_3)_2$ | $N(CH_3)_2$ | $SCH_3$ | H(l = O) | OH |
| 209 | $N(CH_2CH_3)_2$ | $N(CH_2CH_3)_2$ | $SCH_3$ | H(l = O) | OH |
| 210 | $N(CH_3)(CH_2CH_3)$ | $N(CH_3)(CH_2CH_3)$ | $SCH_3$ | H(l = O) | OH |
| 211 | $O—(CH_2CH_2)—O$ | | $SCH_3$ | H(l = O) | OH |

TABLE 1-continued

I1a1

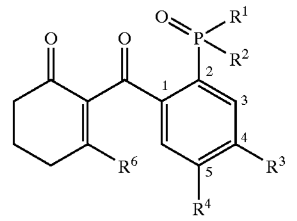

| n | $R^1$ | $R^2$ | $R^3$ | $R^4$ | $R^6$ |
|---|---|---|---|---|---|
| 212 | O—$(CH_2CH_2CH_2)$—O | | $SCH_3$ | H(l = O) | OH |
| 213 | S—$(CH_2CH_2)$—S | | $SCH_3$ | H(l = O) | OH |
| 214 | S—$(CH_2CH_2CH_2)$—S | | $SCH_3$ | H(l = O) | OH |
| 215 | —$(CH_2)_4$— | | $SCH_3$ | H(l = O) | OH |
| 216 | —$(CH_2)_5$— | | $SCH_3$ | H(l = O) | OH |
| 217 | H | H | $SO_2CH_3$ | H(l = O) | OH |
| 218 | $CH_3$ | $CH_3$ | $SO_2CH_3$ | H(l = O) | OH |
| 219 | $CH_2CH_3$ | $CH_2CH_3$ | $SO_2CH_3$ | H(l = O) | OH |
| 220 | $CH_2CH_2CH_3$ | $CH_2CH_2CH_3$ | $SO_2CH_3$ | H(l = O) | OH |
| 221 | $OCH_3$ | $OCH_3$ | $SO_2CH_3$ | H(l = O) | OH |
| 222 | $OCH_2CH_3$ | $OCH_2CH_3$ | $SO_2CH_3$ | H(l = O) | OH |
| 223 | $OCH_2CH_2CH_3$ | $OCH_2CH_2CH_3$ | $SO_2CH_3$ | H(l = O) | OH |
| 224 | $SCH_3$ | $SCH_3$ | $SO_2CH_3$ | H(l = O) | OH |
| 225 | $SCH_2CH_3$ | $SCH_2CH_3$ | $SO_2CH_3$ | H(l = O) | OH |
| 226 | $N(CH_3)_2$ | $N(CH_3)_2$ | $SO_2CH_3$ | H(l = O) | OH |
| 227 | $N(CH_2CH_3)_2$ | $N(CH_2CH_3)_2$ | $SO_2CH_3$ | H(l = O) | OH |
| 228 | $N(CH_3)(CH_2CH_3)$ | $N(CH_3)(CH_2CH_3)$ | $SO_2CH_3$ | H(l = O) | OH |
| 229 | O—$(CH_2CH_2)$—O | | $SO_2CH_3$ | H(l = O) | OH |
| 230 | O—$(CH_2CH_2CH_2)$—O | | $SO_2CH_3$ | H(l = O) | OH |
| 231 | S—$(CH_2CH_2)$—S | | $SO_2CH_3$ | H(l = O) | OH |
| 232 | S—$(CH_2CH_2CH_2)$—S | | $SO_2CH_3$ | H(l = O) | OH |
| 233 | —$(CH_2)_4$— | | $SO_2CH_3$ | H(l = O) | OH |
| 234 | —$(CH_2)_5$— | | $SO_2CH_3$ | H(l = O) | OH |
| 235 | H | H | $PO(OCH_3)_2$ | H(l = O) | OH |
| 236 | $CH_3$ | $CH_3$ | $PO(OCH_3)_2$ | H(l = O) | OH |
| 237 | $CH_2CH_3$ | $CH_2CH_3$ | $PO(OCH_3)_2$ | H(l = O) | OH |
| 238 | $CH_2CH_2CH_3$ | $CH_2CH_2CH_3$ | $PO(OCH_3)_2$ | H(l = O) | OH |
| 239 | $OCH_3$ | $OCH_3$ | $PO(OCH_3)_2$ | H(l = O) | OH |
| 240 | $OCH_2CH_3$ | $OCH_2CH_3$ | $PO(OCH_3)_2$ | H(l = O) | OH |
| 241 | $OCH_2CH_2CH_3$ | $OCH_2CH_2CH_3$ | $PO(OCH_3)_2$ | H(l = O) | OH |
| 242 | $SCH_3$ | $SCH_3$ | $PO(OCH_3)_2$ | H(l = O) | OH |
| 243 | $SCH_2CH_3$ | $SCH_2CH_3$ | $PO(OCH_3)_2$ | H(l = O) | OH |
| 244 | $N(CH_3)_2$ | $N(CH_3)_2$ | $PO(OCH_3)_2$ | H(l = O) | OH |
| 245 | $N(CH_2CH_3)_2$ | $N(CH_2CH_3)_2$ | $PO(OCH_3)_2$ | H(l = O) | OH |
| 246 | $N(CH_3)(CH_2CH_3)$ | $N(CH_3)(CH_2CH_3)$ | $PO(OCH_3)_2$ | H(l = O) | OH |
| 247 | O—$(CH_2CH_2)$—O | | $PO(OCH_3)_2$ | H(l = O) | OH |
| 248 | O—$(CH_2CH_2CH_2)$—O | | $PO(OCH_3)_2$ | H(l = O) | OH |
| 249 | S—$(CH_2CH_2)$—S | | $PO(OCH_3)_2$ | H(l = O) | OH |
| 250 | S—$(CH_2CH_2CH_2)$—S | | $PO(OCH_3)_2$ | H(l = O) | OH |
| 251 | —$(CH_2)_4$— | | $PO(OCH_3)_2$ | H(l = O) | OH |
| 252 | —$(CH_2)_5$— | | $PO(OCH_3)_2$ | H(l = O) | OH |
| 253 | H | H | $PO(OCH_2CH_3)_2$ | H(l = O) | OH |
| 254 | $CH_3$ | $CH_3$ | $PO(OCH_2CH_3)_2$ | H(l = O) | OH |
| 255 | $CH_2CH_3$ | $CH_2CH_3$ | $PO(OCH_2CH_3)_2$ | H(l = O) | OH |
| 256 | $CH_2CH_2CH_3$ | $CH_2CH_2CH_3$ | $PO(OCH_2CH_3)_2$ | H(l = O) | OH |
| 257 | $OCH_3$ | $OCH_3$ | $PO(OCH_2CH_3)_2$ | H(l = O) | OH |
| 258 | $OCH_2CH_3$ | $OCH_2CH_3$ | $PO(OCH_2CH_3)_2$ | H(l = O) | OH |
| 259 | $OCH_2CH_2CH_3$ | $OCH_2CH_2CH_3$ | $PO(OCH_2CH_3)_2$ | H(l = O) | OH |
| 260 | $SCH_3$ | $SCH_3$ | $PO(OCH_2CH_3)_2$ | H(l = O) | OH |
| 261 | $SCH_2CH_3$ | $SCH_2CH_3$ | $PO(OCH_2CH_3)_2$ | H(l = O) | OH |
| 262 | $N(CH_3)_2$ | $N(CH_3)_2$ | $PO(OCH_2CH_3)_2$ | H(l = O) | OH |
| 263 | $N(CH_2CH_3)_2$ | $N(CH_2CH_3)_2$ | $PO(OCH_2CH_3)_2$ | H(l = O) | OH |
| 264 | $N(CH_3)(CH_2CH_3)$ | $N(CH_3)(CH_2CH_3)$ | $PO(OCH_2CH_3)_2$ | H(l = O) | OH |
| 265 | O—$(CH_2CH_2)$—O | | $PO(OCH_2CH_3)_2$ | H(l = O) | OH |
| 266 | O—$(CH_2CH_2CH_2)$—O | | $PO(OCH_2CH_3)_2$ | H(l = O) | OH |
| 267 | S—$(CH_2CH_2)$—S | | $PO(OCH_2CH_3)_2$ | H(l = O) | OH |
| 268 | S—$(CH_2CH_2CH_2)$—S | | $PO(OCH_2CH_3)_2$ | H(l = O) | OH |
| 269 | —$(CH_2)_4$— | | $PO(OCH_2CH_3)_2$ | H(l = O) | OH |
| 270 | —$(CH_2)_5$— | | $PO(OCH_2CH_3)_2$ | H(l = O) | OH |
| 271 | H | H | $PO(CH_3)_2$ | H(l = O) | OH |
| 272 | $CH_3$ | $CH_3$ | $PO(CH_3)_2$ | H(l = O) | OH |
| 273 | $CH_2CH_3$ | $CH_2CH_3$ | $PO(CH_3)_2$ | H(l = O) | OH |
| 274 | $CH_2CH_2CH_3$ | $CH_2CH_2CH_3$ | $PO(CH_3)_2$ | H(l = O) | OH |
| 275 | $OCH_3$ | $OCH_3$ | $PO(CH_3)_2$ | H(l = O) | OH |

TABLE 1-continued

I1a1

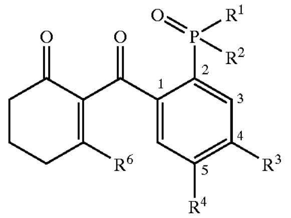

| n | $R^1$ | $R^2$ | $R^3$ | $R^4$ | $R^6$ |
|---|---|---|---|---|---|
| 276 | $OCH_2CH_3$ | $OCH_2CH_3$ | $PO(CH_3)_2$ | H(l = O) | OH |
| 277 | $OCH_2CH_2CH_3$ | $OCH_2CH_2CH_3$ | $PO(CH_3)_2$ | H(l = O) | OH |
| 278 | $SCH_3$ | $SCH_3$ | $PO(CH_3)_2$ | H(l = O) | OH |
| 279 | $SCH_2CH_3$ | $SCH_2CH_3$ | $PO(CH_3)_2$ | H(l = O) | OH |
| 280 | $N(CH_3)_2$ | $N(CH_3)_2$ | $PO(CH_3)_2$ | H(l = O) | OH |
| 281 | $N(CH_2CH_3)_2$ | $N(CH_2CH_3)_2$ | $PO(CH_3)_2$ | H(l = O) | OH |
| 282 | $N(CH_3)(CH_2CH_3)$ | $N(CH_3)(CH_2CH_3)$ | $PO(CH_3)_2$ | H(l = O) | OH |
| 283 | $O—(CH_2CH_2)—O$ | | $PO(CH_3)_2$ | H(l = O) | OH |
| 284 | $O—(CH_2CH_2CH_2)—O$ | | $PO(CH_3)_2$ | H(l = O) | OH |
| 285 | $S—(CH_2CH_2)—S$ | | $PO(CH_3)_2$ | H(l = O) | OH |
| 286 | $S—(CH_2CH_2CH_2)—S$ | | $PO(CH_3)_2$ | H(l = O) | OH |
| 287 | $—(CH_2)_4—$ | | $PO(CH_3)_2$ | H(l = O) | OH |
| 288 | $—(CH_2)_5—$ | | $PO(CH_3)_2$ | H(l = O) | OH |
| 289 | H | H | $PO(CH_2CH_3)_2$ | H(l = O) | OH |
| 290 | $CH_3$ | $CH_3$ | $PO(CH_2CH_3)_2$ | H(l = O) | OH |
| 291 | $CH_2CH_3$ | $CH_2CH_3$ | $PO(CH_2CH_3)_2$ | H(l = O) | OH |
| 292 | $CH_2CH_2CH_3$ | $CH_2CH_2CH_3$ | $PO(CH_2CH_3)_2$ | H(l = O) | OH |
| 293 | $OCH_3$ | $OCH_3$ | $PO(CH_2CH_3)_2$ | H(l = O) | OH |
| 294 | $OCH_2CH_3$ | $OCH_2CH_3$ | $PO(CH_2CH_3)_2$ | H(l = O) | OH |
| 295 | $OCH_2CH_2CH_3$ | $OCH_2CH_2CH_3$ | $PO(CH_2CH_3)_2$ | H(l = O) | OH |
| 296 | $SCH_3$ | $SCH_3$ | $PO(CH_2CH_3)_2$ | H(l = O) | OH |
| 297 | $SCH_2CH_3$ | $SCH_2CH_3$ | $PO(CH_2CH_3)_2$ | H(l = O) | OH |
| 298 | $N(CH_3)_2$ | $N(CH_3)_2$ | $PO(CH_2CH_3)_2$ | H(l = O) | OH |
| 299 | $N(CH_2CH_3)_2$ | $N(CH_2CH_3)_2$ | $PO(CH_2CH_3)_2$ | H(l = O) | OH |
| 300 | $N(CH_3)(CH_2CH_3)$ | $N(CH_3)(CH_2CH_3)$ | $PO(CH_2CH_3)_2$ | H(l = O) | OH |
| 301 | $O—(CH_2CH_2)—O$ | | $PO(CH_2CH_3)_2$ | H(l = O) | OH |
| 302 | $O—(CH_2CH_2CH_2)—O$ | | $PO(CH_2CH_3)_2$ | H(l = O) | OH |
| 303 | $S—(CH_2CH_2)—S$ | | $PO(CH_2CH_3)_2$ | H(l = O) | OH |
| 304 | $S—(CH_2CH_2CH_2)—S$ | | $PO(CH_2CH_3)_2$ | H(l = O) | OH |
| 305 | $—(CH_2)_4—$ | | $PO(CH_2CH_3)_2$ | H(l = O) | OH |
| 306 | $—(CH_2)_5—$ | | $PO(CH_2CH_3)_2$ | H(l = O) | OH |
| 307 | H | H | H | H(l = O) | $OCOC_6H_5$ |
| 308 | $CH_3$ | $CH_3$ | H | H(l = O) | $OCOC_6H_5$ |
| 309 | $CH_2CH_3$ | $CH_2CH_3$ | H | H(l = O) | $OCOC_6H_5$ |
| 310 | $CH_2CH_2CH_3$ | $CH_2CH_2CH_3$ | H | H(l = O) | $OCOC_6H_5$ |
| 311 | $OCH_3$ | $OCH_3$ | H | H(l = O) | $OCOC_6H_5$ |
| 312 | $OCH_2CH_3$ | $OCH_2CH_3$ | H | H(l = O) | $OCOC_6H_5$ |
| 313 | $OCH_2CH_2CH_3$ | $OCH_2CH_2CH_3$ | H | H(l = O) | $OCOC_6H_5$ |
| 314 | $SCH_3$ | $SCH_3$ | H | H(l = O) | $OCOC_6H_5$ |
| 315 | $SCH_2CH_3$ | $SCH_2CH_3$ | H | H(l = O) | $OCOC_6H_5$ |
| 316 | $N(CH_3)_2$ | $N(CH_3)_2$ | H | H(l = O) | $OCOC_6H_5$ |
| 317 | $N(CH_2CH_3)_2$ | $N(CH_2CH_3)_2$ | H | H(l = O) | $OCOC_6H_5$ |
| 318 | $N(CH_3)(CH_2CH_3)$ | $N(CH_3)(CH_2CH_3)$ | H | H(l = O) | $OCOC_6H_5$ |
| 319 | $O—(CH_2CH_2)—O$ | | H | H(l = O) | $OCOC_6H_5$ |
| 320 | $O—(CH_2CH_2CH_2)—O$ | | H | H(l = O) | $OCOC_6H_5$ |
| 321 | $S—(CH_2CH_2)—S$ | | H | H(l = O) | $OCOC_6H_5$ |
| 322 | $S—(CH_2CH_2CH_2)—S$ | | H | H(l = O) | $OCOC_6H_5$ |
| 323 | $—(CH_2)_4—$ | | H | H(l = O) | $OCOC_6H_5$ |
| 324 | $—(CH_2)_5—$ | | H | H(l = O) | $OCOC_6H_5$ |
| 325 | H | H | $NO_2$ | H(l = O) | $OCOC_6H_5$ |
| 326 | $CH_3$ | $CH_3$ | $NO_2$ | H(l = O) | $OCOC_6H_5$ |
| 327 | $CH_2CH_3$ | $CH_2CH_3$ | $NO_2$ | H(l = O) | $OCOC_6H_5$ |
| 328 | $CH_2CH_2CH_3$ | $CH_2CH_2CH_3$ | $NO_2$ | H(l = O) | $OCOC_6H_5$ |
| 329 | $OCH_3$ | $OCH_3$ | $NO_2$ | H(l = O) | $OCOC_6H_5$ |
| 330 | $OCH_2CH_3$ | $OCH_2CH_3$ | $NO_2$ | H(l = O) | $OCOC_6H_5$ |
| 331 | $OCH_2CH_2CH_3$ | $OCH_2CH_2CH_3$ | $NO_2$ | H(l = O) | $OCOC_6H_5$ |
| 332 | $SCH_3$ | $SCH_3$ | $NO_2$ | H(l = O) | $OCOC_6H_5$ |
| 333 | $SCH_2CH_3$ | $SCH_2CH_3$ | $NO_2$ | H(l = O) | $OCOC_6H_5$ |
| 334 | $N(CH_3)_2$ | $N(CH_3)_2$ | $NO_2$ | H(l = O) | $OCOC_6H_5$ |
| 335 | $N(CH_2CH_3)_2$ | $N(CH_2CH_3)_2$ | $NO_2$ | H(l = O) | $OCOC_6H_5$ |
| 336 | $N(CH_3)(CH_2CH_3)$ | $N(CH_3)(CH_2CH_3)$ | $NO_2$ | H(l = O) | $OCOC_6H_5$ |
| 337 | $O—(CH_2CH_2)—O$ | | $NO_2$ | H(l = O) | $OCOC_6H_5$ |
| 338 | $O—(CH_2CH_2CH_2)—O$ | | $NO_2$ | H(l = O) | $OCOC_6H_5$ |
| 339 | $S—(CH_2CH_2)—S$ | | $NO_2$ | H(l = O) | $OCOC_6H_5$ |

TABLE 1-continued

I1a1

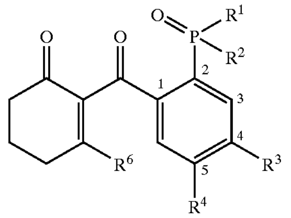

| n | $R^1$ | $R^2$ | $R^3$ | $R^4$ | $R^6$ |
|---|---|---|---|---|---|
| 340 | S—($CH_2CH_2CH_2$)—S | | $NO_2$ | H(l = O) | $OCOC_6H_5$ |
| 341 | —$(CH_2)_4$— | | $NO_2$ | H(l = O) | $OCOC_6H_5$ |
| 342 | —$(CH_2)_5$— | | $NO_2$ | H(l = O) | $OCOC_6H_5$ |
| 343 | H | H | CN | H(l = O) | $OCOC_6H_5$ |
| 344 | $CH_3$ | $CH_3$ | CN | H(l = O) | $OCOC_6H_5$ |
| 345 | $CH_2CH_3$ | $CH_2CH_3$ | CN | H(l = O) | $OCOC_6H_5$ |
| 346 | $CH_2CH_2CH_3$ | $CH_2CH_2CH_3$ | CN | H(l = O) | $OCOC_6H_5$ |
| 347 | $OCH_3$ | $OCH_3$ | CN | H(l = O) | $OCOC_6H_5$ |
| 348 | $OCH_2CH_3$ | $OCH_2CH_3$ | CN | H(l = O) | $OCOC_6H_5$ |
| 349 | $OCH_2CH_2CH_3$ | $OCH_2CH_2CH_3$ | CN | H(l = O) | $OCOC_6H_5$ |
| 350 | $SCH_3$ | $SCH_3$ | CN | H(l = O) | $OCOC_6H_5$ |
| 351 | $SCH_2CH_3$ | $SCH_2CH_3$ | CN | H(l = O) | $OCOC_6H_5$ |
| 352 | $N(CH_3)_2$ | $N(CH_3)_2$ | CN | H(l = O) | $OCOC_6H_5$ |
| 353 | $N(CH_2CH_3)_2$ | $N(CH_2CH_3)_2$ | CN | H(l = O) | $OCOC_6H_5$ |
| 354 | $N(CH_3)(CH_2CH_3)$ | $N(CH_3)(CH_2CH_3)$ | CN | H(l = O) | $OCOC_6H_5$ |
| 355 | O—($CH_2CH_2$)—O | | CN | H(l = O) | $OCOC_6H_5$ |
| 356 | O—($CH_2CH_2CH_2$)—O | | CN | H(l = O) | $OCOC_6H_5$ |
| 357 | S—($CH_2CH_2$)—S | | CN | H(l = O) | $OCOC_6H_5$ |
| 358 | S—($CH_2CH_2CH_2$)—S | | CN | H(l = O) | $OCOC_6H_5$ |
| 359 | —$(CH_2)_4$— | | CN | H(l = O) | $OCOC_6H_5$ |
| 360 | —$(CH_2)_5$— | | CN | H(l = O) | $OCOC_6H_5$ |
| 361 | H | H | F | H(l = O) | $OCOC_6H_5$ |
| 362 | $CH_3$ | $CH_3$ | F | H(l = O) | $OCOC_6H_5$ |
| 363 | $CH_2CH_3$ | $CH_2CH_3$ | F | H(l = O) | $OCOC_6H_5$ |
| 364 | $CH_2CH_2CH_3$ | $CH_2CH_2CH_3$ | F | H(l = O) | $OCOC_6H_5$ |
| 365 | $OCH_3$ | $OCH_3$ | F | H(l = O) | $OCOC_6H_5$ |
| 366 | $OCH_2CH_3$ | $OCH_2CH_3$ | F | H(l = O) | $OCOC_6H_5$ |
| 367 | $OCH_2CH_2CH_3$ | $OCH_2CH_2CH_3$ | F | H(l = O) | $OCOC_6H_5$ |
| 368 | $SCH_3$ | $SCH_3$ | F | H(l = O) | $OCOC_6H_5$ |
| 369 | $SCH_2CH_3$ | $SCH_2CH_3$ | F | H(l = O) | $OCOC_6H_5$ |
| 370 | $N(CH_3)_2$ | $N(CH_3)_2$ | F | H(l = O) | $OCOC_6H_5$ |
| 371 | $N(CH_2CH_3)_2$ | $N(CH_2CH_3)_2$ | F | H(l = O) | $OCOC_6H_5$ |
| 372 | $N(CH_3)(CH_2CH_3)$ | $N(CH_3)(CH_2CH_3)$ | F | H(l = O) | $OCOC_6H_5$ |
| 373 | O—($CH_2CH_2$)—O | | F | H(l = O) | $OCOC_6H_5$ |
| 374 | O—($CH_2CH_2CH_2$)—O | | F | H(l = O) | $OCOC_6H_5$ |
| 375 | S—($CH_2CH_2$)—S | | F | H(l = O) | $OCOC_6H_5$ |
| 376 | S—($CH_2CH_2CH_2$)—S | | F | H(l = O) | $OCOC_6H_5$ |
| 377 | —$(CH_2)_4$— | | F | H(l = O) | $OCOC_6H_5$ |
| 378 | —$(CH_2)_5$— | | F | H(l = O) | $OCOC_6H_5$ |
| 379 | H | H | Cl | H(l = O) | $OCOC_6H_5$ |
| 380 | $CH_3$ | $CH_3$ | Cl | H(l = O) | $OCOC_6H_5$ |
| 381 | $CH_2CH_3$ | $CH_2CH_3$ | Cl | H(l = O) | $OCOC_6H_5$ |
| 382 | $CH_2CH_2CH_3$ | $CH_2CH_2CH_3$ | Cl | H(l = O) | $OCOC_6H_5$ |
| 383 | $OCH_3$ | $OCH_3$ | Cl | H(l = O) | $OCOC_6H_5$ |
| 384 | $OCH_2CH_3$ | $OCH_2CH_3$ | Cl | H(l = O) | $OCOC_6H_5$ |
| 385 | $OCH_2CH_2CH_3$ | $OCH_2CH_2CH_3$ | Cl | H(l = O) | $OCOC_6H_5$ |
| 386 | $SCH_3$ | $SCH_3$ | Cl | H(l = O) | $OCOC_6H_5$ |
| 387 | $SCH_2CH_3$ | $SCH_2CH_3$ | Cl | H(l = O) | $OCOC_6H_5$ |
| 388 | $N(CH_3)_2$ | $N(CH_3)_2$ | Cl | H(l = O) | $OCOC_6H_5$ |
| 389 | $N(CH_2CH_3)_2$ | $N(CH_2CH_3)_2$ | Cl | H(l = O) | $OCOC_6H_5$ |
| 390 | $N(CH_3)(CH_2CH_3)$ | $N(CH_3)(CH_2CH_3)$ | Cl | H(l = O) | $OCOC_6H_5$ |
| 391 | O—($CH_2CH_2$)—O | | Cl | H(l = O) | $OCOC_6H_5$ |
| 392 | O—($CH_2CH_2CH_2$)—O | | Cl | H(l = O) | $OCOC_6H_5$ |
| 393 | S—($CH_2CH_2$)—S | | Cl | H(l = O) | $OCOC_6H_5$ |
| 394 | S—($CH_2CH_2CH_2$)—S | | Cl | H(l = O) | $OCOC_6H_5$ |
| 395 | —$(CH_2)_4$— | | Cl | H(l = O) | $OCOC_6H_5$ |
| 396 | —$(CH_2)_5$— | | Cl | H(l = O) | $OCOC_6H_5$ |
| 397 | H | H | Br | H(l = O) | $OCOC_6H_5$ |
| 398 | $CH_3$ | $CH_3$ | Br | H(l = O) | $OCOC_6H_5$ |
| 399 | $CH_2CH_3$ | $CH_2CH_3$ | Br | H(l = O) | $OCOC_6H_5$ |
| 400 | $CH_2CH_2CH_3$ | $CH_2CH_2CH_3$ | Br | H(l = O) | $OCOC_6H_5$ |
| 401 | $OCH_3$ | $OCH_3$ | Br | H(l = O) | $OCOC_6H_5$ |
| 402 | $OCH_2CH_3$ | $OCH_2CH_3$ | Br | H(l = O) | $OCOC_6H_5$ |
| 403 | $OCH_2CH_2CH_3$ | $OCH_2CH_2CH_3$ | Br | H(l = O) | $OCOC_6H_5$ |

TABLE 1-continued

I1a1

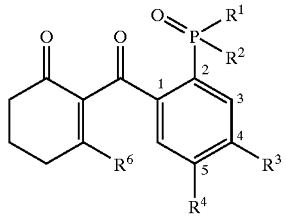

| n | $R^1$ | $R^2$ | $R^3$ | $R^4$ | $R^6$ |
|---|---|---|---|---|---|
| 404 | $SCH_3$ | $SCH_3$ | Br | H(l = O) | $OCOC_6H_5$ |
| 405 | $SCH_2CH_3$ | $SCH_2CH_3$ | Br | H(l = O) | $OCOC_6H_5$ |
| 406 | $N(CH_3)_2$ | $N(CH_3)_2$ | Br | H(l = O) | $OCOC_6H_5$ |
| 407 | $N(CH_2CH_3)_2$ | $N(CH_2CH_3)_2$ | Br | H(l = O) | $OCOC_6H_5$ |
| 408 | $N(CH_3)(CH_2CH_3)$ | $N(CH_3)(CH_2CH_3)$ | Br | H(l = O) | $OCOC_6H_5$ |
| 409 | $O—(CH_2CH_2)—O$ | | Br | H(l = O) | $OCOC_6H_5$ |
| 410 | $O—(CH_2CH_2CH_2)—O$ | | Br | H(l = O) | $OCOC_6H_5$ |
| 411 | $S—(CH_2CH_2)—S$ | | Br | H(l = O) | $OCOC_6H_5$ |
| 412 | $S—(CH_2CH_2CH_2)—S$ | | Br | H(l = O) | $OCOC_6H_5$ |
| 413 | $—(CH_2)_4—$ | | Br | H(l = O) | $OCOC_6H_5$ |
| 414 | $—(CH_2)_5—$ | | Br | H(l = O) | $OCOC_6H_5$ |
| 415 | H | H | $CH_3$ | H(l = O) | $OCOC_6H_5$ |
| 416 | $CH_3$ | $CH_3$ | $CH_3$ | H(l = O) | $OCOC_6H_5$ |
| 417 | $CH_2CH_3$ | $CH_2CH_3$ | $CH_3$ | H(l = O) | $OCOC_6H_5$ |
| 418 | $CH_2CH_2CH_3$ | $CH_2CH_2CH_3$ | $CH_3$ | H(l = O) | $OCOC_6H_5$ |
| 419 | $OCH_3$ | $OCH_3$ | $CH_3$ | H(l = O) | $OCOC_6H_5$ |
| 420 | $OCH_2CH_3$ | $OCH_2CH_3$ | $CH_3$ | H(l = O) | $OCOC_6H_5$ |
| 421 | $OCH_2CH_2CH_3$ | $OCH_2CH_2CH_3$ | $CH_3$ | H(l = O) | $OCOC_6H_5$ |
| 422 | $SCH_3$ | $SCH_3$ | $CH_3$ | H(l = O) | $OCOC_6H_5$ |
| 423 | $SCH_2CH_3$ | $SCH_2CH_3$ | $CH_3$ | H(l = O) | $OCOC_6H_5$ |
| 424 | $N(CH_3)_2$ | $N(CH_3)_2$ | $CH_3$ | H(l = O) | $OCOC_6H_5$ |
| 425 | $N(CH_2CH_3)_2$ | $N(CH_2CH_3)_2$ | $CH_3$ | H(l = O) | $OCOC_6H_5$ |
| 426 | $N(CH_3)(CH_2CH_3)$ | $N(CH_3)(CH_2CH_3)$ | $CH_3$ | H(l = O) | $OCOC_6H_5$ |
| 427 | $O—(CH_2CH_2)—O$ | | $CH_3$ | H(l = O) | $OCOC_6H_5$ |
| 428 | $O—(CH_2CH_2CH_2)—O$ | | $CH_3$ | H(l = O) | $OCOC_6H_5$ |
| 429 | $S—(CH_2CH_2)—S$ | | $CH_3$ | H(l = O) | $OCOC_6H_5$ |
| 430 | $S—(CH_2CH_2CH_2)—S$ | | $CH_3$ | H(l = O) | $OCOC_6H_5$ |
| 431 | $—(CH_2)_4—$ | | $CH_3$ | H(l = O) | $OCOC_6H_5$ |
| 432 | $—(CH_2)_5—$ | | $CH_3$ | H(l = O) | $OCOC_6H_5$ |
| 433 | H | H | $CH_2CH_3$ | H(l = O) | $OCOC_6H_5$ |
| 434 | $CH_3$ | $CH_3$ | $CH_2CH_3$ | H(l = O) | $OCOC_6H_5$ |
| 435 | $CH_2CH_3$ | $CH_2CH_3$ | $CH_2CH_3$ | H(l = O) | $OCOC_6H_5$ |
| 436 | $CH_2CH_2CH_3$ | $CH_2CH_2CH_3$ | $CH_2CH_3$ | H(l = O) | $OCOC_6H_5$ |
| 437 | $OCH_3$ | $OCH_3$ | $CH_2CH_3$ | H(l = O) | $OCOC_6H_5$ |
| 438 | $OCH_2CH_3$ | $OCH_2CH_3$ | $CH_2CH_3$ | H(l = O) | $OCOC_6H_5$ |
| 439 | $OCH_2CH_2CH_3$ | $OCH_2CH_2CH_3$ | $CH_2CH_3$ | H(l = O) | $OCOC_6H_5$ |
| 440 | $SCH_3$ | $SCH_3$ | $CH_2CH_3$ | H(l = O) | $OCOC_6H_5$ |
| 441 | $SCH_2CH_3$ | $SCH_2CH_3$ | $CH_2CH_3$ | H(l = O) | $OCOC_6H_5$ |
| 442 | $N(CH_3)_2$ | $N(CH_3)_2$ | $CH_2CH_3$ | H(l = O) | $OCOC_6H_5$ |
| 443 | $N(CH_2CH_3)_2$ | $N(CH_2CH_3)_2$ | $CH_2CH_3$ | H(l = O) | $OCOC_6H_5$ |
| 444 | $N(CH_3)(CH_2CH_3)$ | $N(CH_3)(CH_2CH_3)$ | $CH_2CH_3$ | H(l = O) | $OCOC_6H_5$ |
| 445 | $O—(CH_2CH_2)—O$ | | $CH_2CH_3$ | H(l = O) | $OCOC_6H_5$ |
| 446 | $O—(CH_2CH_2CH_2)—O$ | | $CH_2CH_3$ | H(l = O) | $OCOC_6H_5$ |
| 447 | $S—(CH_2CH_2)—S$ | | $CH_2CH_3$ | H(l = O) | $OCOC_6H_5$ |
| 448 | $S—(CH_2CH_2CH_2)—S$ | | $CH_2CH_3$ | H(l = O) | $OCOC_6H_5$ |
| 449 | $—(CH_2)_4—$ | | $CH_2CH_3$ | H(l = O) | $OCOC_6H_5$ |
| 450 | $—(CH_2)_5—$ | | $CH_2CH_3$ | H(l = O) | $OCOC_6H_5$ |
| 451 | H | H | $CF_3$ | H(l = O) | $OCOC_6H_5$ |
| 452 | $CH_3$ | $CH_3$ | $CF_3$ | H(l = O) | $OCOC_6H_5$ |
| 453 | $CH_2CH_3$ | $CH_2CH_3$ | $CF_3$ | H(l = O) | $OCOC_6H_5$ |
| 454 | $CH_2CH_2CH_3$ | $CH_2CH_2CH_3$ | $CF_3$ | H(l = O) | $OCOC_6H_5$ |
| 455 | $OCH_3$ | $OCH_3$ | $CF_3$ | H(l = O) | $OCOC_6H_5$ |
| 456 | $OCH_2CH_3$ | $OCH_2CH_3$ | $CF_3$ | H(l = O) | $OCOC_6H_5$ |
| 457 | $OCH_2CH_2CH_3$ | $OCH_2CH_2CH_3$ | $CF_3$ | H(l = O) | $OCOC_6H_5$ |
| 458 | $SCH_3$ | $SCH_3$ | $CF_3$ | H(l = O) | $OCOC_6H_5$ |
| 459 | $SCH_2CH_3$ | $SCH_2CH_3$ | $CF_3$ | H(l = O) | $OCOC_6H_5$ |
| 460 | $N(CH_3)_2$ | $N(CH_3)_2$ | $CF_3$ | H(l = O) | $OCOC_6H_5$ |
| 461 | $N(CH_2CH_3)_2$ | $N(CH_2CH_3)_2$ | $CF_3$ | H(l = O) | $OCOC_6H_5$ |
| 462 | $N(CH_3)(CH_2CH_3)$ | $N(CH_3)(CH_2CH_3)$ | $CF_3$ | H(l = O) | $OCOC_6H_5$ |
| 463 | $O—(CH_2CH_2)—O$ | | $CF_3$ | H(l = O) | $OCOC_6H_5$ |
| 464 | $O—(CH_2CH_2CH_2)—O$ | | $CF_3$ | H(l = O) | $OCOC_6H_5$ |
| 465 | $S—(CH_2CH_2)—S$ | | $CF_3$ | H(l = O) | $OCOC_6H_5$ |
| 466 | $S—(CH_2CH_2CH_2)—S$ | | $CF_3$ | H(l = O) | $OCOC_6H_5$ |
| 467 | $—(CH_2)_4—$ | | $CF_3$ | H(l = O) | $OCOC_6H_5$ |

TABLE 1-continued

I1a1

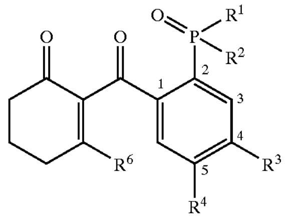

| n | $R^1$ | $R^2$ | $R^3$ | $R^4$ | $R^6$ |
|---|---|---|---|---|---|
| 468 | $-(CH_2)_5-$ | | $CF_3$ | H(l = O) | $OCOC_6H_5$ |
| 469 | H | H | $OCH_3$ | H(l = O) | $OCOC_6H_5$ |
| 470 | $CH_3$ | $CH_3$ | $OCH_3$ | H(l = O) | $OCOC_6H_5$ |
| 471 | $CH_2CH_3$ | $CH_2CH_3$ | $OCH_3$ | H(l = O) | $OCOC_6H_5$ |
| 472 | $CH_2CH_2CH_3$ | $CH_2CH_2CH_3$ | $OCH_3$ | H(l = O) | $OCOC_6H_5$ |
| 473 | $OCH_3$ | $OCH_3$ | $OCH_3$ | H(l = O) | $OCOC_6H_5$ |
| 474 | $OCH_2CH_3$ | $OCH_2CH_3$ | $OCH_3$ | H(l = O) | $OCOC_6H_5$ |
| 475 | $OCH_2CH_2CH_3$ | $OCH_2CH_2CH_3$ | $OCH_3$ | H(l = O) | $OCOC_6H_5$ |
| 476 | $SCH_3$ | $SCH_3$ | $OCH_3$ | H(l = O) | $OCOC_6H_5$ |
| 477 | $SCH_2CH_3$ | $SCH_2CH_3$ | $OCH_3$ | H(l = O) | $OCOC_6H_5$ |
| 478 | $N(CH_3)_2$ | $N(CH_3)_2$ | $OCH_3$ | H(l = O) | $OCOC_6H_5$ |
| 479 | $N(CH_2CH_3)_2$ | $N(CH_2CH_3)_2$ | $OCH_3$ | H(l = O) | $OCOC_6H_5$ |
| 480 | $N(CH_3)(CH_2CH_3)$ | $N(CH_3)(CH_2CH_3)$ | $OCH_3$ | H(l = O) | $OCOC_6H_5$ |
| 481 | $O-(CH_2CH_2)-O$ | | $OCH_3$ | H(l = O) | $OCOC_6H_5$ |
| 482 | $O-(CH_2CH_2CH_2)-O$ | | $OCH_3$ | H(l = O) | $OCOC_6H_5$ |
| 483 | $S-(CH_2CH_2)-S$ | | $OCH_3$ | H(l = O) | $OCOC_6H_5$ |
| 484 | $S-(CH_2CH_2CH_2)-S$ | | $OCH_3$ | H(l = O) | $OCOC_6H_5$ |
| 485 | $-(CH_2)_4-$ | | $OCH_3$ | H(l = O) | $OCOC_6H_5$ |
| 486 | $-(CH_2)_5-$ | | $OCH_3$ | H(l = O) | $OCOC_6H_5$ |
| 487 | H | H | $OCH_2CH_3$ | H(l = O) | $OCOC_6H_5$ |
| 488 | $CH_3$ | $CH_3$ | $OCH_2CH_3$ | H(l = O) | $OCOC_6H_5$ |
| 489 | $CH_2CH_3$ | $CH_2CH_3$ | $OCH_2CH_3$ | H(l = O) | $OCOC_6H_5$ |
| 490 | $CH_2CH_2CH_3$ | $CH_2CH_2CH_3$ | $OCH_2CH_3$ | H(l = O) | $OCOC_6H_5$ |
| 491 | $OCH_3$ | $OCH_3$ | $OCH_2CH_3$ | H(l = O) | $OCOC_6H_5$ |
| 492 | $OCH_2CH_3$ | $OCH_2CH_3$ | $OCH_2CH_3$ | H(l = O) | $OCOC_6H_5$ |
| 493 | $OCH_2CH_2CH_3$ | $OCH_2CH_2CH_3$ | $OCH_2CH_3$ | H(l = O) | $OCOC_6H_5$ |
| 494 | $SCH_3$ | $SCH_3$ | $OCH_2CH_3$ | H(l = O) | $OCOC_6H_5$ |
| 495 | $SCH_2CH_3$ | $SCH_2CH_3$ | $OCH_2CH_3$ | H(l = O) | $OCOC_6H_5$ |
| 496 | $N(CH_3)_2$ | $N(CH_3)_2$ | $OCH_2CH_3$ | H(l = O) | $OCOC_6H_5$ |
| 497 | $N(CH_2CH_3)_2$ | $N(CH_2CH_3)_2$ | $OCH_2CH_3$ | H(l = O) | $OCOC_6H_5$ |
| 498 | $N(CH_3)(CH_2CH_3)$ | $N(CH_3)(CH_2CH_3)$ | $OCH_2CH_3$ | H(l = O) | $OCOC_6H_5$ |
| 499 | $O-(CH_2CH_2)-O$ | | $OCH_2CH_3$ | H(l = O) | $OCOC_6H_5$ |
| 500 | $O-(CH_2CH_2CH_2)-O$ | | $OCH_2CH_3$ | H(l = O) | $OCOC_6H_5$ |
| 501 | $S-(CH_2CH_2)-S$ | | $OCH_2CH_3$ | H(l = O) | $OCOC_6H_5$ |
| 502 | $S-(CH_2CH_2CH_2)-S$ | | $OCH_2CH_3$ | H(l = O) | $OCOC_6H_5$ |
| 503 | $-(CH_2)_4-$ | | $OCH_2CH_3$ | H(l = O) | $OCOC_6H_5$ |
| 504 | $-(CH_2)_5-$ | | $OCH_2CH_3$ | H(l = O) | $OCOC_6H_5$ |
| 505 | H | H | $SCH_3$ | H(l = O) | $OCOC_6H_5$ |
| 506 | $CH_3$ | $CH_3$ | $SCH_3$ | H(l = O) | $OCOC_6H_5$ |
| 507 | $CH_2CH_3$ | $CH_2CH_3$ | $SCH_3$ | H(l = O) | $OCOC_6H_5$ |
| 508 | $CH_2CH_2CH_3$ | $CH_2CH_2CH_3$ | $SCH_3$ | H(l = O) | $OCOC_6H_5$ |
| 509 | $OCH_3$ | $OCH_3$ | $SCH_3$ | H(l = O) | $OCOC_6H_5$ |
| 510 | $OCH_2CH_3$ | $OCH_2CH_3$ | $SCH_3$ | H(l = O) | $OCOC_6H_5$ |
| 511 | $OCH_2CH_2CH_3$ | $OCH_2CH_2CH_3$ | $SCH_3$ | H(l = O) | $OCOC_6H_5$ |
| 512 | $SCH_3$ | $SCH_3$ | $SCH_3$ | H(l = O) | $OCOC_6H_5$ |
| 513 | $SCH_2CH_3$ | $SCH_2CH_3$ | $SCH_3$ | H(l = O) | $OCOC_6H_5$ |
| 514 | $N(CH_3)_2$ | $N(CH_3)_2$ | $SCH_3$ | H(l = O) | $OCOC_6H_5$ |
| 515 | $N(CH_2CH_3)_2$ | $N(CH_2CH_3)_2$ | $SCH_3$ | H(l = O) | $OCOC_6H_5$ |
| 516 | $N(CH_3)(CH_2CH_3)$ | $N(CH_3)(CH_2CH_3)$ | $SCH_3$ | H(l = O) | $OCOC_6H_5$ |
| 517 | $O-(CH_2CH_2)-O$ | | $SCH_3$ | H(l = O) | $OCOC_6H_5$ |
| 518 | $O-(CH_2CH_2CH_2)-O$ | | $SCH_3$ | H(l = O) | $OCOC_6H_5$ |
| 519 | $S-(CH_2CH_2)-S$ | | $SCH_3$ | H(l = O) | $OCOC_6H_5$ |
| 520 | $-(CH_2)_4-$ | | $SCH_3$ | H(l = O) | $OCOC_6H_5$ |
| 521 | $-(CH_2)_5-$ | | $SCH_3$ | H(l = O) | $OCOC_6H_5$ |
| 522 | $S-(CH_2CH_2CH_2)-S$ | | $SCH_3$ | H(l = O) | $OCOC_6H_5$ |
| 523 | $-(CH_2)_4-$ | | $SCH_3$ | H(l = O) | $OCOC_6H_5$ |
| 524 | $-(CH_2)_5-$ | | $SCH_3$ | H(l = O) | $OCOC_6H_5$ |
| 525 | H | H | $SO_2CH_3$ | H(l = O) | $OCOC_6H_5$ |
| 526 | $CH_3$ | $CH_3$ | $SO_2CH_3$ | H(l = O) | $OCOC_6H_5$ |
| 527 | $CH_2CH_3$ | $CH_2CH_3$ | $SO_2CH_3$ | H(l = O) | $OCOC_6H_5$ |
| 528 | $CH_2CH_2CH_3$ | $CH_2CH_2CH_3$ | $SO_2CH_3$ | H(l = O) | $OCOC_6H_5$ |
| 529 | $OCH_3$ | $OCH_3$ | $SO_2CH_3$ | H(l = O) | $OCOC_6H_5$ |
| 530 | $OCH_2CH_3$ | $OCH_2CH_3$ | $SO_2CH_3$ | H(l = O) | $OCOC_6H_5$ |
| 531 | $OCH_2CH_2CH_3$ | $OCH_2CH_2CH_3$ | $SO_2CH_3$ | H(l = O) | $OCOC_6H_5$ |

TABLE 1-continued

I1a1

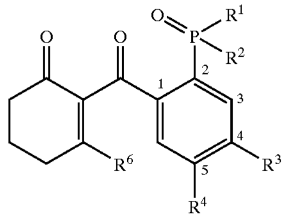

| n | $R^1$ | $R^2$ | $R^3$ | $R^4$ | $R^6$ |
|---|---|---|---|---|---|
| 532 | $SCH_3$ | $SCH_3$ | $SO_2CH_3$ | H(l = O) | $OCOC_6H_5$ |
| 533 | $SCH_2CH_3$ | $SCH_2CH_3$ | $SO_2CH_3$ | H(l = O) | $OCOC_6H_5$ |
| 534 | $N(CH_3)_2$ | $N(CH_3)_2$ | $SO_2CH_3$ | H(l = O) | $OCOC_6H_5$ |
| 535 | $N(CH_2CH_3)_2$ | $N(CH_2CH_3)_2$ | $SO_2CH_3$ | H(l = O) | $OCOC_6H_5$ |
| 536 | $N(CH_3)(CH_2CH_3)$ | $N(CH_3)(CH_2CH_3)$ | $SO_2CH_3$ | H(l = O) | $OCOC_6H_5$ |
| 537 | $O—(CH_2CH_2)—O$ | | $SO_2CH_3$ | H(l = O) | $OCOC_6H_5$ |
| 538 | $O—(CH_2CH_2CH_2)—O$ | | $SO_2CH_3$ | H(l = O) | $OCOC_6H_5$ |
| 539 | $S—(CH_2CH_2)—S$ | | $SO_2CH_3$ | H(l = O) | $OCOC_6H_5$ |
| 540 | $S—(CH_2CH_2CH_2)—S$ | | $SO_2CH_3$ | H(l = O) | $OCOC_6H_5$ |
| 541 | $—(CH_2)_4—$ | | $SO_2CH_3$ | H(l = O) | $OCOC_6H_5$ |
| 542 | $—(CH_2)_5—$ | | $SO_2CH_3$ | H(l = O) | $OCOC_6H_5$ |
| 543 | H | H | $PO(OCH_3)_2$ | H(l = O) | $OCOC_6H_5$ |
| 544 | $CH_3$ | $CH_3$ | $PO(OCH_3)_2$ | H(l = O) | $OCOC_6H_5$ |
| 545 | $CH_2CH_3$ | $CH_2CH_3$ | $PO(OCH_3)_2$ | H(l = O) | $OCOC_6H_5$ |
| 546 | $CH_2CH_2CH_3$ | $CH_2CH_2CH_3$ | $PO(OCH_3)_2$ | H(l = O) | $OCOC_6H_5$ |
| 547 | $OCH_3$ | $OCH_3$ | $PO(OCH_3)_2$ | H(l = O) | $OCOC_6H_5$ |
| 548 | $OCH_2CH_3$ | $OCH_2CH_3$ | $PO(OCH_3)_2$ | H(l = O) | $OCOC_6H_5$ |
| 549 | $OCH_2CH_2CH_3$ | $OCH_2CH_2CH_3$ | $PO(OCH_3)_2$ | H(l = O) | $OCOC_6H_5$ |
| 550 | $SCH_3$ | $SCH_3$ | $PO(OCH_3)_2$ | H(l = O) | $OCOC_6H_5$ |
| 551 | $SCH_2CH_3$ | $SCH_2CH_3$ | $PO(OCH_3)_2$ | H(l = O) | $OCOC_6H_5$ |
| 552 | $N(CH_3)_2$ | $N(CH_3)_2$ | $PO(OCH_3)_2$ | H(l = O) | $OCOC_6H_5$ |
| 553 | $N(CH_2CH_3)_2$ | $N(CH_2CH_3)_2$ | $PO(OCH_3)_2$ | H(l = O) | $OCOC_6H_5$ |
| 554 | $N(CH_3)(CH_2CH_3)$ | $N(CH_3)(CH_2CH_3)$ | $PO(OCH_3)_2$ | H(l = O) | $OCOC_6H_5$ |
| 555 | $O—(CH_2CH_2)—O$ | | $PO(OCH_3)_2$ | H(l = O) | $OCOC_6H_5$ |
| 556 | $O—(CH_2CH_2CH_2)—O$ | | $PO(OCH_3)_2$ | H(l = O) | $OCOC_6H_5$ |
| 557 | $S—(CH_2CH_2)—S$ | | $PO(OCH_3)_2$ | H(l = O) | $OCOC_6H_5$ |
| 558 | $S—(CH_2CH_2CH_2)—S$ | | $PO(OCH_3)_2$ | H(l = O) | $OCOC_6H_5$ |
| 559 | $—(CH_2)_4—$ | | $PO(OCH_3)_2$ | H(l = O) | $OCOC_6H_5$ |
| 560 | $—(CH_2)_5—$ | | $PO(OCH_3)_2$ | H(l = O) | $OCOC_6H_5$ |
| 561 | H | H | $PO(OCH_2CH_3)_2$ | H(l = O) | $OCOC_6H_5$ |
| 562 | $CH_3$ | $CH_3$ | $PO(OCH_2CH_3)_2$ | H(l = O) | $OCOC_6H_5$ |
| 563 | $CH_2CH_3$ | $CH_2CH_3$ | $PO(OCH_2CH_3)_2$ | H(l = O) | $OCOC_6H_5$ |
| 564 | $CH_2CH_2CH_3$ | $CH_2CH_2CH_3$ | $PO(OCH_2CH_3)_2$ | H(l = O) | $OCOC_6H_5$ |
| 565 | $OCH_3$ | $OCH_3$ | $PO(OCH_2CH_3)_2$ | H(l = O) | $OCOC_6H_5$ |
| 566 | $OCH_2CH_3$ | $OCH_2CH_3$ | $PO(OCH_2CH_3)_2$ | H(l = O) | $OCOC_6H_5$ |
| 567 | $OCH_2CH_2CH_3$ | $OCH_2CH_2CH_3$ | $PO(OCH_2CH_3)_2$ | H(l = O) | $OCOC_6H_5$ |
| 568 | $SCH_3$ | $SCH_3$ | $PO(OCH_2CH_3)_2$ | H(l = O) | $OCOC_6H_5$ |
| 569 | $SCH_2CH_3$ | $SCH_2CH_3$ | $PO(OCH_2CH_3)_2$ | H(l = O) | $OCOC_6H_5$ |
| 570 | $N(CH_3)_2$ | $N(CH_3)_2$ | $PO(OCH_2CH_3)_2$ | H(l = O) | $OCOC_6H_5$ |
| 571 | $N(CH_2CH_3)_2$ | $N(CH_2CH_3)_2$ | $PO(OCH_2CH_3)_2$ | H(l = O) | $OCOC_6H_5$ |
| 572 | $N(CH_3)(CH_2CH_3)$ | $N(CH_3)(CH_2CH_3)$ | $PO(OCH_2CH_3)_2$ | H(l = O) | $OCOC_6H_5$ |
| 573 | $O—(CH_2CH_2)—O$ | | $PO(OCH_2CH_3)_2$ | H(l = O) | $OCOC_6H_5$ |
| 574 | $O—(CH_2CH_2CH_2)—O$ | | $PO(OCH_2CH_3)_2$ | H(l = O) | $OCOC_6H_5$ |
| 575 | $S—(CH_2CH_2)—S$ | | $PO(OCH_2CH_3)_2$ | H(l = O) | $OCOC_6H_5$ |
| 576 | $S—(CH_2CH_2CH_2)—S$ | | $PO(OCH_2CH_3)_2$ | H(l = O) | $OCOC_6H_5$ |
| 577 | $—(CH_2)_4—$ | | $PO(OCH_2CH_3)_2$ | H(l = O) | $OCOC_6H_5$ |
| 578 | $—(CH_2)_5—$ | | $PO(OCH_2CH_3)_2$ | H(l = O) | $OCOC_6H_5$ |
| 579 | H | H | $PO(CH_3)_2$ | H(l = O) | $OCOC_6H_5$ |
| 580 | $CH_3$ | $CH_3$ | $PO(CH_3)_2$ | H(l = O) | $OCOC_6H_5$ |
| 581 | $CH_2CH_3$ | $CH_2CH_3$ | $PO(CH_3)_2$ | H(l = O) | $OCOC_6H_5$ |
| 582 | $CH_2CH_2CH_3$ | $CH_2CH_2CH_3$ | $PO(CH_3)_2$ | H(l = O) | $OCOC_6H_5$ |
| 583 | $OCH_3$ | $OCH_3$ | $PO(CH_3)_2$ | H(l = O) | $OCOC_6H_5$ |
| 584 | $OCH_2CH_3$ | $OCH_2CH_3$ | $PO(CH_3)_2$ | H(l = O) | $OCOC_6H_5$ |
| 585 | $OCH_2CH_2CH_3$ | $OCH_2CH_2CH_3$ | $PO(CH_3)_2$ | H(l = O) | $OCOC_6H_5$ |
| 586 | $SCH_3$ | $SCH_3$ | $PO(CH_3)_2$ | H(l = O) | $OCOC_6H_5$ |
| 587 | $SCH_2CH_3$ | $SCH_2CH_3$ | $PO(CH_3)_2$ | H(l = O) | $OCOC_6H_5$ |
| 588 | $N(CH_3)_2$ | $N(CH_3)_2$ | $PO(CH_3)_2$ | H(l = O) | $OCOC_6H_5$ |
| 589 | $N(CH_2CH_3)_2$ | $N(CH_2CH_3)_2$ | $PO(CH_3)_2$ | H(l = O) | $OCOC_6H_5$ |
| 590 | $N(CH_3)(CH_2CH_3)$ | $N(CH_3)(CH_2CH_3)$ | $PO(CH_3)_2$ | H(l = O) | $OCOC_6H_5$ |
| 591 | $O—(CH_2CH_2)—O$ | | $PO(CH_3)_2$ | H(l = O) | $OCOC_6H_5$ |
| 592 | $O—(CH_2CH_2CH_2)—O$ | | $PO(CH_3)_2$ | H(l = O) | $OCOC_6H_5$ |
| 593 | $S—(CH_2CH_2)—S$ | | $PO(CH_3)_2$ | H(l = O) | $OCOC_6H_5$ |
| 594 | $S—(CH_2CH_2CH_2)—S$ | | $PO(CH_3)_2$ | H(l = O) | $OCOC_6H_5$ |
| 595 | $—(CH_2)_4—$ | | $PO(CH_3)_2$ | H(l = O) | $OCOC_6H_5$ |

TABLE 1-continued

I1a1

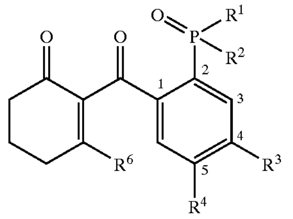

| n | $R^1$ | $R^2$ | $R^3$ | $R^4$ | $R^6$ |
|---|---|---|---|---|---|
| 596 | $-(CH_2)_5-$ | | $PO(CH_3)_2$ | H(l = O) | $OCOC_6H_5$ |
| 597 | H | H | $PO(CH_2CH_3)_2$ | H(l = O) | $OCOC_6H_5$ |
| 598 | $CH_3$ | $CH_3$ | $PO(CH_2CH_3)_2$ | H(l = O) | $OCOC_6H_5$ |
| 599 | $CH_2CH_3$ | $CH_2CH_3$ | $PO(CH_2CH_3)_2$ | H(l = O) | $OCOC_6H_5$ |
| 600 | $CH_2CH_2CH_3$ | $CH_2CH_2CH_3$ | $PO(CH_2CH_3)_2$ | H(l = O) | $OCOC_6H_5$ |
| 601 | $OCH_3$ | $OCH_3$ | $PO(CH_2CH_3)_2$ | H(l = O) | $OCOC_6H_5$ |
| 602 | $OCH_2CH_3$ | $OCH_2CH_3$ | $PO(CH_2CH_3)_2$ | H(l = O) | $OCOC_6H_5$ |
| 603 | $OCH_2CH_2CH_3$ | $OCH_2CH_2CH_3$ | $PO(CH_2CH_3)_2$ | H(l = O) | $OCOC_6H_5$ |
| 604 | $SCH_3$ | $SCH_3$ | $PO(CH_2CH_3)_2$ | H(l = O) | $OCOC_6H_5$ |
| 605 | $SCH_2CH_3$ | $SCH_2CH_3$ | $PO(CH_2CH_3)_2$ | H(l = O) | $OCOC_6H_5$ |
| 606 | $N(CH_3)_2$ | $N(CH_3)_2$ | $PO(CH_2CH_3)_2$ | H(l = O) | $OCOC_6H_5$ |
| 607 | $N(CH_2CH_3)_2$ | $N(CH_2CH_3)_2$ | $PO(CH_2CH_3)_2$ | H(l = O) | $OCOC_6H_5$ |
| 608 | $N(CH_3)(CH_2CH_3)$ | $N(CH_3)(CH_2CH_3)$ | $PO(CH_2CH_3)_2$ | H(l = O) | $OCOC_6H_5$ |
| 609 | $O-(CH_2CH_2)-O$ | | $PO(CH_2CH_3)_2$ | H(l = O) | $OCOC_6H_5$ |
| 610 | $O-(CH_2CH_2CH_2)-O$ | | $PO(CH_2CH_3)_2$ | H(l = O) | $OCOC_6H_5$ |
| 611 | $S-(CH_2CH_2)-S$ | | $PO(CH_2CH_3)_2$ | H(l = O) | $OCOC_6H_5$ |
| 612 | $S-(CH_2CH_2CH_2)-S$ | | $PO(CH_2CH_3)_2$ | H(l = O) | $OCOC_6H_5$ |
| 613 | $-(CH_2)_4-$ | | $PO(CH_2CH_3)_2$ | H(l = O) | $OCOC_6H_5$ |
| 614 | $-(CH_2)_5-$ | | $PO(CH_2CH_3)_2$ | H(l = O) | $OCOC_6H_5$ |
| 615 | H | H | H | H(l = O) | $SCH_3$ |
| 616 | $CH_3$ | $CH_3$ | H | H(l = O) | $SCH_3$ |
| 617 | $CH_2CH_3$ | $CH_2CH_3$ | H | H(l = O) | $SCH_3$ |
| 618 | $CH_2CH_2CH_3$ | $CH_2CH_2CH_3$ | H | H(l = O) | $SCH_3$ |
| 619 | $OCH_3$ | $OCH_3$ | H | H(l = O) | $SCH_3$ |
| 620 | $OCH_2CH_3$ | $OCH_2CH_3$ | H | H(l = O) | $SCH_3$ |
| 621 | $OCH_2CH_2CH_3$ | $OCH_2CH_2CH_3$ | H | H(l = O) | $SCH_3$ |
| 622 | $SCH_3$ | $SCH_3$ | H | H(l = O) | $SCH_3$ |
| 623 | $SCH_2CH_3$ | $SCH_2CH_3$ | H | H(l = O) | $SCH_3$ |
| 624 | $N(CH_3)_2$ | $N(CH_3)_2$ | H | H(l = O) | $SCH_3$ |
| 625 | $N(CH_2CH_3)_2$ | $N(CH_2CH_3)_2$ | H | H(l = O) | $SCH_3$ |
| 626 | $N(CH_3)(CH_2CH_3)$ | $N(CH_3)(CH_2CH_3)$ | H | H(l = O) | $SCH_3$ |
| 627 | $O-(CH_2CH_2)-O$ | | H | H(l = O) | $SCH_3$ |
| 628 | $O-(CH_2CH_2CH_2)-O$ | | H | H(l = O) | $SCH_3$ |
| 629 | $S-(CH_2CH_2)-S$ | | H | H(l = O) | $SCH_3$ |
| 630 | $S-(CH_2CH_2CH_2)-S$ | | H | H(l = O) | $SCH_3$ |
| 631 | $-(CH_2)_4-$ | | H | H(l = O) | $SCH_3$ |
| 632 | $-(CH_2)_5-$ | | H | H(l = O) | $SCH_3$ |
| 633 | H | H | $NO_2$ | H(l = O) | $SCH_3$ |
| 634 | $CH_3$ | $CH_3$ | $NO_2$ | H(l = O) | $SCH_3$ |
| 635 | $CH_2CH_3$ | $CH_2CH_3$ | $NO_2$ | H(l = O) | $SCH_3$ |
| 636 | $CH_2CH_2CH_3$ | $CH_2CH_2CH_3$ | $NO_2$ | H(l = O) | $SCH_3$ |
| 637 | $OCH_3$ | $OCH_3$ | $NO_2$ | H(l = O) | $SCH_3$ |
| 638 | $OCH_2CH_3$ | $OCH_2CH_3$ | $NO_2$ | H(l = O) | $SCH_3$ |
| 639 | $OCH_2CH_2CH_3$ | $OCH_2CH_2CH_3$ | $NO_2$ | H(l = O) | $SCH_3$ |
| 640 | $SCH_3$ | $SCH_3$ | $NO_2$ | H(l = O) | $SCH_3$ |
| 641 | $SCH_2CH_3$ | $SCH_2CH_3$ | $NO_2$ | H(l = O) | $SCH_3$ |
| 642 | $N(CH_3)_2$ | $N(CH_3)_2$ | $NO_2$ | H(l = O) | $SCH_3$ |
| 643 | $N(CH_2CH_3)_2$ | $N(CH_2CH_3)_2$ | $NO_2$ | H(l = O) | $SCH_3$ |
| 644 | $N(CH_3)(CH_2CH_3)$ | $N(CH_3)(CH_2CH_3)$ | $NO_2$ | H(l = O) | $SCH_3$ |
| 645 | $O-(CH_2CH_2)-O$ | | $NO_2$ | H(l = O) | $SCH_3$ |
| 646 | $O-(CH_2CH_2CH_2)-O$ | | $NO_2$ | H(l = O) | $SCH_3$ |
| 647 | $S-(CH_2CH_2)-S$ | | $NO_2$ | H(l = O) | $SCH_3$ |
| 648 | $S-(CH_2CH_2CH_2)-S$ | | $NO_2$ | H(l = O) | $SCH_3$ |
| 649 | $-(CH_2)_4-$ | | $NO_2$ | H(l = O) | $SCH_3$ |
| 650 | $-(CH_2)_5-$ | | $NO_2$ | H(l = O) | $SCH_3$ |
| 651 | H | H | CN | H(l = O) | $SCH_3$ |
| 652 | $CH_3$ | $CH_3$ | CN | H(l = O) | $SCH_3$ |
| 653 | $CH_2CH_3$ | $CH_2CH_3$ | CN | H(l = O) | $SCH_3$ |
| 654 | $CH_2CH_2CH_3$ | $CH_2CH_2CH_3$ | CN | H(l = O) | $SCH_3$ |
| 655 | $OCH_3$ | $OCH_3$ | CN | H(l = O) | $SCH_3$ |
| 656 | $OCH_2CH_3$ | $OCH_2CH_3$ | CN | H(l = O) | $SCH_3$ |
| 657 | $OCH_2CH_2CH_3$ | $OCH_2CH_2CH_3$ | CN | H(l = O) | $SCH_3$ |
| 658 | $SCH_3$ | $SCH_3$ | CN | H(l = O) | $SCH_3$ |
| 659 | $SCH_2CH_3$ | $SCH_2CH_3$ | CN | H(l = O) | $SCH_3$ |

TABLE 1-continued

I1a1

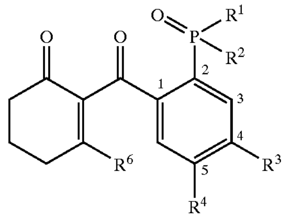

| n | $R^1$ | $R^2$ | $R^3$ | $R^4$ | $R^6$ |
|---|---|---|---|---|---|
| 660 | $N(CH_3)_2$ | $N(CH_3)_2$ | CN | H(l = O) | $SCH_3$ |
| 661 | $N(CH_2CH_3)_2$ | $N(CH_2CH_3)_2$ | CN | H(l = O) | $SCH_3$ |
| 662 | $N(CH_3)(CH_2CH_3)$ | $N(CH_3)(CH_2CH_3)$ | CN | H(l = O) | $SCH_3$ |
| 663 | $O—(CH_2CH_2)—O$ | | CN | H(l = O) | $SCH_3$ |
| 664 | $O—(CH_2CH_2CH_2)—O$ | | CN | H(l = O) | $SCH_3$ |
| 665 | $S—(CH_2CH_2)—S$ | | CN | H(l = O) | $SCH_3$ |
| 666 | $S—(CH_2CH_2CH_2)—S$ | | CN | H(l = O) | $SCH_3$ |
| 667 | $—(CH_2)_4—$ | | CN | H(l = O) | $SCH_3$ |
| 668 | $—(CH_2)_5—$ | | CN | H(l = O) | $SCH_3$ |
| 669 | H | H | F | H(l = O) | $SCH_3$ |
| 670 | $CH_3$ | $CH_3$ | F | H(l = O) | $SCH_3$ |
| 671 | $CH_2CH_3$ | $CH_2CH_3$ | F | H(l = O) | $SCH_3$ |
| 672 | $CH_2CH_2CH_3$ | $CH_2CH_2CH_3$ | F | H(l = O) | $SCH_3$ |
| 673 | $OCH_3$ | $OCH_3$ | F | H(l = O) | $SCH_3$ |
| 674 | $OCH_2CH_3$ | $OCH_2CH_3$ | F | H(l = O) | $SCH_3$ |
| 675 | $OCH_2CH_2CH_3$ | $OCH_2CH_2CH_3$ | F | H(l = O) | $SCH_3$ |
| 676 | $SCH_3$ | $SCH_3$ | F | H(l = O) | $SCH_3$ |
| 677 | $SCH_2CH_3$ | $SCH_2CH_3$ | F | H(l = O) | $SCH_3$ |
| 678 | $N(CH_3)_2$ | $N(CH_3)_2$ | F | H(l = O) | $SCH_3$ |
| 679 | $N(CH_2CH_3)_2$ | $N(CH_2CH_3)_2$ | F | H(l = O) | $SCH_3$ |
| 680 | $N(CH_3)(CH_2CH_3)$ | $N(CH_3)(CH_2CH_3)$ | F | H(l = O) | $SCH_3$ |
| 681 | $O—(CH_2CH_2)—O$ | | F | H(l = O) | $SCH_3$ |
| 682 | $O—(CH_2CH_2CH_2)—O$ | | F | H(l = O) | $SCH_3$ |
| 683 | $S—(CH_2CH_2)—S$ | | F | H(l = O) | $SCH_3$ |
| 684 | $S—(CH_2CH_2CH_2)—S$ | | F | H(l = O) | $SCH_3$ |
| 685 | $—(CH_2)_4—$ | | F | H(l = O) | $SCH_3$ |
| 686 | $—(CH_2)_5—$ | | F | H(l = O) | $SCH_3$ |
| 687 | H | H | Cl | H(l = O) | $SCH_3$ |
| 688 | $CH_3$ | $CH_3$ | Cl | H(l = O) | $SCH_3$ |
| 689 | $CH_2CH_3$ | $CH_2CH_3$ | Cl | H(l = O) | $SCH_3$ |
| 690 | $CH_2CH_2CH_3$ | $CH_2CH_2CH_3$ | Cl | H(l = O) | $SCH_3$ |
| 691 | $OCH_3$ | $OCH_3$ | Cl | H(l = O) | $SCH_3$ |
| 692 | $OCH_2CH_3$ | $OCH_2CH_3$ | Cl | H(l = O) | $SCH_3$ |
| 693 | $OCH_2CH_2CH_3$ | $OCH_2CH_2CH_3$ | Cl | H(l = O) | $SCH_3$ |
| 694 | $SCH_3$ | $SCH_3$ | Cl | H(l = O) | $SCH_3$ |
| 695 | $SCH_2CH_3$ | $SCH_2CH_3$ | Cl | H(l = O) | $SCH_3$ |
| 696 | $N(CH_3)_2$ | $N(CH_3)_2$ | Cl | H(l = O) | $SCH_3$ |
| 697 | $N(CH_2CH_3)_2$ | $N(CH_2CH_3)_2$ | Cl | H(l = O) | $SCH_3$ |
| 698 | $N(CH_3)(CH_2CH_3)$ | $N(CH_3)(CH_2CH_3)$ | Cl | H(l = O) | $SCH_3$ |
| 699 | $O—(CH_2CH_2)—O$ | | Cl | H(l = O) | $SCH_3$ |
| 700 | $O—(CH_2CH_2CH_2)—O$ | | Cl | H(l = O) | $SCH_3$ |
| 701 | $S—(CH_2CH_2)—S$ | | Cl | H(l = O) | $SCH_3$ |
| 702 | $S—(CH_2CH_2CH_2)—S$ | | Cl | H(l = O) | $SCH_3$ |
| 703 | $—(CH_2)_4—$ | | Cl | H(l = O) | $SCH_3$ |
| 704 | $—(CH_2)_5—$ | | Cl | H(l = O) | $SCH_3$ |
| 705 | H | H | Br | H(l = O) | $SCH_3$ |
| 706 | $CH_3$ | $CH_3$ | Br | H(l = O) | $SCH_3$ |
| 707 | $CH_2CH_3$ | $CH_2CH_3$ | Br | H(l = O) | $SCH_3$ |
| 708 | $CH_2CH_2CH_3$ | $CH_2CH_2CH_3$ | Br | H(l = O) | $SCH_3$ |
| 709 | $OCH_3$ | $OCH_3$ | Br | H(l = O) | $SCH_3$ |
| 710 | $OCH_2CH_3$ | $OCH_2CH_3$ | Br | H(l = O) | $SCH_3$ |
| 711 | $OCH_2CH_2CH_3$ | $OCH_2CH_2CH_3$ | Br | H(l = O) | $SCH_3$ |
| 712 | $SCH_3$ | $SCH_3$ | Br | H(l = O) | $SCH_3$ |
| 713 | $SCH_2CH_3$ | $SCH_2CH_3$ | Br | H(l = O) | $SCH_3$ |
| 714 | $N(CH_3)_2$ | $N(CH_3)_2$ | Br | H(l = O) | $SCH_3$ |
| 715 | $N(CH_2CH_3)_2$ | $N(CH_2CH_3)_2$ | Br | H(l = O) | $SCH_3$ |
| 716 | $N(CH_3)(CH_2CH_3)$ | $N(CH_3)(CH_2CH_3)$ | Br | H(l = O) | $SCH_3$ |
| 717 | $O—(CH_2CH_2)—O$ | | Br | H(l = O) | $SCH_3$ |
| 718 | $O—(CH_2CH_2CH_2)—O$ | | Br | H(l = O) | $SCH_3$ |
| 719 | $S—(CH_2CH_2)—S$ | | Br | H(l = O) | $SCH_3$ |
| 720 | $S—(CH_2CH_2CH_2)—S$ | | Br | H(l = O) | $SCH_3$ |
| 721 | $—(CH_2)_4—$ | | Br | H(l = O) | $SCH_3$ |
| 722 | $—(CH_2)_5—$ | | Br | H(l = O) | $SCH_3$ |
| 723 | H | H | $CH_3$ | H(l = O) | $SCH_3$ |

TABLE 1-continued

I1a1

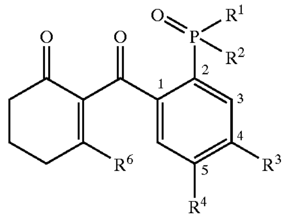

| n | $R^1$ | $R^2$ | $R^3$ | $R^4$ | $R^6$ |
|---|---|---|---|---|---|
| 724 | $CH_3$ | $CH_3$ | $CH_3$ | H(l = O) | $SCH_3$ |
| 725 | $CH_2CH_3$ | $CH_2CH_3$ | $CH_3$ | H(l = O) | $SCH_3$ |
| 726 | $CH_2CH_2CH_3$ | $CH_2CH_2CH_3$ | $CH_3$ | H(l = O) | $SCH_3$ |
| 727 | $OCH_3$ | $OCH_3$ | $CH_3$ | H(l = O) | $SCH_3$ |
| 728 | $OCH_2CH_3$ | $OCH_2CH_3$ | $CH_3$ | H(l = O) | $SCH_3$ |
| 729 | $OCH_2CH_2CH_3$ | $OCH_2CH_2CH_3$ | $CH_3$ | H(l = O) | $SCH_3$ |
| 730 | $SCH_3$ | $SCH_3$ | $CH_3$ | H(l = O) | $SCH_3$ |
| 731 | $SCH_2CH_3$ | $SCH_2CH_3$ | $CH_3$ | H(l = O) | $SCH_3$ |
| 732 | $N(CH_3)_2$ | $N(CH_3)_2$ | $CH_3$ | H(l = O) | $SCH_3$ |
| 733 | $N(CH_2CH_3)_2$ | $N(CH_2CH_3)_2$ | $CH_3$ | H(l = O) | $SCH_3$ |
| 734 | $N(CH_3)(CH_2CH_3)$ | $N(CH_3)(CH_2CH_3)$ | $CH_3$ | H(l = O) | $SCH_3$ |
| 735 | $O—(CH_2CH_2)—O$ | | $CH_3$ | H(l = O) | $SCH_3$ |
| 736 | $O—(CH_2CH_2CH_2)—O$ | | $CH_3$ | H(l = O) | $SCH_3$ |
| 737 | $S—(CH_2CH_2)—S$ | | $CH_3$ | H(l = O) | $SCH_3$ |
| 738 | $S—(CH_2CH_2CH_2)—S$ | | $CH_3$ | H(l = O) | $SCH_3$ |
| 739 | $—(CH_2)_4—$ | | $CH_3$ | H(l = O) | $SCH_3$ |
| 740 | $—(CH_2)_5—$ | | $CH_3$ | H(l = O) | $SCH_3$ |
| 741 | H | H | $CH_2CH_3$ | H(l = O) | $SCH_3$ |
| 742 | $CH_3$ | $CH_3$ | $CH_2CH_3$ | H(l = O) | $SCH_3$ |
| 743 | $CH_2CH_3$ | $CH_2CH_3$ | $CH_2CH_3$ | H(l = O) | $SCH_3$ |
| 744 | $CH_2CH_2CH_3$ | $CH_2CH_2CH_3$ | $CH_2CH_3$ | H(l = O) | $SCH_3$ |
| 745 | $OCH_3$ | $OCH_3$ | $CH_2CH_3$ | H(l = O) | $SCH_3$ |
| 746 | $OCH_2CH_3$ | $OCH_2CH_3$ | $CH_2CH_3$ | H(l = O) | $SCH_3$ |
| 747 | $OCH_2CH_2CH_3$ | $OCH_2CH_2CH_3$ | $CH_2CH_3$ | H(l = O) | $SCH_3$ |
| 748 | $SCH_3$ | $SCH_3$ | $CH_2CH_3$ | H(l = O) | $SCH_3$ |
| 749 | $SCH_2CH_3$ | $SCH_2CH_3$ | $CH_2CH_3$ | H(l = O) | $SCH_3$ |
| 750 | $N(CH_3)_2$ | $N(CH_3)_2$ | $CH_2CH_3$ | H(l = O) | $SCH_3$ |
| 751 | $N(CH_2CH_3)_2$ | $N(CH_2CH_3)_2$ | $CH_2CH_3$ | H(l = O) | $SCH_3$ |
| 752 | $N(CH_3)(CH_2CH_3)$ | $N(CH_3)(CH_2CH_3)$ | $CH_2CH_3$ | H(l = O) | $SCH_3$ |
| 753 | $O—(CH_2CH_2)—O$ | | $CH_2CH_3$ | H(l = O) | $SCH_3$ |
| 754 | $O—(CH_2CH_2CH_2)—O$ | | $CH_2CH_3$ | H(l = O) | $SCH_3$ |
| 755 | $S—(CH_2CH_2)—S$ | | $CH_2CH_3$ | H(l = O) | $SCH_3$ |
| 756 | $S—(CH_2CH_2CH_2)—S$ | | $CH_2CH_3$ | H(l = O) | $SCH_3$ |
| 757 | $—(CH_2)_4—$ | | $CH_2CH_3$ | H(l = O) | $SCH_3$ |
| 758 | $—(CH_2)_5—$ | | $CH_2CH_3$ | H(l = O) | $SCH_3$ |
| 759 | H | H | $CF_3$ | H(l = O) | $SCH_3$ |
| 760 | $CH_3$ | $CH_3$ | $CF_3$ | H(l = O) | $SCH_3$ |
| 761 | $CH_2CH_3$ | $CH_2CH_3$ | $CF_3$ | H(l = O) | $SCH_3$ |
| 762 | $CH_2CH_2CH_3$ | $CH_2CH_2CH_3$ | $CF_3$ | H(l = O) | $SCH_3$ |
| 763 | $OCH_3$ | $OCH_3$ | $CF_3$ | H(l = O) | $SCH_3$ |
| 764 | $OCH_2CH_3$ | $OCH_2CH_3$ | $CF_3$ | H(l = O) | $SCH_3$ |
| 765 | $OCH_2CH_2CH_3$ | $OCH_2CH_2CH_3$ | $CF_3$ | H(l = O) | $SCH_3$ |
| 766 | $SCH_3$ | $SCH_3$ | $CF_3$ | H(l = O) | $SCH_3$ |
| 767 | $SCH_2CH_3$ | $SCH_2CH_3$ | $CF_3$ | H(l = O) | $SCH_3$ |
| 768 | $N(CH_3)_2$ | $N(CH_3)_2$ | $CF_3$ | H(l = O) | $SCH_3$ |
| 769 | $N(CH_2CH_3)_2$ | $N(CH_2CH_3)_2$ | $CF_3$ | H(l = O) | $SCH_3$ |
| 770 | $N(CH_3)(CH_2CH_3)$ | $N(CH_3)(CH_2CH_3)$ | $CF_3$ | H(l = O) | $SCH_3$ |
| 771 | $O—(CH_2CH_2)—O$ | | $CF_3$ | H(l = O) | $SCH_3$ |
| 772 | $O—(CH_2CH_2CH_2)—O$ | | $CF_3$ | H(l = O) | $SCH_3$ |
| 773 | $S—(CH_2CH_2)—S$ | | $CF_3$ | H(l = O) | $SCH_3$ |
| 774 | $S—(CH_2CH_2CH_2)—S$ | | $CF_3$ | H(l = O) | $SCH_3$ |
| 775 | $—(CH_2)_4—$ | | $CF_3$ | H(l = O) | $SCH_3$ |
| 776 | $—(CH_2)_5—$ | | $CF_3$ | H(l = O) | $SCH_3$ |
| 777 | H | H | $OCH_3$ | H(l = O) | $SCH_3$ |
| 778 | $CH_3$ | $CH_3$ | $OCH_3$ | H(l = O) | $SCH_3$ |
| 779 | $CH_2CH_3$ | $CH_2CH_3$ | $OCH_3$ | H(l = O) | $SCH_3$ |
| 780 | $CH_2CH_2CH_3$ | $CH_2CH_2CH_3$ | $OCH_3$ | H(l = O) | $SCH_3$ |
| 781 | $OCH_3$ | $OCH_3$ | $OCH_3$ | H(l = O) | $SCH_3$ |
| 782 | $OCH_2CH_3$ | $OCH_2CH_3$ | $OCH_3$ | H(l = O) | $SCH_3$ |
| 783 | $OCH_2CH_2CH_3$ | $OCH_2CH_2CH_3$ | $OCH_3$ | H(l = O) | $SCH_3$ |
| 784 | $SCH_3$ | $SCH_3$ | $OCH_3$ | H(l = O) | $SCH_3$ |
| 785 | $SCH_2CH_3$ | $SCH_2CH_3$ | $OCH_3$ | H(l = O) | $SCH_3$ |
| 786 | $N(CH_3)_2$ | $N(CH_3)_2$ | $OCH_3$ | H(l = O) | $SCH_3$ |
| 787 | $N(CH_2CH_3)_2$ | $N(CH_2CH_3)_2$ | $OCH_3$ | H(l = O) | $SCH_3$ |

TABLE 1-continued

I1a1

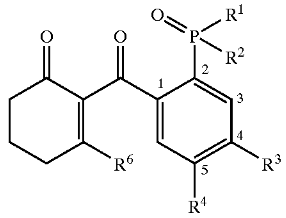

| n | $R^1$ | $R^2$ | $R^3$ | $R^4$ | $R^6$ |
|---|---|---|---|---|---|
| 788 | $N(CH_3)(CH_2CH_3)$ | $N(CH_3)(CH_2CH_3)$ | $OCH_3$ | H(l = O) | $SCH_3$ |
| 789 | O—$(CH_2CH_2)$—O | | $OCH_3$ | H(l = O) | $SCH_3$ |
| 790 | O—$(CH_2CH_2CH_2)$—O | | $OCH_3$ | H(l = O) | $SCH_3$ |
| 791 | S—$(CH_2CH_2)$—S | | $OCH_3$ | H(l = O) | $SCH_3$ |
| 792 | S—$(CH_2CH_2CH_2)$—S | | $OCH_3$ | H(l = O) | $SCH_3$ |
| 793 | —$(CH_2)_4$— | | $OCH_3$ | H(l = O) | $SCH_3$ |
| 794 | —$(CH_2)_5$— | | $OCH_3$ | H(l = O) | $SCH_3$ |
| 795 | H | H | $OCH_2CH_3$ | H(l = O) | $SCH_3$ |
| 796 | $CH_3$ | $CH_3$ | $OCH_2CH_3$ | H(l = O) | $SCH_3$ |
| 797 | $CH_2CH_3$ | $CH_2CH_3$ | $OCH_2CH_3$ | H(l = O) | $SCH_3$ |
| 798 | $CH_2CH_2CH_3$ | $CH_2CH_2CH_3$ | $OCH_2CH_3$ | H(l = O) | $SCH_3$ |
| 799 | $OCH_3$ | $OCH_3$ | $OCH_2CH_3$ | H(l = O) | $SCH_3$ |
| 800 | $OCH_2CH_3$ | $OCH_2CH_3$ | $OCH_2CH_3$ | H(l = O) | $SCH_3$ |
| 801 | $OCH_2CH_2CH_3$ | $OCH_2CH_2CH_3$ | $OCH_2CH_3$ | H(l = O) | $SCH_3$ |
| 802 | $SCH_3$ | $SCH_3$ | $OCH_2CH_3$ | H(l = O) | $SCH_3$ |
| 803 | $SCH_2CH_3$ | $SCH_2CH_3$ | $OCH_2CH_3$ | H(l = O) | $SCH_3$ |
| 804 | $N(CH_3)_2$ | $N(CH_3)_2$ | $OCH_2CH_3$ | H(l = O) | $SCH_3$ |
| 805 | $N(CH_2CH_3)_2$ | $N(CH_2CH_3)_2$ | $OCH_2CH_3$ | H(l = O) | $SCH_3$ |
| 806 | $N(CH_3)(CH_2CH_3)$ | $N(CH_3)(CH_2CH_3)$ | $OCH_2CH_3$ | H(l = O) | $SCH_3$ |
| 807 | O—$(CH_2CH_2)$—O | | $OCH_2CH_3$ | H(l = O) | $SCH_3$ |
| 808 | O—$(CH_2CH_2CH_2)$—O | | $OCH_2CH_3$ | H(l = O) | $SCH_3$ |
| 809 | S—$(CH_2CH_2)$—S | | $OCH_2CH_3$ | H(l = O) | $SCH_3$ |
| 810 | S—$(CH_2CH_2CH_2)$—S | | $OCH_2CH_3$ | H(l = O) | $SCH_3$ |
| 811 | —$(CH_2)_4$— | | $OCH_2CH_3$ | H(l = O) | $SCH_3$ |
| 812 | —$(CH_2)_5$— | | $OCH_2CH_3$ | H(l = O) | $SCH_3$ |
| 813 | H | H | $SCH_3$ | H(l = O) | $SCH_3$ |
| 814 | $CH_3$ | $CH_3$ | $SCH_3$ | H(l = O) | $SCH_3$ |
| 815 | $CH_2CH_3$ | $CH_2CH_3$ | $SCH_3$ | H(l = O) | $SCH_3$ |
| 816 | $CH_2CH_2CH_3$ | $CH_2CH_2CH_3$ | $SCH_3$ | H(l = O) | $SCH_3$ |
| 817 | $OCH_3$ | $OCH_3$ | $SCH_3$ | H(l = O) | $SCH_3$ |
| 818 | $OCH_2CH_3$ | $OCH_2CH_3$ | $SCH_3$ | H(l = O) | $SCH_3$ |
| 819 | $OCH_2CH_2CH_3$ | $OCH_2CH_2CH_3$ | $SCH_3$ | H(l = O) | $SCH_3$ |
| 820 | $SCH_3$ | $SCH_3$ | $SCH_3$ | H(l = O) | $SCH_3$ |
| 821 | $SCH_2CH_3$ | $SCH_2CH_3$ | $SCH_3$ | H(l = O) | $SCH_3$ |
| 822 | $N(CH_3)_2$ | $N(CH_3)_2$ | $SCH_3$ | H(l = O) | $SCH_3$ |
| 823 | $N(CH_2CH_3)_2$ | $N(CH_2CH_3)_2$ | $SCH_3$ | H(l = O) | $SCH_3$ |
| 824 | $N(CH_3)(CH_2CH_3)$ | $N(CH_3)(CH_2CH_3)$ | $SCH_3$ | H(l = O) | $SCH_3$ |
| 825 | O—$(CH_2CH_2)$—O | | $SCH_3$ | H(l = O) | $SCH_3$ |
| 826 | O—$(CH_2CH_2CH_2)$—O | | $SCH_3$ | H(l = O) | $SCH_3$ |
| 827 | S—$(CH_2CH_2)$—S | | $SCH_3$ | H(l = O) | $SCH_3$ |
| 828 | S—$(CH_2CH_2CH_2)$—S | | $SCH_3$ | H(l = O) | $SCH_3$ |
| 829 | —$(CH_2)_4$— | | $SCH_3$ | H(l = O) | $SCH_3$ |
| 830 | —$(CH_2)_5$— | | $SCH_3$ | H(l = O) | $SCH_3$ |
| 831 | H | H | $SO_2CH_3$ | H(l = O) | $SCH_3$ |
| 832 | $CH_3$ | $CH_3$ | $SO_2CH_3$ | H(l = O) | $SCH_3$ |
| 833 | $CH_2CH_3$ | $CH_2CH_3$ | $SO_2CH_3$ | H(l = O) | $SCH_3$ |
| 834 | $CH_2CH_2CH_3$ | $CH_2CH_2CH_3$ | $SO_2CH_3$ | H(l = O) | $SCH_3$ |
| 835 | $OCH_3$ | $OCH_3$ | $SO_2CH_3$ | H(l = O) | $SCH_3$ |
| 836 | $OCH_2CH_3$ | $OCH_2CH_3$ | $SO_2CH_3$ | H(l = O) | $SCH_3$ |
| 837 | $OCH_2CH_2CH_3$ | $OCH_2CH_2CH_3$ | $SO_2CH_3$ | H(l = O) | $SCH_3$ |
| 838 | $SCH_3$ | $SCH_3$ | $SO_2CH_3$ | H(l = O) | $SCH_3$ |
| 839 | $SCH_2CH_3$ | $SCH_2CH_3$ | $SO_2CH_3$ | H(l = O) | $SCH_3$ |
| 840 | $N(CH_3)_2$ | $N(CH_3)_2$ | $SO_2CH_3$ | H(l = O) | $SCH_3$ |
| 841 | $N(CH_2CH_3)_2$ | $N(CH_2CH_3)_2$ | $SO_2CH_3$ | H(l = O) | $SCH_3$ |
| 842 | $N(CH_3)(CH_2CH_3)$ | $N(CH_3)(CH_2CH_3)$ | $SO_2CH_3$ | H(l = O) | $SCH_3$ |
| 843 | O—$(CH_2CH_2)$—O | | $SO_2CH_3$ | H(l = O) | $SCH_3$ |
| 844 | O—$(CH_2CH_2CH_2)$—O | | $SO_2CH_3$ | H(l = O) | $SCH_3$ |
| 845 | S—$(CH_2CH_2)$—S | | $SO_2CH_3$ | H(l = O) | $SCH_3$ |
| 846 | S—$(CH_2CH_2CH_2)$—S | | $SO_2CH_3$ | H(l = O) | $SCH_3$ |
| 847 | —$(CH_2)_4$— | | $SO_2CH_3$ | H(l = O) | $SCH_3$ |
| 848 | —$(CH_2)_5$— | | $SO_2CH_3$ | H(l = O) | $SCH_3$ |
| 849 | H | H | $PO(OCH_3)_2$ | H(l = O) | $SCH_3$ |
| 850 | $CH_3$ | $CH_3$ | $PO(OCH_3)_2$ | H(l = O) | $SCH_3$ |
| 851 | $CH_2CH_3$ | $CH_2CH_3$ | $PO(OCH_3)_2$ | H(l = O) | $SCH_3$ |

TABLE 1-continued

I1a1

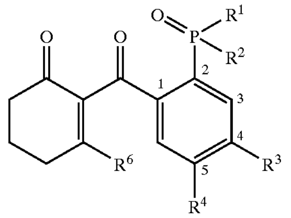

| n | $R^1$ | $R^2$ | $R^3$ | $R^4$ | $R^6$ |
|---|---|---|---|---|---|
| 852 | $CH_2CH_2CH_3$ | $CH_2CH_2CH_3$ | $PO(OCH_3)_2$ | H(l = O) | $SCH_3$ |
| 853 | $OCH_3$ | $OCH_3$ | $PO(OCH_3)_2$ | H(l = O) | $SCH_3$ |
| 854 | $OCH_2CH_3$ | $OCH_2CH_3$ | $PO(OCH_3)_2$ | H(l = O) | $SCH_3$ |
| 855 | $OCH_2CH_2CH_3$ | $OCH_2CH_2CH_3$ | $PO(OCH_3)_2$ | H(l = O) | $SCH_3$ |
| 856 | $SCH_3$ | $SCH_3$ | $PO(OCH_3)_2$ | H(l = O) | $SCH_3$ |
| 857 | $SCH_2CH_3$ | $SCH_2CH_3$ | $PO(OCH_3)_2$ | H(l = O) | $SCH_3$ |
| 858 | $N(CH_3)_2$ | $N(CH_3)_2$ | $PO(OCH_3)_2$ | H(l = O) | $SCH_3$ |
| 859 | $N(CH_2CH_3)_2$ | $N(CH_2CH_3)_2$ | $PO(OCH_3)_2$ | H(l = O) | $SCH_3$ |
| 860 | $N(CH_3)(CH_2CH_3)$ | $N(CH_3)(CH_2CH_3)$ | $PO(OCH_3)_2$ | H(l = O) | $SCH_3$ |
| 861 | $O—(CH_2CH_2)—O$ | | $PO(OCH_3)_2$ | H(l = O) | $SCH_3$ |
| 862 | $O—(CH_2CH_2CH_2)—O$ | | $PO(OCH_3)_2$ | H(l = O) | $SCH_3$ |
| 863 | $S—(CH_2CH_2)—S$ | | $PO(OCH_3)_2$ | H(l = O) | $SCH_3$ |
| 864 | $S—(CH_2CH_2CH_2)—S$ | | $PO(OCH_3)_2$ | H(l = O) | $SCH_3$ |
| 865 | $—(CH_2)_4—$ | | $PO(OCH_3)_2$ | H(l = O) | $SCH_3$ |
| 866 | $—(CH_2)_5—$ | | $PO(OCH_3)_2$ | H(l = O) | $SCH_3$ |
| 867 | H | H | $PO(OCH_2CH_3)_2$ | H(l = O) | $SCH_3$ |
| 868 | $CH_3$ | $CH_3$ | $PO(OCH_2CH_3)_2$ | H(l = O) | $SCH_3$ |
| 869 | $CH_2CH_3$ | $CH_2CH_3$ | $PO(OCH_2CH_3)_2$ | H(l = O) | $SCH_3$ |
| 870 | $CH_2CH_2CH_3$ | $CH_2CH_2CH_3$ | $PO(OCH_2CH_3)_2$ | H(l = O) | $SCH_3$ |
| 871 | $OCH_3$ | $OCH_3$ | $PO(OCH_2CH_3)_2$ | H(l = O) | $SCH_3$ |
| 872 | $OCH_2CH_3$ | $OCH_2CH_3$ | $PO(OCH_2CH_3)_2$ | H(l = O) | $SCH_3$ |
| 873 | $OCH_2CH_2CH_3$ | $OCH_2CH_2CH_3$ | $PO(OCH_2CH_3)_2$ | H(l = O) | $SCH_3$ |
| 874 | $SCH_3$ | $SCH_3$ | $PO(OCH_2CH_3)_2$ | H(l = O) | $SCH_3$ |
| 875 | $SCH_2CH_3$ | $SCH_2CH_3$ | $PO(OCH_2CH_3)_2$ | H(l = O) | $SCH_3$ |
| 876 | $N(CH_3)_2$ | $N(CH_3)_2$ | $PO(OCH_2CH_3)_2$ | H(l = O) | $SCH_3$ |
| 877 | $N(CH_2CH_3)_2$ | $N(CH_2CH_3)_2$ | $PO(OCH_2CH_3)_2$ | H(l = O) | $SCH_3$ |
| 878 | $N(CH_3)(CH_2CH_3)$ | $N(CH_3)(CH_2CH_3)$ | $PO(OCH_2CH_3)_2$ | H(l = O) | $SCH_3$ |
| 879 | $O—(CH_2CH_2)—O$ | | $PO(OCH_2CH_3)_2$ | H(l = O) | $SCH_3$ |
| 880 | $O—(CH_2CH_2CH_2)—O$ | | $PO(OCH_2CH_3)_2$ | H(l = O) | $SCH_3$ |
| 881 | $S—(CH_2CH_2)—S$ | | $PO(OCH_2CH_3)_2$ | H(l = O) | $SCH_3$ |
| 882 | $S—(CH_2CH_2CH_2)—S$ | | $PO(OCH_2CH_3)_2$ | H(l = O) | $SCH_3$ |
| 883 | $—(CH_2)_4—$ | | $PO(OCH_2CH_3)_2$ | H(l = O) | $SCH_3$ |
| 884 | $—(CH_2)_5—$ | | $PO(OCH_2CH_3)_2$ | H(l = O) | $SCH_3$ |
| 885 | H | H | $PO(CH_3)_2$ | H(l = O) | $SCH_3$ |
| 886 | $CH_3$ | $CH_3$ | $PO(CH_3)_2$ | H(l = O) | $SCH_3$ |
| 887 | $CH_2CH_3$ | $CH_2CH_3$ | $PO(CH_3)_2$ | H(l = O) | $SCH_3$ |
| 888 | $CH_2CH_2CH_3$ | $CH_2CH_2CH_3$ | $PO(CH_3)_2$ | H(l = O) | $SCH_3$ |
| 889 | $OCH_3$ | $OCH_3$ | $PO(CH_3)_2$ | H(l = O) | $SCH_3$ |
| 890 | $OCH_2CH_3$ | $OCH_2CH_3$ | $PO(CH_3)_2$ | H(l = O) | $SCH_3$ |
| 891 | $OCH_2CH_2CH_3$ | $OCH_2CH_2CH_3$ | $PO(CH_3)_2$ | H(l = O) | $SCH_3$ |
| 892 | $SCH_3$ | $SCH_3$ | $PO(CH_3)_2$ | H(l = O) | $SCH_3$ |
| 893 | $SCH_2CH_3$ | $SCH_2CH_3$ | $PO(CH_3)_2$ | H(l = O) | $SCH_3$ |
| 894 | $N(CH_3)_2$ | $N(CH_3)_2$ | $PO(CH_3)_2$ | H(l = O) | $SCH_3$ |
| 895 | $N(CH_2CH_3)_2$ | $N(CH_2CH_3)_2$ | $PO(CH_3)_2$ | H(l = O) | $SCH_3$ |
| 896 | $N(CH_3)(CH_2CH_3)$ | $N(CH_3)(CH_2CH_3)$ | $PO(CH_3)_2$ | H(l = O) | $SCH_3$ |
| 897 | $O—(CH_2CH_2)—O$ | | $PO(CH_3)_2$ | H(l = O) | $SCH_3$ |
| 898 | $O—(CH_2CH_2CH_2)—O$ | | $PO(CH_3)_2$ | H(l = O) | $SCH_3$ |
| 899 | $S—(CH_2CH_2)—S$ | | $PO(CH_3)_2$ | H(l = O) | $SCH_3$ |
| 900 | $S—(CH_2CH_2CH_2)—S$ | | $PO(CH_3)_2$ | H(l = O) | $SCH_3$ |
| 901 | $—(CH_2)_4—$ | | $PO(CH_3)_2$ | H(l = O) | $SCH_3$ |
| 902 | $—(CH_2)_5—$ | | $PO(CH_3)_2$ | H(l = O) | $SCH_3$ |
| 903 | H | H | $PO(CH_2CH_3)_2$ | H(l = O) | $SCH_3$ |
| 904 | $CH_3$ | $CH_3$ | $PO(CH_2CH_3)_2$ | H(l = O) | $SCH_3$ |
| 905 | $CH_2CH_3$ | $CH_2CH_3$ | $PO(CH_2CH_3)_2$ | H(l = O) | $SCH_3$ |
| 906 | $CH_2CH_2CH_3$ | $CH_2CH_2CH_3$ | $PO(CH_2CH_3)_2$ | H(l = O) | $SCH_3$ |
| 907 | $OCH_3$ | $OCH_3$ | $PO(CH_2CH_3)_2$ | H(l = O) | $SCH_3$ |
| 908 | $OCH_2CH_3$ | $OCH_2CH_3$ | $PO(CH_2CH_3)_2$ | H(l = O) | $SCH_3$ |
| 909 | $OCH_2CH_2CH_3$ | $OCH_2CH_2CH_3$ | $PO(CH_2CH_3)_2$ | H(l = O) | $SCH_3$ |
| 910 | $SCH_3$ | $SCH_3$ | $PO(CH_2CH_3)_2$ | H(l = O) | $SCH_3$ |
| 911 | $SCH_2CH_3$ | $SCH_2CH_3$ | $PO(CH_2CH_3)_2$ | H(l = O) | $SCH_3$ |
| 912 | $N(CH_3)_2$ | $N(CH_3)_2$ | $PO(CH_2CH_3)_2$ | H(l = O) | $SCH_3$ |
| 913 | $N(CH_2CH_3)_2$ | $N(CH_2CH_3)_2$ | $PO(CH_2CH_3)_2$ | H(l = O) | $SCH_3$ |
| 914 | $N(CH_3)(CH_2CH_3)$ | $N(CH_3)(CH_2CH_3)$ | $PO(CH_2CH_3)_2$ | H(l = O) | $SCH_3$ |
| 915 | $O—(CH_2CH_2)—O$ | | $PO(CH_2CH_3)_2$ | H(l = O) | $SCH_3$ |

TABLE 1-continued

I1a1

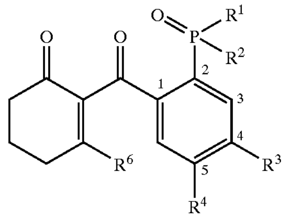

| n | $R^1$ | $R^2$ | $R^3$ | $R^4$ | $R^6$ |
|---|---|---|---|---|---|
| 916 | O—$(CH_2CH_2CH_2)$—O | | $PO(CH_2CH_3)_2$ | H(l = O) | $SCH_3$ |
| 917 | S—$(CH_2CH_2)$—S | | $PO(CH_2CH_3)_2$ | H(l = O) | $SCH_3$ |
| 918 | S—$(CH_2CH_2CH_2)$—S | | $PO(CH_2CH_3)_2$ | H(l = O) | $SCH_3$ |
| 919 | —$(CH_2)_4$— | | $PO(CH_2CH_3)_2$ | H(l = O) | $SCH_3$ |
| 920 | —$(CH_2)_5$— | | $PO(CH_2CH_3)_2$ | H(l = O) | $SCH_3$ |
| 921 | H | H | H | H(l = O) | $SC_6H_5$ |
| 922 | $CH_3$ | $CH_3$ | H | H(l = O) | $SC_6H_5$ |
| 923 | $CH_2CH_3$ | $CH_2CH_3$ | H | H(l = O) | $SC_6H_5$ |
| 924 | $CH_2CH_2CH_3$ | $CH_2CH_2CH_3$ | H | H(l = O) | $SC_6H_5$ |
| 925 | $OCH_3$ | $OCH_3$ | H | H(l = O) | $SC_6H_5$ |
| 926 | $OCH_2CH_3$ | $OCH_2CH_3$ | H | H(l = O) | $SC_6H_5$ |
| 927 | $OCH_2CH_2CH_3$ | $OCH_2CH_2CH_3$ | H | H(l = O) | $SC_6H_5$ |
| 928 | $SCH_3$ | $SCH_3$ | H | H(l = O) | $SC_6H_5$ |
| 929 | $SCH_2CH_3$ | $SCH_2CH_3$ | H | H(l = O) | $SC_6H_5$ |
| 930 | $N(CH_3)_2$ | $N(CH_3)_2$ | H | H(l = O) | $SC_6H_5$ |
| 931 | $N(CH_2CH_3)_2$ | $N(CH_2CH_3)_2$ | H | H(l = O) | $SC_6H_5$ |
| 932 | $N(CH_3)(CH_2CH_3)$ | $N(CH_3)(CH_2CH_3)$ | H | H(l = O) | $SC_6H_5$ |
| 933 | O—$(CH_2CH_2)$—O | | H | H(l = O) | $SC_6H_5$ |
| 934 | O—$(CH_2CH_2CH_2)$—O | | H | H(l = O) | $SC_6H_5$ |
| 935 | S—$(CH_2CH_2)$—S | | H | H(l = O) | $SC_6H_5$ |
| 936 | S—$(CH_2CH_2CH_2)$—S | | H | H(l = O) | $SC_6H_5$ |
| 937 | —$(CH_2)_4$— | | H | H(l = O) | $SC_6H_5$ |
| 938 | —$(CH_2)_5$— | | H | H(l = O) | $SC_6H_5$ |
| 939 | H | H | $NO_2$ | H(l = O) | $SC_6H_5$ |
| 940 | $CH_3$ | $CH_3$ | $NO_2$ | H(l = O) | $SC_6H_5$ |
| 941 | $CH_2CH_3$ | $CH_2CH_3$ | $NO_2$ | H(l = O) | $SC_6H_5$ |
| 942 | $CH_2CH_2CH_3$ | $CH_2CH_2CH_3$ | $NO_2$ | H(l = O) | $SC_6H_5$ |
| 943 | $OCH_3$ | $OCH_3$ | $NO_2$ | H(l = O) | $SC_6H_5$ |
| 944 | $OCH_2CH_3$ | $OCH_2CH_3$ | $NO_2$ | H(l = O) | $SC_6H_5$ |
| 945 | $OCH_2CH_2CH_3$ | $OCH_2CH_2CH_3$ | $NO_2$ | H(l = O) | $SC_6H_5$ |
| 946 | $SCH_3$ | $SCH_3$ | $NO_2$ | H(l = O) | $SC_6H_5$ |
| 947 | $SCH_2CH_3$ | $SCH_2CH_3$ | $NO_2$ | H(l = O) | $SC_6H_5$ |
| 948 | $N(CH_3)_2$ | $N(CH_3)_2$ | $NO_2$ | H(l = O) | $SC_6H_5$ |
| 949 | $N(CH_2CH_3)_2$ | $N(CH_2CH_3)_2$ | $NO_2$ | H(l = O) | $SC_6H_5$ |
| 950 | $N(CH_3)(CH_2CH_3)$ | $N(CH_3)(CH_2CH_3)$ | $NO_2$ | H(l = O) | $SC_6H_5$ |
| 951 | O—$(CH_2CH_2)$—O | | $NO_2$ | H(l = O) | $SC_6H_5$ |
| 952 | O—$(CH_2CH_2CH_2)$—O | | $NO_2$ | H(l = O) | $SC_6H_5$ |
| 953 | S—$(CH_2CH_2)$—S | | $NO_2$ | H(l = O) | $SC_6H_5$ |
| 954 | S—$(CH_2CH_2CH_2)$—S | | $NO_2$ | H(l = O) | $SC_6H_5$ |
| 955 | —$(CH_2)_4$— | | $NO_2$ | H(l = O) | $SC_6H_5$ |
| 956 | —$(CH_2)_5$— | | $NO_2$ | H(l = O) | $SC_6H_5$ |
| 957 | H | H | CN | H(l = O) | $SC_6H_5$ |
| 958 | $CH_3$ | $CH_3$ | CN | H(l = O) | $SC_6H_5$ |
| 959 | $CH_2CH_3$ | $CH_2CH_3$ | CN | H(l = O) | $SC_6H_5$ |
| 960 | $CH_2CH_2CH_3$ | $CH_2CH_2CH_3$ | CN | H(l = O) | $SC_6H_5$ |
| 961 | $OCH_3$ | $OCH_3$ | CN | H(l = O) | $SC_6H_5$ |
| 962 | $OCH_2CH_3$ | $OCH_2CH_3$ | CN | H(l = O) | $SC_6H_5$ |
| 963 | $OCH_2CH_2CH_3$ | $OCH_2CH_2CH_3$ | CN | H(l = O) | $SC_6H_5$ |
| 964 | $SCH_3$ | $SCH_3$ | CN | H(l = O) | $SC_6H_5$ |
| 965 | $SCH_2CH_3$ | $SCH_2CH_3$ | CN | H(l = O) | $SC_6H_5$ |
| 966 | $N(CH_3)_2$ | $N(CH_3)_2$ | CN | H(l = O) | $SC_6H_5$ |
| 967 | $N(CH_2CH_3)_2$ | $N(CH_2CH_3)_2$ | CN | H(l = O) | $SC_6H_5$ |
| 968 | $N(CH_3)(CH_2CH_3)$ | $N(CH_3)(CH_2CH_3)$ | CN | H(l = O) | $SC_6H_5$ |
| 969 | O—$(CH_2CH_2)$—O | | CN | H(l = O) | $SC_6H_5$ |
| 970 | O—$(CH_2CH_2CH_2)$—O | | CN | H(l = O) | $SC_6H_5$ |
| 971 | S—$(CH_2CH_2)$—S | | CN | H(l = O) | $SC_6H_5$ |
| 972 | S—$(CH_2CH_2CH_2)$—S | | CN | H(l = O) | $SC_6H_5$ |
| 973 | —$(CH_2)_4$— | | CN | H(l = O) | $SC_6H_5$ |
| 974 | —$(CH_2)_5$— | | CN | H(l = O) | $SC_6H_5$ |
| 975 | H | H | F | H(l = O) | $SC_6H_5$ |
| 976 | $CH_3$ | $CH_3$ | F | H(l = O) | $SC_6H_5$ |
| 977 | $CH_2CH_3$ | $CH_2CH_3$ | F | H(l = O) | $SC_6H_5$ |
| 978 | $CH_2CH_2CH_3$ | $CH_2CH_2CH_3$ | F | H(l = O) | $SC_6H_5$ |
| 979 | $OCH_3$ | $OCH_3$ | F | H(l = O) | $SC_6H_5$ |

TABLE 1-continued

I1a1

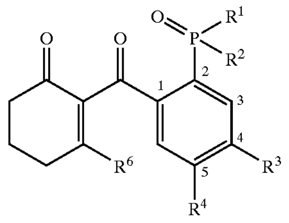

| n | $R^1$ | $R^2$ | $R^3$ | $R^4$ | $R^6$ |
|---|---|---|---|---|---|
| 980 | $OCH_2CH_3$ | $OCH_2CH_3$ | F | H(l = O) | $SC_6H_5$ |
| 981 | $OCH_2CH_2CH_3$ | $OCH_2CH_2CH_3$ | F | H(l = O) | $SC_6H_5$ |
| 982 | $SCH_3$ | $SCH_3$ | F | H(l = O) | $SC_6H_5$ |
| 983 | $SCH_2CH_3$ | $SCH_2CH_3$ | F | H(l = O) | $SC_6H_5$ |
| 984 | $N(CH_3)_2$ | $N(CH_3)_2$ | F | H(l = O) | $SC_6H_5$ |
| 985 | $N(CH_2CH_3)_2$ | $N(CH_2CH_3)_2$ | F | H(l = O) | $SC_6H_5$ |
| 986 | $N(CH_3)(CH_2CH_3)$ | $N(CH_3)(CH_2CH_3)$ | F | H(l = O) | $SC_6H_5$ |
| 987 | $O—(CH_2CH_2)—O$ | | F | H(l = O) | $SC_6H_5$ |
| 988 | $O—(CH_2CH_2CH_2)—O$ | | F | H(l = O) | $SC_6H_5$ |
| 989 | $S—(CH_2CH_2)—S$ | | F | H(l = O) | $SC_6H_5$ |
| 990 | $S—(CH_2CH_2CH_2)—S$ | | F | H(l = O) | $SC_6H_5$ |
| 991 | $—(CH_2)_4—$ | | F | H(l = O) | $SC_6H_5$ |
| 992 | $—(CH_2)_5—$ | | F | H(l = O) | $SC_6H_5$ |
| 993 | H | H | Cl | H(l = O) | $SC_6H_5$ |
| 994 | $CH_3$ | $CH_3$ | Cl | H(l = O) | $SC_6H_5$ |
| 995 | $CH_2CH_3$ | $CH_2CH_3$ | Cl | H(l = O) | $SC_6H_5$ |
| 996 | $CH_2CH_2CH_3$ | $CH_2CH_2CH_3$ | Cl | H(l = O) | $SC_6H_5$ |
| 997 | $OCH_3$ | $OCH_3$ | Cl | H(l = O) | $SC_6H_5$ |
| 998 | $OCH_2CH_3$ | $OCH_2CH_3$ | Cl | H(l = O) | $SC_6H_5$ |
| 999 | $OCH_2CH_2CH_3$ | $OCH_2CH_2CH_3$ | Cl | H(l = O) | $SC_6H_5$ |
| 1000 | $SCH_3$ | $SCH_3$ | Cl | H(l = O) | $SC_6H_5$ |
| 1001 | $SCH_2CH_3$ | $SCH_2CH_3$ | Cl | H(l = O) | $SC_6H_5$ |
| 1002 | $N(CH_3)_2$ | $N(CH_3)_2$ | Cl | H(l = O) | $SC_6H_5$ |
| 1003 | $N(CH_2CH_3)_2$ | $N(CH_2CH_3)_2$ | Cl | H(l = O) | $SC_6H_5$ |
| 1004 | $N(CH_3)(CH_2CH_3)$ | $N(CH_3)(CH_2CH_3)$ | Cl | H(l = O) | $SC_6H_5$ |
| 1005 | $O—(CH_2CH_2)—O$ | | Cl | H(l = O) | $SC_6H_5$ |
| 1006 | $O—(CH_2CH_2CH_2)—O$ | | Cl | H(l = O) | $SC_6H_5$ |
| 1007 | $S—(CH_2CH_2)—S$ | | Cl | H(l = O) | $SC_6H_5$ |
| 1008 | $S—(CH_2CH_2CH_2)—S$ | | Cl | H(l = O) | $SC_6H_5$ |
| 1009 | $—(CH_2)_4—$ | | Cl | H(l = O) | $SC_6H_5$ |
| 1010 | $—(CH_2)_5—$ | | Cl | H(l = O) | $SC_6H_5$ |
| 1011 | H | H | Br | H(l = O) | $SC_6H_5$ |
| 1012 | $CH_3$ | $CH_3$ | Br | H(l = O) | $SC_6H_5$ |
| 1013 | $CH_2CH_3$ | $CH_2CH_3$ | Br | H(l = O) | $SC_6H_5$ |
| 1014 | $CH_2CH_2CH_3$ | $CH_2CH_2CH_3$ | Br | H(l = O) | $SC_6H_5$ |
| 1015 | $OCH_3$ | $OCH_3$ | Br | H(l = O) | $SC_6H_5$ |
| 1016 | $OCH_2CH_3$ | $OCH_2CH_3$ | Br | H(l = O) | $SC_6H_5$ |
| 1017 | $OCH_2CH_2CH_3$ | $OCH_2CH_2CH_3$ | Br | H(l = O) | $SC_6H_5$ |
| 1018 | $SCH_3$ | $SCH_3$ | Br | H(l = O) | $SC_6H_5$ |
| 1019 | $SCH_2CH_3$ | $SCH_2CH_3$ | Br | H(l = O) | $SC_6H_5$ |
| 1020 | $N(CH_3)_2$ | $N(CH_3)_2$ | Br | H(l = O) | $SC_6H_5$ |
| 1021 | $N(CH_2CH_3)_2$ | $N(CH_2CH_3)_2$ | Br | H(l = O) | $SC_6H_5$ |
| 1022 | $N(CH_3)(CH_2CH_3)$ | $N(CH_3)(CH_2CH_3)$ | Br | H(l = O) | $SC_6H_5$ |
| 1023 | $O—(CH_2CH_2)—O$ | | Br | H(l = O) | $SC_6H_5$ |
| 1024 | $O—(CH_2CH_2CH_2)—O$ | | Br | H(l = O) | $SC_6H_5$ |
| 1025 | $S—(CH_2CH_2)—S$ | | Br | H(l = O) | $SC_6H_5$ |
| 1026 | $S—(CH_2CH_2CH_2)—S$ | | Br | H(l = O) | $SC_6H_5$ |
| 1027 | $—(CH_2)_4—$ | | Br | H(l = O) | $SC_6H_5$ |
| 1028 | $—(CH_2)_5—$ | | Br | H(l = O) | $SC_6H_5$ |
| 1029 | H | H | $CH_3$ | H(l = O) | $SC_6H_5$ |
| 1030 | $CH_3$ | $CH_3$ | $CH_3$ | H(l = O) | $SC_6H_5$ |
| 1031 | $CH_2CH_3$ | $CH_2CH_3$ | $CH_3$ | H(l = O) | $SC_6H_5$ |
| 1032 | $CH_2CH_2CH_3$ | $CH_2CH_2CH_3$ | $CH_3$ | H(l = O) | $SC_6H_5$ |
| 1033 | $OCH_3$ | $OCH_3$ | $CH_3$ | H(l = O) | $SC_6H_5$ |
| 1034 | $OCH_2CH_3$ | $OCH_2CH_3$ | $CH_3$ | H(l = O) | $SC_6H_5$ |
| 1035 | $OCH_2CH_2CH_3$ | $OCH_2CH_2CH_3$ | $CH_3$ | H(l = O) | $SC_6H_5$ |
| 1036 | $SCH_3$ | $SCH_3$ | $CH_3$ | H(l = O) | $SC_6H_5$ |
| 1037 | $SCH_2CH_3$ | $SCH_2CH_3$ | $CH_3$ | H(l = O) | $SC_6H_5$ |
| 1038 | $N(CH_3)_2$ | $N(CH_3)_2$ | $CH_3$ | H(l = O) | $SC_6H_5$ |
| 1039 | $N(CH_2CH_3)_2$ | $N(CH_2CH_3)_2$ | $CH_3$ | H(l = O) | $SC_6H_5$ |
| 1040 | $N(CH_3)(CH_2CH_3)$ | $N(CH_3)(CH_2CH_3)$ | $CH_3$ | H(l = O) | $SC_6H_5$ |
| 1041 | $O—(CH_2CH_2)—O$ | | $CH_3$ | H(l = O) | $SC_6H_5$ |
| 1042 | $O—(CH_2CH_2CH_2)—O$ | | $CH_3$ | H(l = O) | $SC_6H_5$ |
| 1043 | $S—(CH_2CH_2)—S$ | | $CH_3$ | H(l = O) | $SC_6H_5$ |

TABLE 1-continued

I1a1

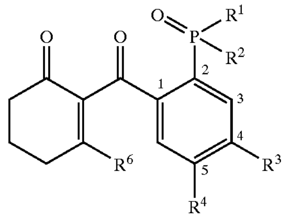

| n | $R^1$ | $R^2$ | $R^3$ | $R^4$ | $R^6$ |
|---|---|---|---|---|---|
| 1044 | S—($CH_2CH_2CH_2$)—S | | $CH_3$ | H(l = O) | $SC_6H_5$ |
| 1045 | —$(CH_2)_4$— | | $CH_3$ | H(l = O) | $SC_6H_5$ |
| 1046 | —$(CH_2)_5$— | | $CH_3$ | H(l = O) | $SC_6H_5$ |
| 1047 | H | H | $CH_2CH_3$ | H(l = O) | $SC_6H_5$ |
| 1048 | $CH_3$ | $CH_3$ | $CH_2CH_3$ | H(l = O) | $SC_6H_5$ |
| 1049 | $CH_2CH_3$ | $CH_2CH_3$ | $CH_2CH_3$ | H(l = O) | $SC_6H_5$ |
| 1050 | $CH_2CH_2CH_3$ | $CH_2CH_2CH_3$ | $CH_2CH_3$ | H(l = O) | $SC_6H_5$ |
| 1051 | $OCH_3$ | $OCH_3$ | $CH_2CH_3$ | H(l = O) | $SC_6H_5$ |
| 1052 | $OCH_2CH_3$ | $OCH_2CH_3$ | $CH_2CH_3$ | H(l = O) | $SC_6H_5$ |
| 1053 | $OCH_2CH_2CH_3$ | $OCH_2CH_2CH_3$ | $CH_2CH_3$ | H(l = O) | $SC_6H_5$ |
| 1054 | $SCH_3$ | $SCH_3$ | $CH_2CH_3$ | H(l = O) | $SC_6H_5$ |
| 1055 | $SCH_2CH_3$ | $SCH_2CH_3$ | $CH_2CH_3$ | H(l = O) | $SC_6H_5$ |
| 1056 | $N(CH_3)_2$ | $N(CH_3)_2$ | $CH_2CH_3$ | H(l = O) | $SC_6H_5$ |
| 1057 | $N(CH_2CH_3)_2$ | $N(CH_2CH_3)_2$ | $CH_2CH_3$ | H(l = O) | $SC_6H_5$ |
| 1058 | $N(CH_3)(CH_2CH_3)$ | $N(CH_3)(CH_2CH_3)$ | $CH_2CH_3$ | H(l = O) | $SC_6H_5$ |
| 1059 | O—($CH_2CH_2$)—O | | $CH_2CH_3$ | H(l = O) | $SC_6H_5$ |
| 1060 | O—($CH_2CH_2CH_2$)—O | | $CH_2CH_3$ | H(l = O) | $SC_6H_5$ |
| 1061 | S—($CH_2CH_2$)—S | | $CH_2CH_3$ | H(l = O) | $SC_6H_5$ |
| 1062 | S—($CH_2CH_2CH_2$)—S | | $CH_2CH_3$ | H(l = O) | $SC_6H_5$ |
| 1063 | —$(CH_2)_4$— | | $CH_2CH_3$ | H(l = O) | $SC_6H_5$ |
| 1064 | —$(CH_2)_5$— | | $CH_2CH_3$ | H(l = O) | $SC_6H_5$ |
| 1065 | H | H | $CF_3$ | H(l = O) | $SC_6H_5$ |
| 1066 | $CH_3$ | $CH_3$ | $CF_3$ | H(l = O) | $SC_6H_5$ |
| 1067 | $CH_2CH_3$ | $CH_2CH_3$ | $CF_3$ | H(l = O) | $SC_6H_5$ |
| 1068 | $CH_2CH_2CH_3$ | $CH_2CH_2CH_3$ | $CF_3$ | H(l = O) | $SC_6H_5$ |
| 1069 | $OCH_3$ | $OCH_3$ | $CF_3$ | H(l = O) | $SC_6H_5$ |
| 1070 | $OCH_2CH_3$ | $OCH_2CH_3$ | $CF_3$ | H(l = O) | $SC_6H_5$ |
| 1071 | $OCH_2CH_2CH_3$ | $OCH_2CH_2CH_3$ | $CF_3$ | H(l = O) | $SC_6H_5$ |
| 1072 | $SCH_3$ | $SCH_3$ | $CF_3$ | H(l = O) | $SC_6H_5$ |
| 1073 | $SCH_2CH_3$ | $SCH_2CH_3$ | $CF_3$ | H(l = O) | $SC_6H_5$ |
| 1074 | $N(CH_3)_2$ | $N(CH_3)_2$ | $CF_3$ | H(l = O) | $SC_6H_5$ |
| 1075 | $N(CH_2CH_3)_2$ | $N(CH_2CH_3)_2$ | $CF_3$ | H(l = O) | $SC_6H_5$ |
| 1076 | $N(CH_3)(CH_2CH_3)$ | $N(CH_3)(CH_2CH_3)$ | $CF_3$ | H(l = O) | $SC_6H_5$ |
| 1077 | O—($CH_2CH_2$)—O | | $CF_3$ | H(l = O) | $SC_6H_5$ |
| 1078 | O—($CH_2CH_2CH_2$)—O | | $CF_3$ | H(l = O) | $SC_6H_5$ |
| 1079 | S—($CH_2CH_2$)—S | | $CF_3$ | H(l = O) | $SC_6H_5$ |
| 1080 | S—($CH_2CH_2CH_2$)—S | | $CF_3$ | H(l = O) | $SC_6H_5$ |
| 1081 | —$(CH_2)_4$— | | $CF_3$ | H(l = O) | $SC_6H_5$ |
| 1082 | —$(CH_2)_5$— | | $CF_3$ | H(l = O) | $SC_6H_5$ |
| 1083 | H | H | $OCH_3$ | H(l = O) | $SC_6H_5$ |
| 1084 | $CH_3$ | $CH_3$ | $OCH_3$ | H(l = O) | $SC_6H_5$ |
| 1085 | $CH_2CH_3$ | $CH_2CH_3$ | $OCH_3$ | H(l = O) | $SC_6H_5$ |
| 1086 | $CH_2CH_2CH_3$ | $CH_2CH_2CH_3$ | $OCH_3$ | H(l = O) | $SC_6H_5$ |
| 1087 | $OCH_3$ | $OCH_3$ | $OCH_3$ | H(l = O) | $SC_6H_5$ |
| 1088 | $OCH_2CH_3$ | $OCH_2CH_3$ | $OCH_3$ | H(l = O) | $SC_6H_5$ |
| 1089 | $OCH_2CH_2CH_3$ | $OCH_2CH_2CH_3$ | $OCH_3$ | H(l = O) | $SC_6H_5$ |
| 1090 | $SCH_3$ | $SCH_3$ | $OCH_3$ | H(l = O) | $SC_6H_5$ |
| 1091 | $SCH_2CH_3$ | $SCH_2CH_3$ | $OCH_3$ | H(l = O) | $SC_6H_5$ |
| 1092 | $N(CH_3)_2$ | $N(CH_3)_2$ | $OCH_3$ | H(l = O) | $SC_6H_5$ |
| 1093 | $N(CH_2CH_3)_2$ | $N(CH_2CH_3)_2$ | $OCH_3$ | H(l = O) | $SC_6H_5$ |
| 1094 | $N(CH_3)(CH_2CH_3)$ | $N(CH_3)(CH_2CH_3)$ | $OCH_3$ | H(l = O) | $SC_6H_5$ |
| 1095 | O—($CH_2CH_2$)—O | | $OCH_3$ | H(l = O) | $SC_6H_5$ |
| 1096 | O—($CH_2CH_2CH_2$)—O | | $OCH_3$ | H(l = O) | $SC_6H_5$ |
| 1097 | S—($CH_2CH_2$)—S | | $OCH_3$ | H(l = O) | $SC_6H_5$ |
| 1098 | S—($CH_2CH_2CH_2$)—S | | $OCH_3$ | H(l = O) | $SC_6H_5$ |
| 1099 | —$(CH_2)_4$— | | $OCH_3$ | H(l = O) | $SC_6H_5$ |
| 1100 | —$(CH_2)_5$— | | $OCH_3$ | H(l = O) | $SC_6H_5$ |
| 1101 | H | H | $OCH_2CH_3$ | H(l = O) | $SC_6H_5$ |
| 1102 | $CH_3$ | $CH_3$ | $OCH_2CH_3$ | H(l = O) | $SC_6H_5$ |
| 1103 | $CH_2CH_3$ | $CH_2CH_3$ | $OCH_2CH_3$ | H(l = O) | $SC_6H_5$ |
| 1104 | $CH_2CH_2CH_3$ | $CH_2CH_2CH_3$ | $OCH_2CH_3$ | H(l = O) | $SC_6H_5$ |
| 1105 | $OCH_3$ | $OCH_3$ | $OCH_2CH_3$ | H(l = O) | $SC_6H_5$ |
| 1106 | $OCH_2CH_3$ | $OCH_2CH_3$ | $OCH_2CH_3$ | H(l = O) | $SC_6H_5$ |
| 1107 | $OCH_2CH_2CH_3$ | $OCH_2CH_2CH_3$ | $OCH_2CH_3$ | H(l = O) | $SC_6H_5$ |

TABLE 1-continued

I1a1

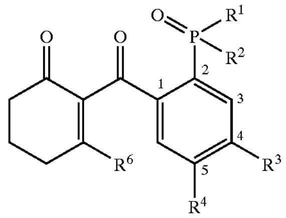

| n | $R^1$ | $R^2$ | $R^3$ | $R^4$ | $R^6$ |
|---|---|---|---|---|---|
| 1108 | $SCH_3$ | $SCH_3$ | $OCH_2CH_3$ | H(l = O) | $SC_6H_5$ |
| 1109 | $SCH_2CH_3$ | $SCH_2CH_3$ | $OCH_2CH_3$ | H(l = O) | $SC_6H_5$ |
| 1110 | $N(CH_3)_2$ | $N(CH_3)_2$ | $OCH_2CH_3$ | H(l = O) | $SC_6H_5$ |
| 1111 | $N(CH_2CH_3)_2$ | $N(CH_2CH_3)_2$ | $OCH_2CH_3$ | H(l = O) | $SC_6H_5$ |
| 1112 | $N(CH_3)(CH_2CH_3)$ | $N(CH_3)(CH_2CH_3)$ | $OCH_2CH_3$ | H(l = O) | $SC_6H_5$ |
| 1113 | O—$(CH_2CH_2)$—O | | $OCH_2CH_3$ | H(l = O) | $SC_6H_5$ |
| 1114 | O—$(CH_2CH_2CH_2)$—O | | $OCH_2CH_3$ | H(l = O) | $SC_6H_5$ |
| 1115 | S—$(CH_2CH_2)$—S | | $OCH_2CH_3$ | H(l = O) | $SC_6H_5$ |
| 1116 | S—$(CH_2CH_2CH_2)$—S | | $OCH_2CH_3$ | H(l = O) | $SC_6H_5$ |
| 1117 | —$(CH_2)_4$— | | $OCH_2CH_3$ | H(l = O) | $SC_6H_5$ |
| 1118 | —$(CH_2)_5$— | | $OCH_2CH_3$ | H(l = O) | $SC_6H_5$ |
| 1119 | H | H | $SCH_3$ | H(l = O) | $SC_6H_5$ |
| 1120 | $CH_3$ | $CH_3$ | $SCH_3$ | H(l = O) | $SC_6H_5$ |
| 1121 | $CH_2CH_3$ | $CH_2CH_3$ | $SCH_3$ | H(l = O) | $SC_6H_5$ |
| 1122 | $CH_2CH_2CH_3$ | $CH_2CH_2CH_3$ | $SCH_3$ | H(l = O) | $SC_6H_5$ |
| 1123 | $OCH_3$ | $OCH_3$ | $SCH_3$ | H(l = O) | $SC_6H_5$ |
| 1124 | $OCH_2CH_3$ | $OCH_2CH_3$ | $SCH_3$ | H(l = O) | $SC_6H_5$ |
| 1125 | $OCH_2CH_2CH_3$ | $OCH_2CH_2CH_3$ | $SCH_3$ | H(l = O) | $SC_6H_5$ |
| 1126 | $SCH_3$ | $SCH_3$ | $SCH_3$ | H(l = O) | $SC_6H_5$ |
| 1127 | $SCH_2CH_3$ | $SCH_2CH_3$ | $SCH_3$ | H(l = O) | $SC_6H_5$ |
| 1128 | $N(CH_3)_2$ | $N(CH_3)_2$ | $SCH_3$ | H(l = O) | $SC_6H_5$ |
| 1129 | $N(CH_2CH_3)_2$ | $N(CH_2CH_3)_2$ | $SCH_3$ | H(l = O) | $SC_6H_5$ |
| 1130 | $N(CH_3)(CH_2CH_3)$ | $N(CH_3)(CH_2CH_3)$ | $SCH_3$ | H(l = O) | $SC_6H_5$ |
| 1131 | O—$(CH_2CH_2)$—O | | $SCH_3$ | H(l = O) | $SC_6H_5$ |
| 1132 | O—$(CH_2CH_2CH_2)$—O | | $SCH_3$ | H(l = O) | $SC_6H_5$ |
| 1133 | S—$(CH_2CH_2)$—S | | $SCH_3$ | H(l = O) | $SC_6H_5$ |
| 1134 | S—$(CH_2CH_2CH_2)$—S | | $SCH_3$ | H(l = O) | $SC_6H_5$ |
| 1135 | —$(CH_2)_4$— | | $SCH_3$ | H(l = O) | $SC_6H_5$ |
| 1136 | —$(CH_2)_5$— | | $SCH_3$ | H(l = O) | $SC_6H_5$ |
| 1137 | H | H | $SO_2CH_3$ | H(l = O) | $SC_6H_5$ |
| 1138 | $CH_3$ | $CH_3$ | $SO_2CH_3$ | H(l = O) | $SC_6H_5$ |
| 1139 | $CH_2CH_3$ | $CH_2CH_3$ | $SO_2CH_3$ | H(l = O) | $SC_6H_5$ |
| 1140 | $CH_2CH_2CH_3$ | $CH_2CH_2CH_3$ | $SO_2CH_3$ | H(l = O) | $SC_6H_5$ |
| 1141 | $OCH_3$ | $OCH_3$ | $SO_2CH_3$ | H(l = O) | $SC_6H_5$ |
| 1142 | $OCH_2CH_3$ | $OCH_2CH_3$ | $SO_2CH_3$ | H(l = O) | $SC_6H_5$ |
| 1143 | $OCH_2CH_2CH_3$ | $OCH_2CH_2CH_3$ | $SO_2CH_3$ | H(l = O) | $SC_6H_5$ |
| 1144 | $SCH_3$ | $SCH_3$ | $SO_2CH_3$ | H(l = O) | $SC_6H_5$ |
| 1145 | $SCH_2CH_3$ | $SCH_2CH_3$ | $SO_2CH_3$ | H(l = O) | $SC_6H_5$ |
| 1146 | $N(CH_3)_2$ | $N(CH_3)_2$ | $SO_2CH_3$ | H(l = O) | $SC_6H_5$ |
| 1147 | $N(CH_2CH_3)_2$ | $N(CH_2CH_3)_2$ | $SO_2CH_3$ | H(l = O) | $SC_6H_5$ |
| 1148 | $N(CH_3)(CH_2CH_3)$ | $N(CH_3)(CH_2CH_3)$ | $SO_2CH_3$ | H(l = O) | $SC_6H_5$ |
| 1149 | O—$(CH_2CH_2)$—O | | $SO_2CH_3$ | H(l = O) | $SC_6H_5$ |
| 1150 | O—$(CH_2CH_2CH_2)$—O | | $SO_2CH_3$ | H(l = O) | $SC_6H_5$ |
| 1151 | S—$(CH_2CH_2)$—S | | $SO_2CH_3$ | H(l = O) | $SC_6H_5$ |
| 1152 | S—$(CH_2CH_2CH_2)$—S | | $SO_2CH_3$ | H(l = O) | $SC_6H_5$ |
| 1153 | —$(CH_2)_4$— | | $SO_2CH_3$ | H(l = O) | $SC_6H_5$ |
| 1154 | —$(CH_2)_5$— | | $SO_2CH_3$ | H(l = O) | $SC_6H_5$ |
| 1155 | H | H | $PO(OCH_3)_2$ | H(l = O) | $SC_6H_5$ |
| 1156 | $CH_3$ | $CH_3$ | $PO(OCH_3)_2$ | H(l = O) | $SC_6H_5$ |
| 1157 | $CH_2CH_3$ | $CH_2CH_3$ | $PO(OCH_3)_2$ | H(l = O) | $SC_6H_5$ |
| 1158 | $CH_2CH_2CH_3$ | $CH_2CH_2CH_3$ | $PO(OCH_3)_2$ | H(l = O) | $SC_6H_5$ |
| 1159 | $OCH_3$ | $OCH_3$ | $PO(OCH_3)_2$ | H(l = O) | $SC_6H_5$ |
| 1160 | $OCH_2CH_3$ | $OCH_2CH_3$ | $PO(OCH_3)_2$ | H(l = O) | $SC_6H_5$ |
| 1161 | $OCH_2CH_2CH_3$ | $OCH_2CH_2CH_3$ | $PO(OCH_3)_2$ | H(l = O) | $SC_6H_5$ |
| 1162 | $SCH_3$ | $SCH_3$ | $PO(OCH_3)_2$ | H(l = O) | $SC_6H_5$ |
| 1163 | $SCH_2CH_3$ | $SCH_2CH_3$ | $PO(OCH_3)_2$ | H(l = O) | $SC_6H_5$ |
| 1164 | $N(CH_3)_2$ | $N(CH_3)_2$ | $PO(OCH_3)_2$ | H(l = O) | $SC_6H_5$ |
| 1165 | $N(CH_2CH_3)_2$ | $N(CH_2CH_3)_2$ | $PO(OCH_3)_2$ | H(l = O) | $SC_6H_5$ |
| 1166 | $N(CH_3)(CH_2CH_3)$ | $N(CH_3)(CH_2CH_3)$ | $PO(OCH_3)_2$ | H(l = O) | $SC_6H_5$ |
| 1167 | O—$(CH_2CH_2)$—O | | $PO(OCH_3)_2$ | H(l = O) | $SC_6H_5$ |
| 1168 | O—$(CH_2CH_2CH_2)$—O | | $PO(OCH_3)_2$ | H(l = O) | $SC_6H_5$ |
| 1169 | S—$(CH_2CH_2)$—S | | $PO(OCH_3)_2$ | H(l = O) | $SC_6H_5$ |
| 1170 | S—$(CH_2CH_2CH_2)$—S | | $PO(OCH_3)_2$ | H(l = O) | $SC_6H_5$ |
| 1171 | —$(CH_2)_4$— | | $PO(OCH_3)_2$ | H(l = O) | $SC_6H_5$ |

TABLE 1-continued

I1a1

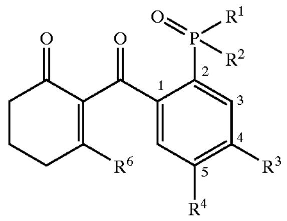

| n | $R^1$ | $R^2$ | $R^3$ | $R^4$ | $R^6$ |
|---|---|---|---|---|---|
| 1172 | $-(CH_2)_5-$ | | $PO(OCH_3)_2$ | H(l = O) | $SC_6H_5$ |
| 1173 | H | H | $PO(OCH_2CH_3)_2$ | H(l = O) | $SC_6H_5$ |
| 1174 | $CH_3$ | $CH_3$ | $PO(OCH_2CH_3)_2$ | H(l = O) | $SC_6H_5$ |
| 1175 | $CH_2CH_3$ | $CH_2CH_3$ | $PO(OCH_2CH_3)_2$ | H(l = O) | $SC_6H_5$ |
| 1176 | $CH_2CH_2CH_3$ | $CH_2CH_2CH_3$ | $PO(OCH_2CH_3)_2$ | H(l = O) | $SC_6H_5$ |
| 1177 | $OCH_3$ | $OCH_3$ | $PO(OCH_2CH_3)_2$ | H(l = O) | $SC_6H_5$ |
| 1178 | $OCH_2CH_3$ | $OCH_2CH_3$ | $PO(OCH_2CH_3)_2$ | H(l = O) | $SC_6H_5$ |
| 1179 | $OCH_2CH_2CH_3$ | $OCH_2CH_2CH_3$ | $PO(OCH_2CH_3)_2$ | H(l = O) | $SC_6H_5$ |
| 1180 | $SCH_3$ | $SCH_3$ | $PO(OCH_2CH_3)_2$ | H(l = O) | $SC_6H_5$ |
| 1181 | $SCH_2CH_3$ | $SCH_2CH_3$ | $PO(OCH_2CH_3)_2$ | H(l = O) | $SC_6H_5$ |
| 1182 | $N(CH_3)_2$ | $N(CH_3)_2$ | $PO(OCH_2CH_3)_2$ | H(l = O) | $SC_6H_5$ |
| 1183 | $N(CH_2CH_3)_2$ | $N(CH_2CH_3)_2$ | $PO(OCH_2CH_3)_2$ | H(l = O) | $SC_6H_5$ |
| 1184 | $N(CH_3)(CH_2CH_3)$ | $N(CH_3)(CH_2CH_3)$ | $PO(OCH_2CH_3)_2$ | H(l = O) | $SC_6H_5$ |
| 1185 | $O-(CH_2CH_2)-O$ | | $PO(OCH_2CH_3)_2$ | H(l = O) | $SC_6H_5$ |
| 1186 | $O-(CH_2CH_2CH_2)-O$ | | $PO(OCH_2CH_3)_2$ | H(l = O) | $SC_6H_5$ |
| 1187 | $S-(CH_2CH_2)-S$ | | $PO(OCH_2CH_3)_2$ | H(l = O) | $SC_6H_5$ |
| 1188 | $S-(CH_2CH_2CH_2)-S$ | | $PO(OCH_2CH_3)_2$ | H(l = O) | $SC_6H_5$ |
| 1189 | $-(CH_2)_4-$ | | $PO(OCH_2CH_3)_2$ | H(l = O) | $SC_6H_5$ |
| 1190 | $-(CH_2)_5-$ | | $PO(OCH_2CH_3)_2$ | H(l = O) | $SC_6H_5$ |
| 1191 | H | H | $PO(CH_3)_2$ | H(l = O) | $SC_6H_5$ |
| 1192 | $CH_3$ | $CH_3$ | $PO(CH_3)_2$ | H(l = O) | $SC_6H_5$ |
| 1193 | $CH_2CH_3$ | $CH_2CH_3$ | $PO(CH_3)_2$ | H(l = O) | $SC_6H_5$ |
| 1194 | $CH_2CH_2CH_3$ | $CH_2CH_2CH_3$ | $PO(CH_3)_2$ | H(l = O) | $SC_6H_5$ |
| 1195 | $OCH_3$ | $OCH_3$ | $PO(CH_3)_2$ | H(l = O) | $SC_6H_5$ |
| 1196 | $OCH_2CH_3$ | $OCH_2CH_3$ | $PO(CH_3)_2$ | H(l = O) | $SC_6H_5$ |
| 1197 | $OCH_2CH_2CH_3$ | $OCH_2CH_2CH_3$ | $PO(CH_3)_2$ | H(l = O) | $SC_6H_5$ |
| 1198 | $SCH_3$ | $SCH_3$ | $PO(CH_3)_2$ | H(l = O) | $SC_6H_5$ |
| 1199 | $SCH_2CH_3$ | $SCH_2CH_3$ | $PO(CH_3)_2$ | H(l = O) | $SC_6H_5$ |
| 1200 | $N(CH_3)_2$ | $N(CH_3)_2$ | $PO(CH_3)_2$ | H(l = O) | $SC_6H_5$ |
| 1201 | $N(CH_2CH_3)_2$ | $N(CH_2CH_3)_2$ | $PO(CH_3)_2$ | H(l = O) | $SC_6H_5$ |
| 1202 | $N(CH_3)(CH_2CH_3)$ | $N(CH_3)(CH_2CH_3)$ | $PO(CH_3)_2$ | H(l = O) | $SC_6H_5$ |
| 1203 | $O-(CH_2CH_2)-O$ | | $PO(CH_3)_2$ | H(l = O) | $SC_6H_5$ |
| 1204 | $O-(CH_2CH_2CH_2)-O$ | | $PO(CH_3)_2$ | H(l = O) | $SC_6H_5$ |
| 1205 | $S-(CH_2CH_2)-S$ | | $PO(CH_3)_2$ | H(l = O) | $SC_6H_5$ |
| 1206 | $S-(CH_2CH_2CH_2)-S$ | | $PO(CH_3)_2$ | H(l = O) | $SC_6H_5$ |
| 1207 | $-(CH_2)_4-$ | | $PO(CH_3)_2$ | H(l = O) | $SC_6H_5$ |
| 1208 | $-(CH_2)_5-$ | | $PO(CH_3)_2$ | H(l = O) | $SC_6H_5$ |
| 1209 | H | H | $PO(CH_2CH_3)_2$ | H(l = O) | $SC_6H_5$ |
| 1210 | $CH_3$ | $CH_3$ | $PO(CH_2CH_3)_2$ | H(l = O) | $SC_6H_5$ |
| 1211 | $CH_2CH_3$ | $CH_2CH_3$ | $PO(CH_2CH_3)_2$ | H(l = O) | $SC_6H_5$ |
| 1212 | $CH_2CH_2CH_3$ | $CH_2CH_2CH_3$ | $PO(CH_2CH_3)_2$ | H(l = O) | $SC_6H_5$ |
| 1213 | $OCH_3$ | $OCH_3$ | $PO(CH_2CH_3)_2$ | H(l = O) | $SC_6H_5$ |
| 1214 | $OCH_2CH_3$ | $OCH_2CH_3$ | $PO(CH_2CH_3)_2$ | H(l = O) | $SC_6H_5$ |
| 1215 | $OCH_2CH_2CH_3$ | $OCH_2CH_2CH_3$ | $PO(CH_2CH_3)_2$ | H(l = O) | $SC_6H_5$ |
| 1216 | $SCH_3$ | $SCH_3$ | $PO(CH_2CH_3)_2$ | H(l = O) | $SC_6H_5$ |
| 1217 | $SCH_2CH_3$ | $SCH_2CH_3$ | $PO(CH_2CH_3)_2$ | H(l = O) | $SC_6H_5$ |
| 1218 | $N(CH_3)_2$ | $N(CH_3)_2$ | $PO(CH_2CH_3)_2$ | H(l = O) | $SC_6H_5$ |
| 1219 | $N(CH_2CH_3)_2$ | $N(CH_2CH_3)_2$ | $PO(CH_2CH_3)_2$ | H(l = O) | $SC_6H_5$ |
| 1220 | $N(CH_3)(CH_2CH_3)$ | $N(CH_3)(CH_2CH_3)$ | $PO(CH_2CH_3)_2$ | H(l = O) | $SC_6H_5$ |
| 1221 | $O-(CH_2CH_2)-O$ | | $PO(CH_2CH_3)_2$ | H(l = O) | $SC_6H_5$ |
| 1222 | $O-(CH_2CH_2CH_2)-O$ | | $PO(CH_2CH_3)_2$ | H(l = O) | $SC_6H_5$ |
| 1223 | $S-(CH_2CH_2)-S$ | | $PO(CH_2CH_3)_2$ | H(l = O) | $SC_6H_5$ |
| 1224 | $S-(CH_2CH_2CH_2)-S$ | | $PO(CH_2CH_3)_2$ | H(l = O) | $SC_6H_5$ |
| 1225 | $-(CH_2)_4-$ | | $PO(CH_2CH_3)_2$ | H(l = O) | $SC_6H_5$ |
| 1226 | $-(CH_2)_5-$ | | $PO(CH_2CH_3)_2$ | H(l = O) | $SC_6H_5$ |
| 1227 | H | H | H | H(l = O) | Het1 |
| 1228 | $CH_3$ | $CH_3$ | H | H(l = O) | Het1 |
| 1229 | $CH_2CH_3$ | $CH_2CH_3$ | H | H(l = O) | Het1 |
| 1230 | $CH_2CH_2CH_3$ | $CH_2CH_2CH_3$ | H | H(l = O) | Het1 |
| 1231 | $OCH_3$ | $OCH_3$ | H | H(l = O) | Het1 |
| 1232 | $OCH_2CH_3$ | $OCH_2CH_3$ | H | H(l = O) | Het1 |
| 1233 | $OCH_2CH_2CH_3$ | $OCH_2CH_2CH_3$ | H | H(l = O) | Het1 |
| 1234 | $SCH_3$ | $SCH_3$ | H | H(l = O) | Het1 |
| 1235 | $SCH_2CH_3$ | $SCH_2CH_3$ | H | H(l = O) | Het1 |

TABLE 1-continued

I1a1

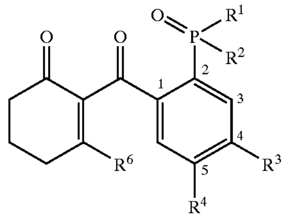

| n | $R^1$ | $R^2$ | $R^3$ | $R^4$ | $R^6$ |
|---|---|---|---|---|---|
| 1236 | $N(CH_3)_2$ | $N(CH_3)_2$ | H | H(l = O) | Het1 |
| 1237 | $N(CH_2CH_3)_2$ | $N(CH_2CH_3)_2$ | H | H(l = O) | Het1 |
| 1238 | $N(CH_3)(CH_2CH_3)$ | $N(CH_3)(CH_2CH_3)$ | H | H(l = O) | Het1 |
| 1239 | $O—(CH_2CH_2)—O$ | | H | H(l = O) | Het1 |
| 1240 | $O—(CH_2CH_2CH_2)—O$ | | H | H(l = O) | Het1 |
| 1241 | $S—(CH_2CH_2)—S$ | | H | H(l = O) | Het1 |
| 1242 | $S—(CH_2CH_2CH_2)—S$ | | H | H(l = O) | Het1 |
| 1243 | $—(CH_2)_4—$ | | H | H(l = O) | Het1 |
| 1244 | $—(CH_2)_5—$ | | H | H(l = O) | Het1 |
| 1245 | H | H | $NO_2$ | H(l = O) | Het1 |
| 1246 | $CH_3$ | $CH_3$ | $NO_2$ | H(l = O) | Het1 |
| 1247 | $CH_2CH_3$ | $CH_2CH_3$ | $NO_2$ | H(l = O) | Het1 |
| 1248 | $CH_2CH_2CH_3$ | $CH_2CH_2CH_3$ | $NO_2$ | H(l = O) | Het1 |
| 1249 | $OCH_3$ | $OCH_3$ | $NO_2$ | H(l = O) | Het1 |
| 1250 | $OCH_2CH_3$ | $OCH_2CH_3$ | $NO_2$ | H(l = O) | Het1 |
| 1251 | $OCH_2CH_2CH_3$ | $OCH_2CH_2CH_3$ | $NO_2$ | H(l = O) | Het1 |
| 1252 | $SCH_3$ | $SCH_3$ | $NO_2$ | H(l = O) | Het1 |
| 1253 | $SCH_2CH_3$ | $SCH_2CH_3$ | $NO_2$ | H(l = O) | Het1 |
| 1254 | $N(CH_3)_2$ | $N(CH_3)_2$ | $NO_2$ | H(l = O) | Het1 |
| 1255 | $N(CH_2CH_3)_2$ | $N(CH_2CH_3)_2$ | $NO_2$ | H(l = O) | Het1 |
| 1256 | $N(CH_3)(CH_2CH_3)$ | $N(CH_3)(CH_2CH_3)$ | $NO_2$ | H(l = O) | Het1 |
| 1257 | $O—(CH_2CH_2)—O$ | | $NO_2$ | H(l = O) | Het1 |
| 1258 | $O—(CH_2CH_2CH_2)—O$ | | $NO_2$ | H(l = O) | Het1 |
| 1259 | $S—(CH_2CH_2)—S$ | | $NO_2$ | H(l = O) | Het1 |
| 1260 | $S—(CH_2CH_2CH_2)—S$ | | $NO_2$ | H(l = O) | Het1 |
| 1261 | $—(CH_2)_4—$ | | $NO_2$ | H(l = O) | Het1 |
| 1262 | $—(CH_2)_5—$ | | $NO_2$ | H(l = O) | Het1 |
| 1263 | H | H | CN | H(l = O) | Het1 |
| 1264 | $CH_3$ | $CH_3$ | CN | H(l = O) | Het1 |
| 1265 | $CH_2CH_3$ | $CH_2CH_3$ | CN | H(l = O) | Het1 |
| 1266 | $CH_2CH_2CH_3$ | $CH_2CH_2CH_3$ | CN | H(l = O) | Het1 |
| 1267 | $OCH_3$ | $OCH_3$ | CN | H(l = O) | Het1 |
| 1268 | $OCH_2CH_3$ | $OCH_2CH_3$ | CN | H(l = O) | Het1 |
| 1269 | $OCH_2CH_2CH_3$ | $OCH_2CH_2CH_3$ | CN | H(l = O) | Het1 |
| 1270 | $SCH_3$ | $SCH_3$ | CN | H(l = O) | Het1 |
| 1271 | $SCH_2CH_3$ | $SCH_2CH_3$ | CN | H(l = O) | Het1 |
| 1272 | $N(CH_3)_2$ | $N(CH_3)_2$ | CN | H(l = O) | Het1 |
| 1273 | $N(CH_2CH_3)_2$ | $N(CH_2CH_3)_2$ | CN | H(l = O) | Het1 |
| 1274 | $N(CH_3)(CH_2CH_3)$ | $N(CH_3)(CH_2CH_3)$ | CN | H(l = O) | Het1 |
| 1275 | $O—(CH_2CH_2)—O$ | | CN | H(l = O) | Het1 |
| 1276 | $O—(CH_2CH_2CH_2)—O$ | | CN | H(l = O) | Het1 |
| 1277 | $S—(CH_2CH_2)—S$ | | CN | H(l = O) | Het1 |
| 1278 | $S—(CH_2CH_2CH_2)—S$ | | CN | H(l = O) | Het1 |
| 1279 | $—(CH_2)_4—$ | | CN | H(l = O) | Het1 |
| 1280 | $—(CH_2)_5—$ | | CN | H(l = O) | Het1 |
| 1281 | H | H | F | H(l = O) | Het1 |
| 1282 | $CH_3$ | $CH_3$ | F | H(l = O) | Het1 |
| 1283 | $CH_2CH_3$ | $CH_2CH_3$ | F | H(l = O) | Het1 |
| 1284 | $CH_2CH_2CH_3$ | $CH_2CH_2CH_3$ | F | H(l = O) | Het1 |
| 1285 | $OCH_3$ | $OCH_3$ | F | H(l = O) | Het1 |
| 1286 | $OCH_2CH_3$ | $OCH_2CH_3$ | F | H(l = O) | Het1 |
| 1287 | $OCH_2CH_2CH_3$ | $OCH_2CH_2CH_3$ | F | H(l = O) | Het1 |
| 1288 | $SCH_3$ | $SCH_3$ | F | H(l = O) | Het1 |
| 1289 | $SCH_2CH_3$ | $SCH_2CH_3$ | F | H(l = O) | Het1 |
| 1290 | $N(CH_3)_2$ | $N(CH_3)_2$ | F | H(l = O) | Het1 |
| 1291 | $N(CH_2CH_3)_2$ | $N(CH_2CH_3)_2$ | F | H(l = O) | Het1 |
| 1292 | $N(CH_3)(CH_2CH_3)$ | $N(CH_3)(CH_2CH_3)$ | F | H(l = O) | Het1 |
| 1293 | $O—(CH_2CH_2)—O$ | | F | H(l = O) | Het1 |
| 1294 | $O—(CH_2CH_2CH_2)—O$ | | F | H(l = O) | Het1 |
| 1295 | $S—(CH_2CH_2)—S$ | | F | H(l = O) | Het1 |
| 1296 | $S—(CH_2CH_2CH_2)—S$ | | F | H(l = O) | Het1 |
| 1297 | $—(CH_2)_4—$ | | F | H(l = O) | Het1 |
| 1298 | $—(CH_2)_5—$ | | F | H(l = O) | Het1 |
| 1299 | H | H | Cl | H(l = O) | Het1 |

TABLE 1-continued

I1a1

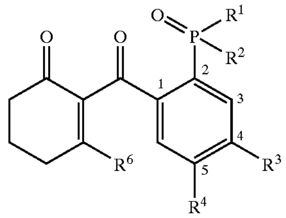

| n | $R^1$ | $R^2$ | $R^3$ | $R^4$ | $R^6$ |
|---|---|---|---|---|---|
| 1300 | $CH_3$ | $CH_3$ | Cl | H(l = O) | Het1 |
| 1301 | $CH_2CH_3$ | $CH_2CH_3$ | Cl | H(l = O) | Het1 |
| 1302 | $CH_2CH_2CH_3$ | $CH_2CH_2CH_3$ | Cl | H(l = O) | Het1 |
| 1303 | $OCH_3$ | $OCH_3$ | Cl | H(l = O) | Het1 |
| 1304 | $OCH_2CH_3$ | $OCH_2CH_3$ | Cl | H(l = O) | Het1 |
| 1305 | $OCH_2CH_2CH_3$ | $OCH_2CH_2CH_3$ | Cl | H(l = O) | Het1 |
| 1306 | $SCH_3$ | $SCH_3$ | Cl | H(l = O) | Het1 |
| 1307 | $SCH_2CH_3$ | $SCH_2CH_3$ | Cl | H(l = O) | Het1 |
| 1308 | $N(CH_3)_2$ | $N(CH_3)_2$ | Cl | H(l = O) | Het1 |
| 1309 | $N(CH_2CH_3)_2$ | $N(CH_2CH_3)_2$ | Cl | H(l = O) | Het1 |
| 1310 | $N(CH_3)(CH_2CH_3)$ | $N(CH_3)(CH_2CH_3)$ | Cl | H(l = O) | Het1 |
| 1311 | $O—(CH_2CH_2)—O$ | | Cl | H(l = O) | Het1 |
| 1312 | $O—(CH_2CH_2CH_2)—O$ | | Cl | H(l = O) | Het1 |
| 1313 | $S—(CH_2CH_2)—S$ | | Cl | H(l = O) | Het1 |
| 1314 | $S—(CH_2CH_2CH_2)—S$ | | | H(l = O) | Het1 |
| 1315 | $—(CH_2)_4—$ | | Cl | H(l = O) | Het1 |
| 1316 | $—(CH_2)_5—$ | | Cl | H(l = O) | Het1 |
| 1317 | H | H | Br | H(l = O) | Het1 |
| 1318 | $CH_3$ | $CH_3$ | Br | H(l = O) | Het1 |
| 1319 | $CH_2CH_3$ | $CH_2CH_3$ | Br | H(l = O) | Het1 |
| 1320 | $CH_2CH_2CH_3$ | $CH_2CH_2CH_3$ | Br | H(l = O) | Het1 |
| 1321 | $OCH_3$ | $OCH_3$ | Br | H(l = O) | Het1 |
| 1322 | $OCH_2CH_3$ | $OCH_2CH_3$ | Br | H(l = O) | Het1 |
| 1323 | $OCH_2CH_2CH_3$ | $OCH_2CH_2CH_3$ | Br | H(l = O) | Het1 |
| 1324 | $SCH_3$ | $SCH_3$ | Br | H(l = O) | Het1 |
| 1325 | $SCH_2CH_3$ | $SCH_2CH_3$ | Br | H(l = O) | Het1 |
| 1326 | $N(CH_3)_2$ | $N(CH_3)_2$ | Br | H(l = O) | Het1 |
| 1327 | $N(CH_2CH_3)_2$ | $N(CH_2CH_3)_2$ | Br | H(l = O) | Het1 |
| 1328 | $N(CH_3)(CH_2CH_3)$ | $N(CH_3)(CH_2CH_3)$ | Br | H(l = O) | Het1 |
| 1329 | $O—(CH_2CH_2)—O$ | | Br | H(l = O) | Het1 |
| 1330 | $O—(CH_2CH_2CH_2)—O$ | | Br | H(l = O) | Het1 |
| 1331 | $S—(CH_2CH_2)—S$ | | Br | H(l = O) | Het1 |
| 1332 | $S—(CH_2CH_2CH_2)—S$ | | Br | H(l = O) | Het1 |
| 1333 | $—(CH_2)_4—$ | | Br | H(l = O) | Het1 |
| 1334 | $—(CH_2)_5—$ | | Br | H(l = O) | Het1 |
| 1335 | H | H | $CH_3$ | H(l = O) | Het1 |
| 1336 | $CH_3$ | $CH_3$ | $CH_3$ | H(l = O) | Het1 |
| 1337 | $CH_2CH_3$ | $CH_2CH_3$ | $CH_3$ | H(l = O) | Het1 |
| 1338 | $CH_2CH_2CH_3$ | $CH_2CH_2CH_3$ | $CH_3$ | H(l = O) | Het1 |
| 1339 | $OCH_3$ | $OCH_3$ | $CH_3$ | H(l = O) | Het1 |
| 1340 | $OCH_2CH_3$ | $OCH_2CH_3$ | $CH_3$ | H(l = O) | Het1 |
| 1341 | $OCH_2CH_2CH_3$ | $OCH_2CH_2CH_3$ | $CH_3$ | H(l = O) | Het1 |
| 1342 | $SCH_3$ | $SCH_3$ | $CH_3$ | H(l = O) | Het1 |
| 1343 | $SCH_2CH_3$ | $SCH_2CH_3$ | $CH_3$ | H(l = O) | Het1 |
| 1344 | $N(CH_3)_2$ | $N(CH_3)_2$ | $CH_3$ | H(l = O) | Het1 |
| 1345 | $N(CH_2CH_3)_2$ | $N(CH_2CH_3)_2$ | $CH_3$ | H(l = O) | Het1 |
| 1346 | $N(CH_3)(CH_2CH_3)$ | $N(CH_3)(CH_2CH_3)$ | $CH_3$ | H(l = O) | Het1 |
| 1347 | $O—(CH_2CH_2)—O$ | | $CH_3$ | H(l = O) | Het1 |
| 1348 | $O—(CH_2CH_2CH_2)—O$ | | $CH_3$ | H(l = O) | Het1 |
| 1349 | $S—(CH_2CH_2)—S$ | | $CH_3$ | H(l = O) | Het1 |
| 1350 | $S—(CH_2CH_2CH_2)—S$ | | $CH_3$ | H(l = O) | Het1 |
| 1351 | $—(CH_2)_4—$ | | $CH_3$ | H(l = O) | Het1 |
| 1352 | $—(CH_2)_5—$ | | $CH_3$ | H(l = O) | Het1 |
| 1353 | H | H | $CH_2CH_3$ | H(l = O) | Het1 |
| 1354 | $CH_3$ | $CH_3$ | $CH_2CH_3$ | H(l = O) | Het1 |
| 1355 | $CH_2CH_3$ | $CH_2CH_3$ | $CH_2CH_3$ | H(l = O) | Het1 |
| 1356 | $CH_2CH_2CH_3$ | $CH_2CH_2CH_3$ | $CH_2CH_3$ | H(l = O) | Het1 |
| 1357 | $OCH_3$ | $OCH_3$ | $CH_2CH_3$ | H(l = O) | Het1 |
| 1358 | $OCH_2CH_3$ | $OCH_2CH_3$ | $CH_2CH_3$ | H(l = O) | Het1 |
| 1359 | $OCH_2CH_2CH_3$ | $OCH_2CH_2CH_3$ | $CH_2CH_3$ | H(l = O) | Het1 |
| 1360 | $SCH_3$ | $SCH_3$ | $CH_2CH_3$ | H(l = O) | Het1 |
| 1361 | $SCH_2CH_3$ | $SCH_2CH_3$ | $CH_2CH_3$ | H(l = O) | Het1 |
| 1362 | $N(CH_3)_2$ | $N(CH_3)_2$ | $CH_2CH_3$ | H(l = O) | Het1 |
| 1363 | $N(CH_2CH_3)_2$ | $N(CH_2CH_3)_2$ | $CH_2CH_3$ | H(l = O) | Het1 |

TABLE 1-continued

I1a1

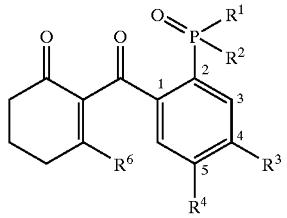

| n | $R^1$ | $R^2$ | $R^3$ | $R^4$ | $R^6$ |
|---|---|---|---|---|---|
| 1364 | $N(CH_3)(CH_2CH_3)$ | $N(CH_3)(CH_2CH_3)$ | $CH_2CH_3$ | H(l = O) | Het1 |
| 1365 | $O—(CH_2CH_2)—O$ | | $CH_2CH_3$ | H(l = O) | Het1 |
| 1366 | $O—(CH_2CH_2CH_2)—O$ | | $CH_2CH_3$ | H(l = O) | Het1 |
| 1367 | $S—(CH_2CH_2)—S$ | | $CH_2CH_3$ | H(l = O) | Het1 |
| 1368 | $S—(CH_2CH_2CH_2)—S$ | | $CH_2CH_3$ | H(l = O) | Het1 |
| 1369 | $—(CH_2)_4—$ | | $CH_2CH_3$ | H(l = O) | Het1 |
| 1370 | $—(CH_2)_5—$ | | $CH_2CH_3$ | H(l = O) | Het1 |
| 1371 | H | H | $CF_3$ | H(l = O) | Het1 |
| 1372 | $CH_3$ | $CH_3$ | $CF_3$ | H(l = O) | Het1 |
| 1373 | $CH_2CH_3$ | $CH_2CH_3$ | $CF_3$ | H(l = O) | Het1 |
| 1374 | $CH_2CH_2CH_3$ | $CH_2CH_2CH_3$ | $CF_3$ | H(l = O) | Het1 |
| 1375 | $OCH_3$ | $OCH_3$ | $CF_3$ | H(l = O) | Het1 |
| 1376 | $OCH_2CH_3$ | $OCH_2CH_3$ | $CF_3$ | H(l = O) | Het1 |
| 1377 | $OCH_2CH_2CH_3$ | $OCH_2CH_2CH_3$ | $CF_3$ | H(l = O) | Het1 |
| 1378 | $SCH_3$ | $SCH_3$ | $CF_3$ | H(l = O) | Het1 |
| 1379 | $SCH_2CH_3$ | $SCH_2CH_3$ | $CF_3$ | H(l = O) | Het1 |
| 1380 | $N(CH_3)_2$ | $N(CH_3)_2$ | $CF_3$ | H(l = O) | Het1 |
| 1381 | $N(CH_2CH_3)_2$ | $N(CH_2CH_3)_2$ | $CF_3$ | H(l = O) | Het1 |
| 1382 | $N(CH_3)(CH_2CH_3)$ | $N(CH_3)(CH_2CH_3)$ | $CF_3$ | H(l = O) | Het1 |
| 1383 | $O—(CH_2CH_2)—O$ | | $CF_3$ | H(l = O) | Het1 |
| 1384 | $O—(CH_2CH_2CH_2)—O$ | | $CF_3$ | H(l = O) | Het1 |
| 1385 | $S—(CH_2CH_2)—S$ | | $CF_3$ | H(l = O) | Het1 |
| 1386 | $S—(CH_2CH_2CH_2)—S$ | | $CF_3$ | H(l = O) | Het1 |
| 1387 | $—(CH_2)_4—$ | | $CF_3$ | H(l = O) | Het1 |
| 1388 | $—(CH_2)_5—$ | | $CF_3$ | H(l = O) | Het1 |
| 1389 | H | H | $OCH_3$ | H(l = O) | Het1 |
| 1390 | $CH_3$ | $CH_3$ | $OCH_3$ | H(l = O) | Het1 |
| 1391 | $CH_2CH_3$ | $CH_2CH_3$ | $OCH_3$ | H(l = O) | Het1 |
| 1392 | $CH_2CH_2CH_3$ | $CH_2CH_2CH_3$ | $OCH_3$ | H(l = O) | Het1 |
| 1393 | $OCH_3$ | $OCH_3$ | $OCH_3$ | H(l = O) | Het1 |
| 1394 | $OCH_2CH_3$ | $OCH_2CH_3$ | $OCH_3$ | H(l = O) | Het1 |
| 1395 | $OCH_2CH_2CH_3$ | $OCH_2CH_2CH_3$ | $OCH_3$ | H(l = O) | Het1 |
| 1396 | $SCH_3$ | $SCH_3$ | $OCH_3$ | H(l = O) | Het1 |
| 1397 | $SCH_2CH_3$ | $SCH_2CH_3$ | $OCH_3$ | H(l = O) | Het1 |
| 1398 | $N(CH_3)_2$ | $N(CH_3)_2$ | $OCH_3$ | H(l = O) | Het1 |
| 1399 | $N(CH_2CH_3)_2$ | $N(CH_2CH_3)_2$ | $OCH_3$ | H(l = O) | Het1 |
| 1400 | $N(CH_3)(CH_2CH_3)$ | $N(CH_3)(CH_2CH_3)$ | $OCH_3$ | H(l = O) | Het1 |
| 1401 | $O—(CH_2CH_2)—O$ | | $OCH_3$ | H(l = O) | Het1 |
| 1402 | $O—(CH_2CH_2CH_2)—O$ | | $OCH_3$ | H(l = O) | Het1 |
| 1403 | $S—(CH_2CH_2)—S$ | | $OCH_3$ | H(l = O) | Het1 |
| 1404 | $S—(CH_2CH_2CH_2)—S$ | | $OCH_3$ | H(l = O) | Het1 |
| 1405 | $—(CH_2)_4—$ | | $OCH_3$ | H(l = O) | Het1 |
| 1406 | $—(CH_2)_5—$ | | $OCH_3$ | H(l = O) | Het1 |
| 1407 | H | H | $OCH_2CH_3$ | H(l = O) | Het1 |
| 1408 | $CH_3$ | $CH_3$ | $OCH_2CH_3$ | H(l = O) | Het1 |
| 1409 | $CH_2CH_3$ | $CH_2CH_3$ | $OCH_2CH_3$ | H(l = O) | Het1 |
| 1410 | $CH_2CH_2CH_3$ | $CH_2CH_2CH_3$ | $OCH_2CH_3$ | H(l = O) | Het1 |
| 1411 | $OCH_3$ | $OCH_3$ | $OCH_2CH_3$ | H(l = O) | Het1 |
| 1412 | $OCH_2CH_3$ | $OCH_2CH_3$ | $OCH_2CH_3$ | H(l = O) | Het1 |
| 1413 | $OCH_2CH_2CH_3$ | $OCH_2CH_2CH_3$ | $OCH_2CH_3$ | H(l = O) | Het1 |
| 1414 | $SCH_3$ | $SCH_3$ | $OCH_2CH_3$ | H(l = O) | Het1 |
| 1415 | $SCH_2CH_3$ | $SCH_2CH_3$ | $OCH_2CH_3$ | H(l = O) | Het1 |
| 1416 | $N(CH_3)_2$ | $N(CH_3)_2$ | $OCH_2CH_3$ | H(l = O) | Het1 |
| 1417 | $N(CH_2CH_3)_2$ | $N(CH_2CH_3)_2$ | $OCH_2CH_3$ | H(l = O) | Het1 |
| 1418 | $N(CH_3)(CH_2CH_3)$ | $N(CH_3)(CH_2CH_3)$ | $OCH_2CH_3$ | H(l = O) | Het1 |
| 1419 | $O—(CH_2CH_2)—O$ | | $OCH_2CH_3$ | H(l = O) | Het1 |
| 1420 | $O—(CH_2CH_2CH_2)—O$ | | $OCH_2CH_3$ | H(l = O) | Het1 |
| 1421 | $S—(CH_2CH_2)—S$ | | $OCH_2CH_3$ | H(l = O) | Het1 |
| 1422 | $S—(CH_2CH_2CH_2)—S$ | | $OCH_2CH_3$ | H(l = O) | Het1 |
| 1423 | $—(CH_2)_4—$ | | $OCH_2CH_3$ | H(l = O) | Het1 |
| 1424 | $—(CH_2)_5—$ | | $OCH_2CH_3$ | H(l = O) | Het1 |
| 1425 | H | H | $SCH_3$ | H(l = O) | Het1 |
| 1426 | $CH_3$ | $CH_3$ | $SCH_3$ | H(l = O) | Het1 |
| 1427 | $CH_2CH_3$ | $CH_2CH_3$ | $SCH_3$ | H(l = O) | Het1 |

TABLE 1-continued

I1a1

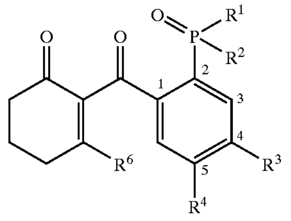

| n | $R^1$ | $R^2$ | $R^3$ | $R^4$ | $R^6$ |
|---|---|---|---|---|---|
| 1428 | $CH_2CH_2CH_3$ | $CH_2CH_2CH_3$ | $SCH_3$ | H(l = O) | Het1 |
| 1429 | $OCH_3$ | $OCH_3$ | $SCH_3$ | H(l = O) | Het1 |
| 1430 | $OCH_2CH_3$ | $OCH_2CH_3$ | $SCH_3$ | H(l = O) | Het1 |
| 1431 | $OCH_2CH_2CH_3$ | $OCH_2CH_2CH_3$ | $SCH_3$ | H(l = O) | Het1 |
| 1432 | $SCH_3$ | $SCH_3$ | $SCH_3$ | H(l = O) | Het1 |
| 1433 | $SCH_2CH_3$ | $SCH_2CH_3$ | $SCH_3$ | H(l = O) | Het1 |
| 1434 | $N(CH_3)_2$ | $N(CH_3)_2$ | $SCH_3$ | H(l = O) | Het1 |
| 1435 | $N(CH_2CH_3)_2$ | $N(CH_2CH_3)_2$ | $SCH_3$ | H(l = O) | Het1 |
| 1436 | $N(CH_3)(CH_2CH_3)$ | $N(CH_3)(CH_2CH_3)$ | $SCH_3$ | H(l = O) | Het1 |
| 1437 | $O—(CH_2CH_2)—O$ | | $SCH_3$ | H(l = O) | Het1 |
| 1438 | $O—(CH_2CH_2CH_2)—O$ | | $SCH_3$ | H(l = O) | Het1 |
| 1439 | $S—(CH_2CH_2)—S$ | | $SCH_3$ | H(l = O) | Het1 |
| 1440 | $S—(CH_2CH_2CH_2)—S$ | | | H(l = O) | Het1 |
| 1441 | $—(CH_2)_4—$ | | $SCH_3$ | H(l = O) | Het1 |
| 1442 | $—(CH_2)_5—$ | | $SCH_3$ | H(l = O) | Het1 |
| 1443 | H | H | $SO_2CH_3$ | H(l = O) | Het1 |
| 1444 | $CH_3$ | $CH_3$ | $SO_2CH_3$ | H(l = O) | Het1 |
| 1445 | $CH_2CH_3$ | $CH_2CH_3$ | $SO_2CH_3$ | H(l = O) | Het1 |
| 1446 | $CH_2CH_2CH_3$ | $CH_2CH_2CH_3$ | $SO_2CH_3$ | H(l = O) | Het1 |
| 1447 | $OCH_3$ | $OCH_3$ | $SO_2CH_3$ | H(l = O) | Het1 |
| 1448 | $OCH_2CH_3$ | $OCH_2CH_3$ | $SO_2CH_3$ | H(l = O) | Het1 |
| 1449 | $OCH_2CH_2CH_3$ | $OCH_2CH_2CH_3$ | $SO_2CH_3$ | H(l = O) | Het1 |
| 1450 | $SCH_3$ | $SCH_3$ | $SO_2CH_3$ | H(l = O) | Het1 |
| 1451 | $SCH_2CH_3$ | $SCH_2CH_3$ | $SO_2CH_3$ | H(l = O) | Het1 |
| 1452 | $N(CH_3)_2$ | $N(CH_3)_2$ | $SO_2CH_3$ | H(l = O) | Het1 |
| 1453 | $N(CH_2CH_3)_2$ | $N(CH_2CH_3)_2$ | $SO_2CH_3$ | H(l = O) | Het1 |
| 1454 | $N(CH_3)(CH_2CH_3)$ | $N(CH_3)(CH_2CH_3)$ | $SO_2CH_3$ | H(l = O) | Het1 |
| 1455 | $O—(CH_2CH_2)—O$ | | $SO_2CH_3$ | H(l = O) | Het1 |
| 1456 | $O—(CH_2CH_2CH_2)—O$ | | $SO_2CH_3$ | H(l = O) | Het1 |
| 1457 | $S—(CH_2CH_2)—S$ | | $SO_2CH_3$ | H(l = O) | Het1 |
| 1458 | $S—(CH_2CH_2CH_2)—S$ | | $SO_2CH_3$ | H(l = O) | Het1 |
| 1459 | $—(CH_2)_4—$ | | $SO_2CH_3$ | H(l = O) | Het1 |
| 1460 | $—(CH_2)_5—$ | | $SO_2CH_3$ | H(l = O) | Het1 |
| 1461 | H | H | $PO(OCH_3)_2$ | H(l = O) | Het1 |
| 1462 | $CH_3$ | $CH_3$ | $PO(OCH_3)_2$ | H(l = O) | Het1 |
| 1463 | $CH_2CH_3$ | $CH_2CH_3$ | $PO(OCH_3)_2$ | H(l = O) | Het1 |
| 1464 | $CH_2CH_2CH_3$ | $CH_2CH_2CH_3$ | $PO(OCH_3)_2$ | H(l = O) | Het1 |
| 1465 | $OCH_3$ | $OCH_3$ | $PO(OCH_3)_2$ | H(l = O) | Het1 |
| 1466 | $OCH_2CH_3$ | $OCH_2CH_3$ | $PO(OCH_3)_2$ | H(l = O) | Het1 |
| 1467 | $OCH_2CH_2CH_3$ | $OCH_2CH_2CH_3$ | $PO(OCH_3)_2$ | H(l = O) | Het1 |
| 1468 | $SCH_3$ | $SCH_3$ | $PO(OCH_3)_2$ | H(l = O) | Het1 |
| 1469 | $SCH_2CH_3$ | $SCH_2CH_3$ | $PO(OCH_3)_2$ | H(l = O) | Het1 |
| 1470 | $N(CH_3)_2$ | $N(CH_3)_2$ | $PO(OCH_3)_2$ | H(l = O) | Het1 |
| 1471 | $N(CH_2CH_3)_2$ | $N(CH_2CH_3)_2$ | $PO(OCH_3)_2$ | H(l = O) | Het1 |
| 1472 | $N(CH_3)(CH_2CH_3)$ | $N(CH_3)(CH_2CH_3)$ | $PO(OCH_3)_2$ | H(l = O) | Het1 |
| 1473 | $O—(CH_2CH_2)—O$ | | $PO(OCH_3)_2$ | H(l = O) | Het1 |
| 1474 | $O—(CH_2CH_2CH_2)—O$ | | $PO(OCH_3)_2$ | H(l = O) | Het1 |
| 1475 | $S—(CH_2CH_2)—S$ | | $PO(OCH_3)_2$ | H(l = O) | Het1 |
| 1476 | $S—(CH_2CH_2CH_2)—S$ | | $PO(OCH_3)_2$ | H(l = O) | Het1 |
| 1477 | $—(CH_2)_4—$ | | $PO(OCH_3)_2$ | H(l = O) | Het1 |
| 1478 | $—(CH_2)_5—$ | | $PO(OCH_3)_2$ | H(l = O) | Het1 |
| 1479 | H | H | $PO(OCH_2CH_3)_2$ | H(l = O) | Het1 |
| 1480 | $CH_3$ | $CH_3$ | $PO(OCH_2CH_3)_2$ | H(l = O) | Het1 |
| 1481 | $CH_2CH_3$ | $CH_2CH_3$ | $PO(OCH_2CH_3)_2$ | H(l = O) | Het1 |
| 1482 | $CH_2CH_2CH_3$ | $CH_2CH_2CH_3$ | $PO(OCH_2CH_3)_2$ | H(l = O) | Het1 |
| 1483 | $OCH_3$ | $OCH_3$ | $PO(OCH_2CH_3)_2$ | H(l = O) | Het1 |
| 1484 | $OCH_2CH_3$ | $OCH_2CH_3$ | $PO(OCH_2CH_3)_2$ | H(l = O) | Het1 |
| 1485 | $OCH_2CH_2CH_3$ | $OCH_2CH_2CH_3$ | $PO(OCH_2CH_3)_2$ | H(l = O) | Het1 |
| 1486 | $SCH_3$ | $SCH_3$ | $PO(OCH_2CH_3)_2$ | H(l = O) | Het1 |
| 1487 | $SCH_2CH_3$ | $SCH_2CH_3$ | $PO(OCH_2CH_3)_2$ | H(l = O) | Het1 |
| 1488 | $N(CH_3)_2$ | $N(CH_3)_2$ | $PO(OCH_2CH_3)_2$ | H(l = O) | Het1 |
| 1489 | $N(CH_2CH_3)_2$ | $N(CH_2CH_3)_2$ | $PO(OCH_2CH_3)_2$ | H(l = O) | Het1 |
| 1490 | $N(CH_3)(CH_2CH_3)$ | $N(CH_3)(CH_2CH_3)$ | $PO(OCH_2CH_3)_2$ | H(l = O) | Het1 |
| 1491 | $O—(CH_2CH_2)—O$ | | $PO(OCH_2CH_3)_2$ | H(l = O) | Het1 |

TABLE 1-continued

I1a1

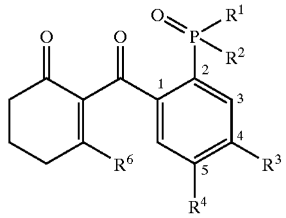

| n | $R^1$ | $R^2$ | $R^3$ | $R^4$ | $R^6$ |
|---|---|---|---|---|---|
| 1492 | O—$(CH_2CH_2CH_2)$—O | | $PO(OCH_2CH_3)_2$ | H(l = O) | Het1 |
| 1493 | S—$(CH_2CH_2)$—S | | $PO(OCH_2CH_3)_2$ | H(l = O) | Het1 |
| 1494 | S—$(CH_2CH_2CH_2)$—S | | $PO(OCH_2CH_3)_2$ | H(l = O) | Het1 |
| 1495 | —$(CH_2)_4$— | | $PO(OCH_2CH_3)_2$ | H(l = O) | Het1 |
| 1496 | —$(CH_2)_5$— | | $PO(OCH_2CH_3)_2$ | H(l = O) | Het1 |
| 1497 | H | H | $PO(CH_3)_2$ | H(l = O) | Het1 |
| 1498 | $CH_3$ | $CH_3$ | $PO(CH_3)_2$ | H(l = O) | Het1 |
| 1499 | $CH_2CH_3$ | $CH_2CH_3$ | $PO(CH_3)_2$ | H(l = O) | Het1 |
| 1500 | $CH_2CH_2CH_3$ | $CH_2CH_2CH_3$ | $PO(CH_3)_2$ | H(l = O) | Het1 |
| 1501 | $OCH_3$ | $OCH_3$ | $PO(CH_3)_2$ | H(l = O) | Het1 |
| 1502 | $OCH_2CH_3$ | $OCH_2CH_3$ | $PO(CH_3)_2$ | H(l = O) | Het1 |
| 1503 | $OCH_2CH_2CH_3$ | $OCH_2CH_2CH_3$ | $PO(CH_3)_2$ | H(l = O) | Het1 |
| 1504 | $SCH_3$ | $SCH_3$ | $PO(CH_3)_2$ | H(l = O) | Het1 |
| 1505 | $SCH_2CH_3$ | $SCH_2CH_3$ | $PO(CH_3)_2$ | H(l = O) | Het1 |
| 1506 | $N(CH_3)_2$ | $N(CH_3)_2$ | $PO(CH_3)_2$ | H(l = O) | Het1 |
| 1507 | $N(CH_2CH_3)_2$ | $N(CH_2CH_3)_2$ | $PO(CH_3)_2$ | H(l = O) | Het1 |
| 1508 | $N(CH_3)(CH_2CH_3)$ | $N(CH_3)(CH_2CH_3)$ | $PO(CH_3)_2$ | H(l = O) | Het1 |
| 1509 | O—$(CH_2CH_2)$—O | | $PO(CH_3)_2$ | H(l = O) | Het1 |
| 1510 | O—$(CH_2CH_2CH_2)$—O | | $PO(CH_3)_2$ | H(l = O) | Het1 |
| 1511 | S—$(CH_2CH_2)$—S | | $PO(CH_3)_2$ | H(l = O) | Het1 |
| 1512 | S—$(CH_2CH_2CH_2)$—S | | $PO(CH_3)_2$ | H(l = O) | Het1 |
| 1513 | —$(CH_2)_4$— | | $PO(CH_3)_2$ | H(l = O) | Het1 |
| 1514 | —$(CH_2)_5$— | | $PO(CH_3)_2$ | H(l = O) | Het1 |
| 1515 | H | H | $PO(CH_2CH_3)_2$ | H(l = O) | Het1 |
| 1516 | $CH_3$ | $CH_3$ | $PO(CH_2CH_3)_2$ | H(l = O) | Het1 |
| 1517 | $CH_2CH_3$ | $CH_2CH_3$ | $PO(CH_2CH_3)_2$ | H(l = O) | Het1 |
| 1518 | $CH_2CH_2CH_3$ | $CH_2CH_2CH_3$ | $PO(CH_2CH_3)_2$ | H(l = O) | Het1 |
| 1519 | $OCH_3$ | $OCH_3$ | $PO(CH_2CH_3)_2$ | H(l = O) | Het1 |
| 1520 | $OCH_2CH_3$ | $OCH_2CH_3$ | $PO(CH_2CH_3)_2$ | H(l = O) | Het1 |
| 1521 | $OCH_2CH_2CH_3$ | $OCH_2CH_2CH_3$ | $PO(CH_2CH_3)_2$ | H(l = O) | Het1 |
| 1522 | $SCH_3$ | $SCH_3$ | $PO(CH_2CH_3)_2$ | H(l = O) | Het1 |
| 1523 | $SCH_2CH_3$ | $SCH_2CH_3$ | $PO(CH_2CH_3)_2$ | H(l = O) | Het1 |
| 1524 | $N(CH_3)_2$ | $N(CH_3)_2$ | $PO(CH_2CH_3)_2$ | H(l = O) | Het1 |
| 1525 | $N(CH_2CH_3)_2$ | $N(CH_2CH_3)_2$ | $PO(CH_2CH_3)_2$ | H(l = O) | Het1 |
| 1526 | $N(CH_3)(CH_2CH_3)$ | $N(CH_3)(CH_2CH_3)$ | $PO(CH_2CH_3)_2$ | H(l = O) | Het1 |
| 1527 | O—$(CH_2CH_2)$—O | | $PO(CH_2CH_3)_2$ | H(l = O) | Het1 |
| 1528 | O—$(CH_2CH_2CH_2)$—O | | $PO(CH_2CH_3)_2$ | H(l = O) | Het1 |
| 1529 | S—$(CH_2CH_2)$—S | | $PO(CH_2CH_3)_2$ | H(l = O) | Het1 |
| 1530 | S—$(CH_2CH_2CH_2)$—S | | $PO(CH_2CH_3)_2$ | H(l = O) | Het1 |
| 1531 | —$(CH_2)_4$— | | $PO(CH_2CH_3)_2$ | H(l = O) | Het1 |
| 1532 | —$(CH_2)_5$— | | $PO(CH_2CH_3)_2$ | H(l = O) | Het1 |
| 1533 | H | H | H | H(l = O) | Het2 |
| 1534 | $CH_3$ | $CH_3$ | H | H(l = O) | Het2 |
| 1535 | $CH_2CH_3$ | $CH_2CH_3$ | H | H(l = O) | Het2 |
| 1536 | $CH_2CH_2CH_3$ | $CH_2CH_2CH_3$ | H | H(l = O) | Het2 |
| 1537 | $OCH_3$ | $OCH_3$ | H | H(l = O) | Het2 |
| 1538 | $OCH_2CH_3$ | $OCH_2CH_3$ | H | H(l = O) | Het2 |
| 1539 | $OCH_2CH_2CH_3$ | $OCH_2CH_2CH_3$ | H | H(l = O) | Het2 |
| 1540 | $SCH_3$ | $SCH_3$ | H | H(l = O) | Het2 |
| 1541 | $SCH_2CH_3$ | $SCH_2CH_3$ | H | H(l = O) | Het2 |
| 1542 | $N(CH_3)_2$ | $N(CH_3)_2$ | H | H(l = O) | Het2 |
| 1543 | $N(CH_2CH_3)_2$ | $N(CH_2CH_3)_2$ | H | H(l = O) | Het2 |
| 1544 | $N(CH_3)(CH_2CH_3)$ | $N(CH_3)(CH_2CH_3)$ | H | H(l = O) | Het2 |
| 1545 | O—$(CH_2CH_2)$—O | | H | H(l = O) | Het2 |
| 1546 | O—$(CH_2CH_2CH_2)$—O | | H | H(l = O) | Het2 |
| 1547 | S—$(CH_2CH_2)$—S | | H | H(l = O) | Het2 |
| 1548 | S—$(CH_2CH_2CH_2)$—S | | H | H(l = O) | Het2 |
| 1549 | —$(CH_2)_4$— | | H | H(l = O) | Het2 |
| 1550 | —$(CH_2)_5$— | | H | H(l = O) | Het2 |
| 1551 | H | H | $NO_2$ | H(l = O) | Het2 |
| 1552 | $CH_3$ | $CH_3$ | $NO_2$ | H(l = O) | Het2 |
| 1553 | $CH_2CH_3$ | $CH_2CH_3$ | $NO_2$ | H(l = O) | Het2 |
| 1554 | $CH_2CH_2CH_3$ | $CH_2CH_2CH_3$ | $NO_2$ | H(l = O) | Het2 |
| 1555 | $OCH_3$ | $OCH_3$ | $NO_2$ | H(l = O) | Het2 |

TABLE 1-continued

I1a1

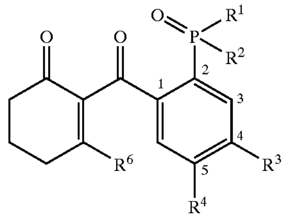

| n | $R^1$ | $R^2$ | $R^3$ | $R^4$ | $R^6$ |
|---|---|---|---|---|---|
| 1556 | $OCH_2CH_3$ | $OCH_2CH_3$ | $NO_2$ | H(l = O) | Het2 |
| 1557 | $OCH_2CH_2CH_3$ | $OCH_2CH_2CH_3$ | $NO_2$ | H(l = O) | Het2 |
| 1558 | $SCH_3$ | $SCH_3$ | $NO_2$ | H(l = O) | Het2 |
| 1559 | $SCH_2CH_3$ | $SCH_2CH_3$ | $NO_2$ | H(l = O) | Het2 |
| 1560 | $N(CH_3)_2$ | $N(CH_3)_2$ | $NO_2$ | H(l = O) | Het2 |
| 1561 | $N(CH_2CH_3)_2$ | $N(CH_2CH_3)_2$ | $NO_2$ | H(l = O) | Het2 |
| 1562 | $N(CH_3)(CH_2CH_3)$ | $N(CH_3)(CH_2CH_3)$ | $NO_2$ | H(l = O) | Het2 |
| 1563 | $O—(CH_2CH_2)—O$ | | $NO_2$ | H(l = O) | Het2 |
| 1564 | $O—(CH_2CH_2CH_2)—O$ | | $NO_2$ | H(l = O) | Het2 |
| 1565 | $S—(CH_2CH_2)—S$ | | $NO_2$ | H(l = O) | Het2 |
| 1566 | $S—(CH_2CH_2CH_2)—S$ | | $NO_2$ | H(l = O) | Het2 |
| 1567 | $—(CH_2)_4—$ | | $NO_2$ | H(l = O) | Het2 |
| 1568 | $—(CH_2)_5—$ | | $NO_2$ | H(l = O) | Het2 |
| 1569 | H | H | CN | H(l = O) | Het2 |
| 1570 | $CH_3$ | $CH_3$ | CN | H(l = O) | Het2 |
| 1571 | $CH_2CH_3$ | $CH_2CH_3$ | CN | H(l = O) | Het2 |
| 1572 | $CH_2CH_2CH_3$ | $CH_2CH_2CH_3$ | CN | H(l = O) | Het2 |
| 1573 | $OCH_3$ | $OCH_3$ | CN | H(l = O) | Het2 |
| 1574 | $OCH_2CH_3$ | $OCH_2CH_3$ | CN | H(l = O) | Het2 |
| 1575 | $OCH_2CH_2CH_3$ | $OCH_2CH_2CH_3$ | CN | H(l = O) | Het2 |
| 1576 | $SCH_3$ | $SCH_3$ | CN | H(l = O) | Het2 |
| 1577 | $SCH_2CH_3$ | $SCH_2CH_3$ | CN | H(l = O) | Het2 |
| 1578 | $N(CH_3)_2$ | $N(CH_3)_2$ | CN | H(l = O) | Het2 |
| 1579 | $N(CH_2CH_3)_2$ | $N(CH_2CH_3)_2$ | CN | H(l = O) | Het2 |
| 1580 | $N(CH_3)(CH_2CH_3)$ | $N(CH_3)(CH_2CH_3)$ | CN | H(l = O) | Het2 |
| 1581 | $O—(CH_2CH_2)—O$ | | CN | H(l = O) | Het2 |
| 1582 | $O—(CH_2CH_2CH_2)—O$ | | CN | H(l = O) | Het2 |
| 1583 | $S—(CH_2CH_2)—S$ | | CN | H(l = O) | Het2 |
| 1584 | $S—(CH_2CH_2CH_2)—S$ | | CN | H(l = O) | Het2 |
| 1585 | $—(CH_2)_4—$ | | CN | H(l = O) | Het2 |
| 1586 | $—(CH_2)_5—$ | | CN | H(l = O) | Het2 |
| 1587 | H | H | F | H(l = O) | Het2 |
| 1588 | $CH_3$ | $CH_3$ | F | H(l = O) | Het2 |
| 1589 | $CH_2CH_3$ | $CH_2CH_3$ | F | H(l = O) | Het2 |
| 1590 | $CH_2CH_2CH_3$ | $CH_2CH_2CH_3$ | F | H(l = O) | Het2 |
| 1591 | $OCH_3$ | $OCH_3$ | F | H(l = O) | Het2 |
| 1592 | $OCH_2CH_3$ | $OCH_2CH_3$ | F | H(l = O) | Het2 |
| 1593 | $OCH_2CH_2CH_3$ | $OCH_2CH_2CH_3$ | F | H(l = O) | Het2 |
| 1594 | $SCH_3$ | $SCH_3$ | F | H(l = O) | Het2 |
| 1595 | $SCH_2CH_3$ | $SCH_2CH_3$ | F | H(l = O) | Het2 |
| 1596 | $N(CH_3)_2$ | $N(CH_3)_2$ | F | H(l = O) | Het2 |
| 1597 | $N(CH_2CH_3)_2$ | $N(CH_2CH_3)_2$ | F | H(l = O) | Het2 |
| 1598 | $N(CH_3)(CH_2CH_3)$ | $N(CH_3)(CH_2CH_3)$ | F | H(l = O) | Het2 |
| 1599 | $O—(CH_2CH_2)—O$ | | F | H(l = O) | Het2 |
| 1600 | $O—(CH_2CH_2CH_2)—O$ | | F | H(l = O) | Het2 |
| 1601 | $S—(CH_2CH_2)—S$ | | F | H(l = O) | Het2 |
| 1602 | $S—(CH_2CH_2CH_2)—S$ | | F | H(l = O) | Het2 |
| 1603 | $—(CH_2)_4—$ | | F | H(l = O) | Het2 |
| 1604 | $—(CH_2)_5—$ | | F | H(l = O) | Het2 |
| 1605 | H | H | Cl | H(l = O) | Het2 |
| 1606 | $CH_3$ | $CH_3$ | Cl | H(l = O) | Het2 |
| 1607 | $CH_2CH_3$ | $CH_2CH_3$ | Cl | H(l = O) | Het2 |
| 1608 | $CH_2CH_2CH_3$ | $CH_2CH_2CH_3$ | Cl | H(l = O) | Het2 |
| 1609 | $OCH_3$ | $OCH_3$ | Cl | H(l = O) | Het2 |
| 1610 | $OCH_2CH_3$ | $OCH_2CH_3$ | Cl | H(l = O) | Het2 |
| 1611 | $OCH_2CH_2CH_3$ | $OCH_2CH_2CH_3$ | Cl | H(l = O) | Het2 |
| 1612 | $SCH_3$ | $SCH_3$ | Cl | H(l = O) | Het2 |
| 1613 | $SCH_2CH_3$ | $SCH_2CH_3$ | Cl | H(l = O) | Het2 |
| 1614 | $N(CH_3)_2$ | $N(CH_3)_2$ | Cl | H(l = O) | Het2 |
| 1615 | $N(CH_2CH_3)_2$ | $N(CH_2CH_3)_2$ | Cl | H(l = O) | Het2 |
| 1616 | $N(CH_3)(CH_2CH_3)$ | $N(CH_3)(CH_2CH_3)$ | Cl | H(l = O) | Het2 |
| 1617 | $O—(CH_2CH_2)—O$ | | Cl | H(l = O) | Het2 |
| 1618 | $O—(CH_2CH_2CH_2)—O$ | | Cl | H(l = O) | Het2 |
| 1619 | $S—(CH_2CH_2)—S$ | | Cl | H(l = O) | Het2 |

TABLE 1-continued

I1a1

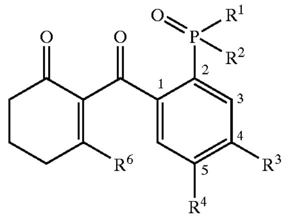

| n | $R^1$ | $R^2$ | $R^3$ | $R^4$ | $R^6$ |
|---|---|---|---|---|---|
| 1620 | S—($CH_2CH_2CH_2$)—S | | Cl | H(l = O) | Het2 |
| 1621 | —$(CH_2)_4$— | | Cl | H(l = O) | Het2 |
| 1622 | —$(CH_2)_5$— | | Cl | H(l = O) | Het2 |
| 1623 | H | H | Br | H(l = O) | Het2 |
| 1624 | $CH_3$ | $CH_3$ | Br | H(l = O) | Het2 |
| 1625 | $CH_2CH_3$ | $CH_2CH_3$ | Br | H(l = O) | Het2 |
| 1626 | $CH_2CH_2CH_3$ | $CH_2CH_2CH_3$ | Br | H(l = O) | Het2 |
| 1627 | $OCH_3$ | $OCH_3$ | Br | H(l = O) | Het2 |
| 1628 | $OCH_2CH_3$ | $OCH_2CH_3$ | Br | H(l = O) | Het2 |
| 1629 | $OCH_2CH_2CH_3$ | $OCH_2CH_2CH_3$ | Br | H(l = O) | Het2 |
| 1630 | $SCH_3$ | $SCH_3$ | Br | H(l = O) | Het2 |
| 1631 | $SCH_2CH_3$ | $SCH_2CH_3$ | Br | H(l = O) | Het2 |
| 1632 | $N(CH_3)_2$ | $N(CH_3)_2$ | Br | H(l = O) | Het2 |
| 1633 | $N(CH_2CH_3)_2$ | $N(CH_2CH_3)_2$ | Br | H(l = O) | Het2 |
| 1634 | $N(CH_3)(CH_2CH_3)$ | $N(CH_3)(CH_2CH_3)$ | Br | H(l = O) | Het2 |
| 1635 | O—($CH_2CH_2$)—O | | Br | H(l = O) | Het2 |
| 1636 | O—($CH_2CH_2CH_2$)—O | | Br | H(l = O) | Het2 |
| 1637 | S—($CH_2CH_2$)—S | | Br | H(l = O) | Het2 |
| 1638 | S—($CH_2CH_2CH_2$)—S | | Br | H(l = O) | Het2 |
| 1639 | —$(CH_2)_4$— | | Br | H(l = O) | Het2 |
| 1640 | —$(CH_2)_5$— | | Br | H(l = O) | Het2 |
| 1641 | H | H | $CH_3$ | H(l = O) | Het2 |
| 1642 | $CH_3$ | $CH_3$ | $CH_3$ | H(l = O) | Het2 |
| 1643 | $CH_2CH_3$ | $CH_2CH_3$ | $CH_3$ | H(l = O) | Het2 |
| 1644 | $CH_2CH_2CH_3$ | $CH_2CH_2CH_3$ | $CH_3$ | H(l = O) | Het2 |
| 1645 | $OCH_3$ | $OCH_3$ | $CH_3$ | H(l = O) | Het2 |
| 1646 | $OCH_2CH_3$ | $OCH_2CH_3$ | $CH_3$ | H(l = O) | Het2 |
| 1647 | $OCH_2CH_2CH_3$ | $OCH_2CH_2CH_3$ | $CH_3$ | H(l = O) | Het2 |
| 1648 | $SCH_3$ | $SCH_3$ | $CH_3$ | H(l = O) | Het2 |
| 1649 | $SCH_2CH_3$ | $SCH_2CH_3$ | $CH_3$ | H(l = O) | Het2 |
| 1650 | $N(CH_3)_2$ | $N(CH_3)_2$ | $CH_3$ | H(l = O) | Het2 |
| 1651 | $N(CH_2CH_3)_2$ | $N(CH_2CH_3)_2$ | $CH_3$ | H(l = O) | Het2 |
| 1652 | $N(CH_3)(CH_2CH_3)$ | $N(CH_3)(CH_2CH_3)$ | $CH_3$ | H(l = O) | Het2 |
| 1653 | O—($CH_2CH_2$)—O | | $CH_3$ | H(l = O) | Het2 |
| 1654 | O—($CH_2CH_2CH_2$)—O | | $CH_3$ | H(l = O) | Het2 |
| 1655 | S—($CH_2CH_2$)—S | | $CH_3$ | H(l = O) | Het2 |
| 1656 | S—($CH_2CH_2CH_2$)—S | | $CH_3$ | H(l = O) | Het2 |
| 1657 | —$(CH_2)_4$— | | $CH_3$ | H(l = O) | Het2 |
| 1658 | —$(CH_2)_5$— | | $CH_3$ | H(l = O) | Het2 |
| 1659 | H | H | $CH_2CH_3$ | H(l = O) | Het2 |
| 1660 | $CH_3$ | $CH_3$ | $CH_2CH_3$ | H(l = O) | Het2 |
| 1661 | $CH_2CH_3$ | $CH_2CH_3$ | $CH_2CH_3$ | H(l = O) | Het2 |
| 1662 | $CH_2CH_2CH_3$ | $CH_2CH_2CH_3$ | $CH_2CH_3$ | H(l = O) | Het2 |
| 1663 | $OCH_3$ | $OCH_3$ | $CH_2CH_3$ | H(l = O) | Het2 |
| 1664 | $OCH_2CH_3$ | $OCH_2CH_3$ | $CH_2CH_3$ | H(l = O) | Het2 |
| 1665 | $OCH_2CH_2CH_3$ | $OCH_2CH_2CH_3$ | $CH_2CH_3$ | H(l = O) | Het2 |
| 1666 | $SCH_3$ | $SCH_3$ | $CH_2CH_3$ | H(l = O) | Het2 |
| 1667 | $SCH_2CH_3$ | $SCH_2CH_3$ | $CH_2CH_3$ | H(l = O) | Het2 |
| 1668 | $N(CH_3)_2$ | $N(CH_3)_2$ | $CH_2CH_3$ | H(l = O) | Het2 |
| 1669 | $N(CH_2CH_3)_2$ | $N(CH_2CH_3)_2$ | $CH_2CH_3$ | H(l = O) | Het2 |
| 1670 | $N(CH_3)(CH_2CH_3)$ | $N(CH_3)(CH_2CH_3)$ | $CH_2CH_3$ | H(l = O) | Het2 |
| 1671 | O—($CH_2CH_2$)—O | | $CH_2CH_3$ | H(l = O) | Het2 |
| 1672 | O—($CH_2CH_2CH_2$)—O | | $CH_2CH_3$ | H(l = O) | Het2 |
| 1673 | S—($CH_2CH_2$)—S | | $CH_2CH_3$ | H(l = O) | Het2 |
| 1674 | S—($CH_2CH_2CH_2$)—S | | $CH_2CH_3$ | H(l = O) | Het2 |
| 1675 | —$(CH_2)_4$— | | $CH_2CH_3$ | H(l = O) | Het2 |
| 1676 | —$(CH_2)_5$— | | $CH_2CH_3$ | H(l = O) | Het2 |
| 1677 | H | H | $CF_3$ | H(l = O) | Het2 |
| 1678 | $CH_3$ | $CH_3$ | $CF_3$ | H(l = O) | Het2 |
| 1679 | $CH_2CH_3$ | $CH_2CH_3$ | $CF_3$ | H(l = O) | Het2 |
| 1680 | $CH_2CH_2CH_3$ | $CH_2CH_2CH_3$ | $CF_3$ | H(l = O) | Het2 |
| 1681 | $OCH_3$ | $OCH_3$ | $CF_3$ | H(l = O) | Het2 |
| 1682 | $OCH_2CH_3$ | $OCH_2CH_3$ | $CF_3$ | H(l = O) | Het2 |
| 1683 | $OCH_2CH_2CH_3$ | $OCH_2CH_2CH_3$ | $CF_3$ | H(l = O) | Het2 |

TABLE 1-continued

I1a1

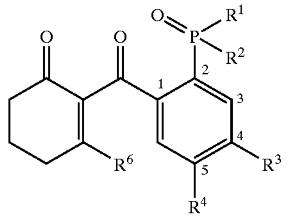

| n | $R^1$ | $R^2$ | $R^3$ | $R^4$ | $R^6$ |
|---|---|---|---|---|---|
| 1684 | $SCH_3$ | $SCH_3$ | $CF_3$ | H(l = O) | Het2 |
| 1685 | $SCH_2CH_3$ | $SCH_2CH_3$ | $CF_3$ | H(l = O) | Het2 |
| 1686 | $N(CH_3)_2$ | $N(CH_3)_2$ | $CF_3$ | H(l = O) | Het2 |
| 1687 | $N(CH_2CH_3)_2$ | $N(CH_2CH_3)_2$ | $CF_3$ | H(l = O) | Het2 |
| 1688 | $N(CH_3)(CH_2CH_3)$ | $N(CH_3)(CH_2CH_3)$ | $CF_3$ | H(l = O) | Het2 |
| 1689 | $O-(CH_2CH_2)-O$ | | $CF_3$ | H(l = O) | Het2 |
| 1690 | $O-(CH_2CH_2CH_2)-O$ | | $CF_3$ | H(l = O) | Het2 |
| 1691 | $S-(CH_2CH_2)-S$ | | $CF_3$ | H(l = O) | Het2 |
| 1692 | $S-(CH_2CH_2CH_2)-S$ | | $CF_3$ | H(l = O) | Het2 |
| 1693 | $-(CH_2)_4-$ | | $CF_3$ | H(l = O) | Het2 |
| 1694 | $-(CH_2)_5-$ | | $CF_3$ | H(l = O) | Het2 |
| 1695 | H | H | $OCH_3$ | H(l = O) | Het2 |
| 1696 | $CH_3$ | $CH_3$ | $OCH_3$ | H(l = O) | Het2 |
| 1697 | $CH_2CH_3$ | $CH_2CH_3$ | $OCH_3$ | H(l = O) | Het2 |
| 1698 | $CH_2CH_2CH_3$ | $CH_2CH_2CH_3$ | $OCH_3$ | H(l = O) | Het2 |
| 1699 | $OCH_3$ | $OCH_3$ | $OCH_3$ | H(l = O) | Het2 |
| 1700 | $OCH_2CH_3$ | $OCH_2CH_3$ | $OCH_3$ | H(l = O) | Het2 |
| 1701 | $OCH_2CH_2CH_3$ | $OCH_2CH_2CH_3$ | $OCH_3$ | H(l = O) | Het2 |
| 1702 | $SCH_3$ | $SCH_3$ | $OCH_3$ | H(l = O) | Het2 |
| 1703 | $SCH_2CH_3$ | $SCH_2CH_3$ | $OCH_3$ | H(l = O) | Het2 |
| 1704 | $N(CH_3)_2$ | $N(CH_3)_2$ | $OCH_3$ | H(l = O) | Het2 |
| 1705 | $N(CH_2CH_3)_2$ | $N(CH_2CH_3)_2$ | $OCH_3$ | H(l = O) | Het2 |
| 1706 | $N(CH_3)(CH_2CH_3)$ | $N(CH_3)(CH_2CH_3)$ | $OCH_3$ | H(l = O) | Het2 |
| 1707 | $O-(CH_2CH_2)-O$ | | $OCH_3$ | H(l = O) | Het2 |
| 1708 | $O-(CH_2CH_2CH_2)-O$ | | $OCH_3$ | H(l = O) | Het2 |
| 1709 | $S-(CH_2CH_2)-S$ | | $OCH_3$ | H(l = O) | Het2 |
| 1710 | $S-(CH_2CH_2CH_2)-S$ | | $OCH_3$ | H(l = O) | Het2 |
| 1711 | $-(CH_2)_4-$ | | $OCH_3$ | H(l = O) | Het2 |
| 1712 | $-(CH_2)_5-$ | | $OCH_3$ | H(l = O) | Het2 |
| 1713 | H | H | $OCH_2CH_3$ | H(l = O) | Het2 |
| 1714 | $CH_3$ | $CH_3$ | $OCH_2CH_3$ | H(l = O) | Het2 |
| 1715 | $CH_2CH_3$ | $CH_2CH_3$ | $OCH_2CH_3$ | H(l = O) | Het2 |
| 1716 | $CH_2CH_2CH_3$ | $CH_2CH_2CH_3$ | $OCH_2CH_3$ | H(l = O) | Het2 |
| 1717 | $OCH_3$ | $OCH_3$ | $OCH_2CH_3$ | H(l = O) | Het2 |
| 1718 | $OCH_2CH_3$ | $OCH_2CH_3$ | $OCH_2CH_3$ | H(l = O) | Het2 |
| 1719 | $OCH_2CH_2CH_3$ | $OCH_2CH_2CH_3$ | $OCH_2CH_3$ | H(l = O) | Het2 |
| 1720 | $SCH_3$ | $SCH_3$ | $OCH_2CH_3$ | H(l = O) | Het2 |
| 1721 | $SCH_2CH_3$ | $SCH_2CH_3$ | $OCH_2CH_3$ | H(l = O) | Het2 |
| 1722 | $N(CH_3)_2$ | $N(CH_3)_2$ | $OCH_2CH_3$ | H(l = O) | Het2 |
| 1723 | $N(CH_2CH_3)_2$ | $N(CH_2CH_3)_2$ | $OCH_2CH_3$ | H(l = O) | Het2 |
| 1724 | $N(CH_3)(CH_2CH_3)$ | $N(CH_3)(CH_2CH_3)$ | $OCH_2CH_3$ | H(l = O) | Het2 |
| 1725 | $O-(CH_2CH_2)-O$ | | $OCH_2CH_3$ | H(l = O) | Het2 |
| 1726 | $O-(CH_2CH_2CH_2)-O$ | | $OCH_2CH_3$ | H(l = O) | Het2 |
| 1727 | $S-(CH_2CH_2)-S$ | | $OCH_2CH_3$ | H(l = O) | Het2 |
| 1728 | $S-(CH_2CH_2CH_2)-S$ | | $OCH_2CH_3$ | H(l = O) | Het2 |
| 1729 | $-(CH_2)_4-$ | | $OCH_2CH_3$ | H(l = O) | Het2 |
| 1730 | $-(CH_2)_5-$ | | $OCH_2CH_3$ | H(l = O) | Het2 |
| 1731 | H | H | $SCH_3$ | H(l = O) | Het2 |
| 1732 | $CH_3$ | $CH_3$ | $SCH_3$ | H(l = O) | Het2 |
| 1733 | $CH_2CH_3$ | $CH_2CH_3$ | $SCH_3$ | H(l = O) | Het2 |
| 1734 | $CH_2CH_2CH_3$ | $CH_2CH_2CH_3$ | $SCH_3$ | H(l = O) | Het2 |
| 1735 | $OCH_3$ | $OCH_3$ | $SCH_3$ | H(l = O) | Het2 |
| 1736 | $OCH_2CH_3$ | $OCH_2CH_3$ | $SCH_3$ | H(l = O) | Het2 |
| 1737 | $OCH_2CH_2CH_3$ | $OCH_2CH_2CH_3$ | $SCH_3$ | H(l = O) | Het2 |
| 1738 | $SCH_3$ | $SCH_3$ | $SCH_3$ | H(l = O) | Het2 |
| 1739 | $SCH_2CH_3$ | $SCH_2CH_3$ | $SCH_3$ | H(l = O) | Het2 |
| 1740 | $N(CH_3)_2$ | $N(CH_3)_2$ | $SCH_3$ | H(l = O) | Het2 |
| 1741 | $N(CH_2CH_3)_2$ | $N(CH_2CH_3)_2$ | $SCH_3$ | H(l = O) | Het2 |
| 1742 | $N(CH_3)(CH_2CH_3)$ | $N(CH_3)(CH_2CH_3)$ | $SCH_3$ | H(l = O) | Het2 |
| 1743 | $O-(CH_2CH_2)-O$ | | $SCH_3$ | H(l = O) | Het2 |
| 1744 | $O-(CH_2CH_2CH_2)-O$ | | $SCH_3$ | H(l = O) | Het2 |
| 1745 | $S-(CH_2CH_2)-S$ | | $SCH_3$ | H(l = O) | Het2 |
| 1746 | $S-(CH_2CH_2CH_2)-S$ | | $SCH_3$ | H(l = O) | Het2 |
| 1747 | $-(CH_2)_4-$ | | $SCH_3$ | H(l = O) | Het2 |

TABLE 1-continued

I1a1

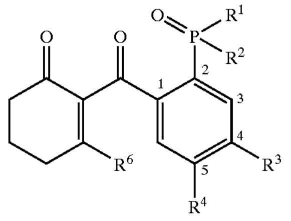

| n | $R^1$ | $R^2$ | $R^3$ | $R^4$ | $R^6$ |
|---|---|---|---|---|---|
| 1748 | $-(CH_2)_5-$ | | $SCH_3$ | H(l = O) | Het2 |
| 1749 | H | H | $SO_2CH_3$ | H(l = O) | Het2 |
| 1750 | $CH_3$ | $CH_3$ | $SO_2CH_3$ | H(l = O) | Het2 |
| 1751 | $CH_2CH_3$ | $CH_2CH_3$ | $SO_2CH_3$ | H(l = O) | Het2 |
| 1752 | $CH_2CH_2CH_3$ | $CH_2CH_2CH_3$ | $SO_2CH_3$ | H(l = O) | Het2 |
| 1753 | $OCH_3$ | $OCH_3$ | $SO_2CH_3$ | H(l = O) | Het2 |
| 1754 | $OCH_2CH_3$ | $OCH_2CH_3$ | $SO_2CH_3$ | H(l = O) | Het2 |
| 1755 | $OCH_2CH_2CH_3$ | $OCH_2CH_2CH_3$ | $SO_2CH_3$ | H(l = O) | Het2 |
| 1756 | $SCH_3$ | $SCH_3$ | $SO_2CH_3$ | H(l = O) | Het2 |
| 1757 | $SCH_2CH_3$ | $SCH_2CH_3$ | $SO_2CH_3$ | H(l = O) | Het2 |
| 1758 | $N(CH_3)_2$ | $N(CH_3)_2$ | $SO_2CH_3$ | H(l = O) | Het2 |
| 1759 | $N(CH_2CH_3)_2$ | $N(CH_2CH_3)_2$ | $SO_2CH_3$ | H(l = O) | Het2 |
| 1760 | $N(CH_3)(CH_2CH_3)$ | $N(CH_3)(CH_2CH_3)$ | $SO_2CH_3$ | H(l = O) | Het2 |
| 1761 | $O-(CH_2CH_2)-O$ | | $SO_2CH_3$ | H(l = O) | Het2 |
| 1762 | $O-(CH_2CH_2CH_2)-O$ | | $SO_2CH_3$ | H(l = O) | Het2 |
| 1763 | $S-(CH_2CH_2)-S$ | | $SO_2CH_3$ | H(l = O) | Het2 |
| 1764 | $S-(CH_2CH_2CH_2)-S$ | | $SO_2CH_3$ | H(l = O) | Het2 |
| 1765 | $-(CH_2)_4-$ | | $SO_2CH_3$ | H(l = O) | Het2 |
| 1766 | $-(CH_2)_5-$ | | $SO_2CH_3$ | H(l = O) | Het2 |
| 1767 | H | H | $PO(OCH_3)_2$ | H(l = O) | Het2 |
| 1768 | $CH_3$ | $CH_3$ | $PO(OCH_3)_2$ | H(l = O) | Het2 |
| 1769 | $CH_2CH_3$ | $CH_2CH_3$ | $PO(OCH_3)_2$ | H(l = O) | Het2 |
| 1770 | $CH_2CH_2CH_3$ | $CH_2CH_2CH_3$ | $PO(OCH_3)_2$ | H(l = O) | Het2 |
| 1771 | $OCH_3$ | $OCH_3$ | $PO(OCH_3)_2$ | H(l = O) | Het2 |
| 1772 | $OCH_2CH_3$ | $OCH_2CH_3$ | $PO(OCH_3)_2$ | H(l = O) | Het2 |
| 1773 | $OCH_2CH_2CH_3$ | $OCH_2CH_2CH_3$ | $PO(OCH_3)_2$ | H(l = O) | Het2 |
| 1774 | $SCH_3$ | $SCH_3$ | $PO(OCH_3)_2$ | H(l = O) | Het2 |
| 1775 | $SCH_2CH_3$ | $SCH_2CH_3$ | $PO(OCH_3)_2$ | H(l = O) | Het2 |
| 1776 | $N(CH_3)_2$ | $N(CH_3)_2$ | $PO(OCH_3)_2$ | H(l = O) | Het2 |
| 1777 | $N(CH_2CH_3)_2$ | $N(CH_2CH_3)_2$ | $PO(OCH_3)_2$ | H(l = O) | Het2 |
| 1778 | $N(CH_3)(CH_2CH_3)$ | $N(CH_3)(CH_2CH_3)$ | $PO(OCH_3)_2$ | H(l = O) | Het2 |
| 1779 | $O-(CH_2CH_2)-O$ | | $PO(OCH_3)_2$ | H(l = O) | Het2 |
| 1780 | $O-(CH_2CH_2CH_2)-O$ | | $PO(OCH_3)_2$ | H(l = O) | Het2 |
| 1781 | $S-(CH_2CH_2)-S$ | | $PO(OCH_3)_2$ | H(l = O) | Het2 |
| 1782 | $S-(CH_2CH_2CH_2)-S$ | | $PO(OCH_3)_2$ | H(l = O) | Het2 |
| 1783 | $-(CH_2)_4-$ | | $PO(OCH_3)_2$ | H(l = O) | Het2 |
| 1784 | $-(CH_2)_5-$ | | $PO(OCH_3)_2$ | H(l = O) | Het2 |
| 1785 | H | H | $PO(OCH_2CH_3)_2$ | H(l = O) | Het2 |
| 1786 | $CH_3$ | $CH_3$ | $PO(OCH_2CH_3)_2$ | H(l = O) | Het2 |
| 1787 | $CH_2CH_3$ | $CH_2CH_3$ | $PO(OCH_2CH_3)_2$ | H(l = O) | Het2 |
| 1788 | $CH_2CH_2CH_3$ | $CH_2CH_2CH_3$ | $PO(OCH_2CH_3)_2$ | H(l = O) | Het2 |
| 1789 | $OCH_3$ | $OCH_3$ | $PO(OCH_2CH_3)_2$ | H(l = O) | Het2 |
| 1790 | $OCH_2CH_3$ | $OCH_2CH_3$ | $PO(OCH_2CH_3)_2$ | H(l = O) | Het2 |
| 1791 | $OCH_2CH_2CH_3$ | $OCH_2CH_2CH_3$ | $PO(OCH_2CH_3)_2$ | H(l = O) | Het2 |
| 1792 | $SCH_3$ | $SCH_3$ | $PO(OCH_2CH_3)_2$ | H(l = O) | Het2 |
| 1793 | $SCH_2CH_3$ | $SCH_2CH_3$ | $PO(OCH_2CH_3)_2$ | H(l = O) | Het2 |
| 1794 | $N(CH_3)_2$ | $N(CH_3)_2$ | $PO(OCH_2CH_3)_2$ | H(l = O) | Het2 |
| 1795 | $N(CH_2CH_3)_2$ | $N(CH_2CH_3)_2$ | $PO(OCH_2CH_3)_2$ | H(l = O) | Het2 |
| 1796 | $N(CH_3)(CH_2CH_3)$ | $N(CH_3)(CH_2CH_3)$ | $PO(OCH_2CH_3)_2$ | H(l = O) | Het2 |
| 1797 | $O-(CH_2CH_2)-O$ | | $PO(OCH_2CH_3)_2$ | H(l = O) | Het2 |
| 1798 | $O-(CH_2CH_2CH_2)-O$ | | $PO(OCH_2CH_3)_2$ | H(l = O) | Het2 |
| 1799 | $S-(CH_2CH_2)-S$ | | $PO(OCH_2CH_3)_2$ | H(l = O) | Het2 |
| 1800 | $S-(CH_2CH_2CH_2)-S$ | | $PO(OCH_2CH_3)_2$ | H(l = O) | Het2 |
| 1801 | $-(CH_2)_4-$ | | $PO(OCH_2CH_3)_2$ | H(l = O) | Het2 |
| 1802 | $-(CH_2)_5-$ | | $PO(OCH_2CH_3)_2$ | H(l = O) | Het2 |
| 1803 | H | H | $PO(CH_3)_2$ | H(l = O) | Het2 |
| 1804 | $CH_3$ | $CH_3$ | $PO(CH_3)_2$ | H(l = O) | Het2 |
| 1805 | $CH_2CH_3$ | $CH_2CH_3$ | $PO(CH_3)_2$ | H(l = O) | Het2 |
| 1806 | $CH_2CH_2CH_3$ | $CH_2CH_2CH_3$ | $PO(CH_3)_2$ | H(l = O) | Het2 |
| 1807 | $OCH_3$ | $OCH_3$ | $PO(CH_3)_2$ | H(l = O) | Het2 |
| 1808 | $OCH_2CH_3$ | $OCH_2CH_3$ | $PO(CH_3)_2$ | H(l = O) | Het2 |
| 1809 | $OCH_2CH_2CH_3$ | $OCH_2CH_2CH_3$ | $PO(CH_3)_2$ | H(l = O) | Het2 |
| 1810 | $SCH_3$ | $SCH_3$ | $PO(CH_3)_2$ | H(l = O) | Het2 |
| 1811 | $SCH_2CH_3$ | $SCH_2CH_3$ | $PO(CH_3)_2$ | H(l = O) | Het2 |

TABLE 1-continued

I1a1

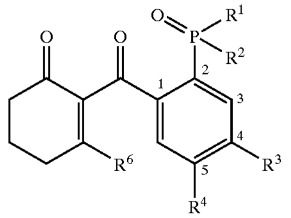

| n | $R^1$ | $R^2$ | $R^3$ | $R^4$ | $R^6$ |
|---|---|---|---|---|---|
| 1812 | $N(CH_3)_2$ | $N(CH_3)_2$ | $PO(CH_3)_2$ | H(l = O) | Het2 |
| 1813 | $N(CH_2CH_3)_2$ | $N(CH_2CH_3)_2$ | $PO(CH_3)_2$ | H(l = O) | Het2 |
| 1814 | $N(CH_3)(CH_2CH_3)$ | $N(CH_3)(CH_2CH_3)$ | $PO(CH_3)_2$ | H(l = O) | Het2 |
| 1815 | $O-(CH_2CH_2)-O$ | | $PO(CH_3)_2$ | H(l = O) | Het2 |
| 1816 | $O-(CH_2CH_2CH_2)-O$ | | $PO(CH_3)_2$ | H(l = O) | Het2 |
| 1817 | $S-(CH_2CH_2)-S$ | | $PO(CH_3)_2$ | H(l = O) | Het2 |
| 1818 | $S-(CH_2CH_2CH_2)-S$ | | $PO(CH_3)_2$ | H(l = O) | Het2 |
| 1819 | $-(CH_2)_4-$ | | $PO(CH_3)_2$ | H(l = O) | Het2 |
| 1820 | $-(CH_2)_5-$ | | $PO(CH_3)_2$ | H(l = O) | Het2 |
| 1821 | H | H | $PO(CH_2CH_3)_2$ | H(l = O) | Het2 |
| 1822 | $CH_3$ | $CH_3$ | $PO(CH_2CH_3)_2$ | H(l = O) | Het2 |
| 1823 | $CH_2CH_3$ | $CH_2CH_3$ | $PO(CH_2CH_3)_2$ | H(l = O) | Het2 |
| 1824 | $CH_2CH_2CH_3$ | $CH_2CH_2CH_3$ | $PO(CH_2CH_3)_2$ | H(l = O) | Het2 |
| 1825 | $OCH_3$ | $OCH_3$ | $PO(CH_2CH_3)_2$ | H(l = O) | Het2 |
| 1826 | $OCH_2CH_3$ | $OCH_2CH_3$ | $PO(CH_2CH_3)_2$ | H(l = O) | Het2 |
| 1827 | $OCH_2CH_2CH_3$ | $OCH_2CH_2CH_3$ | $PO(CH_2CH_3)_2$ | H(l = O) | Het2 |
| 1828 | $SCH_3$ | $SCH_3$ | $PO(CH_2CH_3)_2$ | H(l = O) | Het2 |
| 1829 | $SCH_2CH_3$ | $SCH_2CH_3$ | $PO(CH_2CH_3)_2$ | H(l = O) | Het2 |
| 1830 | $N(CH_3)_2$ | $N(CH_3)_2$ | $PO(CH_2CH_3)_2$ | H(l = O) | Het2 |
| 1831 | $N(CH_2CH_3)_2$ | $N(CH_2CH_3)_2$ | $PO(CH_2CH_3)_2$ | H(l = O) | Het2 |
| 1832 | $N(CH_3)(CH_2CH_3)$ | $N(CH_3)(CH_2CH_3)$ | $PO(CH_2CH_3)_2$ | H(l = O) | Het2 |
| 1833 | $O-(CH_2CH_2)-O$ | | $PO(CH_2CH_3)_2$ | H(l = O) | Het2 |
| 1834 | $O-(CH_2CH_2CH_2)-O$ | | $PO(CH_2CH_3)_2$ | H(l = O) | Het2 |
| 1835 | $S-(CH_2CH_2)-S$ | | $PO(CH_2CH_3)_2$ | H(l = O) | Het2 |
| 1836 | $S-(CH_2CH_2CH_2)-S$ | | $PO(CH_2CH_3)_2$ | H(l = O) | Het2 |
| 1837 | $-(CH_2)_4-$ | | $PO(CH_2CH_3)_2$ | H(l = O) | Het2 |
| 1838 | $-(CH_2)_5-$ | | $PO(CH_2CH_3)_2$ | H(l = O) | Het2 |
| 1839 | H | H | H | H(l = O) | Het3 |
| 1840 | $CH_3$ | $CH_3$ | H | H(l = O) | Het3 |
| 1841 | $CH_2CH_3$ | $CH_2CH_3$ | H | H(l = O) | Het3 |
| 1842 | $CH_2CH_2CH_3$ | $CH_2CH_2CH_3$ | H | H(l = O) | Het3 |
| 1843 | $OCH_3$ | $OCH_3$ | H | H(l = O) | Het3 |
| 1844 | $OCH_2CH_3$ | $OCH_2CH_3$ | H | H(l = O) | Het3 |
| 1845 | $OCH_2CH_2CH_3$ | $OCH_2CH_2CH_3$ | H | H(l = O) | Het3 |
| 1846 | $SCH_3$ | $SCH_3$ | H | H(l = O) | Het3 |
| 1847 | $SCH_2CH_3$ | $SCH_2CH_3$ | H | H(l = O) | Het3 |
| 1848 | $N(CH_3)_2$ | $N(CH_3)_2$ | H | H(l = O) | Het3 |
| 1849 | $N(CH_2CH_3)_2$ | $N(CH_2CH_3)_2$ | H | H(l = O) | Het3 |
| 1850 | $N(CH_3)(CH_2CH_3)$ | $N(CH_3)(CH_2CH_3)$ | H | H(l = O) | Het3 |
| 1851 | $O-(CH_2CH_2)-O$ | | H | H(l = O) | Het3 |
| 1852 | $O-(CH_2CH_2CH_2)-O$ | | H | H(l = O) | Het3 |
| 1853 | $S-(CH_2CH_2)-S$ | | H | H(l = O) | Het3 |
| 1854 | $S-(CH_2CH_2CH_2)-S$ | | H | H(l = O) | Het3 |
| 1855 | $-(CH_2)_4-$ | | H | H(l = O) | Het3 |
| 1856 | $-(CH_2)_5-$ | | H | H(l = O) | Het3 |
| 1857 | H | H | $NO_2$ | H(l = O) | Het3 |
| 1858 | $CH_3$ | $CH_3$ | $NO_2$ | H(l = O) | Het3 |
| 1859 | $CH_2CH_3$ | $CH_2CH_3$ | $NO_2$ | H(l = O) | Het3 |
| 1860 | $CH_2CH_2CH_3$ | $CH_2CH_2CH_3$ | $NO_2$ | H(l = O) | Het3 |
| 1861 | $OCH_3$ | $OCH_3$ | $NO_2$ | H(l = O) | Het3 |
| 1862 | $OCH_2CH_3$ | $OCH_2CH_3$ | $NO_2$ | H(l = O) | Het3 |
| 1863 | $OCH_2CH_2CH_3$ | $OCH_2CH_2CH_3$ | $NO_2$ | H(l = O) | Het3 |
| 1864 | $SCH_3$ | $SCH_3$ | $NO_2$ | H(l = O) | Het3 |
| 1865 | $SCH_2CH_3$ | $SCH_2CH_3$ | $NO_2$ | H(l = O) | Het3 |
| 1866 | $N(CH_3)_2$ | $N(CH_3)_2$ | $NO_2$ | H(l = O) | Het3 |
| 1867 | $N(CH_2CH_3)_2$ | $N(CH_2CH_3)_2$ | $NO_2$ | H(l = O) | Het3 |
| 1868 | $N(CH_3)(CH_2CH_3)$ | $N(CH_3)(CH_2CH_3)$ | $NO_2$ | H(l = O) | Het3 |
| 1869 | $O-(CH_2CH_2)-O$ | | $NO_2$ | H(l = O) | Het3 |
| 1870 | $O-(CH_2CH_2CH_2)-O$ | | $NO_2$ | H(l = O) | Het3 |
| 1871 | $S-(CH_2CH_2)-S$ | | $NO_2$ | H(l = O) | Het3 |
| 1872 | $S-(CH_2CH_2CH_2)-S$ | | $NO_2$ | H(l = O) | Het3 |
| 1873 | $-(CH_2)_4-$ | | $NO_2$ | H(l = O) | Het3 |
| 1874 | $-(CH_2)_5-$ | | $NO_2$ | H(l = O) | Het3 |
| 1875 | H | H | CN | H(l = O) | Het3 |

TABLE 1-continued

I1a1

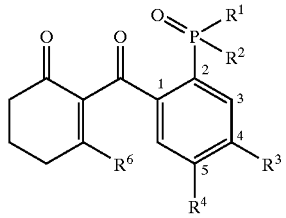

| n | $R^1$ | $R^2$ | $R^3$ | $R^4$ | $R^6$ |
|---|---|---|---|---|---|
| 1876 | $CH_3$ | $CH_3$ | CN | H(l = O) | Het3 |
| 1877 | $CH_2CH_3$ | $CH_2CH_3$ | CN | H(l = O) | Het3 |
| 1878 | $CH_2CH_2CH_3$ | $CH_2CH_2CH_3$ | CN | H(l = O) | Het3 |
| 1879 | $OCH_3$ | $OCH_3$ | CN | H(l = O) | Het3 |
| 1880 | $OCH_2CH_3$ | $OCH_2CH_3$ | CN | H(l = O) | Het3 |
| 1881 | $OCH_2CH_2CH_3$ | $OCH_2CH_2CH_3$ | CN | H(l = O) | Het3 |
| 1882 | $SCH_3$ | $SCH_3$ | CN | H(l = O) | Het3 |
| 1883 | $SCH_2CH_3$ | $SCH_2CH_3$ | CN | H(l = O) | Het3 |
| 1884 | $N(CH_3)_2$ | $N(CH_3)_2$ | CN | H(l = O) | Het3 |
| 1885 | $N(CH_2CH_3)_2$ | $N(CH_2CH_3)_2$ | CN | H(l = O) | Het3 |
| 1886 | $N(CH_3)(CH_2CH_3)$ | $N(CH_3)(CH_2CH_3)$ | CN | H(l = O) | Het3 |
| 1887 | $O—(CH_2CH_2)—O$ | | CN | H(l = O) | Het3 |
| 1888 | $O—(CH_2CH_2CH_2)—O$ | | CN | H(l = O) | Het3 |
| 1889 | $S—(CH_2CH_2)—S$ | | CN | H(l = O) | Het3 |
| 1890 | $S—(CH_2CH_2CH_2)—S$ | | CN | H(l = O) | Het3 |
| 1891 | $—(CH_2)_4—$ | | CN | H(l = O) | Het3 |
| 1892 | $—(CH_2)_5—$ | | CN | H(l = O) | Het3 |
| 1893 | H | H | F | H(l = O) | Het3 |
| 1894 | $CH_3$ | $CH_3$ | F | H(l = O) | Het3 |
| 1895 | $CH_2CH_3$ | $CH_2CH_3$ | F | H(l = O) | Het3 |
| 1896 | $CH_2CH_2CH_3$ | $CH_2CH_2CH_3$ | F | H(l = O) | Het3 |
| 1897 | $OCH_3$ | $OCH_3$ | F | H(l = O) | Het3 |
| 1898 | $OCH_2CH_3$ | $OCH_2CH_3$ | F | H(l = O) | Het3 |
| 1899 | $OCH_2CH_2CH_3$ | $OCH_2CH_2CH_3$ | F | H(l = O) | Het3 |
| 1900 | $SCH_3$ | $SCH_3$ | F | H(l = O) | Het3 |
| 1901 | $SCH_2CH_3$ | $SCH_2CH_3$ | F | H(l = O) | Het3 |
| 1902 | $N(CH_3)_2$ | $N(CH_3)_2$ | F | H(l = O) | Het3 |
| 1903 | $N(CH_2CH_3)_2$ | $N(CH_2CH_3)_2$ | F | H(l = O) | Het3 |
| 1904 | $N(CH_3)(CH_2CH_3)$ | $N(CH_3)(CH_2CH_3)$ | F | H(l = O) | Het3 |
| 1905 | $O—(CH_2CH_2)—O$ | | F | H(l = O) | Het3 |
| 1906 | $O—(CH_2CH_2CH_2)—O$ | | F | H(l = O) | Het3 |
| 1907 | $S—(CH_2CH_2)—S$ | | F | H(l = O) | Het3 |
| 1908 | $S—(CH_2CH_2CH_2)—S$ | | F | H(l = O) | Het3 |
| 1909 | $—(CH_2)_4—$ | | F | H(l = O) | Het3 |
| 1910 | $—(CH_2)_5—$ | | F | H(l = O) | Het3 |
| 1911 | H | H | Cl | H(l = O) | Het3 |
| 1912 | $CH_3$ | $CH_3$ | Cl | H(l = O) | Het3 |
| 1913 | $CH_2CH_3$ | $CH_2CH_3$ | Cl | H(l = O) | Het3 |
| 1914 | $CH_2CH_2CH_3$ | $CH_2CH_2CH_3$ | Cl | H(l = O) | Het3 |
| 1915 | $OCH_3$ | $OCH_3$ | Cl | H(l = O) | Het3 |
| 1916 | $OCH_2CH_3$ | $OCH_2CH_3$ | Cl | H(l = O) | Het3 |
| 1917 | $OCH_2CH_2CH_3$ | $OCH_2CH_2CH_3$ | Cl | H(l = O) | Het3 |
| 1918 | $SCH_3$ | $SCH_3$ | Cl | H(l = O) | Het3 |
| 1919 | $SCH_2CH_3$ | $SCH_2CH_3$ | Cl | H(l = O) | Het3 |
| 1920 | $N(CH_3)_2$ | $N(CH_3)_2$ | Cl | H(l = O) | Het3 |
| 1921 | $N(CH_2CH_3)_2$ | $N(CH_2CH_3)_2$ | Cl | H(l = O) | Het3 |
| 1922 | $N(CH_3)(CH_2CH_3)$ | $N(CH_3)(CH_2CH_3)$ | Cl | H(l = O) | Het3 |
| 1923 | $O—(CH_2CH_2)—O$ | | Cl | H(l = O) | Het3 |
| 1924 | $O—(CH_2CH_2CH_2)—O$ | | Cl | H(l = O) | Het3 |
| 1925 | $S—(CH_2CH_2)—S$ | | Cl | H(l = O) | Het3 |
| 1926 | $S—(CH_2CH_2CH_2)—S$ | | Cl | H(l = O) | Het3 |
| 1927 | $—(CH_2)_4—$ | | Cl | H(l = O) | Het3 |
| 1928 | $—(CH_2)_5—$ | | Cl | H(l = O) | Het3 |
| 1929 | H | H | Br | H(l = O) | Het3 |
| 1930 | $CH_3$ | $CH_3$ | Br | H(l = O) | Het3 |
| 1931 | $CH_2CH_3$ | $CH_2CH_3$ | Br | H(l = O) | Het3 |
| 1932 | $CH_2CH_2CH_3$ | $CH_2CH_2CH_3$ | Br | H(l = O) | Het3 |
| 1933 | $OCH_3$ | $OCH_3$ | Br | H(l = O) | Het3 |
| 1934 | $OCH_2CH_3$ | $OCH_2CH_3$ | Br | H(l = O) | Het3 |
| 1935 | $OCH_2CH_2CH_3$ | $OCH_2CH_2CH_3$ | Br | H(l = O) | Het3 |
| 1936 | $SCH_3$ | $SCH_3$ | Br | H(l = O) | Het3 |
| 1937 | $SCH_2CH_3$ | $SCH_2CH_3$ | Br | H(l = O) | Het3 |
| 1938 | $N(CH_3)_2$ | $N(CH_3)_2$ | Br | H(l = O) | Het3 |
| 1939 | $N(CH_2CH_3)_2$ | $N(CH_2CH_3)_2$ | Br | H(l = O) | Het3 |

TABLE 1-continued

I1a1

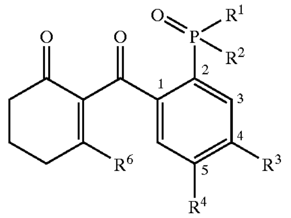

| n | $R^1$ | $R^2$ | $R^3$ | $R^4$ | $R^6$ |
|---|---|---|---|---|---|
| 1940 | $N(CH_3)(CH_2CH_3)$ | $N(CH_3)(CH_2CH_3)$ | Br | H(l = O) | Het3 |
| 1941 | $O—(CH_2CH_2)—O$ | | Br | H(l = O) | Het3 |
| 1942 | $O—(CH_2CH_2CH_2)—O$ | | Br | H(l = O) | Het3 |
| 1943 | $S—(CH_2CH_2)—S$ | | Br | H(l = O) | Het3 |
| 1944 | $S—(CH_2CH_2CH_2)—S$ | | Br | H(l = O) | Het3 |
| 1945 | $—(CH_2)_4—$ | | Br | H(l = O) | Het3 |
| 1946 | $—(CH_2)_5—$ | | Br | H(l = O) | Het3 |
| 1947 | H | H | $CH_3$ | H(l = O) | Het3 |
| 1948 | $CH_3$ | $CH_3$ | $CH_3$ | H(l = O) | Het3 |
| 1949 | $CH_2CH_3$ | $CH_2CH_3$ | $CH_3$ | H(l = O) | Het3 |
| 1950 | $CH_2CH_2CH_3$ | $CH_2CH_2CH_3$ | $CH_3$ | H(l = O) | Het3 |
| 1951 | $OCH_3$ | $OCH_3$ | $CH_3$ | H(l = O) | Het3 |
| 1952 | $OCH_2CH_3$ | $OCH_2CH_3$ | $CH_3$ | H(l = O) | Het3 |
| 1953 | $OCH_2CH_2CH_3$ | $OCH_2CH_2CH_3$ | $CH_3$ | H(l = O) | Het3 |
| 1954 | $SCH_3$ | $SCH_3$ | $CH_3$ | H(l = O) | Het3 |
| 1955 | $SCH_2CH_3$ | $SCH_2CH_3$ | $CH_3$ | H(l = O) | Het3 |
| 1956 | $N(CH_3)_2$ | $N(CH_3)_2$ | $CH_3$ | H(l = O) | Het3 |
| 1957 | $N(CH_2CH_3)_2$ | $N(CH_2CH_3)_2$ | $CH_3$ | H(l = O) | Het3 |
| 1958 | $N(CH_3)(CH_2CH_3)$ | $N(CH_3)(CH_2CH_3)$ | $CH_3$ | H(l = O) | Het3 |
| 1959 | $O—(CH_2CH_2)—O$ | | $CH_3$ | H(l = O) | Het3 |
| 1960 | $O—(CH_2CH_2CH_2)—O$ | | $CH_3$ | H(l = O) | Het3 |
| 1961 | $S—(CH_2CH_2)—S$ | | $CH_3$ | H(l = O) | Het3 |
| 1962 | $S—(CH_2CH_2CH_2)—S$ | | $CH_3$ | H(l = O) | Het3 |
| 1963 | $—(CH_2)_4—$ | | $CH_3$ | H(l = O) | Het3 |
| 1964 | $—(CH_2)_5—$ | | $CH_3$ | H(l = O) | Het3 |
| 1965 | H | H | $CH_2CH_3$ | H(l = O) | Het3 |
| 1966 | $CH_3$ | $CH_3$ | $CH_2CH_3$ | H(l = O) | Het3 |
| 1967 | $CH_2CH_3$ | $CH_2CH_3$ | $CH_2CH_3$ | H(l = O) | Het3 |
| 1968 | $CH_2CH_2CH_3$ | $CH_2CH_2CH_3$ | $CH_2CH_3$ | H(l = O) | Het3 |
| 1969 | $OCH_3$ | $OCH_3$ | $CH_2CH_3$ | H(l = O) | Het3 |
| 1970 | $OCH_2CH_3$ | $OCH_2CH_3$ | $CH_2CH_3$ | H(l = O) | Het3 |
| 1971 | $OCH_2CH_2CH_3$ | $OCH_2CH_2CH_3$ | $CH_2CH_3$ | H(l = O) | Het3 |
| 1972 | $SCH_3$ | $SCH_3$ | $CH_2CH_3$ | H(l = O) | Het3 |
| 1973 | $SCH_2CH_3$ | $SCH_2CH_3$ | $CH_2CH_3$ | H(l = O) | Het3 |
| 1974 | $N(CH_3)_2$ | $N(CH_3)_2$ | $CH_2CH_3$ | H(l = O) | Het3 |
| 1975 | $N(CH_2CH_3)_2$ | $N(CH_2CH_3)_2$ | $CH_2CH_3$ | H(l = O) | Het3 |
| 1976 | $N(CH_3)(CH_2CH_3)$ | $N(CH_3)(CH_2CH_3)$ | $CH_2CH_3$ | H(l = O) | Het3 |
| 1977 | $O—(CH_2CH_2)—O$ | | $CH_2CH_3$ | H(l = O) | Het3 |
| 1978 | $O—(CH_2CH_2CH_2)—O$ | | $CH_2CH_3$ | H(l = O) | Het3 |
| 1979 | $S—(CH_2CH_2)—S$ | | $CH_2CH_3$ | H(l = O) | Het3 |
| 1980 | $S—(CH_2CH_2CH_2)—S$ | | $CH_2CH_3$ | H(l = O) | Het3 |
| 1981 | $—(CH_2)_4—$ | | $CH_2CH_3$ | H(l = O) | Het3 |
| 1982 | $—(CH_2)_5—$ | | $CH_2CH_3$ | H(l = O) | Het3 |
| 1983 | H | H | $CF_3$ | H(l = O) | Het3 |
| 1984 | $CH_3$ | $CH_3$ | $CF_3$ | H(l = O) | Het3 |
| 1985 | $CH_2CH_3$ | $CH_2CH_3$ | $CF_3$ | H(l = O) | Het3 |
| 1986 | $CH_2CH_2CH_3$ | $CH_2CH_2CH_3$ | $CF_3$ | H(l = O) | Het3 |
| 1987 | $OCH_3$ | $OCH_3$ | $CF_3$ | H(l = O) | Het3 |
| 1988 | $OCH_2CH_3$ | $OCH_2CH_3$ | $CF_3$ | H(l = O) | Het3 |
| 1989 | $OCH_2CH_2CH_3$ | $OCH_2CH_2CH_3$ | $CF_3$ | H(l = O) | Het3 |
| 1990 | $SCH_3$ | $SCH_3$ | $CF_3$ | H(l = O) | Het3 |
| 1991 | $SCH_2CH_3$ | $SCH_2CH_3$ | $CF_3$ | H(l = O) | Het3 |
| 1992 | $N(CH_3)_2$ | $N(CH_3)_2$ | $CF_3$ | H(l = O) | Het3 |
| 1993 | $N(CH_2CH_3)_2$ | $N(CH_2CH_3)_2$ | $CF_3$ | H(l = O) | Het3 |
| 1994 | $N(CH_3)(CH_2CH_3)$ | $N(CH_3)(CH_2CH_3)$ | $CF_3$ | H(l = O) | Het3 |
| 1995 | $O—(CH_2CH_2)—O$ | | $CF_3$ | H(l = O) | Het3 |
| 1996 | $O—(CH_2CH_2CH_2)—O$ | | $CF_3$ | H(l = O) | Het3 |
| 1997 | $S—(CH_2CH_2)—S$ | | $CF_3$ | H(l = O) | Het3 |
| 1998 | $S—(CH_2CH_2CH_2)—S$ | | $CF_3$ | H(l = O) | Het3 |
| 1999 | $—(CH_2)_4—$ | | $CF_3$ | H(l = O) | Het3 |
| 2000 | $—(CH_2)_5—$ | | $CF_3$ | H(l = O) | Het3 |
| 2001 | H | H | $OCH_3$ | H(l = O) | Het3 |
| 2002 | $CH_3$ | $CH_3$ | $OCH_3$ | H(l = O) | Het3 |
| 2003 | $CH_2CH_3$ | $CH_2CH_3$ | $OCH_3$ | H(l = O) | Het3 |

TABLE 1-continued

I1a1

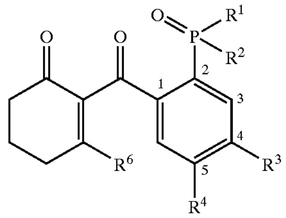

| n | $R^1$ | $R^2$ | $R^3$ | $R^4$ | $R^6$ |
|---|---|---|---|---|---|
| 2004 | $CH_2CH_2CH_3$ | $CH_2CH_2CH_3$ | $OCH_3$ | H(l = O) | Het3 |
| 2005 | $OCH_3$ | $OCH_3$ | $OCH_3$ | H(l = O) | Het3 |
| 2006 | $OCH_2CH_3$ | $OCH_2CH_3$ | $OCH_3$ | H(l = O) | Het3 |
| 2007 | $OCH_2CH_2CH_3$ | $OCH_2CH_2CH_3$ | $OCH_3$ | H(l = O) | Het3 |
| 2008 | $SCH_3$ | $SCH_3$ | $OCH_3$ | H(l = O) | Het3 |
| 2009 | $SCH_2CH_3$ | $SCH_2CH_3$ | $OCH_3$ | H(l = O) | Het3 |
| 2010 | $N(CH_3)_2$ | $N(CH_3)_2$ | $OCH_3$ | H(l = O) | Het3 |
| 2011 | $N(CH_2CH_3)_2$ | $N(CH_2CH_3)_2$ | $OCH_3$ | H(l = O) | Het3 |
| 2012 | $N(CH_3)(CH_2CH_3)$ | $N(CH_3)(CH_2CH_3)$ | $OCH_3$ | H(l = O) | Het3 |
| 2013 | $O—(CH_2CH_2)—O$ | | $OCH_3$ | H(l = O) | Het3 |
| 2014 | $O—(CH_2CH_2CH_2)—O$ | | $OCH_3$ | H(l = O) | Het3 |
| 2015 | $S—(CH_2CH_2)—S$ | | $OCH_3$ | H(l = O) | Het3 |
| 2016 | $S—(CH_2CH_2CH_2)—S$ | | $OCH_3$ | H(l = O) | Het3 |
| 2017 | $—(CH_2)_4—$ | | $OCH_3$ | H(l = O) | Het3 |
| 2018 | $—(CH_2)_5—$ | | $OCH_3$ | H(l = O) | Het3 |
| 2019 | H | H | $OCH_2CH_3$ | H(l = O) | Het3 |
| 2020 | $CH_3$ | $CH_3$ | $OCH_2CH_3$ | H(l = O) | Het3 |
| 2021 | $CH_2CH_3$ | $CH_2CH_3$ | $OCH_2CH_3$ | H(l = O) | Het3 |
| 2022 | $CH_2CH_2CH_3$ | $CH_2CH_2CH_3$ | $OCH_2CH_3$ | H(l = O) | Het3 |
| 2023 | $OCH_3$ | $OCH_3$ | $OCH_2CH_3$ | H(l = O) | Het3 |
| 2024 | $OCH_2CH_3$ | $OCH_2CH_3$ | $OCH_2CH_3$ | H(l = O) | Het3 |
| 2025 | $OCH_2CH_2CH_3$ | $OCH_2CH_2CH_3$ | $OCH_2CH_3$ | H(l = O) | Het3 |
| 2026 | $SCH_3$ | $SCH_3$ | $OCH_2CH_3$ | H(l = O) | Het3 |
| 2027 | $SCH_2CH_3$ | $SCH_2CH_3$ | $OCH_2CH_3$ | H(l = O) | Het3 |
| 2028 | $N(CH_3)_2$ | $N(CH_3)_2$ | $OCH_2CH_3$ | H(l = O) | Het3 |
| 2029 | $N(CH_2CH_3)_2$ | $N(CH_2CH_3)_2$ | $OCH_2CH_3$ | H(l = O) | Het3 |
| 2030 | $N(CH_3)(CH_2CH_3)$ | $N(CH_3)(CH_2CH_3)$ | $OCH_2CH_3$ | H(l = O) | Het3 |
| 2031 | $O—(CH_2CH_2)—O$ | | $OCH_2CH_3$ | H(l = O) | Het3 |
| 2032 | $O—(CH_2CH_2CH_2)—O$ | | $OCH_2CH_3$ | H(l = O) | Het3 |
| 2033 | $S—(CH_2CH_2)—S$ | | $OCH_2CH_3$ | H(l = O) | Het3 |
| 2034 | $S—(CH_2CH_2CH_2)—S$ | | $OCH_2CH_3$ | H(l = O) | Het3 |
| 2035 | $—(CH_2)_4—$ | | $OCH_2CH_3$ | H(l = O) | Het3 |
| 2036 | $—(CH_2)_5—$ | | $OCH_2CH_3$ | H(l = O) | Het3 |
| 2037 | H | H | $SCH_3$ | H(l = O) | Het3 |
| 2038 | $CH_3$ | $CH_3$ | $SCH_3$ | H(l = O) | Het3 |
| 2039 | $CH_2CH_3$ | $CH_2CH_3$ | $SCH_3$ | H(l = O) | Het3 |
| 2040 | $CH_2CH_2CH_3$ | $CH_2CH_2CH_3$ | $SCH_3$ | H(l = O) | Het3 |
| 2041 | $OCH_3$ | $OCH_3$ | $SCH_3$ | H(l = O) | Het3 |
| 2042 | $OCH_2CH_3$ | $OCH_2CH_3$ | $SCH_3$ | H(l = O) | Het3 |
| 2043 | $OCH_2CH_2CH_3$ | $OCH_2CH_2CH_3$ | $SCH_3$ | H(l = O) | Het3 |
| 2044 | $SCH_3$ | $SCH_3$ | $SCH_3$ | H(l = O) | Het3 |
| 2045 | $SCH_2CH_3$ | $SCH_2CH_3$ | $SCH_3$ | H(l = O) | Het3 |
| 2046 | $N(CH_3)_2$ | $N(CH_3)_2$ | $SCH_3$ | H(l = O) | Het3 |
| 2047 | $N(CH_2CH_3)_2$ | $N(CH_2CH_3)_2$ | $SCH_3$ | H(l = O) | Het3 |
| 2048 | $N(CH_3)(CH_2CH_3)$ | $N(CH_3)(CH_2CH_3)$ | $SCH_3$ | H(l = O) | Het3 |
| 2049 | $O—(CH_2CH_2)—O$ | | $SCH_3$ | H(l = O) | Het3 |
| 2050 | $O—(CH_2CH_2CH_2)—O$ | | $SCH_3$ | H(l = O) | Het3 |
| 2051 | $S—(CH_2CH_2)—S$ | | $SCH_3$ | H(l = O) | Het3 |
| 2052 | $S—(CH_2CH_2CH_2)—S$ | | $SCH_3$ | H(l = O) | Het3 |
| 2053 | $—(CH_2)_4—$ | | $SCH_3$ | H(l = O) | Het3 |
| 2054 | $—(CH_2)_5—$ | | $SCH_3$ | H(l = O) | Het3 |
| 2055 | H | H | $SO_2CH_3$ | H(l = O) | Het3 |
| 2056 | $CH_3$ | $CH_3$ | $SO_2CH_3$ | H(l = O) | Het3 |
| 2057 | $CH_2CH_3$ | $CH_2CH_3$ | $SO_2CH_3$ | H(l = O) | Het3 |
| 2058 | $CH_2CH_2CH_3$ | $CH_2CH_2CH_3$ | $SO_2CH_3$ | H(l = O) | Het3 |
| 2059 | $OCH_3$ | $OCH_3$ | $SO_2CH_3$ | H(l = O) | Het3 |
| 2060 | $OCH_2CH_3$ | $OCH_2CH_3$ | $SO_2CH_3$ | H(l = O) | Het3 |
| 2061 | $OCH_2CH_2CH_3$ | $OCH_2CH_2CH_3$ | $SO_2CH_3$ | H(l = O) | Het3 |
| 2062 | $SCH_3$ | $SCH_3$ | $SO_2CH_3$ | H(l = O) | Het3 |
| 2063 | $SCH_2CH_3$ | $SCH_2CH_3$ | $SO_2CH_3$ | H(l = O) | Het3 |
| 2064 | $N(CH_3)_2$ | $N(CH_3)_2$ | $SO_2CH_3$ | H(l = O) | Het3 |
| 2065 | $N(CH_2CH_3)_2$ | $N(CH_2CH_3)_2$ | $SO_2CH_3$ | H(l = O) | Het3 |
| 2066 | $N(CH_3)(CH_2CH_3)$ | $N(CH_3)(CH_2CH_3)$ | $SO_2CH_3$ | H(l = O) | Het3 |
| 2067 | $O—(CH_2CH_2)—O$ | | $SO_2CH_3$ | H(l = O) | Het3 |

TABLE 1-continued

I1a1

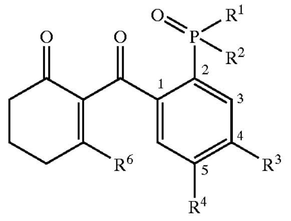

| n | $R^1$ | $R^2$ | $R^3$ | $R^4$ | $R^6$ |
|---|---|---|---|---|---|
| 2068 | O—($CH_2CH_2CH_2$)—O | | $SO_2CH_3$ | H(l = O) | Het3 |
| 2069 | S—($CH_2CH_2$)—S | | $SO_2CH_3$ | H(l = O) | Het3 |
| 2070 | S—($CH_2CH_2CH_2$)—S | | $SO_2CH_3$ | H(l = O) | Het3 |
| 2071 | —$(CH_2)_4$— | | $SO_2CH_3$ | H(l = O) | Het3 |
| 2072 | —$(CH_2)_5$— | | $SO_2CH_3$ | H(l = O) | Het3 |
| 2073 | H | H | $PO(OCH_3)_2$ | H(l = O) | Het3 |
| 2074 | $CH_3$ | $CH_3$ | $PO(OCH_3)_2$ | H(l = O) | Het3 |
| 2075 | $CH_2CH_3$ | $CH_2CH_3$ | $PO(OCH_3)_2$ | H(l = O) | Het3 |
| 2076 | $CH_2CH_2CH_3$ | $CH_2CH_2CH_3$ | $PO(OCH_3)_2$ | H(l = O) | Het3 |
| 2077 | $OCH_3$ | $OCH_3$ | $PO(OCH_3)_2$ | H(l = O) | Het3 |
| 2078 | $OCH_2CH_3$ | $OCH_2CH_3$ | $PO(OCH_3)_2$ | H(l = O) | Het3 |
| 2079 | $OCH_2CH_2CH_3$ | $OCH_2CH_2CH_3$ | $PO(OCH_3)_2$ | H(l = O) | Het3 |
| 2080 | $SCH_3$ | $SCH_3$ | $PO(OCH_3)_2$ | H(l = O) | Het3 |
| 2081 | $SCH_2CH_3$ | $SCH_2CH_3$ | $PO(OCH_3)_2$ | H(l = O) | Het3 |
| 2082 | $N(CH_3)_2$ | $N(CH_3)_2$ | $PO(OCH_3)_2$ | H(l = O) | Het3 |
| 2083 | $N(CH_2CH_3)_2$ | $N(CH_2CH_3)_2$ | $PO(OCH_3)_2$ | H(l = O) | Het3 |
| 2084 | $N(CH_3)(CH_2CH_3)$ | $N(CH_3)(CH_2CH_3)$ | $PO(OCH_3)_2$ | H(l = O) | Het3 |
| 2085 | O—($CH_2CH_2$)—O | | $PO(OCH_3)_2$ | H(l = O) | Het3 |
| 2086 | O—($CH_2CH_2CH_2$)—O | | $PO(OCH_3)_2$ | H(l = O) | Het3 |
| 2087 | S—($CH_2CH_2$)—S | | $PO(OCH_3)_2$ | H(l = O) | Het3 |
| 2088 | S—($CH_2CH_2CH_2$)—S | | $PO(OCH_3)_2$ | H(l = O) | Het3 |
| 2089 | —$(CH_2)_4$— | | $PO(OCH_3)_2$ | H(l = O) | Het3 |
| 2090 | —$(CH_2)_5$— | | $PO(OCH_3)_2$ | H(l = O) | Het3 |
| 2091 | H | H | $PO(OCH_2CH_3)_2$ | H(l = O) | Het3 |
| 2092 | $CH_3$ | $CH_3$ | $PO(OCH_2CH_3)_2$ | H(l = O) | Het3 |
| 2093 | $CH_2CH_3$ | $CH_2CH_3$ | $PO(OCH_2CH_3)_2$ | H(l = O) | Het3 |
| 2094 | $CH_2CH_2CH_3$ | $CH_2CH_2CH_3$ | $PO(OCH_2CH_3)_2$ | H(l = O) | Het3 |
| 2095 | $OCH_3$ | $OCH_3$ | $PO(OCH_2CH_3)_2$ | H(l = O) | Het3 |
| 2096 | $OCH_2CH_3$ | $OCH_2CH_3$ | $PO(OCH_2CH_3)_2$ | H(l = O) | Het3 |
| 2097 | $OCH_2CH_2CH_3$ | $OCH_2CH_2CH_3$ | $PO(OCH_2CH_3)_2$ | H(l = O) | Het3 |
| 2098 | $SCH_3$ | $SCH_3$ | $PO(OCH_2CH_3)_2$ | H(l = O) | Het3 |
| 2099 | $SCH_2CH_3$ | $SCH_2CH_3$ | $PO(OCH_2CH_3)_2$ | H(l = O) | Het3 |
| 2100 | $N(CH_3)_2$ | $N(CH_3)_2$ | $PO(OCH_2CH_3)_2$ | H(l = O) | Het3 |
| 2101 | $N(CH_2CH_3)_2$ | $N(CH_2CH_3)_2$ | $PO(OCH_2CH_3)_2$ | H(l = O) | Het3 |
| 2102 | $N(CH_3)(CH_2CH_3)$ | $N(CH_3)(CH_2CH_3)$ | $PO(OCH_2CH_3)_2$ | H(l = O) | Het3 |
| 2103 | O—($CH_2CH_2$)—O | | $PO(OCH_2CH_3)_2$ | H(l = O) | Het3 |
| 2104 | O—($CH_2CH_2CH_2$)—O | | $PO(OCH_2CH_3)_2$ | H(l = O) | Het3 |
| 2105 | S—($CH_2CH_2$)—S | | $PO(OCH_2CH_3)_2$ | H(l = O) | Het3 |
| 2106 | S—($CH_2CH_2CH_2$)—S | | $PO(OCH_2CH_3)_2$ | H(l = O) | Het3 |
| 2107 | —$(CH_2)_4$— | | $PO(OCH_2CH_3)_2$ | H(l = O) | Het3 |
| 2108 | —$(CH_2)_5$— | | $PO(OCH_2CH_3)_2$ | H(l = O) | Het3 |
| 2109 | H | H | $PO(CH_3)_2$ | H(l = O) | Het3 |
| 2110 | $CH_3$ | $CH_3$ | $PO(CH_3)_2$ | H(l = O) | Het3 |
| 2111 | $CH_2CH_3$ | $CH_2CH_3$ | $PO(CH_3)_2$ | H(l = O) | Het3 |
| 2112 | $CH_2CH_2CH_3$ | $CH_2CH_2CH_3$ | $PO(CH_3)_2$ | H(l = O) | Het3 |
| 2113 | $OCH_3$ | $OCH_3$ | $PO(CH_3)_2$ | H(l = O) | Het3 |
| 2114 | $OCH_2CH_3$ | $OCH_2CH_3$ | $PO(CH_3)_2$ | H(l = O) | Het3 |
| 2115 | $OCH_2CH_2CH_3$ | $OCH_2CH_2CH_3$ | $PO(CH_3)_2$ | H(l = O) | Het3 |
| 2116 | $SCH_3$ | $SCH_3$ | $PO(CH_3)_2$ | H(l = O) | Het3 |
| 2117 | $SCH_2CH_3$ | $SCH_2CH_3$ | $PO(CH_3)_2$ | H(l = O) | Het3 |
| 2118 | $N(CH_3)_2$ | $N(CH_3)_2$ | $PO(CH_3)_2$ | H(l = O) | Het3 |
| 2119 | $N(CH_2CH_3)_2$ | $N(CH_2CH_3)_2$ | $PO(CH_3)_2$ | H(l = O) | Het3 |
| 2120 | $N(CH_3)(CH_2CH_3)$ | $N(CH_3)(CH_2CH_3)$ | $PO(CH_3)_2$ | H(l = O) | Het3 |
| 2121 | O—($CH_2CH_2$)—O | | $PO(CH_3)_2$ | H(l = O) | Het3 |
| 2122 | O—($CH_2CH_2CH_2$)—O | | $PO(CH_3)_2$ | H(l = O) | Het3 |
| 2123 | S—($CH_2CH_2$)—S | | $PO(CH_3)_2$ | H(l = O) | Het3 |
| 2124 | S—($CH_2CH_2CH_2$)—S | | $PO(CH_3)_2$ | H(l = O) | Het3 |
| 2125 | —$(CH_2)_4$— | | $PO(CH_3)_2$ | H(l = O) | Het3 |
| 2126 | —$(CH_2)_5$— | | $PO(CH_3)_2$ | H(l = O) | Het3 |
| 2127 | H | H | $PO(CH_2CH_3)_2$ | H(l = O) | Het3 |
| 2128 | $CH_3$ | $CH_3$ | $PO(CH_2CH_3)_2$ | H(l = O) | Het3 |
| 2129 | $CH_2CH_3$ | $CH_2CH_3$ | $PO(CH_2CH_3)_2$ | H(l = O) | Het3 |
| 2130 | $CH_2CH_2CH_3$ | $CH_2CH_2CH_3$ | $PO(CH_2CH_3)_2$ | H(l = O) | Het3 |
| 2131 | $OCH_3$ | $OCH_3$ | $PO(CH_2CH_3)_2$ | H(l = O) | Het3 |

TABLE 1-continued

I1a1

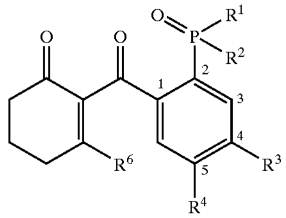

| n | $R^1$ | $R^2$ | $R^3$ | $R^4$ | $R^6$ |
|---|---|---|---|---|---|
| 2132 | $OCH_2CH_3$ | $OCH_2CH_3$ | $PO(CH_2CH_3)_2$ | H(l = O) | Het3 |
| 2133 | $OCH_2CH_2CH_3$ | $OCH_2CH_2CH_3$ | $PO(CH_2CH_3)_2$ | H(l = O) | Het3 |
| 2134 | $SCH_3$ | $SCH_3$ | $PO(CH_2CH_3)_2$ | H(l = O) | Het3 |
| 2135 | $SCH_2CH_3$ | $SCH_2CH_3$ | $PO(CH_2CH_3)_2$ | H(l = O) | Het3 |
| 2136 | $N(CH_3)_2$ | $N(CH_3)_2$ | $PO(CH_2CH_3)_2$ | H(l = O) | Het3 |
| 2137 | $N(CH_2CH_3)_2$ | $N(CH_2CH_3)_2$ | $PO(CH_2CH_3)_2$ | H(l = O) | Het3 |
| 2138 | $N(CH_3)(CH_2CH_3)$ | $N(CH_3)(CH_2CH_3)$ | $PO(CH_2CH_3)_2$ | H(l = O) | Het3 |
| 2139 | $O—(CH_2CH_2)—O$ | | $PO(CH_2CH_3)_2$ | H(l = O) | Het3 |
| 2140 | $O—(CH_2CH_2CH_2)—O$ | | $PO(CH_2CH_3)_2$ | H(l = O) | Het3 |
| 2141 | $S—(CH_2CH_2)—S$ | | $PO(CH_2CH_3)_2$ | H(l = O) | Het3 |
| 2142 | $S—(CH_2CH_2CH_2)—S$ | | $PO(CH_2CH_3)_2$ | H(l = O) | Het3 |
| 2143 | $—(CH_2)_4—$ | | $PO(CH_2CH_3)_2$ | H(l = O) | Het3 |
| 2144 | $—(CH_2)_5—$ | | $PO(CH_2CH_3)_2$ | H(l = O) | Het3 |
| 2145 | H | H | H | $CH_3$ | OH |
| 2146 | $CH_3$ | $CH_3$ | H | $CH_3$ | OH |
| 2147 | $CH_2CH_3$ | $CH_2CH_3$ | H | $CH_3$ | OH |
| 2148 | $CH_2CH_2CH_3$ | $CH_2CH_2CH_3$ | H | $CH_3$ | OH |
| 2149 | $OCH_3$ | $OCH_3$ | H | $CH_3$ | OH |
| 2150 | $OCH_2CH_3$ | $OCH_2CH_3$ | H | $CH_3$ | OH |
| 2151 | $OCH_2CH_2CH_3$ | $OCH_2CH_2CH_3$ | H | $CH_3$ | OH |
| 2152 | $SCH_3$ | $SCH_3$ | H | $CH_3$ | OH |
| 2153 | $SCH_2CH_3$ | $SCH_2CH_3$ | H | $CH_3$ | OH |
| 2154 | $N(CH_3)_2$ | $N(CH_3)_2$ | H | $CH_3$ | OH |
| 2155 | $N(CH_2CH_3)_2$ | $N(CH_2CH_3)_2$ | H | $CH_3$ | OH |
| 2156 | $N(CH_3)(CH_2CH_3)$ | $N(CH_3)(CH_2CH_3)$ | H | $CH_3$ | OH |
| 2157 | $O—(CH_2CH_2)—O$ | | H | $CH_3$ | OH |
| 2158 | $O—(CH_2CH_2CH_2)—O$ | | H | $CH_3$ | OH |
| 2159 | $S—(CH_2CH_2)—S$ | | H | $CH_3$ | OH |
| 2160 | $S—(CH_2CH_2CH_2)—S$ | | H | $CH_3$ | OH |
| 2161 | $—(CH_2)_4—$ | | H | $CH_3$ | OH |
| 2162 | $—(CH_2)_5—$ | | H | $CH_3$ | OH |
| 2163 | H | H | $NO_2$ | $CH_3$ | OH |
| 2164 | $CH_3$ | $CH_3$ | $NO_2$ | $CH_3$ | OH |
| 2165 | $CH_2CH_3$ | $CH_2CH_3$ | $NO_2$ | $CH_3$ | OH |
| 2166 | $CH_2CH_2CH_3$ | $CH_2CH_2CH_3$ | $NO_2$ | $CH_3$ | OH |
| 2167 | $OCH_3$ | $OCH_3$ | $NO_2$ | $CH_3$ | OH |
| 2168 | $OCH_2CH_3$ | $OCH_2CH_3$ | $NO_2$ | $CH_3$ | OH |
| 2169 | $OCH_2CH_2CH_3$ | $OCH_2CH_2CH_3$ | $NO_2$ | $CH_3$ | OH |
| 2170 | $SCH_3$ | $SCH_3$ | $NO_2$ | $CH_3$ | OH |
| 2171 | $SCH_2CH_3$ | $SCH_2CH_3$ | $NO_2$ | $CH_3$ | OH |
| 2172 | $N(CH_3)_2$ | $N(CH_3)_2$ | $NO_2$ | $CH_3$ | OH |
| 2173 | $N(CH_2CH_3)_2$ | $N(CH_2CH_3)_2$ | $NO_2$ | $CH_3$ | OH |
| 2174 | $N(CH_3)(CH_2CH_3)$ | $N(CH_3)(CH_2CH_3)$ | $NO_2$ | $CH_3$ | OH |
| 2175 | $O—(CH_2CH_2)—O$ | | $NO_2$ | $CH_3$ | OH |
| 2176 | $O—(CH_2CH_2CH_2)—O$ | | $NO_2$ | $CH_3$ | OH |
| 2177 | $S—(CH_2CH_2)—S$ | | $NO_2$ | $CH_3$ | OH |
| 2178 | $S—(CH_2CH_2CH_2)—S$ | | $NO_2$ | $CH_3$ | OH |
| 2179 | $—(CH_2)_4—$ | | $NO_2$ | $CH_3$ | OH |
| 2180 | $—(CH_2)_5—$ | | $NO_2$ | $CH_3$ | OH |
| 2181 | H | H | CN | $CH_3$ | OH |
| 2182 | $CH_3$ | $CH_3$ | CN | $CH_3$ | OH |
| 2183 | $CH_2CH_3$ | $CH_2CH_3$ | CN | $CH_3$ | OH |
| 2184 | $CH_2CH_2CH_3$ | $CH_2CH_2CH_3$ | CN | $CH_3$ | OH |
| 2185 | $OCH_3$ | $OCH_3$ | CN | $CH_3$ | OH |
| 2186 | $OCH_2CH_3$ | $OCH_2CH_3$ | CN | $CH_3$ | OH |
| 2187 | $OCH_2CH_2CH_3$ | $OCH_2CH_2CH_3$ | CN | $CH_3$ | OH |
| 2188 | $SCH_3$ | $SCH_3$ | CN | $CH_3$ | OH |
| 2189 | $SCH_2CH_3$ | $SCH_2CH_3$ | CN | $CH_3$ | OH |
| 2190 | $N(CH_3)_2$ | $N(CH_3)_2$ | CN | $CH_3$ | OH |
| 2191 | $N(CH_2CH_3)_2$ | $N(CH_2CH_3)_2$ | CN | $CH_3$ | OH |
| 2192 | $N(CH_3)(CH_2CH_3)$ | $N(CH_3)(CH_2CH_3)$ | CN | $CH_3$ | OH |
| 2193 | $O—(CH_2CH_2)—O$ | | CN | $CH_3$ | OH |
| 2194 | $O—(CH_2CH_2CH_2)—O$ | | CN | $CH_3$ | OH |
| 2195 | $S—(CH_2CH_2)—S$ | | CN | $CH_3$ | OH |

TABLE 1-continued

I1a1

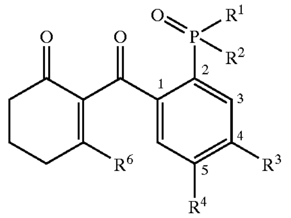

| n | $R^1$ | $R^2$ | $R^3$ | $R^4$ | $R^6$ |
|---|---|---|---|---|---|
| 2196 | S—($CH_2CH_2CH_2$)—S | | CN | $CH_3$ | OH |
| 2197 | —$(CH_2)_4$— | | CN | $CH_3$ | OH |
| 2198 | —$(CH_2)_5$— | | CN | $CH_3$ | OH |
| 2199 | H | H | F | $CH_3$ | OH |
| 2200 | $CH_3$ | $CH_3$ | F | $CH_3$ | OH |
| 2201 | $CH_2CH_3$ | $CH_2CH_3$ | F | $CH_3$ | OH |
| 2202 | $CH_2CH_2CH_3$ | $CH_2CH_2CH_3$ | F | $CH_3$ | OH |
| 2203 | $OCH_3$ | $OCH_3$ | F | $CH_3$ | OH |
| 2204 | $OCH_2CH_3$ | $OCH_2CH_3$ | F | $CH_3$ | OH |
| 2205 | $OCH_2CH_2CH_3$ | $OCH_2CH_2CH_3$ | F | $CH_3$ | OH |
| 2206 | $SCH_3$ | $SCH_3$ | F | $CH_3$ | OH |
| 2207 | $SCH_2CH_3$ | $SCH_2CH_3$ | F | $CH_3$ | OH |
| 2208 | $N(CH_3)_2$ | $N(CH_3)_2$ | F | $CH_3$ | OH |
| 2209 | $N(CH_2CH_3)_2$ | $N(CH_2CH_3)_2$ | F | $CH_3$ | OH |
| 2210 | $N(CH_3)(CH_2CH_3)$ | $N(CH_3)(CH_2CH_3)$ | F | $CH_3$ | OH |
| 2211 | O—($CH_2CH_2$)—O | | F | $CH_3$ | OH |
| 2212 | O—($CH_2CH_2CH_2$)—O | | F | $CH_3$ | OH |
| 2213 | S—($CH_2CH_2$)—S | | F | $CH_3$ | OH |
| 2214 | S—($CH_2CH_2CH_2$)—S | | F | $CH_3$ | OH |
| 2215 | —$(CH_2)_4$— | | F | $CH_3$ | OH |
| 2216 | —$(CH_2)_5$— | | F | $CH_3$ | OH |
| 2217 | H | H | Cl | $CH_3$ | OH |
| 2218 | $CH_3$ | $CH_3$ | Cl | $CH_3$ | OH |
| 2219 | $CH_2CH_3$ | $CH_2CH_3$ | Cl | $CH_3$ | OH |
| 2220 | $CH_2CH_2CH_3$ | $CH_2CH_2CH_3$ | Cl | $CH_3$ | OH |
| 2221 | $OCH_3$ | $OCH_3$ | Cl | $CH_3$ | OH |
| 2222 | $OCH_2CH_3$ | $OCH_2CH_3$ | Cl | $CH_3$ | OH |
| 2223 | $OCH_2CH_2CH_3$ | $OCH_2CH_2CH_3$ | Cl | $CH_3$ | OH |
| 2224 | $SCH_3$ | $SCH_3$ | Cl | $CH_3$ | OH |
| 2225 | $SCH_2CH_3$ | $SCH_2CH_3$ | Cl | $CH_3$ | OH |
| 2226 | $N(CH_3)_2$ | $N(CH_3)_2$ | Cl | $CH_3$ | OH |
| 2227 | $N(CH_2CH_3)_2$ | $N(CH_2CH_3)_2$ | Cl | $CH_3$ | OH |
| 2228 | $N(CH_3)(CH_2CH_3)$ | $N(CH_3)(CH_2CH_3)$ | Cl | $CH_3$ | OH |
| 2229 | O—($CH_2CH_2$)—O | | Cl | $CH_3$ | OH |
| 2230 | O—($CH_2CH_2CH_2$)—O | | Cl | $CH_3$ | OH |
| 2231 | S—($CH_2CH_2$)—S | | Cl | $CH_3$ | OH |
| 2232 | S—($CH_2CH_2CH_2$)—S | | Cl | $CH_3$ | OH |
| 2233 | —$(CH_2)_4$— | | Cl | $CH_3$ | OH |
| 2234 | —$(CH_2)_5$— | | Cl | $CH_3$ | OH |
| 2235 | H | H | Br | $CH_3$ | OH |
| 2236 | $CH_3$ | $CH_3$ | Br | $CH_3$ | OH |
| 2237 | $CH_2CH_3$ | $CH_2CH_3$ | Br | $CH_3$ | OH |
| 2238 | $CH_2CH_2CH_3$ | $CH_2CH_2CH_3$ | Br | $CH_3$ | OH |
| 2239 | $OCH_3$ | $OCH_3$ | Br | $CH_3$ | OH |
| 2240 | $OCH_2CH_3$ | $OCH_2CH_3$ | Br | $CH_3$ | OH |
| 2241 | $OCH_2CH_2CH_3$ | $OCH_2CH_2CH_3$ | Br | $CH_3$ | OH |
| 2242 | $SCH_3$ | $SCH_3$ | Br | $CH_3$ | OH |
| 2243 | $SCH_2CH_3$ | $SCH_2CH_3$ | Br | $CH_3$ | OH |
| 2244 | $N(CH_3)_2$ | $N(CH_3)_2$ | Br | $CH_3$ | OH |
| 2245 | $N(CH_2CH_3)_2$ | $N(CH_2CH_3)_2$ | Br | $CH_3$ | OH |
| 2246 | $N(CH_3)(CH_2CH_3)$ | $N(CH_3)(CH_2CH_3)$ | Br | $CH_3$ | OH |
| 2247 | O—($CH_2CH_2$)—O | | Br | $CH_3$ | OH |
| 2248 | O—($CH_2CH_2CH_2$)—O | | Br | $CH_3$ | OH |
| 2249 | S—($CH_2CH_2$)—S | | Br | $CH_3$ | OH |
| 2250 | S—($CH_2CH_2CH_2$)—S | | Br | $CH_3$ | OH |
| 2251 | —$(CH_2)_4$— | | Br | $CH_3$ | OH |
| 2252 | —$(CH_2)_5$— | | Br | $CH_3$ | OH |
| 2253 | H | H | $CH_3$ | $CH_3$ | OH |
| 2254 | $CH_3$ | $CH_3$ | $CH_3$ | $CH_3$ | OH |
| 2255 | $CH_2CH_3$ | $CH_2CH_3$ | $CH_3$ | $CH_3$ | OH |
| 2256 | $CH_2CH_2CH_3$ | $CH_2CH_2CH_3$ | $CH_3$ | $CH_3$ | OH |
| 2257 | $OCH_3$ | $OCH_3$ | $CH_3$ | $CH_3$ | OH |
| 2258 | $OCH_2CH_3$ | $OCH_2CH_3$ | $CH_3$ | $CH_3$ | OH |
| 2259 | $OCH_2CH_2CH_3$ | $OCH_2CH_2CH_3$ | $CH_3$ | $CH_3$ | OH |

TABLE 1-continued

I1a1

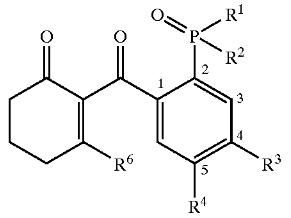

| n | $R^1$ | $R^2$ | $R^3$ | $R^4$ | $R^6$ |
|---|---|---|---|---|---|
| 2260 | $SCH_3$ | $SCH_3$ | $CH_3$ | $CH_3$ | OH |
| 2261 | $SCH_2CH_3$ | $SCH_2CH_3$ | $CH_3$ | $CH_3$ | OH |
| 2262 | $N(CH_3)_2$ | $N(CH_3)_2$ | $CH_3$ | $CH_3$ | OH |
| 2263 | $N(CH_2CH_3)_2$ | $N(CH_2CH_3)_2$ | $CH_3$ | $CH_3$ | OH |
| 2264 | $N(CH_3)(CH_2CH_3)$ | $N(CH_3)(CH_2CH_3)$ | $CH_3$ | $CH_3$ | OH |
| 2265 | $O—(CH_2CH_2)—O$ | | $CH_3$ | $CH_3$ | OH |
| 2266 | $O—(CH_2CH_2CH_2)—O$ | | $CH_3$ | $CH_3$ | OH |
| 2267 | $S—(CH_2CH_2)—S$ | | $CH_3$ | $CH_3$ | OH |
| 2268 | $S—(CH_2CH_2CH_2)—S$ | | $CH_3$ | $CH_3$ | OH |
| 2269 | $—(CH_2)_4—$ | | $CH_3$ | $CH_3$ | OH |
| 2270 | $—(CH_2)_5—$ | | $CH_3$ | $CH_3$ | OH |
| 2271 | H | H | $CH_2CH_3$ | $CH_3$ | OH |
| 2272 | $CH_3$ | $CH_3$ | $CH_2CH_3$ | $CH_3$ | OH |
| 2273 | $CH_2CH_3$ | $CH_2CH_3$ | $CH_2CH_3$ | $CH_3$ | OH |
| 2274 | $CH_2CH_2CH_3$ | $CH_2CH_2CH_3$ | $CH_2CH_3$ | $CH_3$ | OH |
| 2275 | $OCH_3$ | $OCH_3$ | $CH_2CH_3$ | $CH_3$ | OH |
| 2276 | $OCH_2CH_3$ | $OCH_2CH_3$ | $CH_2CH_3$ | $CH_3$ | OH |
| 2277 | $OCH_2CH_2CH_3$ | $OCH_2CH_2CH_3$ | $CH_2CH_3$ | $CH_3$ | OH |
| 2278 | $SCH_3$ | $SCH_3$ | $CH_2CH_3$ | $CH_3$ | OH |
| 2279 | $SCH_2CH_3$ | $SCH_2CH_3$ | $CH_2CH_3$ | $CH_3$ | OH |
| 2280 | $N(CH_3)_2$ | $N(CH_3)_2$ | $CH_2CH_3$ | $CH_3$ | OH |
| 2281 | $N(CH_2CH_3)_2$ | $N(CH_2CH_3)_2$ | $CH_2CH_3$ | $CH_3$ | OH |
| 2282 | $N(CH_3)(CH_2CH_3)$ | $N(CH_3)(CH_2CH_3)$ | $CH_2CH_3$ | $CH_3$ | OH |
| 2283 | $O—(CH_2CH_2)—O$ | | $CH_2CH_3$ | $CH_3$ | OH |
| 2284 | $O—(CH_2CH_2CH_2)—O$ | | $CH_2CH_3$ | $CH_3$ | OH |
| 2285 | $S—(CH_2CH_2)—S$ | | $CH_2CH_3$ | $CH_3$ | OH |
| 2286 | $S—(CH_2CH_2CH_2)—S$ | | $CH_2CH_3$ | $CH_3$ | OH |
| 2287 | $—(CH_2)_4—$ | | $CH_2CH_3$ | $CH_3$ | OH |
| 2288 | $—(CH_2)_5—$ | | $CH_2CH_3$ | $CH_3$ | OH |
| 2289 | H | H | $CF_3$ | $CH_3$ | OH |
| 2290 | $CH_3$ | $CH_3$ | $CF_3$ | $CH_3$ | OH |
| 2291 | $CH_2CH_3$ | $CH_2CH_3$ | $CF_3$ | $CH_3$ | OH |
| 2292 | $CH_2CH_2CH_3$ | $CH_2CH_2CH_3$ | $CF_3$ | $CH_3$ | OH |
| 2293 | $OCH_3$ | $OCH_3$ | $CF_3$ | $CH_3$ | OH |
| 2294 | $OCH_2CH_3$ | $OCH_2CH_3$ | $CF_3$ | $CH_3$ | OH |
| 2295 | $OCH_2CH_2CH_3$ | $OCH_2CH_2CH_3$ | $CF_3$ | $CH_3$ | OH |
| 2296 | $SCH_3$ | $SCH_3$ | $CF_3$ | $CH_3$ | OH |
| 2297 | $SCH_2CH_3$ | $SCH_2CH_3$ | $CF_3$ | $CH_3$ | OH |
| 2298 | $N(CH_3)_2$ | $N(CH_3)_2$ | $CF_3$ | $CH_3$ | OH |
| 2299 | $N(CH_2CH_3)_2$ | $N(CH_2CH_3)_2$ | $CF_3$ | $CH_3$ | OH |
| 2300 | $N(CH_3)(CH_2CH_3)$ | $N(CH_3)(CH_2CH_3)$ | $CF_3$ | $CH_3$ | OH |
| 2301 | $O—(CH_2CH_2)—O$ | | $CF_3$ | $CH_3$ | OH |
| 2302 | $O—(CH_2CH_2CH_2)—O$ | | $CF_3$ | $CH_3$ | OH |
| 2303 | $S—(CH_2CH_2)—S$ | | $CF_3$ | $CH_3$ | OH |
| 2304 | $S—(CH_2CH_2CH_2)—S$ | | $CF_3$ | $CH_3$ | OH |
| 2305 | $—(CH_2)_4—$ | | $CF_3$ | $CH_3$ | OH |
| 2306 | $—(CH_2)_5—$ | | $CF_3$ | $CH_3$ | OH |
| 2307 | H | H | $OCH_3$ | $CH_3$ | OH |
| 2308 | $CH_3$ | $CH_3$ | $OCH_3$ | $CH_3$ | OH |
| 2309 | $CH_2CH_3$ | $CH_2CH_3$ | $OCH_3$ | $CH_3$ | OH |
| 2310 | $CH_2CH_2CH_3$ | $CH_2CH_2CH_3$ | $OCH_3$ | $CH_3$ | OH |
| 2311 | $OCH_3$ | $OCH_3$ | $OCH_3$ | $CH_3$ | OH |
| 2312 | $OCH_2CH_3$ | $OCH_2CH_3$ | $OCH_3$ | $CH_3$ | OH |
| 2313 | $OCH_2CH_2CH_3$ | $OCH_2CH_2CH_3$ | $OCH_3$ | $CH_3$ | OH |
| 2314 | $SCH_3$ | $SCH_3$ | $OCH_3$ | $CH_3$ | OH |
| 2315 | $SCH_2CH_3$ | $SCH_2CH_3$ | $OCH_3$ | $CH_3$ | OH |
| 2316 | $N(CH_3)_2$ | $N(CH_3)_2$ | $OCH_3$ | $CH_3$ | OH |
| 2317 | $N(CH_2CH_3)_2$ | $N(CH_2CH_3)_2$ | $OCH_3$ | $CH_3$ | OH |
| 2318 | $N(CH_3)(CH_2CH_3)$ | $N(CH_3)(CH_2CH_3)$ | $OCH_3$ | $CH_3$ | OH |
| 2319 | $O—(CH_2CH_2)—O$ | | $OCH_3$ | $CH_3$ | OH |
| 2320 | $O—(CH_2CH_2CH_2)—O$ | | $OCH_3$ | $CH_3$ | OH |
| 2321 | $S—(CH_2CH_2)—S$ | | $OCH_3$ | $CH_3$ | OH |
| 2322 | $S—(CH_2CH_2CH_2)—S$ | | $OCH_3$ | $CH_3$ | OH |
| 2323 | $—(CH_2)_4—$ | | $OCH_3$ | $CH_3$ | OH |

TABLE 1-continued

I1a1

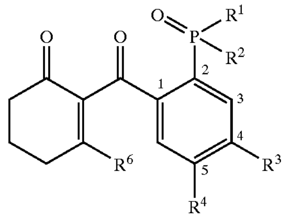

| n | $R^1$ | $R^2$ | $R^3$ | $R^4$ | $R^6$ |
|---|---|---|---|---|---|
| 2324 | $-(CH_2)_5-$ | | $OCH_3$ | $CH_3$ | OH |
| 2325 | H | H | $OCH_2CH_3$ | $CH_3$ | OH |
| 2326 | $CH_3$ | $CH_3$ | $OCH_2CH_3$ | $CH_3$ | OH |
| 2327 | $CH_2CH_3$ | $CH_2CH_3$ | $OCH_2CH_3$ | $CH_3$ | OH |
| 2328 | $CH_2CH_2CH_3$ | $CH_2CH_2CH_3$ | $OCH_2CH_3$ | $CH_3$ | OH |
| 2329 | $OCH_3$ | $OCH_3$ | $OCH_2CH_3$ | $CH_3$ | OH |
| 2330 | $OCH_2CH_3$ | $OCH_2CH_3$ | $OCH_2CH_3$ | $CH_3$ | OH |
| 2331 | $OCH_2CH_2CH_3$ | $OCH_2CH_2CH_3$ | $OCH_2CH_3$ | $CH_3$ | OH |
| 2332 | $SCH_3$ | $SCH_3$ | $OCH_2CH_3$ | $CH_3$ | OH |
| 2333 | $SCH_2CH_3$ | $SCH_2CH_3$ | $OCH_2CH_3$ | $CH_3$ | OH |
| 2334 | $N(CH_3)_2$ | $N(CH_3)_2$ | $OCH_2CH_3$ | $CH_3$ | OH |
| 2335 | $N(CH_2CH_3)_2$ | $N(CH_2CH_3)_2$ | $OCH_2CH_3$ | $CH_3$ | OH |
| 2336 | $N(CH_3)(CH_2CH_3)$ | $N(CH_3)(CH_2CH_3)$ | $OCH_2CH_3$ | $CH_3$ | OH |
| 2337 | $O-(CH_2CH_2)-O$ | | $OCH_2CH_3$ | $CH_3$ | OH |
| 2338 | $O-(CH_2CH_2CH_2)-O$ | | $OCH_2CH_3$ | $CH_3$ | OH |
| 2339 | $S-(CH_2CH_2)-S$ | | $OCH_2CH_3$ | $CH_3$ | OH |
| 2340 | $S-(CH_2CH_2CH_2)-S$ | | $OCH_2CH_3$ | $CH_3$ | OH |
| 2341 | $-(CH_2)_4-$ | | $OCH_2CH_3$ | $CH_3$ | OH |
| 2342 | $-(CH_2)_5-$ | | $OCH_2CH_3$ | $CH_3$ | OH |
| 2343 | H | H | $SCH_3$ | $CH_3$ | OH |
| 2344 | $CH_3$ | $CH_3$ | $SCH_3$ | $CH_3$ | OH |
| 2345 | $CH_2CH_3$ | $CH_2CH_3$ | $SCH_3$ | $CH_3$ | OH |
| 2346 | $CH_2CH_2CH_3$ | $CH_2CH_2CH_3$ | $SCH_3$ | $CH_3$ | OH |
| 2347 | $OCH_3$ | $OCH_3$ | $SCH_3$ | $CH_3$ | OH |
| 2348 | $OCH_2CH_3$ | $OCH_2CH_3$ | $SCH_3$ | $CH_3$ | OH |
| 2349 | $OCH_2CH_2CH_3$ | $OCH_2CH_2CH_3$ | $SCH_3$ | $CH_3$ | OH |
| 2350 | $SCH_3$ | $SCH_3$ | $SCH_3$ | $CH_3$ | OH |
| 2351 | $SCH_2CH_3$ | $SCH_2CH_3$ | $SCH_3$ | $CH_3$ | OH |
| 2352 | $N(CH_3)_2$ | $N(CH_3)_2$ | $SCH_3$ | $CH_3$ | OH |
| 2353 | $N(CH_2CH_3)_2$ | $N(CH_2CH_3)_2$ | $SCH_3$ | $CH_3$ | OH |
| 2354 | $N(CH_3)(CH_2CH_3)$ | $N(CH_3)(CH_2CH_3)$ | $SCH_3$ | $CH_3$ | OH |
| 2355 | $O-(CH_2CH_2)-O$ | | $SCH_3$ | $CH_3$ | OH |
| 2356 | $O-(CH_2CH_2CH_2)-O$ | | $SCH_3$ | $CH_3$ | OH |
| 2357 | $S-(CH_2CH_2)-S$ | | $SCH_3$ | $CH_3$ | OH |
| 2358 | $S-(CH_2CH_2CH_2)-S$ | | $SCH_3$ | $CH_3$ | OH |
| 2359 | $-(CH_2)_4-$ | | $SCH_3$ | $CH_3$ | OH |
| 2360 | $-(CH_2)_5-$ | | $SCH_3$ | $CH_3$ | OH |
| 2361 | H | H | $SO_2CH_3$ | $CH_3$ | OH |
| 2362 | $CH_3$ | $CH_3$ | $SO_2CH_3$ | $CH_3$ | OH |
| 2363 | $CH_2CH_3$ | $CH_2CH_3$ | $SO_2CH_3$ | $CH_3$ | OH |
| 2364 | $CH_2CH_2CH_3$ | $CH_2CH_2CH_3$ | $SO_2CH_3$ | $CH_3$ | OH |
| 2365 | $OCH_3$ | $OCH_3$ | $SO_2CH_3$ | $CH_3$ | OH |
| 2366 | $OCH_2CH_3$ | $OCH_2CH_3$ | $SO_2CH_3$ | $CH_3$ | OH |
| 2367 | $OCH_2CH_2CH_3$ | $OCH_2CH_2CH_3$ | $SO_2CH_3$ | $CH_3$ | OH |
| 2368 | $SCH_3$ | $SCH_3$ | $SO_2CH_3$ | $CH_3$ | OH |
| 2369 | $SCH_2CH_3$ | $SCH_2CH_3$ | $SO_2CH_3$ | $CH_3$ | OH |
| 2370 | $N(CH_3)_2$ | $N(CH_3)_2$ | $SO_2CH_3$ | $CH_3$ | OH |
| 2371 | $N(CH_2CH_3)_2$ | $N(CH_2CH_3)_2$ | $SO_2CH_3$ | $CH_3$ | OH |
| 2372 | $N(CH_3)(CH_2CH_3)$ | $N(CH_3)(CH_2CH_3)$ | $SO_2CH_3$ | $CH_3$ | OH |
| 2373 | $O-(CH_2CH_2)-O$ | | $SO_2CH_3$ | $CH_3$ | OH |
| 2374 | $O-(CH_2CH_2CH_2)-O$ | | $SO_2CH_3$ | $CH_3$ | OH |
| 2375 | $S-(CH_2CH_2)-S$ | | $SO_2CH_3$ | $CH_3$ | OH |
| 2376 | $S-(CH_2CH_2CH_2)-S$ | | $SO_2CH_3$ | $CH_3$ | OH |
| 2377 | $-(CH_2)_4-$ | | $SO_2CH_3$ | $CH_3$ | OH |
| 2378 | $-(CH_2)_5-$ | | $SO_2CH_3$ | $CH_3$ | OH |
| 2379 | H | H | $PO(OCH_3)_2$ | $CH_3$ | OH |
| 2380 | $CH_3$ | $CH_3$ | $PO(OCH_3)_2$ | $CH_3$ | OH |
| 2381 | $CH_2CH_3$ | $CH_2CH_3$ | $PO(OCH_3)_2$ | $CH_3$ | OH |
| 2382 | $CH_2CH_2CH_3$ | $CH_2CH_2CH_3$ | $PO(OCH_3)_2$ | $CH_3$ | OH |
| 2383 | $OCH_3$ | $OCH_3$ | $PO(OCH_3)_2$ | $CH_3$ | OH |
| 2384 | $OCH_2CH_3$ | $OCH_2CH_3$ | $PO(OCH_3)_2$ | $CH_3$ | OH |
| 2385 | $OCH_2CH_2CH_3$ | $OCH_2CH_2CH_3$ | $PO(OCH_3)_2$ | $CH_3$ | OH |
| 2386 | $SCH_3$ | $SCH_3$ | $PO(OCH_3)_2$ | $CH_3$ | OH |
| 2387 | $SCH_2CH_3$ | $SCH_2CH_3$ | $PO(OCH_3)_2$ | $CH_3$ | OH |

TABLE 1-continued

I1a1

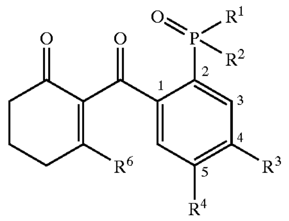

| n | $R^1$ | $R^2$ | $R^3$ | $R^4$ | $R^6$ |
|---|---|---|---|---|---|
| 2388 | $N(CH_3)_2$ | $N(CH_3)_2$ | $PO(OCH_3)_2$ | $CH_3$ | OH |
| 2389 | $N(CH_2CH_3)_2$ | $N(CH_2CH_3)_2$ | $PO(OCH_3)_2$ | $CH_3$ | OH |
| 2390 | $N(CH_3)(CH_2CH_3)$ | $N(CH_3)(CH_2CH_3)$ | $PO(OCH_3)_2$ | $CH_3$ | OH |
| 2391 | $O-(CH_2CH_2)-O$ | | $PO(OCH_3)_2$ | $CH_3$ | OH |
| 2392 | $O-(CH_2CH_2CH_2)-O$ | | $PO(OCH_3)_2$ | $CH_3$ | OH |
| 2393 | $S-(CH_2CH_2)-S$ | | $PO(OCH_3)_2$ | $CH_3$ | OH |
| 2394 | $S-(CH_2CH_2CH_2)-S$ | | $PO(OCH_3)_2$ | $CH_3$ | OH |
| 2395 | $-(CH_2)_4-$ | | $PO(OCH_3)_2$ | $CH_3$ | OH |
| 2396 | $-(CH_2)_5-$ | | $PO(OCH_3)_2$ | $CH_3$ | OH |
| 2397 | H | H | $PO(OCH_2CH_3)_2$ | $CH_3$ | OH |
| 2398 | $CH_3$ | $CH_3$ | $PO(OCH_2CH_3)_2$ | $CH_3$ | OH |
| 2399 | $CH_2CH_3$ | $CH_2CH_3$ | $PO(OCH_2CH_3)_2$ | $CH_3$ | OH |
| 2400 | $CH_2CH_2CH_3$ | $CH_2CH_2CH_3$ | $PO(OCH_2CH_3)_2$ | $CH_3$ | OH |
| 2401 | $OCH_3$ | $OCH_3$ | $PO(OCH_2CH_3)_2$ | $CH_3$ | OH |
| 2402 | $OCH_2CH_3$ | $OCH_2CH_3$ | $PO(OCH_2CH_3)_2$ | $CH_3$ | OH |
| 2403 | $OCH_2CH_2CH_3$ | $OCH_2CH_2CH_3$ | $PO(OCH_2CH_3)_2$ | $CH_3$ | OH |
| 2404 | $SCH_3$ | $SCH_3$ | $PO(OCH_2CH_3)_2$ | $CH_3$ | OH |
| 2405 | $SCH_2CH_3$ | $SCH_2CH_3$ | $PO(OCH_2CH_3)_2$ | $CH_3$ | OH |
| 2406 | $N(CH_3)_2$ | $N(CH_3)_2$ | $PO(OCH_2CH_3)_2$ | $CH_3$ | OH |
| 2407 | $N(CH_2CH_3)_2$ | $N(CH_2CH_3)_2$ | $PO(OCH_2CH_3)_2$ | $CH_3$ | OH |
| 2408 | $N(CH_3)(CH_2CH_3)$ | $N(CH_3)(CH_2CH_3)$ | $PO(OCH_2CH_3)_2$ | $CH_3$ | OH |
| 2409 | $O-(CH_2CH_2)-O$ | | $PO(OCH_2CH_3)_2$ | $CH_3$ | OH |
| 2410 | $O-(CH_2CH_2CH_2)-O$ | | $PO(OCH_2CH_3)_2$ | $CH_3$ | OH |
| 2411 | $S-(CH_2CH_2)-S$ | | $PO(OCH_2CH_3)_2$ | $CH_3$ | OH |
| 2412 | $S-(CH_2CH_2CH_2)-S$ | | $PO(OCH_2CH_3)_2$ | $CH_3$ | OH |
| 2413 | $-(CH_2)_4-$ | | $PO(OCH_2CH_3)_2$ | $CH_3$ | OH |
| 2414 | $-(CH_2)_5-$ | | $PO(OCH_2CH_3)_2$ | $CH_3$ | OH |
| 2415 | H | H | $PO(CH_3)_2$ | $CH_3$ | OH |
| 2416 | $CH_3$ | $CH_3$ | $PO(CH_3)_2$ | $CH_3$ | OH |
| 2417 | $CH_2CH_3$ | $CH_2CH_3$ | $PO(CH_3)_2$ | $CH_3$ | OH |
| 2418 | $CH_2CH_2CH_3$ | $CH_2CH_2CH_3$ | $PO(CH_3)_2$ | $CH_3$ | OH |
| 2419 | $OCH_3$ | $OCH_3$ | $PO(CH_3)_2$ | $CH_3$ | OH |
| 2420 | $OCH_2CH_3$ | $OCH_2CH_3$ | $PO(CH_3)_2$ | $CH_3$ | OH |
| 2421 | $OCH_2CH_2CH_3$ | $OCH_2CH_2CH_3$ | $PO(CH_3)_2$ | $CH_3$ | OH |
| 2422 | $SCH_3$ | $SCH_3$ | $PO(CH_3)_2$ | $CH_3$ | OH |
| 2423 | $SCH_2CH_3$ | $SCH_2CH_3$ | $PO(CH_3)_2$ | $CH_3$ | OH |
| 2424 | $N(CH_3)_2$ | $N(CH_3)_2$ | $PO(CH_3)_2$ | $CH_3$ | OH |
| 2425 | $N(CH_2CH_3)_2$ | $N(CH_2CH_3)_2$ | $PO(CH_3)_2$ | $CH_3$ | OH |
| 2426 | $N(CH_3)(CH_2CH_3)$ | $N(CH_3)(CH_2CH_3)$ | $PO(CH_3)_2$ | $CH_3$ | OH |
| 2427 | $O-(CH_2CH_2)-O$ | | $PO(CH_3)_2$ | $CH_3$ | OH |
| 2428 | $O-(CH_2CH_2CH_2)-O$ | | $PO(CH_3)_2$ | $CH_3$ | OH |
| 2429 | $S-(CH_2CH_2)-S$ | | $PO(CH_3)_2$ | $CH_3$ | OH |
| 2430 | $S-(CH_2CH_2CH_2)-S$ | | $PO(CH_3)_2$ | $CH_3$ | OH |
| 2431 | $-(CH_2)_4-$ | | $PO(CH_3)_2$ | $CH_3$ | OH |
| 2432 | $-(CH_2)_5-$ | | $PO(CH_3)_2$ | $CH_3$ | OH |
| 2433 | H | H | $PO(CH_2CH_3)_2$ | $CH_3$ | OH |
| 2434 | $CH_3$ | $CH_3$ | $PO(CH_2CH_3)_2$ | $CH_3$ | OH |
| 2435 | $CH_2CH_3$ | $CH_2CH_3$ | $PO(CH_2CH_3)_2$ | $CH_3$ | OH |
| 2436 | $CH_2CH_2CH_3$ | $CH_2CH_2CH_3$ | $PO(CH_2CH_3)_2$ | $CH_3$ | OH |
| 2437 | $OCH_3$ | $OCH_3$ | $PO(CH_2CH_3)_2$ | $CH_3$ | OH |
| 2438 | $OCH_2CH_3$ | $OCH_2CH_3$ | $PO(CH_2CH_3)_2$ | $CH_3$ | OH |
| 2439 | $OCH_2CH_2CH_3$ | $OCH_2CH_2CH_3$ | $PO(CH_2CH_3)_2$ | $CH_3$ | OH |
| 2440 | $SCH_3$ | $SCH_3$ | $PO(CH_2CH_3)_2$ | $CH_3$ | OH |
| 2441 | $SCH_2CH_3$ | $SCH_2CH_3$ | $PO(CH_2CH_3)_2$ | $CH_3$ | OH |
| 2442 | $N(CH_3)_2$ | $N(CH_3)_2$ | $PO(CH_2CH_3)_2$ | $CH_3$ | OH |
| 2443 | $N(CH_2CH_3)_2$ | $N(CH_2CH_3)_2$ | $PO(CH_2CH_3)_2$ | $CH_3$ | OH |
| 2444 | $N(CH_3)(CH_2CH_3)$ | $N(CH_3)(CH_2CH_3)$ | $PO(CH_2CH_3)_2$ | $CH_3$ | OH |
| 2445 | $O-(CH_2CH_2)-O$ | | $PO(CH_2CH_3)_2$ | $CH_3$ | OH |
| 2446 | $O-(CH_2CH_2CH_2)-O$ | | $PO(CH_2CH_3)_2$ | $CH_3$ | OH |
| 2447 | $S-(CH_2CH_2)-S$ | | $PO(CH_2CH_3)_2$ | $CH_3$ | OH |
| 2448 | $S-(CH_2CH_2CH_2)-S$ | | $PO(CH_2CH_3)_2$ | $CH_3$ | OH |
| 2449 | $-(CH_2)_4-$ | | $PO(CH_2CH_3)_2$ | $CH_3$ | OH |
| 2450 | $-(CH_2)_5-$ | | $PO(CH_2CH_3)_2$ | $CH_3$ | OH |
| 2451 | H | H | H | $CH_3$ | $OCOC_6H_5$ |

TABLE 1-continued

I1a1

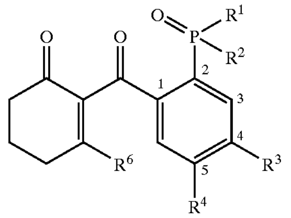

| n | $R^1$ | $R^2$ | $R^3$ | $R^4$ | $R^6$ |
|---|---|---|---|---|---|
| 2452 | $CH_3$ | $CH_3$ | H | $CH_3$ | $OCOC_6H_5$ |
| 2453 | $CH_2CH_3$ | $CH_2CH_3$ | H | $CH_3$ | $OCOC_6H_5$ |
| 2454 | $CH_2CH_2CH_3$ | $CH_2CH_2CH_3$ | H | $CH_3$ | $OCOC_6H_5$ |
| 2455 | $OCH_3$ | $OCH_3$ | H | $CH_3$ | $OCOC_6H_5$ |
| 2456 | $OCH_2CH_3$ | $OCH_2CH_3$ | H | $CH_3$ | $OCOC_6H_5$ |
| 2457 | $OCH_2CH_2CH_3$ | $OCH_2CH_2CH_3$ | H | $CH_3$ | $OCOC_6H_5$ |
| 2458 | $SCH_3$ | $SCH_3$ | H | $CH_3$ | $OCOC_6H_5$ |
| 2459 | $SCH_2CH_3$ | $SCH_2CH_3$ | H | $CH_3$ | $OCOC_6H_5$ |
| 2460 | $N(CH_3)_2$ | $N(CH_3)_2$ | H | $CH_3$ | $OCOC_6H_5$ |
| 2461 | $N(CH_2CH_3)_2$ | $N(CH_2CH_3)_2$ | H | $CH_3$ | $OCOC_6H_5$ |
| 2462 | $N(CH_3)(CH_2CH_3)$ | $N(CH_3)(CH_2CH_3)$ | H | $CH_3$ | $OCOC_6H_5$ |
| 2463 | $O—(CH_2CH_2)—O$ | | H | $CH_3$ | $OCOC_6H_5$ |
| 2464 | $O—(CH_2CH_2CH_2)—O$ | | H | $CH_3$ | $OCOC_6H_5$ |
| 2465 | $S—(CH_2CH_2)—S$ | | H | $CH_3$ | $OCOC_6H_5$ |
| 2466 | $S—(CH_2CH_2CH_2)—S$ | | H | $CH_3$ | $OCOC_6H_5$ |
| 2467 | $—(CH_2)_4—$ | | H | $CH_3$ | $OCOC_6H_5$ |
| 2468 | $—(CH_2)_5—$ | | H | $CH_3$ | $OCOC_6H_5$ |
| 2469 | H | H | $NO_2$ | $CH_3$ | $OCOC_6H_5$ |
| 2470 | $CH_3$ | $CH_3$ | $NO_2$ | $CH_3$ | $OCOC_6H_5$ |
| 2471 | $CH_2CH_3$ | $CH_2CH_3$ | $NO_2$ | $CH_3$ | $OCOC_6H_5$ |
| 2472 | $CH_2CH_2CH_3$ | $CH_2CH_2CH_3$ | $NO_2$ | $CH_3$ | $OCOC_6H_5$ |
| 2473 | $OCH_3$ | $OCH_3$ | $NO_2$ | $CH_3$ | $OCOC_6H_5$ |
| 2474 | $OCH_2CH_3$ | $OCH_2CH_3$ | $NO_2$ | $CH_3$ | $OCOC_6H_5$ |
| 2475 | $OCH_2CH_2CH_3$ | $OCH_2CH_2CH_3$ | $NO_2$ | $CH_3$ | $OCOC_6H_5$ |
| 2476 | $SCH_3$ | $SCH_3$ | $NO_2$ | $CH_3$ | $OCOC_6H_5$ |
| 2477 | $SCH_2CH_3$ | $SCH_2CH_3$ | $NO_2$ | $CH_3$ | $OCOC_6H_5$ |
| 2478 | $N(CH_3)_2$ | $N(CH_3)_2$ | $NO_2$ | $CH_3$ | $OCOC_6H_5$ |
| 2479 | $N(CH_2CH_3)_2$ | $N(CH_2CH_3)_2$ | $NO_2$ | $CH_3$ | $OCOC_6H_5$ |
| 2480 | $N(CH_3)(CH_2CH_3)$ | $N(CH_3)(CH_2CH_3)$ | $NO_2$ | $CH_3$ | $OCOC_6H_5$ |
| 2481 | $O—(CH_2CH_2)—O$ | | $NO_2$ | $CH_3$ | $OCOC_6H_5$ |
| 2482 | $O—(CH_2CH_2CH_2)—O$ | | $NO_2$ | $CH_3$ | $OCOC_6H_5$ |
| 2483 | $S—(CH_2CH_2)—S$ | | $NO_2$ | $CH_3$ | $OCOC_6H_5$ |
| 2484 | $S—(CH_2CH_2CH_2)—S$ | | $NO_2$ | $CH_3$ | $OCOC_6H_5$ |
| 2485 | $—(CH_2)_4—$ | | $NO_2$ | $CH_3$ | $OCOC_6H_5$ |
| 2486 | $—(CH_2)_5—$ | | $NO_2$ | $CH_3$ | $OCOC_6H_5$ |
| 2487 | H | H | CN | $CH_3$ | $OCOC_6H_5$ |
| 2488 | $CH_3$ | $CH_3$ | CN | $CH_3$ | $OCOC_6H_5$ |
| 2489 | $CH_2CH_3$ | $CH_2CH_3$ | CN | $CH_3$ | $OCOC_6H_5$ |
| 2490 | $CH_2CH_2CH_3$ | $CH_2CH_2CH_3$ | CN | $CH_3$ | $OCOC_6H_5$ |
| 2491 | $OCH_3$ | $OCH_3$ | CN | $CH_3$ | $OCOC_6H_5$ |
| 2492 | $OCH_2CH_3$ | $OCH_2CH_3$ | CN | $CH_3$ | $OCOC_6H_5$ |
| 2493 | $OCH_2CH_2CH_3$ | $OCH_2CH_2CH_3$ | CN | $CH_3$ | $OCOC_6H_5$ |
| 2494 | $SCH_3$ | $SCH_3$ | CN | $CH_3$ | $OCOC_6H_5$ |
| 2495 | $SCH_2CH_3$ | $SCH_2CH_3$ | CN | $CH_3$ | $OCOC_6H_5$ |
| 2496 | $N(CH_3)_2$ | $N(CH_3)_2$ | CN | $CH_3$ | $OCOC_6H_5$ |
| 2497 | $N(CH_2CH_3)_2$ | $N(CH_2CH_3)_2$ | CN | $CH_3$ | $OCOC_6H_5$ |
| 2498 | $N(CH_3)(CH_2CH_3)$ | $N(CH_3)(CH_2CH_3)$ | CN | $CH_3$ | $OCOC_6H_5$ |
| 2499 | $O—(CH_2CH_2)—O$ | | CN | $CH_3$ | $OCOC_6H_5$ |
| 2500 | $O—(CH_2CH_2CH_2)—O$ | | CN | $CH_3$ | $OCOC_6H_5$ |
| 2501 | $S—(CH_2CH_2)—S$ | | CN | $CH_3$ | $OCOC_6H_5$ |
| 2502 | $S—(CH_2CH_2CH_2)—S$ | | CN | $CH_3$ | $OCOC_6H_5$ |
| 2503 | $—(CH_2)_4—$ | | CN | $CH_3$ | $OCOC_6H_5$ |
| 2504 | $—(CH_2)_5—$ | | CN | $CH_3$ | $OCOC_6H_5$ |
| 2505 | H | H | F | $CH_3$ | $OCOC_6H_5$ |
| 2506 | $CH_3$ | $CH_3$ | F | $CH_3$ | $OCOC_6H_5$ |
| 2507 | $CH_2CH_3$ | $CH_2CH_3$ | F | $CH_3$ | $OCOC_6H_5$ |
| 2508 | $CH_2CH_2CH_3$ | $CH_2CH_2CH_3$ | F | $CH_3$ | $OCOC_6H_5$ |
| 2509 | $OCH_3$ | $OCH_3$ | F | $CH_3$ | $OCOC_6H_5$ |
| 2510 | $OCH_2CH_3$ | $OCH_2CH_3$ | F | $CH_3$ | $OCOC_6H_5$ |
| 2511 | $OCH_2CH_2CH_3$ | $OCH_2CH_2CH_3$ | F | $CH_3$ | $OCOC_6H_5$ |
| 2512 | $SCH_3$ | $SCH_3$ | F | $CH_3$ | $OCOC_6H_5$ |
| 2513 | $SCH_2CH_3$ | $SCH_2CH_3$ | F | $CH_3$ | $OCOC_6H_5$ |
| 2514 | $N(CH_3)_2$ | $N(CH_3)_2$ | F | $CH_3$ | $OCOC_6H_5$ |
| 2515 | $N(CH_2CH_3)_2$ | $N(CH_2CH_3)_2$ | F | $CH_3$ | $OCOC_6H_5$ |

TABLE 1-continued

I1a1

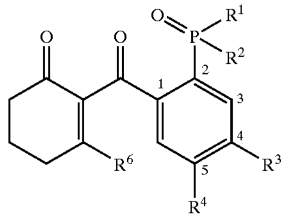

| n | $R^1$ | $R^2$ | $R^3$ | $R^4$ | $R^6$ |
|---|---|---|---|---|---|
| 2516 | $N(CH_3)(CH_2CH_3)$ | $N(CH_3)(CH_2CH_3)$ | F | $CH_3$ | $OCOC_6H_5$ |
| 2517 | $O—(CH_2CH_2)—O$ | | F | $CH_3$ | $OCOC_6H_5$ |
| 2518 | $O—(CH_2CH_2CH_2)—O$ | | F | $CH_3$ | $OCOC_6H_5$ |
| 2519 | $S—(CH_2CH_2)—S$ | | F | $CH_3$ | $OCOC_6H_5$ |
| 2520 | $S—(CH_2CH_2CH_2)—S$ | | F | $CH_3$ | $OCOC_6H_5$ |
| 2521 | $—(CH_2)_4—$ | | F | $CH_3$ | $OCOC_6H_5$ |
| 2522 | $—(CH_2)_5—$ | | F | $CH_3$ | $OCOC_6H_5$ |
| 2523 | H | H | Cl | $CH_3$ | $OCOC_6H_5$ |
| 2524 | $CH_3$ | $CH_3$ | Cl | $CH_3$ | $OCOC_6H_5$ |
| 2525 | $CH_2CH_3$ | $CH_2CH_3$ | Cl | $CH_3$ | $OCOC_6H_5$ |
| 2526 | $CH_2CH_2CH_3$ | $CH_2CH_2CH_3$ | Cl | $CH_3$ | $OCOC_6H_5$ |
| 2527 | $OCH_3$ | $OCH_3$ | Cl | $CH_3$ | $OCOC_6H_5$ |
| 2528 | $OCH_2CH_3$ | $OCH_2CH_3$ | Cl | $CH_3$ | $OCOC_6H_5$ |
| 2529 | $OCH_2CH_2CH_3$ | $OCH_2CH_2CH_3$ | Cl | $CH_3$ | $OCOC_6H_5$ |
| 2530 | $SCH_3$ | $SCH_3$ | Cl | $CH_3$ | $OCOC_6H_5$ |
| 2531 | $SCH_2CH_3$ | $SCH_2CH_3$ | Cl | $CH_3$ | $OCOC_6H_5$ |
| 2532 | $N(CH_3)_2$ | $N(CH_3)_2$ | Cl | $CH_3$ | $OCOC_6H_5$ |
| 2533 | $N(CH_2CH_3)_2$ | $N(CH_2CH_3)_2$ | Cl | $CH_3$ | $OCOC_6H_5$ |
| 2534 | $N(CH_3)(CH_2CH_3)$ | $N(CH_3)(CH_2CH_3)$ | Cl | $CH_3$ | $OCOC_6H_5$ |
| 2535 | $O—(CH_2CH_2)—O$ | | Cl | $CH_3$ | $OCOC_6H_5$ |
| 2536 | $O—(CH_2CH_2CH_2)—O$ | | Cl | $CH_3$ | $OCOC_6H_5$ |
| 2537 | $S—(CH_2CH_2)—S$ | | Cl | $CH_3$ | $OCOC_6H_5$ |
| 2538 | $S—(CH_2CH_2CH_2)—S$ | | Cl | $CH_3$ | $OCOC_6H_5$ |
| 2539 | $—(CH_2)_4—$ | | Cl | $CH_3$ | $OCOC_6H_5$ |
| 2540 | $—(CH_2)_5—$ | | Cl | $CH_3$ | $OCOC_6H_5$ |
| 2541 | H | H | Br | $CH_3$ | $OCOC_6H_5$ |
| 2542 | $CH_3$ | $CH_3$ | Br | $CH_3$ | $OCOC_6H_5$ |
| 2543 | $CH_2CH_3$ | $CH_2CH_3$ | Br | $CH_3$ | $OCOC_6H_5$ |
| 2544 | $CH_2CH_2CH_3$ | $CH_2CH_2CH_3$ | Br | $CH_3$ | $OCOC_6H_5$ |
| 2545 | $OCH_3$ | $OCH_3$ | Br | $CH_3$ | $OCOC_6H_5$ |
| 2546 | $OCH_2CH_3$ | $OCH_2CH_3$ | Br | $CH_3$ | $OCOC_6H_5$ |
| 2547 | $OCH_2CH_2CH_3$ | $OCH_2CH_2CH_3$ | Br | $CH_3$ | $OCOC_6H_5$ |
| 2548 | $SCH_3$ | $SCH_3$ | Br | $CH_3$ | $OCOC_6H_5$ |
| 2549 | $SCH_2CH_3$ | $SCH_2CH_3$ | Br | $CH_3$ | $OCOC_6H_5$ |
| 2550 | $N(CH_3)_2$ | $N(CH_3)_2$ | Br | $CH_3$ | $OCOC_6H_5$ |
| 2551 | $N(CH_2CH_3)_2$ | $N(CH_2CH_3)_2$ | Br | $CH_3$ | $OCOC_6H_5$ |
| 2552 | $N(CH_3)(CH_2CH_3)$ | $N(CH_3)(CH_2CH_3)$ | Br | $CH_3$ | $OCOC_6H_5$ |
| 2553 | $O—(CH_2CH_2)—O$ | | Br | $CH_3$ | $OCOC_6H_5$ |
| 2554 | $O—(CH_2CH_2CH_2)—O$ | | Br | $CH_3$ | $OCOC_6H_5$ |
| 2555 | $S—(CH_2CH_2)—S$ | | Br | $CH_3$ | $OCOC_6H_5$ |
| 2556 | $S—(CH_2CH_2CH_2)—S$ | | Br | $CH_3$ | $OCOC_6H_5$ |
| 2557 | $—(CH_2)_4—$ | | Br | $CH_3$ | $OCOC_6H_5$ |
| 2558 | $—(CH_2)_5—$ | | Br | $CH_3$ | $OCOC_6H_5$ |
| 2559 | H | H | $CH_3$ | $CH_3$ | $OCOC_6H_5$ |
| 2560 | $CH_3$ | $CH_3$ | $CH_3$ | $CH_3$ | $OCOC_6H_5$ |
| 2561 | $CH_2CH_3$ | $CH_2CH_3$ | $CH_3$ | $CH_3$ | $OCOC_6H_5$ |
| 2562 | $CH_2CH_2CH_3$ | $CH_2CH_2CH_3$ | $CH_3$ | $CH_3$ | $OCOC_6H_5$ |
| 2563 | $OCH_3$ | $OCH_3$ | $CH_3$ | $CH_3$ | $OCOC_6H_5$ |
| 2564 | $OCH_2CH_3$ | $OCH_2CH_3$ | $CH_3$ | $CH_3$ | $OCOC_6H_5$ |
| 2565 | $OCH_2CH_2CH_3$ | $OCH_2CH_2CH_3$ | $CH_3$ | $CH_3$ | $OCOC_6H_5$ |
| 2566 | $SCH_3$ | $SCH_3$ | $CH_3$ | $CH_3$ | $OCOC_6H_5$ |
| 2567 | $SCH_2CH_3$ | $SCH_2CH_3$ | $CH_3$ | $CH_3$ | $OCOC_6H_5$ |
| 2568 | $N(CH_3)_2$ | $N(CH_3)_2$ | $CH_3$ | $CH_3$ | $OCOC_6H_5$ |
| 2569 | $N(CH_2CH_3)_2$ | $N(CH_2CH_3)_2$ | $CH_3$ | $CH_3$ | $OCOC_6H_5$ |
| 2570 | $N(CH_3)(CH_2CH_3)$ | $N(CH_3)(CH_2CH_3)$ | $CH_3$ | $CH_3$ | $OCOC_6H_5$ |
| 2571 | $O—(CH_2CH_2)—O$ | | $CH_3$ | $CH_3$ | $OCOC_6H_5$ |
| 2572 | $O—(CH_2CH_2CH_2)—O$ | | $CH_3$ | $CH_3$ | $OCOC_6H_5$ |
| 2573 | $S—(CH_2CH_2)—S$ | | $CH_3$ | $CH_3$ | $OCOC_6H_5$ |
| 2574 | $S—(CH_2CH_2CH_2)—S$ | | $CH_3$ | $CH_3$ | $OCOC_6H_5$ |
| 2575 | $—(CH_2)_4—$ | | $CH_3$ | $CH_3$ | $OCOC_6H_5$ |
| 2576 | $—(CH_2)_5—$ | | $CH_3$ | $CH_3$ | $OCOC_6H_5$ |
| 2577 | H | H | $CH_2CH_3$ | $CH_3$ | $OCOC_6H_5$ |
| 2578 | $CH_3$ | $CH_3$ | $CH_2CH_3$ | $CH_3$ | $OCOC_6H_5$ |
| 2579 | $CH_2CH_3$ | $CH_2CH_3$ | $CH_2CH_3$ | $CH_3$ | $OCOC_6H_5$ |

TABLE 1-continued

I1a1

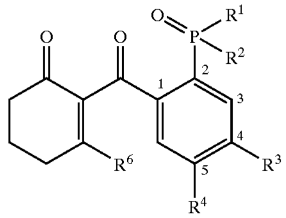

| n | $R^1$ | $R^2$ | $R^3$ | $R^4$ | $R^6$ |
|---|---|---|---|---|---|
| 2580 | $CH_2CH_2CH_3$ | $CH_2CH_2CH_3$ | $CH_2CH_3$ | $CH_3$ | $OCOC_6H_5$ |
| 2581 | $OCH_3$ | $OCH_3$ | $CH_2CH_3$ | $CH_3$ | $OCOC_6H_5$ |
| 2582 | $OCH_2CH_3$ | $OCH_2CH_3$ | $CH_2CH_3$ | $CH_3$ | $OCOC_6H_5$ |
| 2583 | $OCH_2CH_2CH_3$ | $OCH_2CH_2CH_3$ | $CH_2CH_3$ | $CH_3$ | $OCOC_6H_5$ |
| 2584 | $SCH_3$ | $SCH_3$ | $CH_2CH_3$ | $CH_3$ | $OCOC_6H_5$ |
| 2585 | $SCH_2CH_3$ | $SCH_2CH_3$ | $CH_2CH_3$ | $CH_3$ | $OCOC_6H_5$ |
| 2586 | $N(CH_3)_2$ | $N(CH_3)_2$ | $CH_2CH_3$ | $CH_3$ | $OCOC_6H_5$ |
| 2587 | $N(CH_2CH_3)_2$ | $N(CH_2CH_3)_2$ | $CH_2CH_3$ | $CH_3$ | $OCOC_6H_5$ |
| 2588 | $N(CH_3)(CH_2CH_3)$ | $N(CH_3)(CH_2CH_3)$ | $CH_2CH_3$ | $CH_3$ | $OCOC_6H_5$ |
| 2589 | $O—(CH_2CH_2)—O$ | | $CH_2CH_3$ | $CH_3$ | $OCOC_6H_5$ |
| 2590 | $O—(CH_2CH_2CH_2)—O$ | | $CH_2CH_3$ | $CH_3$ | $OCOC_6H_5$ |
| 2591 | $S—(CH_2CH_2)—S$ | | $CH_2CH_3$ | $CH_3$ | $OCOC_6H_5$ |
| 2592 | $S—(CH_2CH_2CH_2)—S$ | | $CH_2CH_3$ | $CH_3$ | $OCOC_6H_5$ |
| 2593 | $—(CH_2)_4—$ | | $CH_2CH_3$ | $CH_3$ | $OCOC_6H_5$ |
| 2594 | $—(CH_2)_5—$ | | $CH_2CH_3$ | $CH_3$ | $OCOC_6H_5$ |
| 2595 | H | H | $CF_3$ | $CH_3$ | $OCOC_6H_5$ |
| 2596 | $CH_3$ | $CH_3$ | $CF_3$ | $CH_3$ | $OCOC_6H_5$ |
| 2597 | $CH_2CH_3$ | $CH_2CH_3$ | $CF_3$ | $CH_3$ | $OCOC_6H_5$ |
| 2598 | $CH_2CH_2CH_3$ | $CH_2CH_2CH_3$ | $CF_3$ | $CH_3$ | $OCOC_6H_5$ |
| 2599 | $OCH_3$ | $OCH_3$ | $CF_3$ | $CH_3$ | $OCOC_6H_5$ |
| 2600 | $OCH_2CH_3$ | $OCH_2CH_3$ | $CF_3$ | $CH_3$ | $OCOC_6H_5$ |
| 2601 | $OCH_2CH_2CH_3$ | $OCH_2CH_2CH_3$ | $CF_3$ | $CH_3$ | $OCOC_6H_5$ |
| 2602 | $SCH_3$ | $SCH_3$ | $CF_3$ | $CH_3$ | $OCOC_6H_5$ |
| 2603 | $SCH_2CH_3$ | $SCH_2CH_3$ | $CF_3$ | $CH_3$ | $OCOC_6H_5$ |
| 2604 | $N(CH_3)_2$ | $N(CH_3)_2$ | $CF_3$ | $CH_3$ | $OCOC_6H_5$ |
| 2605 | $N(CH_2CH_3)_2$ | $N(CH_2CH_3)_2$ | $CF_3$ | $CH_3$ | $OCOC_6H_5$ |
| 2606 | $N(CH_3)(CH_2CH_3)$ | $N(CH_3)(CH_2CH_3)$ | $CF_3$ | $CH_3$ | $OCOC_6H_5$ |
| 2607 | $O—(CH_2CH_2)—O$ | | $CF_3$ | $CH_3$ | $OCOC_6H_5$ |
| 2608 | $O—(CH_2CH_2CH_2)—O$ | | $CF_3$ | $CH_3$ | $OCOC_6H_5$ |
| 2609 | $S—(CH_2CH_2)—S$ | | $CF_3$ | $CH_3$ | $OCOC_6H_5$ |
| 2610 | $S—(CH_2CH_2CH_2)—S$ | | $CF_3$ | $CH_3$ | $OCOC_6H_5$ |
| 2611 | $—(CH_2)_4—$ | | $CF_3$ | $CH_3$ | $OCOC_6H_5$ |
| 2612 | $—(CH_2)_5—$ | | $CF_3$ | $CH_3$ | $OCOC_6H_5$ |
| 2613 | H | H | $OCH_3$ | $CH_3$ | $OCOC_6H_5$ |
| 2614 | $CH_3$ | $CH_3$ | $OCH_3$ | $CH_3$ | $OCOC_6H_5$ |
| 2615 | $CH_2CH_3$ | $CH_2CH_3$ | $OCH_3$ | $CH_3$ | $OCOC_6H_5$ |
| 2616 | $CH_2CH_2CH_3$ | $CH_2CH_2CH_3$ | $OCH_3$ | $CH_3$ | $OCOC_6H_5$ |
| 2617 | $OCH_3$ | $OCH_3$ | $OCH_3$ | $CH_3$ | $OCOC_6H_5$ |
| 2618 | $OCH_2CH_3$ | $OCH_2CH_3$ | $OCH_3$ | $CH_3$ | $OCOC_6H_5$ |
| 2619 | $OCH_2CH_2CH_3$ | $OCH_2CH_2CH_3$ | $OCH_3$ | $CH_3$ | $OCOC_6H_5$ |
| 2620 | $SCH_3$ | $SCH_3$ | $OCH_3$ | $CH_3$ | $OCOC_6H_5$ |
| 2621 | $SCH_2CH_3$ | $SCH_2CH_3$ | $OCH_3$ | $CH_3$ | $OCOC_6H_5$ |
| 2622 | $N(CH_3)_2$ | $N(CH_3)_2$ | $OCH_3$ | $CH_3$ | $OCOC_6H_5$ |
| 2623 | $N(CH_2CH_3)_2$ | $N(CH_2CH_3)_2$ | $OCH_3$ | $CH_3$ | $OCOC_6H_5$ |
| 2624 | $N(CH_3)(CH_2CH_3)$ | $N(CH_3)(CH_2CH_3)$ | $OCH_3$ | $CH_3$ | $OCOC_6H_5$ |
| 2625 | $O—(CH_2CH_2)—O$ | | $OCH_3$ | $CH_3$ | $OCOC_6H_5$ |
| 2626 | $O—(CH_2CH_2CH_2)—O$ | | $OCH_3$ | $CH_3$ | $OCOC_6H_5$ |
| 2627 | $S—(CH_2CH_2)—S$ | | $OCH_3$ | $CH_3$ | $OCOC_6H_5$ |
| 2628 | $S—(CH_2CH_2CH_2)—S$ | | $OCH_3$ | $CH_3$ | $OCOC_6H_5$ |
| 2629 | $—(CH_2)_4—$ | | $OCH_3$ | $CH_3$ | $OCOC_6H_5$ |
| 2630 | $—(CH_2)_5—$ | | $OCH_3$ | $CH_3$ | $OCOC_6H_5$ |
| 2631 | H | H | $OCH_2CH_3$ | $CH_3$ | $OCOC_6H_5$ |
| 2632 | $CH_3$ | $CH_3$ | $OCH_2CH_3$ | $CH_3$ | $OCOC_6H_5$ |
| 2633 | $CH_2CH_3$ | $CH_2CH_3$ | $OCH_2CH_3$ | $CH_3$ | $OCOC_6H_5$ |
| 2634 | $CH_2CH_2CH_3$ | $CH_2CH_2CH_3$ | $OCH_2CH_3$ | $CH_3$ | $OCOC_6H_5$ |
| 2635 | $OCH_3$ | $OCH_3$ | $OCH_2CH_3$ | $CH_3$ | $OCOC_6H_5$ |
| 2636 | $OCH_2CH_3$ | $OCH_2CH_3$ | $OCH_2CH_3$ | $CH_3$ | $OCOC_6H_5$ |
| 2637 | $OCH_2CH_2CH_3$ | $OCH_2CH_2CH_3$ | $OCH_2CH_3$ | $CH_3$ | $OCOC_6H_5$ |
| 2638 | $SCH_3$ | $SCH_3$ | $OCH_2CH_3$ | $CH_3$ | $OCOC_6H_5$ |
| 2639 | $SCH_2CH_3$ | $SCH_2CH_3$ | $OCH_2CH_3$ | $CH_3$ | $OCOC_6H_5$ |
| 2640 | $N(CH_3)_2$ | $N(CH_3)_2$ | $OCH_2CH_3$ | $CH_3$ | $OCOC_6H_5$ |
| 2641 | $N(CH_2CH_3)_2$ | $N(CH_2CH_3)_2$ | $OCH_2CH_3$ | $CH_3$ | $OCOC_6H_5$ |
| 2642 | $N(CH_3)(CH_2CH_3)$ | $N(CH_3)(CH_2CH_3)$ | $OCH_2CH_3$ | $CH_3$ | $OCOC_6H_5$ |
| 2643 | $O—(CH_2CH_2)—O$ | | $OCH_2CH_3$ | $CH_3$ | $OCOC_6H_5$ |

TABLE 1-continued

I1a1

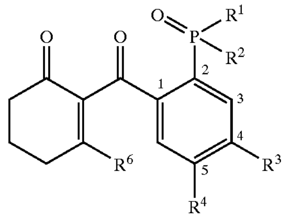

| n | $R^1$ | $R^2$ | $R^3$ | $R^4$ | $R^6$ |
|---|---|---|---|---|---|
| 2644 | O—$(CH_2CH_2CH_2)$—O | | $OCH_2CH_3$ | $CH_3$ | $OCOC_6H_5$ |
| 2645 | S—$(CH_2CH_2)$—S | | $OCH_2CH_3$ | $CH_3$ | $OCOC_6H_5$ |
| 2646 | S—$(CH_2CH_2CH_2)$—S | | $OCH_2CH_3$ | $CH_3$ | $OCOC_6H_5$ |
| 2647 | —$(CH_2)_4$— | | $OCH_2CH_3$ | $CH_3$ | $OCOC_6H_5$ |
| 2648 | —$(CH_2)_5$— | | $OCH_2CH_3$ | $CH_3$ | $OCOC_6H_5$ |
| 2649 | H | H | $SCH_3$ | $CH_3$ | $OCOC_6H_5$ |
| 2650 | $CH_3$ | $CH_3$ | $SCH_3$ | $CH_3$ | $OCOC_6H_5$ |
| 2651 | $CH_2CH_3$ | $CH_2CH_3$ | $SCH_3$ | $CH_3$ | $OCOC_6H_5$ |
| 2652 | $CH_2CH_2CH_3$ | $CH_2CH_2CH_3$ | $SCH_3$ | $CH_3$ | $OCOC_6H_5$ |
| 2653 | $OCH_3$ | $OCH_3$ | $SCH_3$ | $CH_3$ | $OCOC_6H_5$ |
| 2654 | $OCH_2CH_3$ | $OCH_2CH_3$ | $SCH_3$ | $CH_3$ | $OCOC_6H_5$ |
| 2655 | $OCH_2CH_2CH_3$ | $OCH_2CH_2CH_3$ | $SCH_3$ | $CH_3$ | $OCOC_6H_5$ |
| 2656 | $SCH_3$ | $SCH_3$ | $SCH_3$ | $CH_3$ | $OCOC_6H_5$ |
| 2657 | $SCH_2CH_3$ | $SCH_2CH_3$ | $SCH_3$ | $CH_3$ | $OCOC_6H_5$ |
| 2658 | $N(CH_3)_2$ | $N(CH_3)_2$ | $SCH_3$ | $CH_3$ | $OCOC_6H_5$ |
| 2659 | $N(CH_2CH_3)_2$ | $N(CH_2CH_3)_2$ | $SCH_3$ | $CH_3$ | $OCOC_6H_5$ |
| 2660 | $N(CH_3)(CH_2CH_3)$ | $N(CH_3)(CH_2CH_3)$ | $SCH_3$ | $CH_3$ | $OCOC_6H_5$ |
| 2661 | O—$(CH_2CH_2)$—O | | $SCH_3$ | $CH_3$ | $OCOC_6H_5$ |
| 2662 | O—$(CH_2CH_2CH_2)$—O | | $SCH_3$ | $CH_3$ | $OCOC_6H_5$ |
| 2663 | S—$(CH_2CH_2)$—S | | $SCH_3$ | $CH_3$ | $OCOC_6H_5$ |
| 2664 | S—$(CH_2CH_2CH_2)$—S | | $SCH_3$ | $CH_3$ | $OCOC_6H_5$ |
| 2665 | —$(CH_2)_4$— | | $SCH_3$ | $CH_3$ | $OCOC_6H_5$ |
| 2666 | —$(CH_2)_5$— | | $SCH_3$ | $CH_3$ | $OCOC_6H_5$ |
| 2667 | H | H | $SO_2CH_3$ | $CH_3$ | $OCOC_6H_5$ |
| 2668 | $CH_3$ | $CH_3$ | $SO_2CH_3$ | $CH_3$ | $OCOC_6H_5$ |
| 2669 | $CH_2CH_3$ | $CH_2CH_3$ | $SO_2CH_3$ | $CH_3$ | $OCOC_6H_5$ |
| 2670 | $CH_2CH_2CH_3$ | $CH_2CH_2CH_3$ | $SO_2CH_3$ | $CH_3$ | $OCOC_6H_5$ |
| 2671 | $OCH_3$ | $OCH_3$ | $SO_2CH_3$ | $CH_3$ | $OCOC_6H_5$ |
| 2672 | $OCH_2CH_3$ | $OCH_2CH_3$ | $SO_2CH_3$ | $CH_3$ | $OCOC_6H_5$ |
| 2673 | $OCH_2CH_2CH_3$ | $OCH_2CH_2CH_3$ | $SO_2CH_3$ | $CH_3$ | $OCOC_6H_5$ |
| 2674 | $SCH_3$ | $SCH_3$ | $SO_2CH_3$ | $CH_3$ | $OCOC_6H_5$ |
| 2675 | $SCH_2CH_3$ | $SCH_2CH_3$ | $SO_2CH_3$ | $CH_3$ | $OCOC_6H_5$ |
| 2676 | $N(CH_3)_2$ | $N(CH_3)_2$ | $SO_2CH_3$ | $CH_3$ | $OCOC_6H_5$ |
| 2677 | $N(CH_2CH_3)_2$ | $N(CH_2CH_3)_2$ | $SO_2CH_3$ | $CH_3$ | $OCOC_6H_5$ |
| 2678 | $N(CH_3)(CH_2CH_3)$ | $N(CH_3)(CH_2CH_3)$ | $SO_2CH_3$ | $CH_3$ | $OCOC_6H_5$ |
| 2679 | O—$(CH_2CH_2)$—O | | $SO_2CH_3$ | $CH_3$ | $OCOC_6H_5$ |
| 2680 | O—$(CH_2CH_2CH_2)$—O | | $SO_2CH_3$ | $CH_3$ | $OCOC_6H_5$ |
| 2681 | S—$(CH_2CH_2)$—S | | $SO_2CH_3$ | $CH_3$ | $OCOC_6H_5$ |
| 2682 | S—$(CH_2CH_2CH_2)$—S | | $SO_2CH_3$ | $CH_3$ | $OCOC_6H_5$ |
| 2683 | —$(CH_2)_4$— | | $SO_2CH_3$ | $CH_3$ | $OCOC_6H_5$ |
| 2684 | —$(CH_2)_5$— | | $SO_2CH_3$ | $CH_3$ | $OCOC_6H_5$ |
| 2685 | H | H | $PO(OCH_3)_2$ | $CH_3$ | $OCOC_6H_5$ |
| 2686 | $CH_3$ | $CH_3$ | $PO(OCH_3)_2$ | $CH_3$ | $OCOC_6H_5$ |
| 2687 | $CH_2CH_3$ | $CH_2CH_3$ | $PO(OCH_3)_2$ | $CH_3$ | $OCOC_6H_5$ |
| 2688 | $CH_2CH_2CH_3$ | $CH_2CH_2CH_3$ | $PO(OCH_3)_2$ | $CH_3$ | $OCOC_6H_5$ |
| 2689 | $OCH_3$ | $OCH_3$ | $PO(OCH_3)_2$ | $CH_3$ | $OCOC_6H_5$ |
| 2690 | $OCH_2CH_3$ | $OCH_2CH_3$ | $PO(OCH_3)_2$ | $CH_3$ | $OCOC_6H_5$ |
| 2691 | $OCH_2CH_2CH_3$ | $OCH_2CH_2CH_3$ | $PO(OCH_3)_2$ | $CH_3$ | $OCOC_6H_5$ |
| 2692 | $SCH_3$ | $SCH_3$ | $PO(OCH_3)_2$ | $CH_3$ | $OCOC_6H_5$ |
| 2693 | $SCH_2CH_3$ | $SCH_2CH_3$ | $PO(OCH_3)_2$ | $CH_3$ | $OCOC_6H_5$ |
| 2694 | $N(CH_3)_2$ | $N(CH_3)_2$ | $PO(OCH_3)_2$ | $CH_3$ | $OCOC_6H_5$ |
| 2695 | $N(CH_2CH_3)_2$ | $N(CH_2CH_3)_2$ | $PO(OCH_3)_2$ | $CH_3$ | $OCOC_6H_5$ |
| 2696 | $N(CH_3)(CH_2CH_3)$ | $N(CH_3)(CH_2CH_3)$ | $PO(OCH_3)_2$ | $CH_3$ | $OCOC_6H_5$ |
| 2697 | O—$(CH_2CH_2)$—O | | $PO(OCH_3)_2$ | $CH_3$ | $OCOC_6H_5$ |
| 2698 | O—$(CH_2CH_2CH_2)$—O | | $PO(OCH_3)_2$ | $CH_3$ | $OCOC_6H_5$ |
| 2699 | S—$(CH_2CH_2)$—S | | $PO(OCH_3)_2$ | $CH_3$ | $OCOC_6H_5$ |
| 2700 | S—$(CH_2CH_2CH_2)$—S | | $PO(OCH_3)_2$ | $CH_3$ | $OCOC_6H_5$ |
| 2701 | —$(CH_2)_4$— | | $PO(OCH_3)_2$ | $CH_3$ | $OCOC_6H_5$ |
| 2702 | —$(CH_2)_5$— | | $PO(OCH_3)_2$ | $CH_3$ | $OCOC_6H_5$ |
| 2703 | H | H | $PO(OCH_2CH_3)_2$ | $CH_3$ | $OCOC_6H_5$ |
| 2704 | $CH_3$ | $CH_3$ | $PO(OCH_2CH_3)_2$ | $CH_3$ | $OCOC_6H_5$ |
| 2705 | $CH_2CH_3$ | $CH_2CH_3$ | $PO(OCH_2CH_3)_2$ | $CH_3$ | $OCOC_6H_5$ |
| 2706 | $CH_2CH_2CH_3$ | $CH_2CH_2CH_3$ | $PO(OCH_2CH_3)_2$ | $CH_3$ | $OCOC_6H_5$ |
| 2707 | $OCH_3$ | $OCH_3$ | $PO(OCH_2CH_3)_2$ | $CH_3$ | $OCOC_6H_5$ |

TABLE 1-continued

I1a1

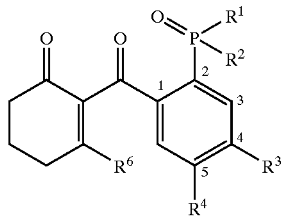

| n | $R^1$ | $R^2$ | $R^3$ | $R^4$ | $R^6$ |
|---|---|---|---|---|---|
| 2708 | $OCH_2CH_3$ | $OCH_2CH_3$ | $PO(OCH_2CH_3)_2$ | $CH_3$ | $OCOC_6H_5$ |
| 2709 | $OCH_2CH_2CH_3$ | $OCH_2CH_2CH_3$ | $PO(OCH_2CH_3)_2$ | $CH_3$ | $OCOC_6H_5$ |
| 2710 | $SCH_3$ | $SCH_3$ | $PO(OCH_2CH_3)_2$ | $CH_3$ | $OCOC_6H_5$ |
| 2711 | $SCH_2CH_3$ | $SCH_2CH_3$ | $PO(OCH_2CH_3)_2$ | $CH_3$ | $OCOC_6H_5$ |
| 2712 | $N(CH_3)_2$ | $N(CH_3)_2$ | $PO(OCH_2CH_3)_2$ | $CH_3$ | $OCOC_6H_5$ |
| 2713 | $N(CH_2CH_3)_2$ | $N(CH_2CH_3)_2$ | $PO(OCH_2CH_3)_2$ | $CH_3$ | $OCOC_6H_5$ |
| 2714 | $N(CH_3)(CH_2CH_3)$ | $N(CH_3)(CH_2CH_3)$ | $PO(OCH_2CH_3)_2$ | $CH_3$ | $OCOC_6H_5$ |
| 2715 | $O—(CH_2CH_2)—O$ | | $PO(OCH_2CH_3)_2$ | $CH_3$ | $OCOC_6H_5$ |
| 2716 | $O—(CH_2CH_2CH_2)—O$ | | $PO(OCH_2CH_3)_2$ | $CH_3$ | $OCOC_6H_5$ |
| 2717 | $S—(CH_2CH_2)—S$ | | $PO(OCH_2CH_3)_2$ | $CH_3$ | $OCOC_6H_5$ |
| 2718 | $S—(CH_2CH_2CH_2)—S$ | | $PO(OCH_2CH_3)_2$ | $CH_3$ | $OCOC_6H_5$ |
| 2719 | $—(CH_2)_4—$ | | $PO(OCH_2CH_3)_2$ | $CH_3$ | $OCOC_6H_5$ |
| 2720 | $—(CH_2)_5—$ | | $PO(OCH_2CH_3)_2$ | $CH_3$ | $OCOC_6H_5$ |
| 2721 | H | H | $PO(CH_3)_2$ | $CH_3$ | $OCOC_6H_5$ |
| 2722 | $CH_3$ | $CH_3$ | $PO(CH_3)_2$ | $CH_3$ | $OCOC_6H_5$ |
| 2723 | $CH_2CH_3$ | $CH_2CH_3$ | $PO(CH_3)_2$ | $CH_3$ | $OCOC_6H_5$ |
| 2724 | $CH_2CH_2CH_3$ | $CH_2CH_2CH_3$ | $PO(CH_3)_2$ | $CH_3$ | $OCOC_6H_5$ |
| 2725 | $OCH_3$ | $OCH_3$ | $PO(CH_3)_2$ | $CH_3$ | $OCOC_6H_5$ |
| 2726 | $OCH_2CH_3$ | $OCH_2CH_3$ | $PO(CH_3)_2$ | $CH_3$ | $OCOC_6H_5$ |
| 2727 | $OCH_2CH_2CH_3$ | $OCH_2CH_2CH_3$ | $PO(CH_3)_2$ | $CH_3$ | $OCOC_6H_5$ |
| 2728 | $SCH_3$ | $SCH_3$ | $PO(CH_3)_2$ | $CH_3$ | $OCOC_6H_5$ |
| 2729 | $SCH_2CH_3$ | $SCH_2CH_3$ | $PO(CH_3)_2$ | $CH_3$ | $OCOC_6H_5$ |
| 2730 | $N(CH_3)_2$ | $N(CH_3)_2$ | $PO(CH_3)_2$ | $CH_3$ | $OCOC_6H_5$ |
| 2731 | $N(CH_2CH_3)_2$ | $N(CH_2CH_3)_2$ | $PO(CH_3)_2$ | $CH_3$ | $OCOC_6H_5$ |
| 2732 | $N(CH_3)(CH_2CH_3)$ | $N(CH_3)(CH_2CH_3)$ | $PO(CH_3)_2$ | $CH_3$ | $OCOC_6H_5$ |
| 2733 | $O—(CH_2CH_2)—O$ | | $PO(CH_3)_2$ | $CH_3$ | $OCOC_6H_5$ |
| 2734 | $O—(CH_2CH_2CH_2)—O$ | | $PO(CH_3)_2$ | $CH_3$ | $OCOC_6H_5$ |
| 2735 | $S—(CH_2CH_2)—S$ | | $PO(CH_3)_2$ | $CH_3$ | $OCOC_6H_5$ |
| 2736 | $S—(CH_2CH_2CH_2)—S$ | | $PO(CH_3)_2$ | $CH_3$ | $OCOC_6H_5$ |
| 2737 | $—(CH_2)_4—$ | | $PO(CH_3)_2$ | $CH_3$ | $OCOC_6H_5$ |
| 2738 | $—(CH_2)_5—$ | | $PO(CH_3)_2$ | $CH_3$ | $OCOC_6H_5$ |
| 2739 | H | H | $PO(CH_2CH_3)_2$ | $CH_3$ | $OCOC_6H_5$ |
| 2740 | $CH_3$ | $CH_3$ | $PO(CH_2CH_3)_2$ | $CH_3$ | $OCOC_6H_5$ |
| 2741 | $CH_2CH_3$ | $CH_2CH_3$ | $PO(CH_2CH_3)_2$ | $CH_3$ | $OCOC_6H_5$ |
| 2742 | $CH_2CH_2CH_3$ | $CH_2CH_2CH_3$ | $PO(CH_2CH_3)_2$ | $CH_3$ | $OCOC_6H_5$ |
| 2743 | $OCH_3$ | $OCH_3$ | $PO(CH_2CH_3)_2$ | $CH_3$ | $OCOC_6H_5$ |
| 2744 | $OCH_2CH_3$ | $OCH_2CH_3$ | $PO(CH_2CH_3)_2$ | $CH_3$ | $OCOC_6H_5$ |
| 2745 | $OCH_2CH_2CH_3$ | $OCH_2CH_2CH_3$ | $PO(CH_2CH_3)_2$ | $CH_3$ | $OCOC_6H_5$ |
| 2746 | $SCH_3$ | $SCH_3$ | $PO(CH_2CH_3)_2$ | $CH_3$ | $OCOC_6H_5$ |
| 2747 | $SCH_2CH_3$ | $SCH_2CH_3$ | $PO(CH_2CH_3)_2$ | $CH_3$ | $OCOC_6H_5$ |
| 2748 | $N(CH_3)_2$ | $N(CH_3)_2$ | $PO(CH_2CH_3)_2$ | $CH_3$ | $OCOC_6H_5$ |
| 2749 | $N(CH_2CH_3)_2$ | $N(CH_2CH_3)_2$ | $PO(CH_2CH_3)_2$ | $CH_3$ | $OCOC_6H_5$ |
| 2750 | $N(CH_3)(CH_2CH_3)$ | $N(CH_3)(CH_2CH_3)$ | $PO(CH_2CH_3)_2$ | $CH_3$ | $OCOC_6H_5$ |
| 2751 | $O—(CH_2CH_2)—O$ | | $PO(CH_2CH_3)_2$ | $CH_3$ | $OCOC_6H_5$ |
| 2752 | $O—(CH_2CH_2CH_2)—O$ | | $PO(CH_2CH_3)_2$ | $CH_3$ | $OCOC_6H_5$ |
| 2753 | $S—(CH_2CH_2)—S$ | | $PO(CH_2CH_3)_2$ | $CH_3$ | $OCOC_6H_5$ |
| 2754 | $S—(CH_2CH_2CH_2)—S$ | | $PO(CH_2CH_3)_2$ | $CH_3$ | $OCOC_6H_5$ |
| 2755 | $—(CH_2)_4—$ | | $PO(CH_2CH_3)_2$ | $CH_3$ | $OCOC_6H_5$ |
| 2756 | $—(CH_2)_5—$ | | $PO(CH_2CH_3)_2$ | $CH_3$ | $OCOC_6H_5$ |
| 2757 | H | H | H | $CH_3$ | $SCH_3$ |
| 2758 | $CH_3$ | $CH_3$ | H | $CH_3$ | $SCH_3$ |
| 2759 | $CH_2CH_3$ | $CH_2CH_3$ | H | $CH_3$ | $SCH_3$ |
| 2760 | $CH_2CH_2CH_3$ | $CH_2CH_2CH_3$ | H | $CH_3$ | $SCH_3$ |
| 2761 | $OCH_3$ | $OCH_3$ | H | $CH_3$ | $SCH_3$ |
| 2762 | $OCH_2CH_3$ | $OCH_2CH_3$ | H | $CH_3$ | $SCH_3$ |
| 2763 | $OCH_2CH_2CH_3$ | $OCH_2CH_2CH_3$ | H | $CH_3$ | $SCH_3$ |
| 2764 | $SCH_3$ | $SCH_3$ | H | $CH_3$ | $SCH_3$ |
| 2765 | $SCH_2CH_3$ | $SCH_2CH_3$ | H | $CH_3$ | $SCH_3$ |
| 2766 | $N(CH_3)_2$ | $N(CH_3)_2$ | H | $CH_3$ | $SCH_3$ |
| 2767 | $N(CH_2CH_3)_2$ | $N(CH_2CH_3)_2$ | H | $CH_3$ | $SCH_3$ |
| 2768 | $N(CH_3)(CH_2CH_3)$ | $N(CH_3)(CH_2CH_3)$ | H | $CH_3$ | $SCH_3$ |
| 2769 | $O—(CH_2CH_2)—O$ | | H | $CH_3$ | $SCH_3$ |
| 2770 | $O—(CH_2CH_2CH_2)—O$ | | H | $CH_3$ | $SCH_3$ |
| 2771 | $S—(CH_2CH_2)—S$ | | H | $CH_3$ | $SCH_3$ |

TABLE 1-continued

I1a1

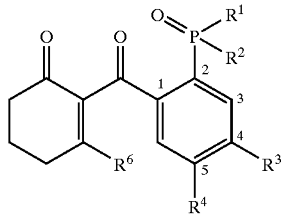

| n | $R^1$ | $R^2$ | $R^3$ | $R^4$ | $R^6$ |
|---|---|---|---|---|---|
| 2772 | S—$(CH_2CH_2CH_2)$—S | | H | $CH_3$ | $SCH_3$ |
| 2773 | —$(CH_2)_4$— | | H | $CH_3$ | $SCH_3$ |
| 2774 | —$(CH_2)_5$— | | H | $CH_3$ | $SCH_3$ |
| 2775 | H | H | $NO_2$ | $CH_3$ | $SCH_3$ |
| 2776 | $CH_3$ | $CH_3$ | $NO_2$ | $CH_3$ | $SCH_3$ |
| 2777 | $CH_2CH_3$ | $CH_2CH_3$ | $NO_2$ | $CH_3$ | $SCH_3$ |
| 2778 | $CH_2CH_2CH_3$ | $CH_2CH_2CH_3$ | $NO_2$ | $CH_3$ | $SCH_3$ |
| 2779 | $OCH_3$ | $OCH_3$ | $NO_2$ | $CH_3$ | $SCH_3$ |
| 2780 | $OCH_2CH_3$ | $OCH_2CH_3$ | $NO_2$ | $CH_3$ | $SCH_3$ |
| 2781 | $OCH_2CH_2CH_3$ | $OCH_2CH_2CH_3$ | $NO_2$ | $CH_3$ | $SCH_3$ |
| 2782 | $SCH_3$ | $SCH_3$ | $NO_2$ | $CH_3$ | $SCH_3$ |
| 2783 | $SCH_2CH_3$ | $SCH_2CH_3$ | $NO_2$ | $CH_3$ | $SCH_3$ |
| 2784 | $N(CH_3)_2$ | $N(CH_3)_2$ | $NO_2$ | $CH_3$ | $SCH_3$ |
| 2785 | $N(CH_2CH_3)_2$ | $N(CH_2CH_3)_2$ | $NO_2$ | $CH_3$ | $SCH_3$ |
| 2786 | $N(CH_3)(CH_2CH_3)$ | $N(CH_3)(CH_2CH_3)$ | $NO_2$ | $CH_3$ | $SCH_3$ |
| 2787 | O—$(CH_2CH_2)$—O | | $NO_2$ | $CH_3$ | $SCH_3$ |
| 2788 | O—$(CH_2CH_2CH_2)$—O | | $NO_2$ | $CH_3$ | $SCH_3$ |
| 2789 | S—$(CH_2CH_2)$—S | | $NO_2$ | $CH_3$ | $SCH_3$ |
| 2790 | S—$(CH_2CH_2CH_2)$—S | | $NO_2$ | $CH_3$ | $SCH_3$ |
| 2791 | —$(CH_2)_4$— | | $NO_2$ | $CH_3$ | $SCH_3$ |
| 2792 | —$(CH_2)_5$— | | $NO_2$ | $CH_3$ | $SCH_3$ |
| 2793 | H | H | CN | $CH_3$ | $SCH_3$ |
| 2794 | $CH_3$ | $CH_3$ | CN | $CH_3$ | $SCH_3$ |
| 2795 | $CH_2CH_3$ | $CH_2CH_3$ | CN | $CH_3$ | $SCH_3$ |
| 2796 | $CH_2CH_2CH_3$ | $CH_2CH_2CH_3$ | CN | $CH_3$ | $SCH_3$ |
| 2797 | $OCH_3$ | $OCH_3$ | CN | $CH_3$ | $SCH_3$ |
| 2798 | $OCH_2CH_3$ | $OCH_2CH_3$ | CN | $CH_3$ | $SCH_3$ |
| 2799 | $OCH_2CH_2CH_3$ | $OCH_2CH_2CH_3$ | CN | $CH_3$ | $SCH_3$ |
| 2800 | $SCH_3$ | $SCH_3$ | CN | $CH_3$ | $SCH_3$ |
| 2801 | $SCH_2CH_3$ | $SCH_2CH_3$ | CN | $CH_3$ | $SCH_3$ |
| 2802 | $N(CH_3)_2$ | $N(CH_3)_2$ | CN | $CH_3$ | $SCH_3$ |
| 2803 | $N(CH_2CH_3)_2$ | $N(CH_2CH_3)_2$ | CN | $CH_3$ | $SCH_3$ |
| 2804 | $N(CH_3)(CH_2CH_3)$ | $N(CH_3)(CH_2CH_3)$ | CN | $CH_3$ | $SCH_3$ |
| 2805 | O—$(CH_2CH_2)$—O | | CN | $CH_3$ | $SCH_3$ |
| 2806 | O—$(CH_2CH_2CH_2)$—O | | CN | $CH_3$ | $SCH_3$ |
| 2807 | S—$(CH_2CH_2)$—S | | CN | $CH_3$ | $SCH_3$ |
| 2808 | S—$(CH_2CH_2CH_2)$—S | | CN | $CH_3$ | $SCH_3$ |
| 2809 | —$(CH_2)_4$— | | CN | $CH_3$ | $SCH_3$ |
| 2810 | —$(CH_2)_5$— | | CN | $CH_3$ | $SCH_3$ |
| 2811 | H | H | F | $CH_3$ | $SCH_3$ |
| 2812 | $CH_3$ | $CH_3$ | F | $CH_3$ | $SCH_3$ |
| 2813 | $CH_2CH_3$ | $CH_2CH_3$ | F | $CH_3$ | $SCH_3$ |
| 2814 | $CH_2CH_2CH_3$ | $CH_2CH_2CH_3$ | F | $CH_3$ | $SCH_3$ |
| 2815 | $OCH_3$ | $OCH_3$ | F | $CH_3$ | $SCH_3$ |
| 2816 | $OCH_2CH_3$ | $OCH_2CH_3$ | F | $CH_3$ | $SCH_3$ |
| 2817 | $OCH_2CH_2CH_3$ | $OCH_2CH_2CH_3$ | F | $CH_3$ | $SCH_3$ |
| 2818 | $SCH_3$ | $SCH_3$ | F | $CH_3$ | $SCH_3$ |
| 2819 | $SCH_2CH_3$ | $SCH_2CH_3$ | F | $CH_3$ | $SCH_3$ |
| 2820 | $N(CH_3)_2$ | $N(CH_3)_2$ | F | $CH_3$ | $SCH_3$ |
| 2821 | $N(CH_2CH_3)_2$ | $N(CH_2CH_3)_2$ | F | $CH_3$ | $SCH_3$ |
| 2822 | $N(CH_3)(CH_2CH_3)$ | $N(CH_3)(CH_2CH_3)$ | F | $CH_3$ | $SCH_3$ |
| 2823 | O—$(CH_2CH_2)$—O | | F | $CH_3$ | $SCH_3$ |
| 2824 | O—$(CH_2CH_2CH_2)$—O | | F | $CH_3$ | $SCH_3$ |
| 2825 | S—$(CH_2CH_2)$—S | | F | $CH_3$ | $SCH_3$ |
| 2826 | S—$(CH_2CH_2CH_2)$—S | | F | $CH_3$ | $SCH_3$ |
| 2827 | —$(CH_2)_4$— | | F | $CH_3$ | $SCH_3$ |
| 2828 | —$(CH_2)_5$— | | F | $CH_3$ | $SCH_3$ |
| 2829 | H | H | Cl | $CH_3$ | $SCH_3$ |
| 2830 | $CH_3$ | $CH_3$ | Cl | $CH_3$ | $SCH_3$ |
| 2831 | $CH_2CH_3$ | $CH_2CH_3$ | Cl | $CH_3$ | $SCH_3$ |
| 2832 | $CH_2CH_2CH_3$ | $CH_2CH_2CH_3$ | Cl | $CH_3$ | $SCH_3$ |
| 2833 | $OCH_3$ | $OCH_3$ | Cl | $CH_3$ | $SCH_3$ |
| 2834 | $OCH_2CH_3$ | $OCH_2CH_3$ | Cl | $CH_3$ | $SCH_3$ |
| 2835 | $OCH_2CH_2CH_3$ | $OCH_2CH_2CH_3$ | Cl | $CH_3$ | $SCH_3$ |

TABLE 1-continued

I1a1

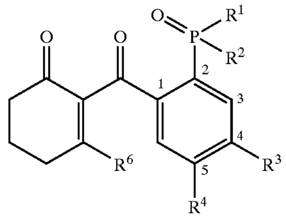

| n | $R^1$ | $R^2$ | $R^3$ | $R^4$ | $R^6$ |
|---|---|---|---|---|---|
| 2836 | $SCH_3$ | $SCH_3$ | Cl | $CH_3$ | $SCH_3$ |
| 2837 | $SCH_2CH_3$ | $SCH_2CH_3$ | Cl | $CH_3$ | $SCH_3$ |
| 2838 | $N(CH_3)_2$ | $N(CH_3)_2$ | Cl | $CH_3$ | $SCH_3$ |
| 2839 | $N(CH_2CH_3)_2$ | $N(CH_2CH_3)_2$ | Cl | $CH_3$ | $SCH_3$ |
| 2840 | $N(CH_3)(CH_2CH_3)$ | $N(CH_3)(CH_2CH_3)$ | Cl | $CH_3$ | $SCH_3$ |
| 2841 | $O—(CH_2CH_2)—O$ | | Cl | $CH_3$ | $SCH_3$ |
| 2842 | $O—(CH_2CH_2CH_2)—O$ | | Cl | $CH_3$ | $SCH_3$ |
| 2843 | $S—(CH_2CH_2)—S$ | | Cl | $CH_3$ | $SCH_3$ |
| 2844 | $S—(CH_2CH_2CH_2)—S$ | | Cl | $CH_3$ | $SCH_3$ |
| 2845 | $—(CH_2)_4—$ | | Cl | $CH_3$ | $SCH_3$ |
| 2846 | $—(CH_2)_5—$ | | Cl | $CH_3$ | $SCH_3$ |
| 2847 | H | H | Br | $CH_3$ | $SCH_3$ |
| 2848 | $CH_3$ | $CH_3$ | Br | $CH_3$ | $SCH_3$ |
| 2849 | $CH_2CH_3$ | $CH_2CH_3$ | Br | $CH_3$ | $SCH_3$ |
| 2850 | $CH_2CH_2CH_3$ | $CH_2CH_2CH_3$ | Br | $CH_3$ | $SCH_3$ |
| 2851 | $OCH_3$ | $OCH_3$ | Br | $CH_3$ | $SCH_3$ |
| 2852 | $OCH_2CH_3$ | $OCH_2CH_3$ | Br | $CH_3$ | $SCH_3$ |
| 2853 | $OCH_2CH_2CH_3$ | $OCH_2CH_2CH_3$ | Br | $CH_3$ | $SCH_3$ |
| 2854 | $SCH_3$ | $SCH_3$ | Br | $CH_3$ | $SCH_3$ |
| 2855 | $SCH_2CH_3$ | $SCH_2CH_3$ | Br | $CH_3$ | $SCH_3$ |
| 2856 | $N(CH_3)_2$ | $N(CH_3)_2$ | Br | $CH_3$ | $SCH_3$ |
| 2857 | $N(CH_2CH_3)_2$ | $N(CH_2CH_3)_2$ | Br | $CH_3$ | $SCH_3$ |
| 2858 | $N(CH_3)(CH_2CH_3)$ | $N(CH_3)(CH_2CH_3)$ | Br | $CH_3$ | $SCH_3$ |
| 2859 | $O—(CH_2CH_2)—O$ | | Br | $CH_3$ | $SCH_3$ |
| 2860 | $O—(CH_2CH_2CH_2)—O$ | | Br | $CH_3$ | $SCH_3$ |
| 2861 | $S—(CH_2CH_2)—S$ | | Br | $CH_3$ | $SCH_3$ |
| 2862 | $S—(CH_2CH_2CH_2)—S$ | | Br | $CH_3$ | $SCH_3$ |
| 2863 | $—(CH_2)_4—$ | | Br | $CH_3$ | $SCH_3$ |
| 2864 | $—(CH_2)_5—$ | | Br | $CH_3$ | $SCH_3$ |
| 2865 | H | H | $CH_3$ | $CH_3$ | $SCH_3$ |
| 2866 | $CH_3$ | $CH_3$ | $CH_3$ | $CH_3$ | $SCH_3$ |
| 2867 | $CH_2CH_3$ | $CH_2CH_3$ | $CH_3$ | $CH_3$ | $SCH_3$ |
| 2868 | $CH_2CH_2CH_3$ | $CH_2CH_2CH_3$ | $CH_3$ | $CH_3$ | $SCH_3$ |
| 2869 | $OCH_3$ | $OCH_3$ | $CH_3$ | $CH_3$ | $SCH_3$ |
| 2870 | $OCH_2CH_3$ | $OCH_2CH_3$ | $CH_3$ | $CH_3$ | $SCH_3$ |
| 2871 | $OCH_2CH_2CH_3$ | $OCH_2CH_2CH_3$ | $CH_3$ | $CH_3$ | $SCH_3$ |
| 2872 | $SCH_3$ | $SCH_3$ | $CH_3$ | $CH_3$ | $SCH_3$ |
| 2873 | $SCH_2CH_3$ | $SCH_2CH_3$ | $CH_3$ | $CH_3$ | $SCH_3$ |
| 2874 | $N(CH_3)_2$ | $N(CH_3)_2$ | $CH_3$ | $CH_3$ | $SCH_3$ |
| 2875 | $N(CH_2CH_3)_2$ | $N(CH_2CH_3)_2$ | $CH_3$ | $CH_3$ | $SCH_3$ |
| 2876 | $N(CH_3)(CH_2CH_3)$ | $N(CH_3)(CH_2CH_3)$ | $CH_3$ | $CH_3$ | $SCH_3$ |
| 2877 | $O—(CH_2CH_2)—O$ | | $CH_3$ | $CH_3$ | $SCH_3$ |
| 2878 | $O—(CH_2CH_2CH_2)—O$ | | $CH_3$ | $CH_3$ | $SCH_3$ |
| 2879 | $S—(CH_2CH_2)—S$ | | $CH_3$ | $CH_3$ | $SCH_3$ |
| 2880 | $S—(CH_2CH_2CH_2)—S$ | | $CH_3$ | $CH_3$ | $SCH_3$ |
| 2881 | $—(CH_2)_4—$ | | $CH_3$ | $CH_3$ | $SCH_3$ |
| 2882 | $—(CH_2)_5—$ | | $CH_3$ | $CH_3$ | $SCH_3$ |
| 2883 | H | H | $CH_2CH_3$ | $CH_3$ | $SCH_3$ |
| 2884 | $CH_3$ | $CH_3$ | $CH_2CH_3$ | $CH_3$ | $SCH_3$ |
| 2885 | $CH_2CH_3$ | $CH_2CH_3$ | $CH_2CH_3$ | $CH_3$ | $SCH_3$ |
| 2886 | $CH_2CH_2CH_3$ | $CH_2CH_2CH_3$ | $CH_2CH_3$ | $CH_3$ | $SCH_3$ |
| 2887 | $OCH_3$ | $OCH_3$ | $CH_2CH_3$ | $CH_3$ | $SCH_3$ |
| 2888 | $OCH_2CH_3$ | $OCH_2CH_3$ | $CH_2CH_3$ | $CH_3$ | $SCH_3$ |
| 2889 | $OCH_2CH_2CH_3$ | $OCH_2CH_2CH_3$ | $CH_2CH_3$ | $CH_3$ | $SCH_3$ |
| 2890 | $SCH_3$ | $SCH_3$ | $CH_2CH_3$ | $CH_3$ | $SCH_3$ |
| 2891 | $SCH_2CH_3$ | $SCH_2CH_3$ | $CH_2CH_3$ | $CH_3$ | $SCH_3$ |
| 2892 | $N(CH_3)_2$ | $N(CH_3)_2$ | $CH_2CH_3$ | $CH_3$ | $SCH_3$ |
| 2893 | $N(CH_2CH_3)_2$ | $N(CH_2CH_3)_2$ | $CH_2CH_3$ | $CH_3$ | $SCH_3$ |
| 2894 | $N(CH_3)(CH_2CH_3)$ | $N(CH_3)(CH_2CH_3)$ | $CH_2CH_3$ | $CH_3$ | $SCH_3$ |
| 2895 | $O—(CH_2CH_2)—O$ | | $CH_2CH_3$ | $CH_3$ | $SCH_3$ |
| 2896 | $O—(CH_2CH_2CH_2)—O$ | | $CH_2CH_3$ | $CH_3$ | $SCH_3$ |
| 2897 | $S—(CH_2CH_2)—S$ | | $CH_2CH_3$ | $CH_3$ | $SCH_3$ |
| 2898 | $S—(CH_2CH_2CH_2)—S$ | | $CH_2CH_3$ | $CH_3$ | $SCH_3$ |
| 2899 | $—(CH_2)_4—$ | | $CH_2CH_3$ | $CH_3$ | $SCH_3$ |

TABLE 1-continued

I1a1

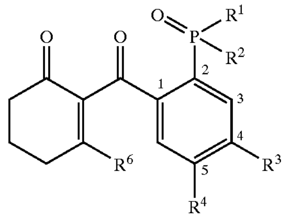

| n | $R^1$ | $R^2$ | $R^3$ | $R^4$ | $R^6$ |
|---|---|---|---|---|---|
| 2900 | $-(CH_2)_5-$ | | $CH_2CH_3$ | $CH_3$ | $SCH_3$ |
| 2901 | H | H | $CF_3$ | $CH_3$ | $SCH_3$ |
| 2902 | $CH_3$ | $CH_3$ | $CF_3$ | $CH_3$ | $SCH_3$ |
| 2903 | $CH_2CH_3$ | $CH_2CH_3$ | $CF_3$ | $CH_3$ | $SCH_3$ |
| 2904 | $CH_2CH_2CH_3$ | $CH_2CH_2CH_3$ | $CF_3$ | $CH_3$ | $SCH_3$ |
| 2905 | $OCH_3$ | $OCH_3$ | $CF_3$ | $CH_3$ | $SCH_3$ |
| 2906 | $OCH_2CH_3$ | $OCH_2CH_3$ | $CF_3$ | $CH_3$ | $SCH_3$ |
| 2907 | $OCH_2CH_2CH_3$ | $OCH_2CH_2CH_3$ | $CF_3$ | $CH_3$ | $SCH_3$ |
| 2908 | $SCH_3$ | $SCH_3$ | $CF_3$ | $CH_3$ | $SCH_3$ |
| 2909 | $SCH_2CH_3$ | $SCH_2CH_3$ | $CF_3$ | $CH_3$ | $SCH_3$ |
| 2910 | $N(CH_3)_2$ | $N(CH_3)_2$ | $CF_3$ | $CH_3$ | $SCH_3$ |
| 2911 | $N(CH_2CH_3)_2$ | $N(CH_2CH_3)_2$ | $CF_3$ | $CH_3$ | $SCH_3$ |
| 2912 | $N(CH_3)(CH_2CH_3)$ | $N(CH_3)(CH_2CH_3)$ | $CF_3$ | $CH_3$ | $SCH_3$ |
| 2913 | $O-(CH_2CH_2)-O$ | | $CF_3$ | $CH_3$ | $SCH_3$ |
| 2914 | $O-(CH_2CH_2CH_2)-O$ | | $CF_3$ | $CH_3$ | $SCH_3$ |
| 2915 | $S-(CH_2CH_2)-S$ | | $CF_3$ | $CH_3$ | $SCH_3$ |
| 2916 | $S-(CH_2CH_2CH_2)-S$ | | $CF_3$ | $CH_3$ | $SCH_3$ |
| 2917 | $-(CH_2)_4-$ | | $CF_3$ | $CH_3$ | $SCH_3$ |
| 2918 | $-(CH_2)_5-$ | | $CF_3$ | $CH_3$ | $SCH_3$ |
| 2919 | H | H | $OCH_3$ | $CH_3$ | $SCH_3$ |
| 2920 | $CH_3$ | $CH_3$ | $OCH_3$ | $CH_3$ | $SCH_3$ |
| 2921 | $CH_2CH_3$ | $CH_2CH_3$ | $OCH_3$ | $CH_3$ | $SCH_3$ |
| 2922 | $CH_2CH_2CH_3$ | $CH_2CH_2CH_3$ | $OCH_3$ | $CH_3$ | $SCH_3$ |
| 2923 | $OCH_3$ | $OCH_3$ | $OCH_3$ | $CH_3$ | $SCH_3$ |
| 2924 | $OCH_2CH_3$ | $OCH_2CH_3$ | $OCH_3$ | $CH_3$ | $SCH_3$ |
| 2925 | $OCH_2CH_2CH_3$ | $OCH_2CH_2CH_3$ | $OCH_3$ | $CH_3$ | $SCH_3$ |
| 2926 | $SCH_3$ | $SCH_3$ | $OCH_3$ | $CH_3$ | $SCH_3$ |
| 2927 | $SCH_2CH_3$ | $SCH_2CH_3$ | $OCH_3$ | $CH_3$ | $SCH_3$ |
| 2928 | $N(CH_3)_2$ | $N(CH_3)_2$ | $OCH_3$ | $CH_3$ | $SCH_3$ |
| 2929 | $N(CH_2CH_3)_2$ | $N(CH_2CH_3)_2$ | $OCH_3$ | $CH_3$ | $SCH_3$ |
| 2930 | $N(CH_3)(CH_2CH_3)$ | $N(CH_3)(CH_2CH_3)$ | $OCH_3$ | $CH_3$ | $SCH_3$ |
| 2931 | $O-(CH_2CH_2)-O$ | | $OCH_3$ | $CH_3$ | $SCH_3$ |
| 2932 | $O-(CH_2CH_2CH_2)-O$ | | $OCH_3$ | $CH_3$ | $SCH_3$ |
| 2933 | $S-(CH_2CH_2)-S$ | | $OCH_3$ | $CH_3$ | $SCH_3$ |
| 2934 | $S-(CH_2CH_2CH_2)-S$ | | $OCH_3$ | $CH_3$ | $SCH_3$ |
| 2935 | $-(CH_2)_4-$ | | $OCH_3$ | $CH_3$ | $SCH_3$ |
| 2936 | $-(CH_2)_5-$ | | $OCH_3$ | $CH_3$ | $SCH_3$ |
| 2937 | H | H | $OCH_2CH_3$ | $CH_3$ | $SCH_3$ |
| 2938 | $CH_3$ | $CH_3$ | $OCH_2CH_3$ | $CH_3$ | $SCH_3$ |
| 2939 | $CH_2CH_3$ | $CH_2CH_3$ | $OCH_2CH_3$ | $CH_3$ | $SCH_3$ |
| 2940 | $CH_2CH_2CH_3$ | $CH_2CH_2CH_3$ | $OCH_2CH_3$ | $CH_3$ | $SCH_3$ |
| 2941 | $OCH_3$ | $OCH_3$ | $OCH_2CH_3$ | $CH_3$ | $SCH_3$ |
| 2942 | $OCH_2CH_3$ | $OCH_2CH_3$ | $OCH_2CH_3$ | $CH_3$ | $SCH_3$ |
| 2943 | $OCH_2CH_2CH_3$ | $OCH_2CH_2CH_3$ | $OCH_2CH_3$ | $CH_3$ | $SCH_3$ |
| 2944 | $SCH_3$ | $SCH_3$ | $OCH_2CH_3$ | $CH_3$ | $SCH_3$ |
| 2945 | $SCH_2CH_3$ | $SCH_2CH_3$ | $OCH_2CH_3$ | $CH_3$ | $SCH_3$ |
| 2946 | $N(CH_3)_2$ | $N(CH_3)_2$ | $OCH_2CH_3$ | $CH_3$ | $SCH_3$ |
| 2947 | $N(CH_2CH_3)_2$ | $N(CH_2CH_3)_2$ | $OCH_2CH_3$ | $CH_3$ | $SCH_3$ |
| 2948 | $N(CH_3)(CH_2CH_3)$ | $N(CH_3)(CH_2CH_3)$ | $OCH_2CH_3$ | $CH_3$ | $SCH_3$ |
| 2949 | $O-(CH_2CH_2)-O$ | | $OCH_2CH_3$ | $CH_3$ | $SCH_3$ |
| 2950 | $O-(CH_2CH_2CH_2)-O$ | | $OCH_2CH_3$ | $CH_3$ | $SCH_3$ |
| 2951 | $S-(CH_2CH_2)-S$ | | $OCH_2CH_3$ | $CH_3$ | $SCH_3$ |
| 2952 | $S-(CH_2CH_2CH_2)-S$ | | $OCH_2CH_3$ | $CH_3$ | $SCH_3$ |
| 2953 | $-(CH_2)_4-$ | | $OCH_2CH_3$ | $CH_3$ | $SCH_3$ |
| 2954 | $-(CH_2)_5-$ | | $OCH_2CH_3$ | $CH_3$ | $SCH_3$ |
| 2955 | H | H | $SCH_3$ | $CH_3$ | $SCH_3$ |
| 2956 | $CH_3$ | $CH_3$ | $SCH_3$ | $CH_3$ | $SCH_3$ |
| 2957 | $CH_2CH_3$ | $CH_2CH_3$ | $SCH_3$ | $CH_3$ | $SCH_3$ |
| 2958 | $CH_2CH_2CH_3$ | $CH_2CH_2CH_3$ | $SCH_3$ | $CH_3$ | $SCH_3$ |
| 2959 | $OCH_3$ | $OCH_3$ | $SCH_3$ | $CH_3$ | $SCH_3$ |
| 2960 | $OCH_2CH_3$ | $OCH_2CH_3$ | $SCH_3$ | $CH_3$ | $SCH_3$ |
| 2961 | $OCH_2CH_2CH_3$ | $OCH_2CH_2CH_3$ | $SCH_3$ | $CH_3$ | $SCH_3$ |
| 2962 | $SCH_3$ | $SCH_3$ | $SCH_3$ | $CH_3$ | $SCH_3$ |
| 2963 | $SCH_2CH_3$ | $SCH_2CH_3$ | $SCH_3$ | $CH_3$ | $SCH_3$ |

TABLE 1-continued

I1a1

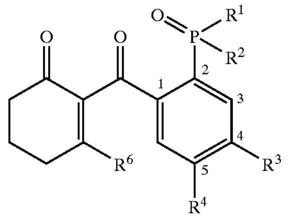

| n | $R^1$ | $R^2$ | $R^3$ | $R^4$ | $R^6$ |
|---|---|---|---|---|---|
| 2964 | $N(CH_3)_2$ | $N(CH_3)_2$ | $SCH_3$ | $CH_3$ | $SCH_3$ |
| 2965 | $N(CH_2CH_3)_2$ | $N(CH_2CH_3)_2$ | $SCH_3$ | $CH_3$ | $SCH_3$ |
| 2966 | $N(CH_3)(CH_2CH_3)$ | $N(CH_3)(CH_2CH_3)$ | $SCH_3$ | $CH_3$ | $SCH_3$ |
| 2967 | $O—(CH_2CH_2)—O$ | | $SCH_3$ | $CH_3$ | $SCH_3$ |
| 2968 | $O—(CH_2CH_2CH_2)—O$ | | $SCH_3$ | $CH_3$ | $SCH_3$ |
| 2969 | $S—(CH_2CH_2)—S$ | | $SCH_3$ | $CH_3$ | $SCH_3$ |
| 2970 | $S—(CH_2CH_2CH_2)—S$ | | $SCH_3$ | $CH_3$ | $SCH_3$ |
| 2971 | $—(CH_2)_4—$ | | $SCH_3$ | $CH_3$ | $SCH_3$ |
| 2972 | $—(CH_2)_5—$ | | $SCH_3$ | $CH_3$ | $SCH_3$ |
| 2973 | H | H | $SO_2CH_3$ | $CH_3$ | $SCH_3$ |
| 2974 | $CH_3$ | $CH_3$ | $SO_2CH_3$ | $CH_3$ | $SCH_3$ |
| 2975 | $CH_2CH_3$ | $CH_2CH_3$ | $SO_2CH_3$ | $CH_3$ | $SCH_3$ |
| 2976 | $CH_2CH_2CH_3$ | $CH_2CH_2CH_3$ | $SO_2CH_3$ | $CH_3$ | $SCH_3$ |
| 2977 | $OCH_3$ | $OCH_3$ | $SO_2CH_3$ | $CH_3$ | $SCH_3$ |
| 2978 | $OCH_2CH_3$ | $OCH_2CH_3$ | $SO_2CH_3$ | $CH_3$ | $SCH_3$ |
| 2979 | $OCH_2CH_2CH_3$ | $OCH_2CH_2CH_3$ | $SO_2CH_3$ | $CH_3$ | $SCH_3$ |
| 2980 | $SCH_3$ | $SCH_3$ | $SO_2CH_3$ | $CH_3$ | $SCH_3$ |
| 2981 | $SCH_2CH_3$ | $SCH_2CH_3$ | $SO_2CH_3$ | $CH_3$ | $SCH_3$ |
| 2982 | $N(CH_3)_2$ | $N(CH_3)_2$ | $SO_2CH_3$ | $CH_3$ | $SCH_3$ |
| 2983 | $N(CH_2CH_3)_2$ | $N(CH_2CH_3)_2$ | $SO_2CH_3$ | $CH_3$ | $SCH_3$ |
| 2984 | $N(CH_3)(CH_2CH_3)$ | $N(CH_3)(CH_2CH_3)$ | $SO_2CH_3$ | $CH_3$ | $SCH_3$ |
| 2985 | $O—(CH_2CH_2)—O$ | | $SO_2CH_3$ | $CH_3$ | $SCH_3$ |
| 2986 | $O—(CH_2CH_2CH_2)—O$ | | $SO_2CH_3$ | $CH_3$ | $SCH_3$ |
| 2987 | $S—(CH_2CH_2)—S$ | | $SO_2CH_3$ | $CH_3$ | $SCH_3$ |
| 2988 | $S—(CH_2CH_2CH_2)—S$ | | $SO_2CH_3$ | $CH_3$ | $SCH_3$ |
| 2989 | $—(CH_2)_4—$ | | $SO_2CH_3$ | $CH_3$ | $SCH_3$ |
| 2990 | $—(CH_2)_5—$ | | $SO_2CH_3$ | $CH_3$ | $SCH_3$ |
| 2991 | H | H | $PO(OCH_3)_2$ | $CH_3$ | $SCH_3$ |
| 2992 | $CH_3$ | $CH_3$ | $PO(OCH_3)_2$ | $CH_3$ | $SCH_3$ |
| 2993 | $CH_2CH_3$ | $CH_2CH_3$ | $PO(OCH_3)_2$ | $CH_3$ | $SCH_3$ |
| 2994 | $CH_2CH_2CH_3$ | $CH_2CH_2CH_3$ | $PO(OCH_3)_2$ | $CH_3$ | $SCH_3$ |
| 2995 | $OCH_3$ | $OCH_3$ | $PO(OCH_3)_2$ | $CH_3$ | $SCH_3$ |
| 2996 | $OCH_2CH_3$ | $OCH_2CH_3$ | $PO(OCH_3)_2$ | $CH_3$ | $SCH_3$ |
| 2997 | $OCH_2CH_2CH_3$ | $OCH_2CH_2CH_3$ | $PO(OCH_3)_2$ | $CH_3$ | $SCH_3$ |
| 2998 | $SCH_3$ | $SCH_3$ | $PO(OCH_3)_2$ | $CH_3$ | $SCH_3$ |
| 2999 | $SCH_2CH_3$ | $SCH_2CH_3$ | $PO(OCH_3)_2$ | $CH_3$ | $SCH_3$ |
| 3000 | $N(CH_3)_2$ | $N(CH_3)_2$ | $PO(OCH_3)_2$ | $CH_3$ | $SCH_3$ |
| 3001 | $N(CH_2CH_3)_2$ | $N(CH_2CH_3)_2$ | $PO(OCH_3)_2$ | $CH_3$ | $SCH_3$ |
| 3002 | $N(CH_3)(CH_2CH_3)$ | $N(CH_3)(CH_2CH_3)$ | $PO(OCH_3)_2$ | $CH_3$ | $SCH_3$ |
| 3003 | $O—(CH_2CH_2)—O$ | | $PO(OCH_3)_2$ | $CH_3$ | $SCH_3$ |
| 3004 | $O—(CH_2CH_2CH_2)—O$ | | $PO(OCH_3)_2$ | $CH_3$ | $SCH_3$ |
| 3005 | $S—(CH_2CH_2)—S$ | | $PO(OCH_3)_2$ | $CH_3$ | $SCH_3$ |
| 3006 | $S—(CH_2CH_2CH_2)—S$ | | $PO(OCH_3)_2$ | $CH_3$ | $SCH_3$ |
| 3007 | $—(CH_2)_4—$ | | $PO(OCH_3)_2$ | $CH_3$ | $SCH_3$ |
| 3008 | $—(CH_2)_5—$ | | $PO(OCH_3)_2$ | $CH_3$ | $SCH_3$ |
| 3009 | H | H | $PO(OCH_2CH_3)_2$ | $CH_3$ | $SCH_3$ |
| 3010 | $CH_3$ | $CH_3$ | $PO(OCH_2CH_3)_2$ | $CH_3$ | $SCH_3$ |
| 3011 | $CH_2CH_3$ | $CH_2CH_3$ | $PO(OCH_2CH_3)_2$ | $CH_3$ | $SCH_3$ |
| 3012 | $CH_2CH_2CH_3$ | $CH_2CH_2CH_3$ | $PO(OCH_2CH_3)_2$ | $CH_3$ | $SCH_3$ |
| 3013 | $OCH_3$ | $OCH_3$ | $PO(OCH_2CH_3)_2$ | $CH_3$ | $SCH_3$ |
| 3014 | $OCH_2CH_3$ | $OCH_2CH_3$ | $PO(OCH_2CH_3)_2$ | $CH_3$ | $SCH_3$ |
| 3015 | $OCH_2CH_2CH_3$ | $OCH_2CH_2CH_3$ | $PO(OCH_2CH_3)_2$ | $CH_3$ | $SCH_3$ |
| 3016 | $SCH_3$ | $SCH_3$ | $PO(OCH_2CH_3)_2$ | $CH_3$ | $SCH_3$ |
| 3017 | $SCH_2CH_3$ | $SCH_2CH_3$ | $PO(OCH_2CH_3)_2$ | $CH_3$ | $SCH_3$ |
| 3018 | $N(CH_3)_2$ | $N(CH_3)_2$ | $PO(OCH_2CH_3)_2$ | $CH_3$ | $SCH_3$ |
| 3019 | $N(CH_2CH_3)_2$ | $N(CH_2CH_3)_2$ | $PO(OCH_2CH_3)_2$ | $CH_3$ | $SCH_3$ |
| 3020 | $N(CH_3)(CH_2CH_3)$ | $N(CH_3)(CH_2CH_3)$ | $PO(OCH_2CH_3)_2$ | $CH_3$ | $SCH_3$ |
| 3021 | $O—(CH_2CH_2)—O$ | | $PO(OCH_2CH_3)_2$ | $CH_3$ | $SCH_3$ |
| 3022 | $O—(CH_2CH_2CH_2)—O$ | | $PO(OCH_2CH_3)_2$ | $CH_3$ | $SCH_3$ |
| 3023 | $S—(CH_2CH_2)—S$ | | $PO(OCH_2CH_3)_2$ | $CH_3$ | $SCH_3$ |
| 3024 | $S—(CH_2CH_2CH_2)—S$ | | $PO(OCH_2CH_3)_2$ | $CH_3$ | $SCH_3$ |
| 3025 | $—(CH_2)_4—$ | | $PO(OCH_2CH_3)_2$ | $CH_3$ | $SCH_3$ |
| 3026 | $—(CH_2)_5—$ | | $PO(OCH_2CH_3)_2$ | $CH_3$ | $SCH_3$ |
| 3027 | H | H | $PO(CH_3)_2$ | $CH_3$ | $SCH_3$ |

TABLE 1-continued

I1a1

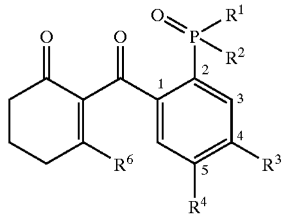

| n | $R^1$ | $R^2$ | $R^3$ | $R^4$ | $R^6$ |
|---|---|---|---|---|---|
| 3028 | $CH_3$ | $CH_3$ | $PO(CH_3)_2$ | $CH_3$ | $SCH_3$ |
| 3029 | $CH_2CH_3$ | $CH_2CH_3$ | $PO(CH_3)_2$ | $CH_3$ | $SCH_3$ |
| 3030 | $CH_2CH_2CH_3$ | $CH_2CH_2CH_3$ | $PO(CH_3)_2$ | $CH_3$ | $SCH_3$ |
| 3031 | $OCH_3$ | $OCH_3$ | $PO(CH_3)_2$ | $CH_3$ | $SCH_3$ |
| 3032 | $OCH_2CH_3$ | $OCH_2CH_3$ | $PO(CH_3)_2$ | $CH_3$ | $SCH_3$ |
| 3033 | $OCH_2CH_2CH_3$ | $OCH_2CH_2CH_3$ | $PO(CH_3)_2$ | $CH_3$ | $SCH_3$ |
| 3034 | $SCH_3$ | $SCH_3$ | $PO(CH_3)_2$ | $CH_3$ | $SCH_3$ |
| 3035 | $SCH_2CH_3$ | $SCH_2CH_3$ | $PO(CH_3)_2$ | $CH_3$ | $SCH_3$ |
| 3036 | $N(CH_3)_2$ | $N(CH_3)_2$ | $PO(CH_3)_2$ | $CH_3$ | $SCH_3$ |
| 3037 | $N(CH_2CH_3)_2$ | $N(CH_2CH_3)_2$ | $PO(CH_3)_2$ | $CH_3$ | $SCH_3$ |
| 3038 | $N(CH_3)(CH_2CH_3)$ | $N(CH_3)(CH_2CH_3)$ | $PO(CH_3)_2$ | $CH_3$ | $SCH_3$ |
| 3039 | $O—(CH_2CH_2)—O$ | | $PO(CH_3)_2$ | $CH_3$ | $SCH_3$ |
| 3040 | $O—(CH_2CH_2CH_2)—O$ | | $PO(CH_3)_2$ | $CH_3$ | $SCH_3$ |
| 3041 | $S—(CH_2CH_2)—S$ | | $PO(CH_3)_2$ | $CH_3$ | $SCH_3$ |
| 3042 | $S—(CH_2CH_2CH_2)—S$ | | $PO(CH_3)_2$ | $CH_3$ | $SCH_3$ |
| 3043 | $—(CH_2)_4—$ | | $PO(CH_3)_2$ | $CH_3$ | $SCH_3$ |
| 3044 | $—(CH_2)_5—$ | | $PO(CH_3)_2$ | $CH_3$ | $SCH_3$ |
| 3045 | H | H | $PO(CH_2CH_3)_2$ | $CH_3$ | $SCH_3$ |
| 3046 | $CH_3$ | $CH_3$ | $PO(CH_2CH_3)_2$ | $CH_3$ | $SCH_3$ |
| 3047 | $CH_2CH_3$ | $CH_2CH_3$ | $PO(CH_2CH_3)_2$ | $CH_3$ | $SCH_3$ |
| 3048 | $CH_2CH_2CH_3$ | $CH_2CH_2CH_3$ | $PO(CH_2CH_3)_2$ | $CH_3$ | $SCH_3$ |
| 3049 | $OCH_3$ | $OCH_3$ | $PO(CH_2CH_3)_2$ | $CH_3$ | $SCH_3$ |
| 3050 | $OCH_2CH_3$ | $OCH_2CH_3$ | $PO(CH_2CH_3)_2$ | $CH_3$ | $SCH_3$ |
| 3051 | $OCH_2CH_2CH_3$ | $OCH_2CH_2CH_3$ | $PO(CH_2CH_3)_2$ | $CH_3$ | $SCH_3$ |
| 3052 | $SCH_3$ | $SCH_3$ | $PO(CH_2CH_3)_2$ | $CH_3$ | $SCH_3$ |
| 3053 | $SCH_2CH_3$ | $SCH_2CH_3$ | $PO(CH_2CH_3)_2$ | $CH_3$ | $SCH_3$ |
| 3054 | $N(CH_3)_2$ | $N(CH_3)_2$ | $PO(CH_2CH_3)_2$ | $CH_3$ | $SCH_3$ |
| 3055 | $N(CH_2CH_3)_2$ | $N(CH_2CH_3)_2$ | $PO(CH_2CH_3)_2$ | $CH_3$ | $SCH_3$ |
| 3056 | $N(CH_3)(CH_2CH_3)$ | $N(CH_3)(CH_2CH_3)$ | $PO(CH_2CH_3)_2$ | $CH_3$ | $SCH_3$ |
| 3057 | $O—(CH_2CH_2)—O$ | | $PO(CH_2CH_3)_2$ | $CH_3$ | $SCH_3$ |
| 3058 | $O—(CH_2CH_2CH_2)—O$ | | $PO(CH_2CH_3)_2$ | $CH_3$ | $SCH_3$ |
| 3059 | $S—(CH_2CH_2)—S$ | | $PO(CH_2CH_3)_2$ | $CH_3$ | $SCH_3$ |
| 3060 | $S—(CH_2CH_2CH_2)—S$ | | $PO(CH_2CH_3)_2$ | $CH_3$ | $SCH_3$ |
| 3061 | $—(CH_2)_4—$ | | $PO(CH_2CH_3)_2$ | $CH_3$ | $SCH_3$ |
| 3062 | $—(CH_2)_5—$ | | $PO(CH_2CH_3)_2$ | $CH_3$ | $SCH_3$ |
| 3063 | H | H | H | $CH_3$ | $SC_6H_5$ |
| 3064 | $CH_3$ | $CH_3$ | H | $CH_3$ | $SC_6H_5$ |
| 3065 | $CH_2CH_3$ | $CH_2CH_3$ | H | $CH_3$ | $SC_6H_5$ |
| 3066 | $CH_2CH_2CH_3$ | $CH_2CH_2CH_3$ | H | $CH_3$ | $SC_6H_5$ |
| 3067 | $OCH_3$ | $OCH_3$ | H | $CH_3$ | $SC_6H_5$ |
| 3068 | $OCH_2CH_3$ | $OCH_2CH_3$ | H | $CH_3$ | $SC_6H_5$ |
| 3069 | $OCH_2CH_2CH_3$ | $OCH_2CH_2CH_3$ | H | $CH_3$ | $SC_6H_5$ |
| 3070 | $SCH_3$ | $SCH_3$ | H | $CH_3$ | $SC_6H_5$ |
| 3071 | $SCH_2CH_3$ | $SCH_2CH_3$ | H | $CH_3$ | $SC_6H_5$ |
| 3072 | $N(CH_3)_2$ | $N(CH_3)_2$ | H | $CH_3$ | $SC_6H_5$ |
| 3073 | $N(CH_2CH_3)_2$ | $N(CH_2CH_3)_2$ | H | $CH_3$ | $SC_6H_5$ |
| 3074 | $N(CH_3)(CH_2CH_3)$ | $N(CH_3)(CH_2CH_3)$ | H | $CH_3$ | $SC_6H_5$ |
| 3075 | $O—(CH_2CH_2)—O$ | | H | $CH_3$ | $SC_6H_5$ |
| 3076 | $O—(CH_2CH_2CH_2)—O$ | | H | $CH_3$ | $SC_6H_5$ |
| 3077 | $S—(CH_2CH_2)—S$ | | H | $CH_3$ | $SC_6H_5$ |
| 3078 | $S—(CH_2CH_2CH_2)—S$ | | H | $CH_3$ | $SC_6H_5$ |
| 3079 | $—(CH_2)_4—$ | | H | $CH_3$ | $SC_6H_5$ |
| 3080 | $—(CH_2)_5—$ | | H | $CH_3$ | $SC_6H_5$ |
| 3081 | H | H | $NO_2$ | $CH_3$ | $SC_6H_5$ |
| 3082 | $CH_3$ | $CH_3$ | $NO_2$ | $CH_3$ | $SC_6H_5$ |
| 3083 | $CH_2CH_3$ | $CH_2CH_3$ | $NO_2$ | $CH_3$ | $SC_6H_5$ |
| 3084 | $CH_2CH_2CH_3$ | $CH_2CH_2CH_3$ | $NO_2$ | $CH_3$ | $SC_6H_5$ |
| 3085 | $OCH_3$ | $OCH_3$ | $NO_2$ | $CH_3$ | $SC_6H_5$ |
| 3086 | $OCH_2CH_3$ | $OCH_2CH_3$ | $NO_2$ | $CH_3$ | $SC_6H_5$ |
| 3087 | $OCH_2CH_2CH_3$ | $OCH_2CH_2CH_3$ | $NO_2$ | $CH_3$ | $SC_6H_5$ |
| 3088 | $SCH_3$ | $SCH_3$ | $NO_2$ | $CH_3$ | $SC_6H_5$ |
| 3089 | $SCH_2CH_3$ | $SCH_2CH_3$ | $NO_2$ | $CH_3$ | $SC_6H_5$ |
| 3090 | $N(CH_3)_2$ | $N(CH_3)_2$ | $NO_2$ | $CH_3$ | $SC_6H_5$ |
| 3091 | $N(CH_2CH_3)_2$ | $N(CH_2CH_3)_2$ | $NO_2$ | $CH_3$ | $SC_6H_5$ |

TABLE 1-continued

I1a1

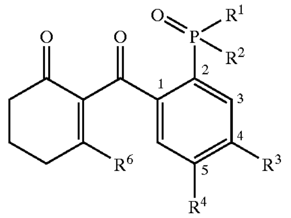

| n | $R^1$ | $R^2$ | $R^3$ | $R^4$ | $R^6$ |
|---|---|---|---|---|---|
| 3092 | $N(CH_3)(CH_2CH_3)$ | $N(CH_3)(CH_2CH_3)$ | $NO_2$ | $CH_3$ | $SC_6H_5$ |
| 3093 | $O-(CH_2CH_2)-O$ | | $NO_2$ | $CH_3$ | $SC_6H_5$ |
| 3094 | $O-(CH_2CH_2CH_2)-O$ | | $NO_2$ | $CH_3$ | $SC_6H_5$ |
| 3095 | $S-(CH_2CH_2)-S$ | | $NO_2$ | $CH_3$ | $SC_6H_5$ |
| 3096 | $S-(CH_2CH_2CH_2)-S$ | | $NO_2$ | $CH_3$ | $SC_6H_5$ |
| 3097 | $-(CH_2)_4-$ | | $NO_2$ | $CH_3$ | $SC_6H_5$ |
| 3098 | $-(CH_2)_5-$ | | $NO_2$ | $CH_3$ | $SC_6H_5$ |
| 3099 | H | H | CN | $CH_3$ | $SC_6H_5$ |
| 3100 | $CH_3$ | $CH_3$ | CN | $CH_3$ | $SC_6H_5$ |
| 3101 | $CH_2CH_3$ | $CH_2CH_3$ | CN | $CH_3$ | $SC_6H_5$ |
| 3102 | $CH_2CH_2CH_3$ | $CH_2CH_2CH_3$ | CN | $CH_3$ | $SC_6H_5$ |
| 3103 | $OCH_3$ | $OCH_3$ | CN | $CH_3$ | $SC_6H_5$ |
| 3104 | $OCH_2CH_3$ | $OCH_2CH_3$ | CN | $CH_3$ | $SC_6H_5$ |
| 3105 | $OCH_2CH_2CH_3$ | $OCH_2CH_2CH_3$ | CN | $CH_3$ | $SC_6H_5$ |
| 3106 | $SCH_3$ | $SCH_3$ | CN | $CH_3$ | $SC_6H_5$ |
| 3107 | $SCH_2CH_3$ | $SCH_2CH_3$ | CN | $CH_3$ | $SC_6H_5$ |
| 3108 | $N(CH_3)_2$ | $N(CH_3)_2$ | CN | $CH_3$ | $SC_6H_5$ |
| 3109 | $N(CH_2CH_3)_2$ | $N(CH_2CH_3)_2$ | CN | $CH_3$ | $SC_6H_5$ |
| 3110 | $N(CH_3)(CH_2CH_3)$ | $N(CH_3)(CH_2CH_3)$ | CN | $CH_3$ | $SC_6H_5$ |
| 3111 | $O-(CH_2CH_2)-O$ | | CN | $CH_3$ | $SC_6H_5$ |
| 3112 | $O-(CH_2CH_2CH_2)-O$ | | CN | $CH_3$ | $SC_6H_5$ |
| 3113 | $S-(CH_2CH_2)-S$ | | CN | $CH_3$ | $SC_6H_5$ |
| 3114 | $S-(CH_2CH_2CH_2)-S$ | | CN | $CH_3$ | $SC_6H_5$ |
| 3115 | $-(CH_2)_4-$ | | CN | $CH_3$ | $SC_6H_5$ |
| 3116 | $-(CH_2)_5-$ | | CN | $CH_3$ | $SC_6H_5$ |
| 3117 | H | H | F | $CH_3$ | $SC_6H_5$ |
| 3118 | $CH_3$ | $CH_3$ | F | $CH_3$ | $SC_6H_5$ |
| 3119 | $CH_2CH_3$ | $CH_2CH_3$ | F | $CH_3$ | $SC_6H_5$ |
| 3120 | $CH_2CH_2CH_3$ | $CH_2CH_2CH_3$ | F | $CH_3$ | $SC_6H_5$ |
| 3121 | $OCH_3$ | $OCH_3$ | F | $CH_3$ | $SC_6H_5$ |
| 3122 | $OCH_2CH_3$ | $OCH_2CH_3$ | F | $CH_3$ | $SC_6H_5$ |
| 3123 | $OCH_2CH_2CH_3$ | $OCH_2CH_2CH_3$ | F | $CH_3$ | $SC_6H_5$ |
| 3124 | $SCH_3$ | $SCH_3$ | F | $CH_3$ | $SC_6H_5$ |
| 3125 | $SCH_2CH_3$ | $SCH_2CH_3$ | F | $CH_3$ | $SC_6H_5$ |
| 3126 | $N(CH_3)_2$ | $N(CH_3)_2$ | F | $CH_3$ | $SC_6H_5$ |
| 3127 | $N(CH_2CH_3)_2$ | $N(CH_2CH_3)_2$ | F | $CH_3$ | $SC_6H_5$ |
| 3128 | $N(CH_3)(CH_2CH_3)$ | $N(CH_3)(CH_2CH_3)$ | F | $CH_3$ | $SC_6H_5$ |
| 3129 | $O-(CH_2CH_2)-O$ | | F | $CH_3$ | $SC_6H_5$ |
| 3130 | $O-(CH_2CH_2CH_2)-O$ | | F | $CH_3$ | $SC_6H_5$ |
| 3131 | $S-(CH_2CH_2)-S$ | | F | $CH_3$ | $SC_6H_5$ |
| 3132 | $S-(CH_2CH_2CH_2)-S$ | | F | $CH_3$ | $SC_6H_5$ |
| 3133 | $-(CH_2)_4-$ | | F | $CH_3$ | $SC_6H_5$ |
| 3134 | $-(CH_2)_5-$ | | F | $CH_3$ | $SC_6H_5$ |
| 3135 | H | H | Cl | $CH_3$ | $SC_6H_5$ |
| 3136 | $CH_3$ | $CH_3$ | Cl | $CH_3$ | $SC_6H_5$ |
| 3137 | $CH_2CH_3$ | $CH_2CH_3$ | Cl | $CH_3$ | $SC_6H_5$ |
| 3138 | $CH_2CH_2CH_3$ | $CH_2CH_2CH_3$ | Cl | $CH_3$ | $SC_6H_5$ |
| 3139 | $OCH_3$ | $OCH_3$ | Cl | $CH_3$ | $SC_6H_5$ |
| 3140 | $OCH_2CH_3$ | $OCH_2CH_3$ | Cl | $CH_3$ | $SC_6H_5$ |
| 3141 | $OCH_2CH_2CH_3$ | $OCH_2CH_2CH_3$ | Cl | $CH_3$ | $SC_6H_5$ |
| 3142 | $SCH_3$ | $SCH_3$ | Cl | $CH_3$ | $SC_6H_5$ |
| 3143 | $SCH_2CH_3$ | $SCH_2CH_3$ | Cl | $CH_3$ | $SC_6H_5$ |
| 3144 | $N(CH_3)_2$ | $N(CH_3)_2$ | Cl | $CH_3$ | $SC_6H_5$ |
| 3145 | $N(CH_2CH_3)_2$ | $N(CH_2CH_3)_2$ | Cl | $CH_3$ | $SC_6H_5$ |
| 3146 | $N(CH_3)(CH_2CH_3)$ | $N(CH_3)(CH_2CH_3)$ | Cl | $CH_3$ | $SC_6H_5$ |
| 3147 | $O-(CH_2CH_2)-O$ | | Cl | $CH_3$ | $SC_6H_5$ |
| 3148 | $O-(CH_2CH_2CH_2)-O$ | | Cl | $CH_3$ | $SC_6H_5$ |
| 3149 | $S-(CH_2CH_2)-S$ | | Cl | $CH_3$ | $SC_6H_5$ |
| 3150 | $S-(CH_2CH_2CH_2)-S$ | | Cl | $CH_3$ | $SC_6H_5$ |
| 3151 | $-(CH_2)_4-$ | | Cl | $CH_3$ | $SC_6H_5$ |
| 3152 | $-(CH_2)_5-$ | | Cl | $CH_3$ | $SC_6H_5$ |
| 3153 | H | H | Br | $CH_3$ | $SC_6H_5$ |
| 3154 | $CH_3$ | $CH_3$ | Br | $CH_3$ | $SC_6H_5$ |
| 3155 | $CH_2CH_3$ | $CH_2CH_3$ | Br | $CH_3$ | $SC_6H_5$ |

TABLE 1-continued

I1a1

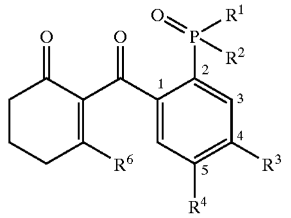

| n | $R^1$ | $R^2$ | $R^3$ | $R^4$ | $R^6$ |
|---|---|---|---|---|---|
| 3156 | $CH_2CH_2CH_3$ | $CH_2CH_2CH_3$ | Br | $CH_3$ | $SC_6H_5$ |
| 3157 | $OCH_3$ | $OCH_3$ | Br | $CH_3$ | $SC_6H_5$ |
| 3158 | $OCH_2CH_3$ | $OCH_2CH_3$ | Br | $CH_3$ | $SC_6H_5$ |
| 3159 | $OCH_2CH_2CH_3$ | $OCH_2CH_2CH_3$ | Br | $CH_3$ | $SC_6H_5$ |
| 3160 | $SCH_3$ | $SCH_3$ | Br | $CH_3$ | $SC_6H_5$ |
| 3161 | $SCH_2CH_3$ | $SCH_2CH_3$ | Br | $CH_3$ | $SC_6H_5$ |
| 3162 | $N(CH_3)_2$ | $N(CH_3)_2$ | Br | $CH_3$ | $SC_6H_5$ |
| 3163 | $N(CH_2CH_3)_2$ | $N(CH_2CH_3)_2$ | Br | $CH_3$ | $SC_6H_5$ |
| 3164 | $N(CH_3)(CH_2CH_3)$ | $N(CH_3)(CH_2CH_3)$ | Br | $CH_3$ | $SC_6H_5$ |
| 3165 | $O—(CH_2CH_2)—O$ | | Br | $CH_3$ | $SC_6H_5$ |
| 3166 | $O—(CH_2CH_2CH_2)—O$ | | Br | $CH_3$ | $SC_6H_5$ |
| 3167 | $S—(CH_2CH_2)—S$ | | Br | $CH_3$ | $SC_6H_5$ |
| 3168 | $S—(CH_2CH_2CH_2)—S$ | | Br | $CH_3$ | $SC_6H_5$ |
| 3169 | $—(CH_2)_4—$ | | Br | $CH_3$ | $SC_6H_5$ |
| 3170 | $—(CH_2)_5—$ | | Br | $CH_3$ | $SC_6H_5$ |
| 3171 | H | H | $CH_3$ | $CH_3$ | $SC_6H_5$ |
| 3172 | $CH_3$ | $CH_3$ | $CH_3$ | $CH_3$ | $SC_6H_5$ |
| 3173 | $CH_2CH_3$ | $CH_2CH_3$ | $CH_3$ | $CH_3$ | $SC_6H_5$ |
| 3174 | $CH_2CH_2CH_3$ | $CH_2CH_2CH_3$ | $CH_3$ | $CH_3$ | $SC_6H_5$ |
| 3175 | $OCH_3$ | $OCH_3$ | $CH_3$ | $CH_3$ | $SC_6H_5$ |
| 3176 | $OCH_2CH_3$ | $OCH_2CH_3$ | $CH_3$ | $CH_3$ | $SC_6H_5$ |
| 3177 | $OCH_2CH_2CH_3$ | $OCH_2CH_2CH_3$ | $CH_3$ | $CH_3$ | $SC_6H_5$ |
| 3178 | $SCH_3$ | $SCH_3$ | $CH_3$ | $CH_3$ | $SC_6H_5$ |
| 3179 | $SCH_2CH_3$ | $SCH_2CH_3$ | $CH_3$ | $CH_3$ | $SC_6H_5$ |
| 3180 | $N(CH_3)_2$ | $N(CH_3)_2$ | $CH_3$ | $CH_3$ | $SC_6H_5$ |
| 3181 | $N(CH_2CH_3)_2$ | $N(CH_2CH_3)_2$ | $CH_3$ | $CH_3$ | $SC_6H_5$ |
| 3182 | $N(CH_3)(CH_2CH_3)$ | $N(CH_3)(CH_2CH_3)$ | $CH_3$ | $CH_3$ | $SC_6H_5$ |
| 3183 | $O—(CH_2CH_2)—O$ | | $CH_3$ | $CH_3$ | $SC_6H_5$ |
| 3184 | $O—(CH_2CH_2CH_2)—O$ | | $CH_3$ | $CH_3$ | $SC_6H_5$ |
| 3185 | $S—(CH_2CH_2)—S$ | | $CH_3$ | $CH_3$ | $SC_6H_5$ |
| 3186 | $S—(CH_2CH_2CH_2)—S$ | | $CH_3$ | $CH_3$ | $SC_6H_5$ |
| 3187 | $—(CH_2)_4—$ | | $CH_3$ | $CH_3$ | $SC_6H_5$ |
| 3188 | $—(CH_2)_5—$ | | $CH_3$ | $CH_3$ | $SC_6H_5$ |
| 3189 | H | H | $CH_2CH_3$ | $CH_3$ | $SC_6H_5$ |
| 3190 | $CH_3$ | $CH_3$ | $CH_2CH_3$ | $CH_3$ | $SC_6H_5$ |
| 3191 | $CH_2CH_3$ | $CH_2CH_3$ | $CH_2CH_3$ | $CH_3$ | $SC_6H_5$ |
| 3192 | $CH_2CH_2CH_3$ | $CH_2CH_2CH_3$ | $CH_2CH_3$ | $CH_3$ | $SC_6H_5$ |
| 3193 | $OCH_3$ | $OCH_3$ | $CH_2CH_3$ | $CH_3$ | $SC_6H_5$ |
| 3194 | $OCH_2CH_3$ | $OCH_2CH_3$ | $CH_2CH_3$ | $CH_3$ | $SC_6H_5$ |
| 3195 | $OCH_2CH_2CH_3$ | $OCH_2CH_2CH_3$ | $CH_2CH_3$ | $CH_3$ | $SC_6H_5$ |
| 3196 | $SCH_3$ | $SCH_3$ | $CH_2CH_3$ | $CH_3$ | $SC_6H_5$ |
| 3197 | $SCH_2CH_3$ | $SCH_2CH_3$ | $CH_2CH_3$ | $CH_3$ | $SC_6H_5$ |
| 3198 | $N(CH_3)_2$ | $N(CH_3)_2$ | $CH_2CH_3$ | $CH_3$ | $SC_6H_5$ |
| 3199 | $N(CH_2CH_3)_2$ | $N(CH_2CH_3)_2$ | $CH_2CH_3$ | $CH_3$ | $SC_6H_5$ |
| 3200 | $N(CH_3)(CH_2CH_3)$ | $N(CH_3)(CH_2CH_3)$ | $CH_2CH_3$ | $CH_3$ | $SC_6H_5$ |
| 3201 | $O—(CH_2CH_2)—O$ | | $CH_2CH_3$ | $CH_3$ | $SC_6H_5$ |
| 3202 | $O—(CH_2CH_2CH_2)—O$ | | $CH_2CH_3$ | $CH_3$ | $SC_6H_5$ |
| 3203 | $S—(CH_2CH_2)—S$ | | $CH_2CH_3$ | $CH_3$ | $SC_6H_5$ |
| 3204 | $S—(CH_2CH_2CH_2)—S$ | | $CH_2CH_3$ | $CH_3$ | $SC_6H_5$ |
| 3205 | $—(CH_2)_4—$ | | $CH_2CH_3$ | $CH_3$ | $SC_6H_5$ |
| 3206 | $—(CH_2)_5—$ | | $CH_2CH_3$ | $CH_3$ | $SC_6H_5$ |
| 3207 | H | H | $CF_3$ | $CH_3$ | $SC_6H_5$ |
| 3208 | $CH_3$ | $CH_3$ | $CF_3$ | $CH_3$ | $SC_6H_5$ |
| 3209 | $CH_2CH_3$ | $CH_2CH_3$ | $CF_3$ | $CH_3$ | $SC_6H_5$ |
| 3210 | $CH_2CH_2CH_3$ | $CH_2CH_2CH_3$ | $CF_3$ | $CH_3$ | $SC_6H_5$ |
| 3211 | $OCH_3$ | $OCH_3$ | $CF_3$ | $CH_3$ | $SC_6H_5$ |
| 3212 | $OCH_2CH_3$ | $OCH_2CH_3$ | $CF_3$ | $CH_3$ | $SC_6H_5$ |
| 3213 | $OCH_2CH_2CH_3$ | $OCH_2CH_2CH_3$ | $CF_3$ | $CH_3$ | $SC_6H_5$ |
| 3214 | $SCH_3$ | $SCH_3$ | $CF_3$ | $CH_3$ | $SC_6H_5$ |
| 3215 | $SCH_2CH_3$ | $SCH_2CH_3$ | $CF_3$ | $CH_3$ | $SC_6H_5$ |
| 3216 | $N(CH_3)_2$ | $N(CH_3)_2$ | $CF_3$ | $CH_3$ | $SC_6H_5$ |
| 3217 | $N(CH_2CH_3)_2$ | $N(CH_2CH_3)_2$ | $CF_3$ | $CH_3$ | $SC_6H_5$ |
| 3218 | $N(CH_3)(CH_2CH_3)$ | $N(CH_3)(CH_2CH_3)$ | $CF_3$ | $CH_3$ | $SC_6H_5$ |
| 3219 | $O—(CH_2CH_2)—O$ | | $CF_3$ | $CH_3$ | $SC_6H_5$ |

TABLE 1-continued

I1a1

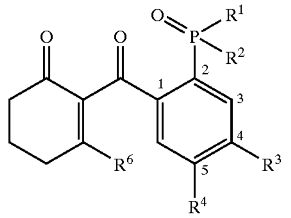

| n | $R^1$ | $R^2$ | $R^3$ | $R^4$ | $R^6$ |
|---|---|---|---|---|---|
| 3220 | O—(CH2CH2CH2)—O | | $CF_3$ | $CH_3$ | $SC_6H_5$ |
| 3221 | S—(CH2CH2)—S | | $CF_3$ | $CH_3$ | $SC_6H_5$ |
| 3222 | S—(CH2CH2CH2)—S | | $CF_3$ | $CH_3$ | $SC_6H_5$ |
| 3223 | —(CH2)4— | | $CF_3$ | $CH_3$ | $SC_6H_5$ |
| 3224 | —(CH2)5— | | $CF_3$ | $CH_3$ | $SC_6H_5$ |
| 3225 | H | H | $OCH_3$ | $CH_3$ | $SC_6H_5$ |
| 3226 | $CH_3$ | $CH_3$ | $OCH_3$ | $CH_3$ | $SC_6H_5$ |
| 3227 | $CH_2CH_3$ | $CH_2CH_3$ | $OCH_3$ | $CH_3$ | $SC_6H_5$ |
| 3228 | $CH_2CH_2CH_3$ | $CH_2CH_2CH_3$ | $OCH_3$ | $CH_3$ | $SC_6H_5$ |
| 3229 | $OCH_3$ | $OCH_3$ | $OCH_3$ | $CH_3$ | $SC_6H_5$ |
| 3230 | $OCH_2CH_3$ | $OCH_2CH_3$ | $OCH_3$ | $CH_3$ | $SC_6H_5$ |
| 3231 | $OCH_2CH_2CH_3$ | $OCH_2CH_2CH_3$ | $OCH_3$ | $CH_3$ | $SC_6H_5$ |
| 3232 | $SCH_3$ | $SCH_3$ | $OCH_3$ | $CH_3$ | $SC_6H_5$ |
| 3233 | $SCH_2CH_3$ | $SCH_2CH_3$ | $OCH_3$ | $CH_3$ | $SC_6H_5$ |
| 3234 | $N(CH_3)_2$ | $N(CH_3)_2$ | $OCH_3$ | $CH_3$ | $SC_6H_5$ |
| 3235 | $N(CH_2CH_3)_2$ | $N(CH_2CH_3)_2$ | $OCH_3$ | $CH_3$ | $SC_6H_5$ |
| 3236 | $N(CH_3)(CH_2CH_3)$ | $N(CH_3)(CH_2CH_3)$ | $OCH_3$ | $CH_3$ | $SC_6H_5$ |
| 3237 | O—(CH2CH2)—O | | $OCH_3$ | $CH_3$ | $SC_6H_5$ |
| 3238 | O—(CH2CH2CH2)—O | | $OCH_3$ | $CH_3$ | $SC_6H_5$ |
| 3239 | S—(CH2CH2)—S | | $OCH_3$ | $CH_3$ | $SC_6H_5$ |
| 3240 | S—(CH2CH2CH2)—S | | $OCH_3$ | $CH_3$ | $SC_6H_5$ |
| 3241 | —(CH2)4— | | $OCH_3$ | $CH_3$ | $SC_6H_5$ |
| 3242 | —(CH2)5— | | $OCH_3$ | $CH_3$ | $SC_6H_5$ |
| 3243 | H | H | $OCH_2CH_3$ | $CH_3$ | $SC_6H_5$ |
| 3244 | $CH_3$ | $CH_3$ | $OCH_2CH_3$ | $CH_3$ | $SC_6H_5$ |
| 3245 | $CH_2CH_3$ | $CH_2CH_3$ | $OCH_2CH_3$ | $CH_3$ | $SC_6H_5$ |
| 3246 | $CH_2CH_2CH_3$ | $CH_2CH_2CH_3$ | $OCH_2CH_3$ | $CH_3$ | $SC_6H_5$ |
| 3247 | $OCH_3$ | $OCH_3$ | $OCH_2CH_3$ | $CH_3$ | $SC_6H_5$ |
| 3248 | $OCH_2CH_3$ | $OCH_2CH_3$ | $OCH_2CH_3$ | $CH_3$ | $SC_6H_5$ |
| 3249 | $OCH_2CH_2CH_3$ | $OCH_2CH_2CH_3$ | $OCH_2CH_3$ | $CH_3$ | $SC_6H_5$ |
| 3250 | $SCH_3$ | $SCH_3$ | $OCH_2CH_3$ | $CH_3$ | $SC_6H_5$ |
| 3251 | $SCH_2CH_3$ | $SCH_2CH_3$ | $OCH_2CH_3$ | $CH_3$ | $SC_6H_5$ |
| 3252 | $N(CH_3)_2$ | $N(CH_3)_2$ | $OCH_2CH_3$ | $CH_3$ | $SC_6H_5$ |
| 3253 | $N(CH_2CH_3)_2$ | $N(CH_2CH_3)_2$ | $OCH_2CH_3$ | $CH_3$ | $SC_6H_5$ |
| 3254 | $N(CH_3)(CH_2CH_3)$ | $N(CH_3)(CH_2CH_3)$ | $OCH_2CH_3$ | $CH_3$ | $SC_6H_5$ |
| 3255 | O—(CH2CH2)—O | | $OCH_2CH_3$ | $CH_3$ | $SC_6H_5$ |
| 3256 | O—(CH2CH2CH2)—O | | $OCH_2CH_3$ | $CH_3$ | $SC_6H_5$ |
| 3257 | S—(CH2CH2)—S | | $OCH_2CH_3$ | $CH_3$ | $SC_6H_5$ |
| 3258 | S—(CH2CH2CH2)—S | | $OCH_2CH_3$ | $CH_3$ | $SC_6H_5$ |
| 3259 | —(CH2)4— | | $OCH_2CH_3$ | $CH_3$ | $SC_6H_5$ |
| 3260 | —(CH2)5— | | $OCH_2CH_3$ | $CH_3$ | $SC_6H_5$ |
| 3261 | H | H | $SCH_3$ | $CH_3$ | $SC_6H_5$ |
| 3262 | $CH_3$ | $CH_3$ | $SCH_3$ | $CH_3$ | $SC_6H_5$ |
| 3263 | $CH_2CH_3$ | $CH_2CH_3$ | $SCH_3$ | $CH_3$ | $SC_6H_5$ |
| 3264 | $CH_2CH_2CH_3$ | $CH_2CH_2CH_3$ | $SCH_3$ | $CH_3$ | $SC_6H_5$ |
| 3265 | $OCH_3$ | $OCH_3$ | $SCH_3$ | $CH_3$ | $SC_6H_5$ |
| 3266 | $OCH_2CH_3$ | $OCH_2CH_3$ | $SCH_3$ | $CH_3$ | $SC_6H_5$ |
| 3267 | $OCH_2CH_2CH_3$ | $OCH_2CH_2CH_3$ | $SCH_3$ | $CH_3$ | $SC_6H_5$ |
| 3268 | $SCH_3$ | $SCH_3$ | $SCH_3$ | $CH_3$ | $SC_6H_5$ |
| 3269 | $SCH_2CH_3$ | $SCH_2CH_3$ | $SCH_3$ | $CH_3$ | $SC_6H_5$ |
| 3270 | $N(CH_3)_2$ | $N(CH_3)_2$ | $SCH_3$ | $CH_3$ | $SC_6H_5$ |
| 3271 | $N(CH_2CH_3)_2$ | $N(CH_2CH_3)_2$ | $SCH_3$ | $CH_3$ | $SC_6H_5$ |
| 3272 | $N(CH_3)(CH_2CH_3)$ | $N(CH_3)(CH_2CH_3)$ | $SCH_3$ | $CH_3$ | $SC_6H_5$ |
| 3273 | O—(CH2CH2)—O | | $SCH_3$ | $CH_3$ | $SC_6H_5$ |
| 3274 | O—(CH2CH2CH2)—O | | $SCH_3$ | $CH_3$ | $SC_6H_5$ |
| 3275 | S—(CH2CH2)—S | | $SCH_3$ | $CH_3$ | $SC_6H_5$ |
| 3276 | S—(CH2CH2CH2)—S | | $SCH_3$ | $CH_3$ | $SC_6H_5$ |
| 3277 | —(CH2)4— | | $SCH_3$ | $CH_3$ | $SC_6H_5$ |
| 3278 | —(CH2)5— | | $SCH_3$ | $CH_3$ | $SC_6H_5$ |
| 3279 | H | H | $SO_2CH_3$ | $CH_3$ | $SC_6H_5$ |
| 3280 | $CH_3$ | $CH_3$ | $SO_2CH_3$ | $CH_3$ | $SC_6H_5$ |
| 3281 | $CH_2CH_3$ | $CH_2CH_3$ | $SO_2CH_3$ | $CH_3$ | $SC_6H_5$ |
| 3282 | $CH_2CH_2CH_3$ | $CH_2CH_2CH_3$ | $SO_2CH_3$ | $CH_3$ | $SC_6H_5$ |
| 3283 | $OCH_3$ | $OCH_3$ | $SO_2CH_3$ | $CH_3$ | $SC_6H_5$ |

TABLE 1-continued

I1a1

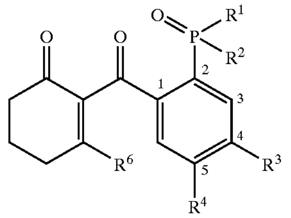

| n | $R^1$ | $R^2$ | $R^3$ | $R^4$ | $R^6$ |
|---|---|---|---|---|---|
| 3284 | $OCH_2CH_3$ | $OCH_2CH_3$ | $SO_2CH_3$ | $CH_3$ | $SC_6H_5$ |
| 3285 | $OCH_2CH_2CH_3$ | $OCH_2CH_2CH_3$ | $SO_2CH_3$ | $CH_3$ | $SC_6H_5$ |
| 3286 | $SCH_3$ | $SCH_3$ | $SO_2CH_3$ | $CH_3$ | $SC_6H_5$ |
| 3287 | $SCH_2CH_3$ | $SCH_2CH_3$ | $SO_2CH_3$ | $CH_3$ | $SC_6H_5$ |
| 3288 | $N(CH_3)_2$ | $N(CH_3)_2$ | $SO_2CH_3$ | $CH_3$ | $SC_6H_5$ |
| 3289 | $N(CH_2CH_3)_2$ | $N(CH_2CH_3)_2$ | $SO_2CH_3$ | $CH_3$ | $SC_6H_5$ |
| 3290 | $N(CH_3)(CH_2CH_3)$ | $N(CH_3)(CH_2CH_3)$ | $SO_2CH_3$ | $CH_3$ | $SC_6H_5$ |
| 3291 | $O—(CH_2CH_2)—O$ | | $SO_2CH_3$ | $CH_3$ | $SC_6H_5$ |
| 3292 | $O—(CH_2CH_2CH_2)—O$ | | $SO_2CH_3$ | $CH_3$ | $SC_6H_5$ |
| 3293 | $S—(CH_2CH_2)—S$ | | $SO_2CH_3$ | $CH_3$ | $SC_6H_5$ |
| 3294 | $S—(CH_2CH_2CH_2)—S$ | | $SO_2CH_3$ | $CH_3$ | $SC_6H_5$ |
| 3295 | $—(CH_2)_4—$ | | $SO_2CH_3$ | $CH_3$ | $SC_6H_5$ |
| 3296 | $—(CH_2)_5—$ | | $SO_2CH_3$ | $CH_3$ | $SC_6H_5$ |
| 3297 | H | H | $PO(OCH_3)_2$ | $CH_3$ | $SC_6H_5$ |
| 3298 | $CH_3$ | $CH_3$ | $PO(OCH_3)_2$ | $CH_3$ | $SC_6H_5$ |
| 3299 | $CH_2CH_3$ | $CH_2CH_3$ | $PO(OCH_3)_2$ | $CH_3$ | $SC_6H_5$ |
| 3300 | $CH_2CH_2CH_3$ | $CH_2CH_2CH_3$ | $PO(OCH_3)_2$ | $CH_3$ | $SC_6H_5$ |
| 3301 | $OCH_3$ | $OCH_3$ | $PO(OCH_3)_2$ | $CH_3$ | $SC_6H_5$ |
| 3302 | $OCH_2CH_3$ | $OCH_2CH_3$ | $PO(OCH_3)_2$ | $CH_3$ | $SC_6H_5$ |
| 3303 | $OCH_2CH_2CH_3$ | $OCH_2CH_2CH_3$ | $PO(OCH_3)_2$ | $CH_3$ | $SC_6H_5$ |
| 3304 | $SCH_3$ | $SCH_3$ | $PO(OCH_3)_2$ | $CH_3$ | $SC_6H_5$ |
| 3305 | $SCH_2CH_3$ | $SCH_2CH_3$ | $PO(OCH_3)_2$ | $CH_3$ | $SC_6H_5$ |
| 3306 | $N(CH_3)_2$ | $N(CH_3)_2$ | $PO(OCH_3)_2$ | $CH_3$ | $SC_6H_5$ |
| 3307 | $N(CH_2CH_3)_2$ | $N(CH_2CH_3)_2$ | $PO(OCH_3)_2$ | $CH_3$ | $SC_6H_5$ |
| 3308 | $N(CH_3)(CH_2CH_3)$ | $N(CH_3)(CH_2CH_3)$ | $PO(OCH_3)_2$ | $CH_3$ | $SC_6H_5$ |
| 3309 | $O—(CH_2CH_2)—O$ | | $PO(OCH_3)_2$ | $CH_3$ | $SC_6H_5$ |
| 3310 | $O—(CH_2CH_2CH_2)—O$ | | $PO(OCH_3)_2$ | $CH_3$ | $SC_6H_5$ |
| 3311 | $S—(CH_2CH_2)—S$ | | $PO(OCH_3)_2$ | $CH_3$ | $SC_6H_5$ |
| 3312 | $S—(CH_2CH_2CH_2)—S$ | | $PO(OCH_3)_2$ | $CH_3$ | $SC_6H_5$ |
| 3313 | $—(CH_2)_4—$ | | $PO(OCH_3)_2$ | $CH_3$ | $SC_6H_5$ |
| 3314 | $—(CH_2)_5—$ | | $PO(OCH_3)_2$ | $CH_3$ | $SC_6H_5$ |
| 3315 | H | H | $PO(OCH_2CH_3)_2$ | $CH_3$ | $SC_6H_5$ |
| 3316 | $CH_3$ | $CH_3$ | $PO(OCH_2CH_3)_2$ | $CH_3$ | $SC_6H_5$ |
| 3317 | $CH_2CH_3$ | $CH_2CH_3$ | $PO(OCH_2CH_3)_2$ | $CH_3$ | $SC_6H_5$ |
| 3318 | $CH_2CH_2CH_3$ | $CH_2CH_2CH_3$ | $PO(OCH_2CH_3)_2$ | $CH_3$ | $SC_6H_5$ |
| 3319 | $OCH_3$ | $OCH_3$ | $PO(OCH_2CH_3)_2$ | $CH_3$ | $SC_6H_5$ |
| 3320 | $OCH_2CH_3$ | $OCH_2CH_3$ | $PO(OCH_2CH_3)_2$ | $CH_3$ | $SC_6H_5$ |
| 3321 | $OCH_2CH_2CH_3$ | $OCH_2CH_2CH_3$ | $PO(OCH_2CH_3)_2$ | $CH_3$ | $SC_6H_5$ |
| 3322 | $SCH_3$ | $SCH_3$ | $PO(OCH_2CH_3)_2$ | $CH_3$ | $SC_6H_5$ |
| 3323 | $SCH_2CH_3$ | $SCH_2CH_3$ | $PO(OCH_2CH_3)_2$ | $CH_3$ | $SC_6H_5$ |
| 3324 | $N(CH_3)_2$ | $N(CH_3)_2$ | $PO(OCH_2CH_3)_2$ | $CH_3$ | $SC_6H_5$ |
| 3325 | $N(CH_2CH_3)_2$ | $N(CH_2CH_3)_2$ | $PO(OCH_2CH_3)_2$ | $CH_3$ | $SC_6H_5$ |
| 3326 | $N(CH_3)(CH_2CH_3)$ | $N(CH_3)(CH_2CH_3)$ | $PO(OCH_2CH_3)_2$ | $CH_3$ | $SC_6H_5$ |
| 3327 | $O—(CH_2CH_2)—O$ | | $PO(OCH_2CH_3)_2$ | $CH_3$ | $SC_6H_5$ |
| 3328 | $O—(CH_2CH_2CH_2)—O$ | | $PO(OCH_2CH_3)_2$ | $CH_3$ | $SC_6H_5$ |
| 3329 | $S—(CH_2CH_2)—S$ | | $PO(OCH_2CH_3)_2$ | $CH_3$ | $SC_6H_5$ |
| 3330 | $S—(CH_2CH_2CH_2)—S$ | | $PO(OCH_2CH_3)_2$ | $CH_3$ | $SC_6H_5$ |
| 3331 | $—(CH_2)_4—$ | | $PO(OCH_2CH_3)_2$ | $CH_3$ | $SC_6H_5$ |
| 3332 | $—(CH_2)_5—$ | | $PO(OCH_2CH_3)_2$ | $CH_3$ | $SC_6H_5$ |
| 3333 | H | H | $PO(CH_3)_2$ | $CH_3$ | $SC_6H_5$ |
| 3334 | $CH_3$ | $CH_3$ | $PO(CH_3)_2$ | $CH_3$ | $SC_6H_5$ |
| 3335 | $CH_2CH_3$ | $CH_2CH_3$ | $PO(CH_3)_2$ | $CH_3$ | $SC_6H_5$ |
| 3336 | $CH_2CH_2CH_3$ | $CH_2CH_2CH_3$ | $PO(CH_3)_2$ | $CH_3$ | $SC_6H_5$ |
| 3337 | $OCH_3$ | $OCH_3$ | $PO(CH_3)_2$ | $CH_3$ | $SC_6H_5$ |
| 3338 | $OCH_2CH_3$ | $OCH_2CH_3$ | $PO(CH_3)_2$ | $CH_3$ | $SC_6H_5$ |
| 3339 | $OCH_2CH_2CH_3$ | $OCH_2CH_2CH_3$ | $PO(CH_3)_2$ | $CH_3$ | $SC_6H_5$ |
| 3340 | $SCH_3$ | $SCH_3$ | $PO(CH_3)_2$ | $CH_3$ | $SC_6H_5$ |
| 3341 | $SCH_2CH_3$ | $SCH_2CH_3$ | $PO(CH_3)_2$ | $CH_3$ | $SC_6H_5$ |
| 3342 | $N(CH_3)_2$ | $N(CH_3)_2$ | $PO(CH_3)_2$ | $CH_3$ | $SC_6H_5$ |
| 3343 | $N(CH_2CH_3)_2$ | $N(CH_2CH_3)_2$ | $PO(CH_3)_2$ | $CH_3$ | $SC_6H_5$ |
| 3344 | $N(CH_3)(CH_2CH_3)$ | $N(CH_3)(CH_2CH_3)$ | $PO(CH_3)_2$ | $CH_3$ | $SC_6H_5$ |
| 3345 | $O—(CH_2CH_2)—O$ | | $PO(CH_3)_2$ | $CH_3$ | $SC_6H_5$ |
| 3346 | $O—(CH_2CH_2CH_2)—O$ | | $PO(CH_3)_2$ | $CH_3$ | $SC_6H_5$ |
| 3347 | $S—(CH_2CH_2)—S$ | | $PO(CH_3)_2$ | $CH_3$ | $SC_6H_5$ |

TABLE 1-continued

I1a1

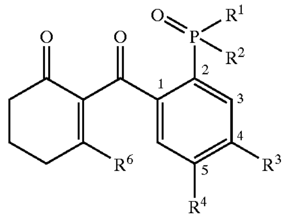

| n | $R^1$ | $R^2$ | $R^3$ | $R^4$ | $R^6$ |
|---|---|---|---|---|---|
| 3348 | S—($CH_2CH_2CH_2$)—S | | $PO(CH_3)_2$ | $CH_3$ | $SC_6H_5$ |
| 3349 | —$(CH_2)_4$— | | $PO(CH_3)_2$ | $CH_3$ | $SC_6H_5$ |
| 3350 | —$(CH_2)_5$— | | $PO(CH_3)_2$ | $CH_3$ | $SC_6H_5$ |
| 3351 | H | H | $PO(CH_2CH_3)_2$ | $CH_3$ | $SC_6H_5$ |
| 3352 | $CH_3$ | $CH_3$ | $PO(CH_2CH_3)_2$ | $CH_3$ | $SC_6H_5$ |
| 3353 | $CH_2CH_3$ | $CH_2CH_3$ | $PO(CH_2CH_3)_2$ | $CH_3$ | $SC_6H_5$ |
| 3354 | $CH_2CH_2CH_3$ | $CH_2CH_2CH_3$ | $PO(CH_2CH_3)_2$ | $CH_3$ | $SC_6H_5$ |
| 3355 | $OCH_3$ | $OCH_3$ | $PO(CH_2CH_3)_2$ | $CH_3$ | $SC_6H_5$ |
| 3356 | $OCH_2CH_3$ | $OCH_2CH_3$ | $PO(CH_2CH_3)_2$ | $CH_3$ | $SC_6H_5$ |
| 3357 | $OCH_2CH_2CH_3$ | $OCH_2CH_2CH_3$ | $PO(CH_2CH_3)_2$ | $CH_3$ | $SC_6H_5$ |
| 3358 | $SCH_3$ | $SCH_3$ | $PO(CH_2CH_3)_2$ | $CH_3$ | $SC_6H_5$ |
| 3359 | $SCH_2CH_3$ | $SCH_2CH_3$ | $PO(CH_2CH_3)_2$ | $CH_3$ | $SC_6H_5$ |
| 3360 | $N(CH_3)_2$ | $N(CH_3)_2$ | $PO(CH_2CH_3)_2$ | $CH_3$ | $SC_6H_5$ |
| 3361 | $N(CH_2CH_3)_2$ | $N(CH_2CH_3)_2$ | $PO(CH_2CH_3)_2$ | $CH_3$ | $SC_6H_5$ |
| 3362 | $N(CH_3)(CH_2CH_3)$ | $N(CH_3)(CH_2CH_3)$ | $PO(CH_2CH_3)_2$ | $CH_3$ | $SC_6H_5$ |
| 3363 | O—($CH_2CH_2$)—O | | $PO(CH_2CH_3)_2$ | $CH_3$ | $SC_6H_5$ |
| 3364 | O—($CH_2CH_2CH_2$)—O | | $PO(CH_2CH_3)_2$ | $CH_3$ | $SC_6H_5$ |
| 3365 | S—($CH_2CH_2$)—S | | $PO(CH_2CH_3)_2$ | $CH_3$ | $SC_6H_5$ |
| 3366 | S—($CH_2CH_2CH_2$)—S | | $PO(CH_2CH_3)_2$ | $CH_3$ | $SC_6H_5$ |
| 3367 | —$(CH_2)_4$— | | $PO(CH_2CH_3)_2$ | $CH_3$ | $SC_6H_5$ |
| 3368 | —$(CH_2)_5$— | | $PO(CH_2CH_3)_2$ | $CH_3$ | $SC_6H_5$ |
| 3369 | H | H | H | $CH_3$ | Het1 |
| 3370 | $CH_3$ | $CH_3$ | H | $CH_3$ | Het1 |
| 3371 | $CH_2CH_3$ | $CH_2CH_3$ | H | $CH_3$ | Het1 |
| 3372 | $CH_2CH_2CH_3$ | $CH_2CH_2CH_3$ | H | $CH_3$ | Het1 |
| 3373 | $OCH_3$ | $OCH_3$ | H | $CH_3$ | Het1 |
| 3374 | $OCH_2CH_3$ | $OCH_2CH_3$ | H | $CH_3$ | Het1 |
| 3375 | $OCH_2CH_2CH_3$ | $OCH_2CH_2CH_3$ | H | $CH_3$ | Het1 |
| 3376 | $SCH_3$ | $SCH_3$ | H | $CH_3$ | Het1 |
| 3377 | $SCH_2CH_3$ | $SCH_2CH_3$ | H | $CH_3$ | Het1 |
| 3378 | $N(CH_3)_2$ | $N(CH_3)_2$ | H | $CH_3$ | Het1 |
| 3379 | $N(CH_2CH_3)_2$ | $N(CH_2CH_3)_2$ | H | $CH_3$ | Het1 |
| 3380 | $N(CH_3)(CH_2CH_3)$ | $N(CH_3)(CH_2CH_3)$ | H | $CH_3$ | Het1 |
| 3381 | O—($CH_2CH_2$)—O | | H | $CH_3$ | Het1 |
| 3382 | O—($CH_2CH_2CH_2$)—O | | H | $CH_3$ | Het1 |
| 3383 | S—($CH_2CH_2$)—S | | H | $CH_3$ | Het1 |
| 3384 | S—($CH_2CH_2CH_2$)—S | | H | $CH_3$ | Het1 |
| 3385 | —$(CH_2)_4$— | | H | $CH_3$ | Het1 |
| 3386 | —$(CH_2)_5$— | | H | $CH_3$ | Het1 |
| 3387 | H | H | $NO_2$ | $CH_3$ | Het1 |
| 3388 | $CH_3$ | $CH_3$ | $NO_2$ | $CH_3$ | Het1 |
| 3389 | $CH_2CH_3$ | $CH_2CH_3$ | $NO_2$ | $CH_3$ | Het1 |
| 3390 | $CH_2CH_2CH_3$ | $CH_2CH_2CH_3$ | $NO_2$ | $CH_3$ | Het1 |
| 3391 | $OCH_3$ | $OCH_3$ | $NO_2$ | $CH_3$ | Het1 |
| 3392 | $OCH_2CH_3$ | $OCH_2CH_3$ | $NO_2$ | $CH_3$ | Het1 |
| 3393 | $OCH_2CH_2CH_3$ | $OCH_2CH_2CH_3$ | $NO_2$ | $CH_3$ | Het1 |
| 3394 | $SCH_3$ | $SCH_3$ | $NO_2$ | $CH_3$ | Het1 |
| 3395 | $SCH_2CH_3$ | $SCH_2CH_3$ | $NO_2$ | $CH_3$ | Het1 |
| 3396 | $N(CH_3)_2$ | $N(CH_3)_2$ | $NO_2$ | $CH_3$ | Het1 |
| 3397 | $N(CH_2CH_3)_2$ | $N(CH_2CH_3)_2$ | $NO_2$ | $CH_3$ | Het1 |
| 3398 | $N(CH_3)(CH_2CH_3)$ | $N(CH_3)(CH_2CH_3)$ | $NO_2$ | $CH_3$ | Het1 |
| 3399 | O—($CH_2CH_2$)—O | | $NO_2$ | $CH_3$ | Het1 |
| 3400 | O—($CH_2CH_2CH_2$)—O | | $NO_2$ | $CH_3$ | Het1 |
| 3401 | S—($CH_2CH_2$)—S | | $NO_2$ | $CH_3$ | Het1 |
| 3402 | S—($CH_2CH_2CH_2$)—S | | $NO_2$ | $CH_3$ | Het1 |
| 3403 | —$(CH_2)_4$— | | $NO_2$ | $CH_3$ | Het1 |
| 3404 | —$(CH_2)_5$— | | $NO_2$ | $CH_3$ | Het1 |
| 3405 | H | H | CN | $CH_3$ | Het1 |
| 3406 | $CH_3$ | $CH_3$ | CN | $CH_3$ | Het1 |
| 3407 | $CH_2CH_3$ | $CH_2CH_3$ | CN | $CH_3$ | Het1 |
| 3408 | $CH_2CH_2CH_3$ | $CH_2CH_2CH_3$ | CN | $CH_3$ | Het1 |
| 3409 | $OCH_3$ | $OCH_3$ | CN | $CH_3$ | Het1 |
| 3410 | $OCH_2CH_3$ | $OCH_2CH_3$ | CN | $CH_3$ | Het1 |
| 3411 | $OCH_2CH_2CH_3$ | $OCH_2CH_2CH_3$ | CN | $CH_3$ | Het1 |

TABLE 1-continued

I1a1

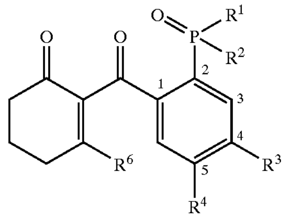

| n | $R^1$ | $R^2$ | $R^3$ | $R^4$ | $R^6$ |
|---|---|---|---|---|---|
| 3412 | $SCH_3$ | $SCH_3$ | CN | $CH_3$ | Het1 |
| 3413 | $SCH_2CH_3$ | $SCH_2CH_3$ | CN | $CH_3$ | Het1 |
| 3414 | $N(CH_3)_2$ | $N(CH_3)_2$ | CN | $CH_3$ | Het1 |
| 3415 | $N(CH_2CH_3)_2$ | $N(CH_2CH_3)_2$ | CN | $CH_3$ | Het1 |
| 3416 | $N(CH_3)(CH_2CH_3)$ | $N(CH_3)(CH_2CH_3)$ | CN | $CH_3$ | Het1 |
| 3417 | $O-(CH_2CH_2)-O$ | | CN | $CH_3$ | Het1 |
| 3418 | $O-(CH_2CH_2CH_2)-O$ | | CN | $CH_3$ | Het1 |
| 3419 | $S-(CH_2CH_2)-S$ | | CN | $CH_3$ | Het1 |
| 3420 | $S-(CH_2CH_2CH_2)-S$ | | CN | $CH_3$ | Het1 |
| 3421 | $-(CH_2)_4-$ | | CN | $CH_3$ | Het1 |
| 3422 | $-(CH_2)_5-$ | | CN | $CH_3$ | Het1 |
| 3423 | H | H | F | $CH_3$ | Het1 |
| 3424 | $CH_3$ | $CH_3$ | F | $CH_3$ | Het1 |
| 3425 | $CH_2CH_3$ | $CH_2CH_3$ | F | $CH_3$ | Het1 |
| 3426 | $CH_2CH_2CH_3$ | $CH_2CH_2CH_3$ | F | $CH_3$ | Het1 |
| 3427 | $OCH_3$ | $OCH_3$ | F | $CH_3$ | Het1 |
| 3428 | $OCH_2CH_3$ | $OCH_2CH_3$ | F | $CH_3$ | Het1 |
| 3429 | $OCH_2CH_2CH_3$ | $OCH_2CH_2CH_3$ | F | $CH_3$ | Het1 |
| 3430 | $SCH_3$ | $SCH_3$ | F | $CH_3$ | Het1 |
| 3431 | $SCH_2CH_3$ | $SCH_2CH_3$ | F | $CH_3$ | Het1 |
| 3432 | $N(CH_3)_2$ | $N(CH_3)_2$ | F | $CH_3$ | Het1 |
| 3433 | $N(CH_2CH_3)_2$ | $N(CH_2CH_3)_2$ | F | $CH_3$ | Het1 |
| 3434 | $N(CH_3)(CH_2CH_3)$ | $N(CH_3)(CH_2CH_3)$ | F | $CH_3$ | Het1 |
| 3435 | $O-(CH_2CH_2)-O$ | | F | $CH_3$ | Het1 |
| 3436 | $O-(CH_2CH_2CH_2)-O$ | | F | $CH_3$ | Het1 |
| 3437 | $S-(CH_2CH_2)-S$ | | F | $CH_3$ | Het1 |
| 3438 | $S-(CH_2CH_2CH_2)-S$ | | F | $CH_3$ | Het1 |
| 3439 | $-(CH_2)_4-$ | | F | $CH_3$ | Het1 |
| 3440 | $-(CH_2)_5-$ | | F | $CH_3$ | Het1 |
| 3441 | H | H | Cl | $CH_3$ | Het1 |
| 3442 | $CH_3$ | $CH_3$ | Cl | $CH_3$ | Het1 |
| 3443 | $CH_2CH_3$ | $CH_2CH_3$ | Cl | $CH_3$ | Het1 |
| 3444 | $CH_2CH_2CH_3$ | $CH_2CH_2CH_3$ | Cl | $CH_3$ | Het1 |
| 3445 | $OCH_3$ | $OCH_3$ | Cl | $CH_3$ | Het1 |
| 3446 | $OCH_2CH_3$ | $OCH_2CH_3$ | Cl | $CH_3$ | Het1 |
| 3447 | $OCH_2CH_2CH_3$ | $OCH_2CH_2CH_3$ | Cl | $CH_3$ | Het1 |
| 3448 | $SCH_3$ | $SCH_3$ | Cl | $CH_3$ | Het1 |
| 3449 | $SCH_2CH_3$ | $SCH_2CH_3$ | Cl | $CH_3$ | Het1 |
| 3450 | $N(CH_3)_2$ | $N(CH_3)_2$ | Cl | $CH_3$ | Het1 |
| 3451 | $N(CH_2CH_3)_2$ | $N(CH_2CH_3)_2$ | Cl | $CH_3$ | Het1 |
| 3452 | $N(CH_3)(CH_2CH_3)$ | $N(CH_3)(CH_2CH_3)$ | Cl | $CH_3$ | Het1 |
| 3453 | $O-(CH_2CH_2)-O$ | | Cl | $CH_3$ | Het1 |
| 3454 | $O-(CH_2CH_2CH_2)-O$ | | Cl | $CH_3$ | Het1 |
| 3455 | $S-(CH_2CH_2)-S$ | | Cl | $CH_3$ | Het1 |
| 3456 | $S-(CH_2CH_2CH_2)-S$ | | Cl | $CH_3$ | Het1 |
| 3457 | $-(CH_2)_4-$ | | Cl | $CH_3$ | Het1 |
| 3458 | $-(CH_2)_5-$ | | Cl | $CH_3$ | Het1 |
| 3459 | H | H | Br | $CH_3$ | Het1 |
| 3460 | $CH_3$ | $CH_3$ | Br | $CH_3$ | Het1 |
| 3461 | $CH_2CH_3$ | $CH_2CH_3$ | Br | $CH_3$ | Het1 |
| 3462 | $CH_2CH_2CH_3$ | $CH_2CH_2CH_3$ | Br | $CH_3$ | Het1 |
| 3463 | $OCH_3$ | $OCH_3$ | Br | $CH_3$ | Het1 |
| 3464 | $OCH_2CH_3$ | $OCH_2CH_3$ | Br | $CH_3$ | Het1 |
| 3465 | $OCH_2CH_2CH_3$ | $OCH_2CH_2CH_3$ | Br | $CH_3$ | Het1 |
| 3466 | $SCH_3$ | $SCH_3$ | Br | $CH_3$ | Het1 |
| 3467 | $SCH_2CH_3$ | $SCH_2CH_3$ | Br | $CH_3$ | Het1 |
| 3468 | $N(CH_3)_2$ | $N(CH_3)_2$ | Br | $CH_3$ | Het1 |
| 3469 | $N(CH_2CH_3)_2$ | $N(CH_2CH_3)_2$ | Br | $CH_3$ | Het1 |
| 3470 | $N(CH_3)(CH_2CH_3)$ | $N(CH_3)(CH_2CH_3)$ | Br | $CH_3$ | Het1 |
| 3471 | $O-(CH_2CH_2)-O$ | | Br | $CH_3$ | Het1 |
| 3472 | $O-(CH_2CH_2CH_2)-O$ | | Br | $CH_3$ | Het1 |
| 3473 | $S-(CH_2CH_2)-S$ | | Br | $CH_3$ | Het1 |
| 3474 | $S-(CH_2CH_2CH_2)-S$ | | Br | $CH_3$ | Het1 |
| 3475 | $-(CH_2)_4-$ | | Br | $CH_3$ | Het1 |

TABLE 1-continued

I1a1

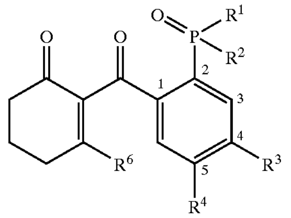

| n | $R^1$ | $R^2$ | $R^3$ | $R^4$ | $R^6$ |
|---|---|---|---|---|---|
| 3476 | —$(CH_2)_5$— | | Br | $CH_3$ | Het1 |
| 3477 | H | H | $CH_3$ | $CH_3$ | Het1 |
| 3478 | $CH_3$ | $CH_3$ | $CH_3$ | $CH_3$ | Het1 |
| 3479 | $CH_2CH_3$ | $CH_2CH_3$ | $CH_3$ | $CH_3$ | Het1 |
| 3480 | $CH_2CH_2CH_3$ | $CH_2CH_2CH_3$ | $CH_3$ | $CH_3$ | Het1 |
| 3481 | $OCH_3$ | $OCH_3$ | $CH_3$ | $CH_3$ | Het1 |
| 3482 | $OCH_2CH_3$ | $OCH_2CH_3$ | $CH_3$ | $CH_3$ | Het1 |
| 3483 | $OCH_2CH_2CH_3$ | $OCH_2CH_2CH_3$ | $CH_3$ | $CH_3$ | Het1 |
| 3484 | $SCH_3$ | $SCH_3$ | $CH_3$ | $CH_3$ | Het1 |
| 3485 | $SCH_2CH_3$ | $SCH_2CH_3$ | $CH_3$ | $CH_3$ | Het1 |
| 3486 | $N(CH_3)_2$ | $N(CH_3)_2$ | $CH_3$ | $CH_3$ | Het1 |
| 3487 | $N(CH_2CH_3)_2$ | $N(CH_2CH_3)_2$ | $CH_3$ | $CH_3$ | Het1 |
| 3488 | $N(CH_3)(CH_2CH_3)$ | $N(CH_3)(CH_2CH_3)$ | $CH_3$ | $CH_3$ | Het1 |
| 3489 | O—$(CH_2CH_2)$—O | | $CH_3$ | $CH_3$ | Het1 |
| 3490 | O—$(CH_2CH_2CH_2)$—O | | $CH_3$ | $CH_3$ | Het1 |
| 3491 | S—$(CH_2CH_2)$—S | | $CH_3$ | $CH_3$ | Het1 |
| 3492 | S—$(CH_2CH_2CH_2)$—S | | $CH_3$ | $CH_3$ | Het1 |
| 3493 | —$(CH_2)_4$— | | $CH_3$ | $CH_3$ | Het1 |
| 3494 | —$(CH_2)_5$— | | $CH_3$ | $CH_3$ | Het1 |
| 3495 | H | H | $CH_2CH_3$ | $CH_3$ | Het1 |
| 3496 | $CH_3$ | $CH_3$ | $CH_2CH_3$ | $CH_3$ | Het1 |
| 3497 | $CH_2CH_3$ | $CH_2CH_3$ | $CH_2CH_3$ | $CH_3$ | Het1 |
| 3498 | $CH_2CH_2CH_3$ | $CH_2CH_2CH_3$ | $CH_2CH_3$ | $CH_3$ | Het1 |
| 3499 | $OCH_3$ | $OCH_3$ | $CH_2CH_3$ | $CH_3$ | Het1 |
| 3500 | $OCH_2CH_3$ | $OCH_2CH_3$ | $CH_2CH_3$ | $CH_3$ | Het1 |
| 3501 | $OCH_2CH_2CH_3$ | $OCH_2CH_2CH_3$ | $CH_2CH_3$ | $CH_3$ | Het1 |
| 3502 | $SCH_3$ | $SCH_3$ | $CH_2CH_3$ | $CH_3$ | Het1 |
| 3503 | $SCH_2CH_3$ | $SCH_2CH_3$ | $CH_2CH_3$ | $CH_3$ | Het1 |
| 3504 | $N(CH_3)_2$ | $N(CH_3)_2$ | $CH_2CH_3$ | $CH_3$ | Het1 |
| 3505 | $N(CH_2CH_3)_2$ | $N(CH_2CH_3)_2$ | $CH_2CH_3$ | $CH_3$ | Het1 |
| 3506 | $N(CH_3)(CH_2CH_3)$ | $N(CH_3)(CH_2CH_3)$ | $CH_2CH_3$ | $CH_3$ | Het1 |
| 3507 | O—$(CH_2CH_2)$—O | | $CH_2CH_3$ | $CH_3$ | Het1 |
| 3508 | O—$(CH_2CH_2CH_2)$—O | | $CH_2CH_3$ | $CH_3$ | Het1 |
| 3509 | S—$(CH_2CH_2)$—S | | $CH_2CH_3$ | $CH_3$ | Het1 |
| 3510 | S—$(CH_2CH_2CH_2)$—S | | $CH_2CH_3$ | $CH_3$ | Het1 |
| 3511 | —$(CH_2)_4$— | | $CH_2CH_3$ | $CH_3$ | Het1 |
| 3512 | —$(CH_2)_5$— | | $CH_2CH_3$ | $CH_3$ | Het1 |
| 3513 | H | H | $CF_3$ | $CH_3$ | Het1 |
| 3514 | $CH_3$ | $CH_3$ | $CF_3$ | $CH_3$ | Het1 |
| 3515 | $CH_2CH_3$ | $CH_2CH_3$ | $CF_3$ | $CH_3$ | Het1 |
| 3516 | $CH_2CH_2CH_3$ | $CH_2CH_2CH_3$ | $CF_3$ | $CH_3$ | Het1 |
| 3517 | $OCH_3$ | $OCH_3$ | $CF_3$ | $CH_3$ | Het1 |
| 3518 | $OCH_2CH_3$ | $OCH_2CH_3$ | $CF_3$ | $CH_3$ | Het1 |
| 3519 | $OCH_2CH_2CH_3$ | $OCH_2CH_2CH_3$ | $CF_3$ | $CH_3$ | Het1 |
| 3520 | $SCH_3$ | $SCH_3$ | $CF_3$ | $CH_3$ | Het1 |
| 3521 | $SCH_2CH_3$ | $SCH_2CH_3$ | $CF_3$ | $CH_3$ | Het1 |
| 3522 | $N(CH_3)_2$ | $N(CH_3)_2$ | $CF_3$ | $CH_3$ | Het1 |
| 3523 | $N(CH_2CH_3)_2$ | $N(CH_2CH_3)_2$ | $CF_3$ | $CH_3$ | Het1 |
| 3524 | $N(CH_3)(CH_2CH_3)$ | $N(CH_3)(CH_2CH_3)$ | $CF_3$ | $CH_3$ | Het1 |
| 3525 | O—$(CH_2CH_2)$—O | | $CF_3$ | $CH_3$ | Het1 |
| 3526 | O—$(CH_2CH_2CH_2)$—O | | $CF_3$ | $CH_3$ | Het1 |
| 3527 | S—$(CH_2CH_2)$—S | | $CF_3$ | $CH_3$ | Het1 |
| 3528 | S—$(CH_2CH_2CH_2)$—S | | $CF_3$ | $CH_3$ | Het1 |
| 3529 | —$(CH_2)_4$— | | $CF_3$ | $CH_3$ | Het1 |
| 3530 | —$(CH_2)_5$— | | $CF_3$ | $CH_3$ | Het1 |
| 3531 | H | H | $OCH_3$ | $CH_3$ | Het1 |
| 3532 | $CH_3$ | $CH_3$ | $OCH_3$ | $CH_3$ | Het1 |
| 3533 | $CH_2CH_3$ | $CH_2CH_3$ | $OCH_3$ | $CH_3$ | Het1 |
| 3534 | $CH_2CH_2CH_3$ | $CH_2CH_2CH_3$ | $OCH_3$ | $CH_3$ | Het1 |
| 3535 | $OCH_3$ | $OCH_3$ | $OCH_3$ | $CH_3$ | Het1 |
| 3536 | $OCH_2CH_3$ | $OCH_2CH_3$ | $OCH_3$ | $CH_3$ | Het1 |
| 3537 | $OCH_2CH_2CH_3$ | $OCH_2CH_2CH_3$ | $OCH_3$ | $CH_3$ | Het1 |
| 3538 | $SCH_3$ | $SCH_3$ | $OCH_3$ | $CH_3$ | Het1 |
| 3539 | $SCH_2CH_3$ | $SCH_2CH_3$ | $OCH_3$ | $CH_3$ | Het1 |

TABLE 1-continued

I1a1

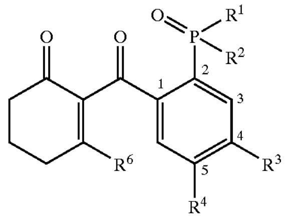

| n | $R^1$ | $R^2$ | $R^3$ | $R^4$ | $R^6$ |
|---|---|---|---|---|---|
| 3540 | $N(CH_3)_2$ | $N(CH_3)_2$ | $OCH_3$ | $CH_3$ | Het1 |
| 3541 | $N(CH_2CH_3)_2$ | $N(CH_2CH_3)_2$ | $OCH_3$ | $CH_3$ | Het1 |
| 3542 | $N(CH_3)(CH_2CH_3)$ | $N(CH_3)(CH_2CH_3)$ | $OCH_3$ | $CH_3$ | Het1 |
| 3543 | $O-(CH_2CH_2)-O$ | | $OCH_3$ | $CH_3$ | Het1 |
| 3544 | $O-(CH_2CH_2CH_2)-O$ | | $OCH_3$ | $CH_3$ | Het1 |
| 3545 | $S-(CH_2CH_2)-S$ | | $OCH_3$ | $CH_3$ | Het1 |
| 3546 | $S-(CH_2CH_2CH_2)-S$ | | $OCH_3$ | $CH_3$ | Het1 |
| 4044 | $N(CH_3)_2$ | $N(CH_3)_2$ | F | $CH_3$ | Het3 |
| 4045 | $N(CH_2CH_3)_2$ | $N(CH_2CH_3)_2$ | F | $CH_3$ | Het3 |
| 4046 | $N(CH_3)(CH_2CH_3)$ | $N(CH_3)(CH_2CH_3)$ | F | $CH_3$ | Het3 |
| 4047 | $O-(CH_2CH_2)-O$ | | F | $CH_3$ | Het3 |
| 4048 | $O-(CH_2CH_2CH_2)-O$ | | F | $CH_3$ | Het3 |
| 4049 | $S-(CH_2CH_2)-S$ | | F | $CH_3$ | Het3 |
| 4050 | $S-(CH_2CH_2CH_2)-S$ | | F | $CH_3$ | Het3 |
| 4051 | $-(CH_2)_4-$ | | F | $CH_3$ | Het3 |
| 4052 | $-(CH_2)_5-$ | | F | $CH_3$ | Het3 |
| 4053 | H | H | Cl | $CH_3$ | Het3 |
| 4054 | $CH_3$ | $CH_3$ | Cl | $CH_3$ | Het3 |
| 4055 | $CH_2CH_3$ | $CH_2CH_3$ | Cl | $CH_3$ | Het3 |
| 4056 | $CH_2CH_2CH_3$ | $CH_2CH_2CH_3$ | Cl | $CH_3$ | Het3 |
| 4057 | $OCH_3$ | $OCH_3$ | Cl | $CH_3$ | Het3 |
| 4058 | $OCH_2CH_3$ | $OCH_2CH_3$ | Cl | $CH_3$ | Het3 |
| 4059 | $OCH_2CH_2CH_3$ | $OCH_2CH_2CH_3$ | Cl | $CH_3$ | Het3 |
| 4060 | $SCH_3$ | $SCH_3$ | Cl | $CH_3$ | Het3 |
| 4061 | $SCH_2CH_3$ | $SCH_2CH_3$ | Cl | $CH_3$ | Het3 |
| 4062 | $N(CH_3)_2$ | $N(CH_3)_2$ | Cl | $CH_3$ | Het3 |
| 4063 | $N(CH_2CH_3)_2$ | $N(CH_2CH_3)_2$ | Cl | $CH_3$ | Het3 |
| 4064 | $N(CH_3)(CH_2CH_3)$ | $N(CH_3)(CH_2CH_3)$ | Cl | $CH_3$ | Het3 |
| 4065 | $O-(CH_2CH_2)-O$ | | Cl | $CH_3$ | Het3 |
| 4066 | $O-(CH_2CH_2CH_2)-O$ | | Cl | $CH_3$ | Het3 |
| 4067 | $S-(CH_2CH_2)-S$ | | Cl | $CH_3$ | Het3 |
| 4068 | $S-(CH_2CH_2CH_2)-S$ | | Cl | $CH_3$ | Het3 |
| 4069 | $-(CH_2)_4-$ | | Cl | $CH_3$ | Het3 |
| 4070 | $-(CH_2)_5-$ | | Cl | $CH_3$ | Het3 |
| 4071 | H | H | Br | $CH_3$ | Het3 |
| 4072 | $CH_3$ | $CH_3$ | Br | $CH_3$ | Het3 |
| 4073 | $CH_2CH_3$ | $CH_2CH_3$ | Br | $CH_3$ | Het3 |
| 4074 | $CH_2CH_2CH_3$ | $CH_2CH_2CH_3$ | Br | $CH_3$ | Het3 |
| 4075 | $OCH_3$ | $OCH_3$ | Br | $CH_3$ | Het3 |
| 4076 | $OCH_2CH_3$ | $OCH_2CH_3$ | Br | $CH_3$ | Het3 |
| 4077 | $OCH_2CH_2CH_3$ | $OCH_2CH_2CH_3$ | Br | $CH_3$ | Het3 |
| 4078 | $SCH_3$ | $SCH_3$ | Br | $CH_3$ | Het3 |
| 4079 | $SCH_2CH_3$ | $SCH_2CH_3$ | Br | $CH_3$ | Het3 |
| 4080 | $N(CH_3)_2$ | $N(CH_3)_2$ | Br | $CH_3$ | Het3 |
| 4081 | $N(CH_2CH_3)_2$ | $N(CH_2CH_3)_2$ | Br | $CH_3$ | Het3 |
| 4082 | $N(CH_3)(CH_2CH_3)$ | $N(CH_3)(CH_2CH_3)$ | Br | $CH_3$ | Het3 |
| 4083 | $O-(CH_2CH_2)-O$ | | Br | $CH_3$ | Het3 |
| 4084 | $O-(CH_2CH_2CH_2)-O$ | | Br | $CH_3$ | Het3 |
| 4085 | $S-(CH_2CH_2)-S$ | | Br | $CH_3$ | Het3 |
| 4086 | $S-(CH_2CH_2CH_2)-S$ | | Br | $CH_3$ | Het3 |
| 4087 | $-(CH_2)_4-$ | | Br | $CH_3$ | Het3 |
| 4088 | $-(CH_2)_5-$ | | Br | $CH_3$ | Het3 |
| 4089 | H | H | $CH_3$ | $CH_3$ | Het3 |
| 4090 | $CH_3$ | $CH_3$ | $CH_3$ | $CH_3$ | Het3 |
| 4091 | $CH_2CH_3$ | $CH_2CH_3$ | $CH_3$ | $CH_3$ | Het3 |
| 4092 | $CH_2CH_2CH_3$ | $CH_2CH_2CH_3$ | $CH_3$ | $CH_3$ | Het3 |
| 4093 | $OCH_3$ | $OCH_3$ | $CH_3$ | $CH_3$ | Het3 |
| 4094 | $OCH_2CH_3$ | $OCH_2CH_3$ | $CH_3$ | $CH_3$ | Het3 |
| 4095 | $OCH_2CH_2CH_3$ | $OCH_2CH_2CH_3$ | $CH_3$ | $CH_3$ | Het3 |
| 4096 | $SCH_3$ | $SCH_3$ | $CH_3$ | $CH_3$ | Het3 |
| 4097 | $SCH_2CH_3$ | $SCH_2CH_3$ | $CH_3$ | $CH_3$ | Het3 |
| 4098 | $N(CH_3)_2$ | $N(CH_3)_2$ | $CH_3$ | $CH_3$ | Het3 |
| 4099 | $N(CH_2CH_3)_2$ | $N(CH_2CH_3)_2$ | $CH_3$ | $CH_3$ | Het3 |
| 4100 | $N(CH_3)(CH_2CH_3)$ | $N(CH_3)(CH_2CH_3)$ | $CH_3$ | $CH_3$ | Het3 |

TABLE 1-continued

I1a1

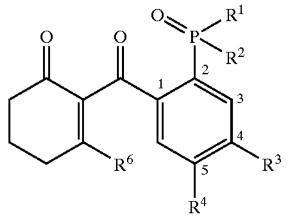

| n | $R^1$ | $R^2$ | $R^3$ | $R^4$ | $R^6$ |
|---|---|---|---|---|---|
| 4101 | O—$(CH_2CH_2)$—O | | $CH_3$ | $CH_3$ | Het3 |
| 4102 | O—$(CH_2CH_2CH_2)$—O | | $CH_3$ | $CH_3$ | Het3 |
| 4103 | S—$(CH_2CH_2)$—S | | $CH_3$ | $CH_3$ | Het3 |
| 4104 | S—$(CH_2CH_2CH_2)$—S | | $CH_3$ | $CH_3$ | Het3 |
| 4105 | —$(CH_2)_4$— | | $CH_3$ | $CH_3$ | Het3 |
| 4106 | —$(CH_2)_5$— | | $CH_3$ | $CH_3$ | Het3 |
| 4107 | H | H | $CH_2CH_3$ | $CH_3$ | Het3 |
| 4108 | $CH_3$ | $CH_3$ | $CH_2CH_3$ | $CH_3$ | Het3 |
| 4109 | $CH_2CH_3$ | $CH_2CH_3$ | $CH_2CH_3$ | $CH_3$ | Het3 |
| 4110 | $CH_2CH_2CH_3$ | $CH_2CH_2CH_3$ | $CH_2CH_3$ | $CH_3$ | Het3 |
| 4111 | $OCH_3$ | $OCH_3$ | $CH_2CH_3$ | $CH_3$ | Het3 |
| 4112 | $OCH_2CH_3$ | $OCH_2CH_3$ | $CH_2CH_3$ | $CH_3$ | Het3 |
| 4113 | $OCH_2CH_2CH_3$ | $OCH_2CH_2CH_3$ | $CH_2CH_3$ | $CH_3$ | Het3 |
| 4114 | $SCH_3$ | $SCH_3$ | $CH_2CH_3$ | $CH_3$ | Het3 |
| 4115 | $SCH_2CH_3$ | $SCH_2CH_3$ | $CH_2CH_3$ | $CH_3$ | Het3 |
| 4116 | $N(CH_3)_2$ | $N(CH_3)_2$ | $CH_2CH_3$ | $CH_3$ | Het3 |
| 4117 | $N(CH_2CH_3)_2$ | $N(CH_2CH_3)_2$ | $CH_2CH_3$ | $CH_3$ | Het3 |
| 4118 | $N(CH_3)(CH_2CH_3)$ | $N(CH_3)(CH_2CH_3)$ | $CH_2CH_3$ | $CH_3$ | Het3 |
| 4119 | O—$(CH_2CH_2)$—O | | $CH_2CH_3$ | $CH_3$ | Het3 |
| 4120 | O—$(CH_2CH_2CH_2)$—O | | $CH_2CH_3$ | $CH_3$ | Het3 |
| 4121 | S—$(CH_2CH_2)$—S | | $CH_2CH_3$ | $CH_3$ | Het3 |
| 4122 | S—$(CH_2CH_2CH_2)$—S | | $CH_2CH_3$ | $CH_3$ | Het3 |
| 4123 | —$(CH_2)_4$— | | $CH_2CH_3$ | $CH_3$ | Het3 |
| 4124 | —$(CH_2)_5$— | | $CH_2CH_3$ | $CH_3$ | Het3 |
| 4125 | H | H | $CF_3$ | $CH_3$ | Het3 |
| 4126 | $CH_3$ | $CH_3$ | $CF_3$ | $CH_3$ | Het3 |
| 4127 | $CH_2CH_3$ | $CH_2CH_3$ | $CF_3$ | $CH_3$ | Het3 |
| 4128 | $CH_2CH_2CH_3$ | $CH_2CH_2CH_3$ | $CF_3$ | $CH_3$ | Het3 |
| 4129 | $OCH_3$ | $OCH_3$ | $CF_3$ | $CH_3$ | Het3 |
| 4130 | $OCH_2CH_3$ | $OCH_2CH_3$ | $CF_3$ | $CH_3$ | Het3 |
| 4131 | $OCH_2CH_2CH_3$ | $OCH_2CH_2CH_3$ | $CF_3$ | $CH_3$ | Het3 |
| 4132 | $SCH_3$ | $SCH_3$ | $CF_3$ | $CH_3$ | Het3 |
| 4133 | $SCH_2CH_3$ | $SCH_2CH_3$ | $CF_3$ | $CH_3$ | Het3 |
| 4134 | $N(CH_3)_2$ | $N(CH_3)_2$ | $CF_3$ | $CH_3$ | Het3 |
| 4135 | $N(CH_2CH_3)_2$ | $N(CH_2CH_3)_2$ | $CF_3$ | $CH_3$ | Het3 |
| 4136 | $N(CH_3)(CH_2CH_3)$ | $N(CH_3)(CH_2CH_3)$ | $CF_3$ | $CH_3$ | Het3 |
| 4137 | O—$(CH_2CH_2)$—O | | $CF_3$ | $CH_3$ | Het3 |
| 4138 | O—$(CH_2CH_2CH_2)$—O | | $CF_3$ | $CH_3$ | Het3 |
| 4139 | S—$(CH_2CH_2)$—S | | $CF_3$ | $CH_3$ | Het3 |
| 4140 | S—$(CH_2CH_2CH_2)$—S | | $CF_3$ | $CH_3$ | Het3 |
| 4141 | —$(CH_2)_4$— | | $CF_3$ | $CH_3$ | Het3 |
| 4142 | —$(CH_2)_5$— | | $CF_3$ | $CH_3$ | Het3 |
| 4143 | H | H | $OCH_3$ | $CH_3$ | Het3 |
| 4144 | $CH_3$ | $CH_3$ | $OCH_3$ | $CH_3$ | Het3 |
| 4145 | $CH_2CH_3$ | $CH_2CH_3$ | $OCH_3$ | $CH_3$ | Het3 |
| 4146 | $CH_2CH_2CH_3$ | $CH_2CH_2CH_3$ | $OCH_3$ | $CH_3$ | Het3 |
| 4147 | $OCH_3$ | $OCH_3$ | $OCH_3$ | $CH_3$ | Het3 |
| 4148 | $OCH_2CH_3$ | $OCH_2CH_3$ | $OCH_3$ | $CH_3$ | Het3 |
| 4149 | $OCH_2CH_2CH_3$ | $OCH_2CH_2CH_3$ | $OCH_3$ | $CH_3$ | Het3 |
| 4150 | $SCH_3$ | $SCH_3$ | $OCH_3$ | $CH_3$ | Het3 |
| 4151 | $SCH_2CH_3$ | $SCH_2CH_3$ | $OCH_3$ | $CH_3$ | Het3 |
| 4152 | $N(CH_3)_2$ | $N(CH_3)_2$ | $OCH_3$ | $CH_3$ | Het3 |
| 4153 | $N(CH_2CH_3)_2$ | $N(CH_2CH_3)_2$ | $OCH_3$ | $CH_3$ | Het3 |
| 4154 | $N(CH_3)(CH_2CH_3)$ | $N(CH_3)(CH_2CH_3)$ | $OCH_3$ | $CH_3$ | Het3 |
| 4155 | O—$(CH_2CH_2)$—O | | $OCH_3$ | $CH_3$ | Het3 |
| 4156 | O—$(CH_2CH_2CH_2)$—O | | $OCH_3$ | $CH_3$ | Het3 |
| 4157 | S—$(CH_2CH_2)$—S | | $OCH_3$ | $CH_3$ | Het3 |
| 4158 | S—$(CH_2CH_2CH_2)$—S | | $OCH_3$ | $CH_3$ | Het3 |
| 4159 | —$(CH_2)_4$— | | $OCH_3$ | $CH_3$ | Het3 |
| 4160 | —$(CH_2)_5$— | | $OCH_3$ | $CH_3$ | Het3 |
| 4161 | H | H | $OCH_2CH_3$ | $CH_3$ | Het3 |
| 4162 | $CH_3$ | $CH_3$ | $OCH_2CH_3$ | $CH_3$ | Het3 |
| 4163 | $CH_2CH_3$ | $CH_2CH_3$ | $OCH_2CH_3$ | $CH_3$ | Het3 |
| 4164 | $CH_2CH_2CH_3$ | $CH_2CH_2CH_3$ | $OCH_2CH_3$ | $CH_3$ | Het3 |

TABLE 1-continued

I1a1

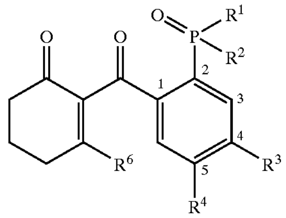

| n | $R^1$ | $R^2$ | $R^3$ | $R^4$ | $R^6$ |
|---|---|---|---|---|---|
| 4165 | $OCH_3$ | $OCH_3$ | $OCH_2CH_3$ | $CH_3$ | Het3 |
| 4166 | $OCH_2CH_3$ | $OCH_2CH_3$ | $OCH_2CH_3$ | $CH_3$ | Het3 |
| 4167 | $OCH_2CH_2CH_3$ | $OCH_2CH_2CH_3$ | $OCH_2CH_3$ | $CH_3$ | Het3 |
| 4168 | $SCH_3$ | $SCH_3$ | $OCH_2CH_3$ | $CH_3$ | Het3 |
| 4169 | $SCH_2CH_3$ | $SCH_2CH_3$ | $OCH_2CH_3$ | $CH_3$ | Het3 |
| 4170 | $N(CH_3)_2$ | $N(CH_3)_2$ | $OCH_2CH_3$ | $CH_3$ | Het3 |
| 4171 | $N(CH_2CH_3)_2$ | $N(CH_2CH_3)_2$ | $OCH_2CH_3$ | $CH_3$ | Het3 |
| 4172 | $N(CH_3)(CH_2CH_3)$ | $N(CH_3)(CH_2CH_3)$ | $OCH_2CH_3$ | $CH_3$ | Het3 |
| 4173 | $O—(CH_2CH_2)—O$ | | $OCH_2CH_3$ | $CH_3$ | Het3 |
| 4174 | $O—(CH_2CH_2CH_2)—O$ | | $OCH_2CH_3$ | $CH_3$ | Het3 |
| 4175 | $S—(CH_2CH_2)—S$ | | $OCH_2CH_3$ | $CH_3$ | Het3 |
| 4176 | $S—(CH_2CH_2CH_2)—S$ | | $OCH_2CH_3$ | $CH_3$ | Het3 |
| 4177 | $—(CH_2)_4—$ | | $OCH_2CH_3$ | $CH_3$ | Het3 |
| 4178 | $—(CH_2)_5—$ | | $OCH_2CH_3$ | $CH_3$ | Het3 |
| 4179 | H | H | $SCH_3$ | $CH_3$ | Het3 |
| 4180 | $CH_3$ | $CH_3$ | $SCH_3$ | $CH_3$ | Het3 |
| 4181 | $CH_2CH_3$ | $CH_2CH_3$ | $SCH_3$ | $CH_3$ | Het3 |
| 4182 | $CH_2CH_2CH_3$ | $CH_2CH_2CH_3$ | $SCH_3$ | $CH_3$ | Het3 |
| 4183 | $OCH_3$ | $OCH_3$ | $SCH_3$ | $CH_3$ | Het3 |
| 4184 | $OCH_2CH_3$ | $OCH_2CH_3$ | $SCH_3$ | $CH_3$ | Het3 |
| 4185 | $OCH_2CH_2CH_3$ | $OCH_2CH_2CH_3$ | $SCH_3$ | $CH_3$ | Het3 |
| 4186 | $SCH_3$ | $SCH_3$ | $SCH_3$ | $CH_3$ | Het3 |
| 4187 | $SCH_2CH_3$ | $SCH_2CH_3$ | $SCH_3$ | $CH_3$ | Het3 |
| 4188 | $N(CH_3)_2$ | $N(CH_3)_2$ | $SCH_3$ | $CH_3$ | Het3 |
| 4189 | $N(CH_2CH_3)_2$ | $N(CH_2CH_3)_2$ | $SCH_3$ | $CH_3$ | Het3 |
| 4190 | $N(CH_3)(CH_2CH_3)$ | $N(CH_3)(CH_2CH_3)$ | $SCH_3$ | $CH_3$ | Het3 |
| 4191 | $O—(CH_2CH_2)—O$ | | $SCH_3$ | $CH_3$ | Het3 |
| 4192 | $O—(CH_2CH_2CH_2)—O$ | | $SCH_3$ | $CH_3$ | Het3 |
| 4193 | $S—(CH_2CH_2)—S$ | | $SCH_3$ | $CH_3$ | Het3 |
| 4194 | $S—(CH_2CH_2CH_2)—S$ | | $SCH_3$ | $CH_3$ | Het3 |
| 4195 | $—(CH_2)_4—$ | | $SCH_3$ | $CH_3$ | Het3 |
| 4196 | $—(CH_2)_5—$ | | $SCH_3$ | $CH_3$ | Het3 |
| 4197 | H | H | $SO_2CH_3$ | $CH_3$ | Het3 |
| 4198 | $CH_3$ | $CH_3$ | $SO_2CH_3$ | $CH_3$ | Het3 |
| 4199 | $CH_2CH_3$ | $CH_2CH_3$ | $SO_2CH_3$ | $CH_3$ | Het3 |
| 4200 | $CH_2CH_2CH_3$ | $CH_2CH_2CH_3$ | $SO_2CH_3$ | $CH_3$ | Het3 |
| 4201 | $OCH_3$ | $OCH_3$ | $SO_2CH_3$ | $CH_3$ | Het3 |
| 4202 | $OCH_2CH_3$ | $OCH_2CH_3$ | $SO_2CH_3$ | $CH_3$ | Het3 |
| 4203 | $OCH_2CH_2CH_3$ | $OCH_2CH_2CH_3$ | $SO_2CH_3$ | $CH_3$ | Het3 |
| 4204 | $SCH_3$ | $SCH_3$ | $SO_2CH_3$ | $CH_3$ | Het3 |
| 4205 | $SCH_2CH_3$ | $SCH_2CH_3$ | $SO_2CH_3$ | $CH_3$ | Het3 |
| 4206 | $N(CH_3)_2$ | $N(CH_3)_2$ | $SO_2CH_3$ | $CH_3$ | Het3 |
| 4207 | $N(CH_2CH_3)_2$ | $N(CH_2CH_3)_2$ | $SO_2CH_3$ | $CH_3$ | Het3 |
| 4208 | $N(CH_3)(CH_2CH_3)$ | $N(CH_3)(CH_2CH_3)$ | $SO_2CH_3$ | $CH_3$ | Het3 |
| 4209 | $O—(CH_2CH_2)—O$ | | $SO_2CH_3$ | $CH_3$ | Het3 |
| 4210 | $O—(CH_2CH_2CH_2)—O$ | | $SO_2CH_3$ | $CH_3$ | Het3 |
| 4211 | $S—(CH_2CH_2)—S$ | | $SO_2CH_3$ | $CH_3$ | Het3 |
| 4212 | $S—(CH_2CH_2CH_2)—S$ | | $SO_2CH_3$ | $CH_3$ | Het3 |
| 4213 | $—(CH_2)_4—$ | | $SO_2CH_3$ | $CH_3$ | Het3 |
| 4214 | $—(CH_2)_5—$ | | $SO_2CH_3$ | $CH_3$ | Het3 |
| 4215 | H | H | $PO(OCH_3)_2$ | $CH_3$ | Het3 |
| 4216 | $CH_3$ | $CH_3$ | $PO(OCH_3)_2$ | $CH_3$ | Het3 |
| 4217 | $CH_2CH_3$ | $CH_2CH_3$ | $PO(OCH_3)_2$ | $CH_3$ | Het3 |
| 4218 | $CH_2CH_2CH_3$ | $CH_2CH_2CH_3$ | $PO(OCH_3)_2$ | $CH_3$ | Het3 |
| 4219 | $OCH_3$ | $OCH_3$ | $PO(OCH_3)_2$ | $CH_3$ | Het3 |
| 4220 | $OCH_2CH_3$ | $OCH_2CH_3$ | $PO(OCH_3)_2$ | $CH_3$ | Het3 |
| 4221 | $OCH_2CH_2CH_3$ | $OCH_2CH_2CH_3$ | $PO(OCH_3)_2$ | $CH_3$ | Het3 |
| 4222 | $SCH_3$ | $SCH_3$ | $PO(OCH_3)_2$ | $CH_3$ | Het3 |
| 4223 | $SCH_2CH_3$ | $SCH_2CH_3$ | $PO(OCH_3)_2$ | $CH_3$ | Het3 |
| 4224 | $N(CH_3)_2$ | $N(CH_3)_2$ | $PO(OCH_3)_2$ | $CH_3$ | Het3 |
| 4225 | $N(CH_2CH_3)_2$ | $N(CH_2CH_3)_2$ | $PO(OCH_3)_2$ | $CH_3$ | Het3 |
| 4226 | $N(CH_3)(CH_2CH_3)$ | $N(CH_3)(CH_2CH_3)$ | $PO(OCH_3)_2$ | $CH_3$ | Het3 |
| 4227 | $O—(CH_2CH_2)—O$ | | $PO(OCH_3)_2$ | $CH_3$ | Het3 |
| 4228 | $O—(CH_2CH_2CH_2)—O$ | | $PO(OCH_3)_2$ | $CH_3$ | Het3 |

TABLE 1-continued

I1a1

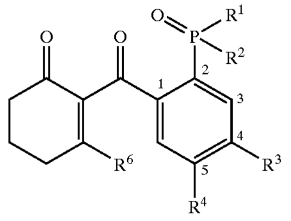

| n | $R^1$ | $R^2$ | $R^3$ | $R^4$ | $R^6$ |
|---|---|---|---|---|---|
| 4229 | S—(CH$_2$CH$_2$)—S | | PO(OCH$_3$)$_2$ | CH$_3$ | Het3 |
| 4230 | S—(CH$_2$CH$_2$CH$_2$)—S | | PO(OCH$_3$)$_2$ | CH$_3$ | Het3 |
| 4231 | —(CH$_2$)$_4$— | | PO(OCH$_3$)$_2$ | CH$_3$ | Het3 |
| 4232 | —(CH$_2$)$_5$— | | PO(OCH$_3$)$_2$ | CH$_3$ | Het3 |
| 4233 | H | H | PO(OCH$_2$CH$_3$)$_2$ | CH$_3$ | Het3 |
| 4234 | CH$_3$ | CH$_3$ | PO(OCH$_2$CH$_3$)$_2$ | CH$_3$ | Het3 |
| 4235 | CH$_2$CH$_3$ | CH$_2$CH$_3$ | PO(OCH$_2$CH$_3$)$_2$ | CH$_3$ | Het3 |
| 4236 | CH$_2$CH$_2$CH$_3$ | CH$_2$CH$_2$CH$_3$ | PO(OCH$_2$CH$_3$)$_2$ | CH$_3$ | Het3 |
| 4237 | OCH$_3$ | OCH$_3$ | PO(OCH$_2$CH$_3$)$_2$ | CH$_3$ | Het3 |
| 4238 | OCH$_2$CH$_3$ | OCH$_2$CH$_3$ | PO(OCH$_2$CH$_3$)$_2$ | CH$_3$ | Het3 |
| 4239 | OCH$_2$CH$_2$CH$_3$ | OCH$_2$CH$_2$CH$_3$ | PO(OCH$_2$CH$_3$)$_2$ | CH$_3$ | Het3 |
| 4240 | SCH$_3$ | SCH$_3$ | PO(OCH$_2$CH$_3$)$_2$ | CH$_3$ | Het3 |
| 4241 | SCH$_2$CH$_3$ | SCH$_2$CH$_3$ | PO(OCH$_2$CH$_3$)$_2$ | CH$_3$ | Het3 |
| 4242 | N(CH$_3$)$_2$ | N(CH$_3$)$_2$ | PO(OCH$_2$CH$_3$)$_2$ | CH$_3$ | Het3 |
| 4243 | N(CH$_2$CH$_3$)$_2$ | N(CH$_2$CH$_3$)$_2$ | PO(OCH$_2$CH$_3$)$_2$ | CH$_3$ | Het3 |
| 4244 | N(CH$_3$)(CH$_2$CH$_3$) | N(CH$_3$)(CH$_2$CH$_3$) | PO(OCH$_2$CH$_3$)$_2$ | CH$_3$ | Het3 |
| 4245 | O—(CH$_2$CH$_2$)—O | | PO(OCH$_2$CH$_3$)$_2$ | CH$_3$ | Het3 |
| 4246 | O—(CH$_2$CH$_2$CH$_2$)—O | | PO(OCH$_2$CH$_3$)$_2$ | CH$_3$ | Het3 |
| 4247 | S—(CH$_2$CH$_2$)—S | | PO(OCH$_2$CH$_3$)$_2$ | CH$_3$ | Het3 |
| 4248 | S—(CH$_2$CH$_2$CH$_2$)—S | | PO(OCH$_2$CH$_3$)$_2$ | CH$_3$ | Het3 |
| 4249 | —(CH$_2$)$_4$— | | PO(OCH$_2$CH$_3$)$_2$ | CH$_3$ | Het3 |
| 4250 | —(CH$_2$)$_5$— | | PO(OCH$_2$CH$_3$)$_2$ | CH$_3$ | Het3 |
| 4251 | H | H | PO(CH$_3$)$_2$ | CH$_3$ | Het3 |
| 4252 | CH$_3$ | CH$_3$ | PO(CH$_3$)$_2$ | CH$_3$ | Het3 |
| 4253 | CH$_2$CH$_3$ | CH$_2$CH$_3$ | PO(CH$_3$)$_2$ | CH$_3$ | Het3 |
| 4254 | CH$_2$CH$_2$CH$_3$ | CH$_2$CH$_2$CH$_3$ | PO(CH$_3$)$_2$ | CH$_3$ | Het3 |
| 4255 | OCH$_3$ | OCH$_3$ | PO(CH$_3$)$_2$ | CH$_3$ | Het3 |
| 4256 | OCH$_2$CH$_3$ | OCH$_2$CH$_3$ | PO(CH$_3$)$_2$ | CH$_3$ | Het3 |
| 4257 | OCH$_2$CH$_2$CH$_3$ | OCH$_2$CH$_2$CH$_3$ | PO(CH$_3$)$_2$ | CH$_3$ | Het3 |
| 4258 | SCH$_3$ | SCH$_3$ | PO(CH$_3$)$_2$ | CH$_3$ | Het3 |
| 4259 | SCH$_2$CH$_3$ | SCH$_2$CH$_3$ | PO(CH$_3$)$_2$ | CH$_3$ | Het3 |
| 4260 | N(CH$_3$)$_2$ | N(CH$_3$)$_2$ | PO(CH$_3$)$_2$ | CH$_3$ | Het3 |
| 4261 | N(CH$_2$CH$_3$)$_2$ | N(CH$_2$CH$_3$)$_2$ | PO(CH$_3$)$_2$ | CH$_3$ | Het3 |
| 4262 | N(CH$_3$)(CH$_2$CH$_3$) | N(CH$_3$)(CH$_2$CH$_3$) | PO(CH$_3$)$_2$ | CH$_3$ | Het3 |
| 4263 | O—(CH$_2$CH$_2$)—O | | PO(CH$_3$)$_2$ | CH$_3$ | Het3 |
| 4264 | O—(CH$_2$CH$_2$CH$_2$)—O | | PO(CH$_3$)$_2$ | CH$_3$ | Het3 |
| 4265 | S—(CH$_2$CH$_2$)—S | | PO(CH$_3$)$_2$ | CH$_3$ | Het3 |
| 4266 | S—(CH$_2$CH$_2$CH$_2$)—S | | PO(CH$_3$)$_2$ | CH$_3$ | Het3 |
| 4267 | —(CH$_2$)$_4$— | | PO(CH$_3$)$_2$ | CH$_3$ | Het3 |
| 4268 | —(CH$_2$)$_5$— | | PO(CH$_3$)$_2$ | CH$_3$ | Het3 |
| 4269 | H | H | PO(CH$_2$CH$_3$)$_2$ | CH$_3$ | Het3 |
| 4270 | CH$_3$ | CH$_3$ | PO(CH$_2$CH$_3$)$_2$ | CH$_3$ | Het3 |
| 4271 | CH$_2$CH$_3$ | CH$_2$CH$_3$ | PO(CH$_2$CH$_3$)$_2$ | CH$_3$ | Het3 |
| 4272 | CH$_2$CH$_2$CH$_3$ | CH$_2$CH$_2$CH$_3$ | PO(CH$_2$CH$_3$)$_2$ | CH$_3$ | Het3 |
| 4273 | OCH$_3$ | OCH$_3$ | PO(CH$_2$CH$_3$)$_2$ | CH$_3$ | Het3 |
| 4274 | OCH$_2$CH$_3$ | OCH$_2$CH$_3$ | PO(CH$_2$CH$_3$)$_2$ | CH$_3$ | Het3 |
| 4275 | OCH$_2$CH$_2$CH$_3$ | OCH$_2$CH$_2$CH$_3$ | PO(CH$_2$CH$_3$)$_2$ | CH$_3$ | Het3 |
| 4276 | SCH$_3$ | SCH$_3$ | PO(CH$_2$CH$_3$)$_2$ | CH$_3$ | Het3 |
| 4277 | SCH$_2$CH$_3$ | SCH$_2$CH$_3$ | PO(CH$_2$CH$_3$)$_2$ | CH$_3$ | Het3 |
| 4278 | N(CH$_3$)$_2$ | N(CH$_3$)$_2$ | PO(CH$_2$CH$_3$)$_2$ | CH$_3$ | Het3 |
| 4279 | N(CH$_2$CH$_3$)$_2$ | N(CH$_2$CH$_3$)$_2$ | PO(CH$_2$CH$_3$)$_2$ | CH$_3$ | Het3 |
| 4280 | N(CH$_3$)(CH$_2$CH$_3$) | N(CH$_3$)(CH$_2$CH$_3$) | PO(CH$_2$CH$_3$)$_2$ | CH$_3$ | Het3 |
| 4281 | O—(CH$_2$CH$_2$)—O | | PO(CH$_2$CH$_3$)$_2$ | CH$_3$ | Het3 |
| 4282 | O—(CH$_2$CH$_2$CH$_2$)—O | | PO(CH$_2$CH$_3$)$_2$ | CH$_3$ | Het3 |
| 4283 | S—(CH$_2$CH$_2$)—S | | PO(CH$_2$CH$_3$)$_2$ | CH$_3$ | Het3 |
| 4284 | S—(CH$_2$CH$_2$CH$_2$)—S | | PO(CH$_2$CH$_3$)$_2$ | CH$_3$ | Het3 |
| 4285 | —(CH$_2$)$_4$— | | PO(CH$_2$CH$_3$)$_2$ | CH$_3$ | Het3 |
| 4286 | —(CH$_2$)$_5$— | | PO(CH$_2$CH$_3$)$_2$ | CH$_3$ | Het3 |
| 4287 | H | H | H | Cl | OH |
| 4288 | CH$_3$ | CH$_3$ | H | Cl | OH |
| 4289 | CH$_2$CH$_3$ | CH$_2$CH$_3$ | H | Cl | OH |
| 4290 | CH$_2$CH$_2$CH$_3$ | CH$_2$CH$_2$CH$_3$ | H | Cl | OH |
| 4291 | OCH$_3$ | OCH$_3$ | H | Cl | OH |
| 4292 | OCH$_2$CH$_3$ | OCH$_2$CH$_3$ | H | Cl | OH |

TABLE 1-continued

I1a1

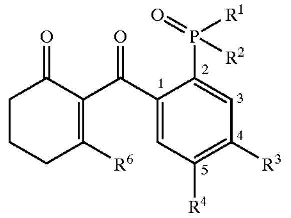

| n | $R^1$ | $R^2$ | $R^3$ | $R^4$ | $R^6$ |
|---|---|---|---|---|---|
| 4293 | $OCH_2CH_2CH_3$ | $OCH_2CH_2CH_3$ | H | Cl | OH |
| 4294 | $SCH_3$ | $SCH_3$ | H | Cl | OH |
| 4295 | $SCH_2CH_3$ | $SCH_2CH_3$ | H | Cl | OH |
| 4296 | $N(CH_3)_2$ | $N(CH_3)_2$ | H | Cl | OH |
| 4297 | $N(CH_2CH_3)_2$ | $N(CH_2CH_3)_2$ | H | Cl | OH |
| 4298 | $N(CH_3)(CH_2CH_3)$ | $N(CH_3)(CH_2CH_3)$ | H | Cl | OH |
| 4299 | $O—(CH_2CH_2)—O$ | | H | Cl | OH |
| 4300 | $O—(CH_2CH_2CH_2)—O$ | | H | Cl | OH |
| 4301 | $S—(CH_2CH_2)—S$ | | H | Cl | OH |
| 4302 | $S—(CH_2CH_2CH_2)—S$ | | H | Cl | OH |
| 4303 | $—(CH_2)_4—$ | | H | Cl | OH |
| 4304 | $—(CH_2)_5—$ | | H | Cl | OH |
| 4305 | H | H | $NO_2$ | Cl | OH |
| 4306 | $CH_3$ | $CH_3$ | $NO_2$ | Cl | OH |
| 4307 | $CH_2CH_3$ | $CH_2CH_3$ | $NO_2$ | Cl | OH |
| 4308 | $CH_2CH_2CH_3$ | $CH_2CH_2CH_3$ | $NO_2$ | Cl | OH |
| 4309 | $OCH_3$ | $OCH_3$ | $NO_2$ | Cl | OH |
| 4310 | $OCH_2CH_3$ | $OCH_2CH_3$ | $NO_2$ | Cl | OH |
| 4311 | $OCH_2CH_2CH_3$ | $OCH_2CH_2CH_3$ | $NO_2$ | Cl | OH |
| 4312 | $SCH_3$ | $SCH_3$ | $NO_2$ | Cl | OH |
| 4313 | $SCH_2CH_3$ | $SCH_2CH_3$ | $NO_2$ | Cl | OH |
| 4314 | $N(CH_3)_2$ | $N(CH_3)_2$ | $NO_2$ | Cl | OH |
| 4315 | $N(CH_2CH_3)_2$ | $N(CH_2CH_3)_2$ | $NO_2$ | Cl | OH |
| 4316 | $N(CH_3)(CH_2CH_3)$ | $N(CH_3)(CH_2CH_3)$ | $NO_2$ | Cl | OH |
| 4317 | $O—(CH_2CH_2)—O$ | | $NO_2$ | Cl | OH |
| 4318 | $O—(CH_2CH_2CH_2)—O$ | | $NO_2$ | Cl | OH |
| 4319 | $S—(CH_2CH_2)—S$ | | $NO_2$ | Cl | OH |
| 4320 | $S—(CH_2CH_2CH_2)—S$ | | $NO_2$ | Cl | OH |
| 4321 | $—(CH_2)_4—$ | | $NO_2$ | Cl | OH |
| 4322 | $—(CH_2)_5—$ | | $NO_2$ | Cl | OH |
| 4323 | H | H | CN | Cl | OH |
| 4324 | $CH_3$ | $CH_3$ | CN | Cl | OH |
| 4325 | $CH_2CH_3$ | $CH_2CH_3$ | CN | Cl | OH |
| 4326 | $CH_2CH_2CH_3$ | $CH_2CH_2CH_3$ | CN | Cl | OH |
| 4327 | $OCH_3$ | $OCH_3$ | CN | Cl | OH |
| 4328 | $OCH_2CH_3$ | $OCH_2CH_3$ | CN | Cl | OH |
| 4329 | $OCH_2CH_2CH_3$ | $OCH_2CH_2CH_3$ | CN | Cl | OH |
| 4330 | $SCH_3$ | $SCH_3$ | CN | Cl | OH |
| 4331 | $SCH_2CH_3$ | $SCH_2CH_3$ | CN | Cl | OH |
| 4332 | $N(CH_3)_2$ | $N(CH_3)_2$ | CN | Cl | OH |
| 4333 | $N(CH_2CH_3)_2$ | $N(CH_2CH_3)_2$ | CN | Cl | OH |
| 4334 | $N(CH_3)(CH_2CH_3)$ | $N(CH_3)(CH_2CH_3)$ | CN | Cl | OH |
| 4335 | $O—(CH_2CH_2)—O$ | | CN | Cl | OH |
| 4336 | $O—(CH_2CH_2CH_2)—O$ | | CN | Cl | OH |
| 4337 | $S—(CH_2CH_2)—S$ | | CN | Cl | OH |
| 4338 | $S—(CH_2CH_2CH_2)—S$ | | CN | Cl | OH |
| 4339 | $—(CH_2)_4—$ | | CN | Cl | OH |
| 4340 | $—(CH_2)_5—$ | | CN | Cl | OH |
| 4341 | H | H | F | Cl | OH |
| 4342 | $CH_3$ | $CH_3$ | F | Cl | OH |
| 4343 | $CH_2CH_3$ | $CH_2CH_3$ | F | Cl | OH |
| 4344 | $CH_2CH_2CH_3$ | $CH_2CH_2CH_3$ | F | Cl | OH |
| 4345 | $OCH_3$ | $OCH_3$ | F | Cl | OH |
| 4346 | $OCH_2CH_3$ | $OCH_2CH_3$ | F | Cl | OH |
| 4347 | $OCH_2CH_2CH_3$ | $OCH_2CH_2CH_3$ | F | Cl | OH |
| 4348 | $SCH_3$ | $SCH_3$ | F | Cl | OH |
| 4349 | $SCH_2CH_3$ | $SCH_2CH_3$ | F | Cl | OH |
| 4350 | $N(CH_3)_2$ | $N(CH_3)_2$ | F | Cl | OH |
| 4351 | $N(CH_2CH_3)_2$ | $N(CH_2CH_3)_2$ | F | Cl | OH |
| 4352 | $N(CH_3)(CH_2CH_3)$ | $N(CH_3)(CH_2CH_3)$ | F | Cl | OH |
| 4353 | $O—(CH_2CH_2)—O$ | | F | Cl | OH |
| 4354 | $O—(CH_2CH_2CH_2)—O$ | | F | Cl | OH |
| 4355 | $S—(CH_2CH_2)—S$ | | F | Cl | OH |
| 4356 | $S—(CH_2CH_2CH_2)—S$ | | F | Cl | OH |

TABLE 1-continued

I1a1

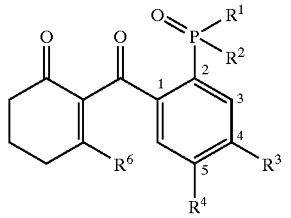

| n | $R^1$ | $R^2$ | $R^3$ | $R^4$ | $R^6$ |
|---|---|---|---|---|---|
| 4357 | $-(CH_2)_4-$ | | F | Cl | OH |
| 4358 | $-(CH_2)_5-$ | | F | Cl | OH |
| 4359 | H | H | Cl | Cl | OH |
| 4360 | $CH_3$ | $CH_3$ | Cl | Cl | OH |
| 4361 | $CH_2CH_3$ | $CH_2CH_3$ | Cl | Cl | OH |
| 4362 | $CH_2CH_2CH_3$ | $CH_2CH_2CH_3$ | Cl | Cl | OH |
| 4363 | $OCH_3$ | $OCH_3$ | Cl | Cl | OH |
| 4364 | $OCH_2CH_3$ | $OCH_2CH_3$ | Cl | Cl | OH |
| 4365 | $OCH_2CH_2CH_3$ | $OCH_2CH_2CH_3$ | Cl | Cl | OH |
| 4366 | $SCH_3$ | $SCH_3$ | Cl | Cl | OH |
| 4367 | $SCH_2CH_3$ | $SCH_2CH_3$ | Cl | Cl | OH |
| 4368 | $N(CH_3)_2$ | $N(CH_3)_2$ | Cl | Cl | OH |
| 4369 | $N(CH_2CH_3)_2$ | $N(CH_2CH_3)_2$ | Cl | Cl | OH |
| 4370 | $N(CH_3)(CH_2CH_3)$ | $N(CH_3)(CH_2CH_3)$ | Cl | Cl | OH |
| 4371 | $O-(CH_2CH_2)-O$ | | Cl | Cl | OH |
| 4372 | $O-(CH_2CH_2CH_2)-O$ | | Cl | Cl | OH |
| 4373 | $S-(CH_2CH_2)-S$ | | Cl | Cl | OH |
| 4374 | $S-(CH_2CH_2CH_2)-S$ | | Cl | Cl | OH |
| 4375 | $-(CH_2)_4-$ | | Cl | Cl | OH |
| 4376 | $-(CH_2)_5-$ | | Cl | Cl | OH |
| 4377 | H | H | Br | Cl | OH |
| 4378 | $CH_3$ | $CH_3$ | Br | Cl | OH |
| 4379 | $CH_2CH_3$ | $CH_2CH_3$ | Br | Cl | OH |
| 4380 | $CH_2CH_2CH_3$ | $CH_2CH_2CH_3$ | Br | Cl | OH |
| 4381 | $OCH_3$ | $OCH_3$ | Br | Cl | OH |
| 4382 | $OCH_2CH_3$ | $OCH_2CH_3$ | Br | Cl | OH |
| 4383 | $OCH_2CH_2CH_3$ | $OCH_2CH_2CH_3$ | Br | Cl | OH |
| 4384 | $SCH_3$ | $SCH_3$ | Br | Cl | OH |
| 4385 | $SCH_2CH_3$ | $SCH_2CH_3$ | Br | Cl | OH |
| 4386 | $N(CH_3)_2$ | $N(CH_3)_2$ | Br | Cl | OH |
| 4387 | $N(CH_2CH_3)_2$ | $N(CH_2CH_3)_2$ | Br | Cl | OH |
| 4388 | $N(CH_3)(CH_2CH_3)$ | $N(CH_3)(CH_2CH_3)$ | Br | Cl | OH |
| 4389 | $O-(CH_2CH_2)-O$ | | Br | Cl | OH |
| 4390 | $O-(CH_2CH_2CH_2)-O$ | | Br | Cl | OH |
| 4391 | $S-(CH_2CH_2)-S$ | | Br | Cl | OH |
| 4392 | $S-(CH_2CH_2CH_2)-S$ | | Br | Cl | OH |
| 4393 | $-(CH_2)_4-$ | | Br | Cl | OH |
| 4394 | $-(CH_2)_5-$ | | Br | Cl | OH |
| 4395 | H | H | $CH_3$ | Cl | OH |
| 4396 | $CH_3$ | $CH_3$ | $CH_3$ | Cl | OH |
| 4397 | $CH_2CH_3$ | $CH_2CH_3$ | $CH_3$ | Cl | OH |
| 4398 | $CH_2CH_2CH_3$ | $CH_2CH_2CH_3$ | $CH_3$ | Cl | OH |
| 4399 | $OCH_3$ | $OCH_3$ | $CH_3$ | Cl | OH |
| 4400 | $OCH_2CH_3$ | $OCH_2CH_3$ | $CH_3$ | Cl | OH |
| 4401 | $OCH_2CH_2CH_3$ | $OCH_2CH_2CH_3$ | $CH_3$ | Cl | OH |
| 4402 | $SCH_3$ | $SCH_3$ | $CH_3$ | Cl | OH |
| 4403 | $SCH_2CH_3$ | $SCH_2CH_3$ | $CH_3$ | Cl | OH |
| 4404 | $N(CH_3)_2$ | $N(CH_3)_2$ | $CH_3$ | Cl | OH |
| 4405 | $N(CH_2CH_3)_2$ | $N(CH_2CH_3)_2$ | $CH_3$ | Cl | OH |
| 4406 | $N(CH_3)(CH_2CH_3)$ | $N(CH_3)(CH_2CH_3)$ | $CH_3$ | Cl | OH |
| 4407 | $O-(CH_2CH_2)-O$ | | $CH_3$ | Cl | OH |
| 4408 | $O-(CH_2CH_2CH_2)-O$ | | $CH_3$ | Cl | OH |
| 4409 | $S-(CH_2CH_2)-S$ | | $CH_3$ | Cl | OH |
| 4410 | $S-(CH_2CH_2CH_2)-S$ | | $CH_3$ | Cl | OH |
| 4411 | $-(CH_2)_4-$ | | $CH_3$ | Cl | OH |
| 4412 | $-(CH_2)_5-$ | | $CH_3$ | Cl | OH |
| 4413 | H | H | $CH_2CH_3$ | Cl | OH |
| 4414 | $CH_3$ | $CH_3$ | $CH_2CH_3$ | Cl | OH |
| 4415 | $CH_2CH_3$ | $CH_2CH_3$ | $CH_2CH_3$ | Cl | OH |
| 4416 | $CH_2CH_2CH_3$ | $CH_2CH_2CH_3$ | $CH_2CH_3$ | Cl | OH |
| 4417 | $OCH_3$ | $OCH_3$ | $CH_2CH_3$ | Cl | OH |
| 4418 | $OCH_2CH_3$ | $OCH_2CH_3$ | $CH_2CH_3$ | Cl | OH |
| 4419 | $OCH_2CH_2CH_3$ | $OCH_2CH_2CH_3$ | $CH_2CH_3$ | Cl | OH |
| 4420 | $SCH_3$ | $SCH_3$ | $CH_2CH_3$ | Cl | OH |

TABLE 1-continued

I1a1

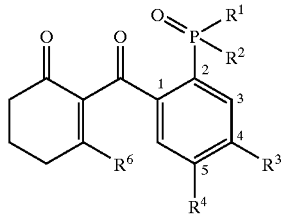

| n | $R^1$ | $R^2$ | $R^3$ | $R^4$ | $R^6$ |
|---|---|---|---|---|---|
| 4421 | $SCH_2CH_3$ | $SCH_2CH_3$ | $CH_2CH_3$ | Cl | OH |
| 4422 | $N(CH_3)_2$ | $N(CH_3)_2$ | $CH_2CH_3$ | Cl | OH |
| 4423 | $N(CH_2CH_3)_2$ | $N(CH_2CH_3)_2$ | $CH_2CH_3$ | Cl | OH |
| 4424 | $N(CH_3)(CH_2CH_3)$ | $N(CH_3)(CH_2CH_3)$ | $CH_2CH_3$ | Cl | OH |
| 4425 | $O—(CH_2CH_2)—O$ | | $CH_2CH_3$ | Cl | OH |
| 4426 | $O—(CH_2CH_2CH_2)—O$ | | $CH_2CH_3$ | Cl | OH |
| 4427 | $S—(CH_2CH_2)—S$ | | $CH_2CH_3$ | Cl | OH |
| 4428 | $S—(CH_2CH_2CH_2)—S$ | | $CH_2CH_3$ | Cl | OH |
| 4429 | $—(CH_2)_4—$ | | $CH_2CH_3$ | Cl | OH |
| 4430 | $—(CH_2)_5—$ | | $CH_2CH_3$ | Cl | OH |
| 4431 | H | H | $CF_3$ | Cl | OH |
| 4432 | $CH_3$ | $CH_3$ | $CF_3$ | Cl | OH |
| 4433 | $CH_2CH_3$ | $CH_2CH_3$ | $CF_3$ | Cl | OH |
| 4434 | $CH_2CH_2CH_3$ | $CH_2CH_2CH_3$ | $CF_3$ | Cl | OH |
| 4435 | $OCH_3$ | $OCH_3$ | $CF_3$ | Cl | OH |
| 4436 | $OCH_2CH_3$ | $OCH_2CH_3$ | $CF_3$ | Cl | OH |
| 4437 | $OCH_2CH_2CH_3$ | $OCH_2CH_2CH_3$ | $CF_3$ | Cl | OH |
| 4438 | $SCH_3$ | $SCH_3$ | $CF_3$ | Cl | OH |
| 4439 | $SCH_2CH_3$ | $SCH_2CH_3$ | $CF_3$ | Cl | OH |
| 4440 | $N(CH_3)_2$ | $N(CH_3)_2$ | $CF_3$ | Cl | OH |
| 4441 | $N(CH_2CH_3)_2$ | $N(CH_2CH_3)_2$ | $CF_3$ | Cl | OH |
| 4442 | $N(CH_3)(CH_2CH_3)$ | $N(CH_3)(CH_2CH_3)$ | $CF_3$ | Cl | OH |
| 4443 | $O—(CH_2CH_2)—O$ | | $CF_3$ | Cl | OH |
| 4444 | $O—(CH_2CH_2CH_2)—O$ | | $CF_3$ | Cl | OH |
| 4445 | $S—(CH_2CH_2)—S$ | | $CF_3$ | Cl | OH |
| 4446 | $S—(CH_2CH_2CH_2)—S$ | | $CF_3$ | Cl | OH |
| 4447 | $—(CH_2)_4—$ | | $CF_3$ | Cl | OH |
| 4448 | $—(CH_2)_5—$ | | $CF_3$ | Cl | OH |
| 4449 | H | H | $OCH_3$ | Cl | OH |
| 4450 | $CH_3$ | $CH_3$ | $OCH_3$ | Cl | OH |
| 4451 | $CH_2CH_3$ | $CH_2CH_3$ | $OCH_3$ | Cl | OH |
| 4452 | $CH_2CH_2CH_3$ | $CH_2CH_2CH_3$ | $OCH_3$ | Cl | OH |
| 4453 | $OCH_3$ | $OCH_3$ | $OCH_3$ | Cl | OH |
| 4454 | $OCH_2CH_3$ | $OCH_2CH_3$ | $OCH_3$ | Cl | OH |
| 4455 | $OCH_2CH_2CH_3$ | $OCH_2CH_2CH_3$ | $OCH_3$ | Cl | OH |
| 4456 | $SCH_3$ | $SCH_3$ | $OCH_3$ | Cl | OH |
| 4457 | $SCH_2CH_3$ | $SCH_2CH_3$ | $OCH_3$ | Cl | OH |
| 4458 | $N(CH_3)_2$ | $N(CH_3)_2$ | $OCH_3$ | Cl | OH |
| 4459 | $N(CH_2CH_3)_2$ | $N(CH_2CH_3)_2$ | $OCH_3$ | Cl | OH |
| 4460 | $N(CH_3)(CH_2CH_3)$ | $N(CH_3)(CH_2CH_3)$ | $OCH_3$ | Cl | OH |
| 4461 | $O—(CH_2CH_2)—O$ | | $OCH_3$ | Cl | OH |
| 4462 | $O—(CH_2CH_2CH_2)—O$ | | $OCH_3$ | Cl | OH |
| 4463 | $S—(CH_2CH_2)—S$ | | $OCH_3$ | Cl | OH |
| 4464 | $S—(CH_2CH_2CH_2)—S$ | | $OCH_3$ | Cl | OH |
| 4465 | $—(CH_2)_4—$ | | $OCH_3$ | Cl | OH |
| 4466 | $—(CH_2)_5—$ | | $OCH_3$ | Cl | OH |
| 4467 | H | H | $OCH_2CH_3$ | Cl | OH |
| 4468 | $CH_3$ | $CH_3$ | $OCH_2CH_3$ | Cl | OH |
| 4469 | $CH_2CH_3$ | $CH_2CH_3$ | $OCH_2CH_3$ | Cl | OH |
| 4470 | $CH_2CH_2CH_3$ | $CH_2CH_2CH_3$ | $OCH_2CH_3$ | Cl | OH |
| 4471 | $OCH_3$ | $OCH_3$ | $OCH_2CH_3$ | Cl | OH |
| 4472 | $OCH_2CH_3$ | $OCH_2CH_3$ | $OCH_2CH_3$ | Cl | OH |
| 4473 | $OCH_2CH_2CH_3$ | $OCH_2CH_2CH_3$ | $OCH_2CH_3$ | Cl | OH |
| 4474 | $SCH_3$ | $SCH_3$ | $OCH_2CH_3$ | Cl | OH |
| 4475 | $SCH_2CH_3$ | $SCH_2CH_3$ | $OCH_2CH_3$ | Cl | OH |
| 4476 | $N(CH_3)_2$ | $N(CH_3)_2$ | $OCH_2CH_3$ | Cl | OH |
| 4477 | $N(CH_2CH_3)_2$ | $N(CH_2CH_3)_2$ | $OCH_2CH_3$ | Cl | OH |
| 4478 | $N(CH_3)(CH_2CH_3)$ | $N(CH_3)(CH_2CH_3)$ | $OCH_2CH_3$ | Cl | OH |
| 4479 | $O—(CH_2CH_2)—O$ | | $OCH_2CH_3$ | Cl | OH |
| 4480 | $O—(CH_2CH_2CH_2)—O$ | | $OCH_2CH_3$ | Cl | OH |
| 4481 | $S—(CH_2CH_2)—S$ | | $OCH_2CH_3$ | Cl | OH |
| 4482 | $S—(CH_2CH_2CH_2)—S$ | | $OCH_2CH_3$ | Cl | OH |
| 4483 | $—(CH_2)_4—$ | | $OCH_2CH_3$ | Cl | OH |
| 4484 | $—(CH_2)_5—$ | | $OCH_2CH_3$ | Cl | OH |

TABLE 1-continued

I1a1

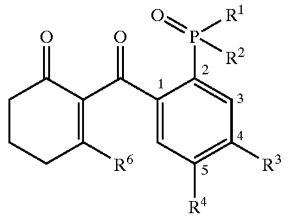

| n | $R^1$ | $R^2$ | $R^3$ | $R^4$ | $R^6$ |
|---|---|---|---|---|---|
| 4485 | H | H | $SCH_3$ | Cl | OH |
| 4486 | $CH_3$ | $CH_3$ | $SCH_3$ | Cl | OH |
| 4487 | $CH_2CH_3$ | $CH_2CH_3$ | $SCH_3$ | Cl | OH |
| 4488 | $CH_2CH_2CH_3$ | $CH_2CH_2CH_3$ | $SCH_3$ | Cl | OH |
| 4489 | $OCH_3$ | $OCH_3$ | $SCH_3$ | Cl | OH |
| 4490 | $OCH_2CH_3$ | $OCH_2CH_3$ | $SCH_3$ | Cl | OH |
| 4491 | $OCH_2CH_2CH_3$ | $OCH_2CH_2CH_3$ | $SCH_3$ | Cl | OH |
| 4492 | $SCH_3$ | $SCH_3$ | $SCH_3$ | Cl | OH |
| 4493 | $SCH_2CH_3$ | $SCH_2CH_3$ | $SCH_3$ | Cl | OH |
| 4494 | $N(CH_3)_2$ | $N(CH_3)_2$ | $SCH_3$ | Cl | OH |
| 4495 | $N(CH_2CH_3)_2$ | $N(CH_2CH_3)_2$ | $SCH_3$ | Cl | OH |
| 4496 | $N(CH_3)(CH_2CH_3)$ | $N(CH_3)(CH_2CH_3)$ | $SCH_3$ | Cl | OH |
| 4497 | $O-(CH_2CH_2)-O$ | | $SCH_3$ | Cl | OH |
| 4498 | $O-(CH_2CH_2CH_2)-O$ | | $SCH_3$ | Cl | OH |
| 4499 | $S-(CH_2CH_2)-S$ | | $SCH_3$ | Cl | OH |
| 4500 | $S-(CH_2CH_2CH_2)-S$ | | $SCH_3$ | Cl | OH |
| 4501 | $-(CH_2)_4-$ | | $SCH_3$ | Cl | OH |
| 4502 | $-(CH_2)_5-$ | | $SCH_3$ | Cl | OH |
| 4503 | H | H | $SO_2CH_3$ | Cl | OH |
| 4504 | $CH_3$ | $CH_3$ | $SO_2CH_3$ | Cl | OH |
| 4505 | $CH_2CH_3$ | $CH_2CH_3$ | $SO_2CH_3$ | Cl | OH |
| 4506 | $CH_2CH_2CH_3$ | $CH_2CH_2CH_3$ | $SO_2CH_3$ | Cl | OH |
| 4507 | $OCH_3$ | $OCH_3$ | $SO_2CH_3$ | Cl | OH |
| 4508 | $OCH_2CH_3$ | $OCH_2CH_3$ | $SO_2CH_3$ | Cl | OH |
| 4509 | $OCH_2CH_2CH_3$ | $OCH_2CH_2CH_3$ | $SO_2CH_3$ | Cl | OH |
| 4510 | $SCH_3$ | $SCH_3$ | $SO_2CH_3$ | Cl | OH |
| 4511 | $SCH_2CH_3$ | $SCH_2CH_3$ | $SO_2CH_3$ | Cl | OH |
| 4512 | $N(CH_3)_2$ | $N(CH_3)_2$ | $SO_2CH_3$ | Cl | OH |
| 4513 | $N(CH_2CH_3)_2$ | $N(CH_2CH_3)_2$ | $SO_2CH_3$ | Cl | OH |
| 4514 | $N(CH_3)(CH_2CH_3)$ | $N(CH_3)(CH_2CH_3)$ | $SO_2CH_3$ | Cl | OH |
| 4515 | $O-(CH_2CH_2)-O$ | | $SO_2CH_3$ | Cl | OH |
| 4516 | $O-(CH_2CH_2CH_2)-O$ | | $SO_2CH_3$ | Cl | OH |
| 4517 | $S-(CH_2CH_2)-S$ | | $SO_2CH_3$ | Cl | OH |
| 4518 | $S-(CH_2CH_2CH_2)-S$ | | $SO_2CH_3$ | Cl | OH |
| 4519 | $-(CH_2)_4-$ | | $SO_2CH_3$ | Cl | OH |
| 4520 | $-(CH_2)_5-$ | | $SO_2CH_3$ | Cl | OH |
| 4521 | H | H | $PO(OCH_3)_2$ | Cl | OH |
| 4522 | $CH_3$ | $CH_3$ | $PO(OCH_3)_2$ | Cl | OH |
| 4523 | $CH_2CH_3$ | $CH_2CH_3$ | $PO(OCH_3)_2$ | Cl | OH |
| 4524 | $CH_2CH_2CH_3$ | $CH_2CH_2CH_3$ | $PO(OCH_3)_2$ | Cl | OH |
| 4525 | $OCH_3$ | $OCH_3$ | $PO(OCH_3)_2$ | Cl | OH |
| 4526 | $OCH_2CH_3$ | $OCH_2CH_3$ | $PO(OCH_3)_2$ | Cl | OH |
| 4527 | $OCH_2CH_2CH_3$ | $OCH_2CH_2CH_3$ | $PO(OCH_3)_2$ | Cl | OH |
| 4528 | $SCH_3$ | $SCH_3$ | $PO(OCH_3)_2$ | Cl | OH |
| 4529 | $SCH_2CH_3$ | $SCH_2CH_3$ | $PO(OCH_3)_2$ | Cl | OH |
| 4530 | $N(CH_3)_2$ | $N(CH_3)_2$ | $PO(OCH_3)_2$ | Cl | OH |
| 4531 | $N(CH_2CH_3)_2$ | $N(CH_2CH_3)_2$ | $PO(OCH_3)_2$ | Cl | OH |
| 4532 | $N(CH_3)(CH_2CH_3)$ | $N(CH_3)(CH_2CH_3)$ | $PO(OCH_3)_2$ | Cl | OH |
| 4533 | $O-(CH_2CH_2)-O$ | | $PO(OCH_3)_2$ | Cl | OH |
| 4534 | $O-(CH_2CH_2CH_2)-O$ | | $PO(OCH_3)_2$ | Cl | OH |
| 4535 | $S-(CH_2CH_2)-S$ | | $PO(OCH_3)_2$ | Cl | OH |
| 4536 | $S-(CH_2CH_2CH_2)-S$ | | $PO(OCH_3)_2$ | Cl | OH |
| 4537 | $-(CH_2)_4-$ | | $PO(OCH_3)_2$ | Cl | OH |
| 4538 | $-(CH_2)_5-$ | | $PO(OCH_3)_2$ | Cl | OH |
| 4539 | H | H | $PO(OCH_2CH_3)_2$ | Cl | OH |
| 4540 | $CH_3$ | $CH_3$ | $PO(OCH_2CH_3)_2$ | Cl | OH |
| 4541 | $CH_2CH_3$ | $CH_2CH_3$ | $PO(OCH_2CH_3)_2$ | Cl | OH |
| 4542 | $CH_2CH_2CH_3$ | $CH_2CH_2CH_3$ | $PO(OCH_2CH_3)_2$ | Cl | OH |
| 4543 | $OCH_3$ | $OCH_3$ | $PO(OCH_2CH_3)_2$ | Cl | OH |
| 4544 | $OCH_2CH_3$ | $OCH_2CH_3$ | $PO(OCH_2CH_3)_2$ | Cl | OH |
| 4545 | $OCH_2CH_2CH_3$ | $OCH_2CH_2CH_3$ | $PO(OCH_2CH_3)_2$ | Cl | OH |
| 4546 | $SCH_3$ | $SCH_3$ | $PO(OCH_2CH_3)_2$ | Cl | OH |
| 4547 | $SCH_2CH_3$ | $SCH_2CH_3$ | $PO(OCH_2CH_3)_2$ | Cl | OH |
| 4548 | $N(CH_3)_2$ | $N(CH_3)_2$ | $PO(OCH_2CH_3)_2$ | Cl | OH |

TABLE 1-continued

I1a1

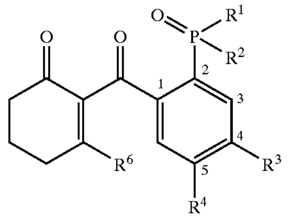

| n | $R^1$ | $R^2$ | $R^3$ | $R^4$ | $R^6$ |
|---|---|---|---|---|---|
| 4549 | $N(CH_2CH_3)_2$ | $N(CH_2CH_3)_2$ | $PO(OCH_2CH_3)_2$ | Cl | OH |
| 4550 | $N(CH_3)(CH_2CH_3)$ | $N(CH_3)(CH_2CH_3)$ | $PO(OCH_2CH_3)_2$ | Cl | OH |
| 4551 | $O—(CH_2CH_2)—O$ | | $PO(OCH_2CH_3)_2$ | Cl | OH |
| 4552 | $O—(CH_2CH_2CH_2)—O$ | | $PO(OCH_2CH_3)_2$ | Cl | OH |
| 4553 | $S—(CH_2CH_2)—S$ | | $PO(OCH_2CH_3)_2$ | Cl | OH |
| 4554 | $S—(CH_2CH_2CH_2)—S$ | | $PO(OCH_2CH_3)_2$ | Cl | OH |
| 4555 | $—(CH_2)_4—$ | | $PO(OCH_2CH_3)_2$ | Cl | OH |
| 4556 | $—(CH_2)_5—$ | | $PO(OCH_2CH_3)_2$ | Cl | OH |
| 4557 | H | H | $PO(CH_3)_2$ | Cl | OH |
| 4558 | $CH_3$ | $CH_3$ | $PO(CH_3)_2$ | Cl | OH |
| 4559 | $CH_2CH_3$ | $CH_2CH_3$ | $PO(CH_3)_2$ | Cl | OH |
| 4560 | $CH_2CH_2CH_3$ | $CH_2CH_2CH_3$ | $PO(CH_3)_2$ | Cl | OH |
| 4561 | $OCH_3$ | $OCH_3$ | $PO(CH_3)_2$ | Cl | OH |
| 4562 | $OCH_2CH_3$ | $OCH_2CH_3$ | $PO(CH_3)_2$ | Cl | OH |
| 4563 | $OCH_2CH_2CH_3$ | $OCH_2CH_2CH_3$ | $PO(CH_3)_2$ | Cl | OH |
| 4564 | $SCH_3$ | $SCH_3$ | $PO(CH_3)_2$ | Cl | OH |
| 4565 | $SCH_2CH_3$ | $SCH_2CH_3$ | $PO(CH_3)_2$ | Cl | OH |
| 4566 | $N(CH_3)_2$ | $N(CH_3)_2$ | $PO(CH_3)_2$ | Cl | OH |
| 4567 | $N(CH_2CH_3)_2$ | $N(CH_2CH_3)_2$ | $PO(CH_3)_2$ | Cl | OH |
| 4568 | $N(CH_3)(CH_2CH_3)$ | $N(CH_3)(CH_2CH_3)$ | $PO(CH_3)_2$ | Cl | OH |
| 4569 | $O—(CH_2CH_2)—O$ | | $PO(CH_3)_2$ | Cl | OH |
| 4570 | $O—(CH_2CH_2CH_2)—O$ | | $PO(CH_3)_2$ | Cl | OH |
| 4571 | $S—(CH_2CH_2)—S$ | | $PO(CH_3)_2$ | Cl | OH |
| 4572 | $S—(CH_2CH_2CH_2)—S$ | | $PO(CH_3)_2$ | Cl | OH |
| 4573 | $—(CH_2)_4—$ | | $PO(CH_3)_2$ | Cl | OH |
| 4574 | $—(CH_2)_5—$ | | $PO(CH_3)_2$ | Cl | OH |
| 4575 | H | H | $PO(CH_2CH_3)_2$ | Cl | OH |
| 4576 | $CH_3$ | $CH_3$ | $PO(CH_2CH_3)_2$ | Cl | OH |
| 4577 | $CH_2CH_3$ | $CH_2CH_3$ | $PO(CH_2CH_3)_2$ | Cl | OH |
| 4578 | $CH_2CH_2CH_3$ | $CH_2CH_2CH_3$ | $PO(CH_2CH_3)_2$ | Cl | OH |
| 4579 | $OCH_3$ | $OCH_3$ | $PO(CH_2CH_3)_2$ | Cl | OH |
| 4580 | $OCH_2CH_3$ | $OCH_2CH_3$ | $PO(CH_2CH_3)_2$ | Cl | OH |
| 4581 | $OCH_2CH_2CH_3$ | $OCH_2CH_2CH_3$ | $PO(CH_2CH_3)_2$ | Cl | OH |
| 4582 | $SCH_3$ | $SCH_3$ | $PO(CH_2CH_3)_2$ | Cl | OH |
| 4583 | $SCH_2CH_3$ | $SCH_2CH_3$ | $PO(CH_2CH_3)_2$ | Cl | OH |
| 4584 | $N(CH_3)_2$ | $N(CH_3)_2$ | $PO(CH_2CH_3)_2$ | Cl | OH |
| 4585 | $N(CH_2CH_3)_2$ | $N(CH_2CH_3)_2$ | $PO(CH_2CH_3)_2$ | Cl | OH |
| 4586 | $N(CH_3)(CH_2CH_3)$ | $N(CH_3)(CH_2CH_3)$ | $PO(CH_2CH_3)_2$ | Cl | OH |
| 4587 | $O—(CH_2CH_2)—O$ | | $PO(CH_2CH_3)_2$ | Cl | OH |
| 4588 | $O—(CH_2CH_2CH_2)—O$ | | $PO(CH_2CH_3)_2$ | Cl | OH |
| 4589 | $S—(CH_2CH_2)—S$ | | $PO(CH_2CH_3)_2$ | Cl | OH |
| 4590 | $S—(CH_2CH_2CH_2)—S$ | | $PO(CH_2CH_3)_2$ | Cl | OH |
| 4591 | $—(CH_2)_4—$ | | $PO(CH_2CH_3)_2$ | Cl | OH |
| 4592 | $—(CH_2)_5—$ | | $PO(CH_2CH_3)_2$ | Cl | OH |
| 4593 | H | H | H | Cl | $OCOC_6H_5$ |
| 4594 | $CH_3$ | $CH_3$ | H | Cl | $OCOC_6H_5$ |
| 4595 | $CH_2CH_3$ | $CH_2CH_3$ | H | Cl | $OCOC_6H_5$ |
| 4596 | $CH_2CH_2CH_3$ | $CH_2CH_2CH_3$ | H | Cl | $OCOC_6H_5$ |
| 4597 | $OCH_3$ | $OCH_3$ | H | Cl | $OCOC_6H_5$ |
| 4598 | $OCH_2CH_3$ | $OCH_2CH_3$ | H | Cl | $OCOC_6H_5$ |
| 4599 | $OCH_2CH_2CH_3$ | $OCH_2CH_2CH_3$ | H | Cl | $OCOC_6H_5$ |
| 4600 | $SCH_3$ | $SCH_3$ | H | Cl | $OCOC_6H_5$ |
| 4601 | $SCH_2CH_3$ | $SCH_2CH_3$ | H | Cl | $OCOC_6H_5$ |
| 4602 | $N(CH_3)_2$ | $N(CH_3)_2$ | H | Cl | $OCOC_6H_5$ |
| 4603 | $N(CH_2CH_3)_2$ | $N(CH_2CH_3)_2$ | H | Cl | $OCOC_6H_5$ |
| 4604 | $N(CH_3)(CH_2CH_3)$ | $N(CH_3)(CH_2CH_3)$ | H | Cl | $OCOC_6H_5$ |
| 4605 | $O—(CH_2CH_2)—O$ | | H | Cl | $OCOC_6H_5$ |
| 4606 | $O—(CH_2CH_2CH_2)—O$ | | H | Cl | $OCOC_6H_5$ |
| 4607 | $S—(CH_2CH_2)—S$ | | H | Cl | $OCOC_6H_5$ |
| 4608 | $S—(CH_2CH_2CH_2)—S$ | | H | Cl | $OCOC_6H_5$ |
| 4609 | $—(CH_2)_4—$ | | H | Cl | $OCOC_6H_5$ |
| 4610 | $—(CH_2)_5—$ | | H | Cl | $OCOC_6H_5$ |
| 4611 | H | H | $NO_2$ | Cl | $OCOC_6H_5$ |
| 4612 | $CH_3$ | $CH_3$ | $NO_2$ | Cl | $OCOC_6H_5$ |

TABLE 1-continued

I1a1

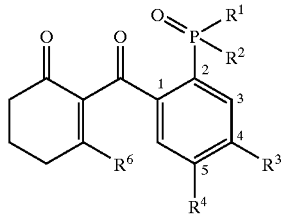

| n | $R^1$ | $R^2$ | $R^3$ | $R^4$ | $R^6$ |
|---|---|---|---|---|---|
| 4613 | $CH_2CH_3$ | $CH_2CH_3$ | $NO_2$ | Cl | $OCOC_6H_5$ |
| 4614 | $CH_2CH_2CH_3$ | $CH_2CH_2CH_3$ | $NO_2$ | Cl | $OCOC_6H_5$ |
| 4615 | $OCH_3$ | $OCH_3$ | $NO_2$ | Cl | $OCOC_6H_5$ |
| 4616 | $OCH_2CH_3$ | $OCH_2CH_3$ | $NO_2$ | Cl | $OCOC_6H_5$ |
| 4617 | $OCH_2CH_2CH_3$ | $OCH_2CH_2CH_3$ | $NO_2$ | Cl | $OCOC_6H_5$ |
| 4618 | $SCH_3$ | $SCH_3$ | $NO_2$ | Cl | $OCOC_6H_5$ |
| 4619 | $SCH_2CH_3$ | $SCH_2CH_3$ | $NO_2$ | Cl | $OCOC_6H_5$ |
| 4620 | $N(CH_3)_2$ | $N(CH_3)_2$ | $NO_2$ | Cl | $OCOC_6H_5$ |
| 4621 | $N(CH_2CH_3)_2$ | $N(CH_2CH_3)_2$ | $NO_2$ | Cl | $OCOC_6H_5$ |
| 4622 | $N(CH_3)(CH_2CH_3)$ | $N(CH_3)(CH_2CH_3)$ | $NO_2$ | Cl | $OCOC_6H_5$ |
| 4623 | $O-(CH_2CH_2)-O$ | | $NO_2$ | Cl | $OCOC_6H_5$ |
| 4624 | $O-(CH_2CH_2CH_2)-O$ | | $NO_2$ | Cl | $OCOC_6H_5$ |
| 4625 | $S-(CH_2CH_2)-S$ | | $NO_2$ | Cl | $OCOC_6H_5$ |
| 4626 | $S-(CH_2CH_2CH_2)-S$ | | $NO_2$ | Cl | $OCOC_6H_5$ |
| 4627 | $-(CH_2)_4-$ | | $NO_2$ | Cl | $OCOC_6H_5$ |
| 4628 | $-(CH_2)_5-$ | | $NO_2$ | Cl | $OCOC_6H_5$ |
| 4629 | H | H | CN | Cl | $OCOC_6H_5$ |
| 4630 | $CH_3$ | $CH_3$ | CN | Cl | $OCOC_6H_5$ |
| 4631 | $CH_2CH_3$ | $CH_2CH_3$ | CN | Cl | $OCOC_6H_5$ |
| 4632 | $CH_2CH_2CH_3$ | $CH_2CH_2CH_3$ | CN | Cl | $OCOC_6H_5$ |
| 4633 | $OCH_3$ | $OCH_3$ | CN | Cl | $OCOC_6H_5$ |
| 4634 | $OCH_2CH_3$ | $OCH_2CH_3$ | CN | Cl | $OCOC_6H_5$ |
| 4635 | $OCH_2CH_2CH_3$ | $OCH_2CH_2CH_3$ | CN | Cl | $OCOC_6H_5$ |
| 4636 | $SCH_3$ | $SCH_3$ | CN | Cl | $OCOC_6H_5$ |
| 4637 | $SCH_2CH_3$ | $SCH_2CH_3$ | CN | Cl | $OCOC_6H_5$ |
| 4638 | $N(CH_3)_2$ | $N(CH_3)_2$ | CN | Cl | $OCOC_6H_5$ |
| 4639 | $N(CH_2CH_3)_2$ | $N(CH_2CH_3)_2$ | CN | Cl | $OCOC_6H_5$ |
| 4640 | $N(CH_3)(CH_2CH_3)$ | $N(CH_3)(CH_2CH_3)$ | CN | Cl | $OCOC_6H_5$ |
| 4641 | $O-(CH_2CH_2)-O$ | | CN | Cl | $OCOC_6H_5$ |
| 4642 | $O-(CH_2CH_2CH_2)-O$ | | CN | Cl | $OCOC_6H_5$ |
| 4643 | $S-(CH_2CH_2)-S$ | | CN | Cl | $OCOC_6H_5$ |
| 4644 | $S-(CH_2CH_2CH_2)-S$ | | CN | Cl | $OCOC_6H_5$ |
| 4645 | $-(CH_2)_4-$ | | CN | Cl | $OCOC_6H_5$ |
| 4646 | $-(CH_2)_5-$ | | CN | Cl | $OCOC_6H_5$ |
| 4647 | H | H | F | Cl | $OCOC_6H_5$ |
| 4648 | $CH_3$ | $CH_3$ | F | Cl | $OCOC_6H_5$ |
| 4649 | $CH_2CH_3$ | $CH_2CH_3$ | F | Cl | $OCOC_6H_5$ |
| 4650 | $CH_2CH_2CH_3$ | $CH_2CH_2CH_3$ | F | Cl | $OCOC_6H_5$ |
| 4651 | $OCH_3$ | $OCH_3$ | F | Cl | $OCOC_6H_5$ |
| 4652 | $OCH_2CH_3$ | $OCH_2CH_3$ | F | Cl | $OCOC_6H_5$ |
| 4653 | $OCH_2CH_2CH_3$ | $OCH_2CH_2CH_3$ | F | Cl | $OCOC_6H_5$ |
| 4654 | $SCH_3$ | $SCH_3$ | F | Cl | $OCOC_6H_5$ |
| 4655 | $SCH_2CH_3$ | $SCH_2CH_3$ | F | Cl | $OCOC_6H_5$ |
| 4656 | $N(CH_3)_2$ | $N(CH_3)_2$ | F | Cl | $OCOC_6H_5$ |
| 4657 | $N(CH_2CH_3)_2$ | $N(CH_2CH_3)_2$ | F | Cl | $OCOC_6H_5$ |
| 4658 | $N(CH_3)(CH_2CH_3)$ | $N(CH_3)(CH_2CH_3)$ | F | Cl | $OCOC_6H_5$ |
| 4659 | $O-(CH_2CH_2)-O$ | | F | Cl | $OCOC_6H_5$ |
| 4660 | $O-(CH_2CH_2CH_2)-O$ | | F | Cl | $OCOC_6H_5$ |
| 4661 | $S-(CH_2CH_2)-S$ | | F | Cl | $OCOC_6H_5$ |
| 4662 | $S-(CH_2CH_2CH_2)-S$ | | F | Cl | $OCOC_6H_5$ |
| 4663 | $-(CH_2)_4-$ | | F | Cl | $OCOC_6H_5$ |
| 4664 | $-(CH_2)_5-$ | | F | Cl | $OCOC_6H_5$ |
| 4665 | H | H | Cl | Cl | $OCOC_6H_5$ |
| 4666 | $CH_3$ | $CH_3$ | Cl | Cl | $OCOC_6H_5$ |
| 4667 | $CH_2CH_3$ | $CH_2CH_3$ | Cl | Cl | $OCOC_6H_5$ |
| 4668 | $CH_2CH_2CH_3$ | $CH_2CH_2CH_3$ | Cl | Cl | $OCOC_6H_5$ |
| 4669 | $OCH_3$ | $OCH_3$ | Cl | Cl | $OCOC_6H_5$ |
| 4670 | $OCH_2CH_3$ | $OCH_2CH_3$ | Cl | Cl | $OCOC_6H_5$ |
| 4671 | $OCH_2CH_2CH_3$ | $OCH_2CH_2CH_3$ | Cl | Cl | $OCOC_6H_5$ |
| 4672 | $SCH_3$ | $SCH_3$ | Cl | Cl | $OCOC_6H_5$ |
| 4673 | $SCH_2CH_3$ | $SCH_2CH_3$ | Cl | Cl | $OCOC_6H_5$ |
| 4674 | $N(CH_3)_2$ | $N(CH_3)_2$ | Cl | Cl | $OCOC_6H_5$ |
| 4675 | $N(CH_2CH_3)_2$ | $N(CH_2CH_3)_2$ | Cl | Cl | $OCOC_6H_5$ |
| 4676 | $N(CH_3)(CH_2CH_3)$ | $N(CH_3)(CH_2CH_3)$ | Cl | Cl | $OCOC_6H_5$ |

TABLE 1-continued

I1a1

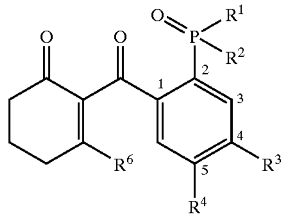

| n | $R^1$ | $R^2$ | $R^3$ | $R^4$ | $R^6$ |
|---|---|---|---|---|---|
| 4677 | O—$(CH_2CH_2)$—O | | Cl | Cl | $OCOC_6H_5$ |
| 4678 | O—$(CH_2CH_2CH_2)$—O | | Cl | Cl | $OCOC_6H_5$ |
| 4679 | S—$(CH_2CH_2)$—S | | Cl | Cl | $OCOC_6H_5$ |
| 4680 | S—$(CH_2CH_2CH_2)$—S | | Cl | Cl | $OCOC_6H_5$ |
| 4681 | —$(CH_2)_4$— | | Cl | Cl | $OCOC_6H_5$ |
| 4682 | —$(CH_2)_5$— | | Cl | Cl | $OCOC_6H_5$ |
| 4683 | H | H | Br | Cl | $OCOC_6H_5$ |
| 4684 | $CH_3$ | $CH_3$ | Br | Cl | $OCOC_6H_5$ |
| 4685 | $CH_2CH_3$ | $CH_2CH_3$ | Br | Cl | $OCOC_6H_5$ |
| 4686 | $CH_2CH_2CH_3$ | $CH_2CH_2CH_3$ | Br | Cl | $OCOC_6H_5$ |
| 4687 | $OCH_3$ | $OCH_3$ | Br | Cl | $OCOC_6H_5$ |
| 4688 | $OCH_2CH_3$ | $OCH_2CH_3$ | Br | Cl | $OCOC_6H_5$ |
| 4689 | $OCH_2CH_2CH_3$ | $OCH_2CH_2CH_3$ | Br | Cl | $OCOC_6H_5$ |
| 4690 | $SCH_3$ | $SCH_3$ | Br | Cl | $OCOC_6H_5$ |
| 4691 | $SCH_2CH_3$ | $SCH_2CH_3$ | Br | Cl | $OCOC_6H_5$ |
| 4692 | $N(CH_3)_2$ | $N(CH_3)_2$ | Br | Cl | $OCOC_6H_5$ |
| 4693 | $N(CH_2CH_3)_2$ | $N(CH_2CH_3)_2$ | Br | Cl | $OCOC_6H_5$ |
| 4694 | $N(CH_3)(CH_2CH_3)$ | $N(CH_3)(CH_2CH_3)$ | Br | Cl | $OCOC_6H_5$ |
| 4695 | O—$(CH_2CH_2)$—O | | Br | Cl | $OCOC_6H_5$ |
| 4696 | O—$(CH_2CH_2CH_2)$—O | | Br | Cl | $OCOC_6H_5$ |
| 4697 | S—$(CH_2CH_2)$—S | | Br | Cl | $OCOC_6H_5$ |
| 4698 | S—$(CH_2CH_2CH_2)$—S | | Br | Cl | $OCOC_6H_5$ |
| 4699 | —$(CH_2)_4$— | | Br | Cl | $OCOC_6H_5$ |
| 4700 | —$(CH_2)_5$— | | Br | Cl | $OCOC_6H_5$ |
| 4701 | H | H | $CH_3$ | Cl | $OCOC_6H_5$ |
| 4702 | $CH_3$ | $CH_3$ | $CH_3$ | Cl | $OCOC_6H_5$ |
| 4703 | $CH_2CH_3$ | $CH_2CH_3$ | $CH_3$ | Cl | $OCOC_6H_5$ |
| 4704 | $CH_2CH_2CH_3$ | $CH_2CH_2CH_3$ | $CH_3$ | Cl | $OCOC_6H_5$ |
| 4705 | $OCH_3$ | $OCH_3$ | $CH_3$ | Cl | $OCOC_6H_5$ |
| 4706 | $OCH_2CH_3$ | $OCH_2CH_3$ | $CH_3$ | Cl | $OCOC_6H_5$ |
| 4707 | $OCH_2CH_2CH_3$ | $OCH_2CH_2CH_3$ | $CH_3$ | Cl | $OCOC_6H_5$ |
| 4708 | $SCH_3$ | $SCH_3$ | $CH_3$ | Cl | $OCOC_6H_5$ |
| 4709 | $SCH_2CH_3$ | $SCH_2CH_3$ | $CH_3$ | Cl | $OCOC_6H_5$ |
| 4710 | $N(CH_3)_2$ | $N(CH_3)_2$ | $CH_3$ | Cl | $OCOC_6H_5$ |
| 4711 | $N(CH_2CH_3)_2$ | $N(CH_2CH_3)_2$ | $CH_3$ | Cl | $OCOC_6H_5$ |
| 4712 | $N(CH_3)(CH_2CH_3)$ | $N(CH_3)(CH_2CH_3)$ | $CH_3$ | Cl | $OCOC_6H_5$ |
| 4713 | O—$(CH_2CH_2)$—O | | $CH_3$ | Cl | $OCOC_6H_5$ |
| 4714 | O—$(CH_2CH_2CH_2)$—O | | $CH_3$ | Cl | $OCOC_6H_5$ |
| 4715 | S—$(CH_2CH_2)$—S | | $CH_3$ | Cl | $OCOC_6H_5$ |
| 4716 | S—$(CH_2CH_2CH_2)$—S | | $CH_3$ | Cl | $OCOC_6H_5$ |
| 4717 | —$(CH_2)_4$— | | $CH_3$ | Cl | $OCOC_6H_5$ |
| 4718 | —$(CH_2)_5$— | | $CH_3$ | Cl | $OCOC_6H_5$ |
| 4719 | H | H | $CH_2CH_3$ | Cl | $OCOC_6H_5$ |
| 4720 | $CH_3$ | $CH_3$ | $CH_2CH_3$ | Cl | $OCOC_6H_5$ |
| 4721 | $CH_2CH_3$ | $CH_2CH_3$ | $CH_2CH_3$ | Cl | $OCOC_6H_5$ |
| 4722 | $CH_2CH_2CH_3$ | $CH_2CH_2CH_3$ | $CH_2CH_3$ | Cl | $OCOC_6H_5$ |
| 4723 | $OCH_3$ | $OCH_3$ | $CH_2CH_3$ | Cl | $OCOC_6H_5$ |
| 4724 | $OCH_2CH_3$ | $OCH_2CH_3$ | $CH_2CH_3$ | Cl | $OCOC_6H_5$ |
| 4725 | $OCH_2CH_2CH_3$ | $OCH_2CH_2CH_3$ | $CH_2CH_3$ | Cl | $OCOC_6H_5$ |
| 4726 | $SCH_3$ | $SCH_3$ | $CH_2CH_3$ | Cl | $OCOC_6H_5$ |
| 4727 | $SCH_2CH_3$ | $SCH_2CH_3$ | $CH_2CH_3$ | Cl | $OCOC_6H_5$ |
| 4728 | $N(CH_3)_2$ | $N(CH_3)_2$ | $CH_2CH_3$ | Cl | $OCOC_6H_5$ |
| 4729 | $N(CH_2CH_3)_2$ | $N(CH_2CH_3)_2$ | $CH_2CH_3$ | Cl | $OCOC_6H_5$ |
| 4730 | $N(CH_3)(CH_2CH_3)$ | $N(CH_3)(CH_2CH_3)$ | $CH_2CH_3$ | Cl | $OCOC_6H_5$ |
| 4731 | O—$(CH_2CH_2)$—O | | $CH_2CH_3$ | Cl | $OCOC_6H_5$ |
| 4732 | O—$(CH_2CH_2CH_2)$—O | | $CH_2CH_3$ | Cl | $OCOC_6H_5$ |
| 4733 | S—$(CH_2CH_2)$—S | | $CH_2CH_3$ | Cl | $OCOC_6H_5$ |
| 4734 | S—$(CH_2CH_2CH_2)$—S | | $CH_2CH_3$ | Cl | $OCOC_6H_5$ |
| 4735 | —$(CH_2)_4$— | | $CH_2CH_3$ | Cl | $OCOC_6H_5$ |
| 4736 | —$(CH_2)_5$— | | $CH_2CH_3$ | Cl | $OCOC_6H_5$ |
| 4737 | H | H | $CF_3$ | Cl | $OCOC_6H_5$ |
| 4738 | $CH_3$ | $CH_3$ | $CF_3$ | Cl | $OCOC_6H_5$ |
| 4739 | $CH_2CH_3$ | $CH_2CH_3$ | $CF_3$ | Cl | $OCOC_6H_5$ |
| 4740 | $CH_2CH_2CH_3$ | $CH_2CH_2CH_3$ | $CF_3$ | Cl | $OCOC_6H_5$ |

TABLE 1-continued

I1a1

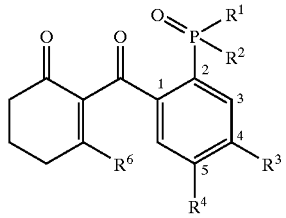

| n | $R^1$ | $R^2$ | $R^3$ | $R^4$ | $R^6$ |
|---|---|---|---|---|---|
| 4741 | $OCH_3$ | $OCH_3$ | $CF_3$ | Cl | $OCOC_6H_5$ |
| 4742 | $OCH_2CH_3$ | $OCH_2CH_3$ | $CF_3$ | Cl | $OCOC_6H_5$ |
| 4743 | $OCH_2CH_2CH_3$ | $OCH_2CH_2CH_3$ | $CF_3$ | Cl | $OCOC_6H_5$ |
| 4744 | $SCH_3$ | $SCH_3$ | $CF_3$ | Cl | $OCOC_6H_5$ |
| 4745 | $SCH_2CH_3$ | $SCH_2CH_3$ | $CF_3$ | Cl | $OCOC_6H_5$ |
| 4746 | $N(CH_3)_2$ | $N(CH_3)_2$ | $CF_3$ | Cl | $OCOC_6H_5$ |
| 4747 | $N(CH_2CH_3)_2$ | $N(CH_2CH_3)_2$ | $CF_3$ | Cl | $OCOC_6H_5$ |
| 4748 | $N(CH_3)(CH_2CH_3)$ | $N(CH_3)(CH_2CH_3)$ | $CF_3$ | Cl | $OCOC_6H_5$ |
| 4749 | $O—(CH_2CH_2)—O$ | | $CF_3$ | Cl | $OCOC_6H_5$ |
| 4750 | $O—(CH_2CH_2CH_2)—O$ | | $CF_3$ | Cl | $OCOC_6H_5$ |
| 4751 | $S—(CH_2CH_2)—S$ | | $CF_3$ | Cl | $OCOC_6H_5$ |
| 4752 | $S—(CH_2CH_2CH_2)—S$ | | $CF_3$ | Cl | $OCOC_6H_5$ |
| 4753 | $—(CH_2)_4—$ | | $CF_3$ | Cl | $OCOC_6H_5$ |
| 4754 | $—(CH_2)_5—$ | | $CF_3$ | Cl | $OCOC_6H_5$ |
| 4755 | H | H | $OCH_3$ | Cl | $OCOC_6H_5$ |
| 4756 | $CH_3$ | $CH_3$ | $OCH_3$ | Cl | $OCOC_6H_5$ |
| 4757 | $CH_2CH_3$ | $CH_2CH_3$ | $OCH_3$ | Cl | $OCOC_6H_5$ |
| 4758 | $CH_2CH_2CH_3$ | $CH_2CH_2CH_3$ | $OCH_3$ | Cl | $OCOC_6H_5$ |
| 4759 | $OCH_3$ | $OCH_3$ | $OCH_3$ | Cl | $OCOC_6H_5$ |
| 4760 | $OCH_2CH_3$ | $OCH_2CH_3$ | $OCH_3$ | Cl | $OCOC_6H_5$ |
| 4761 | $OCH_2CH_2CH_3$ | $OCH_2CH_2CH_3$ | $OCH_3$ | Cl | $OCOC_6H_5$ |
| 4762 | $SCH_3$ | $SCH_3$ | $OCH_3$ | Cl | $OCOC_6H_5$ |
| 4763 | $SCH_2CH_3$ | $SCH_2CH_3$ | $OCH_3$ | Cl | $OCOC_6H_5$ |
| 4764 | $N(CH_3)_2$ | $N(CH_3)_2$ | $OCH_3$ | Cl | $OCOC_6H_5$ |
| 4765 | $N(CH_2CH_3)_2$ | $N(CH_2CH_3)_2$ | $OCH_3$ | Cl | $OCOC_6H_5$ |
| 4766 | $N(CH_3)(CH_2CH_3)$ | $N(CH_3)(CH_2CH_3)$ | $OCH_3$ | Cl | $OCOC_6H_5$ |
| 4767 | $O—(CH_2CH_2)—O$ | | $OCH_3$ | Cl | $OCOC_6H_5$ |
| 4768 | $O—(CH_2CH_2CH_2)—O$ | | $OCH_3$ | Cl | $OCOC_6H_5$ |
| 4769 | $S—(CH_2CH_2)—S$ | | $OCH_3$ | Cl | $OCOC_6H_5$ |
| 4770 | $S—(CH_2CH_2CH_2)—S$ | | $OCH_3$ | Cl | $OCOC_6H_5$ |
| 4771 | $—(CH_2)_4—$ | | $OCH_3$ | Cl | $OCOC_6H_5$ |
| 4772 | $—(CH_2)_5—$ | | $OCH_3$ | Cl | $OCOC_6H_5$ |
| 4773 | H | H | $OCH_2CH_3$ | Cl | $OCOC_6H_5$ |
| 4774 | $CH_3$ | $CH_3$ | $OCH_2CH_3$ | Cl | $OCOC_6H_5$ |
| 4775 | $CH_2CH_3$ | $CH_2CH_3$ | $OCH_2CH_3$ | Cl | $OCOC_6H_5$ |
| 4776 | $CH_2CH_2CH_3$ | $CH_2CH_2CH_3$ | $OCH_2CH_3$ | Cl | $OCOC_6H_5$ |
| 4777 | $OCH_3$ | $OCH_3$ | $OCH_2CH_3$ | Cl | $OCOC_6H_5$ |
| 4778 | $OCH_2CH_3$ | $OCH_2CH_3$ | $OCH_2CH_3$ | Cl | $OCOC_6H_5$ |
| 4779 | $OCH_2CH_2CH_3$ | $OCH_2CH_2CH_3$ | $OCH_2CH_3$ | Cl | $OCOC_6H_5$ |
| 4780 | $SCH_3$ | $SCH_3$ | $OCH_2CH_3$ | Cl | $OCOC_6H_5$ |
| 4781 | $SCH_2CH_3$ | $SCH_2CH_3$ | $OCH_2CH_3$ | Cl | $OCOC_6H_5$ |
| 4782 | $N(CH_3)_2$ | $N(CH_3)_2$ | $OCH_2CH_3$ | Cl | $OCOC_6H_5$ |
| 4783 | $N(CH_2CH_3)_2$ | $N(CH_2CH_3)_2$ | $OCH_2CH_3$ | Cl | $OCOC_6H_5$ |
| 4784 | $N(CH_3)(CH_2CH_3)$ | $N(CH_3)(CH_2CH_3)$ | $OCH_2CH_3$ | Cl | $OCOC_6H_5$ |
| 4785 | $O—(CH_2CH_2)—O$ | | $OCH_2CH_3$ | Cl | $OCOC_6H_5$ |
| 4786 | $O—(CH_2CH_2CH_2)—O$ | | $OCH_2CH_3$ | Cl | $OCOC_6H_5$ |
| 4787 | $S—(CH_2CH_2)—S$ | | $OCH_2CH_3$ | Cl | $OCOC_6H_5$ |
| 4788 | $S—(CH_2CH_2CH_2)—S$ | | $OCH_2CH_3$ | Cl | $OCOC_6H_5$ |
| 4789 | $—(CH_2)_4—$ | | $OCH_2CH_3$ | Cl | $OCOC_6H_5$ |
| 4790 | $—(CH_2)_5—$ | | $OCH_2CH_3$ | Cl | $OCOC_6H_5$ |
| 4791 | H | H | $SCH_3$ | Cl | $OCOC_6H_5$ |
| 4792 | $CH_3$ | $CH_3$ | $SCH_3$ | Cl | $OCOC_6H_5$ |
| 4793 | $CH_2CH_3$ | $CH_2CH_3$ | $SCH_3$ | Cl | $OCOC_6H_5$ |
| 4794 | $CH_2CH_2CH_3$ | $CH_2CH_2CH_3$ | $SCH_3$ | Cl | $OCOC_6H_5$ |
| 4795 | $OCH_3$ | $OCH_3$ | $SCH_3$ | Cl | $OCOC_6H_5$ |
| 4796 | $OCH_2CH_3$ | $OCH_2CH_3$ | $SCH_3$ | Cl | $OCOC_6H_5$ |
| 4797 | $OCH_2CH_2CH_3$ | $OCH_2CH_2CH_3$ | $SCH_3$ | Cl | $OCOC_6H_5$ |
| 4798 | $SCH_3$ | $SCH_3$ | $SCH_3$ | Cl | $OCOC_6H_5$ |
| 4799 | $SCH_2CH_3$ | $SCH_2CH_3$ | $SCH_3$ | Cl | $OCOC_6H_5$ |
| 4800 | $N(CH_3)_2$ | $N(CH_3)_2$ | $SCH_3$ | Cl | $OCOC_6H_5$ |
| 4801 | $N(CH_2CH_3)_2$ | $N(CH_2CH_3)_2$ | $SCH_3$ | Cl | $OCOC_6H_5$ |
| 4802 | $N(CH_3)(CH_2CH_3)$ | $N(CH_3)(CH_2CH_3)$ | $SCH_3$ | Cl | $OCOC_6H_5$ |
| 4803 | $O—(CH_2CH_2)—O$ | | $SCH_3$ | Cl | $OCOC_6H_5$ |
| 4804 | $O—(CH_2CH_2CH_2)—O$ | | $SCH_3$ | Cl | $OCOC_6H_5$ |

TABLE 1-continued

I1a1

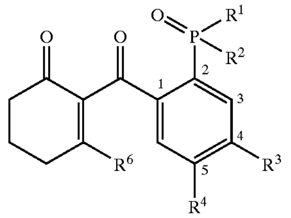

| n | $R^1$ | $R^2$ | $R^3$ | $R^4$ | $R^6$ |
|---|---|---|---|---|---|
| 4805 | S—(CH$_2$CH$_2$)—S | | $SCH_3$ | Cl | $OCOC_6H_5$ |
| 4806 | S—(CH$_2$CH$_2$CH$_2$)—S | | $SCH_3$ | Cl | $OCOC_6H_5$ |
| 4807 | —(CH$_2$)$_4$— | | $SCH_3$ | Cl | $OCOC_6H_5$ |
| 4808 | —(CH$_2$)$_5$— | | $SCH_3$ | Cl | $OCOC_6H_5$ |
| 4809 | H | H | $SO_2CH_3$ | Cl | $OCOC_6H_5$ |
| 4810 | $CH_3$ | $CH_3$ | $SO_2CH_3$ | Cl | $OCOC_6H_5$ |
| 4811 | $CH_2CH_3$ | $CH_2CH_3$ | $SO_2CH_3$ | Cl | $OCOC_6H_5$ |
| 4812 | $CH_2CH_2CH_3$ | $CH_2CH_2CH_3$ | $SO_2CH_3$ | Cl | $OCOC_6H_5$ |
| 4813 | $OCH_3$ | $OCH_3$ | $SO_2CH_3$ | Cl | $OCOC_6H_5$ |
| 4814 | $OCH_2CH_3$ | $OCH_2CH_3$ | $SO_2CH_3$ | Cl | $OCOC_6H_5$ |
| 4815 | $OCH_2CH_2CH_3$ | $OCH_2CH_2CH_3$ | $SO_2CH_3$ | Cl | $OCOC_6H_5$ |
| 4816 | $SCH_3$ | $SCH_3$ | $SO_2CH_3$ | Cl | $OCOC_6H_5$ |
| 4817 | $SCH_2CH_3$ | $SCH_2CH_3$ | $SO_2CH_3$ | Cl | $OCOC_6H_5$ |
| 4818 | $N(CH_3)_2$ | $N(CH_3)_2$ | $SO_2CH_3$ | Cl | $OCOC_6H_5$ |
| 4819 | $N(CH_2CH_3)_2$ | $N(CH_2CH_3)_2$ | $SO_2CH_3$ | Cl | $OCOC_6H_5$ |
| 4820 | $N(CH_3)(CH_2CH_3)$ | $N(CH_3)(CH_2CH_3)$ | $SO_2CH_3$ | Cl | $OCOC_6H_5$ |
| 4821 | O—(CH$_2$CH$_2$)—O | | $SO_2CH_3$ | Cl | $OCOC_6H_5$ |
| 4822 | O—(CH$_2$CH$_2$CH$_2$)—O | | $SO_2CH_3$ | Cl | $OCOC_6H_5$ |
| 4823 | S—(CH$_2$CH$_2$)—S | | $SO_2CH_3$ | Cl | $OCOC_6H_5$ |
| 4824 | S—(CH$_2$CH$_2$CH$_2$)—S | | $SO_2CH_3$ | Cl | $OCOC_6H_5$ |
| 4825 | —(CH$_2$)$_4$— | | $SO_2CH_3$ | Cl | $OCOC_6H_5$ |
| 4826 | —(CH$_2$)$_5$— | | $SO_2CH_3$ | Cl | $OCOC_6H_5$ |
| 4827 | H | H | $PO(OCH_3)_2$ | Cl | $OCOC_6H_5$ |
| 4828 | $CH_3$ | $CH_3$ | $PO(OCH_3)_2$ | Cl | $OCOC_6H_5$ |
| 4829 | $CH_2CH_3$ | $CH_2CH_3$ | $PO(OCH_3)_2$ | Cl | $OCOC_6H_5$ |
| 4830 | $CH_2CH_2CH_3$ | $CH_2CH_2CH_3$ | $PO(OCH_3)_2$ | Cl | $OCOC_6H_5$ |
| 4831 | $OCH_3$ | $OCH_3$ | $PO(OCH_3)_2$ | Cl | $OCOC_6H_5$ |
| 4832 | $OCH_2CH_3$ | $OCH_2CH_3$ | $PO(OCH_3)_2$ | Cl | $OCOC_6H_5$ |
| 4833 | $OCH_2CH_2CH_3$ | $OCH_2CH_2CH_3$ | $PO(OCH_3)_2$ | Cl | $OCOC_6H_5$ |
| 4834 | $SCH_3$ | $SCH_3$ | $PO(OCH_3)_2$ | Cl | $OCOC_6H_5$ |
| 4835 | $SCH_2CH_3$ | $SCH_2CH_3$ | $PO(OCH_3)_2$ | Cl | $OCOC_6H_5$ |
| 4836 | $N(CH_3)_2$ | $N(CH_3)_2$ | $PO(OCH_3)_2$ | Cl | $OCOC_6H_5$ |
| 4837 | $N(CH_2CH_3)_2$ | $N(CH_2CH_3)_2$ | $PO(OCH_3)_2$ | Cl | $OCOC_6H_5$ |
| 4838 | $N(CH_3)(CH_2CH_3)$ | $N(CH_3)(CH_2CH_3)$ | $PO(OCH_3)_2$ | Cl | $OCOC_6H_5$ |
| 4839 | O—(CH$_2$CH$_2$)—O | | $PO(OCH_3)_2$ | Cl | $OCOC_6H_5$ |
| 4840 | O—(CH$_2$CH$_2$CH$_2$)—O | | $PO(OCH_3)_2$ | Cl | $OCOC_6H_5$ |
| 4841 | S—(CH$_2$CH$_2$)—S | | $PO(OCH_3)_2$ | Cl | $OCOC_6H_5$ |
| 4842 | S—(CH$_2$CH$_2$CH$_2$)—S | | $PO(OCH_3)_2$ | Cl | $OCOC_6H_5$ |
| 4843 | —(CH$_2$)$_4$— | | $PO(OCH_3)_2$ | Cl | $OCOC_6H_5$ |
| 4844 | —(CH$_2$)$_5$— | | $PO(OCH_3)_2$ | Cl | $OCOC_6H_5$ |
| 4845 | H | H | $PO(OCH_2CH_3)_2$ | Cl | $OCOC_6H_5$ |
| 4846 | $CH_3$ | $CH_3$ | $PO(OCH_2CH_3)_2$ | Cl | $OCOC_6H_5$ |
| 4847 | $CH_2CH_3$ | $CH_2CH_3$ | $PO(OCH_2CH_3)_2$ | Cl | $OCOC_6H_5$ |
| 4848 | $CH_2CH_2CH_3$ | $CH_2CH_2CH_3$ | $PO(OCH_2CH_3)_2$ | Cl | $OCOC_6H_5$ |
| 4849 | $OCH_3$ | $OCH_3$ | $PO(OCH_2CH_3)_2$ | Cl | $OCOC_6H_5$ |
| 4850 | $OCH_2CH_3$ | $OCH_2CH_3$ | $PO(OCH_2CH_3)_2$ | Cl | $OCOC_6H_5$ |
| 4851 | $OCH_2CH_2CH_3$ | $OCH_2CH_2CH_3$ | $PO(OCH_2CH_3)_2$ | Cl | $OCOC_6H_5$ |
| 4852 | $SCH_3$ | $SCH_3$ | $PO(OCH_2CH_3)_2$ | Cl | $OCOC_6H_5$ |
| 4853 | $SCH_2CH_3$ | $SCH_2CH_3$ | $PO(OCH_2CH_3)_2$ | Cl | $OCOC_6H_5$ |
| 4854 | $N(CH_3)_2$ | $N(CH_3)_2$ | $PO(OCH_2CH_3)_2$ | Cl | $OCOC_6H_5$ |
| 4855 | $N(CH_2CH_3)_2$ | $N(CH_2CH_3)_2$ | $PO(OCH_2CH_3)_2$ | Cl | $OCOC_6H_5$ |
| 4856 | $N(CH_3)(CH_2CH_3)$ | $N(CH_3)(CH_2CH_3)$ | $PO(OCH_2CH_3)_2$ | Cl | $OCOC_6H_5$ |
| 4857 | O—(CH$_2$CH$_2$)—O | | $PO(OCH_2CH_3)_2$ | Cl | $OCOC_6H_5$ |
| 4858 | O—(CH$_2$CH$_2$CH$_2$)—O | | $PO(OCH_2CH_3)_2$ | Cl | $OCOC_6H_5$ |
| 4859 | S—(CH$_2$CH$_2$)—S | | $PO(OCH_2CH_3)_2$ | Cl | $OCOC_6H_5$ |
| 4860 | S—(CH$_2$CH$_2$CH$_2$)—S | | $PO(OCH_2CH_3)_2$ | Cl | $OCOC_6H_5$ |
| 4861 | —(CH$_2$)$_4$— | | $PO(OCH_2CH_3)_2$ | Cl | $OCOC_6H_5$ |
| 4862 | —(CH$_2$)$_5$— | | $PO(OCH_2CH_3)_2$ | Cl | $OCOC_6H_5$ |
| 4863 | H | H | $PO(CH_3)_2$ | Cl | $OCOC_6H_5$ |
| 4864 | $CH_3$ | $CH_3$ | $PO(CH_3)_2$ | Cl | $OCOC_6H_5$ |
| 4865 | $CH_2CH_3$ | $CH_2CH_3$ | $PO(CH_3)_2$ | Cl | $OCOC_6H_5$ |
| 4866 | $CH_2CH_2CH_3$ | $CH_2CH_2CH_3$ | $PO(CH_3)_2$ | Cl | $OCOC_6H_5$ |
| 4867 | $OCH_3$ | $OCH_3$ | $PO(CH_3)_2$ | Cl | $OCOC_6H_5$ |
| 4868 | $OCH_2CH_3$ | $OCH_2CH_3$ | $PO(CH_3)_2$ | Cl | $OCOC_6H_5$ |

TABLE 1-continued

I1a1

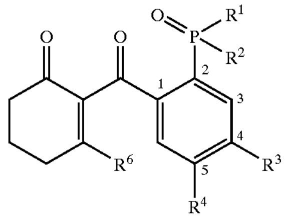

| n | $R^1$ | $R^2$ | $R^3$ | $R^4$ | $R^6$ |
|---|---|---|---|---|---|
| 4869 | $OCH_2CH_2CH_3$ | $OCH_2CH_2CH_3$ | $PO(CH_3)_2$ | Cl | $OCOC_6H_5$ |
| 4870 | $SCH_3$ | $SCH_3$ | $PO(CH_3)_2$ | Cl | $OCOC_6H_5$ |
| 4871 | $SCH_2CH_3$ | $SCH_2CH_3$ | $PO(CH_3)_2$ | Cl | $OCOC_6H_5$ |
| 4872 | $N(CH_3)_2$ | $N(CH_3)_2$ | $PO(CH_3)_2$ | Cl | $OCOC_6H_5$ |
| 4873 | $N(CH_2CH_3)_2$ | $N(CH_2CH_3)_2$ | $PO(CH_3)_2$ | Cl | $OCOC_6H_5$ |
| 4874 | $N(CH_3)(CH_2CH_3)$ | $N(CH_3)(CH_2CH_3)$ | $PO(CH_3)_2$ | Cl | $OCOC_6H_5$ |
| 4875 | $O—(CH_2CH_2)—O$ | | $PO(CH_3)_2$ | Cl | $OCOC_6H_5$ |
| 4876 | $O—(CH_2CH_2CH_2)—O$ | | $PO(CH_3)_2$ | Cl | $OCOC_6H_5$ |
| 4877 | $S—(CH_2CH_2)—S$ | | $PO(CH_3)_2$ | Cl | $OCOC_6H_5$ |
| 4878 | $S—(CH_2CH_2CH_2)—S$ | | $PO(CH_3)_2$ | Cl | $OCOC_6H_5$ |
| 4879 | $—(CH_2)_4—$ | | $PO(CH_3)_2$ | Cl | $OCOC_6H_5$ |
| 4880 | $—(CH_2)_5—$ | | $PO(CH_3)_2$ | Cl | $OCOC_6H_5$ |
| 4881 | H | H | $PO(CH_2CH_3)_2$ | Cl | $OCOC_6H_5$ |
| 4882 | $CH_3$ | $CH_3$ | $PO(CH_2CH_3)_2$ | Cl | $OCOC_6H_5$ |
| 4883 | $CH_2CH_3$ | $CH_2CH_3$ | $PO(CH_2CH_3)_2$ | Cl | $OCOC_6H_5$ |
| 4884 | $CH_2CH_2CH_3$ | $CH_2CH_2CH_3$ | $PO(CH_2CH_3)_2$ | Cl | $OCOC_6H_5$ |
| 4885 | $OCH_3$ | $OCH_3$ | $PO(CH_2CH_3)_2$ | Cl | $OCOC_6H_5$ |
| 4886 | $OCH_2CH_3$ | $OCH_2CH_3$ | $PO(CH_2CH_3)_2$ | Cl | $OCOC_6H_5$ |
| 4887 | $OCH_2CH_2CH_3$ | $OCH_2CH_2CH_3$ | $PO(CH_2CH_3)_2$ | Cl | $OCOC_6H_5$ |
| 4888 | $SCH_3$ | $SCH_3$ | $PO(CH_2CH_3)_2$ | Cl | $OCOC_6H_5$ |
| 4889 | $SCH_2CH_3$ | $SCH_2CH_3$ | $PO(CH_2CH_3)_2$ | Cl | $OCOC_6H_5$ |
| 4890 | $N(CH_3)_2$ | $N(CH_3)_2$ | $PO(CH_2CH_3)_2$ | Cl | $OCOC_6H_5$ |
| 4891 | $N(CH_2CH_3)_2$ | $N(CH_2CH_3)_2$ | $PO(CH_2CH_3)_2$ | Cl | $OCOC_6H_5$ |
| 4892 | $N(CH_3)(CH_2CH_3)$ | $N(CH_3)(CH_2CH_3)$ | $PO(CH_2CH_3)_2$ | Cl | $OCOC_6H_5$ |
| 4893 | $O—(CH_2CH_2)—O$ | | $PO(CH_2CH_3)_2$ | Cl | $OCOC_6H_5$ |
| 4894 | $O—(CH_2CH_2CH_2)—O$ | | $PO(CH_2CH_3)_2$ | Cl | $OCOC_6H_5$ |
| 4895 | $S—(CH_2CH_2)—S$ | | $PO(CH_2CH_3)_2$ | Cl | $OCOC_6H_5$ |
| 4896 | $S—(CH_2CH_2CH_2)—S$ | | $PO(CH_2CH_3)_2$ | Cl | $OCOC_6H_5$ |
| 4897 | $—(CH_2)_4—$ | | $PO(CH_2CH_3)_2$ | Cl | $OCOC_6H_5$ |
| 4898 | $—(CH_2)_5—$ | | $PO(CH_2CH_3)_2$ | Cl | $OCOC_6H_5$ |
| 4899 | H | H | H | Cl | $SCH_3$ |
| 4900 | $CH_3$ | $CH_3$ | H | Cl | $SCH_3$ |
| 4901 | $CH_2CH_3$ | $CH_2CH_3$ | H | Cl | $SCH_3$ |
| 4902 | $CH_2CH_2CH_3$ | $CH_2CH_2CH_3$ | H | Cl | $SCH_3$ |
| 4903 | $OCH_3$ | $OCH_3$ | H | Cl | $SCH_3$ |
| 4904 | $OCH_2CH_3$ | $OCH_2CH_3$ | H | Cl | $SCH_3$ |
| 4905 | $OCH_2CH_2CH_3$ | $OCH_2CH_2CH_3$ | H | Cl | $SCH_3$ |
| 4906 | $SCH_3$ | $SCH_3$ | H | Cl | $SCH_3$ |
| 4907 | $SCH_2CH_3$ | $SCH_2CH_3$ | H | Cl | $SCH_3$ |
| 4908 | $N(CH_3)_2$ | $N(CH_3)_2$ | H | Cl | $SCH_3$ |
| 4909 | $N(CH_2CH_3)_2$ | $N(CH_2CH_3)_2$ | H | Cl | $SCH_3$ |
| 4910 | $N(CH_3)(CH_2CH_3)$ | $N(CH_3)(CH_2CH_3)$ | H | Cl | $SCH_3$ |
| 4911 | $O—(CH_2CH_2)—O$ | | H | Cl | $SCH_3$ |
| 4912 | $O—(CH_2CH_2CH_2)—O$ | | H | Cl | $SCH_3$ |
| 4913 | $S—(CH_2CH_2)—S$ | | H | Cl | $SCH_3$ |
| 4914 | $S—(CH_2CH_2CH_2)—S$ | | H | Cl | $SCH_3$ |
| 4915 | $—(CH_2)_4—$ | | H | Cl | $SCH_3$ |
| 4916 | $—(CH_2)_5—$ | | H | Cl | $SCH_3$ |
| 4917 | H | H | $NO_2$ | Cl | $SCH_3$ |
| 4918 | $CH_3$ | $CH_3$ | $NO_2$ | Cl | $SCH_3$ |
| 4919 | $CH_2CH_3$ | $CH_2CH_3$ | $NO_2$ | Cl | $SCH_3$ |
| 4920 | $CH_2CH_2CH_3$ | $CH_2CH_2CH_3$ | $NO_2$ | Cl | $SCH_3$ |
| 4921 | $OCH_3$ | $OCH_3$ | $NO_2$ | Cl | $SCH_3$ |
| 4922 | $OCH_2CH_3$ | $OCH_2CH_3$ | $NO_2$ | Cl | $SCH_3$ |
| 4923 | $OCH_2CH_2CH_3$ | $OCH_2CH_2CH_3$ | $NO_2$ | Cl | $SCH_3$ |
| 4924 | $SCH_3$ | $SCH_3$ | $NO_2$ | Cl | $SCH_3$ |
| 4925 | $SCH_2CH_3$ | $SCH_2CH_3$ | $NO_2$ | Cl | $SCH_3$ |
| 4926 | $N(CH_3)_2$ | $N(CH_3)_2$ | $NO_2$ | Cl | $SCH_3$ |
| 4927 | $N(CH_2CH_3)_2$ | $N(CH_2CH_3)_2$ | $NO_2$ | Cl | $SCH_3$ |
| 4928 | $N(CH_3)(CH_2CH_3)$ | $N(CH_3)(CH_2CH_3)$ | $NO_2$ | Cl | $SCH_3$ |
| 4929 | $O—(CH_2CH_2)—O$ | | $NO_2$ | Cl | $SCH_3$ |
| 4930 | $O—(CH_2CH_2CH_2)—O$ | | $NO_2$ | Cl | $SCH_3$ |
| 4931 | $S—(CH_2CH_2)—S$ | | $NO_2$ | Cl | $SCH_3$ |
| 4932 | $S—(CH_2CH_2CH_2)—S$ | | $NO_2$ | Cl | $SCH_3$ |

TABLE 1-continued

I1a1

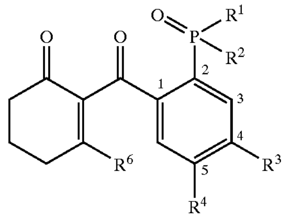

| n | $R^1$ | $R^2$ | $R^3$ | $R^4$ | $R^6$ |
|---|---|---|---|---|---|
| 4933 | $—(CH_2)_4—$ | | $NO_2$ | Cl | $SCH_3$ |
| 4934 | $—(CH_2)_5—$ | | $NO_2$ | Cl | $SCH_3$ |
| 4935 | H | H | CN | Cl | $SCH_3$ |
| 4936 | $CH_3$ | $CH_3$ | CN | Cl | $SCH_3$ |
| 4937 | $CH_2CH_3$ | $CH_2CH_3$ | CN | Cl | $SCH_3$ |
| 4938 | $CH_2CH_2CH_3$ | $CH_2CH_2CH_3$ | CN | Cl | $SCH_3$ |
| 4939 | $OCH_3$ | $OCH_3$ | CN | Cl | $SCH_3$ |
| 4940 | $OCH_2CH_3$ | $OCH_2CH_3$ | CN | Cl | $SCH_3$ |
| 4941 | $OCH_2CH_2CH_3$ | $OCH_2CH_2CH_3$ | CN | Cl | $SCH_3$ |
| 4942 | $SCH_3$ | $SCH_3$ | CN | Cl | $SCH_3$ |
| 4943 | $SCH_2CH_3$ | $SCH_2CH_3$ | CN | Cl | $SCH_3$ |
| 4944 | $N(CH_3)_2$ | $N(CH_3)_2$ | CN | Cl | $SCH_3$ |
| 4945 | $N(CH_2CH_3)_2$ | $N(CH_2CH_3)_2$ | CN | Cl | $SCH_3$ |
| 4946 | $N(CH_3)(CH_2CH_3)$ | $N(CH_3)(CH_2CH_3)$ | CN | Cl | $SCH_3$ |
| 4947 | $O—(CH_2CH_2)—O$ | | CN | Cl | $SCH_3$ |
| 4948 | $O—(CH_2CH_2CH_2)—O$ | | CN | Cl | $SCH_3$ |
| 4949 | $S—(CH_2CH_2)—S$ | | CN | Cl | $SCH_3$ |
| 4950 | $S—(CH_2CH_2CH_2)—S$ | | CN | Cl | $SCH_3$ |
| 4951 | $—(CH_2)_4—$ | | CN | Cl | $SCH_3$ |
| 4952 | $—(CH_2)_5—$ | | CN | Cl | $SCH_3$ |
| 4953 | H | H | F | Cl | $SCH_3$ |
| 4954 | $CH_3$ | $CH_3$ | F | Cl | $SCH_3$ |
| 4955 | $CH_2CH_3$ | $CH_2CH_3$ | F | Cl | $SCH_3$ |
| 4956 | $CH_2CH_2CH_3$ | $CH_2CH_2CH_3$ | F | Cl | $SCH_3$ |
| 4957 | $OCH_3$ | $OCH_3$ | F | Cl | $SCH_3$ |
| 4958 | $OCH_2CH_3$ | $OCH_2CH_3$ | F | Cl | $SCH_3$ |
| 4959 | $OCH_2CH_2CH_3$ | $OCH_2CH_2CH_3$ | F | Cl | $SCH_3$ |
| 4960 | $SCH_3$ | $SCH_3$ | F | Cl | $SCH_3$ |
| 4961 | $SCH_2CH_3$ | $SCH_2CH_3$ | F | Cl | $SCH_3$ |
| 4962 | $N(CH_3)_2$ | $N(CH_3)_2$ | F | Cl | $SCH_3$ |
| 4963 | $N(CH_2CH_3)_2$ | $N(CH_2CH_3)_2$ | F | Cl | $SCH_3$ |
| 4964 | $N(CH_3)(CH_2CH_3)$ | $N(CH_3)(CH_2CH_3)$ | F | Cl | $SCH_3$ |
| 4965 | $O—(CH_2CH_2)—O$ | | F | Cl | $SCH_3$ |
| 4966 | $O—(CH_2CH_2CH_2)—O$ | | F | Cl | $SCH_3$ |
| 4967 | $S—(CH_2CH_2)—S$ | | F | Cl | $SCH_3$ |
| 4968 | $S—(CH_2CH_2CH_2)—S$ | | F | Cl | $SCH_3$ |
| 4969 | $—(CH_2)_4—$ | | F | Cl | $SCH_3$ |
| 4970 | $—(CH_2)_5—$ | | F | Cl | $SCH_3$ |
| 4971 | H | H | Cl | Cl | $SCH_3$ |
| 4972 | $CH_3$ | $CH_3$ | Cl | Cl | $SCH_3$ |
| 4973 | $CH_2CH_3$ | $CH_2CH_3$ | Cl | Cl | $SCH_3$ |
| 4974 | $CH_2CH_2CH_3$ | $CH_2CH_2CH_3$ | Cl | Cl | $SCH_3$ |
| 4975 | $OCH_3$ | $OCH_3$ | Cl | Cl | $SCH_3$ |
| 4976 | $OCH_2CH_3$ | $OCH_2CH_3$ | Cl | Cl | $SCH_3$ |
| 4977 | $OCH_2CH_2CH_3$ | $OCH_2CH_2CH_3$ | Cl | Cl | $SCH_3$ |
| 4978 | $SCH_3$ | $SCH_3$ | Cl | Cl | $SCH_3$ |
| 4979 | $SCH_2CH_3$ | $SCH_2CH_3$ | Cl | Cl | $SCH_3$ |
| 4980 | $N(CH_3)_2$ | $N(CH_3)_2$ | Cl | Cl | $SCH_3$ |
| 4981 | $N(CH_2CH_3)_2$ | $N(CH_2CH_3)_2$ | Cl | Cl | $SCH_3$ |
| 4982 | $N(CH_3)(CH_2CH_3)$ | $N(CH_3)(CH_2CH_3)$ | Cl | Cl | $SCH_3$ |
| 4983 | $O—(CH_2CH_2)—O$ | | Cl | Cl | $SCH_3$ |
| 4984 | $O—(CH_2CH_2CH_2)—O$ | | Cl | Cl | $SCH_3$ |
| 4985 | $S—(CH_2CH_2)—S$ | | Cl | Cl | $SCH_3$ |
| 4986 | $S—(CH_2CH_2CH_2)—S$ | | Cl | Cl | $SCH_3$ |
| 4987 | $—(CH_2)_4—$ | | Cl | Cl | $SCH_3$ |
| 4988 | $—(CH_2)_5—$ | | Cl | Cl | $SCH_3$ |
| 4989 | H | H | Br | Cl | $SCH_3$ |
| 4990 | $CH_3$ | $CH_3$ | Br | Cl | $SCH_3$ |
| 4991 | $CH_2CH_3$ | $CH_2CH_3$ | Br | Cl | $SCH_3$ |
| 4992 | $CH_2CH_2CH_3$ | $CH_2CH_2CH_3$ | Br | Cl | $SCH_3$ |
| 4993 | $OCH_3$ | $OCH_3$ | Br | Cl | $SCH_3$ |
| 4994 | $OCH_2CH_3$ | $OCH_2CH_3$ | Br | Cl | $SCH_3$ |
| 4995 | $OCH_2CH_2CH_3$ | $OCH_2CH_2CH_3$ | Br | Cl | $SCH_3$ |
| 4996 | $SCH_3$ | $SCH_3$ | Br | Cl | $SCH_3$ |

TABLE 1-continued

I1a1

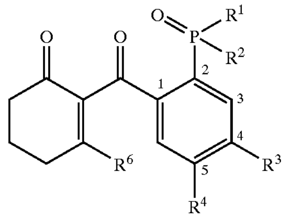

| n | $R^1$ | $R^2$ | $R^3$ | $R^4$ | $R^6$ |
|---|---|---|---|---|---|
| 4997 | $SCH_2CH_3$ | $SCH_2CH_3$ | Br | Cl | $SCH_3$ |
| 4998 | $N(CH_3)_2$ | $N(CH_3)_2$ | Br | Cl | $SCH_3$ |
| 4999 | $N(CH_2CH_3)_2$ | $N(CH_2CH_3)_2$ | Br | Cl | $SCH_3$ |
| 5000 | $N(CH_3)(CH_2CH_3)$ | $N(CH_3)(CH_2CH_3)$ | Br | Cl | $SCH_3$ |
| 5001 | $O—(CH_2CH_2)—O$ | | Br | Cl | $SCH_3$ |
| 5002 | $O—(CH_2CH_2CH_2)—O$ | | Br | Cl | $SCH_3$ |
| 5003 | $S—(CH_2CH_2)—S$ | | Br | Cl | $SCH_3$ |
| 5004 | $S—(CH_2CH_2CH_2)—S$ | | Br | Cl | $SCH_3$ |
| 5005 | $—(CH_2)_4—$ | | Br | Cl | $SCH_3$ |
| 5006 | $—(CH_2)_5—$ | | Br | Cl | $SCH_3$ |
| 5007 | H | H | $CH_3$ | Cl | $SCH_3$ |
| 5008 | $CH_3$ | $CH_3$ | $CH_3$ | Cl | $SCH_3$ |
| 5009 | $CH_2CH_3$ | $CH_2CH_3$ | $CH_3$ | Cl | $SCH_3$ |
| 5010 | $CH_2CH_2CH_3$ | $CH_2CH_2CH_3$ | $CH_3$ | Cl | $SCH_3$ |
| 5011 | $OCH_3$ | $OCH_3$ | $CH_3$ | Cl | $SCH_3$ |
| 5012 | $OCH_2CH_3$ | $OCH_2CH_3$ | $CH_3$ | Cl | $SCH_3$ |
| 5013 | $OCH_2CH_2CH_3$ | $OCH_2CH_2CH_3$ | $CH_3$ | Cl | $SCH_3$ |
| 5014 | $SCH_3$ | $SCH_3$ | $CH_3$ | Cl | $SCH_3$ |
| 5015 | $SCH_2CH_3$ | $SCH_2CH_3$ | $CH_3$ | Cl | $SCH_3$ |
| 5016 | $N(CH_3)_2$ | $N(CH_3)_2$ | $CH_3$ | Cl | $SCH_3$ |
| 5017 | $N(CH_2CH_3)_2$ | $N(CH_2CH_3)_2$ | $CH_3$ | Cl | $SCH_3$ |
| 5018 | $N(CH_3)(CH_2CH_3)$ | $N(CH_3)(CH_2CH_3)$ | $CH_3$ | Cl | $SCH_3$ |
| 5019 | $O—(CH_2CH_2)—O$ | | $CH_3$ | Cl | $SCH_3$ |
| 5020 | $O—(CH_2CH_2CH_2)—O$ | | $CH_3$ | Cl | $SCH_3$ |
| 5021 | $S—(CH_2CH_2)—S$ | | $CH_3$ | Cl | $SCH_3$ |
| 5022 | $S—(CH_2CH_2CH_2)—S$ | | $CH_3$ | Cl | $SCH_3$ |
| 5023 | $—(CH_2)_4—$ | | $CH_3$ | Cl | $SCH_3$ |
| 5024 | $—(CH_2)_5—$ | | $CH_3$ | Cl | $SCH_3$ |
| 5025 | H | H | $CH_2CH_3$ | Cl | $SCH_3$ |
| 5026 | $CH_3$ | $CH_3$ | $CH_2CH_3$ | Cl | $SCH_3$ |
| 5027 | $CH_2CH_3$ | $CH_2CH_3$ | $CH_2CH_3$ | Cl | $SCH_3$ |
| 5028 | $CH_2CH_2CH_3$ | $CH_2CH_2CH_3$ | $CH_2CH_3$ | Cl | $SCH_3$ |
| 5029 | $OCH_3$ | $OCH_3$ | $CH_2CH_3$ | Cl | $SCH_3$ |
| 5030 | $OCH_2CH_3$ | $OCH_2CH_3$ | $CH_2CH_3$ | Cl | $SCH_3$ |
| 5031 | $OCH_2CH_2CH_3$ | $OCH_2CH_2CH_3$ | $CH_2CH_3$ | Cl | $SCH_3$ |
| 5032 | $SCH_3$ | $SCH_3$ | $CH_2CH_3$ | Cl | $SCH_3$ |
| 5033 | $SCH_2CH_3$ | $SCH_2CH_3$ | $CH_2CH_3$ | Cl | $SCH_3$ |
| 5034 | $N(CH_3)_2$ | $N(CH_3)_2$ | $CH_2CH_3$ | Cl | $SCH_3$ |
| 5035 | $N(CH_2CH_3)_2$ | $N(CH_2CH_3)_2$ | $CH_2CH_3$ | Cl | $SCH_3$ |
| 5036 | $N(CH_3)(CH_2CH_3)$ | $N(CH_3)(CH_2CH_3)$ | $CH_2CH_3$ | Cl | $SCH_3$ |
| 5037 | $O—(CH_2CH_2)—O$ | | $CH_2CH_3$ | Cl | $SCH_3$ |
| 5038 | $O—(CH_2CH_2CH_2)—O$ | | $CH_2CH_3$ | Cl | $SCH_3$ |
| 5039 | $S—(CH_2CH_2)—S$ | | $CH_2CH_3$ | Cl | $SCH_3$ |
| 5040 | $S—(CH_2CH_2CH_2)—S$ | | $CH_2CH_3$ | Cl | $SCH_3$ |
| 5041 | $—(CH_2)_4—$ | | $CH_2CH_3$ | Cl | $SCH_3$ |
| 5042 | $—(CH_2)_5—$ | | $CH_2CH_3$ | Cl | $SCH_3$ |
| 5043 | H | H | $CF_3$ | Cl | $SCH_3$ |
| 5044 | $CH_3$ | $CH_3$ | $CF_3$ | Cl | $SCH_3$ |
| 5045 | $CH_2CH_3$ | $CH_2CH_3$ | $CF_3$ | Cl | $SCH_3$ |
| 5046 | $CH_2CH_2CH_3$ | $CH_2CH_2CH_3$ | $CF_3$ | Cl | $SCH_3$ |
| 5047 | $OCH_3$ | $OCH_3$ | $CF_3$ | Cl | $SCH_3$ |
| 5048 | $OCH_2CH_3$ | $OCH_2CH_3$ | $CF_3$ | Cl | $SCH_3$ |
| 5049 | $OCH_2CH_2CH_3$ | $OCH_2CH_2CH_3$ | $CF_3$ | Cl | $SCH_3$ |
| 5050 | $SCH_3$ | $SCH_3$ | $CF_3$ | Cl | $SCH_3$ |
| 5051 | $SCH_2CH_3$ | $SCH_2CH_3$ | $CF_3$ | Cl | $SCH_3$ |
| 5052 | $N(CH_3)_2$ | $N(CH_3)_2$ | $CF_3$ | Cl | $SCH_3$ |
| 5053 | $N(CH_2CH_3)_2$ | $N(CH_2CH_3)_2$ | $CF_3$ | Cl | $SCH_3$ |
| 5054 | $N(CH_3)(CH_2CH_3)$ | $N(CH_3)(CH_2CH_3)$ | $CF_3$ | Cl | $SCH_3$ |
| 5055 | $O—(CH_2CH_2)—O$ | | $CF_3$ | Cl | $SCH_3$ |
| 5056 | $O—(CH_2CH_2CH_2)—O$ | | $CF_3$ | Cl | $SCH_3$ |
| 5057 | $S—(CH_2CH_2)—S$ | | $CF_3$ | Cl | $SCH_3$ |
| 5058 | $S—(CH_2CH_2CH_2)—S$ | | $CF_3$ | Cl | $SCH_3$ |
| 5059 | $—(CH_2)_4—$ | | $CF_3$ | Cl | $SCH_3$ |
| 5060 | $—(CH_2)_5—$ | | $CF_3$ | Cl | $SCH_3$ |

TABLE 1-continued

I1a1

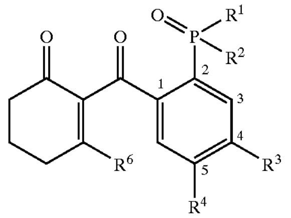

| n | $R^1$ | $R^2$ | $R^3$ | $R^4$ | $R^6$ |
|---|---|---|---|---|---|
| 5061 | H | H | $OCH_3$ | Cl | $SCH_3$ |
| 5062 | $CH_3$ | $CH_3$ | $OCH_3$ | Cl | $SCH_3$ |
| 5063 | $CH_2CH_3$ | $CH_2CH_3$ | $OCH_3$ | Cl | $SCH_3$ |
| 5064 | $CH_2CH_2CH_3$ | $CH_2CH_2CH_3$ | $OCH_3$ | Cl | $SCH_3$ |
| 5065 | $OCH_3$ | $OCH_3$ | $OCH_3$ | Cl | $SCH_3$ |
| 5066 | $OCH_2CH_3$ | $OCH_2CH_3$ | $OCH_3$ | Cl | $SCH_3$ |
| 5067 | $OCH_2CH_2CH_3$ | $OCH_2CH_2CH_3$ | $OCH_3$ | Cl | $SCH_3$ |
| 5068 | $SCH_3$ | $SCH_3$ | $OCH_3$ | Cl | $SCH_3$ |
| 5069 | $SCH_2CH_3$ | $SCH_2CH_3$ | $OCH_3$ | Cl | $SCH_3$ |
| 5070 | $N(CH_3)_2$ | $N(CH_3)_2$ | $OCH_3$ | Cl | $SCH_3$ |
| 5071 | $N(CH_2CH_3)_2$ | $N(CH_2CH_3)_2$ | $OCH_3$ | Cl | $SCH_3$ |
| 5072 | $N(CH_3)(CH_2CH_3)$ | $N(CH_3)(CH_2CH_3)$ | $OCH_3$ | Cl | $SCH_3$ |
| 5073 | $O-(CH_2CH_2)-O$ | | $OCH_3$ | Cl | $SCH_3$ |
| 5074 | $O-(CH_2CH_2CH_2)-O$ | | $OCH_3$ | Cl | $SCH_3$ |
| 5075 | $S-(CH_2CH_2)-S$ | | $OCH_3$ | Cl | $SCH_3$ |
| 5076 | $S-(CH_2CH_2CH_2)-S$ | | $OCH_3$ | Cl | $SCH_3$ |
| 5077 | $-(CH_2)_4-$ | | $OCH_3$ | Cl | $SCH_3$ |
| 5078 | $-(CH_2)_5-$ | | $OCH_3$ | Cl | $SCH_3$ |
| 5079 | H | H | $OCH_2CH_3$ | Cl | $SCH_3$ |
| 5080 | $CH_3$ | $CH_3$ | $OCH_2CH_3$ | Cl | $SCH_3$ |
| 5081 | $CH_2CH_3$ | $CH_2CH_3$ | $OCH_2CH_3$ | Cl | $SCH_3$ |
| 5082 | $CH_2CH_2CH_3$ | $CH_2CH_2CH_3$ | $OCH_2CH_3$ | Cl | $SCH_3$ |
| 5083 | $OCH_3$ | $OCH_3$ | $OCH_2CH_3$ | Cl | $SCH_3$ |
| 5084 | $OCH_2CH_3$ | $OCH_2CH_3$ | $OCH_2CH_3$ | Cl | $SCH_3$ |
| 5085 | $OCH_2CH_2CH_3$ | $OCH_2CH_2CH_3$ | $OCH_2CH_3$ | Cl | $SCH_3$ |
| 5086 | $SCH_3$ | $SCH_3$ | $OCH_2CH_3$ | Cl | $SCH_3$ |
| 5087 | $SCH_2CH_3$ | $SCH_2CH_3$ | $OCH_2CH_3$ | Cl | $SCH_3$ |
| 5088 | $N(CH_3)_2$ | $N(CH_3)_2$ | $OCH_2CH_3$ | Cl | $SCH_3$ |
| 5089 | $N(CH_2CH_3)_2$ | $N(CH_2CH_3)_2$ | $OCH_2CH_3$ | Cl | $SCH_3$ |
| 5090 | $N(CH_3)(CH_2CH_3)$ | $N(CH_3)(CH_2CH_3)$ | $OCH_2CH_3$ | Cl | $SCH_3$ |
| 5091 | $O-(CH_2CH_2)-O$ | | $OCH_2CH_3$ | Cl | $SCH_3$ |
| 5092 | $O-(CH_2CH_2CH_2)-O$ | | $OCH_2CH_3$ | Cl | $SCH_3$ |
| 5093 | $S-(CH_2CH_2)-S$ | | $OCH_2CH_3$ | Cl | $SCH_3$ |
| 5094 | $S-(CH_2CH_2CH_2)-S$ | | $OCH_2CH_3$ | Cl | $SCH_3$ |
| 5095 | $-(CH_2)_4-$ | | $OCH_2CH_3$ | Cl | $SCH_3$ |
| 5096 | $-(CH_2)_5-$ | | $OCH_2CH_3$ | Cl | $SCH_3$ |
| 5097 | H | H | $SCH_3$ | Cl | $SCH_3$ |
| 5098 | $CH_3$ | $CH_3$ | $SCH_3$ | Cl | $SCH_3$ |
| 5099 | $CH_2CH_3$ | $CH_2CH_3$ | $SCH_3$ | Cl | $SCH_3$ |
| 5100 | $CH_2CH_2CH_3$ | $CH_2CH_2CH_3$ | $SCH_3$ | Cl | $SCH_3$ |
| 5101 | $OCH_3$ | $OCH_3$ | $SCH_3$ | Cl | $SCH_3$ |
| 5102 | $OCH_2CH_3$ | $OCH_2CH_3$ | $SCH_3$ | Cl | $SCH_3$ |
| 5103 | $OCH_2CH_2CH_3$ | $OCH_2CH_2CH_3$ | $SCH_3$ | Cl | $SCH_3$ |
| 5104 | $SCH_3$ | $SCH_3$ | $SCH_3$ | Cl | $SCH_3$ |
| 5105 | $SCH_2CH_3$ | $SCH_2CH_3$ | $SCH_3$ | Cl | $SCH_3$ |
| 5106 | $N(CH_3)_2$ | $N(CH_3)_2$ | $SCH_3$ | Cl | $SCH_3$ |
| 5107 | $N(CH_2CH_3)_2$ | $N(CH_2CH_3)_2$ | $SCH_3$ | Cl | $SCH_3$ |
| 5108 | $N(CH_3)(CH_2CH_3)$ | $N(CH_3)(CH_2CH_3)$ | $SCH_3$ | Cl | $SCH_3$ |
| 5109 | $O-(CH_2CH_2)-O$ | | $SCH_3$ | Cl | $SCH_3$ |
| 5110 | $O-(CH_2CH_2CH_2)-O$ | | $SCH_3$ | Cl | $SCH_3$ |
| 5111 | $S-(CH_2CH_2)-S$ | | $SCH_3$ | Cl | $SCH_3$ |
| 5112 | $S-(CH_2CH_2CH_2)-S$ | | $SCH_3$ | Cl | $SCH_3$ |
| 5113 | $-(CH_2)_4-$ | | $SCH_3$ | Cl | $SCH_3$ |
| 5114 | $-(CH_2)_5-$ | | $SCH_3$ | Cl | $SCH_3$ |
| 5115 | H | H | $SO_2CH_3$ | Cl | $SCH_3$ |
| 5116 | $CH_3$ | $CH_3$ | $SO_2CH_3$ | Cl | $SCH_3$ |
| 5117 | $CH_2CH_3$ | $CH_2CH_3$ | $SO_2CH_3$ | Cl | $SCH_3$ |
| 5118 | $CH_2CH_2CH_3$ | $CH_2CH_2CH_3$ | $SO_2CH_3$ | Cl | $SCH_3$ |
| 5119 | $OCH_3$ | $OCH_3$ | $SO_2CH_3$ | Cl | $SCH_3$ |
| 5120 | $OCH_2CH_3$ | $OCH_2CH_3$ | $SO_2CH_3$ | Cl | $SCH_3$ |
| 5121 | $OCH_2CH_2CH_3$ | $OCH_2CH_2CH_3$ | $SO_2CH_3$ | Cl | $SCH_3$ |
| 5122 | $SCH_3$ | $SCH_3$ | $SO_2CH_3$ | Cl | $SCH_3$ |
| 5123 | $SCH_2CH_3$ | $SCH_2CH_3$ | $SO_2CH_3$ | Cl | $SCH_3$ |
| 5124 | $N(CH_3)_2$ | $N(CH_3)_2$ | $SO_2CH_3$ | Cl | $SCH_3$ |

TABLE 1-continued

I1a1

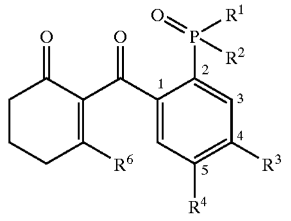

| n | $R^1$ | $R^2$ | $R^3$ | $R^4$ | $R^6$ |
|---|---|---|---|---|---|
| 5125 | $N(CH_2CH_3)_2$ | $N(CH_2CH_3)_2$ | $SO_2CH_3$ | Cl | $SCH_3$ |
| 5126 | $N(CH_3)(CH_2CH_3)$ | $N(CH_3)(CH_2CH_3)$ | $SO_2CH_3$ | Cl | $SCH_3$ |
| 5127 | $O—(CH_2CH_2)—O$ | | $SO_2CH_3$ | Cl | $SCH_3$ |
| 5128 | $O—(CH_2CH_2CH_2)—O$ | | $SO_2CH_3$ | Cl | $SCH_3$ |
| 5129 | $S—(CH_2CH_2)—S$ | | $SO_2CH_3$ | Cl | $SCH_3$ |
| 5130 | $S—(CH_2CH_2CH_2)—S$ | | $SO_2CH_3$ | Cl | $SCH_3$ |
| 5131 | $—(CH_2)_4—$ | | $SO_2CH_3$ | Cl | $SCH_3$ |
| 5132 | $—(CH_2)_5—$ | | $SO_2CH_3$ | Cl | $SCH_3$ |
| 5133 | H | H | $PO(OCH_3)_2$ | Cl | $SCH_3$ |
| 5134 | $CH_3$ | $CH_3$ | $PO(OCH_3)_2$ | Cl | $SCH_3$ |
| 5135 | $CH_2CH_3$ | $CH_2CH_3$ | $PO(OCH_3)_2$ | Cl | $SCH_3$ |
| 5136 | $CH_2CH_2CH_3$ | $CH_2CH_2CH_3$ | $PO(OCH_3)_2$ | Cl | $SCH_3$ |
| 5137 | $OCH_3$ | $OCH_3$ | $PO(OCH_3)_2$ | Cl | $SCH_3$ |
| 5138 | $OCH_2CH_3$ | $OCH_2CH_3$ | $PO(OCH_3)_2$ | Cl | $SCH_3$ |
| 5139 | $OCH_2CH_2CH_3$ | $OCH_2CH_2CH_3$ | $PO(OCH_3)_2$ | Cl | $SCH_3$ |
| 5140 | $SCH_3$ | $SCH_3$ | $PO(OCH_3)_2$ | Cl | $SCH_3$ |
| 5141 | $SCH_2CH_3$ | $SCH_2CH_3$ | $PO(OCH_3)_2$ | Cl | $SCH_3$ |
| 5142 | $N(CH_3)_2$ | $N(CH_3)_2$ | $PO(OCH_3)_2$ | Cl | $SCH_3$ |
| 5143 | $N(CH_2CH_3)_2$ | $N(CH_2CH_3)_2$ | $PO(OCH_3)_2$ | Cl | $SCH_3$ |
| 5144 | $N(CH_3)(CH_2CH_3)$ | $N(CH_3)(CH_2CH_3)$ | $PO(OCH_3)_2$ | Cl | $SCH_3$ |
| 5145 | $O—(CH_2CH_2)—O$ | | $PO(OCH_3)_2$ | Cl | $SCH_3$ |
| 5146 | $O—(CH_2CH_2CH_2)—O$ | | $PO(OCH_3)_2$ | Cl | $SCH_3$ |
| 5147 | $S—(CH_2CH_2)—S$ | | $PO(OCH_3)_2$ | Cl | $SCH_3$ |
| 5148 | $S—(CH_2CH_2CH_2)—S$ | | $PO(OCH_3)_2$ | Cl | $SCH_3$ |
| 5149 | $—(CH_2)_4—$ | | $PO(OCH_3)_2$ | Cl | $SCH_3$ |
| 5150 | $—(CH_2)_5—$ | | $PO(OCH_3)_2$ | Cl | $SCH_3$ |
| 5151 | H | H | $PO(OCH_2CH_3)_2$ | Cl | $SCH_3$ |
| 5152 | $CH_3$ | $CH_3$ | $PO(OCH_2CH_3)_2$ | Cl | $SCH_3$ |
| 5153 | $CH_2CH_3$ | $CH_2CH_3$ | $PO(OCH_2CH_3)_2$ | Cl | $SCH_3$ |
| 5154 | $CH_2CH_2CH_3$ | $CH_2CH_2CH_3$ | $PO(OCH_2CH_3)_2$ | Cl | $SCH_3$ |
| 5155 | $OCH_3$ | $OCH_3$ | $PO(OCH_2CH_3)_2$ | Cl | $SCH_3$ |
| 5156 | $OCH_2CH_3$ | $OCH_2CH_3$ | $PO(OCH_2CH_3)_2$ | Cl | $SCH_3$ |
| 5157 | $OCH_2CH_2CH_3$ | $OCH_2CH_2CH_3$ | $PO(OCH_2CH_3)_2$ | Cl | $SCH_3$ |
| 5158 | $SCH_3$ | $SCH_3$ | $PO(OCH_2CH_3)_2$ | Cl | $SCH_3$ |
| 5159 | $SCH_2CH_3$ | $SCH_2CH_3$ | $PO(OCH_2CH_3)_2$ | Cl | $SCH_3$ |
| 5160 | $N(CH_3)_2$ | $N(CH_3)_2$ | $PO(OCH_2CH_3)_2$ | Cl | $SCH_3$ |
| 5161 | $N(CH_2CH_3)_2$ | $N(CH_2CH_3)_2$ | $PO(OCH_2CH_3)_2$ | Cl | $SCH_3$ |
| 5162 | $N(CH_3)(CH_2CH_3)$ | $N(CH_3)(CH_2CH_3)$ | $PO(OCH_2CH_3)_2$ | Cl | $SCH_3$ |
| 5163 | $O—(CH_2CH_2)—O$ | | $PO(OCH_2CH_3)_2$ | Cl | $SCH_3$ |
| 5164 | $O—(CH_2CH_2CH_2)—O$ | | $PO(OCH_2CH_3)_2$ | Cl | $SCH_3$ |
| 5165 | $S—(CH_2CH_2)—S$ | | $PO(OCH_2CH_3)_2$ | Cl | $SCH_3$ |
| 5166 | $S—(CH_2CH_2CH_2)—S$ | | $PO(OCH_2CH_3)_2$ | Cl | $SCH_3$ |
| 5167 | $—(CH_2)_4—$ | | $PO(OCH_2CH_3)_2$ | Cl | $SCH_3$ |
| 5168 | $—(CH_2)_5—$ | | $PO(OCH_2CH_3)_2$ | Cl | $SCH_3$ |
| 5169 | H | H | $PO(CH_3)_2$ | Cl | $SCH_3$ |
| 5170 | $CH_3$ | $CH_3$ | $PO(CH_3)_2$ | Cl | $SCH_3$ |
| 5171 | $CH_2CH_3$ | $CH_2CH_3$ | $PO(CH_3)_2$ | Cl | $SCH_3$ |
| 5172 | $CH_2CH_2CH_3$ | $CH_2CH_2CH_3$ | $PO(CH_3)_2$ | Cl | $SCH_3$ |
| 5173 | $OCH_3$ | $OCH_3$ | $PO(CH_3)_2$ | Cl | $SCH_3$ |
| 5174 | $OCH_2CH_3$ | $OCH_2CH_3$ | $PO(CH_3)_2$ | Cl | $SCH_3$ |
| 5175 | $OCH_2CH_2CH_3$ | $OCH_2CH_2CH_3$ | $PO(CH_3)_2$ | Cl | $SCH_3$ |
| 5176 | $SCH_3$ | $SCH_3$ | $PO(CH_3)_2$ | Cl | $SCH_3$ |
| 5177 | $SCH_2CH_3$ | $SCH_2CH_3$ | $PO(CH_3)_2$ | Cl | $SCH_3$ |
| 5178 | $N(CH_3)_2$ | $N(CH_3)_2$ | $PO(CH_3)_2$ | Cl | $SCH_3$ |
| 5179 | $N(CH_2CH_3)_2$ | $N(CH_2CH_3)_2$ | $PO(CH_3)_2$ | Cl | $SCH_3$ |
| 5180 | $N(CH_3)(CH_2CH_3)$ | $N(CH_3)(CH_2CH_3)$ | $PO(CH_3)_2$ | Cl | $SCH_3$ |
| 5181 | $O—(CH_2CH_2)—O$ | | $PO(CH_3)_2$ | Cl | $SCH_3$ |
| 5182 | $O—(CH_2CH_2CH_2)—O$ | | $PO(CH_3)_2$ | Cl | $SCH_3$ |
| 5183 | $S—(CH_2CH_2)—S$ | | $PO(CH_3)_2$ | Cl | $SCH_3$ |
| 5184 | $S—(CH_2CH_2CH_2)—S$ | | $PO(CH_3)_2$ | Cl | $SCH_3$ |
| 5185 | $—(CH_2)_4—$ | | $PO(CH_3)_2$ | Cl | $SCH_3$ |
| 5186 | $—(CH_2)_5—$ | | $PO(CH_3)_2$ | Cl | $SCH_3$ |
| 5187 | H | H | $PO(CH_2CH_3)_2$ | Cl | $SCH_3$ |
| 5188 | $CH_3$ | $CH_3$ | $PO(CH_2CH_3)_2$ | Cl | $SCH_3$ |

TABLE 1-continued

I1a1

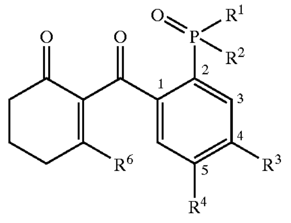

| n | $R^1$ | $R^2$ | $R^3$ | $R^4$ | $R^6$ |
|---|---|---|---|---|---|
| 5189 | $CH_2CH_3$ | $CH_2CH_3$ | $PO(CH_2CH_3)_2$ | Cl | $SCH_3$ |
| 5190 | $CH_2CH_2CH_3$ | $CH_2CH_2CH_3$ | $PO(CH_2CH_3)_2$ | Cl | $SCH_3$ |
| 5191 | $OCH_3$ | $OCH_3$ | $PO(CH_2CH_3)_2$ | Cl | $SCH_3$ |
| 5192 | $OCH_2CH_3$ | $OCH_2CH_3$ | $PO(CH_2CH_3)_2$ | Cl | $SCH_3$ |
| 5193 | $OCH_2CH_2CH_3$ | $OCH_2CH_2CH_3$ | $PO(CH_2CH_3)_2$ | Cl | $SCH_3$ |
| 5194 | $SCH_3$ | $SCH_3$ | $PO(CH_2CH_3)_2$ | Cl | $SCH_3$ |
| 5195 | $SCH_2CH_3$ | $SCH_2CH_3$ | $PO(CH_2CH_3)_2$ | Cl | $SCH_3$ |
| 5196 | $N(CH_3)_2$ | $N(CH_3)_2$ | $PO(CH_2CH_3)_2$ | Cl | $SCH_3$ |
| 5197 | $N(CH_2CH_3)_2$ | $N(CH_2CH_3)_2$ | $PO(CH_2CH_3)_2$ | Cl | $SCH_3$ |
| 5198 | $N(CH_3)(CH_2CH_3)$ | $N(CH_3)(CH_2CH_3)$ | $PO(CH_2CH_3)_2$ | Cl | $SCH_3$ |
| 5199 | $O-(CH_2CH_2)-O$ | | $PO(CH_2CH_3)_2$ | Cl | $SCH_3$ |
| 5200 | $O-(CH_2CH_2CH_2)-O$ | | $PO(CH_2CH_3)_2$ | Cl | $SCH_3$ |
| 5201 | $S-(CH_2CH_2)-S$ | | $PO(CH_2CH_3)_2$ | Cl | $SCH_3$ |
| 5202 | $S-(CH_2CH_2CH_2)-S$ | | $PO(CH_2CH_3)_2$ | Cl | $SCH_3$ |
| 5203 | $-(CH_2)_4-$ | | $PO(CH_2CH_3)_2$ | Cl | $SCH_3$ |
| 5204 | $-(CH_2)_5-$ | | $PO(CH_2CH_3)_2$ | Cl | $SCH_3$ |
| 5205 | H | H | H | Cl | $SC_6H_5$ |
| 5206 | $CH_3$ | $CH_3$ | H | Cl | $SC_6H_5$ |
| 5207 | $CH_2CH_3$ | $CH_2CH_3$ | H | Cl | $SC_6H_5$ |
| 5208 | $CH_2CH_2CH_3$ | $CH_2CH_2CH_3$ | H | Cl | $SC_6H_5$ |
| 5209 | $OCH_3$ | $OCH_3$ | H | Cl | $SC_6H_5$ |
| 5210 | $OCH_2CH_3$ | $OCH_2CH_3$ | H | Cl | $SC_6H_5$ |
| 5211 | $OCH_2CH_2CH_3$ | $OCH_2CH_2CH_3$ | H | Cl | $SC_6H_5$ |
| 5212 | $SCH_3$ | $SCH_3$ | H | Cl | $SC_6H_5$ |
| 5213 | $SCH_2CH_3$ | $SCH_2CH_3$ | H | Cl | $SC_6H_5$ |
| 5214 | $N(CH_3)_2$ | $N(CH_3)_2$ | H | Cl | $SC_6H_5$ |
| 5215 | $N(CH_2CH_3)_2$ | $N(CH_2CH_3)_2$ | H | Cl | $SC_6H_5$ |
| 5216 | $N(CH_3)(CH_2CH_3)$ | $N(CH_3)(CH_2CH_3)$ | H | Cl | $SC_6H_5$ |
| 5217 | $O-(CH_2CH_2)-O$ | | H | Cl | $SC_6H_5$ |
| 5218 | $O-(CH_2CH_2CH_2)-O$ | | H | Cl | $SC_6H_5$ |
| 5219 | $S-(CH_2CH_2)-S$ | | H | Cl | $SC_6H_5$ |
| 5220 | $S-(CH_2CH_2CH_2)-S$ | | H | Cl | $SC_6H_5$ |
| 5221 | $-(CH_2)_4-$ | | H | Cl | $SC_6H_5$ |
| 5222 | $-(CH_2)_5-$ | | H | Cl | $SC_6H_5$ |
| 5223 | H | H | $NO_2$ | Cl | $SC_6H_5$ |
| 5224 | $CH_3$ | $CH_3$ | $NO_2$ | Cl | $SC_6H_5$ |
| 5225 | $CH_2CH_3$ | $CH_2CH_3$ | $NO_2$ | Cl | $SC_6H_5$ |
| 5226 | $CH_2CH_2CH_3$ | $CH_2CH_2CH_3$ | $NO_2$ | Cl | $SC_6H_5$ |
| 5227 | $OCH_3$ | $OCH_3$ | $NO_2$ | Cl | $SC_6H_5$ |
| 5228 | $OCH_2CH_3$ | $OCH_2CH_3$ | $NO_2$ | Cl | $SC_6H_5$ |
| 5229 | $OCH_2CH_2CH_3$ | $OCH_2CH_2CH_3$ | $NO_2$ | Cl | $SC_6H_5$ |
| 5230 | $SCH_3$ | $SCH_3$ | $NO_2$ | Cl | $SC_6H_5$ |
| 5231 | $SCH_2CH_3$ | $SCH_2CH_3$ | $NO_2$ | Cl | $SC_6H_5$ |
| 5232 | $N(CH_3)_2$ | $N(CH_3)_2$ | $NO_2$ | Cl | $SC_6H_5$ |
| 5233 | $N(CH_2CH_3)_2$ | $N(CH_2CH_3)_2$ | $NO_2$ | Cl | $SC_6H_5$ |
| 5234 | $N(CH_3)(CH_2CH_3)$ | $N(CH_3)(CH_2CH_3)$ | $NO_2$ | Cl | $SC_6H_5$ |
| 5235 | $O-(CH_2CH_2)-O$ | | $NO_2$ | Cl | $SC_6H_5$ |
| 5236 | $O-(CH_2CH_2CH_2)-O$ | | $NO_2$ | Cl | $SC_6H_5$ |
| 5237 | $S-(CH_2CH_2)-S$ | | $NO_2$ | Cl | $SC_6H_5$ |
| 5238 | $S-(CH_2CH_2CH_2)-S$ | | $NO_2$ | Cl | $SC_6H_5$ |
| 5239 | $-(CH_2)_4-$ | | $NO_2$ | Cl | $SC_6H_5$ |
| 5240 | $-(CH_2)_5-$ | | $NO_2$ | Cl | $SC_6H_5$ |
| 5241 | H | H | CN | Cl | $SC_6H_5$ |
| 5242 | $CH_3$ | $CH_3$ | CN | Cl | $SC_6H_5$ |
| 5243 | $CH_2CH_3$ | $CH_2CH_3$ | CN | Cl | $SC_6H_5$ |
| 5244 | $CH_2CH_2CH_3$ | $CH_2CH_2CH_3$ | CN | Cl | $SC_6H_5$ |
| 5245 | $OCH_3$ | $OCH_3$ | CN | Cl | $SC_6H_5$ |
| 5246 | $OCH_2CH_3$ | $OCH_2CH_3$ | CN | Cl | $SC_6H_5$ |
| 5247 | $OCH_2CH_2CH_3$ | $OCH_2CH_2CH_3$ | CN | Cl | $SC_6H_5$ |
| 5248 | $SCH_3$ | $SCH_3$ | CN | Cl | $SC_6H_5$ |
| 5249 | $SCH_2CH_3$ | $SCH_2CH_3$ | CN | Cl | $SC_6H_5$ |
| 5250 | $N(CH_3)_2$ | $N(CH_3)_2$ | CN | Cl | $SC_6H_5$ |
| 5251 | $N(CH_2CH_3)_2$ | $N(CH_2CH_3)_2$ | CN | Cl | $SC_6H_5$ |
| 5252 | $N(CH_3)(CH_2CH_3)$ | $N(CH_3)(CH_2CH_3)$ | CN | Cl | $SC_6H_5$ |

TABLE 1-continued

I1a1

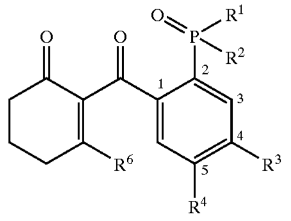

| n | R¹ | R² | R³ | R⁴ | R⁶ |
|---|---|---|---|---|---|
| 5253 | O—(CH$_2$CH$_2$)—O | | CN | Cl | SC$_6$H$_5$ |
| 5254 | O—(CH$_2$CH$_2$CH$_2$)—O | | CN | Cl | SC$_6$H$_5$ |
| 5255 | S—(CH$_2$CH$_2$)—S | | CN | Cl | SC$_6$H$_5$ |
| 5256 | S—(CH$_2$CH$_2$CH$_2$)—S | | CN | Cl | SC$_6$H$_5$ |
| 5257 | —(CH$_2$)$_4$— | | CN | Cl | SC$_6$H$_5$ |
| 5258 | —(CH$_2$)$_5$— | | CN | Cl | SC$_6$H$_5$ |
| 5259 | H | H | F | Cl | SC$_6$H$_5$ |
| 5260 | CH$_3$ | CH$_3$ | F | Cl | SC$_6$H$_5$ |
| 5261 | CH$_2$CH$_3$ | CH$_2$CH$_3$ | F | Cl | SC$_6$H$_5$ |
| 5262 | CH$_2$CH$_2$CH$_3$ | CH$_2$CH$_2$CH$_3$ | F | Cl | SC$_6$H$_5$ |
| 5263 | OCH$_3$ | OCH$_3$ | F | Cl | SC$_6$H$_5$ |
| 5264 | OCH$_2$CH$_3$ | OCH$_2$CH$_3$ | F | Cl | SC$_6$H$_5$ |
| 5265 | OCH$_2$CH$_2$CH$_3$ | OCH$_2$CH$_2$CH$_3$ | F | Cl | SC$_6$H$_5$ |
| 5266 | SCH$_3$ | SCH$_3$ | F | Cl | SC$_6$H$_5$ |
| 5267 | SCH$_2$CH$_3$ | SCH$_2$CH$_3$ | F | Cl | SC$_6$H$_5$ |
| 5268 | N(CH$_3$)$_2$ | N(CH$_3$)$_2$ | F | Cl | SC$_6$H$_5$ |
| 5269 | N(CH$_2$CH$_3$)$_2$ | N(CH$_2$CH$_3$)$_2$ | F | Cl | SC$_6$H$_5$ |
| 5270 | N(CH$_3$)(CH$_2$CH$_3$) | N(CH$_3$)(CH$_2$CH$_3$) | F | Cl | SC$_6$H$_5$ |
| 5271 | O—(CH$_2$CH$_2$)—O | | F | Cl | SC$_6$H$_5$ |
| 5272 | O—(CH$_2$CH$_2$CH$_2$)—O | | F | Cl | SC$_6$H$_5$ |
| 5273 | S—(CH$_2$CH$_2$)—S | | F | Cl | SC$_6$H$_5$ |
| 5274 | S—(CH$_2$CH$_2$CH$_2$)—S | | F | Cl | SC$_6$H$_5$ |
| 5275 | —(CH$_2$)$_4$— | | F | Cl | SC$_6$H$_5$ |
| 5276 | —(CH$_2$)$_5$— | | F | Cl | SC$_6$H$_5$ |
| 5277 | H | H | Cl | Cl | SC$_6$H$_5$ |
| 5278 | CH$_3$ | CH$_3$ | Cl | Cl | SC$_6$H$_5$ |
| 5279 | CH$_2$CH$_3$ | CH$_2$CH$_3$ | Cl | Cl | SC$_6$H$_5$ |
| 5280 | CH$_2$CH$_2$CH$_3$ | CH$_2$CH$_2$CH$_3$ | Cl | Cl | SC$_6$H$_5$ |
| 5281 | OCH$_3$ | OCH$_3$ | Cl | Cl | SC$_6$H$_5$ |
| 5282 | OCH$_2$CH$_3$ | OCH$_2$CH$_3$ | Cl | Cl | SC$_6$H$_5$ |
| 5283 | OCH$_2$CH$_2$CH$_3$ | OCH$_2$CH$_2$CH$_3$ | Cl | Cl | SC$_6$H$_5$ |
| 5284 | SCH$_3$ | SCH$_3$ | Cl | Cl | SC$_6$H$_5$ |
| 5285 | SCH$_2$CH$_3$ | SCH$_2$CH$_3$ | Cl | Cl | SC$_6$H$_5$ |
| 5286 | N(CH$_3$)$_2$ | N(CH$_3$)$_2$ | Cl | Cl | SC$_6$H$_5$ |
| 5287 | N(CH$_2$CH$_3$)$_2$ | N(CH$_2$CH$_3$)$_2$ | Cl | Cl | SC$_6$H$_5$ |
| 5288 | N(CH$_3$)(CH$_2$CH$_3$) | N(CH$_3$)(CH$_2$CH$_3$) | Cl | Cl | SC$_6$H$_5$ |
| 5289 | O—(CH$_2$CH$_2$)—O | | Cl | Cl | SC$_6$H$_5$ |
| 5290 | O—(CH$_2$CH$_2$CH$_2$)—O | | Cl | Cl | SC$_6$H$_5$ |
| 5291 | S—(CH$_2$CH$_2$)—S | | Cl | Cl | SC$_6$H$_5$ |
| 5292 | S—(CH$_2$CH$_2$CH$_2$)—S | | Cl | Cl | SC$_6$H$_5$ |
| 5293 | —(CH$_2$)$_4$— | | Cl | Cl | SC$_6$H$_5$ |
| 5294 | —(CH$_2$)$_5$— | | Cl | Cl | SC$_6$H$_5$ |
| 5295 | H | H | Br | Cl | SC$_6$H$_5$ |
| 5296 | CH$_3$ | CH$_3$ | Br | Cl | SC$_6$H$_5$ |
| 5297 | CH$_2$CH$_3$ | CH$_2$CH$_3$ | Br | Cl | SC$_6$H$_5$ |
| 5298 | CH$_2$CH$_2$CH$_3$ | CH$_2$CH$_2$CH$_3$ | Br | Cl | SC$_6$H$_5$ |
| 5299 | OCH$_3$ | OCH$_3$ | Br | Cl | SC$_6$H$_5$ |
| 5300 | OCH$_2$CH$_3$ | OCH$_2$CH$_3$ | Br | Cl | SC$_6$H$_5$ |
| 5301 | OCH$_2$CH$_2$CH$_3$ | OCH$_2$CH$_2$CH$_3$ | Br | Cl | SC$_6$H$_5$ |
| 5302 | SCH$_3$ | SCH$_3$ | Br | Cl | SC$_6$H$_5$ |
| 5303 | SCH$_2$CH$_3$ | SCH$_2$CH$_3$ | Br | Cl | SC$_6$H$_5$ |
| 5304 | N(CH$_3$)$_2$ | N(CH$_3$)$_2$ | Br | Cl | SC$_6$H$_5$ |
| 5305 | N(CH$_2$CH$_3$)$_2$ | N(CH$_2$CH$_3$)$_2$ | Br | Cl | SC$_6$H$_5$ |
| 5306 | N(CH$_3$)(CH$_2$CH$_3$) | N(CH$_3$)(CH$_2$CH$_3$) | Br | Cl | SC$_6$H$_5$ |
| 5307 | O—(CH$_2$CH$_2$)—O | | Br | Cl | SC$_6$H$_5$ |
| 5308 | O—(CH$_2$CH$_2$CH$_2$)—O | | Br | Cl | SC$_6$H$_5$ |
| 5309 | S—(CH$_2$CH$_2$)—S | | Br | Cl | SC$_6$H$_5$ |
| 5310 | S—(CH$_2$CH$_2$CH$_2$)—S | | Br | Cl | SC$_6$H$_5$ |
| 5311 | —(CH$_2$)$_4$— | | Br | Cl | SC$_6$H$_5$ |
| 5312 | —(CH$_2$)$_5$— | | Br | Cl | SC$_6$H$_5$ |
| 5313 | H | H | CH$_3$ | Cl | SC$_6$H$_5$ |
| 5314 | CH$_3$ | CH$_3$ | CH$_3$ | Cl | SC$_6$H$_5$ |
| 5315 | CH$_2$CH$_3$ | CH$_2$CH$_3$ | CH$_3$ | Cl | SC$_6$H$_5$ |
| 5316 | CH$_2$CH$_2$CH$_3$ | CH$_2$CH$_2$CH$_3$ | CH$_3$ | Cl | SC$_6$H$_5$ |

TABLE 1-continued

I1a1

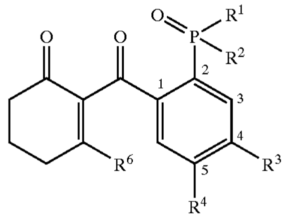

| n | $R^1$ | $R^2$ | $R^3$ | $R^4$ | $R^6$ |
|---|---|---|---|---|---|
| 5317 | $OCH_3$ | $OCH_3$ | $CH_3$ | Cl | $SC_6H_5$ |
| 5318 | $OCH_2CH_3$ | $OCH_2CH_3$ | $CH_3$ | Cl | $SC_6H_5$ |
| 5319 | $OCH_2CH_2CH_3$ | $OCH_2CH_2CH_3$ | $CH_3$ | Cl | $SC_6H_5$ |
| 5320 | $SCH_3$ | $SCH_3$ | $CH_3$ | Cl | $SC_6H_5$ |
| 5321 | $SCH_2CH_3$ | $SCH_2CH_3$ | $CH_3$ | Cl | $SC_6H_5$ |
| 5322 | $N(CH_3)_2$ | $N(CH_3)_2$ | $CH_3$ | Cl | $SC_6H_5$ |
| 5323 | $N(CH_2CH_3)_2$ | $N(CH_2CH_3)_2$ | $CH_3$ | Cl | $SC_6H_5$ |
| 5324 | $N(CH_3)(CH_2CH_3)$ | $N(CH_3)(CH_2CH_3)$ | $CH_3$ | Cl | $SC_6H_5$ |
| 5325 | $O—(CH_2CH_2)—O$ | | $CH_3$ | Cl | $SC_6H_5$ |
| 5326 | $O—(CH_2CH_2CH_2)—O$ | | $CH_3$ | Cl | $SC_6H_5$ |
| 5327 | $S—(CH_2CH_2)—S$ | | $CH_3$ | Cl | $SC_6H_5$ |
| 5328 | $S—(CH_2CH_2CH_2)—S$ | | $CH_3$ | Cl | $SC_6H_5$ |
| 5329 | $—(CH_2)_4—$ | | $CH_3$ | Cl | $SC_6H_5$ |
| 5330 | $—(CH_2)_5—$ | | $CH_3$ | Cl | $SC_6H_5$ |
| 5331 | H | H | $CH_2CH_3$ | Cl | $SC_6H_5$ |
| 5332 | $CH_3$ | $CH_3$ | $CH_2CH_3$ | Cl | $SC_6H_5$ |
| 5333 | $CH_2CH_3$ | $CH_2CH_3$ | $CH_2CH_3$ | Cl | $SC_6H_5$ |
| 5334 | $CH_2CH_2CH_3$ | $CH_2CH_2CH_3$ | $CH_2CH_3$ | Cl | $SC_6H_5$ |
| 5335 | $OCH_3$ | $OCH_3$ | $CH_2CH_3$ | Cl | $SC_6H_5$ |
| 5336 | $OCH_2CH_3$ | $OCH_2CH_3$ | $CH_2CH_3$ | Cl | $SC_6H_5$ |
| 5337 | $OCH_2CH_2CH_3$ | $OCH_2CH_2CH_3$ | $CH_2CH_3$ | Cl | $SC_6H_5$ |
| 5338 | $SCH_3$ | $SCH_3$ | $CH_2CH_3$ | Cl | $SC_6H_5$ |
| 5339 | $SCH_2CH_3$ | $SCH_2CH_3$ | $CH_2CH_3$ | Cl | $SC_6H_5$ |
| 5340 | $N(CH_3)_2$ | $N(CH_3)_2$ | $CH_2CH_3$ | Cl | $SC_6H_5$ |
| 5341 | $N(CH_2CH_3)_2$ | $N(CH_2CH_3)_2$ | $CH_2CH_3$ | Cl | $SC_6H_5$ |
| 5342 | $N(CH_3)(CH_2CH_3)$ | $N(CH_3)(CH_2CH_3)$ | $CH_2CH_3$ | Cl | $SC_6H_5$ |
| 5343 | $O—(CH_2CH_2)—O$ | | $CH_2CH_3$ | Cl | $SC_6H_5$ |
| 5344 | $O—(CH_2CH_2CH_2)—O$ | | $CH_2CH_3$ | Cl | $SC_6H_5$ |
| 5345 | $S—(CH_2CH_2)—S$ | | $CH_2CH_3$ | Cl | $SC_6H_5$ |
| 5346 | $S—(CH_2CH_2CH_2)—S$ | | $CH_2CH_3$ | Cl | $SC_6H_5$ |
| 5347 | $—(CH_2)_4—$ | | $CH_2CH_3$ | Cl | $SC_6H_5$ |
| 5348 | $—(CH_2)_5—$ | | $CH_2CH_3$ | Cl | $SC_6H_5$ |
| 5349 | H | H | $CF_3$ | Cl | $SC_6H_5$ |
| 5350 | $CH_3$ | $CH_3$ | $CF_3$ | Cl | $SC_6H_5$ |
| 5351 | $CH_2CH_3$ | $CH_2CH_3$ | $CF_3$ | Cl | $SC_6H_5$ |
| 5352 | $CH_2CH_2CH_3$ | $CH_2CH_2CH_3$ | $CF_3$ | Cl | $SC_6H_5$ |
| 5353 | $OCH_3$ | $OCH_3$ | $CF_3$ | Cl | $SC_6H_5$ |
| 5354 | $OCH_2CH_3$ | $OCH_2CH_3$ | $CF_3$ | Cl | $SC_6H_5$ |
| 5355 | $OCH_2CH_2CH_3$ | $OCH_2CH_2CH_3$ | $CF_3$ | Cl | $SC_6H_5$ |
| 5356 | $SCH_3$ | $SCH_3$ | $CF_3$ | Cl | $SC_6H_5$ |
| 5357 | $SCH_2CH_3$ | $SCH_2CH_3$ | $CF_3$ | Cl | $SC_6H_5$ |
| 5358 | $N(CH_3)_2$ | $N(CH_3)_2$ | $CF_3$ | Cl | $SC_6H_5$ |
| 5359 | $N(CH_2CH_3)_2$ | $N(CH_2CH_3)_2$ | $CF_3$ | Cl | $SC_6H_5$ |
| 5360 | $N(CH_3)(CH_2CH_3)$ | $N(CH_3)(CH_2CH_3)$ | $CF_3$ | Cl | $SC_6H_5$ |
| 5361 | $O—(CH_2CH_2)—O$ | | $CF_3$ | Cl | $SC_6H_5$ |
| 5362 | $O—(CH_2CH_2CH_2)—O$ | | $CF_3$ | Cl | $SC_6H_5$ |
| 5363 | $S—(CH_2CH_2)—S$ | | $CF_3$ | Cl | $SC_6H_5$ |
| 5364 | $S—(CH_2CH_2CH_2)—S$ | | $CF_3$ | Cl | $SC_6H_5$ |
| 5365 | $—(CH_2)_4—$ | | $CF_3$ | Cl | $SC_6H_5$ |
| 5366 | $—(CH_2)_5—$ | | $CF_3$ | Cl | $SC_6H_5$ |
| 5367 | H | H | $OCH_3$ | Cl | $SC_6H_5$ |
| 5368 | $CH_3$ | $CH_3$ | $OCH_3$ | Cl | $SC_6H_5$ |
| 5369 | $CH_2CH_3$ | $CH_2CH_3$ | $OCH_3$ | Cl | $SC_6H_5$ |
| 5370 | $CH_2CH_2CH_3$ | $CH_2CH_2CH_3$ | $OCH_3$ | Cl | $SC_6H_5$ |
| 5371 | $OCH_3$ | $OCH_3$ | $OCH_3$ | Cl | $SC_6H_5$ |
| 5372 | $OCH_2CH_3$ | $OCH_2CH_3$ | $OCH_3$ | Cl | $SC_6H_5$ |
| 5373 | $OCH_2CH_2CH_3$ | $OCH_2CH_2CH_3$ | $OCH_3$ | Cl | $SC_6H_5$ |
| 5374 | $SCH_3$ | $SCH_3$ | $OCH_3$ | Cl | $SC_6H_5$ |
| 5375 | $SCH_2CH_3$ | $SCH_2CH_3$ | $OCH_3$ | Cl | $SC_6H_5$ |
| 5376 | $N(CH_3)_2$ | $N(CH_3)_2$ | $OCH_3$ | Cl | $SC_6H_5$ |
| 5377 | $N(CH_2CH_3)_2$ | $N(CH_2CH_3)_2$ | $OCH_3$ | Cl | $SC_6H_5$ |
| 5378 | $N(CH_3)(CH_2CH_3)$ | $N(CH_3)(CH_2CH_3)$ | $OCH_3$ | Cl | $SC_6H_5$ |
| 5379 | $O—(CH_2CH_2)—O$ | | $OCH_3$ | Cl | $SC_6H_5$ |
| 5380 | $O—(CH_2CH_2CH_2)—O$ | | $OCH_3$ | Cl | $SC_6H_5$ |

TABLE 1-continued

I1a1

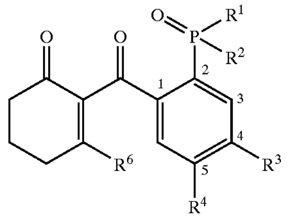

| n | $R^1$ | $R^2$ | $R^3$ | $R^4$ | $R^6$ |
|---|---|---|---|---|---|
| 5381 | S—$(CH_2CH_2)$—S | | $OCH_3$ | Cl | $SC_6H_5$ |
| 5382 | S—$(CH_2CH_2CH_2)$—S | | $OCH_3$ | Cl | $SC_6H_5$ |
| 5383 | —$(CH_2)_4$— | | $OCH_3$ | Cl | $SC_6H_5$ |
| 5384 | —$(CH_2)_5$— | | $OCH_3$ | Cl | $SC_6H_5$ |
| 5385 | H | H | $OCH_2CH_3$ | Cl | $SC_6H_5$ |
| 5386 | $CH_3$ | $CH_3$ | $OCH_2CH_3$ | Cl | $SC_6H_5$ |
| 5387 | $CH_2CH_3$ | $CH_2CH_3$ | $OCH_2CH_3$ | Cl | $SC_6H_5$ |
| 5388 | $CH_2CH_2CH_3$ | $CH_2CH_2CH_3$ | $OCH_2CH_3$ | Cl | $SC_6H_5$ |
| 5389 | $OCH_3$ | $OCH_3$ | $OCH_2CH_3$ | Cl | $SC_6H_5$ |
| 5390 | $OCH_2CH_3$ | $OCH_2CH_3$ | $OCH_2CH_3$ | Cl | $SC_6H_5$ |
| 5391 | $OCH_2CH_2CH_3$ | $OCH_2CH_2CH_3$ | $OCH_2CH_3$ | Cl | $SC_6H_5$ |
| 5392 | $SCH_3$ | $SCH_3$ | $OCH_2CH_3$ | Cl | $SC_6H_5$ |
| 5393 | $SCH_2CH_3$ | $SCH_2CH_3$ | $OCH_2CH_3$ | Cl | $SC_6H_5$ |
| 5394 | $N(CH_3)_2$ | $N(CH_3)_2$ | $OCH_2CH_3$ | Cl | $SC_6H_5$ |
| 5395 | $N(CH_2CH_3)_2$ | $N(CH_2CH_3)_2$ | $OCH_2CH_3$ | Cl | $SC_6H_5$ |
| 5396 | $N(CH_3)(CH_2CH_3)$ | $N(CH_3)(CH_2CH_3)$ | $OCH_2CH_3$ | Cl | $SC_6H_5$ |
| 5397 | O—$(CH_2CH_2)$—O | | $OCH_2CH_3$ | Cl | $SC_6H_5$ |
| 5398 | O—$(CH_2CH_2CH_2)$—O | | $OCH_2CH_3$ | Cl | $SC_6H_5$ |
| 5399 | S—$(CH_2CH_2)$—S | | $OCH_2CH_3$ | Cl | $SC_6H_5$ |
| 5400 | S—$(CH_2CH_2CH_2)$—S | | $OCH_2CH_3$ | Cl | $SC_6H_5$ |
| 5401 | —$(CH_2)_4$— | | $OCH_2CH_3$ | Cl | $SC_6H_5$ |
| 5402 | —$(CH_2)_5$— | | $OCH_2CH_3$ | Cl | $SC_6H_5$ |
| 5403 | H | H | $SCH_3$ | Cl | $SC_6H_5$ |
| 5404 | $CH_3$ | $CH_3$ | $SCH_3$ | Cl | $SC_6H_5$ |
| 5405 | $CH_2CH_3$ | $CH_2CH_3$ | $SCH_3$ | Cl | $SC_6H_5$ |
| 5406 | $CH_2CH_2CH_3$ | $CH_2CH_2CH_3$ | $SCH_3$ | Cl | $SC_6H_5$ |
| 5407 | $OCH_3$ | $OCH_3$ | $SCH_3$ | Cl | $SC_6H_5$ |
| 5408 | $OCH_2CH_3$ | $OCH_2CH_3$ | $SCH_3$ | Cl | $SC_6H_5$ |
| 5409 | $OCH_2CH_2CH_3$ | $OCH_2CH_2CH_3$ | $SCH_3$ | Cl | $SC_6H_5$ |
| 5410 | $SCH_3$ | $SCH_3$ | $SCH_3$ | Cl | $SC_6H_5$ |
| 5411 | $SCH_2CH_3$ | $SCH_2CH_3$ | $SCH_3$ | Cl | $SC_6H_5$ |
| 5412 | $N(CH_3)_2$ | $N(CH_3)_2$ | $SCH_3$ | Cl | $SC_6H_5$ |
| 5413 | $N(CH_2CH_3)_2$ | $N(CH_2CH_3)_2$ | $SCH_3$ | Cl | $SC_6H_5$ |
| 5414 | $N(CH_3)(CH_2CH_3)$ | $N(CH_3)(CH_2CH_3)$ | $SCH_3$ | Cl | $SC_6H_5$ |
| 5415 | O—$(CH_2CH_2)$—O | | $SCH_3$ | Cl | $SC_6H_5$ |
| 5416 | O—$(CH_2CH_2CH_2)$—O | | $SCH_3$ | Cl | $SC_6H_5$ |
| 5417 | S—$(CH_2CH_2)$—S | | $SCH_3$ | Cl | $SC_6H_5$ |
| 5418 | S—$(CH_2CH_2CH_2)$—S | | $SCH_3$ | Cl | $SC_6H_5$ |
| 5419 | —$(CH_2)_4$— | | $SCH_3$ | Cl | $SC_6H_5$ |
| 5420 | —$(CH_2)_5$— | | $SCH_3$ | Cl | $SC_6H_5$ |
| 5421 | H | H | $SO_2CH_3$ | Cl | $SC_6H_5$ |
| 5422 | $CH_3$ | $CH_3$ | $SO_2CH_3$ | Cl | $SC_6H_5$ |
| 5423 | $CH_2CH_3$ | $CH_2CH_3$ | $SO_2CH_3$ | Cl | $SC_6H_5$ |
| 5424 | $CH_2CH_2CH_3$ | $CH_2CH_2CH_3$ | $SO_2CH_3$ | Cl | $SC_6H_5$ |
| 5425 | $OCH_3$ | $OCH_3$ | $SO_2CH_3$ | Cl | $SC_6H_5$ |
| 5426 | $OCH_2CH_3$ | $OCH_2CH_3$ | $SO_2CH_3$ | Cl | $SC_6H_5$ |
| 5427 | $OCH_2CH_2CH_3$ | $OCH_2CH_2CH_3$ | $SO_2CH_3$ | Cl | $SC_6H_5$ |
| 5428 | $SCH_3$ | $SCH_3$ | $SO_2CH_3$ | Cl | $SC_6H_5$ |
| 5429 | $SCH_2CH_3$ | $SCH_2CH_3$ | $SO_2CH_3$ | Cl | $SC_6H_5$ |
| 5430 | $N(CH_3)_2$ | $N(CH_3)_2$ | $SO_2CH_3$ | Cl | $SC_6H_5$ |
| 5431 | $N(CH_2CH_3)_2$ | $N(CH_2CH_3)_2$ | $SO_2CH_3$ | Cl | $SC_6H_5$ |
| 5432 | $N(CH_3)(CH_2CH_3)$ | $N(CH_3)(CH_2CH_3)$ | $SO_2CH_3$ | Cl | $SC_6H_5$ |
| 5433 | O—$(CH_2CH_2)$—O | | $SO_2CH_3$ | Cl | $SC_6H_5$ |
| 5434 | O—$(CH_2CH_2CH_2)$—O | | $SO_2CH_3$ | Cl | $SC_6H_5$ |
| 5435 | S—$(CH_2CH_2)$—S | | $SO_2CH_3$ | Cl | $SC_6H_5$ |
| 5436 | S—$(CH_2CH_2CH_2)$—S | | $SO_2CH_3$ | Cl | $SC_6H_5$ |
| 5437 | —$(CH_2)_4$— | | $SO_2CH_3$ | Cl | $SC_6H_5$ |
| 5438 | —$(CH_2)_5$— | | $SO_2CH_3$ | Cl | $SC_6H_5$ |
| 5439 | H | H | $PO(OCH_3)_2$ | Cl | $SC_6H_5$ |
| 5440 | $CH_3$ | $CH_3$ | $PO(OCH_3)_2$ | Cl | $SC_6H_5$ |
| 5441 | $CH_2CH_3$ | $CH_2CH_3$ | $PO(OCH_3)_2$ | Cl | $SC_6H_5$ |
| 5442 | $CH_2CH_2CH_3$ | $CH_2CH_2CH_3$ | $PO(OCH_3)_2$ | Cl | $SC_6H_5$ |
| 5443 | $OCH_3$ | $OCH_3$ | $PO(OCH_3)_2$ | Cl | $SC_6H_5$ |
| 5444 | $OCH_2CH_3$ | $OCH_2CH_3$ | $PO(OCH_3)_2$ | Cl | $SC_6H_5$ |

TABLE 1-continued

I1a1

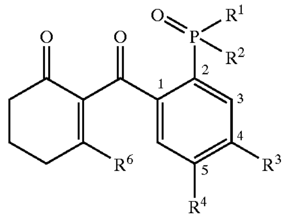

| n | $R^1$ | $R^2$ | $R^3$ | $R^4$ | $R^6$ |
|---|---|---|---|---|---|
| 5445 | $OCH_2CH_2CH_3$ | $OCH_2CH_2CH_3$ | $PO(OCH_3)_2$ | Cl | $SC_6H_5$ |
| 5446 | $SCH_3$ | $SCH_3$ | $PO(OCH_3)_2$ | Cl | $SC_6H_5$ |
| 5447 | $SCH_2CH_3$ | $SCH_2CH_3$ | $PO(OCH_3)_2$ | Cl | $SC_6H_5$ |
| 5448 | $N(CH_3)_2$ | $N(CH_3)_2$ | $PO(OCH_3)_2$ | Cl | $SC_6H_5$ |
| 5449 | $N(CH_2CH_3)_2$ | $N(CH_2CH_3)_2$ | $PO(OCH_3)_2$ | Cl | $SC_6H_5$ |
| 5450 | $N(CH_3)(CH_2CH_3)$ | $N(CH_3)(CH_2CH_3)$ | $PO(OCH_3)_2$ | Cl | $SC_6H_5$ |
| 5451 | $O—(CH_2CH_2)—O$ | | $PO(OCH_3)_2$ | Cl | $SC_6H_5$ |
| 5452 | $O—(CH_2CH_2CH_2)—O$ | | $PO(OCH_3)_2$ | Cl | $SC_6H_5$ |
| 5453 | $S—(CH_2CH_2)—S$ | | $PO(OCH_3)_2$ | Cl | $SC_6H_5$ |
| 5454 | $S—(CH_2CH_2CH_2)—S$ | | $PO(OCH_3)_2$ | Cl | $SC_6H_5$ |
| 5455 | $—(CH_2)_4—$ | | $PO(OCH_3)_2$ | Cl | $SC_6H_5$ |
| 5456 | $—(CH_2)_5—$ | | $PO(OCH_3)_2$ | Cl | $SC_6H_5$ |
| 5457 | H | H | $PO(OCH_2CH_3)_2$ | Cl | $SC_6H_5$ |
| 5458 | $CH_3$ | $CH_3$ | $PO(OCH_2CH_3)_2$ | Cl | $SC_6H_5$ |
| 5459 | $CH_2CH_3$ | $CH_2CH_3$ | $PO(OCH_2CH_3)_2$ | Cl | $SC_6H_5$ |
| 5460 | $CH_2CH_2CH_3$ | $CH_2CH_2CH_3$ | $PO(OCH_2CH_3)_2$ | Cl | $SC_6H_5$ |
| 5461 | $OCH_3$ | $OCH_3$ | $PO(OCH_2CH_3)_2$ | Cl | $SC_6H_5$ |
| 5462 | $OCH_2CH_3$ | $OCH_2CH_3$ | $PO(OCH_2CH_3)_2$ | Cl | $SC_6H_5$ |
| 5463 | $OCH_2CH_2CH_3$ | $OCH_2CH_2CH_3$ | $PO(OCH_2CH_3)_2$ | Cl | $SC_6H_5$ |
| 5464 | $SCH_3$ | $SCH_3$ | $PO(OCH_2CH_3)_2$ | Cl | $SC_6H_5$ |
| 5465 | $SCH_2CH_3$ | $SCH_2CH_3$ | $PO(OCH_2CH_3)_2$ | Cl | $SC_6H_5$ |
| 5466 | $N(CH_3)_2$ | $N(CH_3)_2$ | $PO(OCH_2CH_3)_2$ | Cl | $SC_6H_5$ |
| 5467 | $N(CH_2CH_3)_2$ | $N(CH_2CH_3)_2$ | $PO(OCH_2CH_3)_2$ | Cl | $SC_6H_5$ |
| 5468 | $N(CH_3)(CH_2CH_3)$ | $N(CH_3)(CH_2CH_3)$ | $PO(OCH_2CH_3)_2$ | Cl | $SC_6H_5$ |
| 5469 | $O—(CH_2CH_2)—O$ | | $PO(OCH_2CH_3)_2$ | Cl | $SC_6H_5$ |
| 5470 | $O—(CH_2CH_2CH_2)—O$ | | $PO(OCH_2CH_3)_2$ | Cl | $SC_6H_5$ |
| 5471 | $S—(CH_2CH_2)—S$ | | $PO(OCH_2CH_3)_2$ | Cl | $SC_6H_5$ |
| 5472 | $S—(CH_2CH_2CH_2)—S$ | | $PO(OCH_2CH_3)_2$ | Cl | $SC_6H_5$ |
| 5473 | $—(CH_2)_4—$ | | $PO(OCH_2CH_3)_2$ | Cl | $SC_6H_5$ |
| 5474 | $—(CH_2)_5—$ | | $PO(OCH_2CH_3)_2$ | Cl | $SC_6H_5$ |
| 5475 | H | H | $PO(CH_3)_2$ | Cl | $SC_6H_5$ |
| 5476 | $CH_3$ | $CH_3$ | $PO(CH_3)_2$ | Cl | $SC_6H_5$ |
| 5477 | $CH_2CH_3$ | $CH_2CH_3$ | $PO(CH_3)_2$ | Cl | $SC_6H_5$ |
| 5478 | $CH_2CH_2CH_3$ | $CH_2CH_2CH_3$ | $PO(CH_3)_2$ | Cl | $SC_6H_5$ |
| 5479 | $OCH_3$ | $OCH_3$ | $PO(CH_3)_2$ | Cl | $SC_6H_5$ |
| 5480 | $OCH_2CH_3$ | $OCH_2CH_3$ | $PO(CH_3)_2$ | Cl | $SC_6H_5$ |
| 5481 | $OCH_2CH_2CH_3$ | $OCH_2CH_2CH_3$ | $PO(CH_3)_2$ | Cl | $SC_6H_5$ |
| 5482 | $SCH_3$ | $SCH_3$ | $PO(CH_3)_2$ | Cl | $SC_6H_5$ |
| 5483 | $SCH_2CH_3$ | $SCH_2CH_3$ | $PO(CH_3)_2$ | Cl | $SC_6H_5$ |
| 5484 | $N(CH_3)_2$ | $N(CH_3)_2$ | $PO(CH_3)_2$ | Cl | $SC_6H_5$ |
| 5485 | $N(CH_2CH_3)_2$ | $N(CH_2CH_3)_2$ | $PO(CH_3)_2$ | Cl | $SC_6H_5$ |
| 5486 | $N(CH_3)(CH_2CH_3)$ | $N(CH_3)(CH_2CH_3)$ | $PO(CH_3)_2$ | Cl | $SC_6H_5$ |
| 5487 | $O—(CH_2CH_2)—O$ | | $PO(CH_3)_2$ | Cl | $SC_6H_5$ |
| 5488 | $O—(CH_2CH_2CH_2)—O$ | | $PO(CH_3)_2$ | Cl | $SC_6H_5$ |
| 5489 | $S—(CH_2CH_2)—S$ | | $PO(CH_3)_2$ | Cl | $SC_6H_5$ |
| 5490 | $S—(CH_2CH_2CH_2)—S$ | | $PO(CH_3)_2$ | Cl | $SC_6H_5$ |
| 5491 | $—(CH_2)_4—$ | | $PO(CH_3)_2$ | Cl | $SC_6H_5$ |
| 5492 | $—(CH_2)_5—$ | | $PO(CH_3)_2$ | Cl | $SC_6H_5$ |
| 5493 | H | H | $PC(CH_2CH_3)_2$ | Cl | $SC_6H_5$ |
| 5494 | $CH_3$ | $CH_3$ | $PC(CH_2CH_3)_2$ | Cl | $SC_6H_5$ |
| 5495 | $CH_2CH_3$ | $CH_2CH_3$ | $PC(CH_2CH_3)_2$ | Cl | $SC_6H_5$ |
| 5496 | $CH_2CH_2CH_3$ | $CH_2CH_2CH_3$ | $PC(CH_2CH_3)_2$ | Cl | $SC_6H_5$ |
| 5497 | $OCH_3$ | $OCH_3$ | $PC(CH_2CH_3)_2$ | Cl | $SC_6H_5$ |
| 5498 | $OCH_2CH_3$ | $OCH_2CH_3$ | $PC(CH_2CH_3)_2$ | Cl | $SC_6H_5$ |
| 5499 | $OCH_2CH_2CH_3$ | $OCH_2CH_2CH_3$ | $PC(CH_2CH_3)_2$ | Cl | $SC_6H_5$ |
| 5500 | $SCH_3$ | $SCH_3$ | $PC(CH_2CH_3)_2$ | Cl | $SC_6H_5$ |
| 5501 | $SCH_2CH_3$ | $SCH_2CH_3$ | $PC(CH_2CH_3)_2$ | Cl | $SC_6H_5$ |
| 5502 | $N(CH_3)_2$ | $N(CH_3)_2$ | $PC(CH_2CH_3)_2$ | Cl | $SC_6H_5$ |
| 5503 | $N(CH_2CH_3)_2$ | $N(CH_2CH_3)_2$ | $PC(CH_2CH_3)_2$ | Cl | $SC_6H_5$ |
| 5504 | $N(CH_3)(CH_2CH_3)$ | $N(CH_3)(CH_2CH_3)$ | $PC(CH_2CH_3)_2$ | Cl | $SC_6H_5$ |
| 5505 | $O—(CH_2CH_2)—O$ | | $PC(CH_2CH_3)_2$ | Cl | $SC_6H_5$ |
| 5506 | $O—(CH_2CH_2CH_2)—O$ | | $PC(CH_2CH_3)_2$ | Cl | $SC_6H_5$ |
| 5507 | $S—(CH_2CH_2)—S$ | | $PC(CH_2CH_3)_2$ | Cl | $SC_6H_5$ |
| 5508 | $S—(CH_2CH_2CH_2)—S$ | | $PC(CH_2CH_3)_2$ | Cl | $SC_6H_5$ |

TABLE 1-continued

I1a1

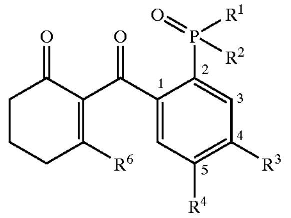

| n | $R^1$ | $R^2$ | $R^3$ | $R^4$ | $R^6$ |
|---|---|---|---|---|---|
| 5509 | $-(CH_2)_4-$ | | $PC(CH_2CH_3)_2$ | Cl | $SC_6H_5$ |
| 5510 | $-(CH_2)_5-$ | | $PC(CH_2CH_3)_2$ | Cl | $SC_6H_5$ |
| 5511 | H | H | H | Cl | Het1 |
| 5512 | $CH_3$ | $CH_3$ | H | Cl | Het1 |
| 5513 | $CH_2CH_3$ | $CH_2CH_3$ | H | Cl | Het1 |
| 5514 | $CH_2CH_2CH_3$ | $CH_2CH_2CH_3$ | H | Cl | Het1 |
| 5515 | $OCH_3$ | $OCH_3$ | H | Cl | Het1 |
| 5516 | $OCH_2CH_3$ | $OCH_2CH_3$ | H | Cl | Het1 |
| 5517 | $OCH_2CH_2CH_3$ | $OCH_2CH_2CH_3$ | H | Cl | Het1 |
| 5518 | $SCH_3$ | $SCH_3$ | H | Cl | Het1 |
| 5519 | $SCH_2CH_3$ | $SCH_2CH_3$ | H | Cl | Het1 |
| 5520 | $N(CH_3)_2$ | $N(CH_3)_2$ | H | Cl | Het1 |
| 5521 | $N(CH_2CH_3)_2$ | $N(CH_2CH_3)_2$ | H | Cl | Het1 |
| 5522 | $N(CH_3)(CH_2CH_3)$ | $N(CH_3)(CH_2CH_3)$ | H | Cl | Het1 |
| 5523 | $O-(CH_2CH_2)-O$ | | H | Cl | Het1 |
| 5524 | $O-(CH_2CH_2CH_2)-O$ | | H | Cl | Het1 |
| 5525 | $S-(CH_2CH_2)-S$ | | H | Cl | Het1 |
| 5526 | $S-(CH_2CH_2CH_2)-S$ | | H | Cl | Het1 |
| 5527 | $-(CH_2)_4-$ | | H | Cl | Het1 |
| 5528 | $-(CH_2)_5-$ | | H | Cl | Het1 |
| 5529 | H | H | $NO_2$ | Cl | Het1 |
| 5530 | $CH_3$ | $CH_3$ | $NO_2$ | Cl | Het1 |
| 5531 | $CH_2CH_3$ | $CH_2CH_3$ | $NO_2$ | Cl | Het1 |
| 5532 | $CH_2CH_2CH_3$ | $CH_2CH_2CH_3$ | $NO_2$ | Cl | Het1 |
| 5533 | $OCH_3$ | $OCH_3$ | $NO_2$ | Cl | Het1 |
| 5534 | $OCH_2CH_3$ | $OCH_2CH_3$ | $NO_2$ | Cl | Het1 |
| 5535 | $OCH_2CH_2CH_3$ | $OCH_2CH_2CH_3$ | $NO_2$ | Cl | Het1 |
| 5536 | $SCH_3$ | $SCH_3$ | $NO_2$ | Cl | Het1 |
| 5537 | $SCH_2CH_3$ | $SCH_2CH_3$ | $NO_2$ | Cl | Het1 |
| 5538 | $N(CH_3)_2$ | $N(CH_3)_2$ | $NO_2$ | Cl | Het1 |
| 5539 | $N(CH_2CH_3)_2$ | $N(CH_2CH_3)_2$ | $NO_2$ | Cl | Het1 |
| 5540 | $N(CH_3)(CH_2CH_3)$ | $N(CH_3)(CH_2CH_3)$ | $NO_2$ | Cl | Het1 |
| 5541 | $O-(CH_2CH_2)-O$ | | $NO_2$ | Cl | Het1 |
| 5542 | $O-(CH_2CH_2CH_2)-O$ | | $NO_2$ | Cl | Het1 |
| 5543 | $S-(CH_2CH_2)-S$ | | $NO_2$ | Cl | Het1 |
| 5544 | $S-(CH_2CH_2CH_2)-S$ | | $NO_2$ | Cl | Het1 |
| 5545 | $-(CH_2)_4-$ | | $NO_2$ | Cl | Het1 |
| 5546 | $-(CH_2)_5-$ | | $NO_2$ | Cl | Het1 |
| 5547 | H | H | CN | Cl | Het1 |
| 5548 | $CH_3$ | $CH_3$ | CN | Cl | Het1 |
| 5549 | $CH_2CH_3$ | $CH_2CH_3$ | CN | Cl | Het1 |
| 5550 | $CH_2CH_2CH_3$ | $CH_2CH_2CH_3$ | CN | Cl | Het1 |
| 5551 | $OCH_3$ | $OCH_3$ | CN | Cl | Het1 |
| 5552 | $OCH_2CH_3$ | $OCH_2CH_3$ | CN | Cl | Het1 |
| 5553 | $OCH_2CH_2CH_3$ | $OCH_2CH_2CH_3$ | CN | Cl | Het1 |
| 5554 | $SCH_3$ | $SCH_3$ | CN | Cl | Het1 |
| 5555 | $SCH_2CH_3$ | $SCH_2CH_3$ | CN | Cl | Het1 |
| 5556 | $N(CH_3)_2$ | $N(CH_3)_2$ | CN | Cl | Het1 |
| 5557 | $N(CH_2CH_3)_2$ | $N(CH_2CH_3)_2$ | CN | Cl | Het1 |
| 5558 | $N(CH_3)(CH_2CH_3)$ | $N(CH_3)(CH_2CH_3)$ | CN | Cl | Het1 |
| 5559 | $O-(CH_2CH_2)-O$ | | CN | Cl | Het1 |
| 5560 | $O-(CH_2CH_2CH_2)-O$ | | CN | Cl | Het1 |
| 5561 | $S-(CH_2CH_2)-S$ | | CN | Cl | Het1 |
| 5562 | $S-(CH_2CH_2CH_2)-S$ | | CN | Cl | Het1 |
| 5563 | $-(CH_2)_4-$ | | CN | Cl | Het1 |
| 5564 | $-(CH_2)_5-$ | | CN | Cl | Het1 |
| 5565 | H | H | F | Cl | Het1 |
| 5566 | $CH_3$ | $CH_3$ | F | Cl | Het1 |
| 5567 | $CH_2CH_3$ | $CH_2CH_3$ | F | Cl | Het1 |
| 5568 | $CH_2CH_2CH_3$ | $CH_2CH_2CH_3$ | F | Cl | Het1 |
| 5569 | $OCH_3$ | $OCH_3$ | F | Cl | Het1 |
| 5570 | $OCH_2CH_3$ | $OCH_2CH_3$ | F | Cl | Het1 |
| 5571 | $OCH_2CH_2CH_3$ | $OCH_2CH_2CH_3$ | F | Cl | Het1 |
| 5572 | $SCH_3$ | $SCH_3$ | F | Cl | Het1 |

TABLE 1-continued

I1a1

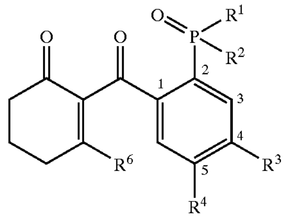

| n | $R^1$ | $R^2$ | $R^3$ | $R^4$ | $R^6$ |
|---|---|---|---|---|---|
| 5573 | $SCH_2CH_3$ | $SCH_2CH_3$ | F | Cl | Het1 |
| 5574 | $N(CH_3)_2$ | $N(CH_3)_2$ | F | Cl | Het1 |
| 5575 | $N(CH_2CH_3)_2$ | $N(CH_2CH_3)_2$ | F | Cl | Het1 |
| 5576 | $N(CH_3)(CH_2CH_3)$ | $N(CH_3)(CH_2CH_3)$ | F | Cl | Het1 |
| 5577 | $O—(CH_2CH_2)—O$ | | F | Cl | Het1 |
| 5578 | $O—(CH_2CH_2CH_2)—O$ | | F | Cl | Het1 |
| 5579 | $S—(CH_2CH_2)—S$ | | F | Cl | Het1 |
| 5580 | $S—(CH_2CH_2CH_2)—S$ | | F | Cl | Het1 |
| 5581 | $—(CH_2)_4—$ | | F | Cl | Het1 |
| 5582 | $—(CH_2)_5—$ | | F | Cl | Het1 |
| 5583 | H | H | Cl | Cl | Het1 |
| 5584 | $CH_3$ | $CH_3$ | Cl | Cl | Het1 |
| 5585 | $CH_2CH_3$ | $CH_2CH_3$ | Cl | Cl | Het1 |
| 5586 | $CH_2CH_2CH_3$ | $CH_2CH_2CH_3$ | Cl | Cl | Het1 |
| 5587 | $OCH_3$ | $OCH_3$ | Cl | Cl | Het1 |
| 5588 | $OCH_2CH_3$ | $OCH_2CH_3$ | Cl | Cl | Het1 |
| 5589 | $OCH_2CH_2CH_3$ | $OCH_2CH_2CH_3$ | Cl | Cl | Het1 |
| 5590 | $SCH_3$ | $SCH_3$ | Cl | Cl | Het1 |
| 5591 | $SCH_2CH_3$ | $SCH_2CH_3$ | Cl | Cl | Het1 |
| 5592 | $N(CH_3)_2$ | $N(CH_3)_2$ | Cl | Cl | Het1 |
| 5593 | $N(CH_2CH_3)_2$ | $N(CH_2CH_3)_2$ | Cl | Cl | Het1 |
| 5594 | $N(CH_3)(CH_2CH_3)$ | $N(CH_3)(CH_2CH_3)$ | Cl | Cl | Het1 |
| 5595 | $O—(CH_2CH_2)—O$ | | Cl | Cl | Het1 |
| 5596 | $O—(CH_2CH_2CH_2)—O$ | | Cl | Cl | Het1 |
| 5597 | $S—(CH_2CH_2)—S$ | | Cl | Cl | Het1 |
| 5598 | $S—(CH_2CH_2CH_2)—S$ | | Cl | Cl | Het1 |
| 5599 | $—(CH_2)_4—$ | | Cl | Cl | Het1 |
| 5600 | $—(CH_2)_5—$ | | Cl | Cl | Het1 |
| 5601 | H | H | Br | Cl | Het1 |
| 5602 | $CH_3$ | $CH_3$ | Br | Cl | Het1 |
| 5603 | $CH_2CH_3$ | $CH_2CH_3$ | Br | Cl | Het1 |
| 5604 | $CH_2CH_2CH_3$ | $CH_2CH_2CH_3$ | Br | Cl | Het1 |
| 5605 | $OCH_3$ | $OCH_3$ | Br | Cl | Het1 |
| 5606 | $OCH_2CH_3$ | $OCH_2CH_3$ | Br | Cl | Het1 |
| 5607 | $OCH_2CH_2CH_3$ | $OCH_2CH_2CH_3$ | Br | Cl | Het1 |
| 5608 | $SCH_3$ | $SCH_3$ | Br | Cl | Het1 |
| 5609 | $SCH_2CH_3$ | $SCH_2CH_3$ | Br | Cl | Het1 |
| 5610 | $N(CH_3)_2$ | $N(CH_3)_2$ | Br | Cl | Het1 |
| 5611 | $N(CH_2CH_3)_2$ | $N(CH_2CH_3)_2$ | Br | Cl | Het1 |
| 5612 | $N(CH_3)(CH_2CH_3)$ | $N(CH_3)(CH_2CH_3)$ | Br | Cl | Het1 |
| 5613 | $O—(CH_2CH_2)—O$ | | Br | Cl | Het1 |
| 5614 | $O—(CH_2CH_2CH_2)—O$ | | Br | Cl | Het1 |
| 5615 | $S—(CH_2CH_2)—S$ | | Br | Cl | Het1 |
| 5616 | $S—(CH_2CH_2CH_2)—S$ | | Br | Cl | Het1 |
| 5617 | $—(CH_2)_4—$ | | Br | Cl | Het1 |
| 5618 | $—(CH_2)_5—$ | | Br | Cl | Het1 |
| 5619 | H | H | $CH_3$ | Cl | Het1 |
| 5620 | $CH_3$ | $CH_3$ | $CH_3$ | Cl | Het1 |
| 5621 | $CH_2CH_3$ | $CH_2CH_3$ | $CH_3$ | Cl | Het1 |
| 5622 | $CH_2CH_2CH_3$ | $CH_2CH_2CH_3$ | $CH_3$ | Cl | Het1 |
| 5623 | $OCH_3$ | $OCH_3$ | $CH_3$ | Cl | Het1 |
| 5624 | $OCH_2CH_3$ | $OCH_2CH_3$ | $CH_3$ | Cl | Het1 |
| 5625 | $OCH_2CH_2CH_3$ | $OCH_2CH_2CH_3$ | $CH_3$ | Cl | Het1 |
| 5626 | $SCH_3$ | $SCH_3$ | $CH_3$ | Cl | Het1 |
| 5627 | $SCH_2CH_3$ | $SCH_2CH_3$ | $CH_3$ | Cl | Het1 |
| 5628 | $N(CH_3)_2$ | $N(CH_3)_2$ | $CH_3$ | Cl | Het1 |
| 5629 | $N(CH_2CH_3)_2$ | $N(CH_2CH_3)_2$ | $CH_3$ | Cl | Het1 |
| 5630 | $N(CH_3)(CH_2CH_3)$ | $N(CH_3)(CH_2CH_3)$ | $CH_3$ | Cl | Het1 |
| 5631 | $O—(CH_2CH_2)—O$ | | $CH_3$ | Cl | Het1 |
| 5632 | $O—(CH_2CH_2CH_2)—O$ | | $CH_3$ | Cl | Het1 |
| 5633 | $S—(CH_2CH_2)—S$ | | $CH_3$ | Cl | Het1 |
| 5634 | $S—(CH_2CH_2CH_2)—S$ | | $CH_3$ | Cl | Het1 |
| 5635 | $—(CH_2)_4—$ | | $CH_3$ | Cl | Het1 |
| 5636 | $—(CH_2)_5—$ | | $CH_3$ | Cl | Het1 |

TABLE 1-continued

I1a1

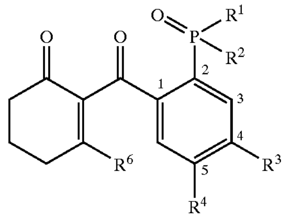

| n | $R^1$ | $R^2$ | $R^3$ | $R^4$ | $R^6$ |
|---|---|---|---|---|---|
| 5637 | H | H | $CH_2CH_3$ | Cl | Het1 |
| 5638 | $CH_3$ | $CH_3$ | $CH_2CH_3$ | Cl | Het1 |
| 5639 | $CH_2CH_3$ | $CH_2CH_3$ | $CH_2CH_3$ | Cl | Het1 |
| 5640 | $CH_2CH_2CH_3$ | $CH_2CH_2CH_3$ | $CH_2CH_3$ | Cl | Het1 |
| 5641 | $OCH_3$ | $OCH_3$ | $CH_2CH_3$ | Cl | Het1 |
| 5642 | $OCH_2CH_3$ | $OCH_2CH_3$ | $CH_2CH_3$ | Cl | Het1 |
| 5643 | $OCH_2CH_2CH_3$ | $OCH_2CH_2CH_3$ | $CH_2CH_3$ | Cl | Het1 |
| 5644 | $SCH_3$ | $SCH_3$ | $CH_2CH_3$ | Cl | Het1 |
| 5645 | $SCH_2CH_3$ | $SCH_2CH_3$ | $CH_2CH_3$ | Cl | Het1 |
| 5646 | $N(CH_3)_2$ | $N(CH_3)_2$ | $CH_2CH_3$ | Cl | Het1 |
| 5647 | $N(CH_2CH_3)_2$ | $N(CH_2CH_3)_2$ | $CH_2CH_3$ | Cl | Het1 |
| 5648 | $N(CH_3)(CH_2CH_3)$ | $N(CH_3)(CH_2CH_3)$ | $CH_2CH_3$ | Cl | Het1 |
| 5649 | $O-(CH_2CH_2)-O$ | | $CH_2CH_3$ | Cl | Het1 |
| 5650 | $O-(CH_2CH_2CH_2)-O$ | | $CH_2CH_3$ | Cl | Het1 |
| 5651 | $S-(CH_2CH_2)-S$ | | $CH_2CH_3$ | Cl | Het1 |
| 5652 | $S-(CH_2CH_2CH_2)-S$ | | $CH_2CH_3$ | Cl | Het1 |
| 5653 | $-(CH_2)_4-$ | | $CH_2CH_3$ | Cl | Het1 |
| 5654 | $-(CH_2)_5-$ | | $CH_2CH_3$ | Cl | Het1 |
| 5655 | H | H | $CF_3$ | Cl | Het1 |
| 5656 | $CH_3$ | $CH_3$ | $CF_3$ | Cl | Het1 |
| 5657 | $CH_2CH_3$ | $CH_2CH_3$ | $CF_3$ | Cl | Het1 |
| 5658 | $CH_2CH_2CH_3$ | $CH_2CH_2CH_3$ | $CF_3$ | Cl | Het1 |
| 5659 | $OCH_3$ | $OCH_3$ | $CF_3$ | Cl | Het1 |
| 5660 | $OCH_2CH_3$ | $OCH_2CH_3$ | $CF_3$ | Cl | Het1 |
| 5661 | $OCH_2CH_2CH_3$ | $OCH_2CH_2CH_3$ | $CF_3$ | Cl | Het1 |
| 5662 | $SCH_3$ | $SCH_3$ | $CF_3$ | Cl | Het1 |
| 5663 | $SCH_2CH_3$ | $SCH_2CH_3$ | $CF_3$ | Cl | Het1 |
| 5664 | $N(CH_3)_2$ | $N(CH_3)_2$ | $CF_3$ | Cl | Het1 |
| 5665 | $N(CH_2CH_3)_2$ | $N(CH_2CH_3)_2$ | $CF_3$ | Cl | Het1 |
| 5666 | $N(CH_3)(CH_2CH_3)$ | $N(CH_3)(CH_2CH_3)$ | $CF_3$ | Cl | Het1 |
| 5667 | $O-(CH_2CH_2)-O$ | | $CF_3$ | Cl | Het1 |
| 5668 | $O-(CH_2CH_2CH_2)-O$ | | $CF_3$ | Cl | Het1 |
| 5669 | $S-(CH_2CH_2)-S$ | | $CF_3$ | Cl | Het1 |
| 5670 | $S-(CH_2CH_2CH_2)-S$ | | $CF_3$ | Cl | Het1 |
| 5671 | $-(CH_2)_4-$ | | $CF_3$ | Cl | Het1 |
| 5672 | $-(CH_2)_5-$ | | $CF_3$ | Cl | Het1 |
| 5673 | H | H | $OCH_3$ | Cl | Het1 |
| 5674 | $CH_3$ | $CH_3$ | $OCH_3$ | Cl | Het1 |
| 5675 | $CH_2CH_3$ | $CH_2CH_3$ | $OCH_3$ | Cl | Het1 |
| 5676 | $CH_2CH_2CH_3$ | $CH_2CH_2CH_3$ | $OCH_3$ | Cl | Het1 |
| 5677 | $OCH_3$ | $OCH_3$ | $OCH_3$ | Cl | Het1 |
| 5678 | $OCH_2CH_3$ | $OCH_2CH_3$ | $OCH_3$ | Cl | Het1 |
| 5679 | $OCH_2CH_2CH_3$ | $OCH_2CH_2CH_3$ | $OCH_3$ | Cl | Het1 |
| 5680 | $SCH_3$ | $SCH_3$ | $OCH_3$ | Cl | Het1 |
| 5681 | $SCH_2CH_3$ | $SCH_2CH_3$ | $OCH_3$ | Cl | Het1 |
| 5682 | $N(CH_3)_2$ | $N(CH_3)_2$ | $OCH_3$ | Cl | Het1 |
| 5683 | $N(CH_2CH_3)_2$ | $N(CH_2CH_3)_2$ | $OCH_3$ | Cl | Het1 |
| 5684 | $N(CH_3)(CH_2CH_3)$ | $N(CH_3)(CH_2CH_3)$ | $OCH_3$ | Cl | Het1 |
| 5685 | $O-(CH_2CH_2)-O$ | | $OCH_3$ | Cl | Het1 |
| 5686 | $O-(CH_2CH_2CH_2)-O$ | | $OCH_3$ | Cl | Het1 |
| 5687 | $S-(CH_2CH_2)-S$ | | $OCH_3$ | Cl | Het1 |
| 5688 | $S-(CH_2CH_2CH_2)-S$ | | $OCH_3$ | Cl | Het1 |
| 5689 | $-(CH_2)_4-$ | | $OCH_3$ | Cl | Het1 |
| 5690 | $-(CH_2)_5-$ | | $OCH_3$ | Cl | Het1 |
| 5691 | H | H | $OCH_2CH_3$ | Cl | Het1 |
| 5692 | $CH_3$ | $CH_3$ | $OCH_2CH_3$ | Cl | Het1 |
| 5693 | $CH_2CH_3$ | $CH_2CH_3$ | $OCH_2CH_3$ | Cl | Het1 |
| 5694 | $CH_2CH_2CH_3$ | $CH_2CH_2CH_3$ | $OCH_2CH_3$ | Cl | Het1 |
| 5695 | $OCH_3$ | $OCH_3$ | $OCH_2CH_3$ | Cl | Het1 |
| 5696 | $OCH_2CH_3$ | $OCH_2CH_3$ | $OCH_2CH_3$ | Cl | Het1 |
| 5697 | $OCH_2CH_2CH_3$ | $OCH_2CH_2CH_3$ | $OCH_2CH_3$ | Cl | Het1 |
| 5698 | $SCH_3$ | $SCH_3$ | $OCH_2CH_3$ | Cl | Het1 |
| 5699 | $SCH_2CH_3$ | $SCH_2CH_3$ | $OCH_2CH_3$ | Cl | Het1 |
| 5700 | $N(CH_3)_2$ | $N(CH_3)_2$ | $OCH_2CH_3$ | Cl | Het1 |

TABLE 1-continued

I1a1

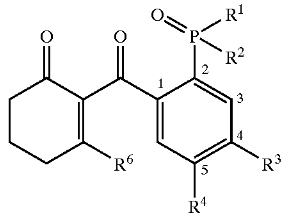

| n | $R^1$ | $R^2$ | $R^3$ | $R^4$ | $R^6$ |
|---|---|---|---|---|---|
| 5701 | $N(CH_2CH_3)_2$ | $N(CH_2CH_3)_2$ | $OCH_2CH_3$ | Cl | Het1 |
| 5702 | $N(CH_3)(CH_2CH_3)$ | $N(CH_3)(CH_2CH_3)$ | $OCH_2CH_3$ | Cl | Het1 |
| 5703 | $O—(CH_2CH_2)—O$ | | $OCH_2CH_3$ | Cl | Het1 |
| 5704 | $O—(CH_2CH_2CH_2)—O$ | | $OCH_2CH_3$ | Cl | Het1 |
| 5705 | $S—(CH_2CH_2)—S$ | | $OCH_2CH_3$ | Cl | Het1 |
| 5706 | $S—(CH_2CH_2CH_2)—S$ | | $OCH_2CH_3$ | Cl | Het1 |
| 5707 | $—(CH_2)_4—$ | | $OCH_2CH_3$ | Cl | Het1 |
| 5708 | $—(CH_2)_5—$ | | $OCH_2CH_3$ | Cl | Het1 |
| 5709 | H | H | $SCH_3$ | Cl | Het1 |
| 5710 | $CH_3$ | $CH_3$ | $SCH_3$ | Cl | Het1 |
| 5711 | $CH_2CH_3$ | $CH_2CH_3$ | $SCH_3$ | Cl | Het1 |
| 5712 | $CH_2CH_2CH_3$ | $CH_2CH_2CH_3$ | $SCH_3$ | Cl | Het1 |
| 5713 | $OCH_3$ | $OCH_3$ | $SCH_3$ | Cl | Het1 |
| 5714 | $OCH_2CH_3$ | $OCH_2CH_3$ | $SCH_3$ | Cl | Het1 |
| 5715 | $OCH_2CH_2CH_3$ | $OCH_2CH_2CH_3$ | $SCH_3$ | Cl | Het1 |
| 5716 | $SCH_3$ | $SCH_3$ | $SCH_3$ | Cl | Het1 |
| 5717 | $SCH_2CH_3$ | $SCH_2CH_3$ | $SCH_3$ | Cl | Het1 |
| 5718 | $N(CH_3)_2$ | $N(CH_3)_2$ | $SCH_3$ | Cl | Het1 |
| 5719 | $N(CH_2CH_3)_2$ | $N(CH_2CH_3)_2$ | $SCH_3$ | Cl | Het1 |
| 5720 | $N(CH_3)(CH_2CH_3)$ | $N(CH_3)(CH_2CH_3)$ | $SCH_3$ | Cl | Het1 |
| 5721 | $O—(CH_2CH_2)—O$ | | $SCH_3$ | Cl | Het1 |
| 5722 | $O—(CH_2CH_2CH_2)—O$ | | $SCH_3$ | Cl | Het1 |
| 5723 | $S—(CH_2CH_2)—S$ | | $SCH_3$ | Cl | Het1 |
| 5724 | $S—(CH_2CH_2CH_2)—S$ | | $SCH_3$ | Cl | Het1 |
| 5725 | $—(CH_2)_4—$ | | $SCH_3$ | Cl | Het1 |
| 5726 | $—(CH_2)_5—$ | | $SCH_3$ | Cl | Het1 |
| 5727 | H | H | $SO_2CH_3$ | Cl | Het1 |
| 5728 | $CH_3$ | $CH_3$ | $SO_2CH_3$ | Cl | Het1 |
| 5729 | $CH_2CH_3$ | $CH_2CH_3$ | $SO_2CH_3$ | Cl | Het1 |
| 5730 | $CH_2CH_2CH_3$ | $CH_2CH_2CH_3$ | $SO_2CH_3$ | Cl | Het1 |
| 5731 | $OCH_3$ | $OCH_3$ | $SO_2CH_3$ | Cl | Het1 |
| 5732 | $OCH_2CH_3$ | $OCH_2CH_3$ | $SO_2CH_3$ | Cl | Het1 |
| 5733 | $OCH_2CH_2CH_3$ | $OCH_2CH_2CH_3$ | $SO_2CH_3$ | Cl | Het1 |
| 5734 | $SCH_3$ | $SCH_3$ | $SO_2CH_3$ | Cl | Het1 |
| 5735 | $SCH_2CH_3$ | $SCH_2CH_3$ | $SO_2CH_3$ | Cl | Het1 |
| 5736 | $N(CH_3)_2$ | $N(CH_3)_2$ | $SO_2CH_3$ | Cl | Het1 |
| 5737 | $N(CH_2CH_3)_2$ | $N(CH_2CH_3)_2$ | $SO_2CH_3$ | Cl | Het1 |
| 5738 | $N(CH_3)(CH_2CH_3)$ | $N(CH_3)(CH_2CH_3)$ | $SO_2CH_3$ | Cl | Het1 |
| 5739 | $O—(CH_2CH_2)—O$ | | $SO_2CH_3$ | Cl | Het1 |
| 5740 | $O—(CH_2CH_2CH_2)—O$ | | $SO_2CH_3$ | Cl | Het1 |
| 5741 | $S—(CH_2CH_2)—S$ | | $SO_2CH_3$ | Cl | Het1 |
| 5742 | $S—(CH_2CH_2CH_2)—S$ | | $SO_2CH_3$ | Cl | Het1 |
| 5743 | $—(CH_2)_4—$ | | $SO_2CH_3$ | Cl | Het1 |
| 5744 | $—(CH_2)_5—$ | | $SO_2CH_3$ | Cl | Het1 |
| 5745 | H | H | $PO(OCH_3)_2$ | Cl | Het1 |
| 5746 | $CH_3$ | $CH_3$ | $PO(OCH_3)_2$ | Cl | Het1 |
| 5747 | $CH_2CH_3$ | $CH_2CH_3$ | $PO(OCH_3)_2$ | Cl | Het1 |
| 5748 | $CH_2CH_2CH_3$ | $CH_2CH_2CH_3$ | $PO(OCH_3)_2$ | Cl | Het1 |
| 5749 | $OCH_3$ | $OCH_3$ | $PO(OCH_3)_2$ | Cl | Het1 |
| 5750 | $OCH_2CH_3$ | $OCH_2CH_3$ | $PO(OCH_3)_2$ | Cl | Het1 |
| 5751 | $OCH_2CH_2CH_3$ | $OCH_2CH_2CH_3$ | $PO(OCH_3)_2$ | Cl | Het1 |
| 5752 | $SCH_3$ | $SCH_3$ | $PO(OCH_3)_2$ | Cl | Het1 |
| 5753 | $SCH_2CH_3$ | $SCH_2CH_3$ | $PO(OCH_3)_2$ | Cl | Het1 |
| 5754 | $N(CH_3)_2$ | $N(CH_3)_2$ | $PO(OCH_3)_2$ | Cl | Het1 |
| 5755 | $N(CH_2CH_3)_2$ | $N(CH_2CH_3)_2$ | $PO(OCH_3)_2$ | Cl | Het1 |
| 5756 | $N(CH_3)(CH_2CH_3)$ | $N(CH_3)(CH_2CH_3)$ | $PO(OCH_3)_2$ | Cl | Het1 |
| 5757 | $O—(CH_2CH_2)—O$ | | $PO(OCH_3)_2$ | Cl | Het1 |
| 5758 | $O—(CH_2CH_2CH_2)—O$ | | $PO(OCH_3)_2$ | Cl | Het1 |
| 5759 | $S—(CH_2CH_2)—S$ | | $PO(OCH_3)_2$ | Cl | Het1 |
| 5760 | $S—(CH_2CH_2CH_2)—S$ | | $PO(OCH_3)_2$ | Cl | Het1 |
| 5761 | $—(CH_2)_4—$ | | $PO(OCH_3)_2$ | Cl | Het1 |
| 5762 | $—(CH_2)_5—$ | | $PO(OCH_3)_2$ | Cl | Het1 |
| 5763 | H | H | $PO(OCH_2CH_3)_2$ | Cl | Het1 |
| 5764 | $CH_3$ | $CH_3$ | $PO(OCH_2CH_3)_2$ | Cl | Het1 |

TABLE 1-continued

I1a1

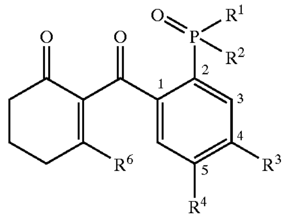

| n | $R^1$ | $R^2$ | $R^3$ | $R^4$ | $R^6$ |
|---|---|---|---|---|---|
| 5765 | $CH_2CH_3$ | $CH_2CH_3$ | $PO(OCH_2CH_3)_2$ | Cl | Het1 |
| 5766 | $CH_2CH_2CH_3$ | $CH_2CH_2CH_3$ | $PO(OCH_2CH_3)_2$ | Cl | Het1 |
| 5767 | $OCH_3$ | $OCH_3$ | $PO(OCH_2CH_3)_2$ | Cl | Het1 |
| 5768 | $OCH_2CH_3$ | $OCH_2CH_3$ | $PO(OCH_2CH_3)_2$ | Cl | Het1 |
| 5769 | $OCH_2CH_2CH_3$ | $OCH_2CH_2CH_3$ | $PO(OCH_2CH_3)_2$ | Cl | Het1 |
| 5770 | $SCH_3$ | $SCH_3$ | $PO(OCH_2CH_3)_2$ | Cl | Het1 |
| 5771 | $SCH_2CH_3$ | $SCH_2CH_3$ | $PO(OCH_2CH_3)_2$ | Cl | Het1 |
| 5772 | $N(CH_3)_2$ | $N(CH_3)_2$ | $PO(OCH_2CH_3)_2$ | Cl | Het1 |
| 5773 | $N(CH_2CH_3)_2$ | $N(CH_2CH_3)_2$ | $PO(OCH_2CH_3)_2$ | Cl | Het1 |
| 5774 | $N(CH_3)(CH_2CH_3)$ | $N(CH_3)(CH_2CH_3)$ | $PO(OCH_2CH_3)_2$ | Cl | Het1 |
| 5775 | $O-(CH_2CH_2)-O$ | | $PO(OCH_2CH_3)_2$ | Cl | Het1 |
| 5776 | $O-(CH_2CH_2CH_2)-O$ | | $PO(OCH_2CH_3)_2$ | Cl | Het1 |
| 5777 | $S-(CH_2CH_2)-S$ | | $PO(OCH_2CH_3)_2$ | Cl | Het1 |
| 5778 | $S-(CH_2CH_2CH_2)-S$ | | $PO(OCH_2CH_3)_2$ | Cl | Het1 |
| 5779 | $-(CH_2)_4-$ | | $PO(OCH_2CH_3)_2$ | Cl | Het1 |
| 5780 | $-(CH_2)_5-$ | | $PO(OCH_2CH_3)_2$ | Cl | Het1 |
| 5781 | H | H | $PO(CH_3)_2$ | Cl | Het1 |
| 5782 | $CH_3$ | $CH_3$ | $PO(CH_3)_2$ | Cl | Het1 |
| 5783 | $CH_2CH_3$ | $CH_2CH_3$ | $PO(CH_3)_2$ | Cl | Het1 |
| 5784 | $CH_2CH_2CH_3$ | $CH_2CH_2CH_3$ | $PO(CH_3)_2$ | Cl | Het1 |
| 5785 | $OCH_3$ | $OCH_3$ | $PO(CH_3)_2$ | Cl | Het1 |
| 5786 | $OCH_2CH_3$ | $OCH_2CH_3$ | $PO(CH_3)_2$ | Cl | Het1 |
| 5787 | $OCH_2CH_2CH_3$ | $OCH_2CH_2CH_3$ | $PO(CH_3)_2$ | Cl | Het1 |
| 5788 | $SCH_3$ | $SCH_3$ | $PO(CH_3)_2$ | Cl | Het1 |
| 5789 | $SCH_2CH_3$ | $SCH_2CH_3$ | $PO(CH_3)_2$ | Cl | Het1 |
| 5790 | $N(CH_3)_2$ | $N(CH_3)_2$ | $PO(CH_3)_2$ | Cl | Het1 |
| 5791 | $N(CH_2CH_3)_2$ | $N(CH_2CH_3)_2$ | $PO(CH_3)_2$ | Cl | Het1 |
| 5792 | $N(CH_3)(CH_2CH_3)$ | $N(CH_3)(CH_2CH_3)$ | $PO(CH_3)_2$ | Cl | Het1 |
| 5793 | $O-(CH_2CH_2)-O$ | | $PO(CH_3)_2$ | Cl | Het1 |
| 5794 | $O-(CH_2CH_2CH_2)-O$ | | $PO(CH_3)_2$ | Cl | Het1 |
| 5795 | $S-(CH_2CH_2)-S$ | | $PO(CH_3)_2$ | Cl | Het1 |
| 5796 | $S-(CH_2CH_2CH_2)-S$ | | $PO(CH_3)_2$ | Cl | Het1 |
| 5797 | $-(CH_2)_4-$ | | $PO(CH_3)_2$ | Cl | Het1 |
| 5798 | $-(CH_2)_5-$ | | $PO(CH_3)_2$ | Cl | Het1 |
| 5799 | H | H | $PC(CH_2CH_3)_2$ | Cl | Het1 |
| 5800 | $CH_3$ | $CH_3$ | $PC(CH_2CH_3)_2$ | Cl | Het1 |
| 5801 | $CH_2CH_3$ | $CH_2CH_3$ | $PC(CH_2CH_3)_2$ | Cl | Het1 |
| 5802 | $CH_2CH_2CH_3$ | $CH_2CH_2CH_3$ | $PC(CH_2CH_3)_2$ | Cl | Het1 |
| 5803 | $OCH_3$ | $OCH_3$ | $PC(CH_2CH_3)_2$ | Cl | Het1 |
| 5804 | $OCH_2CH_3$ | $OCH_2CH_3$ | $PC(CH_2CH_3)_2$ | Cl | Het1 |
| 5805 | $OCH_2CH_2CH_3$ | $OCH_2CH_2CH_3$ | $PC(CH_2CH_3)_2$ | Cl | Het1 |
| 5806 | $SCH_3$ | $SCH_3$ | $PC(CH_2CH_3)_2$ | Cl | Het1 |
| 5807 | $SCH_2CH_3$ | $SCH_2CH_3$ | $PC(CH_2CH_3)_2$ | Cl | Het1 |
| 5808 | $N(CH_3)_2$ | $N(CH_3)_2$ | $PC(CH_2CH_3)_2$ | Cl | Het1 |
| 5809 | $N(CH_2CH_3)_2$ | $N(CH_2CH_3)_2$ | $PC(CH_2CH_3)_2$ | Cl | Het1 |
| 5810 | $N(CH_3)(CH_2CH_3)$ | $N(CH_3)(CH_2CH_3)$ | $PC(CH_2CH_3)_2$ | Cl | Het1 |
| 5811 | $O-(CH_2CH_2)-O$ | | $PC(CH_2CH_3)_2$ | Cl | Het1 |
| 5812 | $O-(CH_2CH_2CH_2)-O$ | | $PC(CH_2CH_3)_2$ | Cl | Het1 |
| 5813 | $S-(CH_2CH_2)-S$ | | $PC(CH_2CH_3)_2$ | Cl | Het1 |
| 5814 | $S-(CH_2CH_2CH_2)-S$ | | $PC(CH_2CH_3)_2$ | Cl | Het1 |
| 5815 | $-(CH_2)_4-$ | | $PC(CH_2CH_3)_2$ | Cl | Het1 |
| 5816 | $-(CH_2)_5-$ | | $PC(CH_2CH_3)_2$ | Cl | Het1 |
| 5817 | H | H | H | Cl | Het2 |
| 5818 | $CH_3$ | $CH_3$ | H | Cl | Het2 |
| 5819 | $CH_2CH_3$ | $CH_2CH_3$ | H | Cl | Het2 |
| 5820 | $CH_2CH_2CH_3$ | $CH_2CH_2CH_3$ | H | Cl | Het2 |
| 5821 | $OCH_3$ | $OCH_3$ | H | Cl | Het2 |
| 5822 | $OCH_2CH_3$ | $OCH_2CH_3$ | H | Cl | Het2 |
| 5823 | $OCH_2CH_2CH_3$ | $OCH_2CH_2CH_3$ | H | Cl | Het2 |
| 5824 | $SCH_3$ | $SCH_3$ | H | Cl | Het2 |
| 5825 | $SCH_2CH_3$ | $SCH_2CH_3$ | H | Cl | Het2 |
| 5826 | $N(CH_3)_2$ | $N(CH_3)_2$ | H | Cl | Het2 |
| 5827 | $N(CH_2CH_3)_2$ | $N(CH_2CH_3)_2$ | H | Cl | Het2 |
| 5828 | $N(CH_3)(CH_2CH_3)$ | $N(CH_3)(CH_2CH_3)$ | H | Cl | Het2 |

TABLE 1-continued

I1a1

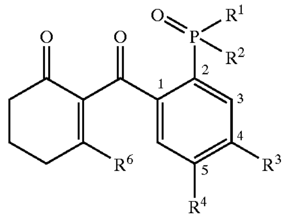

| n | $R^1$ | $R^2$ | $R^3$ | $R^4$ | $R^6$ |
|---|---|---|---|---|---|
| 5829 | O—$(CH_2CH_2)$—O | | H | Cl | Het2 |
| 5830 | O—$(CH_2CH_2CH_2)$—O | | H | Cl | Het2 |
| 5831 | S—$(CH_2CH_2)$—S | | H | Cl | Het2 |
| 5832 | S—$(CH_2CH_2CH_2)$—S | | H | Cl | Het2 |
| 5833 | —$(CH_2)_4$— | | H | Cl | Het2 |
| 5834 | —$(CH_2)_5$— | | H | Cl | Het2 |
| 5835 | H | H | $NO_2$ | Cl | Het2 |
| 5836 | $CH_3$ | $CH_3$ | $NO_2$ | Cl | Het2 |
| 5837 | $CH_2CH_3$ | $CH_2CH_3$ | $NO_2$ | Cl | Het2 |
| 5838 | $CH_2CH_2CH_3$ | $CH_2CH_2CH_3$ | $NO_2$ | Cl | Het2 |
| 5839 | $OCH_3$ | $OCH_3$ | $NO_2$ | Cl | Het2 |
| 5840 | $OCH_2CH_3$ | $OCH_2CH_3$ | $NO_2$ | Cl | Het2 |
| 5841 | $OCH_2CH_2CH_3$ | $OCH_2CH_2CH_3$ | $NO_2$ | Cl | Het2 |
| 5842 | $SCH_3$ | $SCH_3$ | $NO_2$ | Cl | Het2 |
| 5843 | $SCH_2CH_3$ | $SCH_2CH_3$ | $NO_2$ | Cl | Het2 |
| 5844 | $N(CH_3)_2$ | $N(CH_3)_2$ | $NO_2$ | Cl | Het2 |
| 5845 | $N(CH_2CH_3)_2$ | $N(CH_2CH_3)_2$ | $NO_2$ | Cl | Het2 |
| 5846 | $N(CH_3)(CH_2CH_3)$ | $N(CH_3)(CH_2CH_3)$ | $NO_2$ | Cl | Het2 |
| 5847 | O—$(CH_2CH_2)$—O | | $NO_2$ | Cl | Het2 |
| 5848 | O—$(CH_2CH_2CH_2)$—O | | $NO_2$ | Cl | Het2 |
| 5849 | S—$(CH_2CH_2)$—S | | $NO_2$ | Cl | Het2 |
| 5850 | S—$(CH_2CH_2CH_2)$—S | | $NO_2$ | Cl | Het2 |
| 5851 | —$(CH_2)_4$— | | $NO_2$ | Cl | Het2 |
| 5852 | —$(CH_2)_5$— | | $NO_2$ | Cl | Het2 |
| 5853 | H | H | CN | Cl | Het2 |
| 5854 | $CH_3$ | $CH_3$ | CN | Cl | Het2 |
| 5855 | $CH_2CH_3$ | $CH_2CH_3$ | CN | Cl | Het2 |
| 5856 | $CH_2CH_2CH_3$ | $CH_2CH_2CH_3$ | CN | Cl | Het2 |
| 5857 | $OCH_3$ | $OCH_3$ | CN | Cl | Het2 |
| 5858 | $OCH_2CH_3$ | $OCH_2CH_3$ | CN | Cl | Het2 |
| 5859 | $OCH_2CH_2CH_3$ | $OCH_2CH_2CH_3$ | CN | Cl | Het2 |
| 5860 | $SCH_3$ | $SCH_3$ | CN | Cl | Het2 |
| 5861 | $SCH_2CH_3$ | $SCH_2CH_3$ | CN | Cl | Het2 |
| 5862 | $N(CH_3)_2$ | $N(CH_3)_2$ | CN | Cl | Het2 |
| 5863 | $N(CH_2CH_3)_2$ | $N(CH_2CH_3)_2$ | CN | Cl | Het2 |
| 5864 | $N(CH_3)(CH_2CH_3)$ | $N(CH_3)(CH_2CH_3)$ | CN | Cl | Het2 |
| 5865 | O—$(CH_2CH_2)$—O | | CN | Cl | Het2 |
| 5866 | O—$(CH_2CH_2CH_2)$—O | | CN | Cl | Het2 |
| 5867 | S—$(CH_2CH_2)$—S | | CN | Cl | Het2 |
| 5868 | S—$(CH_2CH_2CH_2)$—S | | CN | Cl | Het2 |
| 5869 | —$(CH_2)_4$— | | CN | Cl | Het2 |
| 5870 | —$(CH_2)_5$— | | CN | Cl | Het2 |
| 5871 | H | H | F | Cl | Het2 |
| 5872 | $CH_3$ | $CH_3$ | F | Cl | Het2 |
| 5873 | $CH_2CH_3$ | $CH_2CH_3$ | F | Cl | Het2 |
| 5874 | $CH_2CH_2CH_3$ | $CH_2CH_2CH_3$ | F | Cl | Het2 |
| 5875 | $OCH_3$ | $OCH_3$ | F | Cl | Het2 |
| 5876 | $OCH_2CH_3$ | $OCH_2CH_3$ | F | Cl | Het2 |
| 5877 | $OCH_2CH_2CH_3$ | $OCH_2CH_2CH_3$ | F | Cl | Het2 |
| 5878 | $SCH_3$ | $SCH_3$ | F | Cl | Het2 |
| 5879 | $SCH_2CH_3$ | $SCH_2CH_3$ | F | Cl | Het2 |
| 5880 | $N(CH_3)_2$ | $N(CH_3)_2$ | F | Cl | Het2 |
| 5881 | $N(CH_2CH_3)_2$ | $N(CH_2CH_3)_2$ | F | Cl | Het2 |
| 5882 | $N(CH_3)(CH_2CH_3)$ | $N(CH_3)(CH_2CH_3)$ | F | Cl | Het2 |
| 5883 | O—$(CH_2CH_2)$—O | | F | Cl | Het2 |
| 5884 | O—$(CH_2CH_2CH_2)$—O | | F | Cl | Het2 |
| 5885 | S—$(CH_2CH_2)$—S | | F | Cl | Het2 |
| 5886 | S—$(CH_2CH_2CH_2)$—S | | F | Cl | Het2 |
| 5887 | —$(CH_2)_4$— | | F | Cl | Het2 |
| 5888 | —$(CH_2)_5$— | | F | Cl | Het2 |
| 5889 | H | H | Cl | Cl | Het2 |
| 5890 | $CH_3$ | $CH_3$ | Cl | Cl | Het2 |
| 5891 | $CH_2CH_3$ | $CH_2CH_3$ | Cl | Cl | Het2 |
| 5892 | $CH_2CH_2CH_3$ | $CH_2CH_2CH_3$ | Cl | Cl | Het2 |

TABLE 1-continued

I1a1

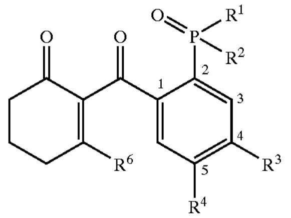

| n | $R^1$ | $R^2$ | $R^3$ | $R^4$ | $R^6$ |
|---|---|---|---|---|---|
| 5893 | $OCH_3$ | $OCH_3$ | Cl | Cl | Het2 |
| 5894 | $OCH_2CH_3$ | $OCH_2CH_3$ | Cl | Cl | Het2 |
| 5895 | $OCH_2CH_2CH_3$ | $OCH_2CH_2CH_3$ | Cl | Cl | Het2 |
| 5896 | $SCH_3$ | $SCH_3$ | Cl | Cl | Het2 |
| 5897 | $SCH_2CH_3$ | $SCH_2CH_3$ | Cl | Cl | Het2 |
| 5898 | $N(CH_3)_2$ | $N(CH_3)_2$ | Cl | Cl | Het2 |
| 5899 | $N(CH_2CH_3)_2$ | $N(CH_2CH_3)_2$ | Cl | Cl | Het2 |
| 5900 | $N(CH_3)(CH_2CH_3)$ | $N(CH_3)(CH_2CH_3)$ | Cl | Cl | Het2 |
| 5901 | $O—(CH_2CH_2)—O$ | | Cl | Cl | Het2 |
| 5902 | $O—(CH_2CH_2CH_2)—O$ | | Cl | Cl | Het2 |
| 5903 | $S—(CH_2CH_2)—S$ | | Cl | Cl | Het2 |
| 5904 | $S—(CH_2CH_2CH_2)—S$ | | Cl | Cl | Het2 |
| 5905 | $—(CH_2)_4—$ | | Cl | Cl | Het2 |
| 5906 | $—(CH_2)_5—$ | | Cl | Cl | Het2 |
| 5907 | H | H | Br | Cl | Het2 |
| 5908 | $CH_3$ | $CH_3$ | Br | Cl | Het2 |
| 5909 | $CH_2CH_3$ | $CH_2CH_3$ | Br | Cl | Het2 |
| 5910 | $CH_2CH_2CH_3$ | $CH_2CH_2CH_3$ | Br | Cl | Het2 |
| 5911 | $OCH_3$ | $OCH_3$ | Br | Cl | Het2 |
| 5912 | $OCH_2CH_3$ | $OCH_2CH_3$ | Br | Cl | Het2 |
| 5913 | $OCH_2CH_2CH_3$ | $OCH_2CH_2CH_3$ | Br | Cl | Het2 |
| 5914 | $SCH_3$ | $SCH_3$ | Br | Cl | Het2 |
| 5915 | $SCH_2CH_3$ | $SCH_2CH_3$ | Br | Cl | Het2 |
| 5916 | $N(CH_3)_2$ | $N(CH_3)_2$ | Br | Cl | Het2 |
| 5917 | $N(CH_2CH_3)_2$ | $N(CH_2CH_3)_2$ | Br | Cl | Het2 |
| 5918 | $N(CH_3)(CH_2CH_3)$ | $N(CH_3)(CH_2CH_3)$ | Br | Cl | Het2 |
| 5919 | $O—(CH_2CH_2)—O$ | | Br | Cl | Het2 |
| 5920 | $O—(CH_2CH_2CH_2)—O$ | | Br | Cl | Het2 |
| 5921 | $S—(CH_2CH_2)—S$ | | Br | Cl | Het2 |
| 5922 | $S—(CH_2CH_2CH_2)—S$ | | Br | Cl | Het2 |
| 5923 | $—(CH_2)_4—$ | | Br | Cl | Het2 |
| 5924 | $—(CH_2)_5—$ | | Br | Cl | Het2 |
| 5925 | H | H | $CH_3$ | Cl | Het2 |
| 5926 | $CH_3$ | $CH_3$ | $CH_3$ | Cl | Het2 |
| 5927 | $CH_2CH_3$ | $CH_2CH_3$ | $CH_3$ | Cl | Het2 |
| 5928 | $CH_2CH_2CH_3$ | $CH_2CH_2CH_3$ | $CH_3$ | Cl | Het2 |
| 5929 | $OCH_3$ | $OCH_3$ | $CH_3$ | Cl | Het2 |
| 5930 | $OCH_2CH_3$ | $OCH_2CH_3$ | $CH_3$ | Cl | Het2 |
| 5931 | $OCH_2CH_2CH_3$ | $OCH_2CH_2CH_3$ | $CH_3$ | Cl | Het2 |
| 5932 | $SCH_3$ | $SCH_3$ | $CH_3$ | Cl | Het2 |
| 5933 | $SCH_2CH_3$ | $SCH_2CH_3$ | $CH_3$ | Cl | Het2 |
| 5934 | $N(CH_3)_2$ | $N(CH_3)_2$ | $CH_3$ | Cl | Het2 |
| 5935 | $N(CH_2CH_3)_2$ | $N(CH_2CH_3)_2$ | $CH_3$ | Cl | Het2 |
| 5936 | $N(CH_3)(CH_2CH_3)$ | $N(CH_3)(CH_2CH_3)$ | $CH_3$ | Cl | Het2 |
| 5937 | $O—(CH_2CH_2)—O$ | | $CH_3$ | Cl | Het2 |
| 5938 | $O—(CH_2CH_2CH_2)—O$ | | $CH_3$ | Cl | Het2 |
| 5939 | $S—(CH_2CH_2)—S$ | | $CH_3$ | Cl | Het2 |
| 5940 | $S—(CH_2CH_2CH_2)—S$ | | $CH_3$ | Cl | Het2 |
| 5941 | $—(CH_2)_4—$ | | $CH_3$ | Cl | Het2 |
| 5942 | $—(CH_2)_5—$ | | $CH_3$ | Cl | Het2 |
| 5943 | H | H | $CH_2CH_3$ | Cl | Het2 |
| 5944 | $CH_3$ | $CH_3$ | $CH_2CH_3$ | Cl | Het2 |
| 5945 | $CH_2CH_3$ | $CH_2CH_3$ | $CH_2CH_3$ | Cl | Het2 |
| 5946 | $CH_2CH_2CH_3$ | $CH_2CH_2CH_3$ | $CH_2CH_3$ | Cl | Het2 |
| 5947 | $OCH_3$ | $OCH_3$ | $CH_2CH_3$ | Cl | Het2 |
| 5948 | $OCH_2CH_3$ | $OCH_2CH_3$ | $CH_2CH_3$ | Cl | Het2 |
| 5949 | $OCH_2CH_2CH_3$ | $OCH_2CH_2CH_3$ | $CH_2CH_3$ | Cl | Het2 |
| 5950 | $SCH_3$ | $SCH_3$ | $CH_2CH_3$ | Cl | Het2 |
| 5951 | $SCH_2CH_3$ | $SCH_2CH_3$ | $CH_2CH_3$ | Cl | Het2 |
| 5952 | $N(CH_3)_2$ | $N(CH_3)_2$ | $CH_2CH_3$ | Cl | Het2 |
| 5953 | $N(CH_2CH_3)_2$ | $N(CH_2CH_3)_2$ | $CH_2CH_3$ | Cl | Het2 |
| 5954 | $N(CH_3)(CH_2CH_3)$ | $N(CH_3)(CH_2CH_3)$ | $CH_2CH_3$ | Cl | Het2 |
| 5955 | $O—(CH_2CH_2)—O$ | | $CH_2CH_3$ | Cl | Het2 |
| 5956 | $O—(CH_2CH_2CH_2)—O$ | | $CH_2CH_3$ | Cl | Het2 |

TABLE 1-continued

I1a1

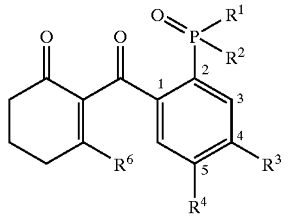

| n | $R^1$ | $R^2$ | $R^3$ | $R^4$ | $R^6$ |
|---|---|---|---|---|---|
| 5957 | S—$(CH_2CH_2)$—S | | $CH_2CH_3$ | Cl | Het2 |
| 5958 | S—$(CH_2CH_2CH_2)$—S | | $CH_2CH_3$ | Cl | Het2 |
| 5959 | —$(CH_2)_4$— | | $CH_2CH_3$ | Cl | Het2 |
| 5960 | —$(CH_2)_5$— | | $CH_2CH_3$ | Cl | Het2 |
| 5961 | H | H | $CF_3$ | Cl | Het2 |
| 5962 | $CH_3$ | $CH_3$ | $CF_3$ | Cl | Het2 |
| 5963 | $CH_2CH_3$ | $CH_2CH_3$ | $CF_3$ | Cl | Het2 |
| 5964 | $CH_2CH_2CH_3$ | $CH_2CH_2CH_3$ | $CF_3$ | Cl | Het2 |
| 5965 | $OCH_3$ | $OCH_3$ | $CF_3$ | Cl | Het2 |
| 5966 | $OCH_2CH_3$ | $OCH_2CH_3$ | $CF_3$ | Cl | Het2 |
| 5967 | $OCH_2CH_2CH_3$ | $OCH_2CH_2CH_3$ | $CF_3$ | Cl | Het2 |
| 5968 | $SCH_3$ | $SCH_3$ | $CF_3$ | Cl | Het2 |
| 5969 | $SCH_2CH_3$ | $SCH_2CH_3$ | $CF_3$ | Cl | Het2 |
| 5970 | $N(CH_3)_2$ | $N(CH_3)_2$ | $CF_3$ | Cl | Het2 |
| 5971 | $N(CH_2CH_3)_2$ | $N(CH_2CH_3)_2$ | $CF_3$ | Cl | Het2 |
| 5972 | $N(CH_3)(CH_2CH_3)$ | $N(CH_3)(CH_2CH_3)$ | $CF_3$ | Cl | Het2 |
| 5973 | O—$(CH_2CH_2)$—O | | $CF_3$ | Cl | Het2 |
| 5974 | O—$(CH_2CH_2CH_2)$—O | | $CF_3$ | Cl | Het2 |
| 5975 | S—$(CH_2CH_2)$—S | | $CF_3$ | Cl | Het2 |
| 5976 | S—$(CH_2CH_2CH_2)$—S | | $CF_3$ | Cl | Het2 |
| 5977 | —$(CH_2)_4$— | | $CF_3$ | Cl | Het2 |
| 5978 | —$(CH_2)_5$— | | $CF_3$ | Cl | Het2 |
| 5979 | H | H | $OCH_3$ | Cl | Het2 |
| 5980 | $CH_3$ | $CH_3$ | $OCH_3$ | Cl | Het2 |
| 5981 | $CH_2CH_3$ | $CH_2CH_3$ | $OCH_3$ | Cl | Het2 |
| 5982 | $CH_2CH_2CH_3$ | $CH_2CH_2CH_3$ | $OCH_3$ | Cl | Het2 |
| 5983 | $OCH_3$ | $OCH_3$ | $OCH_3$ | Cl | Het2 |
| 5984 | $OCH_2CH_3$ | $OCH_2CH_3$ | $OCH_3$ | Cl | Het2 |
| 5985 | $OCH_2CH_2CH_3$ | $OCH_2CH_2CH_3$ | $OCH_3$ | Cl | Het2 |
| 5986 | $SCH_3$ | $SCH_3$ | $OCH_3$ | Cl | Het2 |
| 5987 | $SCH_2CH_3$ | $SCH_2CH_3$ | $OCH_3$ | Cl | Het2 |
| 5988 | $N(CH_3)_2$ | $N(CH_3)_2$ | $OCH_3$ | Cl | Het2 |
| 5989 | $N(CH_2CH_3)_2$ | $N(CH_2CH_3)_2$ | $OCH_3$ | Cl | Het2 |
| 5990 | $N(CH_3)(CH_2CH_3)$ | $N(CH_3)(CH_2CH_3)$ | $OCH_3$ | Cl | Het2 |
| 5991 | O—$(CH_2CH_2)$—O | | $OCH_3$ | Cl | Het2 |
| 5992 | O—$(CH_2CH_2CH_2)$—O | | $OCH_3$ | Cl | Het2 |
| 5993 | S—$(CH_2CH_2)$—S | | $OCH_3$ | Cl | Het2 |
| 5994 | S—$(CH_2CH_2CH_2)$—S | | $OCH_3$ | Cl | Het2 |
| 5995 | —$(CH_2)_4$— | | $OCH_3$ | Cl | Het2 |
| 5996 | —$(CH_2)_5$— | | $OCH_3$ | Cl | Het2 |
| 5997 | H | H | $OCH_2CH_3$ | Cl | Het2 |
| 5998 | $CH_3$ | $CH_3$ | $OCH_2CH_3$ | Cl | Het2 |
| 5999 | $CH_2CH_3$ | $CH_2CH_3$ | $OCH_2CH_3$ | Cl | Het2 |
| 6000 | $CH_2CH_2CH_3$ | $CH_2CH_2CH_3$ | $OCH_2CH_3$ | Cl | Het2 |
| 6001 | $OCH_3$ | $OCH_3$ | $OCH_2CH_3$ | Cl | Het2 |
| 6002 | $OCH_2CH_3$ | $OCH_2CH_3$ | $OCH_2CH_3$ | Cl | Het2 |
| 6003 | $OCH_2CH_2CH_3$ | $OCH_2CH_2CH_3$ | $OCH_2CH_3$ | Cl | Het2 |
| 6004 | $SCH_3$ | $SCH_3$ | $OCH_2CH_3$ | Cl | Het2 |
| 6005 | $SCH_2CH_3$ | $SCH_2CH_3$ | $OCH_2CH_3$ | Cl | Het2 |
| 6006 | $N(CH_3)_2$ | $N(CH_3)_2$ | $OCH_2CH_3$ | Cl | Het2 |
| 6007 | $N(CH_2CH_3)_2$ | $N(CH_2CH_3)_2$ | $OCH_2CH_3$ | Cl | Het2 |
| 6008 | $N(CH_3)(CH_2CH_3)$ | $N(CH_3)(CH_2CH_3)$ | $OCH_2CH_3$ | Cl | Het2 |
| 6009 | O—$(CH_2CH_2)$—O | | $OCH_2CH_3$ | Cl | Het2 |
| 6010 | O—$(CH_2CH_2CH_2)$—O | | $OCH_2CH_3$ | Cl | Het2 |
| 6011 | S—$(CH_2CH_2)$—S | | $OCH_2CH_3$ | Cl | Het2 |
| 6012 | S—$(CH_2CH_2CH_2)$—S | | $OCH_2CH_3$ | Cl | Het2 |
| 6013 | —$(CH_2)_4$— | | $OCH_2CH_3$ | Cl | Het2 |
| 6014 | —$(CH_2)_5$— | | $OCH_2CH_3$ | Cl | Het2 |
| 6015 | H | H | $SCH_3$ | Cl | Het2 |
| 6016 | $CH_3$ | $CH_3$ | $SCH_3$ | Cl | Het2 |
| 6017 | $CH_2CH_3$ | $CH_2CH_3$ | $SCH_3$ | Cl | Het2 |
| 6018 | $CH_2CH_2CH_3$ | $CH_2CH_2CH_3$ | $SCH_3$ | Cl | Het2 |
| 6019 | $OCH_3$ | $OCH_3$ | $SCH_3$ | Cl | Het2 |
| 6020 | $OCH_2CH_3$ | $OCH_2CH_3$ | $SCH_3$ | Cl | Het2 |

TABLE 1-continued

I1a1

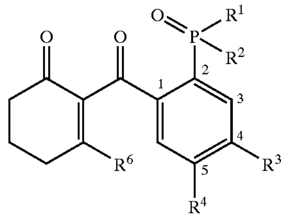

| n | $R^1$ | $R^2$ | $R^3$ | $R^4$ | $R^6$ |
|---|---|---|---|---|---|
| 6021 | $OCH_2CH_2CH_3$ | $OCH_2CH_2CH_3$ | $SCH_3$ | Cl | Het2 |
| 6022 | $SCH_3$ | $SCH_3$ | $SCH_3$ | Cl | Het2 |
| 6023 | $SCH_2CH_3$ | $SCH_2CH_3$ | $SCH_3$ | Cl | Het2 |
| 6024 | $N(CH_3)_2$ | $N(CH_3)_2$ | $SCH_3$ | Cl | Het2 |
| 6025 | $N(CH_2CH_3)_2$ | $N(CH_2CH_3)_2$ | $SCH_3$ | Cl | Het2 |
| 6026 | $N(CH_3)(CH_2CH_3)$ | $N(CH_3)(CH_2CH_3)$ | $SCH_3$ | Cl | Het2 |
| 6027 | $O-(CH_2CH_2)-O$ | | $SCH_3$ | Cl | Het2 |
| 6028 | $O-(CH_2CH_2CH_2)-O$ | | $SCH_3$ | Cl | Het2 |
| 6029 | $S-(CH_2CH_2)-S$ | | $SCH_3$ | Cl | Het2 |
| 6030 | $S-(CH_2CH_2CH_2)-S$ | | $SCH_3$ | Cl | Het2 |
| 6031 | $-(CH_2)_4-$ | | $SCH_3$ | Cl | Het2 |
| 6032 | $-(CH_2)_5-$ | | $SCH_3$ | Cl | Het2 |
| 6033 | H | H | $SO_2CH_3$ | Cl | Het2 |
| 6034 | $CH_3$ | $CH_3$ | $SO_2CH_3$ | Cl | Het2 |
| 6035 | $CH_2CH_3$ | $CH_2CH_3$ | $SO_2CH_3$ | Cl | Het2 |
| 6036 | $CH_2CH_2CH_3$ | $CH_2CH_2CH_3$ | $SO_2CH_3$ | Cl | Het2 |
| 6037 | $OCH_3$ | $OCH_3$ | $SO_2CH_3$ | Cl | Het2 |
| 6038 | $OCH_2CH_3$ | $OCH_2CH_3$ | $SO_2CH_3$ | Cl | Het2 |
| 6039 | $OCH_2CH_2CH_3$ | $OCH_2CH_2CH_3$ | $SO_2CH_3$ | Cl | Het2 |
| 6040 | $SCH_3$ | $SCH_3$ | $SO_2CH_3$ | Cl | Het2 |
| 6041 | $SCH_2CH_3$ | $SCH_2CH_3$ | $SO_2CH_3$ | Cl | Het2 |
| 6042 | $N(CH_3)_2$ | $N(CH_3)_2$ | $SO_2CH_3$ | Cl | Het2 |
| 6043 | $N(CH_2CH_3)_2$ | $N(CH_2CH_3)_2$ | $SO_2CH_3$ | Cl | Het2 |
| 6044 | $N(CH_3)(CH_2CH_3)$ | $N(CH_3)(CH_2CH_3)$ | $SO_2CH_3$ | Cl | Het2 |
| 6045 | $O-(CH_2CH_2)-O$ | | $SO_2CH_3$ | Cl | Het2 |
| 6046 | $O-(CH_2CH_2CH_2)-O$ | | $SO_2CH_3$ | Cl | Het2 |
| 6047 | $S-(CH_2CH_2)-S$ | | $SO_2CH_3$ | Cl | Het2 |
| 6048 | $S-(CH_2CH_2CH_2)-S$ | | $SO_2CH_3$ | Cl | Het2 |
| 6049 | $-(CH_2)_4-$ | | $SO_2CH_3$ | Cl | Het2 |
| 6050 | $-(CH_2)_5-$ | | $SO_2CH_3$ | Cl | Het2 |
| 6051 | H | H | $PO(OCH_3)_2$ | Cl | Het2 |
| 6052 | $CH_3$ | $CH_3$ | $PO(OCH_3)_2$ | Cl | Het2 |
| 6053 | $CH_2CH_3$ | $CH_2CH_3$ | $PO(OCH_3)_2$ | Cl | Het2 |
| 6054 | $CH_2CH_2CH_3$ | $CH_2CH_2CH_3$ | $PO(OCH_3)_2$ | Cl | Het2 |
| 6055 | $OCH_3$ | $OCH_3$ | $PO(OCH_3)_2$ | Cl | Het2 |
| 6056 | $OCH_2CH_3$ | $OCH_2CH_3$ | $PO(OCH_3)_2$ | Cl | Het2 |
| 6057 | $OCH_2CH_2CH_3$ | $OCH_2CH_2CH_3$ | $PO(OCH_3)_2$ | Cl | Het2 |
| 6058 | $SCH_3$ | $SCH_3$ | $PO(OCH_3)_2$ | Cl | Het2 |
| 6059 | $SCH_2CH_3$ | $SCH_2CH_3$ | $PO(OCH_3)_2$ | Cl | Het2 |
| 6060 | $N(CH_3)_2$ | $N(CH_3)_2$ | $PO(OCH_3)_2$ | Cl | Het2 |
| 6061 | $N(CH_2CH_3)_2$ | $N(CH_2CH_3)_2$ | $PO(OCH_3)_2$ | Cl | Het2 |
| 6062 | $N(CH_3)(CH_2CH_3)$ | $N(CH_3)(CH_2CH_3)$ | $PO(OCH_3)_2$ | Cl | Het2 |
| 6063 | $O-(CH_2CH_2)-O$ | | $PO(OCH_3)_2$ | Cl | Het2 |
| 6064 | $O-(CH_2CH_2CH_2)-O$ | | $PO(OCH_3)_2$ | Cl | Het2 |
| 6065 | $S-(CH_2CH_2)-S$ | | $PO(OCH_3)_2$ | Cl | Het2 |
| 6066 | $S-(CH_2CH_2CH_2)-S$ | | $PO(OCH_3)_2$ | Cl | Het2 |
| 6067 | $-(CH_2)_4-$ | | $PO(OCH_3)_2$ | Cl | Het2 |
| 6068 | $-(CH_2)_5-$ | | $PO(OCH_3)_2$ | Cl | Het2 |
| 6069 | H | H | $PO(OCH_2CH_3)_2$ | Cl | Het2 |
| 6070 | $CH_3$ | $CH_3$ | $PO(OCH_2CH_3)_2$ | Cl | Het2 |
| 6071 | $CH_2CH_3$ | $CH_2CH_3$ | $PO(OCH_2CH_3)_2$ | Cl | Het2 |
| 6072 | $CH_2CH_2CH_3$ | $CH_2CH_2CH_3$ | $PO(OCH_2CH_3)_2$ | Cl | Het2 |
| 6073 | $OCH_3$ | $OCH_3$ | $PO(OCH_2CH_3)_2$ | Cl | Het2 |
| 6074 | $OCH_2CH_3$ | $OCH_2CH_3$ | $PO(OCH_2CH_3)_2$ | Cl | Het2 |
| 6075 | $OCH_2CH_2CH_3$ | $OCH_2CH_2CH_3$ | $PO(OCH_2CH_3)_2$ | Cl | Het2 |
| 6076 | $SCH_3$ | $SCH_3$ | $PO(OCH_2CH_3)_2$ | Cl | Het2 |
| 6077 | $SCH_2CH_3$ | $SCH_2CH_3$ | $PO(OCH_2CH_3)_2$ | Cl | Het2 |
| 6078 | $N(CH_3)_2$ | $N(CH_3)_2$ | $PO(OCH_2CH_3)_2$ | Cl | Het2 |
| 6079 | $N(CH_2CH_3)_2$ | $N(CH_2CH_3)_2$ | $PO(OCH_2CH_3)_2$ | Cl | Het2 |
| 6080 | $N(CH_3)(CH_2CH_3)$ | $N(CH_3)(CH_2CH_3)$ | $PO(OCH_2CH_3)_2$ | Cl | Het2 |
| 6081 | $O-(CH_2CH_2)-O$ | | $PO(OCH_2CH_3)_2$ | Cl | Het2 |
| 6082 | $O-(CH_2CH_2CH_2)-O$ | | $PO(OCH_2CH_3)_2$ | Cl | Het2 |
| 6083 | $S-(CH_2CH_2)-S$ | | $PO(OCH_2CH_3)_2$ | Cl | Het2 |
| 6084 | $S-(CH_2CH_2CH_2)-S$ | | $PO(OCH_2CH_3)_2$ | Cl | Het2 |

TABLE 1-continued

I1a1

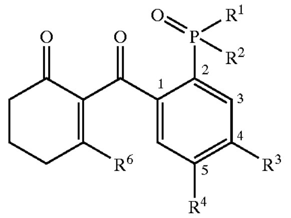

| n | $R^1$ | $R^2$ | $R^3$ | $R^4$ | $R^6$ |
|---|---|---|---|---|---|
| 6085 | —$(CH_2)_4$— | | $PO(OCH_2CH_3)_2$ | Cl | Het2 |
| 6086 | —$(CH_2)_5$— | | $PO(OCH_2CH_3)_2$ | Cl | Het2 |
| 6087 | H | H | $PO(CH_3)_2$ | Cl | Het2 |
| 6088 | $CH_3$ | $CH_3$ | $PO(CH_3)_2$ | Cl | Het2 |
| 6089 | $CH_2CH_3$ | $CH_2CH_3$ | $PO(CH_3)_2$ | Cl | Het2 |
| 6090 | $CH_2CH_2CH_3$ | $CH_2CH_2CH_3$ | $PO(CH_3)_2$ | Cl | Het2 |
| 6091 | $OCH_3$ | $OCH_3$ | $PO(CH_3)_2$ | Cl | Het2 |
| 6092 | $OCH_2CH_3$ | $OCH_2CH_3$ | $PO(CH_3)_2$ | Cl | Het2 |
| 6093 | $OCH_2CH_2CH_3$ | $OCH_2CH_2CH_3$ | $PO(CH_3)_2$ | Cl | Het2 |
| 6094 | $SCH_3$ | $SCH_3$ | $PO(CH_3)_2$ | Cl | Het2 |
| 6095 | $SCH_2CH_3$ | $SCH_2CH_3$ | $PO(CH_3)_2$ | Cl | Het2 |
| 6096 | $N(CH_3)_2$ | $N(CH_3)_2$ | $PO(CH_3)_2$ | Cl | Het2 |
| 6097 | $N(CH_2CH_3)_2$ | $N(CH_2CH_3)_2$ | $PO(CH_3)_2$ | Cl | Het2 |
| 6098 | $N(CH_3)(CH_2CH_3)$ | $N(CH_3)(CH_2CH_3)$ | $PO(CH_3)_2$ | Cl | Het2 |
| 6099 | O—$(CH_2CH_2)$—O | | $PO(CH_3)_2$ | Cl | Het2 |
| 6100 | O—$(CH_2CH_2CH_2)$—O | | $PO(CH_3)_2$ | Cl | Het2 |
| 6101 | S—$(CH_2CH_2)$—S | | $PO(CH_3)_2$ | Cl | Het2 |
| 6102 | S—$(CH_2CH_2CH_2)$—S | | $PO(CH_3)_2$ | Cl | Het2 |
| 6103 | —$(CH_2)_4$— | | $PO(CH_3)_2$ | Cl | Het2 |
| 6104 | —$(CH_2)_5$— | | $PO(CH_3)_2$ | Cl | Het2 |
| 6105 | H | H | $PC(CH_2CH_3)_2$ | Cl | Het2 |
| 6106 | $CH_3$ | $CH_3$ | $PC(CH_2CH_3)_2$ | Cl | Het2 |
| 6107 | $CH_2CH_3$ | $CH_2CH_3$ | $PC(CH_2CH_3)_2$ | Cl | Het2 |
| 6108 | $CH_2CH_2CH_3$ | $CH_2CH_2CH_3$ | $PC(CH_2CH_3)_2$ | Cl | Het2 |
| 6109 | $OCH_3$ | $OCH_3$ | $PC(CH_2CH_3)_2$ | Cl | Het2 |
| 6110 | $OCH_2CH_3$ | $OCH_2CH_3$ | $PC(CH_2CH_3)_2$ | Cl | Het2 |
| 6111 | $OCH_2CH_2CH_3$ | $OCH_2CH_2CH_3$ | $PC(CH_2CH_3)_2$ | Cl | Het2 |
| 6112 | $SCH_3$ | $SCH_3$ | $PC(CH_2CH_3)_2$ | Cl | Het2 |
| 6113 | $SCH_2CH_3$ | $SCH_2CH_3$ | $PC(CH_2CH_3)_2$ | Cl | Het2 |
| 6114 | $N(CH_3)_2$ | $N(CH_3)_2$ | $PC(CH_2CH_3)_2$ | Cl | Het2 |
| 6115 | $N(CH_2CH_3)_2$ | $N(CH_2CH_3)_2$ | $PC(CH_2CH_3)_2$ | Cl | Het2 |
| 6116 | $N(CH_3)(CH_2CH_3)$ | $N(CH_3)(CH_2CH_3)$ | $PC(CH_2CH_3)_2$ | Cl | Het2 |
| 6117 | O—$(CH_2CH_2)$—O | | $PC(CH_2CH_3)_2$ | Cl | Het2 |
| 6118 | O—$(CH_2CH_2CH_2)$—O | | $PC(CH_2CH_3)_2$ | Cl | Het2 |
| 6119 | S—$(CH_2CH_2)$—S | | $PC(CH_2CH_3)_2$ | Cl | Het2 |
| 6120 | S—$(CH_2CH_2CH_2)$—S | | $PC(CH_2CH_3)_2$ | Cl | Het2 |
| 6121 | —$(CH_2)_4$— | | $PC(CH_2CH_3)_2$ | Cl | Het2 |
| 6122 | —$(CH_2)_5$— | | $PC(CH_2CH_3)_2$ | Cl | Het2 |
| 6123 | H | H | H | Cl | Het3 |
| 6124 | $CH_3$ | $CH_3$ | H | Cl | Het3 |
| 6125 | $CH_2CH_3$ | $CH_2CH_3$ | H | Cl | Het3 |
| 6126 | $CH_2CH_2CH_3$ | $CH_2CH_2CH_3$ | H | Cl | Het3 |
| 6127 | $OCH_3$ | $OCH_3$ | H | Cl | Het3 |
| 6128 | $OCH_2CH_3$ | $OCH_2CH_3$ | H | Cl | Het3 |
| 6129 | $OCH_2CH_2CH_3$ | $OCH_2CH_2CH_3$ | H | Cl | Het3 |
| 6130 | $SCH_3$ | $SCH_3$ | H | Cl | Het3 |
| 6131 | $SCH_2CH_3$ | $SCH_2CH_3$ | H | Cl | Het3 |
| 6132 | $N(CH_3)_2$ | $N(CH_3)_2$ | H | Cl | Het3 |
| 6133 | $N(CH_2CH_3)_2$ | $N(CH_2CH_3)_2$ | H | Cl | Het3 |
| 6134 | $N(CH_3)(CH_2CH_3)$ | $N(CH_3)(CH_2CH_3)$ | H | Cl | Het3 |
| 6135 | O—$(CH_2CH_2)$—O | | H | Cl | Het3 |
| 6136 | O—$(CH_2CH_2CH_2)$—O | | H | Cl | Het3 |
| 6137 | S—$(CH_2CH_2)$—S | | H | Cl | Het3 |
| 6138 | S—$(CH_2CH_2CH_2)$—S | | H | Cl | Het3 |
| 6139 | —$(CH_2)_4$— | | H | Cl | Het3 |
| 6140 | —$(CH_2)_5$— | | H | Cl | Het3 |
| 6141 | H | H | $NO_2$ | Cl | Het3 |
| 6142 | $CH_3$ | $CH_3$ | $NO_2$ | Cl | Het3 |
| 6143 | $CH_2CH_3$ | $CH_2CH_3$ | $NO_2$ | Cl | Het3 |
| 6144 | $CH_2CH_2CH_3$ | $CH_2CH_2CH_3$ | $NO_2$ | Cl | Het3 |
| 6145 | $OCH_3$ | $OCH_3$ | $NO_2$ | Cl | Het3 |
| 6146 | $OCH_2CH_3$ | $OCH_2CH_3$ | $NO_2$ | Cl | Het3 |
| 6147 | $OCH_2CH_2CH_3$ | $OCH_2CH_2CH_3$ | $NO_2$ | Cl | Het3 |
| 6148 | $SCH_3$ | $SCH_3$ | $NO_2$ | Cl | Het3 |

TABLE 1-continued

I1a1

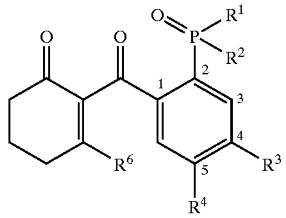

| n | $R^1$ | $R^2$ | $R^3$ | $R^4$ | $R^6$ |
|---|---|---|---|---|---|
| 6149 | $SCH_2CH_3$ | $SCH_2CH_3$ | $NO_2$ | Cl | Het3 |
| 6150 | $N(CH_3)_2$ | $N(CH_3)_2$ | $NO_2$ | Cl | Het3 |
| 6151 | $N(CH_2CH_3)_2$ | $N(CH_2CH_3)_2$ | $NO_2$ | Cl | Het3 |
| 6152 | $N(CH_3)(CH_2CH_3)$ | $N(CH_3)(CH_2CH_3)$ | $NO_2$ | Cl | Het3 |
| 6153 | $O—(CH_2CH_2)—O$ | | $NO_2$ | Cl | Het3 |
| 6154 | $O—(CH_2CH_2CH_2)—O$ | | $NO_2$ | Cl | Het3 |
| 6155 | $S—(CH_2CH_2)—S$ | | $NO_2$ | Cl | Het3 |
| 6156 | $S—(CH_2CH_2CH_2)—S$ | | $NO_2$ | Cl | Het3 |
| 6157 | $—(CH_2)_4—$ | | $NO_2$ | Cl | Het3 |
| 6158 | $—(CH_2)_5—$ | | $NO_2$ | Cl | Het3 |
| 6159 | H | H | CN | Cl | Het3 |
| 6160 | $CH_3$ | $CH_3$ | CN | Cl | Het3 |
| 6161 | $CH_2CH_3$ | $CH_2CH_3$ | CN | Cl | Het3 |
| 6162 | $CH_2CH_2CH_3$ | $CH_2CH_2CH_3$ | CN | Cl | Het3 |
| 6163 | $OCH_3$ | $OCH_3$ | CN | Cl | Het3 |
| 6164 | $OCH_2CH_3$ | $OCH_2CH_3$ | CN | Cl | Het3 |
| 6165 | $OCH_2CH_2CH_3$ | $OCH_2CH_2CH_3$ | CN | Cl | Het3 |
| 6166 | $SCH_3$ | $SCH_3$ | CN | Cl | Het3 |
| 6167 | $SCH_2CH_3$ | $SCH_2CH_3$ | CN | Cl | Het3 |
| 6168 | $N(CH_3)_2$ | $N(CH_3)_2$ | CN | Cl | Het3 |
| 6169 | $N(CH_2CH_3)_2$ | $N(CH_2CH_3)_2$ | CN | Cl | Het3 |
| 6170 | $N(CH_3)(CH_2CH_3)$ | $N(CH_3)(CH_2CH_3)$ | CN | Cl | Het3 |
| 6171 | $O—(CH_2CH_2)—O$ | | CN | Cl | Het3 |
| 6172 | $O—(CH_2CH_2CH_2)—O$ | | CN | Cl | Het3 |
| 6173 | $S—(CH_2CH_2)—S$ | | CN | Cl | Het3 |
| 6174 | $S—(CH_2CH_2CH_2)—S$ | | CN | Cl | Het3 |
| 6175 | $—(CH_2)_4—$ | | CN | Cl | Het3 |
| 6176 | $—(CH_2)_5—$ | | CN | Cl | Het3 |
| 6177 | H | H | F | Cl | Het3 |
| 6178 | $CH_3$ | $CH_3$ | F | Cl | Het3 |
| 6179 | $CH_2CH_3$ | $CH_2CH_3$ | F | Cl | Het3 |
| 6180 | $CH_2CH_2CH_3$ | $CH_2CH_2CH_3$ | F | Cl | Het3 |
| 6181 | $OCH_3$ | $OCH_3$ | F | Cl | Het3 |
| 6182 | $OCH_2CH_3$ | $OCH_2CH_3$ | F | Cl | Het3 |
| 6183 | $OCH_2CH_2CH_3$ | $OCH_2CH_2CH_3$ | F | Cl | Het3 |
| 6184 | $SCH_3$ | $SCH_3$ | F | Cl | Het3 |
| 6185 | $SCH_2CH_3$ | $SCH_2CH_3$ | F | Cl | Het3 |
| 6186 | $N(CH_3)_2$ | $N(CH_3)_2$ | F | Cl | Het3 |
| 6187 | $N(CH_2CH_3)_2$ | $N(CH_2CH_3)_2$ | F | Cl | Het3 |
| 6188 | $N(CH_3)(CH_2CH_3)$ | $N(CH_3)(CH_2CH_3)$ | F | Cl | Het3 |
| 6189 | $O—(CH_2CH_2)—O$ | | F | Cl | Het3 |
| 6190 | $O—(CH_2CH_2CH_2)—O$ | | F | Cl | Het3 |
| 6191 | $S—(CH_2CH_2)—S$ | | F | Cl | Het3 |
| 6192 | $S—(CH_2CH_2CH_2)—S$ | | F | Cl | Het3 |
| 6193 | $—(CH_2)_4—$ | | F | Cl | Het3 |
| 6194 | $—(CH_2)_5—$ | | F | Cl | Het3 |
| 6195 | H | H | Cl | Cl | Het3 |
| 6196 | $CH_3$ | $CH_3$ | Cl | Cl | Het3 |
| 6197 | $CH_2CH_3$ | $CH_2CH_3$ | Cl | Cl | Het3 |
| 6198 | $CH_2CH_2CH_3$ | $CH_2CH_2CH_3$ | Cl | Cl | Het3 |
| 6199 | $OCH_3$ | $OCH_3$ | Cl | Cl | Het3 |
| 6200 | $OCH_2CH_3$ | $OCH_2CH_3$ | Cl | Cl | Het3 |
| 6201 | $OCH_2CH_2CH_3$ | $OCH_2CH_2CH_3$ | Cl | Cl | Het3 |
| 6202 | $SCH_3$ | $SCH_3$ | Cl | Cl | Het3 |
| 6203 | $SCH_2CH_3$ | $SCH_2CH_3$ | Cl | Cl | Het3 |
| 6204 | $N(CH_3)_2$ | $N(CH_3)_2$ | Cl | Cl | Het3 |
| 6205 | $N(CH_2CH_3)_2$ | $N(CH_2CH_3)_2$ | Cl | Cl | Het3 |
| 6206 | $N(CH_3)(CH_2CH_3)$ | $N(CH_3)(CH_2CH_3)$ | Cl | Cl | Het3 |
| 6207 | $O—(CH_2CH_2)—O$ | | Cl | Cl | Het3 |
| 6208 | $O—(CH_2CH_2CH_2)—O$ | | Cl | Cl | Het3 |
| 6209 | $S—(CH_2CH_2)—S$ | | Cl | Cl | Het3 |
| 6210 | $S—(CH_2CH_2CH_2)—S$ | | Cl | Cl | Het3 |
| 6211 | $—(CH_2)_4—$ | | Cl | Cl | Het3 |
| 6212 | $—(CH_2)_5—$ | | Cl | Cl | Het3 |

TABLE 1-continued

I1a1

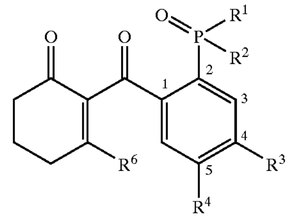

| n | $R^1$ | $R^2$ | $R^3$ | $R^4$ | $R^6$ |
|---|---|---|---|---|---|
| 6213 | H | H | Br | Cl | Het3 |
| 6214 | $CH_3$ | $CH_3$ | Br | Cl | Het3 |
| 6215 | $CH_2CH_3$ | $CH_2CH_3$ | Br | Cl | Het3 |
| 6216 | $CH_2CH_2CH_3$ | $CH_2CH_2CH_3$ | Br | Cl | Het3 |
| 6217 | $OCH_3$ | $OCH_3$ | Br | Cl | Het3 |
| 6218 | $OCH_2CH_3$ | $OCH_2CH_3$ | Br | Cl | Het3 |
| 6219 | $OCH_2CH_2CH_3$ | $OCH_2CH_2CH_3$ | Br | Cl | Het3 |
| 6220 | $SCH_3$ | $SCH_3$ | Br | Cl | Het3 |
| 6221 | $SCH_2CH_3$ | $SCH_2CH_3$ | Br | Cl | Het3 |
| 6222 | $N(CH_3)_2$ | $N(CH_3)_2$ | Br | Cl | Het3 |
| 6223 | $N(CH_2CH_3)_2$ | $N(CH_2CH_3)_2$ | Br | Cl | Het3 |
| 6224 | $N(CH_3)(CH_2CH_3)$ | $N(CH_3)(CH_2CH_3)$ | Br | Cl | Het3 |
| 6225 | $O—(CH_2CH_2)—O$ | | Br | Cl | Het3 |
| 6226 | $O—(CH_2CH_2CH_2)—O$ | | Br | Cl | Het3 |
| 6227 | $S—(CH_2CH_2)—S$ | | Br | Cl | Het3 |
| 6228 | $S—(CH_2CH_2CH_2)—S$ | | Br | Cl | Het3 |
| 6229 | $—(CH_2)_4—$ | | Br | Cl | Het3 |
| 6230 | $—(CH_2)_5—$ | | Br | Cl | Het3 |
| 6231 | H | H | $CH_3$ | Cl | Het3 |
| 6232 | $CH_3$ | $CH_3$ | $CH_3$ | Cl | Het3 |
| 6233 | $CH_2CH_3$ | $CH_2CH_3$ | $CH_3$ | Cl | Het3 |
| 6234 | $CH_2CH_2CH_3$ | $CH_2CH_2CH_3$ | $CH_3$ | Cl | Het3 |
| 6235 | $OCH_3$ | $OCH_3$ | $CH_3$ | Cl | Het3 |
| 6236 | $OCH_2CH_3$ | $OCH_2CH_3$ | $CH_3$ | Cl | Het3 |
| 6237 | $OCH_2CH_2CH_3$ | $OCH_2CH_2CH_3$ | $CH_3$ | Cl | Het3 |
| 6238 | $SCH_3$ | $SCH_3$ | $CH_3$ | Cl | Het3 |
| 6239 | $SCH_2CH_3$ | $SCH_2CH_3$ | $CH_3$ | Cl | Het3 |
| 6240 | $N(CH_3)_2$ | $N(CH_3)_2$ | $CH_3$ | Cl | Het3 |
| 6241 | $N(CH_2CH_3)_2$ | $N(CH_2CH_3)_2$ | $CH_3$ | Cl | Het3 |
| 6242 | $N(CH_3)(CH_2CH_3)$ | $N(CH_3)(CH_2CH_3)$ | $CH_3$ | Cl | Het3 |
| 6243 | $O—(CH_2CH_2)—O$ | | $CH_3$ | Cl | Het3 |
| 6244 | $O—(CH_2CH_2CH_2)—O$ | | $CH_3$ | Cl | Het3 |
| 6245 | $S—(CH_2CH_2)—S$ | | $CH_3$ | Cl | Het3 |
| 6246 | $S—(CH_2CH_2CH_2)—S$ | | $CH_3$ | Cl | Het3 |
| 6247 | $—(CH_2)_4—$ | | $CH_3$ | Cl | Het3 |
| 6248 | $—(CH_2)_5—$ | | $CH_3$ | Cl | Het3 |
| 6249 | H | H | $CH_2CH_3$ | Cl | Het3 |
| 6250 | $CH_3$ | $CH_3$ | $CH_2CH_3$ | Cl | Het3 |
| 6251 | $CH_2CH_3$ | $CH_2CH_3$ | $CH_2CH_3$ | Cl | Het3 |
| 6252 | $CH_2CH_2CH_3$ | $CH_2CH_2CH_3$ | $CH_2CH_3$ | Cl | Het3 |
| 6253 | $OCH_3$ | $OCH_3$ | $CH_2CH_3$ | Cl | Het3 |
| 6254 | $OCH_2CH_3$ | $OCH_2CH_3$ | $CH_2CH_3$ | Cl | Het3 |
| 6255 | $OCH_2CH_2CH_3$ | $OCH_2CH_2CH_3$ | $CH_2CH_3$ | Cl | Het3 |
| 6256 | $SCH_3$ | $SCH_3$ | $CH_2CH_3$ | Cl | Het3 |
| 6257 | $SCH_2CH_3$ | $SCH_2CH_3$ | $CH_2CH_3$ | Cl | Het3 |
| 6258 | $N(CH_3)_2$ | $N(CH_3)_2$ | $CH_2CH_3$ | Cl | Het3 |
| 6259 | $N(CH_2CH_3)_2$ | $N(CH_2CH_3)_2$ | $CH_2CH_3$ | Cl | Het3 |
| 6260 | $N(CH_3)(CH_2CH_3)$ | $N(CH_3)(CH_2CH_3)$ | $CH_2CH_3$ | Cl | Het3 |
| 6261 | $O—(CH_2CH_2)—O$ | | $CH_2CH_3$ | Cl | Het3 |
| 6262 | $O—(CH_2CH_2CH_2)—O$ | | $CH_2CH_3$ | Cl | Het3 |
| 6263 | $S—(CH_2CH_2)—S$ | | $CH_2CH_3$ | Cl | Het3 |
| 6264 | $S—(CH_2CH_2CH_2)—S$ | | $CH_2CH_3$ | Cl | Het3 |
| 6265 | $—(CH_2)_4—$ | | $CH_2CH_3$ | Cl | Het3 |
| 6266 | $—(CH_2)_5—$ | | $CH_2CH_3$ | Cl | Het3 |
| 6267 | H | H | $CF_3$ | Cl | Het3 |
| 6268 | $CH_3$ | $CH_3$ | $CF_3$ | Cl | Het3 |
| 6269 | $CH_2CH_3$ | $CH_2CH_3$ | $CF_3$ | Cl | Het3 |
| 6270 | $CH_2CH_2CH_3$ | $CH_2CH_2CH_3$ | $CF_3$ | Cl | Het3 |
| 6271 | $OCH_3$ | $OCH_3$ | $CF_3$ | Cl | Het3 |
| 6272 | $OCH_2CH_3$ | $OCH_2CH_3$ | $CF_3$ | Cl | Het3 |
| 6273 | $OCH_2CH_2CH_3$ | $OCH_2CH_2CH_3$ | $CF_3$ | Cl | Het3 |
| 6274 | $SCH_3$ | $SCH_3$ | $CF_3$ | Cl | Het3 |
| 6275 | $SCH_2CH_3$ | $SCH_2CH_3$ | $CF_3$ | Cl | Het3 |
| 6276 | $N(CH_3)_2$ | $N(CH_3)_2$ | $CF_3$ | Cl | Het3 |

TABLE 1-continued

I1a1

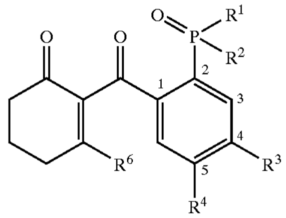

| n | $R^1$ | $R^2$ | $R^3$ | $R^4$ | $R^6$ |
|---|---|---|---|---|---|
| 6277 | $N(CH_2CH_3)_2$ | $N(CH_2CH_3)_2$ | $CF_3$ | Cl | Het3 |
| 6278 | $N(CH_3)(CH_2CH_3)$ | $N(CH_3)(CH_2CH_3)$ | $CF_3$ | Cl | Het3 |
| 6279 | O—($CH_2CH_2$)—O | | $CF_3$ | Cl | Het3 |
| 6280 | O—($CH_2CH_2CH_2$)—O | | $CF_3$ | Cl | Het3 |
| 6281 | S—($CH_2CH_2$)—S | | $CF_3$ | Cl | Het3 |
| 6282 | S—($CH_2CH_2CH_2$)—S | | $CF_3$ | Cl | Het3 |
| 6283 | —$(CH_2)_4$— | | $CF_3$ | Cl | Het3 |
| 6284 | —$(CH_2)_5$— | | $CF_3$ | Cl | Het3 |
| 6285 | H | H | $OCH_3$ | Cl | Het3 |
| 6286 | $CH_3$ | $CH_3$ | $OCH_3$ | Cl | Het3 |
| 6287 | $CH_2CH_3$ | $CH_2CH_3$ | $OCH_3$ | Cl | Het3 |
| 6288 | $CH_2CH_2CH_3$ | $CH_2CH_2CH_3$ | $OCH_3$ | Cl | Het3 |
| 6289 | $OCH_3$ | $OCH_3$ | $OCH_3$ | Cl | Het3 |
| 6290 | $OCH_2CH_3$ | $OCH_2CH_3$ | $OCH_3$ | Cl | Het3 |
| 6291 | $OCH_2CH_2CH_3$ | $OCH_2CH_2CH_3$ | $OCH_3$ | Cl | Het3 |
| 6292 | $SCH_3$ | $SCH_3$ | $OCH_3$ | Cl | Het3 |
| 6293 | $SCH_2CH_3$ | $SCH_2CH_3$ | $OCH_3$ | Cl | Het3 |
| 6294 | $N(CH_3)_2$ | $N(CH_3)_2$ | $OCH_3$ | Cl | Het3 |
| 6295 | $N(CH_2CH_3)_2$ | $N(CH_2CH_3)_2$ | $OCH_3$ | Cl | Het3 |
| 6296 | $N(CH_3)(CH_2CH_3)$ | $N(CH_3)(CH_2CH_3)$ | $OCH_3$ | Cl | Het3 |
| 6297 | O—($CH_2CH_2$)—O | | $OCH_3$ | Cl | Het3 |
| 6298 | O—($CH_2CH_2CH_2$)—O | | $OCH_3$ | Cl | Het3 |
| 6299 | S—($CH_2CH_2$)—S | | $OCH_3$ | Cl | Het3 |
| 6300 | S—($CH_2CH_2CH_2$)—S | | $OCH_3$ | Cl | Het3 |
| 6301 | —$(CH_2)_4$— | | $OCH_3$ | Cl | Het3 |
| 6302 | —$(CH_2)_5$— | | $OCH_3$ | Cl | Het3 |
| 6303 | H | H | $OCH_2CH_3$ | Cl | Het3 |
| 6304 | $CH_3$ | $CH_3$ | $OCH_2CH_3$ | Cl | Het3 |
| 6305 | $CH_2CH_3$ | $CH_2CH_3$ | $OCH_2CH_3$ | Cl | Het3 |
| 6306 | $CH_2CH_2CH_3$ | $CH_2CH_2CH_3$ | $OCH_2CH_3$ | Cl | Het3 |
| 6307 | $OCH_3$ | $OCH_3$ | $OCH_2CH_3$ | Cl | Het3 |
| 6308 | $OCH_2CH_3$ | $OCH_2CH_3$ | $OCH_2CH_3$ | Cl | Het3 |
| 6309 | $OCH_2CH_2CH_3$ | $OCH_2CH_2CH_3$ | $OCH_2CH_3$ | Cl | Het3 |
| 6310 | $SCH_3$ | $SCH_3$ | $OCH_2CH_3$ | Cl | Het3 |
| 6311 | $SCH_2CH_3$ | $SCH_2CH_3$ | $OCH_2CH_3$ | Cl | Het3 |
| 6312 | $N(CH_3)_2$ | $N(CH_3)_2$ | $OCH_2CH_3$ | Cl | Het3 |
| 6313 | $N(CH_2CH_3)_2$ | $N(CH_2CH_3)_2$ | $OCH_2CH_3$ | Cl | Het3 |
| 6314 | $N(CH_3)(CH_2CH_3)$ | $N(CH_3)(CH_2CH_3)$ | $OCH_2CH_3$ | Cl | Het3 |
| 6315 | O—($CH_2CH_2$)—O | | $OCH_2CH_3$ | Cl | Het3 |
| 6316 | O—($CH_2CH_2CH_2$)—O | | $OCH_2CH_3$ | Cl | Het3 |
| 6317 | S—($CH_2CH_2$)—S | | $OCH_2CH_3$ | Cl | Het3 |
| 6318 | S—($CH_2CH_2CH_2$)—S | | $OCH_2CH_3$ | Cl | Het3 |
| 6319 | —$(CH_2)_4$— | | $OCH_2CH_3$ | Cl | Het3 |
| 6320 | —$(CH_2)_5$— | | $OCH_2CH_3$ | Cl | Het3 |
| 6331 | H | H | $SCH_3$ | Cl | Het3 |
| 6332 | $CH_3$ | $CH_3$ | $SCH_3$ | Cl | Het3 |
| 6333 | $CH_2CH_3$ | $CH_2CH_3$ | $SCH_3$ | Cl | Het3 |
| 6334 | $CH_2CH_2CH_3$ | $CH_2CH_2CH_3$ | $SCH_3$ | Cl | Het3 |
| 6335 | $OCH_3$ | $OCH_3$ | $SCH_3$ | Cl | Het3 |
| 6336 | $OCH_2CH_3$ | $OCH_2CH_3$ | $SCH_3$ | Cl | Het3 |
| 6337 | $OCH_2CH_2CH_3$ | $OCH_2CH_2CH_3$ | $SCH_3$ | Cl | Het3 |
| 6338 | $SCH_3$ | $SCH_3$ | $SCH_3$ | Cl | Het3 |
| 6339 | $SCH_2CH_3$ | $SCH_2CH_3$ | $SCH_3$ | Cl | Het3 |
| 6340 | $N(CH_3)_2$ | $N(CH_3)_2$ | $SCH_3$ | Cl | Het3 |
| 6341 | $N(CH_2CH_3)_2$ | $N(CH_2CH_3)_2$ | $SCH_3$ | Cl | Het3 |
| 6342 | $N(CH_3)(CH_2CH_3)$ | $N(CH_3)(CH_2CH_3)$ | $SCH_3$ | Cl | Het3 |
| 6343 | O—($CH_2CH_2$)—O | | $SCH_3$ | Cl | Het3 |
| 6344 | O—($CH_2CH_2CH_2$)—O | | $SCH_3$ | Cl | Het3 |
| 6345 | S—($CH_2CH_2$)—S | | $SCH_3$ | Cl | Het3 |
| 6346 | S—($CH_2CH_2CH_2$)—S | | $SCH_3$ | Cl | Het3 |
| 6347 | —$(CH_2)_4$— | | $SCH_3$ | Cl | Het3 |
| 6348 | —$(CH_2)_5$— | | $SCH_3$ | Cl | Het3 |
| 6349 | H | H | $SO_2CH_3$ | Cl | Het3 |
| 6350 | $CH_3$ | $CH_3$ | $SO_2CH_3$ | Cl | Het3 |

TABLE 1-continued

I1a1

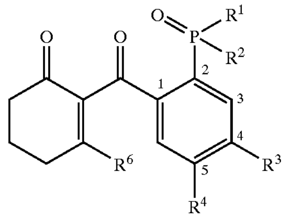

| n | $R^1$ | $R^2$ | $R^3$ | $R^4$ | $R^6$ |
|---|---|---|---|---|---|
| 6351 | $CH_2CH_3$ | $CH_2CH_3$ | $SO_2CH_3$ | Cl | Het3 |
| 6352 | $CH_2CH_2CH_3$ | $CH_2CH_2CH_3$ | $SO_2CH_3$ | Cl | Het3 |
| 6353 | $OCH_3$ | $OCH_3$ | $SO_2CH_3$ | Cl | Het3 |
| 6354 | $OCH_2CH_3$ | $OCH_2CH_3$ | $SO_2CH_3$ | Cl | Het3 |
| 6355 | $OCH_2CH_2CH_3$ | $OCH_2CH_2CH_3$ | $SO_2CH_3$ | Cl | Het3 |
| 6356 | $SCH_3$ | $SCH_3$ | $SO_2CH_3$ | Cl | Het3 |
| 6357 | $SCH_2CH_3$ | $SCH_2CH_3$ | $SO_2CH_3$ | Cl | Het3 |
| 6358 | $N(CH_3)_2$ | $N(CH_3)_2$ | $SO_2CH_3$ | Cl | Het3 |
| 6359 | $N(CH_2CH_3)_2$ | $N(CH_2CH_3)_2$ | $SO_2CH_3$ | Cl | Het3 |
| 6360 | $N(CH_3)(CH_2CH_3)$ | $N(CH_3)(CH_2CH_3)$ | $SO_2CH_3$ | Cl | Het3 |
| 6361 | $O—(CH_2CH_2)—O$ | | $SO_2CH_3$ | Cl | Het3 |
| 6362 | $O—(CH_2CH_2CH_2)—O$ | | $SO_2CH_3$ | Cl | Het3 |
| 6363 | $S—(CH_2CH_2)—S$ | | $SO_2CH_3$ | Cl | Het3 |
| 6364 | $S—(CH_2CH_2CH_2)—S$ | | $SO_2CH_3$ | Cl | Het3 |
| 6365 | $—(CH_2)_4—$ | | $SO_2CH_3$ | Cl | Het3 |
| 6366 | $—(CH_2)_5—$ | | $SO_2CH_3$ | Cl | Het3 |
| 6367 | H | H | $PO(OCH_3)_2$ | Cl | Het3 |
| 6368 | $CH_3$ | $CH_3$ | $PO(OCH_3)_2$ | Cl | Het3 |
| 6369 | $CH_2CH_3$ | $CH_2CH_3$ | $PO(OCH_3)_2$ | Cl | Het3 |
| 6370 | $CH_2CH_2CH_3$ | $CH_2CH_2CH_3$ | $PO(OCH_3)_2$ | Cl | Het3 |
| 6371 | $OCH_3$ | $OCH_3$ | $PO(OCH_3)_2$ | Cl | Het3 |
| 6372 | $OCH_2CH_3$ | $OCH_2CH_3$ | $PO(OCH_3)_2$ | Cl | Het3 |
| 6373 | $OCH_2CH_2CH_3$ | $OCH_2CH_2CH_3$ | $PO(OCH_3)_2$ | Cl | Het3 |
| 6374 | $SCH_3$ | $SCH_3$ | $PO(OCH_3)_2$ | Cl | Het3 |
| 6375 | $SCH_2CH_3$ | $SCH_2CH_3$ | $PO(OCH_3)_2$ | Cl | Het3 |
| 6376 | $N(CH_3)_2$ | $N(CH_3)_2$ | $PO(OCH_3)_2$ | Cl | Het3 |
| 6377 | $N(CH_2CH_3)_2$ | $N(CH_2CH_3)_2$ | $PO(OCH_3)_2$ | Cl | Het3 |
| 6378 | $N(CH_3)(CH_2CH_3)$ | $N(CH_3)(CH_2CH_3)$ | $PO(OCH_3)_2$ | Cl | Het3 |
| 6379 | $O—(CH_2CH_2)—O$ | | $PO(OCH_3)_2$ | Cl | Het3 |
| 6380 | $O—(CH_2CH_2CH_2)—O$ | | $PO(OCH_3)_2$ | Cl | Het3 |
| 6381 | $S—(CH_2CH_2)—S$ | | $PO(OCH_3)_2$ | Cl | Het3 |
| 6382 | $S—(CH_2CH_2CH_2)—S$ | | $PO(OCH_3)_2$ | Cl | Het3 |
| 6383 | $—(CH_2)_4—$ | | $PO(OCH_3)_2$ | Cl | Het3 |
| 6384 | $—(CH_2)_5—$ | | $PO(OCH_3)_2$ | Cl | Het3 |
| 6385 | H | H | $PO(OCH_2CH_3)_2$ | Cl | Het3 |
| 6386 | $CH_3$ | $CH_3$ | $PO(OCH_2CH_3)_2$ | Cl | Het3 |
| 6387 | $CH_2CH_3$ | $CH_2CH_3$ | $PO(OCH_2CH_3)_2$ | Cl | Het3 |
| 6388 | $CH_2CH_2CH_3$ | $CH_2CH_2CH_3$ | $PO(OCH_2CH_3)_2$ | Cl | Het3 |
| 6389 | $OCH_3$ | $OCH_3$ | $PO(OCH_2CH_3)_2$ | Cl | Het3 |
| 6390 | $OCH_2CH_3$ | $OCH_2CH_3$ | $PO(OCH_2CH_3)_2$ | Cl | Het3 |
| 6391 | $OCH_2CH_2CH_3$ | $OCH_2CH_2CH_3$ | $PO(OCH_2CH_3)_2$ | Cl | Het3 |
| 6392 | $SCH_3$ | $SCH_3$ | $PO(OCH_2CH_3)_2$ | Cl | Het3 |
| 6393 | $SCH_2CH_3$ | $SCH_2CH_3$ | $PO(OCH_2CH_3)_2$ | Cl | Het3 |
| 6394 | $N(CH_3)_2$ | $N(CH_3)_2$ | $PO(OCH_2CH_3)_2$ | Cl | Het3 |
| 6395 | $N(CH_2CH_3)_2$ | $N(CH_2CH_3)_2$ | $PO(OCH_2CH_3)_2$ | Cl | Het3 |
| 6396 | $N(CH_3)(CH_2CH_3)$ | $N(CH_3)(CH_2CH_3)$ | $PO(OCH_2CH_3)_2$ | Cl | Het3 |
| 6397 | $O—(CH_2CH_2)—O$ | | $PO(OCH_2CH_3)_2$ | Cl | Het3 |
| 6398 | $O—(CH_2CH_2CH_2)—O$ | | $PO(OCH_2CH_3)_2$ | Cl | Het3 |
| 6399 | $S—(CH_2CH_2)—S$ | | $PO(OCH_2CH_3)_2$ | Cl | Het3 |
| 6400 | $S—(CH_2CH_2CH_2)—S$ | | $PO(OCH_2CH_3)_2$ | Cl | Het3 |
| 6401 | $—(CH_2)_4—$ | | $PO(OCH_2CH_3)_2$ | Cl | Het3 |
| 6402 | $—(CH_2)_5—$ | | $PO(OCH_2CH_3)_2$ | Cl | Het3 |
| 6403 | H | H | $PO(CH_3)_2$ | Cl | Het3 |
| 6404 | $CH_3$ | $CH_3$ | $PO(CH_3)_2$ | Cl | Het3 |
| 6405 | $CH_2CH_3$ | $CH_2CH_3$ | $PO(CH_3)_2$ | Cl | Het3 |
| 6406 | $CH_2CH_2CH_3$ | $CH_2CH_2CH_3$ | $PO(CH_3)_2$ | Cl | Het3 |
| 6407 | $OCH_3$ | $OCH_3$ | $PO(CH_3)_2$ | Cl | Het3 |
| 6408 | $OCH_2CH_3$ | $OCH_2CH_3$ | $PO(CH_3)_2$ | Cl | Het3 |
| 6409 | $OCH_2CH_2CH_3$ | $OCH_2CH_2CH_3$ | $PO(CH_3)_2$ | Cl | Het3 |
| 6410 | $SCH_3$ | $SCH_3$ | $PO(CH_3)_2$ | Cl | Het3 |
| 6411 | $SCH_2CH_3$ | $SCH_2CH_3$ | $PO(CH_3)_2$ | Cl | Het3 |
| 6412 | $N(CH_3)_2$ | $N(CH_3)_2$ | $PO(CH_3)_2$ | Cl | Het3 |
| 6413 | $N(CH_2CH_3)_2$ | $N(CH_2CH_3)_2$ | $PO(CH_3)_2$ | Cl | Het3 |
| 6414 | $N(CH_3)(CH_2CH_3)$ | $N(CH_3)(CH_2CH_3)$ | $PO(CH_3)_2$ | Cl | Het3 |

TABLE 1-continued

I1a1

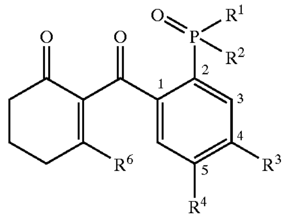

| n | $R^1$ | $R^2$ | $R^3$ | $R^4$ | $R^6$ |
|---|---|---|---|---|---|
| 6415 | O—$(CH_2CH_2)$—O | | $PO(CH_3)_2$ | Cl | Het3 |
| 6416 | O—$(CH_2CH_2CH_2)$—O | | $PO(CH_3)_2$ | Cl | Het3 |
| 6417 | S—$(CH_2CH_2)$—S | | $PO(CH_3)_2$ | Cl | Het3 |
| 6418 | S—$(CH_2CH_2CH_2)$—S | | $PO(CH_3)_2$ | Cl | Het3 |
| 6419 | —$(CH_2)_4$— | | $PO(CH_3)_2$ | Cl | Het3 |
| 6420 | —$(CH_2)_5$— | | $PO(CH_3)_2$ | Cl | Het3 |
| 6421 | H | H | $PC(CH_2CH_3)_2$ | Cl | Het3 |
| 6422 | $CH_3$ | $CH_3$ | $PC(CH_2CH_3)_2$ | Cl | Het3 |
| 6423 | $CH_2CH_3$ | $CH_2CH_3$ | $PC(CH_2CH_3)_2$ | Cl | Het3 |
| 6424 | $CH_2CH_2CH_3$ | $CH_2CH_2CH_3$ | $PC(CH_2CH_3)_2$ | Cl | Het3 |
| 6425 | $OCH_3$ | $OCH_3$ | $PC(CH_2CH_3)_2$ | Cl | Het3 |
| 6426 | $OCH_2CH_3$ | $OCH_2CH_3$ | $PC(CH_2CH_3)_2$ | Cl | Het3 |
| 6427 | $OCH_2CH_2CH_3$ | $OCH_2CH_2CH_3$ | $PC(CH_2CH_3)_2$ | Cl | Het3 |
| 6428 | $SCH_3$ | $SCH_3$ | $PC(CH_2CH_3)_2$ | Cl | Het3 |
| 6429 | $SCH_2CH_3$ | $SCH_2CH_3$ | $PC(CH_2CH_3)_2$ | Cl | Het3 |
| 6430 | $N(CH_3)_2$ | $N(CH_3)_2$ | $PC(CH_2CH_3)_2$ | Cl | Het3 |
| 6431 | $N(CH_2CH_3)_2$ | $N(CH_2CH_3)_2$ | $PC(CH_2CH_3)_2$ | Cl | Het3 |
| 6432 | $N(CH_3)(CH_2CH_3)$ | $N(CH_3)(CH_2CH_3)$ | $PC(CH_2CH_3)_2$ | Cl | Het3 |
| 6433 | O—$(CH_2CH_2)$—O | | $PC(CH_2CH_3)_2$ | Cl | Het3 |
| 6434 | O—$(CH_2CH_2CH_2)$—O | | $PC(CH_2CH_3)_2$ | Cl | Het3 |
| 6435 | S—$(CH_2CH_2)$—S | | $PC(CH_2CH_3)_2$ | Cl | Het3 |
| 6436 | S—$(CH_2CH_2CH_2)$—S | | $PC(CH_2CH_3)_2$ | Cl | Het3 |
| 6437 | —$(CH_2)_4$— | | $PC(CH_2CH_3)_2$ | Cl | Het3 |
| 6438 | —$(CH_2)_5$— | | $PC(CH_2CH_3)_2$ | Cl | Het3 |
| 6439 | H | H | H | Br | OH |
| 6440 | $CH_3$ | $CH_3$ | H | Br | OH |
| 6441 | $CH_2CH_3$ | $CH_2CH_3$ | H | Br | OH |
| 6442 | $CH_2CH_2CH_3$ | $CH_2CH_2CH_3$ | H | Br | OH |
| 6443 | $OCH_3$ | $OCH_3$ | H | Br | OH |
| 6444 | $OCH_2CH_3$ | $OCH_2CH_3$ | H | Br | OH |
| 6445 | $OCH_2CH_2CH_3$ | $OCH_2CH_2CH_3$ | H | Br | OH |
| 6446 | $SCH_3$ | $SCH_3$ | H | Br | OH |
| 6447 | $SCH_2CH_3$ | $SCH_2CH_3$ | H | Br | OH |
| 6448 | $N(CH_3)_2$ | $N(CH_3)_2$ | H | Br | OH |
| 6449 | $N(CH_2CH_3)_2$ | $N(CH_2CH_3)_2$ | H | Br | OH |
| 6450 | $N(CH_3)(CH_2CH_3)$ | $N(CH_3)(CH_2CH_3)$ | H | Br | OH |
| 6451 | O—$(CH_2CH_2)$—O | | H | Br | OH |
| 6452 | O—$(CH_2CH_2CH_2)$—O | | H | Br | OH |
| 6453 | S—$(CH_2CH_2)$—S | | H | Br | OH |
| 6454 | S—$(CH_2CH_2CH_2)$—S | | H | Br | OH |
| 6455 | —$(CH_2)_4$— | | H | Br | OH |
| 6456 | —$(CH_2)_5$— | | H | Br | OH |
| 6457 | H | H | $NO_2$ | Br | OH |
| 6458 | $CH_3$ | $CH_3$ | $NO_2$ | Br | OH |
| 6459 | $CH_2CH_3$ | $CH_2CH_3$ | $NO_2$ | Br | OH |
| 6460 | $CH_2CH_2CH_3$ | $CH_2CH_2CH_3$ | $NO_2$ | Br | OH |
| 6461 | $OCH_3$ | $OCH_3$ | $NO_2$ | Br | OH |
| 6462 | $OCH_2CH_3$ | $OCH_2CH_3$ | $NO_2$ | Br | OH |
| 6463 | $OCH_2CH_2CH_3$ | $OCH_2CH_2CH_3$ | $NO_2$ | Br | OH |
| 6464 | $SCH_3$ | $SCH_3$ | $NO_2$ | Br | OH |
| 6465 | $SCH_2CH_3$ | $SCH_2CH_3$ | $NO_2$ | Br | OH |
| 6466 | $N(CH_3)_2$ | $N(CH_3)_2$ | $NO_2$ | Br | OH |
| 6467 | $N(CH_2CH_3)_2$ | $N(CH_2CH_3)_2$ | $NO_2$ | Br | OH |
| 6468 | $N(CH_3)(CH_2CH_3)$ | $N(CH_3)(CH_2CH_3)$ | $NO_2$ | Br | OH |
| 6469 | O—$(CH_2CH_2)$—O | | $NO_2$ | Br | OH |
| 6470 | O—$(CH_2CH_2CH_2)$—O | | $NO_2$ | Br | OH |
| 6471 | S—$(CH_2CH_2)$—S | | $NO_2$ | Br | OH |
| 6472 | S—$(CH_2CH_2CH_2)$—S | | $NO_2$ | Br | OH |
| 6473 | —$(CH_2)_4$— | | $NO_2$ | Br | OH |
| 6474 | —$(CH_2)_5$— | | $NO_2$ | Br | OH |
| 6475 | H | H | CN | Br | OH |
| 6476 | $CH_3$ | $CH_3$ | CN | Br | OH |
| 6477 | $CH_2CH_3$ | $CH_2CH_3$ | CN | Br | OH |
| 6478 | $CH_2CH_2CH_3$ | $CH_2CH_2CH_3$ | CN | Br | OH |

TABLE 1-continued

I1a1

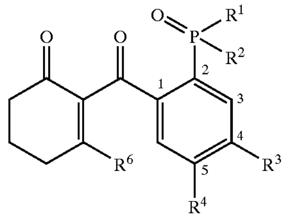

| n | $R^1$ | $R^2$ | $R^3$ | $R^4$ | $R^6$ |
|---|---|---|---|---|---|
| 6479 | $OCH_3$ | $OCH_3$ | CN | Br | OH |
| 6480 | $OCH_2CH_3$ | $OCH_2CH_3$ | CN | Br | OH |
| 6481 | $OCH_2CH_2CH_3$ | $OCH_2CH_2CH_3$ | CN | Br | OH |
| 6482 | $SCH_3$ | $SCH_3$ | CN | Br | OH |
| 6483 | $SCH_2CH_3$ | $SCH_2CH_3$ | CN | Br | OH |
| 6484 | $N(CH_3)_2$ | $N(CH_3)_2$ | CN | Br | OH |
| 6485 | $N(CH_2CH_3)_2$ | $N(CH_2CH_3)_2$ | CN | Br | OH |
| 6486 | $N(CH_3)(CH_2CH_3)$ | $N(CH_3)(CH_2CH_3)$ | CN | Br | OH |
| 6487 | $O—(CH_2CH_2)—O$ | | CN | Br | OH |
| 6488 | $O—(CH_2CH_2CH_2)—O$ | | CN | Br | OH |
| 6489 | $S—(CH_2CH_2)—S$ | | CN | Br | OH |
| 6490 | $S—(CH_2CH_2CH_2)—S$ | | CN | Br | OH |
| 6491 | $—(CH_2)_4—$ | | CN | Br | OH |
| 6492 | $—(CH_2)_5—$ | | CN | Br | OH |
| 6493 | H | H | F | Br | OH |
| 6494 | $CH_3$ | $CH_3$ | F | Br | OH |
| 6495 | $CH_2CH_3$ | $CH_2CH_3$ | F | Br | OH |
| 6496 | $CH_2CH_2CH_3$ | $CH_2CH_2CH_3$ | F | Br | OH |
| 6497 | $OCH_3$ | $OCH_3$ | F | Br | OH |
| 6498 | $OCH_2CH_3$ | $OCH_2CH_3$ | F | Br | OH |
| 6499 | $OCH_2CH_2CH_3$ | $OCH_2CH_2CH_3$ | F | Br | OH |
| 6500 | $SCH_3$ | $SCH_3$ | F | Br | OH |
| 6501 | $SCH_2CH_3$ | $SCH_2CH_3$ | F | Br | OH |
| 6502 | $N(CH_3)_2$ | $N(CH_3)_2$ | F | Br | OH |
| 6503 | $N(CH_2CH_3)_2$ | $N(CH_2CH_3)_2$ | F | Br | OH |
| 6504 | $N(CH_3)(CH_2CH_3)$ | $N(CH_3)(CH_2CH_3)$ | F | Br | OH |
| 6505 | $O—(CH_2CH_2)—O$ | | F | Br | OH |
| 6506 | $O—(CH_2CH_2CH_2)—O$ | | F | Br | OH |
| 6507 | $S—(CH_2CH_2)—S$ | | F | Br | OH |
| 6508 | $S—(CH_2CH_2CH_2)—S$ | | F | Br | OH |
| 6509 | $—(CH_2)_4—$ | | F | Br | OH |
| 6510 | $—(CH_2)_5—$ | | F | Br | OH |
| 6511 | H | H | Cl | Br | OH |
| 6512 | $CH_3$ | $CH_3$ | Cl | Br | OH |
| 6513 | $CH_2CH_3$ | $CH_2CH_3$ | Cl | Br | OH |
| 6514 | $CH_2CH_2CH_3$ | $CH_2CH_2CH_3$ | Cl | Br | OH |
| 6515 | $OCH_3$ | $OCH_3$ | Cl | Br | OH |
| 6516 | $OCH_2CH_3$ | $OCH_2CH_3$ | Cl | Br | OH |
| 6517 | $OCH_2CH_2CH_3$ | $OCH_2CH_2CH_3$ | Cl | Br | OH |
| 6518 | $SCH_3$ | $SCH_3$ | Cl | Br | OH |
| 6519 | $SCH_2CH_3$ | $SCH_2CH_3$ | Cl | Br | OH |
| 6520 | $N(CH_3)_2$ | $N(CH_3)_2$ | Cl | Br | OH |
| 6521 | $N(CH_2CH_3)_2$ | $N(CH_2CH_3)_2$ | Cl | Br | OH |
| 6522 | $N(CH_3)(CH_2CH_3)$ | $N(CH_3)(CH_2CH_3)$ | Cl | Br | OH |
| 6523 | $O—(CH_2CH_2)—O$ | | Cl | Br | OH |
| 6524 | $O—(CH_2CH_2CH_2)—O$ | | Cl | Br | OH |
| 6525 | $S—(CH_2CH_2)—S$ | | Cl | Br | OH |
| 6526 | $S—(CH_2CH_2CH_2)—S$ | | Cl | Br | OH |
| 6527 | $—(CH_2)_4—$ | | Cl | Br | OH |
| 6528 | $—(CH_2)_5—$ | | Cl | Br | OH |
| 6529 | H | H | Br | Br | OH |
| 6530 | $CH_3$ | $CH_3$ | Br | Br | OH |
| 6531 | $CH_2CH_3$ | $CH_2CH_3$ | Br | Br | OH |
| 6532 | $CH_2CH_2CH_3$ | $CH_2CH_2CH_3$ | Br | Br | OH |
| 6533 | $OCH_3$ | $OCH_3$ | Br | Br | OH |
| 6534 | $OCH_2CH_3$ | $OCH_2CH_3$ | Br | Br | OH |
| 6535 | $OCH_2CH_2CH_3$ | $OCH_2CH_2CH_3$ | Br | Br | OH |
| 6536 | $SCH_3$ | $SCH_3$ | Br | Br | OH |
| 6537 | $SCH_2CH_3$ | $SCH_2CH_3$ | Br | Br | OH |
| 6538 | $N(CH_3)_2$ | $N(CH_3)_2$ | Br | Br | OH |
| 6539 | $N(CH_2CH_3)_2$ | $N(CH_2CH_3)_2$ | Br | Br | OH |
| 6540 | $N(CH_3)(CH_2CH_3)$ | $N(CH_3)(CH_2CH_3)$ | Br | Br | OH |
| 6541 | $O—(CH_2CH_2)—O$ | | Br | Br | OH |
| 6542 | $O—(CH_2CH_2CH_2)—O$ | | Br | Br | OH |

TABLE 1-continued

I1a1

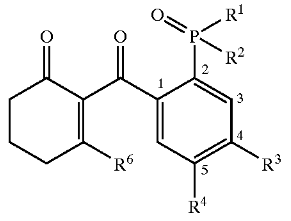

| n | $R^1$ | $R^2$ | $R^3$ | $R^4$ | $R^6$ |
|---|---|---|---|---|---|
| 6543 | S—($CH_2CH_2$)—S | | Br | Br | OH |
| 6544 | S—($CH_2CH_2CH_2$)—S | | Br | Br | OH |
| 6545 | —$(CH_2)_4$— | | Br | Br | OH |
| 6546 | —$(CH_2)_5$— | | Br | Br | OH |
| 6547 | H | H | $CH_3$ | Br | OH |
| 6548 | $CH_3$ | $CH_3$ | $CH_3$ | Br | OH |
| 6549 | $CH_2CH_3$ | $CH_2CH_3$ | $CH_3$ | Br | OH |
| 6550 | $CH_2CH_2CH_3$ | $CH_2CH_2CH_3$ | $CH_3$ | Br | OH |
| 6551 | $OCH_3$ | $OCH_3$ | $CH_3$ | Br | OH |
| 6552 | $OCH_2CH_3$ | $OCH_2CH_3$ | $CH_3$ | Br | OH |
| 6553 | $OCH_2CH_2CH_3$ | $OCH_2CH_2CH_3$ | $CH_3$ | Br | OH |
| 6554 | $SCH_3$ | $SCH_3$ | $CH_3$ | Br | OH |
| 6555 | $SCH_2CH_3$ | $SCH_2CH_3$ | $CH_3$ | Br | OH |
| 6556 | $N(CH_3)_2$ | $N(CH_3)_2$ | $CH_3$ | Br | OH |
| 6557 | $N(CH_2CH_3)_2$ | $N(CH_2CH_3)_2$ | $CH_3$ | Br | OH |
| 6558 | $N(CH_3)(CH_2CH_3)$ | $N(CH_3)(CH_2CH_3)$ | $CH_3$ | Br | OH |
| 6559 | O—($CH_2CH_2$)—O | | $CH_3$ | Br | OH |
| 6560 | O—($CH_2CH_2CH_2$)—O | | $CH_3$ | Br | OH |
| 6561 | S—($CH_2CH_2$)—S | | $CH_3$ | Br | OH |
| 6562 | S—($CH_2CH_2CH_2$)—S | | $CH_3$ | Br | OH |
| 6563 | —$(CH_2)_4$— | | $CH_3$ | Br | OH |
| 6564 | —$(CH_2)_5$— | | $CH_3$ | Br | OH |
| 6565 | H | H | $CH_2CH_3$ | Br | OH |
| 6566 | $CH_3$ | $CH_3$ | $CH_2CH_3$ | Br | OH |
| 6567 | $CH_2CH_3$ | $CH_2CH_3$ | $CH_2CH_3$ | Br | OH |
| 6568 | $CH_2CH_2CH_3$ | $CH_2CH_2CH_3$ | $CH_2CH_3$ | Br | OH |
| 6569 | $OCH_3$ | $OCH_3$ | $CH_2CH_3$ | Br | OH |
| 6570 | $OCH_2CH_3$ | $OCH_2CH_3$ | $CH_2CH_3$ | Br | OH |
| 6571 | $OCH_2CH_2CH_3$ | $OCH_2CH_2CH_3$ | $CH_2CH_3$ | Br | OH |
| 6572 | $SCH_3$ | $SCH_3$ | $CH_2CH_3$ | Br | OH |
| 6573 | $SCH_2CH_3$ | $SCH_2CH_3$ | $CH_2CH_3$ | Br | OH |
| 6574 | $N(CH_3)_2$ | $N(CH_3)_2$ | $CH_2CH_3$ | Br | OH |
| 6575 | $N(CH_2CH_3)_2$ | $N(CH_2CH_3)_2$ | $CH_2CH_3$ | Br | OH |
| 6576 | $N(CH_3)(CH_2CH_3)$ | $N(CH_3)(CH_2CH_3)$ | $CH_2CH_3$ | Br | OH |
| 6577 | O—($CH_2CH_2$)—O | | $CH_2CH_3$ | Br | OH |
| 6578 | O—($CH_2CH_2CH_2$)—O | | $CH_2CH_3$ | Br | OH |
| 6579 | S—($CH_2CH_2$)—S | | $CH_2CH_3$ | Br | OH |
| 6580 | S—($CH_2CH_2CH_2$)—S | | $CH_2CH_3$ | Br | OH |
| 6581 | —$(CH_2)_4$— | | $CH_2CH_3$ | Br | OH |
| 6582 | —$(CH_2)_5$— | | $CH_2CH_3$ | Br | OH |
| 6583 | H | H | $CF_3$ | Br | OH |
| 6584 | $CH_3$ | $CH_3$ | $CF_3$ | Br | OH |
| 6585 | $CH_2CH_3$ | $CH_2CH_3$ | $CF_3$ | Br | OH |
| 6586 | $CH_2CH_2CH_3$ | $CH_2CH_2CH_3$ | $CF_3$ | Br | OH |
| 6587 | $OCH_3$ | $OCH_3$ | $CF_3$ | Br | OH |
| 6588 | $OCH_2CH_3$ | $OCH_2CH_3$ | $CF_3$ | Br | OH |
| 6589 | $OCH_2CH_2CH_3$ | $OCH_2CH_2CH_3$ | $CF_3$ | Br | OH |
| 6590 | $SCH_3$ | $SCH_3$ | $CF_3$ | Br | OH |
| 6591 | $SCH_2CH_3$ | $SCH_2CH_3$ | $CF_3$ | Br | OH |
| 6592 | $N(CH_3)_2$ | $N(CH_3)_2$ | $CF_3$ | Br | OH |
| 6593 | $N(CH_2CH_3)_2$ | $N(CH_2CH_3)_2$ | $CF_3$ | Br | OH |
| 6594 | $N(CH_3)(CH_2CH_3)$ | $N(CH_3)(CH_2CH_3)$ | $CF_3$ | Br | OH |
| 6595 | O—($CH_2CH_2$)—O | | $CF_3$ | Br | OH |
| 6596 | O—($CH_2CH_2CH_2$)—O | | $CF_3$ | Br | OH |
| 6597 | S—($CH_2CH_2$)—S | | $CF_3$ | Br | OH |
| 6598 | S—($CH_2CH_2CH_2$)—S | | $CF_3$ | Br | OH |
| 6599 | —$(CH_2)_4$— | | $CF_3$ | Br | OH |
| 6600 | —$(CH_2)_5$— | | $CF_3$ | Br | OH |
| 6601 | H | H | $OCH_3$ | Br | OH |
| 6602 | $CH_3$ | $CH_3$ | $OCH_3$ | Br | OH |
| 6603 | $CH_2CH_3$ | $CH_2CH_3$ | $OCH_3$ | Br | OH |
| 6604 | $CH_2CH_2CH_3$ | $CH_2CH_2CH_3$ | $OCH_3$ | Br | OH |
| 6605 | $OCH_3$ | $OCH_3$ | $OCH_3$ | Br | OH |
| 6606 | $OCH_2CH_3$ | $OCH_2CH_3$ | $OCH_3$ | Br | OH |

TABLE 1-continued

I1a1

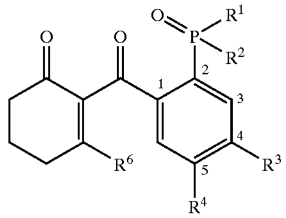

| n | $R^1$ | $R^2$ | $R^3$ | $R^4$ | $R^6$ |
|---|---|---|---|---|---|
| 6607 | $OCH_2CH_2CH_3$ | $OCH_2CH_2CH_3$ | $OCH_3$ | Br | OH |
| 6608 | $SCH_3$ | $SCH_3$ | $OCH_3$ | Br | OH |
| 6609 | $SCH_2CH_3$ | $SCH_2CH_3$ | $OCH_3$ | Br | OH |
| 6610 | $N(CH_3)_2$ | $N(CH_3)_2$ | $OCH_3$ | Br | OH |
| 6611 | $N(CH_2CH_3)_2$ | $N(CH_2CH_3)_2$ | $OCH_3$ | Br | OH |
| 6612 | $N(CH_3)(CH_2CH_3)$ | $N(CH_3)(CH_2CH_3)$ | $OCH_3$ | Br | OH |
| 6613 | $O-(CH_2CH_2)-O$ | | $OCH_3$ | Br | OH |
| 6614 | $O-(CH_2CH_2CH_2)-O$ | | $OCH_3$ | Br | OH |
| 6615 | $S-(CH_2CH_2)-S$ | | $OCH_3$ | Br | OH |
| 6616 | $S-(CH_2CH_2CH_2)-S$ | | $OCH_3$ | Br | OH |
| 6617 | $-(CH_2)_4-$ | | $OCH_3$ | Br | OH |
| 6618 | $-(CH_2)_5-$ | | $OCH_3$ | Br | OH |
| 6619 | H | H | $OCH_2CH_3$ | Br | OH |
| 6620 | $CH_3$ | $CH_3$ | $OCH_2CH_3$ | Br | OH |
| 6621 | $CH_2CH_3$ | $CH_2CH_3$ | $OCH_2CH_3$ | Br | OH |
| 6622 | $CH_2CH_2CH_3$ | $CH_2CH_2CH_3$ | $OCH_2CH_3$ | Br | OH |
| 6623 | $OCH_3$ | $OCH_3$ | $OCH_2CH_3$ | Br | OH |
| 6624 | $OCH_2CH_3$ | $OCH_2CH_3$ | $OCH_2CH_3$ | Br | OH |
| 6625 | $OCH_2CH_2CH_3$ | $OCH_2CH_2CH_3$ | $OCH_2CH_3$ | Br | OH |
| 6626 | $SCH_3$ | $SCH_3$ | $OCH_2CH_3$ | Br | OH |
| 6627 | $SCH_2CH_3$ | $SCH_2CH_3$ | $OCH_2CH_3$ | Br | OH |
| 6628 | $N(CH_3)_2$ | $N(CH_3)_2$ | $OCH_2CH_3$ | Br | OH |
| 6629 | $N(CH_2CH_3)_2$ | $N(CH_2CH_3)_2$ | $OCH_2CH_3$ | Br | OH |
| 6630 | $N(CH_3)(CH_2CH_3)$ | $N(CH_3)(CH_2CH_3)$ | $OCH_2CH_3$ | Br | OH |
| 6631 | $O-(CH_2CH_2)-O$ | | $OCH_2CH_3$ | Br | OH |
| 6632 | $O-(CH_2CH_2CH_2)-O$ | | $OCH_2CH_3$ | Br | OH |
| 6633 | $S-(CH_2CH_2)-S$ | | $OCH_2CH_3$ | Br | OH |
| 6634 | $S-(CH_2CH_2CH_2)-S$ | | $OCH_2CH_3$ | Br | OH |
| 6635 | $-(CH_2)_4-$ | | $OCH_2CH_3$ | Br | OH |
| 6636 | $-(CH_2)_5-$ | | $OCH_2CH_3$ | Br | OH |
| 6637 | H | H | $SCH_3$ | Br | OH |
| 6638 | $CH_3$ | $CH_3$ | $SCH_3$ | Br | OH |
| 6639 | $CH_2CH_3$ | $CH_2CH_3$ | $SCH_3$ | Br | OH |
| 6640 | $CH_2CH_2CH_3$ | $CH_2CH_2CH_3$ | $SCH_3$ | Br | OH |
| 6641 | $OCH_3$ | $OCH_3$ | $SCH_3$ | Br | OH |
| 6642 | $OCH_2CH_3$ | $OCH_2CH_3$ | $SCH_3$ | Br | OH |
| 6643 | $OCH_2CH_2CH_3$ | $OCH_2CH_2CH_3$ | $SCH_3$ | Br | OH |
| 6644 | $SCH_3$ | $SCH_3$ | $SCH_3$ | Br | OH |
| 6645 | $SCH_2CH_3$ | $SCH_2CH_3$ | $SCH_3$ | Br | OH |
| 6646 | $N(CH_3)_2$ | $N(CH_3)_2$ | $SCH_3$ | Br | OH |
| 6647 | $N(CH_2CH_3)_2$ | $N(CH_2CH_3)_2$ | $SCH_3$ | Br | OH |
| 6648 | $N(CH_3)(CH_2CH_3)$ | $N(CH_3)(CH_2CH_3)$ | $SCH_3$ | Br | OH |
| 6649 | $O-(CH_2CH_2)-O$ | | $SCH_3$ | Br | OH |
| 6650 | $O-(CH_2CH_2CH_2)-O$ | | $SCH_3$ | Br | OH |
| 6651 | $S-(CH_2CH_2)-S$ | | $SCH_3$ | Br | OH |
| 6652 | $S-(CH_2CH_2CH_2)-S$ | | $SCH_3$ | Br | OH |
| 6653 | $-(CH_2)_4-$ | | $SCH_3$ | Br | OH |
| 6654 | $-(CH_2)_5-$ | | $SCH_3$ | Br | OH |
| 6655 | H | H | $SO_2CH_3$ | Br | OH |
| 6656 | $CH_3$ | $CH_3$ | $SO_2CH_3$ | Br | OH |
| 6657 | $CH_2CH_3$ | $CH_2CH_3$ | $SO_2CH_3$ | Br | OH |
| 6658 | $CH_2CH_2CH_3$ | $CH_2CH_2CH_3$ | $SO_2CH_3$ | Br | OH |
| 6659 | $OCH_3$ | $OCH_3$ | $SO_2CH_3$ | Br | OH |
| 6660 | $OCH_2CH_3$ | $OCH_2CH_3$ | $SO_2CH_3$ | Br | OH |
| 6661 | $OCH_2CH_2CH_3$ | $OCH_2CH_2CH_3$ | $SO_2CH_3$ | Br | OH |
| 6662 | $SCH_3$ | $SCH_3$ | $SO_2CH_3$ | Br | OH |
| 6663 | $SCH_2CH_3$ | $SCH_2CH_3$ | $SO_2CH_3$ | Br | OH |
| 6664 | $N(CH_3)_2$ | $N(CH_3)_2$ | $SO_2CH_3$ | Br | OH |
| 6665 | $N(CH_2CH_3)_2$ | $N(CH_2CH_3)_2$ | $SO_2CH_3$ | Br | OH |
| 6666 | $N(CH_3)(CH_2CH_3)$ | $N(CH_3)(CH_2CH_3)$ | $SO_2CH_3$ | Br | OH |
| 6667 | $O-(CH_2CH_2)-O$ | | $SO_2CH_3$ | Br | OH |
| 6668 | $O-(CH_2CH_2CH_2)-O$ | | $SO_2CH_3$ | Br | OH |
| 6669 | $S-(CH_2CH_2)-S$ | | $SO_2CH_3$ | Br | OH |
| 6670 | $S-(CH_2CH_2CH_2)-S$ | | $SO_2CH_3$ | Br | OH |

TABLE 1-continued

I1a1

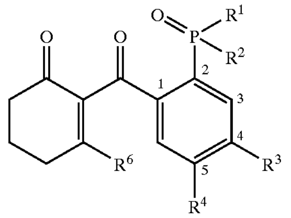

| n | $R^1$ | $R^2$ | $R^3$ | $R^4$ | $R^6$ |
|---|---|---|---|---|---|
| 6671 | $—(CH_2)_4—$ | | $SO_2CH_3$ | Br | OH |
| 6672 | $—(CH_2)_5—$ | | $SO_2CH_3$ | Br | OH |
| 6673 | H | H | $PO(OCH_3)_2$ | Br | OH |
| 6674 | $CH_3$ | $CH_3$ | $PO(OCH_3)_2$ | Br | OH |
| 6675 | $CH_2CH_3$ | $CH_2CH_3$ | $PO(OCH_3)_2$ | Br | OH |
| 6676 | $CH_2CH_2CH_3$ | $CH_2CH_2CH_3$ | $PO(OCH_3)_2$ | Br | OH |
| 6677 | $OCH_3$ | $OCH_3$ | $PO(OCH_3)_2$ | Br | OH |
| 6678 | $OCH_2CH_3$ | $OCH_2CH_3$ | $PO(OCH_3)_2$ | Br | OH |
| 6679 | $OCH_2CH_2CH_3$ | $OCH_2CH_2CH_3$ | $PO(OCH_3)_2$ | Br | OH |
| 6680 | $SCH_3$ | $SCH_3$ | $PO(OCH_3)_2$ | Br | OH |
| 6681 | $SCH_2CH_3$ | $SCH_2CH_3$ | $PO(OCH_3)_2$ | Br | OH |
| 6682 | $N(CH_3)_2$ | $N(CH_3)_2$ | $PO(OCH_3)_2$ | Br | OH |
| 6683 | $N(CH_2CH_3)_2$ | $N(CH_2CH_3)_2$ | $PO(OCH_3)_2$ | Br | OH |
| 6684 | $N(CH_3)(CH_2CH_3)$ | $N(CH_3)(CH_2CH_3)$ | $PO(OCH_3)_2$ | Br | OH |
| 6685 | $O—(CH_2CH_2)—O$ | | $PO(OCH_3)_2$ | Br | OH |
| 6686 | $O—(CH_2CH_2CH_2)—O$ | | $PO(OCH_3)_2$ | Br | OH |
| 6687 | $S—(CH_2CH_2)—S$ | | $PO(OCH_3)_2$ | Br | OH |
| 6688 | $S—(CH_2CH_2CH_2)—S$ | | $PO(OCH_3)_2$ | Br | OH |
| 6689 | $—(CH_2)_4—$ | | $PO(OCH_3)_2$ | Br | OH |
| 6690 | $—(CH_2)_5—$ | | $PO(OCH_3)_2$ | Br | OH |
| 6691 | H | H | $PO(OCH_2CH_3)_2$ | Br | OH |
| 6692 | $CH_3$ | $CH_3$ | $PO(OCH_2CH_3)_2$ | Br | OH |
| 6693 | $CH_2CH_3$ | $CH_2CH_3$ | $PO(OCH_2CH_3)_2$ | Br | OH |
| 6694 | $CH_2CH_2CH_3$ | $CH_2CH_2CH_3$ | $PO(OCH_2CH_3)_2$ | Br | OH |
| 6695 | $OCH_3$ | $OCH_3$ | $PO(OCH_2CH_3)_2$ | Br | OH |
| 6696 | $OCH_2CH_3$ | $OCH_2CH_3$ | $PO(OCH_2CH_3)_2$ | Br | OH |
| 6697 | $OCH_2CH_2CH_3$ | $OCH_2CH_2CH_3$ | $PO(OCH_2CH_3)_2$ | Br | OH |
| 6698 | $SCH_3$ | $SCH_3$ | $PO(OCH_2CH_3)_2$ | Br | OH |
| 6699 | $SCH_2CH_3$ | $SCH_2CH_3$ | $PO(OCH_2CH_3)_2$ | Br | OH |
| 6700 | $N(CH_3)_2$ | $N(CH_3)_2$ | $PO(OCH_2CH_3)_2$ | Br | OH |
| 6701 | $N(CH_2CH_3)_2$ | $N(CH_2CH_3)_2$ | $PO(OCH_2CH_3)_2$ | Br | OH |
| 6702 | $N(CH_3)(CH_2CH_3)$ | $N(CH_3)(CH_2CH_3)$ | $PO(OCH_2CH_3)_2$ | Br | OH |
| 6703 | $O—(CH_2CH_2)—O$ | | $PO(OCH_2CH_3)_2$ | Br | OH |
| 6704 | $O—(CH_2CH_2CH_2)—O$ | | $PO(OCH_2CH_3)_2$ | Br | OH |
| 6705 | $S—(CH_2CH_2)—S$ | | $PO(OCH_2CH_3)_2$ | Br | OH |
| 6706 | $S—(CH_2CH_2CH_2)—S$ | | $PO(OCH_2CH_3)_2$ | Br | OH |
| 6707 | $—(CH_2)_4—$ | | $PO(OCH_2CH_3)_2$ | Br | OH |
| 6708 | $—(CH_2)_5—$ | | $PO(OCH_2CH_3)_2$ | Br | OH |
| 6709 | H | H | $PO(CH_3)_2$ | Br | OH |
| 6710 | $CH_3$ | $CH_3$ | $PO(CH_3)_2$ | Br | OH |
| 6711 | $CH_2CH_3$ | $CH_2CH_3$ | $PO(CH_3)_2$ | Br | OH |
| 6712 | $CH_2CH_2CH_3$ | $CH_2CH_2CH_3$ | $PO(CH_3)_2$ | Br | OH |
| 6713 | $OCH_3$ | $OCH_3$ | $PO(CH_3)_2$ | Br | OH |
| 6714 | $OCH_2CH_3$ | $OCH_2CH_3$ | $PO(CH_3)_2$ | Br | OH |
| 6715 | $OCH_2CH_2CH_3$ | $OCH_2CH_2CH_3$ | $PO(CH_3)_2$ | Br | OH |
| 6716 | $SCH_3$ | $SCH_3$ | $PO(CH_3)_2$ | Br | OH |
| 6717 | $SCH_2CH_3$ | $SCH_2CH_3$ | $PO(CH_3)_2$ | Br | OH |
| 6718 | $N(CH_3)_2$ | $N(CH_3)_2$ | $PO(CH_3)_2$ | Br | OH |
| 6719 | $N(CH_2CH_3)_2$ | $N(CH_2CH_3)_2$ | $PO(CH_3)_2$ | Br | OH |
| 6720 | $N(CH_3)(CH_2CH_3)$ | $N(CH_3)(CH_2CH_3)$ | $PO(CH_3)_2$ | Br | OH |
| 6721 | $O—(CH_2CH_2)—O$ | | $PO(CH_3)_2$ | Br | OH |
| 6722 | $O—(CH_2CH_2CH_2)—O$ | | $PO(CH_3)_2$ | Br | OH |
| 6723 | $S—(CH_2CH_2)—S$ | | $PO(CH_3)_2$ | Br | OH |
| 6724 | $S—(CH_2CH_2CH_2)—S$ | | $PO(CH_3)_2$ | Br | OH |
| 6725 | $—(CH_2)_4—$ | | $PO(CH_3)_2$ | Br | OH |
| 6726 | $—(CH_2)_5—$ | | $PO(CH_3)_2$ | Br | OH |
| 6727 | H | H | $PC(CH_2CH_3)_2$ | Br | OH |
| 6728 | $CH_3$ | $CH_3$ | $PC(CH_2CH_3)_2$ | Br | OH |
| 6729 | $CH_2CH_3$ | $CH_2CH_3$ | $PC(CH_2CH_3)_2$ | Br | OH |
| 6730 | $CH_2CH_2CH_3$ | $CH_2CH_2CH_3$ | $PC(CH_2CH_3)_2$ | Br | OH |
| 6731 | $OCH_3$ | $OCH_3$ | $PC(CH_2CH_3)_2$ | Br | OH |
| 6732 | $OCH_2CH_3$ | $OCH_2CH_3$ | $PC(CH_2CH_3)_2$ | Br | OH |
| 6733 | $OCH_2CH_2CH_3$ | $OCH_2CH_2CH_3$ | $PC(CH_2CH_3)_2$ | Br | OH |
| 6734 | $SCH_3$ | $SCH_3$ | $PC(CH_2CH_3)_2$ | Br | OH |

TABLE 1-continued

I1a1

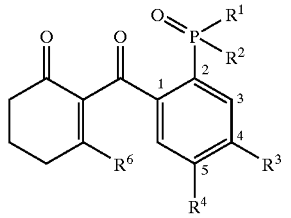

| n | $R^1$ | $R^2$ | $R^3$ | $R^4$ | $R^6$ |
|---|---|---|---|---|---|
| 6735 | $SCH_2CH_3$ | $SCH_2CH_3$ | $PC(CH_2CH_3)_2$ | Br | OH |
| 6736 | $N(CH_3)_2$ | $N(CH_3)_2$ | $PC(CH_2CH_3)_2$ | Br | OH |
| 6737 | $N(CH_2CH_3)_2$ | $N(CH_2CH_3)_2$ | $PC(CH_2CH_3)_2$ | Br | OH |
| 6738 | $N(CH_3)(CH_2CH_3)$ | $N(CH_3)(CH_2CH_3)$ | $PC(CH_2CH_3)_2$ | Br | OH |
| 6739 | $O—(CH_2CH_2)—O$ | | $PC(CH_2CH_3)_2$ | Br | OH |
| 6740 | $O—(CH_2CH_2CH_2)—O$ | | $PC(CH_2CH_3)_2$ | Br | OH |
| 6741 | $S—(CH_2CH_2)—S$ | | $PC(CH_2CH_3)_2$ | Br | OH |
| 6742 | $S—(CH_2CH_2CH_2)—S$ | | $PC(CH_2CH_3)_2$ | Br | OH |
| 6743 | $—(CH_2)_4—$ | | $PC(CH_2CH_3)_2$ | Br | OH |
| 6744 | $—(CH_2)_5—$ | | $PC(CH_2CH_3)_2$ | Br | OH |
| 6745 | H | H | H | Br | $OCOC_6H_5$ |
| 6746 | $CH_3$ | $CH_3$ | H | Br | $OCOC_6H_5$ |
| 6747 | $CH_2CH_3$ | $CH_2CH_3$ | H | Br | $OCOC_6H_5$ |
| 6748 | $CH_2CH_2CH_3$ | $CH_2CH_2CH_3$ | H | Br | $OCOC_6H_5$ |
| 6749 | $OCH_3$ | $OCH_3$ | H | Br | $OCOC_6H_5$ |
| 6750 | $OCH_2CH_3$ | $OCH_2CH_3$ | H | Br | $OCOC_6H_5$ |
| 6751 | $OCH_2CH_2CH_3$ | $OCH_2CH_2CH_3$ | H | Br | $OCOC_6H_5$ |
| 6752 | $SCH_3$ | $SCH_3$ | H | Br | $OCOC_6H_5$ |
| 6753 | $SCH_2CH_3$ | $SCH_2CH_3$ | H | Br | $OCOC_6H_5$ |
| 6754 | $N(CH_3)_2$ | $N(CH_3)_2$ | H | Br | $OCOC_6H_5$ |
| 6755 | $N(CH_2CH_3)_2$ | $N(CH_2CH_3)_2$ | H | Br | $OCOC_6H_5$ |
| 6756 | $N(CH_3)(CH_2CH_3)$ | $N(CH_3)(CH_2CH_3)$ | H | Br | $OCOC_6H_5$ |
| 6757 | $O—(CH_2CH_2)—O$ | | H | Br | $OCOC_6H_5$ |
| 6758 | $O—(CH_2CH_2CH_2)—O$ | | H | Br | $OCOC_6H_5$ |
| 6759 | $S—(CH_2CH_2)—S$ | | H | Br | $OCOC_6H_5$ |
| 6760 | $S—(CH_2CH_2CH_2)—S$ | | H | Br | $OCOC_6H_5$ |
| 6761 | $—(CH_2)_4—$ | | H | Br | $OCOC_6H_5$ |
| 6762 | $—(CH_2)_5—$ | | H | Br | $OCOC_6H_5$ |
| 6763 | H | H | $NO_2$ | Br | $OCOC_6H_5$ |
| 6764 | $CH_3$ | $CH_3$ | $NO_2$ | Br | $OCOC_6H_5$ |
| 6765 | $CH_2CH_3$ | $CH_2CH_3$ | $NO_2$ | Br | $OCOC_6H_5$ |
| 6766 | $CH_2CH_2CH_3$ | $CH_2CH_2CH_3$ | $NO_2$ | Br | $OCOC_6H_5$ |
| 6767 | $OCH_3$ | $OCH_3$ | $NO_2$ | Br | $OCOC_6H_5$ |
| 6768 | $OCH_2CH_3$ | $OCH_2CH_3$ | $NO_2$ | Br | $OCOC_6H_5$ |
| 6769 | $OCH_2CH_2CH_3$ | $OCH_2CH_2CH_3$ | $NO_2$ | Br | $OCOC_6H_5$ |
| 6770 | $SCH_3$ | $SCH_3$ | $NO_2$ | Br | $OCOC_6H_5$ |
| 6771 | $SCH_2CH_3$ | $SCH_2CH_3$ | $NO_2$ | Br | $OCOC_6H_5$ |
| 6772 | $N(CH_3)_2$ | $N(CH_3)_2$ | $NO_2$ | Br | $OCOC_6H_5$ |
| 6773 | $N(CH_2CH_3)_2$ | $N(CH_2CH_3)_2$ | $NO_2$ | Br | $OCOC_6H_5$ |
| 6774 | $N(CH_3)(CH_2CH_3)$ | $N(CH_3)(CH_2CH_3)$ | $NO_2$ | Br | $OCOC_6H_5$ |
| 6775 | $O—(CH_2CH_2)—O$ | | $NO_2$ | Br | $OCOC_6H_5$ |
| 6776 | $O—(CH_2CH_2CH_2)—O$ | | $NO_2$ | Br | $OCOC_6H_5$ |
| 6777 | $S—(CH_2CH_2)—S$ | | $NO_2$ | Br | $OCOC_6H_5$ |
| 6778 | $S—(CH_2CH_2CH_2)—S$ | | $NO_2$ | Br | $OCOC_6H_5$ |
| 6779 | $—(CH_2)_4—$ | | $NO_2$ | Br | $OCOC_6H_5$ |
| 6780 | $—(CH_2)_5—$ | | $NO_2$ | Br | $OCOC_6H_5$ |
| 6781 | H | H | CN | Br | $OCOC_6H_5$ |
| 6782 | $CH_3$ | $CH_3$ | CN | Br | $OCOC_6H_5$ |
| 6783 | $CH_2CH_3$ | $CH_2CH_3$ | CN | Br | $OCOC_6H_5$ |
| 6784 | $CH_2CH_2CH_3$ | $CH_2CH_2CH_3$ | CN | Br | $OCOC_6H_5$ |
| 6785 | $OCH_3$ | $OCH_3$ | CN | Br | $OCOC_6H_5$ |
| 6786 | $OCH_2CH_3$ | $OCH_2CH_3$ | CN | Br | $OCOC_6H_5$ |
| 6787 | $OCH_2CH_2CH_3$ | $OCH_2CH_2CH_3$ | CN | Br | $OCOC_6H_5$ |
| 6788 | $SCH_3$ | $SCH_3$ | CN | Br | $OCOC_6H_5$ |
| 6789 | $SCH_2CH_3$ | $SCH_2CH_3$ | CN | Br | $OCOC_6H_5$ |
| 6790 | $N(CH_3)_2$ | $N(CH_3)_2$ | CN | Br | $OCOC_6H_5$ |
| 6791 | $N(CH_2CH_3)_2$ | $N(CH_2CH_3)_2$ | CN | Br | $OCOC_6H_5$ |
| 6792 | $N(CH_3)(CH_2CH_3)$ | $N(CH_3)(CH_2CH_3)$ | CN | Br | $OCOC_6H_5$ |
| 6793 | $O—(CH_2CH_2)—O$ | | CN | Br | $OCOC_6H_5$ |
| 6794 | $O—(CH_2CH_2CH_2)—O$ | | CN | Br | $OCOC_6H_5$ |
| 6795 | $S—(CH_2CH_2)—S$ | | CN | Br | $OCOC_6H_5$ |
| 6796 | $S—(CH_2CH_2CH_2)—S$ | | CN | Br | $OCOC_6H_5$ |
| 6797 | $—(CH_2)_4—$ | | CN | Br | $OCOC_6H_5$ |
| 6798 | $—(CH_2)_5—$ | | CN | Br | $OCOC_6H_5$ |

TABLE 1-continued

I1a1

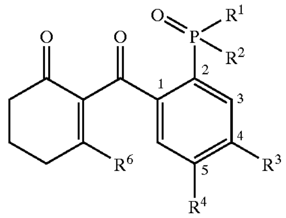

| n | $R^1$ | $R^2$ | $R^3$ | $R^4$ | $R^6$ |
|---|---|---|---|---|---|
| 6799 | H | H | F | Br | $OCOC_6H_5$ |
| 6800 | $CH_3$ | $CH_3$ | F | Br | $OCOC_6H_5$ |
| 6801 | $CH_2CH_3$ | $CH_2CH_3$ | F | Br | $OCOC_6H_5$ |
| 6802 | $CH_2CH_2CH_3$ | $CH_2CH_2CH_3$ | F | Br | $OCOC_6H_5$ |
| 6803 | $OCH_3$ | $OCH_3$ | F | Br | $OCOC_6H_5$ |
| 6804 | $OCH_2CH_3$ | $OCH_2CH_3$ | F | Br | $OCOC_6H_5$ |
| 6805 | $OCH_2CH_2CH_3$ | $OCH_2CH_2CH_3$ | F | Br | $OCOC_6H_5$ |
| 6806 | $SCH_3$ | $SCH_3$ | F | Br | $OCOC_6H_5$ |
| 6807 | $SCH_2CH_3$ | $SCH_2CH_3$ | F | Br | $OCOC_6H_5$ |
| 6808 | $N(CH_3)_2$ | $N(CH_3)_2$ | F | Br | $OCOC_6H_5$ |
| 6809 | $N(CH_2CH_3)_2$ | $N(CH_2CH_3)_2$ | F | Br | $OCOC_6H_5$ |
| 6810 | $N(CH_3)(CH_2CH_3)$ | $N(CH_3)(CH_2CH_3)$ | F | Br | $OCOC_6H_5$ |
| 6811 | $O—(CH_2CH_2)—O$ | | F | Br | $OCOC_6H_5$ |
| 6812 | $O—(CH_2CH_2CH_2)—O$ | | F | Br | $OCOC_6H_5$ |
| 6813 | $S—(CH_2CH_2)—S$ | | F | Br | $OCOC_6H_5$ |
| 6814 | $S—(CH_2CH_2CH_2)—S$ | | F | Br | $OCOC_6H_5$ |
| 6815 | $—(CH_2)_4—$ | | F | Br | $OCOC_6H_5$ |
| 6816 | $—(CH_2)_5—$ | | F | Br | $OCOC_6H_5$ |
| 6817 | H | H | Cl | Br | $OCOC_6H_5$ |
| 6818 | $CH_3$ | $CH_3$ | Cl | Br | $OCOC_6H_5$ |
| 6819 | $CH_2CH_3$ | $CH_2CH_3$ | Cl | Br | $OCOC_6H_5$ |
| 6820 | $CH_2CH_2CH_3$ | $CH_2CH_2CH_3$ | Cl | Br | $OCOC_6H_5$ |
| 6821 | $OCH_3$ | $OCH_3$ | Cl | Br | $OCOC_6H_5$ |
| 6822 | $OCH_2CH_3$ | $OCH_2CH_3$ | Cl | Br | $OCOC_6H_5$ |
| 6823 | $OCH_2CH_2CH_3$ | $OCH_2CH_2CH_3$ | Cl | Br | $OCOC_6H_5$ |
| 6824 | $SCH_3$ | $SCH_3$ | Cl | Br | $OCOC_6H_5$ |
| 6825 | $SCH_2CH_3$ | $SCH_2CH_3$ | Cl | Br | $OCOC_6H_5$ |
| 6826 | $N(CH_3)_2$ | $N(CH_3)_2$ | Cl | Br | $OCOC_6H_5$ |
| 6827 | $N(CH_2CH_3)_2$ | $N(CH_2CH_3)_2$ | Cl | Br | $OCOC_6H_5$ |
| 6828 | $N(CH_3)(CH_2CH_3)$ | $N(CH_3)(CH_2CH_3)$ | Cl | Br | $OCOC_6H_5$ |
| 6829 | $O—(CH_2CH_2)—O$ | | Cl | Br | $OCOC_6H_5$ |
| 6830 | $O—(CH_2CH_2CH_2)—O$ | | Cl | Br | $OCOC_6H_5$ |
| 6831 | $S—(CH_2CH_2)—S$ | | Cl | Br | $OCOC_6H_5$ |
| 6832 | $S—(CH_2CH_2CH_2)—S$ | | Cl | Br | $OCOC_6H_5$ |
| 6833 | $—(CH_2)_4—$ | | Cl | Br | $OCOC_6H_5$ |
| 6834 | $—(CH_2)_5—$ | | Cl | Br | $OCOC_6H_5$ |
| 6835 | H | H | Br | Br | $OCOC_6H_5$ |
| 6836 | $CH_3$ | $CH_3$ | Br | Br | $OCOC_6H_5$ |
| 6837 | $CH_2CH_3$ | $CH_2CH_3$ | Br | Br | $OCOC_6H_5$ |
| 6838 | $CH_2CH_2CH_3$ | $CH_2CH_2CH_3$ | Br | Br | $OCOC_6H_5$ |
| 6839 | $OCH_3$ | $OCH_3$ | Br | Br | $OCOC_6H_5$ |
| 6840 | $OCH_2CH_3$ | $OCH_2CH_3$ | Br | Br | $OCOC_6H_5$ |
| 6841 | $OCH_2CH_2CH_3$ | $OCH_2CH_2CH_3$ | Br | Br | $OCOC_6H_5$ |
| 6842 | $SCH_3$ | $SCH_3$ | Br | Br | $OCOC_6H_5$ |
| 6843 | $SCH_2CH_3$ | $SCH_2CH_3$ | Br | Br | $OCOC_6H_5$ |
| 6844 | $N(CH_3)_2$ | $N(CH_3)_2$ | Br | Br | $OCOC_6H_5$ |
| 6845 | $N(CH_2CH_3)_2$ | $N(CH_2CH_3)_2$ | Br | Br | $OCOC_6H_5$ |
| 6846 | $N(CH_3)(CH_2CH_3)$ | $N(CH_3)(CH_2CH_3)$ | Br | Br | $OCOC_6H_5$ |
| 6847 | $O—(CH_2CH_2)—O$ | | Br | Br | $OCOC_6H_5$ |
| 6848 | $O—(CH_2CH_2CH_2)—O$ | | Br | Br | $OCOC_6H_5$ |
| 6849 | $S—(CH_2CH_2)—S$ | | Br | Br | $OCOC_6H_5$ |
| 6850 | $S—(CH_2CH_2CH_2)—S$ | | Br | Br | $OCOC_6H_5$ |
| 6851 | $—(CH_2)_4—$ | | Br | Br | $OCOC_6H_5$ |
| 6852 | $—(CH_2)_5—$ | | Br | Br | $OCOC_6H_5$ |
| 6853 | H | H | $CH_3$ | Br | $OCOC_6H_5$ |
| 6854 | $CH_3$ | $CH_3$ | $CH_3$ | Br | $OCOC_6H_5$ |
| 6855 | $CH_2CH_3$ | $CH_2CH_3$ | $CH_3$ | Br | $OCOC_6H_5$ |
| 6856 | $CH_2CH_2CH_3$ | $CH_2CH_2CH_3$ | $CH_3$ | Br | $OCOC_6H_5$ |
| 6857 | $OCH_3$ | $OCH_3$ | $CH_3$ | Br | $OCOC_6H_5$ |
| 6858 | $OCH_2CH_3$ | $OCH_2CH_3$ | $CH_3$ | Br | $OCOC_6H_5$ |
| 6859 | $OCH_2CH_2CH_3$ | $OCH_2CH_2CH_3$ | $CH_3$ | Br | $OCOC_6H_5$ |
| 6860 | $SCH_3$ | $SCH_3$ | $CH_3$ | Br | $OCOC_6H_5$ |
| 6861 | $SCH_2CH_3$ | $SCH_2CH_3$ | $CH_3$ | Br | $OCOC_6H_5$ |
| 6862 | $N(CH_3)_2$ | $N(CH_3)_2$ | $CH_3$ | Br | $OCOC_6H_5$ |

TABLE 1-continued

I1a1

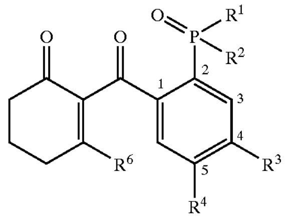

| n | $R^1$ | $R^2$ | $R^3$ | $R^4$ | $R^6$ |
|---|---|---|---|---|---|
| 6863 | $N(CH_2CH_3)_2$ | $N(CH_2CH_3)_2$ | $CH_3$ | Br | $OCOC_6H_5$ |
| 6864 | $N(CH_3)(CH_2CH_3)$ | $N(CH_3)(CH_2CH_3)$ | $CH_3$ | Br | $OCOC_6H_5$ |
| 6865 | $O-(CH_2CH_2)-O$ | | $CH_3$ | Br | $OCOC_6H_5$ |
| 6866 | $O-(CH_2CH_2CH_2)-O$ | | $CH_3$ | Br | $OCOC_6H_5$ |
| 6867 | $S-(CH_2CH_2)-S$ | | $CH_3$ | Br | $OCOC_6H_5$ |
| 6868 | $S-(CH_2CH_2CH_2)-S$ | | $CH_3$ | Br | $OCOC_6H_5$ |
| 6869 | $-(CH_2)_4-$ | | $CH_3$ | Br | $OCOC_6H_5$ |
| 6870 | $-(CH_2)_5-$ | | $CH_3$ | Br | $OCOC_6H_5$ |
| 6871 | H | H | $CH_2CH_3$ | Br | $OCOC_6H_5$ |
| 6872 | $CH_3$ | $CH_3$ | $CH_2CH_3$ | Br | $OCOC_6H_5$ |
| 6873 | $CH_2CH_3$ | $CH_2CH_3$ | $CH_2CH_3$ | Br | $OCOC_6H_5$ |
| 6874 | $CH_2CH_2CH_3$ | $CH_2CH_2CH_3$ | $CH_2CH_3$ | Br | $OCOC_6H_5$ |
| 6875 | $OCH_3$ | $OCH_3$ | $CH_2CH_3$ | Br | $OCOC_6H_5$ |
| 6876 | $OCH_2CH_3$ | $OCH_2CH_3$ | $CH_2CH_3$ | Br | $OCOC_6H_5$ |
| 6877 | $OCH_2CH_2CH_3$ | $OCH_2CH_2CH_3$ | $CH_2CH_3$ | Br | $OCOC_6H_5$ |
| 6878 | $SCH_3$ | $SCH_3$ | $CH_2CH_3$ | Br | $OCOC_6H_5$ |
| 6879 | $SCH_2CH_3$ | $SCH_2CH_3$ | $CH_2CH_3$ | Br | $OCOC_6H_5$ |
| 6880 | $N(CH_3)_2$ | $N(CH_3)_2$ | $CH_2CH_3$ | Br | $OCOC_6H_5$ |
| 6881 | $N(CH_2CH_3)_2$ | $N(CH_2CH_3)_2$ | $CH_2CH_3$ | Br | $OCOC_6H_5$ |
| 6882 | $N(CH_3)(CH_2CH_3)$ | $N(CH_3)(CH_2CH_3)$ | $CH_2CH_3$ | Br | $OCOC_6H_5$ |
| 6883 | $O-(CH_2CH_2)-O$ | | $CH_2CH_3$ | Br | $OCOC_6H_5$ |
| 6884 | $O-(CH_2CH_2CH_2)-O$ | | $CH_2CH_3$ | Br | $OCOC_6H_5$ |
| 6885 | $S-(CH_2CH_2)-S$ | | $CH_2CH_3$ | Br | $OCOC_6H_5$ |
| 6886 | $S-(CH_2CH_2CH_2)-S$ | | $CH_2CH_3$ | Br | $OCOC_6H_5$ |
| 6887 | $-(CH_2)_4-$ | | $CH_2CH_3$ | Br | $OCOC_6H_5$ |
| 6888 | $-(CH_2)_5-$ | | $CH_2CH_3$ | Br | $OCOC_6H_5$ |
| 6889 | H | H | $CF_3$ | Br | $OCOC_6H_5$ |
| 6890 | $CH_3$ | $CH_3$ | $CF_3$ | Br | $OCOC_6H_5$ |
| 6891 | $CH_2CH_3$ | $CH_2CH_3$ | $CF_3$ | Br | $OCOC_6H_5$ |
| 6892 | $CH_2CH_2CH_3$ | $CH_2CH_2CH_3$ | $CF_3$ | Br | $OCOC_6H_5$ |
| 6893 | $OCH_3$ | $OCH_3$ | $CF_3$ | Br | $OCOC_6H_5$ |
| 6894 | $OCH_2CH_3$ | $OCH_2CH_3$ | $CF_3$ | Br | $OCOC_6H_5$ |
| 6895 | $OCH_2CH_2CH_3$ | $OCH_2CH_2CH_3$ | $CF_3$ | Br | $OCOC_6H_5$ |
| 6896 | $SCH_3$ | $SCH_3$ | $CF_3$ | Br | $OCOC_6H_5$ |
| 6897 | $SCH_2CH_3$ | $SCH_2CH_3$ | $CF_3$ | Br | $OCOC_6H_5$ |
| 6898 | $N(CH_3)_2$ | $N(CH_3)_2$ | $CF_3$ | Br | $OCOC_6H_5$ |
| 6899 | $N(CH_2CH_3)_2$ | $N(CH_2CH_3)_2$ | $CF_3$ | Br | $OCOC_6H_5$ |
| 6900 | $N(CH_3)(CH_2CH_3)$ | $N(CH_3)(CH_2CH_3)$ | $CF_3$ | Br | $OCOC_6H_5$ |
| 6901 | $O-(CH_2CH_2)-O$ | | $CF_3$ | Br | $OCOC_6H_5$ |
| 6902 | $O-(CH_2CH_2CH_2)-O$ | | $CF_3$ | Br | $OCOC_6H_5$ |
| 6903 | $S-(CH_2CH_2)-S$ | | $CF_3$ | Br | $OCOC_6H_5$ |
| 6904 | $S-(CH_2CH_2CH_2)-S$ | | $CF_3$ | Br | $OCOC_6H_5$ |
| 6905 | $-(CH_2)_4-$ | | $CF_3$ | Br | $OCOC_6H_5$ |
| 6906 | $-(CH_2)_5-$ | | $CF_3$ | Br | $OCOC_6H_5$ |
| 6907 | H | H | $OCH_3$ | Br | $OCOC_6H_5$ |
| 6908 | $CH_3$ | $CH_3$ | $OCH_3$ | Br | $OCOC_6H_5$ |
| 6909 | $CH_2CH_3$ | $CH_2CH_3$ | $OCH_3$ | Br | $OCOC_6H_5$ |
| 6910 | $CH_2CH_2CH_3$ | $CH_2CH_2CH_3$ | $OCH_3$ | Br | $OCOC_6H_5$ |
| 6911 | $OCH_3$ | $OCH_3$ | $OCH_3$ | Br | $OCOC_6H_5$ |
| 6912 | $OCH_2CH_3$ | $OCH_2CH_3$ | $OCH_3$ | Br | $OCOC_6H_5$ |
| 6913 | $OCH_2CH_2CH_3$ | $OCH_2CH_2CH_3$ | $OCH_3$ | Br | $OCOC_6H_5$ |
| 6914 | $SCH_3$ | $SCH_3$ | $OCH_3$ | Br | $OCOC_6H_5$ |
| 6915 | $SCH_2CH_3$ | $SCH_2CH_3$ | $OCH_3$ | Br | $OCOC_6H_5$ |
| 6916 | $N(CH_3)_2$ | $N(CH_3)_2$ | $OCH_3$ | Br | $OCOC_6H_5$ |
| 6917 | $N(CH_2CH_3)_2$ | $N(CH_2CH_3)_2$ | $OCH_3$ | Br | $OCOC_6H_5$ |
| 6918 | $N(CH_3)(CH_2CH_3)$ | $N(CH_3)(CH_2CH_3)$ | $OCH_3$ | Br | $OCOC_6H_5$ |
| 6919 | $O-(CH_2CH_2)-O$ | | $OCH_3$ | Br | $OCOC_6H_5$ |
| 6920 | $O-(CH_2CH_2CH_2)-O$ | | $OCH_3$ | Br | $OCOC_6H_5$ |
| 6921 | $S-(CH_2CH_2)-S$ | | $OCH_3$ | Br | $OCOC_6H_5$ |
| 6922 | $S-(CH_2CH_2CH_2)-S$ | | $OCH_3$ | Br | $OCOC_6H_5$ |
| 6923 | $-(CH_2)_4-$ | | $OCH_3$ | Br | $OCOC_6H_5$ |
| 6924 | $-(CH_2)_5-$ | | $OCH_3$ | Br | $OCOC_6H_5$ |
| 6925 | H | H | $OCH_2CH_3$ | Br | $OCOC_6H_5$ |
| 6926 | $CH_3$ | $CH_3$ | $OCH_2CH_3$ | Br | $OCOC_6H_5$ |

TABLE 1-continued

I1a1

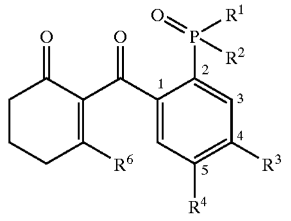

| n | $R^1$ | $R^2$ | $R^3$ | $R^4$ | $R^6$ |
|---|---|---|---|---|---|
| 6927 | $CH_2CH_3$ | $CH_2CH_3$ | $OCH_2CH_3$ | Br | $OCOC_6H_5$ |
| 6928 | $CH_2CH_2CH_3$ | $CH_2CH_2CH_3$ | $OCH_2CH_3$ | Br | $OCOC_6H_5$ |
| 6929 | $OCH_3$ | $OCH_3$ | $OCH_2CH_3$ | Br | $OCOC_6H_5$ |
| 6930 | $OCH_2CH_3$ | $OCH_2CH_3$ | $OCH_2CH_3$ | Br | $OCOC_6H_5$ |
| 6931 | $OCH_2CH_2CH_3$ | $OCH_2CH_2CH_3$ | $OCH_2CH_3$ | Br | $OCOC_6H_5$ |
| 6932 | $SCH_3$ | $SCH_3$ | $OCH_2CH_3$ | Br | $OCOC_6H_5$ |
| 6933 | $SCH_2CH_3$ | $SCH_2CH_3$ | $OCH_2CH_3$ | Br | $OCOC_6H_5$ |
| 6934 | $N(CH_3)_2$ | $N(CH_3)_2$ | $OCH_2CH_3$ | Br | $OCOC_6H_5$ |
| 6935 | $N(CH_2CH_3)_2$ | $N(CH_2CH_3)_2$ | $OCH_2CH_3$ | Br | $OCOC_6H_5$ |
| 6936 | $N(CH_3)(CH_2CH_3)$ | $N(CH_3)(CH_2CH_3)$ | $OCH_2CH_3$ | Br | $OCOC_6H_5$ |
| 6937 | $O—(CH_2CH_2)—O$ | | $OCH_2CH_3$ | Br | $OCOC_6H_5$ |
| 6938 | $O—(CH_2CH_2CH_2)—O$ | | $OCH_2CH_3$ | Br | $OCOC_6H_5$ |
| 6939 | $S—(CH_2CH_2)—S$ | | $OCH_2CH_3$ | Br | $OCOC_6H_5$ |
| 6940 | $S—(CH_2CH_2CH_2)—S$ | | $OCH_2CH_3$ | Br | $OCOC_6H_5$ |
| 6941 | $—(CH_2)_4—$ | | $OCH_2CH_3$ | Br | $OCOC_6H_5$ |
| 6942 | $—(CH_2)_5—$ | | $OCH_2CH_3$ | Br | $OCOC_6H_5$ |
| 6943 | H | H | $SCH_3$ | Br | $OCOC_6H_5$ |
| 6944 | $CH_3$ | $CH_3$ | $SCH_3$ | Br | $OCOC_6H_5$ |
| 6945 | $CH_2CH_3$ | $CH_2CH_3$ | $SCH_3$ | Br | $OCOC_6H_5$ |
| 6946 | $CH_2CH_2CH_3$ | $CH_2CH_2CH_3$ | $SCH_3$ | Br | $OCOC_6H_5$ |
| 6947 | $OCH_3$ | $OCH_3$ | $SCH_3$ | Br | $OCOC_6H_5$ |
| 6948 | $OCH_2CH_3$ | $OCH_2CH_3$ | $SCH_3$ | Br | $OCOC_6H_5$ |
| 6949 | $OCH_2CH_2CH_3$ | $OCH_2CH_2CH_3$ | $SCH_3$ | Br | $OCOC_6H_5$ |
| 6950 | $SCH_3$ | $SCH_3$ | $SCH_3$ | Br | $OCOC_6H_5$ |
| 6951 | $SCH_2CH_3$ | $SCH_2CH_3$ | $SCH_3$ | Br | $OCOC_6H_5$ |
| 6952 | $N(CH_3)_2$ | $N(CH_3)_2$ | $SCH_3$ | Br | $OCOC_6H_5$ |
| 6953 | $N(CH_2CH_3)_2$ | $N(CH_2CH_3)_2$ | $SCH_3$ | Br | $OCOC_6H_5$ |
| 6954 | $N(CH_3)(CH_2CH_3)$ | $N(CH_3)(CH_2CH_3)$ | $SCH_3$ | Br | $OCOC_6H_5$ |
| 6955 | $O—(CH_2CH_2)—O$ | | $SCH_3$ | Br | $OCOC_6H_5$ |
| 6956 | $O—(CH_2CH_2CH_2)—O$ | | $SCH_3$ | Br | $OCOC_6H_5$ |
| 6957 | $S—(CH_2CH_2)—S$ | | $SCH_3$ | Br | $OCOC_6H_5$ |
| 6958 | $S—(CH_2CH_2CH_2)—S$ | | $SCH_3$ | Br | $OCOC_6H_5$ |
| 6959 | $—(CH_2)_4—$ | | $SCH_3$ | Br | $OCOC_6H_5$ |
| 6960 | $—(CH_2)_5—$ | | $SCH_3$ | Br | $OCOC_6H_5$ |
| 6961 | H | H | $SO_2CH_3$ | Br | $OCOC_6H_5$ |
| 6962 | $CH_3$ | $CH_3$ | $SO_2CH_3$ | Br | $OCOC_6H_5$ |
| 6963 | $CH_2CH_3$ | $CH_2CH_3$ | $SO_2CH_3$ | Br | $OCOC_6H_5$ |
| 6964 | $CH_2CH_2CH_3$ | $CH_2CH_2CH_3$ | $SO_2CH_3$ | Br | $OCOC_6H_5$ |
| 6965 | $OCH_3$ | $OCH_3$ | $SO_2CH_3$ | Br | $OCOC_6H_5$ |
| 6966 | $OCH_2CH_3$ | $OCH_2CH_3$ | $SO_2CH_3$ | Br | $OCOC_6H_5$ |
| 6967 | $OCH_2CH_2CH_3$ | $OCH_2CH_2CH_3$ | $SO_2CH_3$ | Br | $OCOC_6H_5$ |
| 6968 | $SCH_3$ | $SCH_3$ | $SO_2CH_3$ | Br | $OCOC_6H_5$ |
| 6969 | $SCH_2CH_3$ | $SCH_2CH_3$ | $SO_2CH_3$ | Br | $OCOC_6H_5$ |
| 6970 | $N(CH_3)_2$ | $N(CH_3)_2$ | $SO_2CH_3$ | Br | $OCOC_6H_5$ |
| 6971 | $N(CH_2CH_3)_2$ | $N(CH_2CH_3)_2$ | $SO_2CH_3$ | Br | $OCOC_6H_5$ |
| 6972 | $N(CH_3)(CH_2CH_3)$ | $N(CH_3)(CH_2CH_3)$ | $SO_2CH_3$ | Br | $OCOC_6H_5$ |
| 6973 | $O—(CH_2CH_2)—O$ | | $SO_2CH_3$ | Br | $OCOC_6H_5$ |
| 6974 | $O—(CH_2CH_2CH_2)—O$ | | $SO_2CH_3$ | Br | $OCOC_6H_5$ |
| 6975 | $S—(CH_2CH_2)—S$ | | $SO_2CH_3$ | Br | $OCOC_6H_5$ |
| 6976 | $S—(CH_2CH_2CH_2)—S$ | | $SO_2CH_3$ | Br | $OCOC_6H_5$ |
| 6977 | $—(CH_2)_4—$ | | $SO_2CH_3$ | Br | $OCOC_6H_5$ |
| 6978 | $—(CH_2)_5—$ | | $SO_2CH_3$ | Br | $OCOC_6H_5$ |
| 6979 | H | H | $PO(OCH_3)_2$ | Br | $OCOC_6H_5$ |
| 6980 | $CH_3$ | $CH_3$ | $PO(OCH_3)_2$ | Br | $OCOC_6H_5$ |
| 6981 | $CH_2CH_3$ | $CH_2CH_3$ | $PO(OCH_3)_2$ | Br | $OCOC_6H_5$ |
| 6982 | $CH_2CH_2CH_3$ | $CH_2CH_2CH_3$ | $PO(OCH_3)_2$ | Br | $OCOC_6H_5$ |
| 6983 | $OCH_3$ | $OCH_3$ | $PO(OCH_3)_2$ | Br | $OCOC_6H_5$ |
| 6984 | $OCH_2CH_3$ | $OCH_2CH_3$ | $PO(OCH_3)_2$ | Br | $OCOC_6H_5$ |
| 6985 | $OCH_2CH_2CH_3$ | $OCH_2CH_2CH_3$ | $PO(OCH_3)_2$ | Br | $OCOC_6H_5$ |
| 6986 | $SCH_3$ | $SCH_3$ | $PO(OCH_3)_2$ | Br | $OCOC_6H_5$ |
| 6987 | $SCH_2CH_3$ | $SCH_2CH_3$ | $PO(OCH_3)_2$ | Br | $OCOC_6H_5$ |
| 6988 | $N(CH_3)_2$ | $N(CH_3)_2$ | $PO(OCH_3)_2$ | Br | $OCOC_6H_5$ |
| 6989 | $N(CH_2CH_3)_2$ | $N(CH_2CH_3)_2$ | $PO(OCH_3)_2$ | Br | $OCOC_6H_5$ |
| 6990 | $N(CH_3)(CH_2CH_3)$ | $N(CH_3)(CH_2CH_3)$ | $PO(OCH_3)_2$ | Br | $OCOC_6H_5$ |

TABLE 1-continued

I1a1

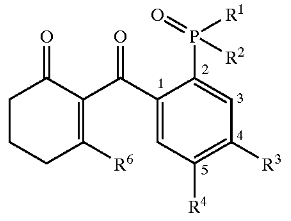

| n | $R^1$ | $R^2$ | $R^3$ | $R^4$ | $R^6$ |
|---|---|---|---|---|---|
| 6991 | O—(CH$_2$CH$_2$)—O | | $PO(OCH_3)_2$ | Br | $OCOC_6H_5$ |
| 6992 | O—(CH$_2$CH$_2$CH$_2$)—O | | $PO(OCH_3)_2$ | Br | $OCOC_6H_5$ |
| 6993 | S—(CH$_2$CH$_2$)—S | | $PO(OCH_3)_2$ | Br | $OCOC_6H_5$ |
| 6994 | S—(CH$_2$CH$_2$CH$_2$)—S | | $PO(OCH_3)_2$ | Br | $OCOC_6H_5$ |
| 6995 | —(CH$_2$)$_4$— | | $PO(OCH_3)_2$ | Br | $OCOC_6H_5$ |
| 6996 | —(CH$_2$)$_5$— | | $PO(OCH_3)_2$ | Br | $OCOC_6H_5$ |
| 6997 | H | H | $PO(OCH_2CH_3)_2$ | Br | $OCOC_6H_5$ |
| 6998 | $CH_3$ | $CH_3$ | $PO(OCH_2CH_3)_2$ | Br | $OCOC_6H_5$ |
| 6999 | $CH_2CH_3$ | $CH_2CH_3$ | $PO(OCH_2CH_3)_2$ | Br | $OCOC_6H_5$ |
| 7000 | $CH_2CH_2CH_3$ | $CH_2CH_2CH_3$ | $PO(OCH_2CH_3)_2$ | Br | $OCOC_6H_5$ |
| 7001 | $OCH_3$ | $OCH_3$ | $PO(OCH_2CH_3)_2$ | Br | $OCOC_6H_5$ |
| 7002 | $OCH_2CH_3$ | $OCH_2CH_3$ | $PO(OCH_2CH_3)_2$ | Br | $OCOC_6H_5$ |
| 7003 | $OCH_2CH_2CH_3$ | $OCH_2CH_2CH_3$ | $PO(OCH_2CH_3)_2$ | Br | $OCOC_6H_5$ |
| 7004 | $SCH_3$ | $SCH_3$ | $PO(OCH_2CH_3)_2$ | Br | $OCOC_6H_5$ |
| 7005 | $SCH_2CH_3$ | $SCH_2CH_3$ | $PO(OCH_2CH_3)_2$ | Br | $OCOC_6H_5$ |
| 7006 | $N(CH_3)_2$ | $N(CH_3)_2$ | $PO(OCH_2CH_3)_2$ | Br | $OCOC_6H_5$ |
| 7007 | $N(CH_2CH_3)_2$ | $N(CH_2CH_3)_2$ | $PO(OCH_2CH_3)_2$ | Br | $OCOC_6H_5$ |
| 7008 | $N(CH_3)(CH_2CH_3)$ | $N(CH_3)(CH_2CH_3)$ | $PO(OCH_2CH_3)_2$ | Br | $OCOC_6H_5$ |
| 7009 | O—(CH$_2$CH$_2$)—O | | $PO(OCH_2CH_3)_2$ | Br | $OCOC_6H_5$ |
| 7010 | O—(CH$_2$CH$_2$CH$_2$)—O | | $PO(OCH_2CH_3)_2$ | Br | $OCOC_6H_5$ |
| 7011 | S—(CH$_2$CH$_2$)—S | | $PO(OCH_2CH_3)_2$ | Br | $OCOC_6H_5$ |
| 7012 | S—(CH$_2$CH$_2$CH$_2$)—S | | $PO(OCH_2CH_3)_2$ | Br | $OCOC_6H_5$ |
| 7013 | —(CH$_2$)$_4$— | | $PO(OCH_2CH_3)_2$ | Br | $OCOC_6H_5$ |
| 7014 | —(CH$_2$)$_5$— | | $PO(OCH_2CH_3)_2$ | Br | $OCOC_6H_5$ |
| 7015 | H | H | $PO(CH_3)_2$ | Br | $OCOC_6H_5$ |
| 7016 | $CH_3$ | $CH_3$ | $PO(CH_3)_2$ | Br | $OCOC_6H_5$ |
| 7017 | $CH_2CH_3$ | $CH_2CH_3$ | $PO(CH_3)_2$ | Br | $OCOC_6H_5$ |
| 7018 | $CH_2CH_2CH_3$ | $CH_2CH_2CH_3$ | $PO(CH_3)_2$ | Br | $OCOC_6H_5$ |
| 7019 | $OCH_3$ | $OCH_3$ | $PO(CH_3)_2$ | Br | $OCOC_6H_5$ |
| 7020 | $OCH_2CH_3$ | $OCH_2CH_3$ | $PO(CH_3)_2$ | Br | $OCOC_6H_5$ |
| 7021 | $OCH_2CH_2CH_3$ | $OCH_2CH_2CH_3$ | $PO(CH_3)_2$ | Br | $OCOC_6H_5$ |
| 7022 | $SCH_3$ | $SCH_3$ | $PO(CH_3)_2$ | Br | $OCOC_6H_5$ |
| 7023 | $SCH_2CH_3$ | $SCH_2CH_3$ | $PO(CH_3)_2$ | Br | $OCOC_6H_5$ |
| 7024 | $N(CH_3)_2$ | $N(CH_3)_2$ | $PO(CH_3)_2$ | Br | $OCOC_6H_5$ |
| 7025 | $N(CH_2CH_3)_2$ | $N(CH_2CH_3)_2$ | $PO(CH_3)_2$ | Br | $OCOC_6H_5$ |
| 7026 | $N(CH_3)(CH_2CH_3)$ | $N(CH_3)(CH_2CH_3)$ | $PO(CH_3)_2$ | Br | $OCOC_6H_5$ |
| 7027 | O—(CH$_2$CH$_2$)—O | | $PO(CH_3)_2$ | Br | $OCOC_6H_5$ |
| 7028 | O—(CH$_2$CH$_2$CH$_2$)—O | | $PO(CH_3)_2$ | Br | $OCOC_6H_5$ |
| 7029 | S—(CH$_2$CH$_2$)—S | | $PO(CH_3)_2$ | Br | $OCOC_6H_5$ |
| 7030 | S—(CH$_2$CH$_2$CH$_2$)—S | | $PO(CH_3)_2$ | Br | $OCOC_6H_5$ |
| 7031 | —(CH$_2$)$_4$— | | $PO(CH_3)_2$ | Br | $OCOC_6H_5$ |
| 7032 | —(CH$_2$)$_5$— | | $PO(CH_3)_2$ | Br | $OCOC_6H_5$ |
| 7033 | H | H | $PC(CH_2CH_3)_2$ | Br | $OCOC_6H_5$ |
| 7034 | $CH_3$ | $CH_3$ | $PC(CH_2CH_3)_2$ | Br | $OCOC_6H_5$ |
| 7035 | $CH_2CH_3$ | $CH_2CH_3$ | $PC(CH_2CH_3)_2$ | Br | $OCOC_6H_5$ |
| 7036 | $CH_2CH_2CH_3$ | $CH_2CH_2CH_3$ | $PC(CH_2CH_3)_2$ | Br | $OCOC_6H_5$ |
| 7037 | $OCH_3$ | $OCH_3$ | $PC(CH_2CH_3)_2$ | Br | $OCOC_6H_5$ |
| 7038 | $OCH_2CH_3$ | $OCH_2CH_3$ | $PC(CH_2CH_3)_2$ | Br | $OCOC_6H_5$ |
| 7039 | $OCH_2CH_2CH_3$ | $OCH_2CH_2CH_3$ | $PC(CH_2CH_3)_2$ | Br | $OCOC_6H_5$ |
| 7040 | $SCH_3$ | $SCH_3$ | $PC(CH_2CH_3)_2$ | Br | $OCOC_6H_5$ |
| 7041 | $SCH_2CH_3$ | $SCH_2CH_3$ | $PC(CH_2CH_3)_2$ | Br | $OCOC_6H_5$ |
| 7042 | $N(CH_3)_2$ | $N(CH_3)_2$ | $PC(CH_2CH_3)_2$ | Br | $OCOC_6H_5$ |
| 7043 | $N(CH_2CH_3)_2$ | $N(CH_2CH_3)_2$ | $PC(CH_2CH_3)_2$ | Br | $OCOC_6H_5$ |
| 7044 | $N(CH_3)(CH_2CH_3)$ | $N(CH_3)(CH_2CH_3)$ | $PC(CH_2CH_3)_2$ | Br | $OCOC_6H_5$ |
| 7045 | O—(CH$_2$CH$_2$)—O | | $PC(CH_2CH_3)_2$ | Br | $OCOC_6H_5$ |
| 7046 | O—(CH$_2$CH$_2$CH$_2$)—O | | $PC(CH_2CH_3)_2$ | Br | $OCOC_6H_5$ |
| 7047 | S—(CH$_2$CH$_2$)—S | | $PC(CH_2CH_3)_2$ | Br | $OCOC_6H_5$ |
| 7048 | S—(CH$_2$CH$_2$CH$_2$)—S | | $PC(CH_2CH_3)_2$ | Br | $OCOC_6H_5$ |
| 7049 | —(CH$_2$)$_4$— | | $PC(CH_2CH_3)_2$ | Br | $OCOC_6H_5$ |
| 7050 | —(CH$_2$)$_5$— | | $PC(CH_2CH_3)_2$ | Br | $OCOC_6H_5$ |
| 7051 | H | H | H | Br | $SCH_3$ |
| 7052 | $CH_3$ | $CH_3$ | H | Br | $SCH_3$ |
| 7053 | $CH_2CH_3$ | $CH_2CH_3$ | H | Br | $SCH_3$ |
| 7054 | $CH_2CH_2CH_3$ | $CH_2CH_2CH_3$ | H | Br | $SCH_3$ |

TABLE 1-continued

I1a1

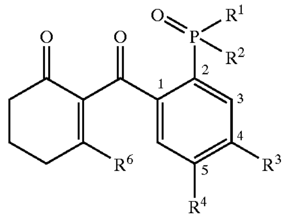

| n | $R^1$ | $R^2$ | $R^3$ | $R^4$ | $R^6$ |
|---|---|---|---|---|---|
| 7055 | $OCH_3$ | $OCH_3$ | H | Br | $SCH_3$ |
| 7056 | $OCH_2CH_3$ | $OCH_2CH_3$ | H | Br | $SCH_3$ |
| 7057 | $OCH_2CH_2CH_3$ | $OCH_2CH_2CH_3$ | H | Br | $SCH_3$ |
| 7058 | $SCH_3$ | $SCH_3$ | H | Br | $SCH_3$ |
| 7059 | $SCH_2CH_3$ | $SCH_2CH_3$ | H | Br | $SCH_3$ |
| 7060 | $N(CH_3)_2$ | $N(CH_3)_2$ | H | Br | $SCH_3$ |
| 7061 | $N(CH_2CH_3)_2$ | $N(CH_2CH_3)_2$ | H | Br | $SCH_3$ |
| 7062 | $N(CH_3)(CH_2CH_3)$ | $N(CH_3)(CH_2CH_3)$ | H | Br | $SCH_3$ |
| 7063 | $O—(CH_2CH_2)—O$ | | H | Br | $SCH_3$ |
| 7064 | $O—(CH_2CH_2CH_2)—O$ | | H | Br | $SCH_3$ |
| 7065 | $S—(CH_2CH_2)—S$ | | H | Br | $SCH_3$ |
| 7066 | $S—(CH_2CH_2CH_2)—S$ | | H | Br | $SCH_3$ |
| 7067 | $—(CH_2)_4—$ | | H | Br | $SCH_3$ |
| 7068 | $—(CH_2)_5—$ | | H | Br | $SCH_3$ |
| 7069 | H | H | $NO_2$ | Br | $SCH_3$ |
| 7070 | $CH_3$ | $CH_3$ | $NO_2$ | Br | $SCH_3$ |
| 7071 | $CH_2CH_3$ | $CH_2CH_3$ | $NO_2$ | Br | $SCH_3$ |
| 7072 | $CH_2CH_2CH_3$ | $CH_2CH_2CH_3$ | $NO_2$ | Br | $SCH_3$ |
| 7073 | $OCH_3$ | $OCH_3$ | $NO_2$ | Br | $SCH_3$ |
| 7074 | $OCH_2CH_3$ | $OCH_2CH_3$ | $NO_2$ | Br | $SCH_3$ |
| 7075 | $OCH_2CH_2CH_3$ | $OCH_2CH_2CH_3$ | $NO_2$ | Br | $SCH_3$ |
| 7076 | $SCH_3$ | $SCH_3$ | $NO_2$ | Br | $SCH_3$ |
| 7077 | $SCH_2CH_3$ | $SCH_2CH_3$ | $NO_2$ | Br | $SCH_3$ |
| 7078 | $N(CH_3)_2$ | $N(CH_3)_2$ | $NO_2$ | Br | $SCH_3$ |
| 7079 | $N(CH_2CH_3)_2$ | $N(CH_2CH_3)_2$ | $NO_2$ | Br | $SCH_3$ |
| 7080 | $N(CH_3)(CH_2CH_3)$ | $N(CH_3)(CH_2CH_3)$ | $NO_2$ | Br | $SCH_3$ |
| 7081 | $O—(CH_2CH_2)—O$ | | $NO_2$ | Br | $SCH_3$ |
| 7082 | $O—(CH_2CH_2CH_2)—O$ | | $NO_2$ | Br | $SCH_3$ |
| 7083 | $S—(CH_2CH_2)—S$ | | $NO_2$ | Br | $SCH_3$ |
| 7084 | $S—(CH_2CH_2CH_2)—S$ | | $NO_2$ | Br | $SCH_3$ |
| 7085 | $—(CH_2)_4—$ | | $NO_2$ | Br | $SCH_3$ |
| 7086 | $—(CH_2)_5—$ | | $NO_2$ | Br | $SCH_3$ |
| 7087 | H | H | CN | Br | $SCH_3$ |
| 7088 | $CH_3$ | $CH_3$ | CN | Br | $SCH_3$ |
| 7089 | $CH_2CH_3$ | $CH_2CH_3$ | CN | Br | $SCH_3$ |
| 7090 | $CH_2CH_2CH_3$ | $CH_2CH_2CH_3$ | CN | Br | $SCH_3$ |
| 7091 | $OCH_3$ | $OCH_3$ | CN | Br | $SCH_3$ |
| 7092 | $OCH_2CH_3$ | $OCH_2CH_3$ | CN | Br | $SCH_3$ |
| 7093 | $OCH_2CH_2CH_3$ | $OCH_2CH_2CH_3$ | CN | Br | $SCH_3$ |
| 7094 | $SCH_3$ | $SCH_3$ | CN | Br | $SCH_3$ |
| 7095 | $SCH_2CH_3$ | $SCH_2CH_3$ | CN | Br | $SCH_3$ |
| 7096 | $N(CH_3)_2$ | $N(CH_3)_2$ | CN | Br | $SCH_3$ |
| 7097 | $N(CH_2CH_3)_2$ | $N(CH_2CH_3)_2$ | CN | Br | $SCH_3$ |
| 7098 | $N(CH_3)(CH_2CH_3)$ | $N(CH_3)(CH_2CH_3)$ | CN | Br | $SCH_3$ |
| 7099 | $O—(CH_2CH_2)—O$ | | CN | Br | $SCH_3$ |
| 7100 | $O—(CH_2CH_2CH_2)—O$ | | CN | Br | $SCH_3$ |
| 7101 | $S—(CH_2CH_2)—S$ | | CN | Br | $SCH_3$ |
| 7102 | $S—(CH_2CH_2CH_2)—S$ | | CN | Br | $SCH_3$ |
| 7103 | $—(CH_2)_4—$ | | CN | Br | $SCH_3$ |
| 7104 | $—(CH_2)_5—$ | | CN | Br | $SCH_3$ |
| 7105 | H | H | F | Br | $SCH_3$ |
| 7106 | $CH_3$ | $CH_3$ | F | Br | $SCH_3$ |
| 7107 | $CH_2CH_3$ | $CH_2CH_3$ | F | Br | $SCH_3$ |
| 7108 | $CH_2CH_2CH_3$ | $CH_2CH_2CH_3$ | F | Br | $SCH_3$ |
| 7109 | $OCH_3$ | $OCH_3$ | F | Br | $SCH_3$ |
| 7110 | $OCH_2CH_3$ | $OCH_2CH_3$ | F | Br | $SCH_3$ |
| 7111 | $OCH_2CH_2CH_3$ | $OCH_2CH_2CH_3$ | F | Br | $SCH_3$ |
| 7112 | $SCH_3$ | $SCH_3$ | F | Br | $SCH_3$ |
| 7113 | $SCH_2CH_3$ | $SCH_2CH_3$ | F | Br | $SCH_3$ |
| 7114 | $N(CH_3)_2$ | $N(CH_3)_2$ | F | Br | $SCH_3$ |
| 7115 | $N(CH_2CH_3)_2$ | $N(CH_2CH_3)_2$ | F | Br | $SCH_3$ |
| 7116 | $N(CH_3)(CH_2CH_3)$ | $N(CH_3)(CH_2CH_3)$ | F | Br | $SCH_3$ |
| 7117 | $O—(CH_2CH_2)—O$ | | F | Br | $SCH_3$ |
| 7118 | $O—(CH_2CH_2CH_2)—O$ | | F | Br | $SCH_3$ |

TABLE 1-continued

I1a1

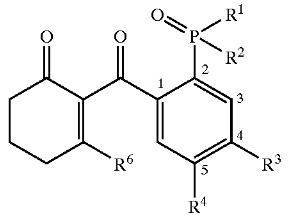

| n | $R^1$ | $R^2$ | $R^3$ | $R^4$ | $R^6$ |
|---|---|---|---|---|---|
| 7119 | S—$(CH_2CH_2)$—S | | F | Br | $SCH_3$ |
| 7120 | S—$(CH_2CH_2CH_2)$—S | | F | Br | $SCH_3$ |
| 7121 | —$(CH_2)_4$— | | F | Br | $SCH_3$ |
| 7122 | —$(CH_2)_5$— | | F | Br | $SCH_3$ |
| 7123 | H | H | Cl | Br | $SCH_3$ |
| 7124 | $CH_3$ | $CH_3$ | Cl | Br | $SCH_3$ |
| 7125 | $CH_2CH_3$ | $CH_2CH_3$ | Cl | Br | $SCH_3$ |
| 7126 | $CH_2CH_2CH_3$ | $CH_2CH_2CH_3$ | Cl | Br | $SCH_3$ |
| 7127 | $OCH_3$ | $OCH_3$ | Cl | Br | $SCH_3$ |
| 7128 | $OCH_2CH_3$ | $OCH_2CH_3$ | Cl | Br | $SCH_3$ |
| 7129 | $OCH_2CH_2CH_3$ | $OCH_2CH_2CH_3$ | Cl | Br | $SCH_3$ |
| 7130 | $SCH_3$ | $SCH_3$ | Cl | Br | $SCH_3$ |
| 7131 | $SCH_2CH_3$ | $SCH_2CH_3$ | Cl | Br | $SCH_3$ |
| 7132 | $N(CH_3)_2$ | $N(CH_3)_2$ | Cl | Br | $SCH_3$ |
| 7133 | $N(CH_2CH_3)_2$ | $N(CH_2CH_3)_2$ | Cl | Br | $SCH_3$ |
| 7134 | $N(CH_3)(CH_2CH_3)$ | $N(CH_3)(CH_2CH_3)$ | Cl | Br | $SCH_3$ |
| 7135 | O—$(CH_2CH_2)$—O | | Cl | Br | $SCH_3$ |
| 7136 | O—$(CH_2CH_2CH_2)$—O | | Cl | Br | $SCH_3$ |
| 7137 | S—$(CH_2CH_2)$—S | | Cl | Br | $SCH_3$ |
| 7138 | S—$(CH_2CH_2CH_2)$—S | | Cl | Br | $SCH_3$ |
| 7139 | —$(CH_2)_4$— | | Cl | Br | $SCH_3$ |
| 7140 | —$(CH_2)_5$— | | Cl | Br | $SCH_3$ |
| 7141 | H | H | Br | Br | $SCH_3$ |
| 7142 | $CH_3$ | $CH_3$ | Br | Br | $SCH_3$ |
| 7143 | $CH_2CH_3$ | $CH_2CH_3$ | Br | Br | $SCH_3$ |
| 7144 | $CH_2CH_2CH_3$ | $CH_2CH_2CH_3$ | Br | Br | $SCH_3$ |
| 7145 | $OCH_3$ | $OCH_3$ | Br | Br | $SCH_3$ |
| 7146 | $OCH_2CH_3$ | $OCH_2CH_3$ | Br | Br | $SCH_3$ |
| 7147 | $OCH_2CH_2CH_3$ | $OCH_2CH_2CH_3$ | Br | Br | $SCH_3$ |
| 7148 | $SCH_3$ | $SCH_3$ | Br | Br | $SCH_3$ |
| 7149 | $SCH_2CH_3$ | $SCH_2CH_3$ | Br | Br | $SCH_3$ |
| 7150 | $N(CH_3)_2$ | $N(CH_3)_2$ | Br | Br | $SCH_3$ |
| 7151 | $N(CH_2CH_3)_2$ | $N(CH_2CH_3)_2$ | Br | Br | $SCH_3$ |
| 7152 | $N(CH_3)(CH_2CH_3)$ | $N(CH_3)(CH_2CH_3)$ | Br | Br | $SCH_3$ |
| 7153 | O—$(CH_2CH_2)$—O | | Br | Br | $SCH_3$ |
| 7154 | O—$(CH_2CH_2CH_2)$—O | | Br | Br | $SCH_3$ |
| 7155 | S—$(CH_2CH_2)$—S | | Br | Br | $SCH_3$ |
| 7156 | S—$(CH_2CH_2CH_2)$—S | | Br | Br | $SCH_3$ |
| 7157 | —$(CH_2)_4$— | | Br | Br | $SCH_3$ |
| 7158 | —$(CH_2)_5$— | | Br | Br | $SCH_3$ |
| 7159 | H | H | $CH_3$ | Br | $SCH_3$ |
| 7160 | $CH_3$ | $CH_3$ | $CH_3$ | Br | $SCH_3$ |
| 7161 | $CH_2CH_3$ | $CH_2CH_3$ | $CH_3$ | Br | $SCH_3$ |
| 7162 | $CH_2CH_2CH_3$ | $CH_2CH_2CH_3$ | $CH_3$ | Br | $SCH_3$ |
| 7163 | $OCH_3$ | $OCH_3$ | $CH_3$ | Br | $SCH_3$ |
| 7164 | $OCH_2CH_3$ | $OCH_2CH_3$ | $CH_3$ | Br | $SCH_3$ |
| 7165 | $OCH_2CH_2CH_3$ | $OCH_2CH_2CH_3$ | $CH_3$ | Br | $SCH_3$ |
| 7166 | $SCH_3$ | $SCH_3$ | $CH_3$ | Br | $SCH_3$ |
| 7167 | $SCH_2CH_3$ | $SCH_2CH_3$ | $CH_3$ | Br | $SCH_3$ |
| 7168 | $N(CH_3)_2$ | $N(CH_3)_2$ | $CH_3$ | Br | $SCH_3$ |
| 7169 | $N(CH_2CH_3)_2$ | $N(CH_2CH_3)_2$ | $CH_3$ | Br | $SCH_3$ |
| 7170 | $N(CH_3)(CH_2CH_3)$ | $N(CH_3)(CH_2CH_3)$ | $CH_3$ | Br | $SCH_3$ |
| 7171 | O—$(CH_2CH_2)$—O | | $CH_3$ | Br | $SCH_3$ |
| 7172 | O—$(CH_2CH_2CH_2)$—O | | $CH_3$ | Br | $SCH_3$ |
| 7173 | S—$(CH_2CH_2)$—S | | $CH_3$ | Br | $SCH_3$ |
| 7174 | S—$(CH_2CH_2CH_2)$—S | | $CH_3$ | Br | $SCH_3$ |
| 7175 | —$(CH_2)_4$— | | $CH_3$ | Br | $SCH_3$ |
| 7176 | —$(CH_2)_5$— | | $CH_3$ | Br | $SCH_3$ |
| 7177 | H | H | $CH_2CH_3$ | Br | $SCH_3$ |
| 7178 | $CH_3$ | $CH_3$ | $CH_2CH_3$ | Br | $SCH_3$ |
| 7179 | $CH_2CH_3$ | $CH_2CH_3$ | $CH_2CH_3$ | Br | $SCH_3$ |
| 7180 | $CH_2CH_2CH_3$ | $CH_2CH_2CH_3$ | $CH_2CH_3$ | Br | $SCH_3$ |
| 7181 | $OCH_3$ | $OCH_3$ | $CH_2CH_3$ | Br | $SCH_3$ |
| 7182 | $OCH_2CH_3$ | $OCH_2CH_3$ | $CH_2CH_3$ | Br | $SCH_3$ |

TABLE 1-continued

I1a1

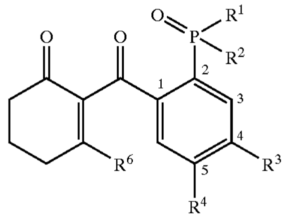

| n | $R^1$ | $R^2$ | $R^3$ | $R^4$ | $R^6$ |
|---|---|---|---|---|---|
| 7183 | $OCH_2CH_2CH_3$ | $OCH_2CH_2CH_3$ | $CH_2CH_3$ | Br | $SCH_3$ |
| 7184 | $SCH_3$ | $SCH_3$ | $CH_2CH_3$ | Br | $SCH_3$ |
| 7185 | $SCH_2CH_3$ | $SCH_2CH_3$ | $CH_2CH_3$ | Br | $SCH_3$ |
| 7186 | $N(CH_3)_2$ | $N(CH_3)_2$ | $CH_2CH_3$ | Br | $SCH_3$ |
| 7187 | $N(CH_2CH_3)_2$ | $N(CH_2CH_3)_2$ | $CH_2CH_3$ | Br | $SCH_3$ |
| 7188 | $N(CH_3)(CH_2CH_3)$ | $N(CH_3)(CH_2CH_3)$ | $CH_2CH_3$ | Br | $SCH_3$ |
| 7189 | $O-(CH_2CH_2)-O$ | | $CH_2CH_3$ | Br | $SCH_3$ |
| 7190 | $O-(CH_2CH_2CH_2)-O$ | | $CH_2CH_3$ | Br | $SCH_3$ |
| 7191 | $S-(CH_2CH_2)-S$ | | $CH_2CH_3$ | Br | $SCH_3$ |
| 7192 | $S-(CH_2CH_2CH_2)-S$ | | $CH_2CH_3$ | Br | $SCH_3$ |
| 7193 | $-(CH_2)_4-$ | | $CH_2CH_3$ | Br | $SCH_3$ |
| 7194 | $-(CH_2)_5-$ | | $CH_2CH_3$ | Br | $SCH_3$ |
| 7195 | H | H | $CF_3$ | Br | $SCH_3$ |
| 7196 | $CH_3$ | $CH_3$ | $CF_3$ | Br | $SCH_3$ |
| 7197 | $CH_2CH_3$ | $CH_2CH_3$ | $CF_3$ | Br | $SCH_3$ |
| 7198 | $CH_2CH_2CH_3$ | $CH_2CH_2CH_3$ | $CF_3$ | Br | $SCH_3$ |
| 7199 | $OCH_3$ | $OCH_3$ | $CF_3$ | Br | $SCH_3$ |
| 7200 | $OCH_2CH_3$ | $OCH_2CH_3$ | $CF_3$ | Br | $SCH_3$ |
| 7201 | $OCH_2CH_2CH_3$ | $OCH_2CH_2CH_3$ | $CF_3$ | Br | $SCH_3$ |
| 7202 | $SCH_3$ | $SCH_3$ | $CF_3$ | Br | $SCH_3$ |
| 7203 | $SCH_2CH_3$ | $SCH_2CH_3$ | $CF_3$ | Br | $SCH_3$ |
| 7204 | $N(CH_3)_2$ | $N(CH_3)_2$ | $CF_3$ | Br | $SCH_3$ |
| 7205 | $N(CH_2CH_3)_2$ | $N(CH_2CH_3)_2$ | $CF_3$ | Br | $SCH_3$ |
| 7206 | $N(CH_3)(CH_2CH_3)$ | $N(CH_3)(CH_2CH_3)$ | $CF_3$ | Br | $SCH_3$ |
| 7207 | $O-(CH_2CH_2)-O$ | | $CF_3$ | Br | $SCH_3$ |
| 7208 | $O-(CH_2CH_2CH_2)-O$ | | $CF_3$ | Br | $SCH_3$ |
| 7209 | $S-(CH_2CH_2)-S$ | | $CF_3$ | Br | $SCH_3$ |
| 7210 | $S-(CH_2CH_2CH_2)-S$ | | $CF_3$ | Br | $SCH_3$ |
| 7211 | $-(CH_2)_4-$ | | $CF_3$ | Br | $SCH_3$ |
| 7212 | $-(CH_2)_5-$ | | $CF_3$ | Br | $SCH_3$ |
| 7213 | H | H | $OCH_3$ | Br | $SCH_3$ |
| 7214 | $CH_3$ | $CH_3$ | $OCH_3$ | Br | $SCH_3$ |
| 7215 | $CH_2CH_3$ | $CH_2CH_3$ | $OCH_3$ | Br | $SCH_3$ |
| 7216 | $CH_2CH_2CH_3$ | $CH_2CH_2CH_3$ | $OCH_3$ | Br | $SCH_3$ |
| 7217 | $OCH_3$ | $OCH_3$ | $OCH_3$ | Br | $SCH_3$ |
| 7218 | $OCH_2CH_3$ | $OCH_2CH_3$ | $OCH_3$ | Br | $SCH_3$ |
| 7219 | $OCH_2CH_2CH_3$ | $OCH_2CH_2CH_3$ | $OCH_3$ | Br | $SCH_3$ |
| 7220 | $SCH_3$ | $SCH_3$ | $OCH_3$ | Br | $SCH_3$ |
| 7221 | $SCH_2CH_3$ | $SCH_2CH_3$ | $OCH_3$ | Br | $SCH_3$ |
| 7222 | $N(CH_3)_2$ | $N(CH_3)_2$ | $OCH_3$ | Br | $SCH_3$ |
| 7223 | $N(CH_2CH_3)_2$ | $N(CH_2CH_3)_2$ | $OCH_3$ | Br | $SCH_3$ |
| 7224 | $N(CH_3)(CH_2CH_3)$ | $N(CH_3)(CH_2CH_3)$ | $OCH_3$ | Br | $SCH_3$ |
| 7225 | $O-(CH_2CH_2)-O$ | | $OCH_3$ | Br | $SCH_3$ |
| 7226 | $O-(CH_2CH_2CH_2)-O$ | | $OCH_3$ | Br | $SCH_3$ |
| 7227 | $S-(CH_2CH_2)-S$ | | $OCH_3$ | Br | $SCH_3$ |
| 7228 | $S-(CH_2CH_2CH_2)-S$ | | $OCH_3$ | Br | $SCH_3$ |
| 7229 | $-(CH_2)_4-$ | | $OCH_3$ | Br | $SCH_3$ |
| 7230 | $-(CH_2)_5-$ | | $OCH_3$ | Br | $SCH_3$ |
| 7231 | H | H | $OCH_2CH_3$ | Br | $SCH_3$ |
| 7232 | $CH_3$ | $CH_3$ | $OCH_2CH_3$ | Br | $SCH_3$ |
| 7233 | $CH_2CH_3$ | $CH_2CH_3$ | $OCH_2CH_3$ | Br | $SCH_3$ |
| 7234 | $CH_2CH_2CH_3$ | $CH_2CH_2CH_3$ | $OCH_2CH_3$ | Br | $SCH_3$ |
| 7235 | $OCH_3$ | $OCH_3$ | $OCH_2CH_3$ | Br | $SCH_3$ |
| 7236 | $OCH_2CH_3$ | $OCH_2CH_3$ | $OCH_2CH_3$ | Br | $SCH_3$ |
| 7237 | $OCH_2CH_2CH_3$ | $OCH_2CH_2CH_3$ | $OCH_2CH_3$ | Br | $SCH_3$ |
| 7238 | $SCH_3$ | $SCH_3$ | $OCH_2CH_3$ | Br | $SCH_3$ |
| 7239 | $SCH_2CH_3$ | $SCH_2CH_3$ | $OCH_2CH_3$ | Br | $SCH_3$ |
| 7240 | $N(CH_3)_2$ | $N(CH_3)_2$ | $OCH_2CH_3$ | Br | $SCH_3$ |
| 7241 | $N(CH_2CH_3)_2$ | $N(CH_2CH_3)_2$ | $OCH_2CH_3$ | Br | $SCH_3$ |
| 7242 | $N(CH_3)(CH_2CH_3)$ | $N(CH_3)(CH_2CH_3)$ | $OCH_2CH_3$ | Br | $SCH_3$ |
| 7243 | $O-(CH_2CH_2)-O$ | | $OCH_2CH_3$ | Br | $SCH_3$ |
| 7244 | $O-(CH_2CH_2CH_2)-O$ | | $OCH_2CH_3$ | Br | $SCH_3$ |
| 7245 | $S-(CH_2CH_2)-S$ | | $OCH_2CH_3$ | Br | $SCH_3$ |
| 7246 | $S-(CH_2CH_2CH_2)-S$ | | $OCH_2CH_3$ | Br | $SCH_3$ |

TABLE 1-continued

I1a1

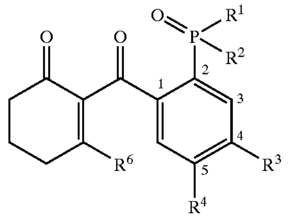

| n | $R^1$ | $R^2$ | $R^3$ | $R^4$ | $R^6$ |
|---|---|---|---|---|---|
| 7247 | $-(CH_2)_4-$ | | $OCH_2CH_3$ | Br | $SCH_3$ |
| 7248 | $-(CH_2)_5-$ | | $OCH_2CH_3$ | Br | $SCH_3$ |
| 7249 | H | H | $SCH_3$ | Br | $SCH_3$ |
| 7250 | $CH_3$ | $CH_3$ | $SCH_3$ | Br | $SCH_3$ |
| 7251 | $CH_2CH_3$ | $CH_2CH_3$ | $SCH_3$ | Br | $SCH_3$ |
| 7252 | $CH_2CH_2CH_3$ | $CH_2CH_2CH_3$ | $SCH_3$ | Br | $SCH_3$ |
| 7253 | $OCH_3$ | $OCH_3$ | $SCH_3$ | Br | $SCH_3$ |
| 7254 | $OCH_2CH_3$ | $OCH_2CH_3$ | $SCH_3$ | Br | $SCH_3$ |
| 7255 | $OCH_2CH_2CH_3$ | $OCH_2CH_2CH_3$ | $SCH_3$ | Br | $SCH_3$ |
| 7256 | $SCH_3$ | $SCH_3$ | $SCH_3$ | Br | $SCH_3$ |
| 7257 | $SCH_2CH_3$ | $SCH_2CH_3$ | $SCH_3$ | Br | $SCH_3$ |
| 7258 | $N(CH_3)_2$ | $N(CH_3)_2$ | $SCH_3$ | Br | $SCH_3$ |
| 7259 | $N(CH_2CH_3)_2$ | $N(CH_2CH_3)_2$ | $SCH_3$ | Br | $SCH_3$ |
| 7260 | $N(CH_3)(CH_2CH_3)$ | $N(CH_3)(CH_2CH_3)$ | $SCH_3$ | Br | $SCH_3$ |
| 7261 | $O-(CH_2CH_2)-O$ | | $SCH_3$ | Br | $SCH_3$ |
| 7262 | $O-(CH_2CH_2CH_2)-O$ | | $SCH_3$ | Br | $SCH_3$ |
| 7263 | $S-(CH_2CH_2)-S$ | | $SCH_3$ | Br | $SCH_3$ |
| 7264 | $S-(CH_2CH_2CH_2)-S$ | | $SCH_3$ | Br | $SCH_3$ |
| 7265 | $-(CH_2)_4-$ | | $SCH_3$ | Br | $SCH_3$ |
| 7266 | $-(CH_2)_5-$ | | $SCH_3$ | Br | $SCH_3$ |
| 7267 | H | H | $SO_2CH_3$ | Br | $SCH_3$ |
| 7268 | $CH_3$ | $CH_3$ | $SO_2CH_3$ | Br | $SCH_3$ |
| 7269 | $CH_2CH_3$ | $CH_2CH_3$ | $SO_2CH_3$ | Br | $SCH_3$ |
| 7270 | $CH_2CH_2CH_3$ | $CH_2CH_2CH_3$ | $SO_2CH_3$ | Br | $SCH_3$ |
| 7271 | $OCH_3$ | $OCH_3$ | $SO_2CH_3$ | Br | $SCH_3$ |
| 7272 | $OCH_2CH_3$ | $OCH_2CH_3$ | $SO_2CH_3$ | Br | $SCH_3$ |
| 7273 | $OCH_2CH_2CH_3$ | $OCH_2CH_2CH_3$ | $SO_2CH_3$ | Br | $SCH_3$ |
| 7274 | $SCH_3$ | $SCH_3$ | $SO_2CH_3$ | Br | $SCH_3$ |
| 7275 | $SCH_2CH_3$ | $SCH_2CH_3$ | $SO_2CH_3$ | Br | $SCH_3$ |
| 7276 | $N(CH_3)_2$ | $N(CH_3)_2$ | $SO_2CH_3$ | Br | $SCH_3$ |
| 7277 | $N(CH_2CH_3)_2$ | $N(CH_2CH_3)_2$ | $SO_2CH_3$ | Br | $SCH_3$ |
| 7278 | $N(CH_3)(CH_2CH_3)$ | $N(CH_3)(CH_2CH_3)$ | $SO_2CH_3$ | Br | $SCH_3$ |
| 7279 | $O-(CH_2CH_2)-O$ | | $SO_2CH_3$ | Br | $SCH_3$ |
| 7280 | $O-(CH_2CH_2CH_2)-O$ | | $SO_2CH_3$ | Br | $SCH_3$ |
| 7281 | $S-(CH_2CH_2)-S$ | | $SO_2CH_3$ | Br | $SCH_3$ |
| 7282 | $S-(CH_2CH_2CH_2)-S$ | | $SO_2CH_3$ | Br | $SCH_3$ |
| 7283 | $-(CH_2)_4-$ | | $SO_2CH_3$ | Br | $SCH_3$ |
| 7284 | $-(CH_2)_5-$ | | $SO_2CH_3$ | Br | $SCH_3$ |
| 7285 | H | H | $PO(OCH_3)_2$ | Br | $SCH_3$ |
| 7286 | $CH_3$ | $CH_3$ | $PO(OCH_3)_2$ | Br | $SCH_3$ |
| 7287 | $CH_2CH_3$ | $CH_2CH_3$ | $PO(OCH_3)_2$ | Br | $SCH_3$ |
| 7288 | $CH_2CH_2CH_3$ | $CH_2CH_2CH_3$ | $PO(OCH_3)_2$ | Br | $SCH_3$ |
| 7289 | $OCH_3$ | $OCH_3$ | $PO(OCH_3)_2$ | Br | $SCH_3$ |
| 7290 | $OCH_2CH_3$ | $OCH_2CH_3$ | $PO(OCH_3)_2$ | Br | $SCH_3$ |
| 7291 | $OCH_2CH_2CH_3$ | $OCH_2CH_2CH_3$ | $PO(OCH_3)_2$ | Br | $SCH_3$ |
| 7292 | $SCH_3$ | $SCH_3$ | $PO(OCH_3)_2$ | Br | $SCH_3$ |
| 7293 | $SCH_2CH_3$ | $SCH_2CH_3$ | $PO(OCH_3)_2$ | Br | $SCH_3$ |
| 7294 | $N(CH_3)_2$ | $N(CH_3)_2$ | $PO(OCH_3)_2$ | Br | $SCH_3$ |
| 7295 | $N(CH_2CH_3)_2$ | $N(CH_2CH_3)_2$ | $PO(OCH_3)_2$ | Br | $SCH_3$ |
| 7296 | $N(CH_3)(CH_2CH_3)$ | $N(CH_3)(CH_2CH_3)$ | $PO(OCH_3)_2$ | Br | $SCH_3$ |
| 7297 | $O-(CH_2CH_2)-O$ | | $PO(OCH_3)_2$ | Br | $SCH_3$ |
| 7298 | $O-(CH_2CH_2CH_2)-O$ | | $PO(OCH_3)_2$ | Br | $SCH_3$ |
| 7299 | $S-(CH_2CH_2)-S$ | | $PO(OCH_3)_2$ | Br | $SCH_3$ |
| 7300 | $S-(CH_2CH_2CH_2)-S$ | | $PO(OCH_3)_2$ | Br | $SCH_3$ |
| 7301 | $-(CH_2)_4-$ | | $PO(OCH_3)_2$ | Br | $SCH_3$ |
| 7302 | $-(CH_2)_5-$ | | $PO(OCH_3)_2$ | Br | $SCH_3$ |
| 7303 | H | H | $PO(OCH_2CH_3)_2$ | Br | $SCH_3$ |
| 7304 | $CH_3$ | $CH_3$ | $PO(OCH_2CH_3)_2$ | Br | $SCH_3$ |
| 7305 | $CH_2CH_3$ | $CH_2CH_3$ | $PO(OCH_2CH_3)_2$ | Br | $SCH_3$ |
| 7306 | $CH_2CH_2CH_3$ | $CH_2CH_2CH_3$ | $PO(OCH_2CH_3)_2$ | Br | $SCH_3$ |
| 7307 | $OCH_3$ | $OCH_3$ | $PO(OCH_2CH_3)_2$ | Br | $SCH_3$ |
| 7308 | $OCH_2CH_3$ | $OCH_2CH_3$ | $PO(OCH_2CH_3)_2$ | Br | $SCH_3$ |
| 7309 | $OCH_2CH_2CH_3$ | $OCH_2CH_2CH_3$ | $PO(OCH_2CH_3)_2$ | Br | $SCH_3$ |
| 7310 | $SCH_3$ | $SCH_3$ | $PO(OCH_2CH_3)_2$ | Br | $SCH_3$ |

TABLE 1-continued

I1a1

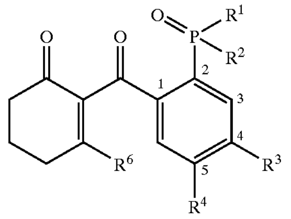

| n | $R^1$ | $R^2$ | $R^3$ | $R^4$ | $R^6$ |
|---|---|---|---|---|---|
| 7311 | $SCH_2CH_3$ | $SCH_2CH_3$ | $PO(OCH_2CH_3)_2$ | Br | $SCH_3$ |
| 7312 | $N(CH_3)_2$ | $N(CH_3)_2$ | $PO(OCH_2CH_3)_2$ | Br | $SCH_3$ |
| 7313 | $N(CH_2CH_3)_2$ | $N(CH_2CH_3)_2$ | $PO(OCH_2CH_3)_2$ | Br | $SCH_3$ |
| 7314 | $N(CH_3)(CH_2CH_3)$ | $N(CH_3)(CH_2CH_3)$ | $PO(OCH_2CH_3)_2$ | Br | $SCH_3$ |
| 7315 | $O—(CH_2CH_2)—O$ | | $PO(OCH_2CH_3)_2$ | Br | $SCH_3$ |
| 7316 | $O—(CH_2CH_2CH_2)—O$ | | $PO(OCH_2CH_3)_2$ | Br | $SCH_3$ |
| 7317 | $S—(CH_2CH_2)—S$ | | $PO(OCH_2CH_3)_2$ | Br | $SCH_3$ |
| 7318 | $S—(CH_2CH_2CH_2)—S$ | | $PO(OCH_2CH_3)_2$ | Br | $SCH_3$ |
| 7319 | $—(CH_2)_4—$ | | $PO(OCH_2CH_3)_2$ | Br | $SCH_3$ |
| 7320 | $—(CH_2)_5—$ | | $PO(OCH_2CH_3)_2$ | Br | $SCH_3$ |
| 7321 | H | H | $PO(CH_3)_2$ | Br | $SCH_3$ |
| 7322 | $CH_3$ | $CH_3$ | $PO(CH_3)_2$ | Br | $SCH_3$ |
| 7323 | $CH_2CH_3$ | $CH_2CH_3$ | $PO(CH_3)_2$ | Br | $SCH_3$ |
| 7324 | $CH_2CH_2CH_3$ | $CH_2CH_2CH_3$ | $PO(CH_3)_2$ | Br | $SCH_3$ |
| 7325 | $OCH_3$ | $OCH_3$ | $PO(CH_3)_2$ | Br | $SCH_3$ |
| 7326 | $OCH_2CH_3$ | $OCH_2CH_3$ | $PO(CH_3)_2$ | Br | $SCH_3$ |
| 7327 | $OCH_2CH_2CH_3$ | $OCH_2CH_2CH_3$ | $PO(CH_3)_2$ | Br | $SCH_3$ |
| 7328 | $SCH_3$ | $SCH_3$ | $PO(CH_3)_2$ | Br | $SCH_3$ |
| 7329 | $SCH_2CH_3$ | $SCH_2CH_3$ | $PO(CH_3)_2$ | Br | $SCH_3$ |
| 7330 | $N(CH_3)_2$ | $N(CH_3)_2$ | $PO(CH_3)_2$ | Br | $SCH_3$ |
| 7331 | $N(CH_2CH_3)_2$ | $N(CH_2CH_3)_2$ | $PO(CH_3)_2$ | Br | $SCH_3$ |
| 7332 | $N(CH_3)(CH_2CH_3)$ | $N(CH_3)(CH_2CH_3)$ | $PO(CH_3)_2$ | Br | $SCH_3$ |
| 7333 | $O—(CH_2CH_2)—O$ | | $PO(CH_3)_2$ | Br | $SCH_3$ |
| 7334 | $O—(CH_2CH_2CH_2)—O$ | | $PO(CH_3)_2$ | Br | $SCH_3$ |
| 7335 | $S—(CH_2CH_2)—S$ | | $PO(CH_3)_2$ | Br | $SCH_3$ |
| 7336 | $S—(CH_2CH_2CH_2)—S$ | | $PO(CH_3)_2$ | Br | $SCH_3$ |
| 7337 | $—(CH_2)_4—$ | | $PO(CH_3)_2$ | Br | $SCH_3$ |
| 7338 | $—(CH_2)_5—$ | | $PO(CH_3)_2$ | Br | $SCH_3$ |
| 7339 | H | H | $PC(CH_2CH_3)_2$ | Br | $SCH_3$ |
| 7340 | $CH_3$ | $CH_3$ | $PC(CH_2CH_3)_2$ | Br | $SCH_3$ |
| 7341 | $CH_2CH_3$ | $CH_2CH_3$ | $PC(CH_2CH_3)_2$ | Br | $SCH_3$ |
| 7342 | $CH_2CH_2CH_3$ | $CH_2CH_2CH_3$ | $PC(CH_2CH_3)_2$ | Br | $SCH_3$ |
| 7343 | $OCH_3$ | $OCH_3$ | $PC(CH_2CH_3)_2$ | Br | $SCH_3$ |
| 7344 | $OCH_2CH_3$ | $OCH_2CH_3$ | $PC(CH_2CH_3)_2$ | Br | $SCH_3$ |
| 7345 | $OCH_2CH_2CH_3$ | $OCH_2CH_2CH_3$ | $PC(CH_2CH_3)_2$ | Br | $SCH_3$ |
| 7346 | $SCH_3$ | $SCH_3$ | $PC(CH_2CH_3)_2$ | Br | $SCH_3$ |
| 7347 | $SCH_2CH_3$ | $SCH_2CH_3$ | $PC(CH_2CH_3)_2$ | Br | $SCH_3$ |
| 7348 | $N(CH_3)_2$ | $N(CH_3)_2$ | $PC(CH_2CH_3)_2$ | Br | $SCH_3$ |
| 7349 | $N(CH_2CH_3)_2$ | $N(CH_2CH_3)_2$ | $PC(CH_2CH_3)_2$ | Br | $SCH_3$ |
| 7350 | $N(CH_3)(CH_2CH_3)$ | $N(CH_3)(CH_2CH_3)$ | $PC(CH_2CH_3)_2$ | Br | $SCH_3$ |
| 7351 | $O—(CH_2CH_2)—O$ | | $PC(CH_2CH_3)_2$ | Br | $SCH_3$ |
| 7352 | $O—(CH_2CH_2CH_2)—O$ | | $PC(CH_2CH_3)_2$ | Br | $SCH_3$ |
| 7353 | $S—(CH_2CH_2)—S$ | | $PC(CH_2CH_3)_2$ | Br | $SCH_3$ |
| 7354 | $S—(CH_2CH_2CH_2)—S$ | | $PC(CH_2CH_3)_2$ | Br | $SCH_3$ |
| 7355 | $—(CH_2)_4—$ | | $PC(CH_2CH_3)_2$ | Br | $SCH_3$ |
| 7356 | $—(CH_2)_5—$ | | $PC(CH_2CH_3)_2$ | Br | $SCH_3$ |
| 7357 | H | H | H | Br | $SC_6H_5$ |
| 7358 | $CH_3$ | $CH_3$ | H | Br | $SC_6H_5$ |
| 7359 | $CH_2CH_3$ | $CH_2CH_3$ | H | Br | $SC_6H_5$ |
| 7360 | $CH_2CH_2CH_3$ | $CH_2CH_2CH_3$ | H | Br | $SC_6H_5$ |
| 7361 | $OCH_3$ | $OCH_3$ | H | Br | $SC_6H_5$ |
| 7362 | $OCH_2CH_3$ | $OCH_2CH_3$ | H | Br | $SC_6H_5$ |
| 7363 | $OCH_2CH_2CH_3$ | $OCH_2CH_2CH_3$ | H | Br | $SC_6H_5$ |
| 7364 | $SCH_3$ | $SCH_3$ | H | Br | $SC_6H_5$ |
| 7365 | $SCH_2CH_3$ | $SCH_2CH_3$ | H | Br | $SC_6H_5$ |
| 7366 | $N(CH_3)_2$ | $N(CH_3)_2$ | H | Br | $SC_6H_5$ |
| 7367 | $N(CH_2CH_3)_2$ | $N(CH_2CH_3)_2$ | H | Br | $SC_6H_5$ |
| 7368 | $N(CH_3)(CH_2CH_3)$ | $N(CH_3)(CH_2CH_3)$ | H | Br | $SC_6H_5$ |
| 7369 | $O—(CH_2CH_2)—O$ | | H | Br | $SC_6H_5$ |
| 7370 | $O—(CH_2CH_2CH_2)—O$ | | H | Br | $SC_6H_5$ |
| 7371 | $S—(CH_2CH_2)—S$ | | H | Br | $SC_6H_5$ |
| 7372 | $S—(CH_2CH_2CH_2)—S$ | | H | Br | $SC_6H_5$ |
| 7373 | $—(CH_2)_4—$ | | H | Br | $SC_6H_5$ |
| 7374 | $—(CH_2)_5—$ | | H | Br | $SC_6H_5$ |

TABLE 1-continued

I1a1

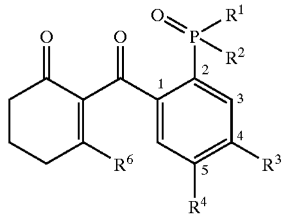

| n | $R^1$ | $R^2$ | $R^3$ | $R^4$ | $R^6$ |
|---|---|---|---|---|---|
| 7375 | H | H | $NO_2$ | Br | $SC_6H_5$ |
| 7376 | $CH_3$ | $CH_3$ | $NO_2$ | Br | $SC_6H_5$ |
| 7377 | $CH_2CH_3$ | $CH_2CH_3$ | $NO_2$ | Br | $SC_6H_5$ |
| 7378 | $CH_2CH_2CH_3$ | $CH_2CH_2CH_3$ | $NO_2$ | Br | $SC_6H_5$ |
| 7379 | $OCH_3$ | $OCH_3$ | $NO_2$ | Br | $SC_6H_5$ |
| 7380 | $OCH_2CH_3$ | $OCH_2CH_3$ | $NO_2$ | Br | $SC_6H_5$ |
| 7381 | $OCH_2CH_2CH_3$ | $OCH_2CH_2CH_3$ | $NO_2$ | Br | $SC_6H_5$ |
| 7382 | $SCH_3$ | $SCH_3$ | $NO_2$ | Br | $SC_6H_5$ |
| 7383 | $SCH_2CH_3$ | $SCH_2CH_3$ | $NO_2$ | Br | $SC_6H_5$ |
| 7384 | $N(CH_3)_2$ | $N(CH_3)_2$ | $NO_2$ | Br | $SC_6H_5$ |
| 7385 | $N(CH_2CH_3)_2$ | $N(CH_2CH_3)_2$ | $NO_2$ | Br | $SC_6H_5$ |
| 7386 | $N(CH_3)(CH_2CH_3)$ | $N(CH_3)(CH_2CH_3)$ | $NO_2$ | Br | $SC_6H_5$ |
| 7387 | $O—(CH_2CH_2)—O$ | | $NO_2$ | Br | $SC_6H_5$ |
| 7388 | $O—(CH_2CH_2CH_2)—O$ | | $NO_2$ | Br | $SC_6H_5$ |
| 7389 | $S—(CH_2CH_2)—S$ | | $NO_2$ | Br | $SC_6H_5$ |
| 7390 | $S—(CH_2CH_2CH_2)—S$ | | $NO_2$ | Br | $SC_6H_5$ |
| 7391 | $—(CH_2)_4—$ | | $NO_2$ | Br | $SC_6H_5$ |
| 7392 | $—(CH_2)_5—$ | | $NO_2$ | Br | $SC_6H_5$ |
| 7393 | H | H | CN | Br | $SC_6H_5$ |
| 7394 | $CH_3$ | $CH_3$ | CN | Br | $SC_6H_5$ |
| 7395 | $CH_2CH_3$ | $CH_2CH_3$ | CN | Br | $SC_6H_5$ |
| 7396 | $CH_2CH_2CH_3$ | $CH_2CH_2CH_3$ | CN | Br | $SC_6H_5$ |
| 7397 | $OCH_3$ | $OCH_3$ | CN | Br | $SC_6H_5$ |
| 7398 | $OCH_2CH_3$ | $OCH_2CH_3$ | CN | Br | $SC_6H_5$ |
| 7399 | $OCH_2CH_2CH_3$ | $OCH_2CH_2CH_3$ | CN | Br | $SC_6H_5$ |
| 7400 | $SCH_3$ | $SCH_3$ | CN | Br | $SC_6H_5$ |
| 7401 | $SCH_2CH_3$ | $SCH_2CH_3$ | CN | Br | $SC_6H_5$ |
| 7402 | $N(CH_3)_2$ | $N(CH_3)_2$ | CN | Br | $SC_6H_5$ |
| 7403 | $N(CH_2CH_3)_2$ | $N(CH_2CH_3)_2$ | CN | Br | $SC_6H_5$ |
| 7404 | $N(CH_3)(CH_2CH_3)$ | $N(CH_3)(CH_2CH_3)$ | CN | Br | $SC_6H_5$ |
| 7405 | $O—(CH_2CH_2)—O$ | | CN | Br | $SC_6H_5$ |
| 7406 | $O—(CH_2CH_2CH_2)—O$ | | CN | Br | $SC_6H_5$ |
| 7407 | $S—(CH_2CH_2)—S$ | | CN | Br | $SC_6H_5$ |
| 7408 | $S—(CH_2CH_2CH_2)—S$ | | CN | Br | $SC_6H_5$ |
| 7409 | $—(CH_2)_4—$ | | CN | Br | $SC_6H_5$ |
| 7410 | $—(CH_2)_5—$ | | CN | Br | $SC_6H_5$ |
| 7411 | H | H | F | Br | $SC_6H_5$ |
| 7412 | $CH_3$ | $CH_3$ | F | Br | $SC_6H_5$ |
| 7413 | $CH_2CH_3$ | $CH_2CH_3$ | F | Br | $SC_6H_5$ |
| 7414 | $CH_2CH_2CH_3$ | $CH_2CH_2CH_3$ | F | Br | $SC_6H_5$ |
| 7415 | $OCH_3$ | $OCH_3$ | F | Br | $SC_6H_5$ |
| 7416 | $OCH_2CH_3$ | $OCH_2CH_3$ | F | Br | $SC_6H_5$ |
| 7417 | $OCH_2CH_2CH_3$ | $OCH_2CH_2CH_3$ | F | Br | $SC_6H_5$ |
| 7418 | $SCH_3$ | $SCH_3$ | F | Br | $SC_6H_5$ |
| 7419 | $SCH_2CH_3$ | $SCH_2CH_3$ | F | Br | $SC_6H_5$ |
| 7420 | $N(CH_3)_2$ | $N(CH_3)_2$ | F | Br | $SC_6H_5$ |
| 7421 | $N(CH_2CH_3)_2$ | $N(CH_2CH_3)_2$ | F | Br | $SC_6H_5$ |
| 7422 | $N(CH_3)(CH_2CH_3)$ | $N(CH_3)(CH_2CH_3)$ | F | Br | $SC_6H_5$ |
| 7423 | $O—(CH_2CH_2)—O$ | | F | Br | $SC_6H_5$ |
| 7424 | $O—(CH_2CH_2CH_2)—O$ | | F | Br | $SC_6H_5$ |
| 7425 | $S—(CH_2CH_2)—S$ | | F | Br | $SC_6H_5$ |
| 7426 | $S—(CH_2CH_2CH_2)—S$ | | F | Br | $SC_6H_5$ |
| 7427 | $—(CH_2)_4—$ | | F | Br | $SC_6H_5$ |
| 7428 | $—(CH_2)_5—$ | | F | Br | $SC_6H_5$ |
| 7429 | H | H | Cl | Br | $SC_6H_5$ |
| 7430 | $CH_3$ | $CH_3$ | Cl | Br | $SC_6H_5$ |
| 7431 | $CH_2CH_3$ | $CH_2CH_3$ | Cl | Br | $SC_6H_5$ |
| 7432 | $CH_2CH_2CH_3$ | $CH_2CH_2CH_3$ | Cl | Br | $SC_6H_5$ |
| 7433 | $OCH_3$ | $OCH_3$ | Cl | Br | $SC_6H_5$ |
| 7434 | $OCH_2CH_3$ | $OCH_2CH_3$ | Cl | Br | $SC_6H_5$ |
| 7435 | $OCH_2CH_2CH_3$ | $OCH_2CH_2CH_3$ | Cl | Br | $SC_6H_5$ |
| 7436 | $SCH_3$ | $SCH_3$ | Cl | Br | $SC_6H_5$ |
| 7437 | $SCH_2CH_3$ | $SCH_2CH_3$ | Cl | Br | $SC_6H_5$ |
| 7438 | $N(CH_3)_2$ | $N(CH_3)_2$ | Cl | Br | $SC_6H_5$ |

TABLE 1-continued

I1a1

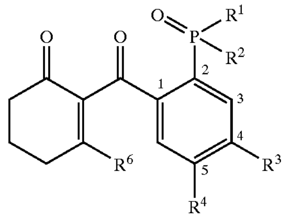

| n | $R^1$ | $R^2$ | $R^3$ | $R^4$ | $R^6$ |
|---|---|---|---|---|---|
| 7439 | $N(CH_2CH_3)_2$ | $N(CH_2CH_3)_2$ | Cl | Br | $SC_6H_5$ |
| 7440 | $N(CH_3)(CH_2CH_3)$ | $N(CH_3)(CH_2CH_3)$ | Cl | Br | $SC_6H_5$ |
| 7441 | $O-(CH_2CH_2)-O$ | | Cl | Br | $SC_6H_5$ |
| 7442 | $O-(CH_2CH_2CH_2)-O$ | | Cl | Br | $SC_6H_5$ |
| 7443 | $S-(CH_2CH_2)-S$ | | Cl | Br | $SC_6H_5$ |
| 7444 | $S-(CH_2CH_2CH_2)-S$ | | Cl | Br | $SC_6H_5$ |
| 7445 | $-(CH_2)_4-$ | | Cl | Br | $SC_6H_5$ |
| 7446 | $-(CH_2)_5-$ | | Cl | Br | $SC_6H_5$ |
| 7447 | H | H | Br | Br | $SC_6H_5$ |
| 7448 | $CH_3$ | $CH_3$ | Br | Br | $SC_6H_5$ |
| 7449 | $CH_2CH_3$ | $CH_2CH_3$ | Br | Br | $SC_6H_5$ |
| 7450 | $CH_2CH_2CH_3$ | $CH_2CH_2CH_3$ | Br | Br | $SC_6H_5$ |
| 7451 | $OCH_3$ | $OCH_3$ | Br | Br | $SC_6H_5$ |
| 7452 | $OCH_2CH_3$ | $OCH_2CH_3$ | Br | Br | $SC_6H_5$ |
| 7453 | $OCH_2CH_2CH_3$ | $OCH_2CH_2CH_3$ | Br | Br | $SC_6H_5$ |
| 7454 | $SCH_3$ | $SCH_3$ | Br | Br | $SC_6H_5$ |
| 7455 | $SCH_2CH_3$ | $SCH_2CH_3$ | Br | Br | $SC_6H_5$ |
| 7456 | $N(CH_3)_2$ | $N(CH_3)_2$ | Br | Br | $SC_6H_5$ |
| 7457 | $N(CH_2CH_3)_2$ | $N(CH_2CH_3)_2$ | Br | Br | $SC_6H_5$ |
| 7458 | $N(CH_3)(CH_2CH_3)$ | $N(CH_3)(CH_2CH_3)$ | Br | Br | $SC_6H_5$ |
| 7459 | $O-(CH_2CH_2)-O$ | | Br | Br | $SC_6H_5$ |
| 7460 | $O-(CH_2CH_2CH_2)-O$ | | Br | Br | $SC_6H_5$ |
| 7461 | $S-(CH_2CH_2)-S$ | | Br | Br | $SC_6H_5$ |
| 7462 | $S-(CH_2CH_2CH_2)-S$ | | Br | Br | $SC_6H_5$ |
| 7463 | $-(CH_2)_4-$ | | Br | Br | $SC_6H_5$ |
| 7464 | $-(CH_2)_5-$ | | Br | Br | $SC_6H_5$ |
| 7465 | H | H | $CH_3$ | Br | $SC_6H_5$ |
| 7466 | $CH_3$ | $CH_3$ | $CH_3$ | Br | $SC_6H_5$ |
| 7467 | $CH_2CH_3$ | $CH_2CH_3$ | $CH_3$ | Br | $SC_6H_5$ |
| 7468 | $CH_2CH_2CH_3$ | $CH_2CH_2CH_3$ | $CH_3$ | Br | $SC_6H_5$ |
| 7469 | $OCH_3$ | $OCH_3$ | $CH_3$ | Br | $SC_6H_5$ |
| 7470 | $OCH_2CH_3$ | $OCH_2CH_3$ | $CH_3$ | Br | $SC_6H_5$ |
| 7471 | $OCH_2CH_2CH_3$ | $OCH_2CH_2CH_3$ | $CH_3$ | Br | $SC_6H_5$ |
| 7472 | $SCH_3$ | $SCH_3$ | $CH_3$ | Br | $SC_6H_5$ |
| 7473 | $SCH_2CH_3$ | $SCH_2CH_3$ | $CH_3$ | Br | $SC_6H_5$ |
| 7474 | $N(CH_3)_2$ | $N(CH_3)_2$ | $CH_3$ | Br | $SC_6H_5$ |
| 7475 | $N(CH_2CH_3)_2$ | $N(CH_2CH_3)_2$ | $CH_3$ | Br | $SC_6H_5$ |
| 7476 | $N(CH_3)(CH_2CH_3)$ | $N(CH_3)(CH_2CH_3)$ | $CH_3$ | Br | $SC_6H_5$ |
| 7477 | $O-(CH_2CH_2)-O$ | | $CH_3$ | Br | $SC_6H_5$ |
| 7478 | $O-(CH_2CH_2CH_2)-O$ | | $CH_3$ | Br | $SC_6H_5$ |
| 7479 | $S-(CH_2CH_2)-S$ | | $CH_3$ | Br | $SC_6H_5$ |
| 7480 | $S-(CH_2CH_2CH_2)-S$ | | $CH_3$ | Br | $SC_6H_5$ |
| 7481 | $-(CH_2)_4-$ | | $CH_3$ | Br | $SC_6H_5$ |
| 7482 | $-(CH_2)_5-$ | | $CH_3$ | Br | $SC_6H_5$ |
| 7483 | H | H | $CH_2CH_3$ | Br | $SC_6H_5$ |
| 7484 | $CH_3$ | $CH_3$ | $CH_2CH_3$ | Br | $SC_6H_5$ |
| 7485 | $CH_2CH_3$ | $CH_2CH_3$ | $CH_2CH_3$ | Br | $SC_6H_5$ |
| 7486 | $CH_2CH_2CH_3$ | $CH_2CH_2CH_3$ | $CH_2CH_3$ | Br | $SC_6H_5$ |
| 7487 | $OCH_3$ | $OCH_3$ | $CH_2CH_3$ | Br | $SC_6H_5$ |
| 7488 | $OCH_2CH_3$ | $OCH_2CH_3$ | $CH_2CH_3$ | Br | $SC_6H_5$ |
| 7489 | $OCH_2CH_2CH_3$ | $OCH_2CH_2CH_3$ | $CH_2CH_3$ | Br | $SC_6H_5$ |
| 7490 | $SCH_3$ | $SCH_3$ | $CH_2CH_3$ | Br | $SC_6H_5$ |
| 7491 | $SCH_2CH_3$ | $SCH_2CH_3$ | $CH_2CH_3$ | Br | $SC_6H_5$ |
| 7492 | $N(CH_3)_2$ | $N(CH_3)_2$ | $CH_2CH_3$ | Br | $SC_6H_5$ |
| 7493 | $N(CH_2CH_3)_2$ | $N(CH_2CH_3)_2$ | $CH_2CH_3$ | Br | $SC_6H_5$ |
| 7494 | $N(CH_3)(CH_2CH_3)$ | $N(CH_3)(CH_2CH_3)$ | $CH_2CH_3$ | Br | $SC_6H_5$ |
| 7495 | $O-(CH_2CH_2)-O$ | | $CH_2CH_3$ | Br | $SC_6H_5$ |
| 7496 | $O-(CH_2CH_2CH_2)-O$ | | $CH_2CH_3$ | Br | $SC_6H_5$ |
| 7497 | $S-(CH_2CH_2)-S$ | | $CH_2CH_3$ | Br | $SC_6H_5$ |
| 7498 | $S-(CH_2CH_2CH_2)-S$ | | $CH_2CH_3$ | Br | $SC_6H_5$ |
| 7499 | $-(CH_2)_4-$ | | $CH_2CH_3$ | Br | $SC_6H_5$ |
| 7500 | $-(CH_2)_5-$ | | $CH_2CH_3$ | Br | $SC_6H_5$ |
| 7501 | H | H | $CF_3$ | Br | $SC_6H_5$ |
| 7502 | $CH_3$ | $CH_3$ | $CF_3$ | Br | $SC_6H_5$ |

TABLE 1-continued

I1a1

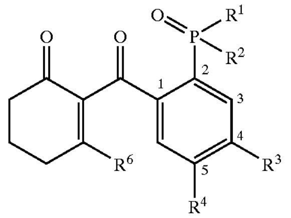

| n | $R^1$ | $R^2$ | $R^3$ | $R^4$ | $R^6$ |
|---|---|---|---|---|---|
| 7503 | $CH_2CH_3$ | $CH_2CH_3$ | $CF_3$ | Br | $SC_6H_5$ |
| 7504 | $CH_2CH_2CH_3$ | $CH_2CH_2CH_3$ | $CF_3$ | Br | $SC_6H_5$ |
| 7505 | $OCH_3$ | $OCH_3$ | $CF_3$ | Br | $SC_6H_5$ |
| 7506 | $OCH_2CH_3$ | $OCH_2CH_3$ | $CF_3$ | Br | $SC_6H_5$ |
| 7507 | $OCH_2CH_2CH_3$ | $OCH_2CH_2CH_3$ | $CF_3$ | Br | $SC_6H_5$ |
| 7508 | $SCH_3$ | $SCH_3$ | $CF_3$ | Br | $SC_6H_5$ |
| 7509 | $SCH_2CH_3$ | $SCH_2CH_3$ | $CF_3$ | Br | $SC_6H_5$ |
| 7510 | $N(CH_3)_2$ | $N(CH_3)_2$ | $CF_3$ | Br | $SC_6H_5$ |
| 7511 | $N(CH_2CH_3)_2$ | $N(CH_2CH_3)_2$ | $CF_3$ | Br | $SC_6H_5$ |
| 7512 | $N(CH_3)(CH_2CH_3)$ | $N(CH_3)(CH_2CH_3)$ | $CF_3$ | Br | $SC_6H_5$ |
| 7513 | $O—(CH_2CH_2)—O$ | | $CF_3$ | Br | $SC_6H_5$ |
| 7514 | $O—(CH_2CH_2CH_2)—O$ | | $CF_3$ | Br | $SC_6H_5$ |
| 7515 | $S—(CH_2CH_2)—S$ | | $CF_3$ | Br | $SC_6H_5$ |
| 7516 | $S—(CH_2CH_2CH_2)—S$ | | $CF_3$ | Br | $SC_6H_5$ |
| 7517 | $—(CH_2)_4—$ | | $CF_3$ | Br | $SC_6H_5$ |
| 7518 | $—(CH_2)_5—$ | | $CF_3$ | Br | $SC_6H_5$ |
| 7519 | H | H | $OCH_3$ | Br | $SC_6H_5$ |
| 7520 | $CH_3$ | $CH_3$ | $OCH_3$ | Br | $SC_6H_5$ |
| 7521 | $CH_2CH_3$ | $CH_2CH_3$ | $OCH_3$ | Br | $SC_6H_5$ |
| 7522 | $CH_2CH_2CH_3$ | $CH_2CH_2CH_3$ | $OCH_3$ | Br | $SC_6H_5$ |
| 7523 | $OCH_3$ | $OCH_3$ | $OCH_3$ | Br | $SC_6H_5$ |
| 7524 | $OCH_2CH_3$ | $OCH_2CH_3$ | $OCH_3$ | Br | $SC_6H_5$ |
| 7525 | $OCH_2CH_2CH_3$ | $OCH_2CH_2CH_3$ | $OCH_3$ | Br | $SC_6H_5$ |
| 7526 | $SCH_3$ | $SCH_3$ | $OCH_3$ | Br | $SC_6H_5$ |
| 7527 | $SCH_2CH_3$ | $SCH_2CH_3$ | $OCH_3$ | Br | $SC_6H_5$ |
| 7528 | $N(CH_3)_2$ | $N(CH_3)_2$ | $OCH_3$ | Br | $SC_6H_5$ |
| 7529 | $N(CH_2CH_3)_2$ | $N(CH_2CH_3)_2$ | $OCH_3$ | Br | $SC_6H_5$ |
| 7530 | $N(CH_3)(CH_2CH_3)$ | $N(CH_3)(CH_2CH_3)$ | $OCH_3$ | Br | $SC_6H_5$ |
| 7531 | $O—(CH_2CH_2)—O$ | | $OCH_3$ | Br | $SC_6H_5$ |
| 7532 | $O—(CH_2CH_2CH_2)—O$ | | $OCH_3$ | Br | $SC_6H_5$ |
| 7533 | $S—(CH_2CH_2)—S$ | | $OCH_3$ | Br | $SC_6H_5$ |
| 7534 | $S—(CH_2CH_2CH_2)—S$ | | $OCH_3$ | Br | $SC_6H_5$ |
| 7535 | $—(CH_2)_4—$ | | $OCH_3$ | Br | $SC_6H_5$ |
| 7536 | $—(CH_2)_5—$ | | $OCH_3$ | Br | $SC_6H_5$ |
| 7537 | H | H | $OCH_2CH_3$ | Br | $SC_6H_5$ |
| 7538 | $CH_3$ | $CH_3$ | $OCH_2CH_3$ | Br | $SC_6H_5$ |
| 7539 | $CH_2CH_3$ | $CH_2CH_3$ | $OCH_2CH_3$ | Br | $SC_6H_5$ |
| 7540 | $CH_2CH_2CH_3$ | $CH_2CH_2CH_3$ | $OCH_2CH_3$ | Br | $SC_6H_5$ |
| 7541 | $OCH_3$ | $OCH_3$ | $OCH_2CH_3$ | Br | $SC_6H_5$ |
| 7542 | $OCH_2CH_3$ | $OCH_2CH_3$ | $OCH_2CH_3$ | Br | $SC_6H_5$ |
| 7543 | $OCH_2CH_2CH_3$ | $OCH_2CH_2CH_3$ | $OCH_2CH_3$ | Br | $SC_6H_5$ |
| 7544 | $SCH_3$ | $SCH_3$ | $OCH_2CH_3$ | Br | $SC_6H_5$ |
| 7545 | $SCH_2CH_3$ | $SCH_2CH_3$ | $OCH_2CH_3$ | Br | $SC_6H_5$ |
| 7546 | $N(CH_3)_2$ | $N(CH_3)_2$ | $OCH_2CH_3$ | Br | $SC_6H_5$ |
| 7547 | $N(CH_2CH_3)_2$ | $N(CH_2CH_3)_2$ | $OCH_2CH_3$ | Br | $SC_6H_5$ |
| 7548 | $N(CH_3)(CH_2CH_3)$ | $N(CH_3)(CH_2CH_3)$ | $OCH_2CH_3$ | Br | $SC_6H_5$ |
| 7549 | $O—(CH_2CH_2)—O$ | | $OCH_2CH_3$ | Br | $SC_6H_5$ |
| 7550 | $O—(CH_2CH_2CH_2)—O$ | | $OCH_2CH_3$ | Br | $SC_6H_5$ |
| 7551 | $S—(CH_2CH_2)—S$ | | $OCH_2CH_3$ | Br | $SC_6H_5$ |
| 7552 | $S—(CH_2CH_2CH_2)—S$ | | $OCH_2CH_3$ | Br | $SC_6H_5$ |
| 7553 | $—(CH_2)_4—$ | | $OCH_2CH_3$ | Br | $SC_6H_5$ |
| 7554 | $—(CH_2)_5—$ | | $OCH_2CH_3$ | Br | $SC_6H_5$ |
| 7555 | H | H | $SCH_3$ | Br | $SC_6H_5$ |
| 7556 | $CH_3$ | $CH_3$ | $SCH_3$ | Br | $SC_6H_5$ |
| 7557 | $CH_2CH_3$ | $CH_2CH_3$ | $SCH_3$ | Br | $SC_6H_5$ |
| 7558 | $CH_2CH_2CH_3$ | $CH_2CH_2CH_3$ | $SCH_3$ | Br | $SC_6H_5$ |
| 7559 | $OCH_3$ | $OCH_3$ | $SCH_3$ | Br | $SC_6H_5$ |
| 7560 | $OCH_2CH_3$ | $OCH_2CH_3$ | $SCH_3$ | Br | $SC_6H_5$ |
| 7561 | $OCH_2CH_2CH_3$ | $OCH_2CH_2CH_3$ | $SCH_3$ | Br | $SC_6H_5$ |
| 7562 | $SCH_3$ | $SCH_3$ | $SCH_3$ | Br | $SC_6H_5$ |
| 7563 | $SCH_2CH_3$ | $SCH_2CH_3$ | $SCH_3$ | Br | $SC_6H_5$ |
| 7564 | $N(CH_3)_2$ | $N(CH_3)_2$ | $SCH_3$ | Br | $SC_6H_5$ |
| 7565 | $N(CH_2CH_3)_2$ | $N(CH_2CH_3)_2$ | $SCH_3$ | Br | $SC_6H_5$ |
| 7566 | $N(CH_3)(CH_2CH_3)$ | $N(CH_3)(CH_2CH_3)$ | $SCH_3$ | Br | $SC_6H_5$ |

TABLE 1-continued

I1a1

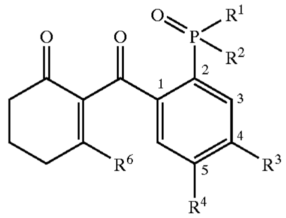

| n | $R^1$ | $R^2$ | $R^3$ | $R^4$ | $R^6$ |
|---|---|---|---|---|---|
| 7567 | O—$(CH_2CH_2)$—O | | $SCH_3$ | Br | $SC_6H_5$ |
| 7568 | O—$(CH_2CH_2CH_2)$—O | | $SCH_3$ | Br | $SC_6H_5$ |
| 7569 | S—$(CH_2CH_2)$—S | | $SCH_3$ | Br | $SC_6H_5$ |
| 7570 | S—$(CH_2CH_2CH_2)$—S | | $SCH_3$ | Br | $SC_6H_5$ |
| 7571 | —$(CH_2)_4$— | | $SCH_3$ | Br | $SC_6H_5$ |
| 7572 | —$(CH_2)_5$— | | $SCH_3$ | Br | $SC_6H_5$ |
| 7573 | H | H | $SO_2CH_3$ | Br | $SC_6H_5$ |
| 7574 | $CH_3$ | $CH_3$ | $SO_2CH_3$ | Br | $SC_6H_5$ |
| 7575 | $CH_2CH_3$ | $CH_2CH_3$ | $SO_2CH_3$ | Br | $SC_6H_5$ |
| 7576 | $CH_2CH_2CH_3$ | $CH_2CH_2CH_3$ | $SO_2CH_3$ | Br | $SC_6H_5$ |
| 7577 | $OCH_3$ | $OCH_3$ | $SO_2CH_3$ | Br | $SC_6H_5$ |
| 7578 | $OCH_2CH_3$ | $OCH_2CH_3$ | $SO_2CH_3$ | Br | $SC_6H_5$ |
| 7579 | $OCH_2CH_2CH_3$ | $OCH_2CH_2CH_3$ | $SO_2CH_3$ | Br | $SC_6H_5$ |
| 7580 | $SCH_3$ | $SCH_3$ | $SO_2CH_3$ | Br | $SC_6H_5$ |
| 7581 | $SCH_2CH_3$ | $SCH_2CH_3$ | $SO_2CH_3$ | Br | $SC_6H_5$ |
| 7582 | $N(CH_3)_2$ | $N(CH_3)_2$ | $SO_2CH_3$ | Br | $SC_6H_5$ |
| 7583 | $N(CH_2CH_3)_2$ | $N(CH_2CH_3)_2$ | $SO_2CH_3$ | Br | $SC_6H_5$ |
| 7584 | $N(CH_3)(CH_2CH_3)$ | $N(CH_3)(CH_2CH_3)$ | $SO_2CH_3$ | Br | $SC_6H_5$ |
| 7585 | O—$(CH_2CH_2)$—O | | $SO_2CH_3$ | Br | $SC_6H_5$ |
| 7586 | O—$(CH_2CH_2CH_2)$—O | | $SO_2CH_3$ | Br | $SC_6H_5$ |
| 7587 | S—$(CH_2CH_2)$—S | | $SO_2CH_3$ | Br | $SC_6H_5$ |
| 7588 | S—$(CH_2CH_2CH_2)$—S | | $SO_2CH_3$ | Br | $SC_6H_5$ |
| 7589 | —$(CH_2)_4$— | | $SO_2CH_3$ | Br | $SC_6H_5$ |
| 7590 | —$(CH_2)_5$— | | $SO_2CH_3$ | Br | $SC_6H_5$ |
| 7591 | H | H | $PO(OCH_3)_2$ | Br | $SC_6H_5$ |
| 7592 | $CH_3$ | $CH_3$ | $PO(OCH_3)_2$ | Br | $SC_6H_5$ |
| 7593 | $CH_2CH_3$ | $CH_2CH_3$ | $PO(OCH_3)_2$ | Br | $SC_6H_5$ |
| 7594 | $CH_2CH_2CH_3$ | $CH_2CH_2CH_3$ | $PO(OCH_3)_2$ | Br | $SC_6H_5$ |
| 7595 | $OCH_3$ | $OCH_3$ | $PO(OCH_3)_2$ | Br | $SC_6H_5$ |
| 7596 | $OCH_2CH_3$ | $OCH_2CH_3$ | $PO(OCH_3)_2$ | Br | $SC_6H_5$ |
| 7597 | $OCH_2CH_2CH_3$ | $OCH_2CH_2CH_3$ | $PO(OCH_3)_2$ | Br | $SC_6H_5$ |
| 7598 | $SCH_3$ | $SCH_3$ | $PO(OCH_3)_2$ | Br | $SC_6H_5$ |
| 7599 | $SCH_2CH_3$ | $SCH_2CH_3$ | $PO(OCH_3)_2$ | Br | $SC_6H_5$ |
| 7600 | $N(CH_3)_2$ | $N(CH_3)_2$ | $PO(OCH_3)_2$ | Br | $SC_6H_5$ |
| 7601 | $N(CH_2CH_3)_2$ | $N(CH_2CH_3)_2$ | $PO(OCH_3)_2$ | Br | $SC_6H_5$ |
| 7602 | $N(CH_3)(CH_2CH_3)$ | $N(CH_3)(CH_2CH_3)$ | $PO(OCH_3)_2$ | Br | $SC_6H_5$ |
| 7603 | O—$(CH_2CH_2)$—O | | $PO(OCH_3)_2$ | Br | $SC_6H_5$ |
| 7604 | O—$(CH_2CH_2CH_2)$—O | | $PO(OCH_3)_2$ | Br | $SC_6H_5$ |
| 7605 | S—$(CH_2CH_2)$—S | | $PO(OCH_3)_2$ | Br | $SC_6H_5$ |
| 7606 | S—$(CH_2CH_2CH_2)$—S | | $PO(OCH_3)_2$ | Br | $SC_6H_5$ |
| 7607 | —$(CH_2)_4$— | | $PO(OCH_3)_2$ | Br | $SC_6H_5$ |
| 7608 | —$(CH_2)_5$— | | $PO(OCH_3)_2$ | Br | $SC_6H_5$ |
| 7609 | H | H | $PO(OCH_2CH_3)_2$ | Br | $SC_6H_5$ |
| 7610 | $CH_3$ | $CH_3$ | $PO(OCH_2CH_3)_2$ | Br | $SC_6H_5$ |
| 7611 | $CH_2CH_3$ | $CH_2CH_3$ | $PO(OCH_2CH_3)_2$ | Br | $SC_6H_5$ |
| 7612 | $CH_2CH_2CH_3$ | $CH_2CH_2CH_3$ | $PO(OCH_2CH_3)_2$ | Br | $SC_6H_5$ |
| 7613 | $OCH_3$ | $OCH_3$ | $PO(OCH_2CH_3)_2$ | Br | $SC_6H_5$ |
| 7614 | $OCH_2CH_3$ | $OCH_2CH_3$ | $PO(OCH_2CH_3)_2$ | Br | $SC_6H_5$ |
| 7615 | $OCH_2CH_2CH_3$ | $OCH_2CH_2CH_3$ | $PO(OCH_2CH_3)_2$ | Br | $SC_6H_5$ |
| 7616 | $SCH_3$ | $SCH_3$ | $PO(OCH_2CH_3)_2$ | Br | $SC_6H_5$ |
| 7617 | $SCH_2CH_3$ | $SCH_2CH_3$ | $PO(OCH_2CH_3)_2$ | Br | $SC_6H_5$ |
| 7618 | $N(CH_3)_2$ | $N(CH_3)_2$ | $PO(OCH_2CH_3)_2$ | Br | $SC_6H_5$ |
| 7619 | $N(CH_2CH_3)_2$ | $N(CH_2CH_3)_2$ | $PO(OCH_2CH_3)_2$ | Br | $SC_6H_5$ |
| 7620 | $N(CH_3)(CH_2CH_3)$ | $N(CH_3)(CH_2CH_3)$ | $PO(OCH_2CH_3)_2$ | Br | $SC_6H_5$ |
| 7621 | O—$(CH_2CH_2)$—O | | $PO(OCH_2CH_3)_2$ | Br | $SC_6H_5$ |
| 7622 | O—$(CH_2CH_2CH_2)$—O | | $PO(OCH_2CH_3)_2$ | Br | $SC_6H_5$ |
| 7623 | S—$(CH_2CH_2)$—S | | $PO(OCH_2CH_3)_2$ | Br | $SC_6H_5$ |
| 7624 | S—$(CH_2CH_2CH_2)$—S | | $PO(OCH_2CH_3)_2$ | Br | $SC_6H_5$ |
| 7625 | —$(CH_2)_4$— | | $PO(OCH_2CH_3)_2$ | Br | $SC_6H_5$ |
| 7626 | —$(CH_2)_5$— | | $PO(OCH_2CH_3)_2$ | Br | $SC_6H_5$ |
| 7627 | H | H | $PO(CH_3)_2$ | Br | $SC_6H_5$ |
| 7628 | $CH_3$ | $CH_3$ | $PO(CH_3)_2$ | Br | $SC_6H_5$ |
| 7629 | $CH_2CH_3$ | $CH_2CH_3$ | $PO(CH_3)_2$ | Br | $SC_6H_5$ |
| 7630 | $CH_2CH_2CH_3$ | $CH_2CH_2CH_3$ | $PO(CH_3)_2$ | Br | $SC_6H_5$ |

TABLE 1-continued

I1a1

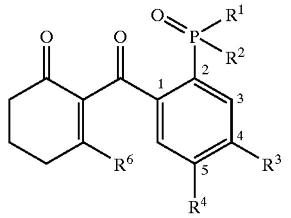

| n | $R^1$ | $R^2$ | $R^3$ | $R^4$ | $R^6$ |
|---|---|---|---|---|---|
| 7631 | $OCH_3$ | $OCH_3$ | $PO(CH_3)_2$ | Br | $SC_6H_5$ |
| 7632 | $OCH_2CH_3$ | $OCH_2CH_3$ | $PO(CH_3)_2$ | Br | $SC_6H_5$ |
| 7633 | $OCH_2CH_2CH_3$ | $OCH_2CH_2CH_3$ | $PO(CH_3)_2$ | Br | $SC_6H_5$ |
| 7634 | $SCH_3$ | $SCH_3$ | $PO(CH_3)_2$ | Br | $SC_6H_5$ |
| 7635 | $SCH_2CH_3$ | $SCH_2CH_3$ | $PO(CH_3)_2$ | Br | $SC_6H_5$ |
| 7636 | $N(CH_3)_2$ | $N(CH_3)_2$ | $PO(CH_3)_2$ | Br | $SC_6H_5$ |
| 7637 | $N(CH_2CH_3)_2$ | $N(CH_2CH_3)_2$ | $PO(CH_3)_2$ | Br | $SC_6H_5$ |
| 7638 | $N(CH_3)(CH_2CH_3)$ | $N(CH_3)(CH_2CH_3)$ | $PO(CH_3)_2$ | Br | $SC_6H_5$ |
| 7639 | $O-(CH_2CH_2)-O$ | | $PO(CH_3)_2$ | Br | $SC_6H_5$ |
| 7640 | $O-(CH_2CH_2CH_2)-O$ | | $PO(CH_3)_2$ | Br | $SC_6H_5$ |
| 7641 | $S-(CH_2CH_2)-S$ | | $PO(CH_3)_2$ | Br | $SC_6H_5$ |
| 7642 | $S-(CH_2CH_2CH_2)-S$ | | $PO(CH_3)_2$ | Br | $SC_6H_5$ |
| 7643 | $-(CH_2)_4-$ | | $PO(CH_3)_2$ | Br | $SC_6H_5$ |
| 7644 | $-(CH_2)_5-$ | | $PO(CH_3)_2$ | Br | $SC_6H_5$ |
| 7645 | H | H | $PC(CH_2CH_3)_2$ | Br | $SC_6H_5$ |
| 7646 | $CH_3$ | $CH_3$ | $PC(CH_2CH_3)_2$ | Br | $SC_6H_5$ |
| 7647 | $CH_2CH_3$ | $CH_2CH_3$ | $PC(CH_2CH_3)_2$ | Br | $SC_6H_5$ |
| 7648 | $CH_2CH_2CH_3$ | $CH_2CH_2CH_3$ | $PC(CH_2CH_3)_2$ | Br | $SC_6H_5$ |
| 7649 | $OCH_3$ | $OCH_3$ | $PC(CH_2CH_3)_2$ | Br | $SC_6H_5$ |
| 7650 | $OCH_2CH_3$ | $OCH_2CH_3$ | $PC(CH_2CH_3)_2$ | Br | $SC_6H_5$ |
| 7651 | $OCH_2CH_2CH_3$ | $OCH_2CH_2CH_3$ | $PC(CH_2CH_3)_2$ | Br | $SC_6H_5$ |
| 7652 | $SCH_3$ | $SCH_3$ | $PC(CH_2CH_3)_2$ | Br | $SC_6H_5$ |
| 7653 | $SCH_2CH_3$ | $SCH_2CH_3$ | $PC(CH_2CH_3)_2$ | Br | $SC_6H_5$ |
| 7654 | $N(CH_3)_2$ | $N(CH_3)_2$ | $PC(CH_2CH_3)_2$ | Br | $SC_6H_5$ |
| 7655 | $N(CH_2CH_3)_2$ | $N(CH_2CH_3)_2$ | $PC(CH_2CH_3)_2$ | Br | $SC_6H_5$ |
| 7656 | $N(CH_3)(CH_2CH_3)$ | $N(CH_3)(CH_2CH_3)$ | $PC(CH_2CH_3)_2$ | Br | $SC_6H_5$ |
| 7657 | $O-(CH_2CH_2)-O$ | | $PC(CH_2CH_3)_2$ | Br | $SC_6H_5$ |
| 7658 | $O-(CH_2CH_2CH_2)-O$ | | $PC(CH_2CH_3)_2$ | Br | $SC_6H_5$ |
| 7659 | $S-(CH_2CH_2)-S$ | | $PC(CH_2CH_3)_2$ | Br | $SC_6H_5$ |
| 7660 | $S-(CH_2CH_2CH_2)-S$ | | $PC(CH_2CH_3)_2$ | Br | $SC_6H_5$ |
| 7661 | $-(CH_2)_4-$ | | $PC(CH_2CH_3)_2$ | Br | $SC_6H_5$ |
| 7662 | $-(CH_2)_5-$ | | $PC(CH_2CH_3)_2$ | Br | $SC_6H_5$ |
| 7663 | H | H | H | Br | Het1 |
| 7664 | $CH_3$ | $CH_3$ | H | Br | Het1 |
| 7665 | $CH_2CH_3$ | $CH_2CH_3$ | H | Br | Het1 |
| 7666 | $CH_2CH_2CH_3$ | $CH_2CH_2CH_3$ | H | Br | Het1 |
| 7667 | $OCH_3$ | $OCH_3$ | H | Br | Het1 |
| 7668 | $OCH_2CH_3$ | $OCH_2CH_3$ | H | Br | Het1 |
| 7669 | $OCH_2CH_2CH_3$ | $OCH_2CH_2CH_3$ | H | Br | Het1 |
| 7670 | $SCH_3$ | $SCH_3$ | H | Br | Het1 |
| 7671 | $SCH_2CH_3$ | $SCH_2CH_3$ | H | Br | Het1 |
| 7672 | $N(CH_3)_2$ | $N(CH_3)_2$ | H | Br | Het1 |
| 7673 | $N(CH_2CH_3)_2$ | $N(CH_2CH_3)_2$ | H | Br | Het1 |
| 7674 | $N(CH_3)(CH_2CH_3)$ | $N(CH_3)(CH_2CH_3)$ | H | Br | Het1 |
| 7675 | $O-(CH_2CH_2)-O$ | | H | Br | Het1 |
| 7676 | $O-(CH_2CH_2CH_2)-O$ | | H | Br | Het1 |
| 7677 | $S-(CH_2CH_2)-S$ | | H | Br | Het1 |
| 7678 | $S-(CH_2CH_2CH_2)-S$ | | H | Br | Het1 |
| 7679 | $-(CH_2)_4-$ | | H | Br | Het1 |
| 7680 | $-(CH_2)_5-$ | | H | Br | Het1 |
| 7681 | H | H | $NO_2$ | Br | Het1 |
| 7682 | $CH_3$ | $CH_3$ | $NO_2$ | Br | Het1 |
| 7683 | $CH_2CH_3$ | $CH_2CH_3$ | $NO_2$ | Br | Het1 |
| 7684 | $CH_2CH_2CH_3$ | $CH_2CH_2CH_3$ | $NO_2$ | Br | Het1 |
| 7685 | $OCH_3$ | $OCH_3$ | $NO_2$ | Br | Het1 |
| 7686 | $OCH_2CH_3$ | $OCH_2CH_3$ | $NO_2$ | Br | Het1 |
| 7687 | $OCH_2CH_2CH_3$ | $OCH_2CH_2CH_3$ | $NO_2$ | Br | Het1 |
| 7688 | $SCH_3$ | $SCH_3$ | $NO_2$ | Br | Het1 |
| 7689 | $SCH_2CH_3$ | $SCH_2CH_3$ | $NO_2$ | Br | Het1 |
| 7690 | $N(CH_3)_2$ | $N(CH_3)_2$ | $NO_2$ | Br | Het1 |
| 7691 | $N(CH_2CH_3)_2$ | $N(CH_2CH_3)_2$ | $NO_2$ | Br | Het1 |
| 7692 | $N(CH_3)(CH_2CH_3)$ | $N(CH_3)(CH_2CH_3)$ | $NO_2$ | Br | Het1 |
| 7693 | $O-(CH_2CH_2)-O$ | | $NO_2$ | Br | Het1 |
| 7694 | $O-(CH_2CH_2CH_2)-O$ | | $NO_2$ | Br | Het1 |

TABLE 1-continued

I1a1

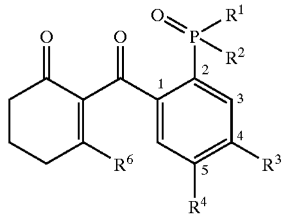

| n | $R^1$ | $R^2$ | $R^3$ | $R^4$ | $R^6$ |
|---|---|---|---|---|---|
| 7695 | S—$(CH_2CH_2)$—S | | $NO_2$ | Br | Het1 |
| 7696 | S—$(CH_2CH_2CH_2)$—S | | $NO_2$ | Br | Het1 |
| 7697 | —$(CH_2)_4$— | | $NO_2$ | Br | Het1 |
| 7698 | —$(CH_2)_5$— | | $NO_2$ | Br | Het1 |
| 7699 | H | H | CN | Br | Het1 |
| 7700 | $CH_3$ | $CH_3$ | CN | Br | Het1 |
| 7701 | $CH_2CH_3$ | $CH_2CH_3$ | CN | Br | Het1 |
| 7702 | $CH_2CH_2CH_3$ | $CH_2CH_2CH_3$ | CN | Br | Het1 |
| 7703 | $OCH_3$ | $OCH_3$ | CN | Br | Het1 |
| 7704 | $OCH_2CH_3$ | $OCH_2CH_3$ | CN | Br | Het1 |
| 7705 | $OCH_2CH_2CH_3$ | $OCH_2CH_2CH_3$ | CN | Br | Het1 |
| 7706 | $SCH_3$ | $SCH_3$ | CN | Br | Het1 |
| 7707 | $SCH_2CH_3$ | $SCH_2CH_3$ | CN | Br | Het1 |
| 7708 | $N(CH_3)_2$ | $N(CH_3)_2$ | CN | Br | Het1 |
| 7709 | $N(CH_2CH_3)_2$ | $N(CH_2CH_3)_2$ | CN | Br | Het1 |
| 7710 | $N(CH_3)(CH_2CH_3)$ | $N(CH_3)(CH_2CH_3)$ | CN | Br | Het1 |
| 7711 | O—$(CH_2CH_2)$—O | | CN | Br | Het1 |
| 7712 | O—$(CH_2CH_2CH_2)$—O | | CN | Br | Het1 |
| 7713 | S—$(CH_2CH_2)$—S | | CN | Br | Het1 |
| 7714 | S—$(CH_2CH_2CH_2)$—S | | CN | Br | Het1 |
| 7715 | —$(CH_2)_4$— | | CN | Br | Het1 |
| 7716 | —$(CH_2)_5$— | | CN | Br | Het1 |
| 7717 | H | H | F | Br | Het1 |
| 7718 | $CH_3$ | $CH_3$ | F | Br | Het1 |
| 7719 | $CH_2CH_3$ | $CH_2CH_3$ | F | Br | Het1 |
| 7720 | $CH_2CH_2CH_3$ | $CH_2CH_2CH_3$ | F | Br | Het1 |
| 7721 | $OCH_3$ | $OCH_3$ | F | Br | Het1 |
| 7722 | $OCH_2CH_3$ | $OCH_2CH_3$ | F | Br | Het1 |
| 7723 | $OCH_2CH_2CH_3$ | $OCH_2CH_2CH_3$ | F | Br | Het1 |
| 7724 | $SCH_3$ | $SCH_3$ | F | Br | Het1 |
| 7725 | $SCH_2CH_3$ | $SCH_2CH_3$ | F | Br | Het1 |
| 7726 | $N(CH_3)_2$ | $N(CH_3)_2$ | F | Br | Het1 |
| 7727 | $N(CH_2CH_3)_2$ | $N(CH_2CH_3)_2$ | F | Br | Het1 |
| 7728 | $N(CH_3)(CH_2CH_3)$ | $N(CH_3)(CH_2CH_3)$ | F | Br | Het1 |
| 7729 | O—$(CH_2CH_2)$—O | | F | Br | Het1 |
| 7730 | O—$(CH_2CH_2CH_2)$—O | | F | Br | Het1 |
| 7731 | S—$(CH_2CH_2)$—S | | F | Br | Het1 |
| 7732 | S—$(CH_2CH_2CH_2)$—S | | F | Br | Het1 |
| 7733 | —$(CH_2)_4$— | | F | Br | Het1 |
| 7734 | —$(CH_2)_5$— | | F | Br | Het1 |
| 7735 | H | H | Cl | Br | Het1 |
| 7736 | $CH_3$ | $CH_3$ | Cl | Br | Het1 |
| 7737 | $CH_2CH_3$ | $CH_2CH_3$ | Cl | Br | Het1 |
| 7738 | $CH_2CH_2CH_3$ | $CH_2CH_2CH_3$ | Cl | Br | Het1 |
| 7739 | $OCH_3$ | $OCH_3$ | Cl | Br | Het1 |
| 7740 | $OCH_2CH_3$ | $OCH_2CH_3$ | Cl | Br | Het1 |
| 7741 | $OCH_2CH_2CH_3$ | $OCH_2CH_2CH_3$ | Cl | Br | Het1 |
| 7742 | $SCH_3$ | $SCH_3$ | Cl | Br | Het1 |
| 7743 | $SCH_2CH_3$ | $SCH_2CH_3$ | Cl | Br | Het1 |
| 7744 | $N(CH_3)_2$ | $N(CH_3)_2$ | Cl | Br | Het1 |
| 7745 | $N(CH_2CH_3)_2$ | $N(CH_2CH_3)_2$ | Cl | Br | Het1 |
| 7746 | $N(CH_3)(CH_2CH_3)$ | $N(CH_3)(CH_2CH_3)$ | Cl | Br | Het1 |
| 7747 | O—$(CH_2CH_2)$—O | | Cl | Br | Het1 |
| 7748 | O—$(CH_2CH_2CH_2)$—O | | Cl | Br | Het1 |
| 7749 | S—$(CH_2CH_2)$—S | | Cl | Br | Het1 |
| 7750 | S—$(CH_2CH_2CH_2)$—S | | Cl | Br | Het1 |
| 7751 | —$(CH_2)_4$— | | Cl | Br | Het1 |
| 7752 | —$(CH_2)_5$— | | Cl | Br | Het1 |
| 7753 | H | H | Br | Br | Het1 |
| 7754 | $CH_3$ | $CH_3$ | Br | Br | Het1 |
| 7755 | $CH_2CH_3$ | $CH_2CH_3$ | Br | Br | Het1 |
| 7756 | $CH_2CH_2CH_3$ | $CH_2CH_2CH_3$ | Br | Br | Het1 |
| 7757 | $OCH_3$ | $OCH_3$ | Br | Br | Het1 |
| 7758 | $OCH_2CH_3$ | $OCH_2CH_3$ | Br | Br | Het1 |

TABLE 1-continued

I1a1

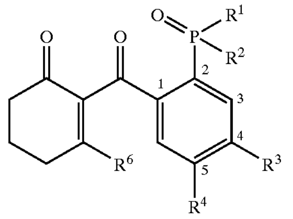

| n | $R^1$ | $R^2$ | $R^3$ | $R^4$ | $R^6$ |
|---|---|---|---|---|---|
| 7759 | $OCH_2CH_2CH_3$ | $OCH_2CH_2CH_3$ | Br | Br | Het1 |
| 7760 | $SCH_3$ | $SCH_3$ | Br | Br | Het1 |
| 7761 | $SCH_2CH_3$ | $SCH_2CH_3$ | Br | Br | Het1 |
| 7762 | $N(CH_3)_2$ | $N(CH_3)_2$ | Br | Br | Het1 |
| 7763 | $N(CH_2CH_3)_2$ | $N(CH_2CH_3)_2$ | Br | Br | Het1 |
| 7764 | $N(CH_3)(CH_2CH_3)$ | $N(CH_3)(CH_2CH_3)$ | Br | Br | Het1 |
| 7765 | $O—(CH_2CH_2)—O$ | | Br | Br | Het1 |
| 7766 | $O—(CH_2CH_2CH_2)—O$ | | Br | Br | Het1 |
| 7767 | $S—(CH_2CH_2)—S$ | | Br | Br | Het1 |
| 7768 | $S—(CH_2CH_2CH_2)—S$ | | Br | Br | Het1 |
| 7769 | $—(CH_2)_4—$ | | Br | Br | Het1 |
| 7770 | $—(CH_2)_5—$ | | Br | Br | Het1 |
| 7771 | H | H | $CH_3$ | Br | Het1 |
| 7772 | $CH_3$ | $CH_3$ | $CH_3$ | Br | Het1 |
| 7773 | $CH_2CH_3$ | $CH_2CH_3$ | $CH_3$ | Br | Het1 |
| 7774 | $CH_2CH_2CH_3$ | $CH_2CH_2CH_3$ | $CH_3$ | Br | Het1 |
| 7775 | $OCH_3$ | $OCH_3$ | $CH_3$ | Br | Het1 |
| 7776 | $OCH_2CH_3$ | $OCH_2CH_3$ | $CH_3$ | Br | Het1 |
| 7777 | $OCH_2CH_2CH_3$ | $OCH_2CH_2CH_3$ | $CH_3$ | Br | Het1 |
| 7778 | $SCH_3$ | $SCH_3$ | $CH_3$ | Br | Het1 |
| 7779 | $SCH_2CH_3$ | $SCH_2CH_3$ | $CH_3$ | Br | Het1 |
| 7780 | $N(CH_3)_2$ | $N(CH_3)_2$ | $CH_3$ | Br | Het1 |
| 7781 | $N(CH_2CH_3)_2$ | $N(CH_2CH_3)_2$ | $CH_3$ | Br | Het1 |
| 7782 | $N(CH_3)(CH_2CH_3)$ | $N(CH_3)(CH_2CH_3)$ | $CH_3$ | Br | Het1 |
| 7783 | $O—(CH_2CH_2)—O$ | | $CH_3$ | Br | Het1 |
| 7784 | $O—(CH_2CH_2CH_2)—O$ | | $CH_3$ | Br | Het1 |
| 7785 | $S—(CH_2CH_2)—S$ | | $CH_3$ | Br | Het1 |
| 7786 | $S—(CH_2CH_2CH_2)—S$ | | $CH_3$ | Br | Het1 |
| 7787 | $—(CH_2)_4—$ | | $CH_3$ | Br | Het1 |
| 7788 | $—(CH_2)_5—$ | | $CH_3$ | Br | Het1 |
| 7789 | H | H | $CH_2CH_3$ | Br | Het1 |
| 7790 | $CH_3$ | $CH_3$ | $CH_2CH_3$ | Br | Het1 |
| 7791 | $CH_2CH_3$ | $CH_2CH_3$ | $CH_2CH_3$ | Br | Het1 |
| 7792 | $CH_2CH_2CH_3$ | $CH_2CH_2CH_3$ | $CH_2CH_3$ | Br | Het1 |
| 7793 | $OCH_3$ | $OCH_3$ | $CH_2CH_3$ | Br | Het1 |
| 7794 | $OCH_2CH_3$ | $OCH_2CH_3$ | $CH_2CH_3$ | Br | Het1 |
| 7795 | $OCH_2CH_2CH_3$ | $OCH_2CH_2CH_3$ | $CH_2CH_3$ | Br | Het1 |
| 7796 | $SCH_3$ | $SCH_3$ | $CH_2CH_3$ | Br | Het1 |
| 7797 | $SCH_2CH_3$ | $SCH_2CH_3$ | $CH_2CH_3$ | Br | Het1 |
| 7798 | $N(CH_3)_2$ | $N(CH_3)_2$ | $CH_2CH_3$ | Br | Het1 |
| 7799 | $N(CH_2CH_3)_2$ | $N(CH_2CH_3)_2$ | $CH_2CH_3$ | Br | Het1 |
| 7800 | $N(CH_3)(CH_2CH_3)$ | $N(CH_3)(CH_2CH_3)$ | $CH_2CH_3$ | Br | Het1 |
| 7801 | $O—(CH_2CH_2)—O$ | | $CH_2CH_3$ | Br | Het1 |
| 7802 | $O—(CH_2CH_2CH_2)—O$ | | $CH_2CH_3$ | Br | Het1 |
| 7803 | $S—(CH_2CH_2)—S$ | | $CH_2CH_3$ | Br | Het1 |
| 7804 | $S—(CH_2CH_2CH_2)—S$ | | $CH_2CH_3$ | Br | Het1 |
| 7805 | $—(CH_2)_4—$ | | $CH_2CH_3$ | Br | Het1 |
| 7806 | $—(CH_2)_5—$ | | $CH_2CH_3$ | Br | Het1 |
| 7807 | H | H | $CF_3$ | Br | Het1 |
| 7808 | $CH_3$ | $CH_3$ | $CF_3$ | Br | Het1 |
| 7809 | $CH_2CH_3$ | $CH_2CH_3$ | $CF_3$ | Br | Het1 |
| 7810 | $CH_2CH_2CH_3$ | $CH_2CH_2CH_3$ | $CF_3$ | Br | Het1 |
| 7811 | $OCH_3$ | $OCH_3$ | $CF_3$ | Br | Het1 |
| 7812 | $OCH_2CH_3$ | $OCH_2CH_3$ | $CF_3$ | Br | Het1 |
| 7813 | $OCH_2CH_2CH_3$ | $OCH_2CH_2CH_3$ | $CF_3$ | Br | Het1 |
| 7814 | $SCH_3$ | $SCH_3$ | $CF_3$ | Br | Het1 |
| 7815 | $SCH_2CH_3$ | $SCH_2CH_3$ | $CF_3$ | Br | Het1 |
| 7816 | $N(CH_3)_2$ | $N(CH_3)_2$ | $CF_3$ | Br | Het1 |
| 7817 | $N(CH_2CH_3)_2$ | $N(CH_2CH_3)_2$ | $CF_3$ | Br | Het1 |
| 7818 | $N(CH_3)(CH_2CH_3)$ | $N(CH_3)(CH_2CH_3)$ | $CF_3$ | Br | Het1 |
| 7819 | $O—(CH_2CH_2)—O$ | | $CF_3$ | Br | Het1 |
| 7820 | $O—(CH_2CH_2CH_2)—O$ | | $CF_3$ | Br | Het1 |
| 7821 | $S—(CH_2CH_2)—S$ | | $CF_3$ | Br | Het1 |
| 7822 | $S—(CH_2CH_2CH_2)—S$ | | $CF_3$ | Br | Het1 |

TABLE 1-continued

I1a1

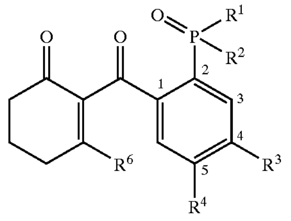

| n | $R^1$ | $R^2$ | $R^3$ | $R^4$ | $R^6$ |
|---|---|---|---|---|---|
| 7823 | $-(CH_2)_4-$ | | $CF_3$ | Br | Het1 |
| 7824 | $-(CH_2)_5-$ | | $CF_3$ | Br | Het1 |
| 7825 | H | H | $OCH_3$ | Br | Het1 |
| 7826 | $CH_3$ | $CH_3$ | $OCH_3$ | Br | Het1 |
| 7827 | $CH_2CH_3$ | $CH_2CH_3$ | $OCH_3$ | Br | Het1 |
| 7828 | $CH_2CH_2CH_3$ | $CH_2CH_2CH_3$ | $OCH_3$ | Br | Het1 |
| 7829 | $OCH_3$ | $OCH_3$ | $OCH_3$ | Br | Het1 |
| 7830 | $OCH_2CH_3$ | $OCH_2CH_3$ | $OCH_3$ | Br | Het1 |
| 7831 | $OCH_2CH_2CH_3$ | $OCH_2CH_2CH_3$ | $OCH_3$ | Br | Het1 |
| 7832 | $SCH_3$ | $SCH_3$ | $OCH_3$ | Br | Het1 |
| 7833 | $SCH_2CH_3$ | $SCH_2CH_3$ | $OCH_3$ | Br | Het1 |
| 7834 | $N(CH_3)_2$ | $N(CH_3)_2$ | $OCH_3$ | Br | Het1 |
| 7835 | $N(CH_2CH_3)_2$ | $N(CH_2CH_3)_2$ | $OCH_3$ | Br | Het1 |
| 7836 | $N(CH_3)(CH_2CH_3)$ | $N(CH_3)(CH_2CH_3)$ | $OCH_3$ | Br | Het1 |
| 7837 | $O-(CH_2CH_2)-O$ | | $OCH_3$ | Br | Het1 |
| 7838 | $O-(CH_2CH_2CH_2)-O$ | | $OCH_3$ | Br | Het1 |
| 7839 | $S-(CH_2CH_2)-S$ | | $OCH_3$ | Br | Het1 |
| 7840 | $S-(CH_2CH_2CH_2)-S$ | | $OCH_3$ | Br | Het1 |
| 7841 | $-(CH_2)_4-$ | | $OCH_3$ | Br | Het1 |
| 7842 | $-(CH_2)_5-$ | | $OCH_3$ | Br | Het1 |
| 7843 | H | H | $OCH_2CH_3$ | Br | Het1 |
| 7844 | $CH_3$ | $CH_3$ | $OCH_2CH_3$ | Br | Het1 |
| 7845 | $CH_2CH_3$ | $CH_2CH_3$ | $OCH_2CH_3$ | Br | Het1 |
| 7846 | $CH_2CH_2CH_3$ | $CH_2CH_2CH_3$ | $OCH_2CH_3$ | Br | Het1 |
| 7847 | $OCH_3$ | $OCH_3$ | $OCH_2CH_3$ | Br | Het1 |
| 7848 | $OCH_2CH_3$ | $OCH_2CH_3$ | $OCH_2CH_3$ | Br | Het1 |
| 7849 | $OCH_2CH_2CH_3$ | $OCH_2CH_2CH_3$ | $OCH_2CH_3$ | Br | Het1 |
| 7850 | $SCH_3$ | $SCH_3$ | $OCH_2CH_3$ | Br | Het1 |
| 7851 | $SCH_2CH_3$ | $SCH_2CH_3$ | $OCH_2CH_3$ | Br | Het1 |
| 7852 | $N(CH_3)_2$ | $N(CH_3)_2$ | $OCH_2CH_3$ | Br | Het1 |
| 7853 | $N(CH_2CH_3)_2$ | $N(CH_2CH_3)_2$ | $OCH_2CH_3$ | Br | Het1 |
| 7854 | $N(CH_3)(CH_2CH_3)$ | $N(CH_3)(CH_2CH_3)$ | $OCH_2CH_3$ | Br | Het1 |
| 7855 | $O-(CH_2CH_2)-O$ | | $OCH_2CH_3$ | Br | Het1 |
| 7856 | $O-(CH_2CH_2CH_2)-O$ | | $OCH_2CH_3$ | Br | Het1 |
| 7857 | $S-(CH_2CH_2)-S$ | | $OCH_2CH_3$ | Br | Het1 |
| 7858 | $S-(CH_2CH_2CH_2)-S$ | | $OCH_2CH_3$ | Br | Het1 |
| 7859 | $-(CH_2)_4-$ | | $OCH_2CH_3$ | Br | Het1 |
| 7860 | $-(CH_2)_5-$ | | $OCH_2CH_3$ | Br | Het1 |
| 7861 | H | H | $SCH_3$ | Br | Het1 |
| 7862 | $CH_3$ | $CH_3$ | $SCH_3$ | Br | Het1 |
| 7863 | $CH_2CH_3$ | $CH_2CH_3$ | $SCH_3$ | Br | Het1 |
| 7864 | $CH_2CH_2CH_3$ | $CH_2CH_2CH_3$ | $SCH_3$ | Br | Het1 |
| 7865 | $OCH_3$ | $OCH_3$ | $SCH_3$ | Br | Het1 |
| 7866 | $OCH_2CH_3$ | $OCH_2CH_3$ | $SCH_3$ | Br | Het1 |
| 7867 | $OCH_2CH_2CH_3$ | $OCH_2CH_2CH_3$ | $SCH_3$ | Br | Het1 |
| 7868 | $SCH_3$ | $SCH_3$ | $SCH_3$ | Br | Het1 |
| 7869 | $SCH_2CH_3$ | $SCH_2CH_3$ | $SCH_3$ | Br | Het1 |
| 7870 | $N(CH_3)_2$ | $N(CH_3)_2$ | $SCH_3$ | Br | Het1 |
| 7871 | $N(CH_2CH_3)_2$ | $N(CH_2CH_3)_2$ | $SCH_3$ | Br | Het1 |
| 7872 | $N(CH_3)(CH_2CH_3)$ | $N(CH_3)(CH_2CH_3)$ | $SCH_3$ | Br | Het1 |
| 7873 | $O-(CH_2CH_2)-O$ | | $SCH_3$ | Br | Het1 |
| 7874 | $O-(CH_2CH_2CH_2)-O$ | | $SCH_3$ | Br | Het1 |
| 7875 | $S-(CH_2CH_2)-S$ | | $SCH_3$ | Br | Het1 |
| 7876 | $S-(CH_2CH_2CH_2)-S$ | | $SCH_3$ | Br | Het1 |
| 7877 | $-(CH_2)_4-$ | | $SCH_3$ | Br | Het1 |
| 7878 | $-(CH_2)_5-$ | | $SCH_3$ | Br | Het1 |
| 7879 | H | H | $SO_2CH_3$ | Br | Het1 |
| 7880 | $CH_3$ | $CH_3$ | $SO_2CH_3$ | Br | Het1 |
| 7881 | $CH_2CH_3$ | $CH_2CH_3$ | $SO_2CH_3$ | Br | Het1 |
| 7882 | $CH_2CH_2CH_3$ | $CH_2CH_2CH_3$ | $SO_2CH_3$ | Br | Het1 |
| 7883 | $OCH_3$ | $OCH_3$ | $SO_2CH_3$ | Br | Het1 |
| 7884 | $OCH_2CH_3$ | $OCH_2CH_3$ | $SO_2CH_3$ | Br | Het1 |
| 7885 | $OCH_2CH_2CH_3$ | $OCH_2CH_2CH_3$ | $SO_2CH_3$ | Br | Het1 |
| 7886 | $SCH_3$ | $SCH_3$ | $SO_2CH_3$ | Br | Het1 |

TABLE 1-continued

I1a1

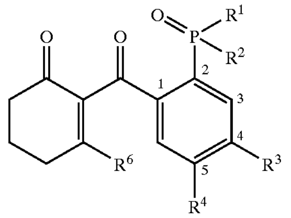

| n | $R^1$ | $R^2$ | $R^3$ | $R^4$ | $R^6$ |
|---|---|---|---|---|---|
| 7887 | $SCH_2CH_3$ | $SCH_2CH_3$ | $SO_2CH_3$ | Br | Het1 |
| 7888 | $N(CH_3)_2$ | $N(CH_3)_2$ | $SO_2CH_3$ | Br | Het1 |
| 7889 | $N(CH_2CH_3)_2$ | $N(CH_2CH_3)_2$ | $SO_2CH_3$ | Br | Het1 |
| 7890 | $N(CH_3)(CH_2CH_3)$ | $N(CH_3)(CH_2CH_3)$ | $SO_2CH_3$ | Br | Het1 |
| 7891 | $O—(CH_2CH_2)—O$ | | $SO_2CH_3$ | Br | Het1 |
| 7892 | $O—(CH_2CH_2CH_2)—O$ | | $SO_2CH_3$ | Br | Het1 |
| 7893 | $S—(CH_2CH_2)—S$ | | $SO_2CH_3$ | Br | Het1 |
| 7894 | $S—(CH_2CH_2CH_2)—S$ | | $SO_2CH_3$ | Br | Het1 |
| 7895 | $—(CH_2)_4—$ | | $SO_2CH_3$ | Br | Het1 |
| 7896 | $—(CH_2)_5—$ | | $SO_2CH_3$ | Br | Het1 |
| 7897 | H | H | $PO(OCH_3)_2$ | Br | Het1 |
| 7898 | $CH_3$ | $CH_3$ | $PO(OCH_3)_2$ | Br | Het1 |
| 7899 | $CH_2CH_3$ | $CH_2CH_3$ | $PO(OCH_3)_2$ | Br | Het1 |
| 7900 | $CH_2CH_2CH_3$ | $CH_2CH_2CH_3$ | $PO(OCH_3)_2$ | Br | Het1 |
| 7901 | $OCH_3$ | $OCH_3$ | $PO(OCH_3)_2$ | Br | Het1 |
| 7902 | $OCH_2CH_3$ | $OCH_2CH_3$ | $PO(OCH_3)_2$ | Br | Het1 |
| 7903 | $OCH_2CH_2CH_3$ | $OCH_2CH_2CH_3$ | $PO(OCH_3)_2$ | Br | Het1 |
| 7904 | $SCH_3$ | $SCH_3$ | $PO(OCH_3)_2$ | Br | Het1 |
| 7905 | $SCH_2CH_3$ | $SCH_2CH_3$ | $PO(OCH_3)_2$ | Br | Het1 |
| 7906 | $N(CH_3)_2$ | $N(CH_3)_2$ | $PO(OCH_3)_2$ | Br | Het1 |
| 7907 | $N(CH_2CH_3)_2$ | $N(CH_2CH_3)_2$ | $PO(OCH_3)_2$ | Br | Het1 |
| 7908 | $N(CH_3)(CH_2CH_3)$ | $N(CH_3)(CH_2CH_3)$ | $PO(OCH_3)_2$ | Br | Het1 |
| 7909 | $O—(CH_2CH_2)—O$ | | $PO(OCH_3)_2$ | Br | Het1 |
| 7910 | $O—(CH_2CH_2CH_2)—O$ | | $PO(OCH_3)_2$ | Br | Het1 |
| 7911 | $S—(CH_2CH_2)—S$ | | $PO(OCH_3)_2$ | Br | Het1 |
| 7912 | $S—(CH_2CH_2CH_2)—S$ | | $PO(OCH_3)_2$ | Br | Het1 |
| 7913 | $—(CH_2)_4—$ | | $PO(OCH_3)_2$ | Br | Het1 |
| 7914 | $—(CH_2)_5—$ | | $PO(OCH_3)_2$ | Br | Het1 |
| 7915 | H | H | $PO(OCH_2CH_3)_2$ | Br | Het1 |
| 7916 | $CH_3$ | $CH_3$ | $PO(OCH_2CH_3)_2$ | Br | Het1 |
| 7917 | $CH_2CH_3$ | $CH_2CH_3$ | $PO(OCH_2CH_3)_2$ | Br | Het1 |
| 7918 | $CH_2CH_2CH_3$ | $CH_2CH_2CH_3$ | $PO(OCH_2CH_3)_2$ | Br | Het1 |
| 7919 | $OCH_3$ | $OCH_3$ | $PO(OCH_2CH_3)_2$ | Br | Het1 |
| 7920 | $OCH_2CH_3$ | $OCH_2CH_3$ | $PO(OCH_2CH_3)_2$ | Br | Het1 |
| 7921 | $OCH_2CH_2CH_3$ | $OCH_2CH_2CH_3$ | $PO(OCH_2CH_3)_2$ | Br | Het1 |
| 7922 | $SCH_3$ | $SCH_3$ | $PO(OCH_2CH_3)_2$ | Br | Het1 |
| 7923 | $SCH_2CH_3$ | $SCH_2CH_3$ | $PO(OCH_2CH_3)_2$ | Br | Het1 |
| 7924 | $N(CH_3)_2$ | $N(CH_3)_2$ | $PO(OCH_2CH_3)_2$ | Br | Het1 |
| 7925 | $N(CH_2CH_3)_2$ | $N(CH_2CH_3)_2$ | $PO(OCH_2CH_3)_2$ | Br | Het1 |
| 7926 | $N(CH_3)(CH_2CH_3)$ | $N(CH_3)(CH_2CH_3)$ | $PO(OCH_2CH_3)_2$ | Br | Het1 |
| 7927 | $O—(CH_2CH_2)—O$ | | $PO(OCH_2CH_3)_2$ | Br | Het1 |
| 7928 | $O—(CH_2CH_2CH_2)—O$ | | $PO(OCH_2CH_3)_2$ | Br | Het1 |
| 7929 | $S—(CH_2CH_2)—S$ | | $PO(OCH_2CH_3)_2$ | Br | Het1 |
| 7930 | $S—(CH_2CH_2CH_2)—S$ | | $PO(OCH_2CH_3)_2$ | Br | Het1 |
| 7931 | $—(CH_2)_4—$ | | $PO(OCH_2CH_3)_2$ | Br | Het1 |
| 7932 | $—(CH_2)_5—$ | | $PO(OCH_2CH_3)_2$ | Br | Het1 |
| 7933 | H | H | $PO(CH_3)_2$ | Br | Het1 |
| 7934 | $CH_3$ | $CH_3$ | $PO(CH_3)_2$ | Br | Het1 |
| 7935 | $CH_2CH_3$ | $CH_2CH_3$ | $PO(CH_3)_2$ | Br | Het1 |
| 7936 | $CH_2CH_2CH_3$ | $CH_2CH_2CH_3$ | $PO(CH_3)_2$ | Br | Het1 |
| 7937 | $OCH_3$ | $OCH_3$ | $PO(CH_3)_2$ | Br | Het1 |
| 7938 | $OCH_2CH_3$ | $OCH_2CH_3$ | $PO(CH_3)_2$ | Br | Het1 |
| 7939 | $OCH_2CH_2CH_3$ | $OCH_2CH_2CH_3$ | $PO(CH_3)_2$ | Br | Het1 |
| 7940 | $SCH_3$ | $SCH_3$ | $PO(CH_3)_2$ | Br | Het1 |
| 7941 | $SCH_2CH_3$ | $SCH_2CH_3$ | $PO(CH_3)_2$ | Br | Het1 |
| 7942 | $N(CH_3)_2$ | $N(CH_3)_2$ | $PO(CH_3)_2$ | Br | Het1 |
| 7943 | $N(CH_2CH_3)_2$ | $N(CH_2CH_3)_2$ | $PO(CH_3)_2$ | Br | Het1 |
| 7944 | $N(CH_3)(CH_2CH_3)$ | $N(CH_3)(CH_2CH_3)$ | $PO(CH_3)_2$ | Br | Het1 |
| 7945 | $O—(CH_2CH_2)—O$ | | $PO(CH_3)_2$ | Br | Het1 |
| 7946 | $O—(CH_2CH_2CH_2)—O$ | | $PO(CH_3)_2$ | Br | Het1 |
| 7947 | $S—(CH_2CH_2)—S$ | | $PO(CH_3)_2$ | Br | Het1 |
| 7948 | $S—(CH_2CH_2CH_2)—S$ | | $PO(CH_3)_2$ | Br | Het1 |
| 7949 | $—(CH_2)_4—$ | | $PO(CH_3)_2$ | Br | Het1 |
| 7950 | $—(CH_2)_5—$ | | $PO(CH_3)_2$ | Br | Het1 |

TABLE 1-continued

I1a1

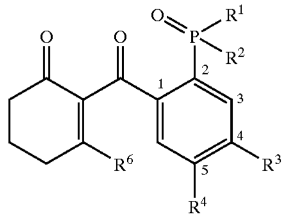

| n | $R^1$ | $R^2$ | $R^3$ | $R^4$ | $R^6$ |
|---|---|---|---|---|---|
| 7951 | H | H | $PC(CH_2CH_3)_2$ | Br | Het1 |
| 7952 | $CH_3$ | $CH_3$ | $PC(CH_2CH_3)_2$ | Br | Het1 |
| 7953 | $CH_2CH_3$ | $CH_2CH_3$ | $PC(CH_2CH_3)_2$ | Br | Het1 |
| 7954 | $CH_2CH_2CH_3$ | $CH_2CH_2CH_3$ | $PC(CH_2CH_3)_2$ | Br | Het1 |
| 7955 | $OCH_3$ | $OCH_3$ | $PC(CH_2CH_3)_2$ | Br | Het1 |
| 7956 | $OCH_2CH_3$ | $OCH_2CH_3$ | $PC(CH_2CH_3)_2$ | Br | Het1 |
| 7957 | $OCH_2CH_2CH_3$ | $OCH_2CH_2CH_3$ | $PC(CH_2CH_3)_2$ | Br | Het1 |
| 7958 | $SCH_3$ | $SCH_3$ | $PC(CH_2CH_3)_2$ | Br | Het1 |
| 7959 | $SCH_2CH_3$ | $SCH_2CH_3$ | $PC(CH_2CH_3)_2$ | Br | Het1 |
| 7960 | $N(CH_3)_2$ | $N(CH_3)_2$ | $PC(CH_2CH_3)_2$ | Br | Het1 |
| 7961 | $N(CH_2CH_3)_2$ | $N(CH_2CH_3)_2$ | $PC(CH_2CH_3)_2$ | Br | Het1 |
| 7962 | $N(CH_3)(CH_2CH_3)$ | $N(CH_3)(CH_2CH_3)$ | $PC(CH_2CH_3)_2$ | Br | Het1 |
| 7963 | $O-(CH_2CH_2)-O$ | | $PC(CH_2CH_3)_2$ | Br | Het1 |
| 7964 | $O-(CH_2CH_2CH_2)-O$ | | $PC(CH_2CH_3)_2$ | Br | Het1 |
| 7965 | $S-(CH_2CH_2)-S$ | | $PC(CH_2CH_3)_2$ | Br | Het1 |
| 7966 | $S-(CH_2CH_2CH_2)-S$ | | $PC(CH_2CH_3)_2$ | Br | Het1 |
| 7967 | $-(CH_2)_4-$ | | $PC(CH_2CH_3)_2$ | Br | Het1 |
| 7968 | $-(CH_2)_5-$ | | $PC(CH_2CH_3)_2$ | Br | Het1 |
| 7969 | H | H | H | Br | Het2 |
| 7970 | $CH_3$ | $CH_3$ | H | Br | Het2 |
| 7971 | $CH_2CH_3$ | $CH_2CH_3$ | H | Br | Het2 |
| 7972 | $CH_2CH_2CH_3$ | $CH_2CH_2CH_3$ | H | Br | Het2 |
| 7973 | $OCH_3$ | $OCH_3$ | H | Br | Het2 |
| 7974 | $OCH_2CH_3$ | $OCH_2CH_3$ | H | Br | Het2 |
| 7975 | $OCH_2CH_2CH_3$ | $OCH_2CH_2CH_3$ | H | Br | Het2 |
| 7976 | $SCH_3$ | $SCH_3$ | H | Br | Het2 |
| 7977 | $SCH_2CH_3$ | $SCH_2CH_3$ | H | Br | Het2 |
| 7978 | $N(CH_3)_2$ | $N(CH_3)_2$ | H | Br | Het2 |
| 7979 | $N(CH_2CH_3)_2$ | $N(CH_2CH_3)_2$ | H | Br | Het2 |
| 7980 | $N(CH_3)(CH_2CH_3)$ | $N(CH_3)(CH_2CH_3)$ | H | Br | Het2 |
| 7981 | $O-(CH_2CH_2)-O$ | | H | Br | Het2 |
| 7982 | $O-(CH_2CH_2CH_2)-O$ | | H | Br | Het2 |
| 7983 | $S-(CH_2CH_2)-S$ | | H | Br | Het2 |
| 7984 | $S-(CH_2CH_2CH_2)-S$ | | H | Br | Het2 |
| 7985 | $-(CH_2)_4-$ | | H | Br | Het2 |
| 7986 | $-(CH_2)_5-$ | | H | Br | Het2 |
| 7987 | H | H | $NO_2$ | Br | Het2 |
| 7988 | $CH_3$ | $CH_3$ | $NO_2$ | Br | Het2 |
| 7989 | $CH_2CH_3$ | $CH_2CH_3$ | $NO_2$ | Br | Het2 |
| 7990 | $CH_2CH_2CH_3$ | $CH_2CH_2CH_3$ | $NO_2$ | Br | Het2 |
| 7991 | $OCH_3$ | $OCH_3$ | $NO_2$ | Br | Het2 |
| 7992 | $OCH_2CH_3$ | $OCH_2CH_3$ | $NO_2$ | Br | Het2 |
| 7993 | $OCH_2CH_2CH_3$ | $OCH_2CH_2CH_3$ | $NO_2$ | Br | Het2 |
| 7994 | $SCH_3$ | $SCH_3$ | $NO_2$ | Br | Het2 |
| 7995 | $SCH_2CH_3$ | $SCH_2CH_3$ | $NO_2$ | Br | Het2 |
| 7996 | $N(CH_3)_2$ | $N(CH_3)_2$ | $NO_2$ | Br | Het2 |
| 7997 | $N(CH_2CH_3)_2$ | $N(CH_2CH_3)_2$ | $NO_2$ | Br | Het2 |
| 7998 | $N(CH_3)(CH_2CH_3)$ | $N(CH_3)(CH_2CH_3)$ | $NO_2$ | Br | Het2 |
| 7999 | $O-(CH_2CH_2)-O$ | | $NO_2$ | Br | Het2 |
| 8000 | $O-(CH_2CH_2CH_2)-O$ | | $NO_2$ | Br | Het2 |
| 8001 | $S-(CH_2CH_2)-S$ | | $NO_2$ | Br | Het2 |
| 8002 | $S-(CH_2CH_2CH_2)-S$ | | $NO_2$ | Br | Het2 |
| 8003 | $-(CH_2)_4-$ | | $NO_2$ | Br | Het2 |
| 8004 | $-(CH_2)_5-$ | | $NO_2$ | Br | Het2 |
| 8005 | H | H | CN | Br | Het2 |
| 8006 | $CH_3$ | $CH_3$ | CN | Br | Het2 |
| 8007 | $CH_2CH_3$ | $CH_2CH_3$ | CN | Br | Het2 |
| 8008 | $CH_2CH_2CH_3$ | $CH_2CH_2CH_3$ | CN | Br | Het2 |
| 8009 | $OCH_3$ | $OCH_3$ | CN | Br | Het2 |
| 8010 | $OCH_2CH_3$ | $OCH_2CH_3$ | CN | Br | Het2 |
| 8011 | $OCH_2CH_2CH_3$ | $OCH_2CH_2CH_3$ | CN | Br | Het2 |
| 8012 | $SCH_3$ | $SCH_3$ | CN | Br | Het2 |
| 8013 | $SCH_2CH_3$ | $SCH_2CH_3$ | CN | Br | Het2 |
| 8014 | $N(CH_3)_2$ | $N(CH_3)_2$ | CN | Br | Het2 |

TABLE 1-continued

I1a1

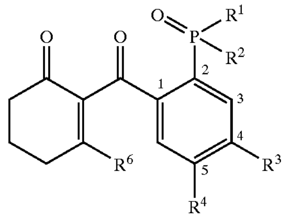

| n | $R^1$ | $R^2$ | $R^3$ | $R^4$ | $R^6$ |
|---|---|---|---|---|---|
| 8015 | $N(CH_2CH_3)_2$ | $N(CH_2CH_3)_2$ | CN | Br | Het2 |
| 8016 | $N(CH_3)(CH_2CH_3)$ | $N(CH_3)(CH_2CH_3)$ | CN | Br | Het2 |
| 8017 | $O-(CH_2CH_2)-O$ | | CN | Br | Het2 |
| 8018 | $O-(CH_2CH_2CH_2)-O$ | | CN | Br | Het2 |
| 8019 | $S-(CH_2CH_2)-S$ | | CN | Br | Het2 |
| 8020 | $S-(CH_2CH_2CH_2)-S$ | | CN | Br | Het2 |
| 8021 | $-(CH_2)_4-$ | | CN | Br | Het2 |
| 8022 | $-(CH_2)_5-$ | | CN | Br | Het2 |
| 8023 | H | H | F | Br | Het2 |
| 8024 | $CH_3$ | $CH_3$ | F | Br | Het2 |
| 8025 | $CH_2CH_3$ | $CH_2CH_3$ | F | Br | Het2 |
| 8026 | $CH_2CH_2CH_3$ | $CH_2CH_2CH_3$ | F | Br | Het2 |
| 8027 | $OCH_3$ | $OCH_3$ | F | Br | Het2 |
| 8028 | $OCH_2CH_3$ | $OCH_2CH_3$ | F | Br | Het2 |
| 8029 | $OCH_2CH_2CH_3$ | $OCH_2CH_2CH_3$ | F | Br | Het2 |
| 8030 | $SCH_3$ | $SCH_3$ | F | Br | Het2 |
| 8031 | $SCH_2CH_3$ | $SCH_2CH_3$ | F | Br | Het2 |
| 8032 | $N(CH_3)_2$ | $N(CH_3)_2$ | F | Br | Het2 |
| 8033 | $N(CH_2CH_3)_2$ | $N(CH_2CH_3)_2$ | F | Br | Het2 |
| 8034 | $N(CH_3)(CH_2CH_3)$ | $N(CH_3)(CH_2CH_3)$ | F | Br | Het2 |
| 8035 | $O-(CH_2CH_2)-O$ | | F | Br | Het2 |
| 8036 | $O-(CH_2CH_2CH_2)-O$ | | F | Br | Het2 |
| 8037 | $S-(CH_2CH_2)-S$ | | F | Br | Het2 |
| 8038 | $S-(CH_2CH_2CH_2)-S$ | | F | Br | Het2 |
| 8039 | $-(CH_2)_4-$ | | F | Br | Het2 |
| 8040 | $-(CH_2)_5-$ | | F | Br | Het2 |
| 8041 | H | H | Cl | Br | Het2 |
| 8042 | $CH_3$ | $CH_3$ | Cl | Br | Het2 |
| 8043 | $CH_2CH_3$ | $CH_2CH_3$ | Cl | Br | Het2 |
| 8044 | $CH_2CH_2CH_3$ | $CH_2CH_2CH_3$ | Cl | Br | Het2 |
| 8045 | $OCH_3$ | $OCH_3$ | Cl | Br | Het2 |
| 8046 | $OCH_2CH_3$ | $OCH_2CH_3$ | Cl | Br | Het2 |
| 8047 | $OCH_2CH_2CH_3$ | $OCH_2CH_2CH_3$ | Cl | Br | Het2 |
| 8048 | $SCH_3$ | $SCH_3$ | Cl | Br | Het2 |
| 8049 | $SCH_2CH_3$ | $SCH_2CH_3$ | Cl | Br | Het2 |
| 8050 | $N(CH_3)_2$ | $N(CH_3)_2$ | Cl | Br | Het2 |
| 8051 | $N(CH_2CH_3)_2$ | $N(CH_2CH_3)_2$ | Cl | Br | Het2 |
| 8052 | $N(CH_3)(CH_2CH_3)$ | $N(CH_3)(CH_2CH_3)$ | Cl | Br | Het2 |
| 8053 | $O-(CH_2CH_2)-O$ | | Cl | Br | Het2 |
| 8054 | $O-(CH_2CH_2CH_2)-O$ | | Cl | Br | Het2 |
| 8055 | $S-(CH_2CH_2)-S$ | | Cl | Br | Het2 |
| 8056 | $S-(CH_2CH_2CH_2)-S$ | | Cl | Br | Het2 |
| 8057 | $-(CH_2)_4-$ | | Cl | Br | Het2 |
| 8058 | $-(CH_2)_5-$ | | Cl | Br | Het2 |
| 8059 | H | H | Br | Br | Het2 |
| 8060 | $CH_3$ | $CH_3$ | Br | Br | Het2 |
| 8061 | $CH_2CH_3$ | $CH_2CH_3$ | Br | Br | Het2 |
| 8062 | $CH_2CH_2CH_3$ | $CH_2CH_2CH_3$ | Br | Br | Het2 |
| 8063 | $OCH_3$ | $OCH_3$ | Br | Br | Het2 |
| 8064 | $OCH_2CH_3$ | $OCH_2CH_3$ | Br | Br | Het2 |
| 8065 | $OCH_2CH_2CH_3$ | $OCH_2CH_2CH_3$ | Br | Br | Het2 |
| 8066 | $SCH_3$ | $SCH_3$ | Br | Br | Het2 |
| 8067 | $SCH_2CH_3$ | $SCH_2CH_3$ | Br | Br | Het2 |
| 8068 | $N(CH_3)_2$ | $N(CH_3)_2$ | Br | Br | Het2 |
| 8069 | $N(CH_2CH_3)_2$ | $N(CH_2CH_3)_2$ | Br | Br | Het2 |
| 8070 | $N(CH_3)(CH_2CH_3)$ | $N(CH_3)(CH_2CH_3)$ | Br | Br | Het2 |
| 8071 | $O-(CH_2CH_2)-O$ | | Br | Br | Het2 |
| 8072 | $O-(CH_2CH_2CH_2)-O$ | | Br | Br | Het2 |
| 8073 | $S-(CH_2CH_2)-S$ | | Br | Br | Het2 |
| 8074 | $S-(CH_2CH_2CH_2)-S$ | | Br | Br | Het2 |
| 8075 | $-(CH_2)_4-$ | | Br | Br | Het2 |
| 8076 | $-(CH_2)_5-$ | | Br | Br | Het2 |
| 8077 | H | H | $CH_3$ | Br | Het2 |
| 8078 | $CH_3$ | $CH_3$ | $CH_3$ | Br | Het2 |

TABLE 1-continued

I1a1

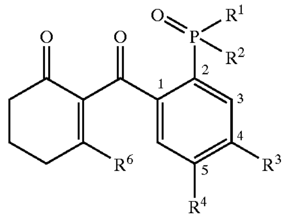

| n | $R^1$ | $R^2$ | $R^3$ | $R^4$ | $R^6$ |
|---|---|---|---|---|---|
| 8079 | $CH_2CH_3$ | $CH_2CH_3$ | $CH_3$ | Br | Het2 |
| 8080 | $CH_2CH_2CH_3$ | $CH_2CH_2CH_3$ | $CH_3$ | Br | Het2 |
| 8081 | $OCH_3$ | $OCH_3$ | $CH_3$ | Br | Het2 |
| 8082 | $OCH_2CH_3$ | $OCH_2CH_3$ | $CH_3$ | Br | Het2 |
| 8083 | $OCH_2CH_2CH_3$ | $OCH_2CH_2CH_3$ | $CH_3$ | Br | Het2 |
| 8084 | $SCH_3$ | $SCH_3$ | $CH_3$ | Br | Het2 |
| 8085 | $SCH_2CH_3$ | $SCH_2CH_3$ | $CH_3$ | Br | Het2 |
| 8086 | $N(CH_3)_2$ | $N(CH_3)_2$ | $CH_3$ | Br | Het2 |
| 8087 | $N(CH_2CH_3)_2$ | $N(CH_2CH_3)_2$ | $CH_3$ | Br | Het2 |
| 8088 | $N(CH_3)(CH_2CH_3)$ | $N(CH_3)(CH_2CH_3)$ | $CH_3$ | Br | Het2 |
| 8089 | $O—(CH_2CH_2)—O$ | | $CH_3$ | Br | Het2 |
| 8090 | $O—(CH_2CH_2CH_2)—O$ | | $CH_3$ | Br | Het2 |
| 8091 | $S—(CH_2CH_2)—S$ | | $CH_3$ | Br | Het2 |
| 8092 | $S—(CH_2CH_2CH_2)—S$ | | $CH_3$ | Br | Het2 |
| 8093 | $—(CH_2)_4—$ | | $CH_3$ | Br | Het2 |
| 8094 | $—(CH_2)_5—$ | | $CH_3$ | Br | Het2 |
| 8095 | H | H | $CH_2CH_3$ | Br | Het2 |
| 8096 | $CH_3$ | $CH_3$ | $CH_2CH_3$ | Br | Het2 |
| 8097 | $CH_2CH_3$ | $CH_2CH_3$ | $CH_2CH_3$ | Br | Het2 |
| 8098 | $CH_2CH_2CH_3$ | $CH_2CH_2CH_3$ | $CH_2CH_3$ | Br | Het2 |
| 8099 | $OCH_3$ | $OCH_3$ | $CH_2CH_3$ | Br | Het2 |
| 8100 | $OCH_2CH_3$ | $OCH_2CH_3$ | $CH_2CH_3$ | Br | Het2 |
| 8101 | $OCH_2CH_2CH_3$ | $OCH_2CH_2CH_3$ | $CH_2CH_3$ | Br | Het2 |
| 8102 | $SCH_3$ | $SCH_3$ | $CH_2CH_3$ | Br | Het2 |
| 8103 | $SCH_2CH_3$ | $SCH_2CH_3$ | $CH_2CH_3$ | Br | Het2 |
| 8104 | $N(CH_3)_2$ | $N(CH_3)_2$ | $CH_2CH_3$ | Br | Het2 |
| 8105 | $N(CH_2CH_3)_2$ | $N(CH_2CH_3)_2$ | $CH_2CH_3$ | Br | Het2 |
| 8106 | $N(CH_3)(CH_2CH_3)$ | $N(CH_3)(CH_2CH_3)$ | $CH_2CH_3$ | Br | Het2 |
| 8107 | $O—(CH_2CH_2)—O$ | | $CH_2CH_3$ | Br | Het2 |
| 8108 | $O—(CH_2CH_2CH_2)—O$ | | $CH_2CH_3$ | Br | Het2 |
| 8109 | $S—(CH_2CH_2)—S$ | | $CH_2CH_3$ | Br | Het2 |
| 8110 | $S—(CH_2CH_2CH_2)—S$ | | $CH_2CH_3$ | Br | Het2 |
| 8111 | $—(CH_2)_4—$ | | $CH_2CH_3$ | Br | Het2 |
| 8112 | $—(CH_2)_5—$ | | $CH_2CH_3$ | Br | Het2 |
| 8113 | H | H | $CF_3$ | Br | Het2 |
| 8114 | $CH_3$ | $CH_3$ | $CF_3$ | Br | Het2 |
| 8115 | $CH_2CH_3$ | $CH_2CH_3$ | $CF_3$ | Br | Het2 |
| 8116 | $CH_2CH_2CH_3$ | $CH_2CH_2CH_3$ | $CF_3$ | Br | Het2 |
| 8117 | $OCH_3$ | $OCH_3$ | $CF_3$ | Br | Het2 |
| 8118 | $OCH_2CH_3$ | $OCH_2CH_3$ | $CF_3$ | Br | Het2 |
| 8119 | $OCH_2CH_2CH_3$ | $OCH_2CH_2CH_3$ | $CF_3$ | Br | Het2 |
| 8120 | $SCH_3$ | $SCH_3$ | $CF_3$ | Br | Het2 |
| 8121 | $SCH_2CH_3$ | $SCH_2CH_3$ | $CF_3$ | Br | Het2 |
| 8122 | $N(CH_3)_2$ | $N(CH_3)_2$ | $CF_3$ | Br | Het2 |
| 8123 | $N(CH_2CH_3)_2$ | $N(CH_2CH_3)_2$ | $CF_3$ | Br | Het2 |
| 8124 | $N(CH_3)(CH_2CH_3)$ | $N(CH_3)(CH_2CH_3)$ | $CF_3$ | Br | Het2 |
| 8125 | $O—(CH_2CH_2)—O$ | | $CF_3$ | Br | Het2 |
| 8126 | $O—(CH_2CH_2CH_2)—O$ | | $CF_3$ | Br | Het2 |
| 8127 | $S—(CH_2CH_2)—S$ | | $CF_3$ | Br | Het2 |
| 8128 | $S—(CH_2CH_2CH_2)—S$ | | $CF_3$ | Br | Het2 |
| 8129 | $—(CH_2)_4—$ | | $CF_3$ | Br | Het2 |
| 8130 | $—(CH_2)_5—$ | | $CF_3$ | Br | Het2 |
| 8131 | H | H | $OCH_3$ | Br | Het2 |
| 8132 | $CH_3$ | $CH_3$ | $OCH_3$ | Br | Het2 |
| 8133 | $CH_2CH_3$ | $CH_2CH_3$ | $OCH_3$ | Br | Het2 |
| 8134 | $CH_2CH_2CH_3$ | $CH_2CH_2CH_3$ | $OCH_3$ | Br | Het2 |
| 8135 | $OCH_3$ | $OCH_3$ | $OCH_3$ | Br | Het2 |
| 8136 | $OCH_2CH_3$ | $OCH_2CH_3$ | $OCH_3$ | Br | Het2 |
| 8137 | $OCH_2CH_2CH_3$ | $OCH_2CH_2CH_3$ | $OCH_3$ | Br | Het2 |
| 8138 | $SCH_3$ | $SCH_3$ | $OCH_3$ | Br | Het2 |
| 8139 | $SCH_2CH_3$ | $SCH_2CH_3$ | $OCH_3$ | Br | Het2 |
| 8140 | $N(CH_3)_2$ | $N(CH_3)_2$ | $OCH_3$ | Br | Het2 |
| 8141 | $N(CH_2CH_3)_2$ | $N(CH_2CH_3)_2$ | $OCH_3$ | Br | Het2 |
| 8142 | $N(CH_3)(CH_2CH_3)$ | $N(CH_3)(CH_2CH_3)$ | $OCH_3$ | Br | Het2 |

TABLE 1-continued

I1a1

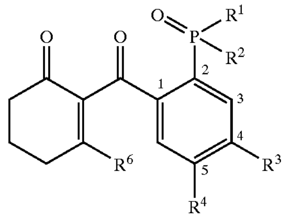

| n | $R^1$ | $R^2$ | $R^3$ | $R^4$ | $R^6$ |
|---|---|---|---|---|---|
| 8143 | O—(CH$_2$CH$_2$)—O | | OCH$_3$ | Br | Het2 |
| 8144 | O—(CH$_2$CH$_2$CH$_2$)—O | | OCH$_3$ | Br | Het2 |
| 8145 | S—(CH$_2$CH$_2$)—S | | OCH$_3$ | Br | Het2 |
| 8146 | S—(CH$_2$CH$_2$CH$_2$)—S | | OCH$_3$ | Br | Het2 |
| 8147 | —(CH$_2$)$_4$— | | OCH$_3$ | Br | Het2 |
| 8148 | —(CH$_2$)$_5$— | | OCH$_3$ | Br | Het2 |
| 8149 | H | H | OCH$_2$CH$_3$ | Br | Het2 |
| 8150 | CH$_3$ | CH$_3$ | OCH$_2$CH$_3$ | Br | Het2 |
| 8151 | CH$_2$CH$_3$ | CH$_2$CH$_3$ | OCH$_2$CH$_3$ | Br | Het2 |
| 8152 | CH$_2$CH$_2$CH$_3$ | CH$_2$CH$_2$CH$_3$ | OCH$_2$CH$_3$ | Br | Het2 |
| 8153 | OCH$_3$ | OCH$_3$ | OCH$_2$CH$_3$ | Br | Het2 |
| 8154 | OCH$_2$CH$_3$ | OCH$_2$CH$_3$ | OCH$_2$CH$_3$ | Br | Het2 |
| 8155 | OCH$_2$CH$_2$CH$_3$ | OCH$_2$CH$_2$CH$_3$ | OCH$_2$CH$_3$ | Br | Het2 |
| 8156 | SCH$_3$ | SCH$_3$ | OCH$_2$CH$_3$ | Br | Het2 |
| 8157 | SCH$_2$CH$_3$ | SCH$_2$CH$_3$ | OCH$_2$CH$_3$ | Br | Het2 |
| 8158 | N(CH$_3$)$_2$ | N(CH$_3$)$_2$ | OCH$_2$CH$_3$ | Br | Het2 |
| 8159 | N(CH$_2$CH$_3$)$_2$ | N(CH$_2$CH$_3$)$_2$ | OCH$_2$CH$_3$ | Br | Het2 |
| 8160 | N(CH$_3$)(CH$_2$CH$_3$) | N(CH$_3$)(CH$_2$CH$_3$) | OCH$_2$CH$_3$ | Br | Het2 |
| 8161 | O—(CH$_2$CH$_2$)—O | | OCH$_2$CH$_3$ | Br | Het2 |
| 8162 | O—(CH$_2$CH$_2$CH$_2$)—O | | OCH$_2$CH$_3$ | Br | Het2 |
| 8163 | S—(CH$_2$CH$_2$)—S | | OCH$_2$CH$_3$ | Br | Het2 |
| 8164 | S—(CH$_2$CH$_2$CH$_2$)—S | | OCH$_2$CH$_3$ | Br | Het2 |
| 8165 | —(CH$_2$)$_4$— | | OCH$_2$CH$_3$ | Br | Het2 |
| 8166 | —(CH$_2$)$_5$— | | OCH$_2$CH$_3$ | Br | Het2 |
| 8167 | H | H | SCH$_3$ | Br | Het2 |
| 8168 | CH$_3$ | CH$_3$ | SCH$_3$ | Br | Het2 |
| 8169 | CH$_2$CH$_3$ | CH$_2$CH$_3$ | SCH$_3$ | Br | Het2 |
| 8170 | CH$_2$CH$_2$CH$_3$ | CH$_2$CH$_2$CH$_3$ | SCH$_3$ | Br | Het2 |
| 8171 | OCH$_3$ | OCH$_3$ | SCH$_3$ | Br | Het2 |
| 8172 | OCH$_2$CH$_3$ | OCH$_2$CH$_3$ | SCH$_3$ | Br | Het2 |
| 8173 | OCH$_2$CH$_2$CH$_3$ | OCH$_2$CH$_2$CH$_3$ | SCH$_3$ | Br | Het2 |
| 8174 | SCH$_3$ | SCH$_3$ | SCH$_3$ | Br | Het2 |
| 8175 | SCH$_2$CH$_3$ | SCH$_2$CH$_3$ | SCH$_3$ | Br | Het2 |
| 8176 | N(CH$_3$)$_2$ | N(CH$_3$)$_2$ | SCH$_3$ | Br | Het2 |
| 8177 | N(CH$_2$CH$_3$)$_2$ | N(CH$_2$CH$_3$)$_2$ | SCH$_3$ | Br | Het2 |
| 8178 | N(CH$_3$)(CH$_2$CH$_3$) | N(CH$_3$)(CH$_2$CH$_3$) | SCH$_3$ | Br | Het2 |
| 8179 | O—(CH$_2$CH$_2$)—O | | SCH$_3$ | Br | Het2 |
| 8180 | O—(CH$_2$CH$_2$CH$_2$)—O | | SCH$_3$ | Br | Het2 |
| 8181 | S—(CH$_2$CH$_2$)—S | | SCH$_3$ | Br | Het2 |
| 8182 | S—(CH$_2$CH$_2$CH$_2$)—S | | SCH$_3$ | Br | Het2 |
| 8183 | —(CH$_2$)$_4$— | | SCH$_3$ | Br | Het2 |
| 8184 | —(CH$_2$)$_5$— | | SCH$_3$ | Br | Het2 |
| 8185 | H | H | SO$_2$CH$_3$ | Br | Het2 |
| 8186 | CH$_3$ | CH$_3$ | SO$_2$CH$_3$ | Br | Het2 |
| 8187 | CH$_2$CH$_3$ | CH$_2$CH$_3$ | SO$_2$CH$_3$ | Br | Het2 |
| 8188 | CH$_2$CH$_2$CH$_3$ | CH$_2$CH$_2$CH$_3$ | SO$_2$CH$_3$ | Br | Het2 |
| 8189 | OCH$_3$ | OCH$_3$ | SO$_2$CH$_3$ | Br | Het2 |
| 8190 | OCH$_2$CH$_3$ | OCH$_2$CH$_3$ | SO$_2$CH$_3$ | Br | Het2 |
| 8191 | OCH$_2$CH$_2$CH$_3$ | OCH$_2$CH$_2$CH$_3$ | SO$_2$CH$_3$ | Br | Het2 |
| 8192 | SCH$_3$ | SCH$_3$ | SO$_2$CH$_3$ | Br | Het2 |
| 8193 | SCH$_2$CH$_3$ | SCH$_2$CH$_3$ | SO$_2$CH$_3$ | Br | Het2 |
| 8194 | N(CH$_3$)$_2$ | N(CH$_3$)$_2$ | SO$_2$CH$_3$ | Br | Het2 |
| 8195 | N(CH$_2$CH$_3$)$_2$ | N(CH$_2$CH$_3$)$_2$ | SO$_2$CH$_3$ | Br | Het2 |
| 8196 | N(CH$_3$)(CH$_2$CH$_3$) | N(CH$_3$)(CH$_2$CH$_3$) | SO$_2$CH$_3$ | Br | Het2 |
| 8197 | O—(CH$_2$CH$_2$)—O | | SO$_2$CH$_3$ | Br | Het2 |
| 8198 | O—(CH$_2$CH$_2$CH$_2$)—O | | SO$_2$CH$_3$ | Br | Het2 |
| 8199 | S—(CH$_2$CH$_2$)—S | | SO$_2$CH$_3$ | Br | Het2 |
| 8200 | S—(CH$_2$CH$_2$CH$_2$)—S | | SO$_2$CH$_3$ | Br | Het2 |
| 8201 | —(CH$_2$)$_4$— | | SO$_2$CH$_3$ | Br | Het2 |
| 8202 | —(CH$_2$)$_5$— | | SO$_2$CH$_3$ | Br | Het2 |
| 8203 | H | H | PO(OCH$_3$)$_2$ | Br | Het2 |
| 8204 | CH$_3$ | CH$_3$ | PO(OCH$_3$)$_2$ | Br | Het2 |
| 8205 | CH$_2$CH$_3$ | CH$_2$CH$_3$ | PO(OCH$_3$)$_2$ | Br | Het2 |
| 8206 | CH$_2$CH$_2$CH$_3$ | CH$_2$CH$_2$CH$_3$ | PO(OCH$_3$)$_2$ | Br | Het2 |

TABLE 1-continued

I1a1

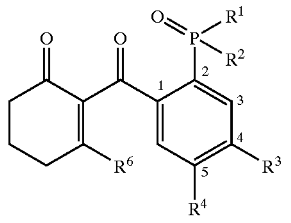

| n | $R^1$ | $R^2$ | $R^3$ | $R^4$ | $R^6$ |
|---|---|---|---|---|---|
| 8207 | $OCH_3$ | $OCH_3$ | $PO(OCH_3)_2$ | Br | Het2 |
| 8208 | $OCH_2CH_3$ | $OCH_2CH_3$ | $PO(OCH_3)_2$ | Br | Het2 |
| 8209 | $OCH_2CH_2CH_3$ | $OCH_2CH_2CH_3$ | $PO(OCH_3)_2$ | Br | Het2 |
| 8210 | $SCH_3$ | $SCH_3$ | $PO(OCH_3)_2$ | Br | Het2 |
| 8211 | $SCH_2CH_3$ | $SCH_2CH_3$ | $PO(OCH_3)_2$ | Br | Het2 |
| 8212 | $N(CH_3)_2$ | $N(CH_3)_2$ | $PO(OCH_3)_2$ | Br | Het2 |
| 8213 | $N(CH_2CH_3)_2$ | $N(CH_2CH_3)_2$ | $PO(OCH_3)_2$ | Br | Het2 |
| 8214 | $N(CH_3)(CH_2CH_3)$ | $N(CH_3)(CH_2CH_3)$ | $PO(OCH_3)_2$ | Br | Het2 |
| 8215 | $O-(CH_2CH_2)-O$ | | $PO(OCH_3)_2$ | Br | Het2 |
| 8216 | $O-(CH_2CH_2CH_2)-O$ | | $PO(OCH_3)_2$ | Br | Het2 |
| 8217 | $S-(CH_2CH_2)-S$ | | $PO(OCH_3)_2$ | Br | Het2 |
| 8218 | $S-(CH_2CH_2CH_2)-S$ | | $PO(OCH_3)_2$ | Br | Het2 |
| 8219 | $-(CH_2)_4-$ | | $PO(OCH_3)_2$ | Br | Het2 |
| 8220 | $-(CH_2)_5-$ | | $PO(OCH_3)_2$ | Br | Het2 |
| 8221 | H | H | $PO(OCH_2CH_3)_2$ | Br | Het2 |
| 8222 | $CH_3$ | $CH_3$ | $PO(OCH_2CH_3)_2$ | Br | Het2 |
| 8223 | $CH_2CH_3$ | $CH_2CH_3$ | $PO(OCH_2CH_3)_2$ | Br | Het2 |
| 8224 | $CH_2CH_2CH_3$ | $CH_2CH_2CH_3$ | $PO(OCH_2CH_3)_2$ | Br | Het2 |
| 8225 | $OCH_3$ | $OCH_3$ | $PO(OCH_2CH_3)_2$ | Br | Het2 |
| 8226 | $OCH_2CH_3$ | $OCH_2CH_3$ | $PO(OCH_2CH_3)_2$ | Br | Het2 |
| 8227 | $OCH_2CH_2CH_3$ | $OCH_2CH_2CH_3$ | $PO(OCH_2CH_3)_2$ | Br | Het2 |
| 8228 | $SCH_3$ | $SCH_3$ | $PO(OCH_2CH_3)_2$ | Br | Het2 |
| 8229 | $SCH_2CH_3$ | $SCH_2CH_3$ | $PO(OCH_2CH_3)_2$ | Br | Het2 |
| 8230 | $N(CH_3)_2$ | $N(CH_3)_2$ | $PO(OCH_2CH_3)_2$ | Br | Het2 |
| 8231 | $N(CH_2CH_3)_2$ | $N(CH_2CH_3)_2$ | $PO(OCH_2CH_3)_2$ | Br | Het2 |
| 8232 | $N(CH_3)(CH_2CH_3)$ | $N(CH_3)(CH_2CH_3)$ | $PO(OCH_2CH_3)_2$ | Br | Het2 |
| 8233 | $O-(CH_2CH_2)-O$ | | $PO(OCH_2CH_3)_2$ | Br | Het2 |
| 8234 | $O-(CH_2CH_2CH_2)-O$ | | $PO(OCH_2CH_3)_2$ | Br | Het2 |
| 8235 | $S-(CH_2CH_2)-S$ | | $PO(OCH_2CH_3)_2$ | Br | Het2 |
| 8236 | $S-(CH_2CH_2CH_2)-S$ | | $PO(OCH_2CH_3)_2$ | Br | Het2 |
| 8237 | $-(CH_2)_4-$ | | $PO(OCH_2CH_3)_2$ | Br | Het2 |
| 8238 | $-(CH_2)_5-$ | | $PO(OCH_2CH_3)_2$ | Br | Het2 |
| 8239 | H | H | $PO(CH_3)_2$ | Br | Het2 |
| 8240 | $CH_3$ | $CH_3$ | $PO(CH_3)_2$ | Br | Het2 |
| 8241 | $CH_2CH_3$ | $CH_2CH_3$ | $PO(CH_3)_2$ | Br | Het2 |
| 8242 | $CH_2CH_2CH_3$ | $CH_2CH_2CH_3$ | $PO(CH_3)_2$ | Br | Het2 |
| 8243 | $OCH_3$ | $OCH_3$ | $PO(CH_3)_2$ | Br | Het2 |
| 8244 | $OCH_2CH_3$ | $OCH_2CH_3$ | $PO(CH_3)_2$ | Br | Het2 |
| 8245 | $OCH_2CH_2CH_3$ | $OCH_2CH_2CH_3$ | $PO(CH_3)_2$ | Br | Het2 |
| 8246 | $SCH_3$ | $SCH_3$ | $PO(CH_3)_2$ | Br | Het2 |
| 8247 | $SCH_2CH_3$ | $SCH_2CH_3$ | $PO(CH_3)_2$ | Br | Het2 |
| 8248 | $N(CH_3)_2$ | $N(CH_3)_2$ | $PO(CH_3)_2$ | Br | Het2 |
| 8249 | $N(CH_2CH_3)_2$ | $N(CH_2CH_3)_2$ | $PO(CH_3)_2$ | Br | Het2 |
| 8250 | $N(CH_3)(CH_2CH_3)$ | $N(CH_3)(CH_2CH_3)$ | $PO(CH_3)_2$ | Br | Het2 |
| 8251 | $O-(CH_2CH_2)-O$ | | $PO(CH_3)_2$ | Br | Het2 |
| 8252 | $O-(CH_2CH_2CH_2)-O$ | | $PO(CH_3)_2$ | Br | Het2 |
| 8253 | $S-(CH_2CH_2)-S$ | | $PO(CH_3)_2$ | Br | Het2 |
| 8254 | $S-(CH_2CH_2CH_2)-S$ | | $PO(CH_3)_2$ | Br | Het2 |
| 8255 | $-(CH_2)_4-$ | | $PO(CH_3)_2$ | Br | Het2 |
| 8256 | $-(CH_2)_5-$ | | $PO(CH_3)_2$ | Br | Het2 |
| 8257 | H | H | $PC(CH_2CH_3)_2$ | Br | Het2 |
| 8258 | $CH_3$ | $CH_3$ | $PC(CH_2CH_3)_2$ | Br | Het2 |
| 8259 | $CH_2CH_3$ | $CH_2CH_3$ | $PC(CH_2CH_3)_2$ | Br | Het2 |
| 8260 | $CH_2CH_2CH_3$ | $CH_2CH_2CH_3$ | $PC(CH_2CH_3)_2$ | Br | Het2 |
| 8261 | $OCH_3$ | $OCH_3$ | $PC(CH_2CH_3)_2$ | Br | Het2 |
| 8262 | $OCH_2CH_3$ | $OCH_2CH_3$ | $PC(CH_2CH_3)_2$ | Br | Het2 |
| 8263 | $OCH_2CH_2CH_3$ | $OCH_2CH_2CH_3$ | $PC(CH_2CH_3)_2$ | Br | Het2 |
| 8264 | $SCH_3$ | $SCH_3$ | $PC(CH_2CH_3)_2$ | Br | Het2 |
| 8265 | $SCH_2CH_3$ | $SCH_2CH_3$ | $PC(CH_2CH_3)_2$ | Br | Het2 |
| 8266 | $N(CH_3)_2$ | $N(CH_3)_2$ | $PC(CH_2CH_3)_2$ | Br | Het2 |
| 8267 | $N(CH_2CH_3)_2$ | $N(CH_2CH_3)_2$ | $PC(CH_2CH_3)_2$ | Br | Het2 |
| 8268 | $N(CH_3)(CH_2CH_3)$ | $N(CH_3)(CH_2CH_3)$ | $PC(CH_2CH_3)_2$ | Br | Het2 |
| 8269 | $O-(CH_2CH_2)-O$ | | $PC(CH_2CH_3)_2$ | Br | Het2 |
| 8270 | $O-(CH_2CH_2CH_2)-O$ | | $PC(CH_2CH_3)_2$ | Br | Het2 |

TABLE 1-continued

I1a1

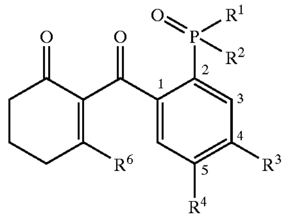

| n | $R^1$ | $R^2$ | $R^3$ | $R^4$ | $R^6$ |
|---|---|---|---|---|---|
| 8271 | S—(CH$_2$CH$_2$)—S | | PC(CH$_2$CH$_3$)$_2$ | Br | Het2 |
| 8272 | S—(CH$_2$CH$_2$CH$_2$)—S | | PC(CH$_2$CH$_3$)$_2$ | Br | Het2 |
| 8273 | —(CH$_2$)$_4$— | | PC(CH$_2$CH$_3$)$_2$ | Br | Het2 |
| 8274 | —(CH$_2$)$_5$— | | PC(CH$_2$CH$_3$)$_2$ | Br | Het2 |
| 8275 | H | H | H | Br | Het3 |
| 8276 | CH$_3$ | CH$_3$ | H | Br | Het3 |
| 8277 | CH$_2$CH$_3$ | CH$_2$CH$_3$ | H | Br | Het3 |
| 8278 | CH$_2$CH$_2$CH$_3$ | CH$_2$CH$_2$CH$_3$ | H | Br | Het3 |
| 8279 | OCH$_3$ | OCH$_3$ | H | Br | Het3 |
| 8280 | OCH$_2$CH$_3$ | OCH$_2$CH$_3$ | H | Br | Het3 |
| 8281 | OCH$_2$CH$_2$CH$_3$ | OCH$_2$CH$_2$CH$_3$ | H | Br | Het3 |
| 8282 | SCH$_3$ | SCH$_3$ | H | Br | Het3 |
| 8283 | SCH$_2$CH$_3$ | SCH$_2$CH$_3$ | H | Br | Het3 |
| 8284 | N(CH$_3$)$_2$ | N(CH$_3$)$_2$ | H | Br | Het3 |
| 8285 | N(CH$_2$CH$_3$)$_2$ | N(CH$_2$CH$_3$)$_2$ | H | Br | Het3 |
| 8286 | N(CH$_3$)(CH$_2$CH$_3$) | N(CH$_3$)(CH$_2$CH$_3$) | H | Br | Het3 |
| 8287 | O—(CH$_2$CH$_2$)—O | | H | Br | Het3 |
| 8288 | O—(CH$_2$CH$_2$CH$_2$)—O | | H | Br | Het3 |
| 8289 | S—(CH$_2$CH$_2$)—S | | H | Br | Het3 |
| 8290 | S—(CH$_2$CH$_2$CH$_2$)—S | | H | Br | Het3 |
| 8291 | —(CH$_2$)$_4$— | | H | Br | Het3 |
| 8292 | —(CH$_2$)$_5$— | | H | Br | Het3 |
| 8293 | H | H | NO$_2$ | Br | Het3 |
| 8294 | CH$_3$ | CH$_3$ | NO$_2$ | Br | Het3 |
| 8295 | CH$_2$CH$_3$ | CH$_2$CH$_3$ | NO$_2$ | Br | Het3 |
| 8296 | CH$_2$CH$_2$CH$_3$ | CH$_2$CH$_2$CH$_3$ | NO$_2$ | Br | Het3 |
| 8297 | OCH$_3$ | OCH$_3$ | NO$_2$ | Br | Het3 |
| 8298 | OCH$_2$CH$_3$ | OCH$_2$CH$_3$ | NO$_2$ | Br | Het3 |
| 8299 | OCH$_2$CH$_2$CH$_3$ | OCH$_2$CH$_2$CH$_3$ | NO$_2$ | Br | Het3 |
| 8300 | SCH$_3$ | SCH$_3$ | NO$_2$ | Br | Het3 |
| 8301 | SCH$_2$CH$_3$ | SCH$_2$CH$_3$ | NO$_2$ | Br | Het3 |
| 8302 | N(CH$_3$)$_2$ | N(CH$_3$)$_2$ | NO$_2$ | Br | Het3 |
| 8303 | N(CH$_2$CH$_3$)$_2$ | N(CH$_2$CH$_3$)$_2$ | NO$_2$ | Br | Het3 |
| 8304 | N(CH$_3$)(CH$_2$CH$_3$) | N(CH$_3$)(CH$_2$CH$_3$) | NO$_2$ | Br | Het3 |
| 8305 | O—(CH$_2$CH$_2$)—O | | NO$_2$ | Br | Het3 |
| 8306 | O—(CH$_2$CH$_2$CH$_2$)—O | | NO$_2$ | Br | Het3 |
| 8307 | S—(CH$_2$CH$_2$)—S | | NO$_2$ | Br | Het3 |
| 8308 | S—(CH$_2$CH$_2$CH$_2$)—S | | NO$_2$ | Br | Het3 |
| 8309 | —(CH$_2$)$_4$— | | NO$_2$ | Br | Het3 |
| 8310 | —(CH$_2$)$_5$— | | NO$_2$ | Br | Het3 |
| 8311 | H | H | CN | Br | Het3 |
| 8312 | CH$_3$ | CH$_3$ | CN | Br | Het3 |
| 8313 | CH$_2$CH$_3$ | CH$_2$CH$_3$ | CN | Br | Het3 |
| 8314 | CH$_2$CH$_2$CH$_3$ | CH$_2$CH$_2$CH$_3$ | CN | Br | Het3 |
| 8315 | OCH$_3$ | OCH$_3$ | CN | Br | Het3 |
| 8316 | OCH$_2$CH$_3$ | OCH$_2$CH$_3$ | CN | Br | Het3 |
| 8317 | OCH$_2$CH$_2$CH$_3$ | OCH$_2$CH$_2$CH$_3$ | CN | Br | Het3 |
| 8318 | SCH$_3$ | SCH$_3$ | CN | Br | Het3 |
| 8319 | SCH$_2$CH$_3$ | SCH$_2$CH$_3$ | CN | Br | Het3 |
| 8320 | N(CH$_3$)$_2$ | N(CH$_3$)$_2$ | CN | Br | Het3 |
| 8321 | N(CH$_2$CH$_3$)$_2$ | N(CH$_2$CH$_3$)$_2$ | CN | Br | Het3 |
| 8322 | N(CH$_3$)(CH$_2$CH$_3$) | N(CH$_3$)(CH$_2$CH$_3$) | CN | Br | Het3 |
| 8323 | O—(CH$_2$CH$_2$)—O | | CN | Br | Het3 |
| 8324 | O—(CH$_2$CH$_2$CH$_2$)—O | | CN | Br | Het3 |
| 8325 | S—(CH$_2$CH$_2$)—S | | CN | Br | Het3 |
| 8326 | S—(CH$_2$CH$_2$CH$_2$)—S | | CN | Br | Het3 |
| 8327 | —(CH$_2$)$_4$— | | CN | Br | Het3 |
| 8328 | —(CH$_2$)$_5$— | | CN | Br | Het3 |
| 8329 | H | H | F | Br | Het3 |
| 8330 | CH$_3$ | CH$_3$ | F | Br | Het3 |
| 8331 | CH$_2$CH$_3$ | CH$_2$CH$_3$ | F | Br | Het3 |
| 8332 | CH$_2$CH$_2$CH$_3$ | CH$_2$CH$_2$CH$_3$ | F | Br | Het3 |
| 8333 | OCH$_3$ | OCH$_3$ | F | Br | Het3 |
| 8334 | OCH$_2$CH$_3$ | OCH$_2$CH$_3$ | F | Br | Het3 |

TABLE 1-continued

I1a1

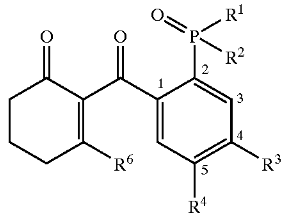

| n | $R^1$ | $R^2$ | $R^3$ | $R^4$ | $R^6$ |
|---|---|---|---|---|---|
| 8335 | $OCH_2CH_2CH_3$ | $OCH_2CH_2CH_3$ | F | Br | Het3 |
| 8336 | $SCH_3$ | $SCH_3$ | F | Br | Het3 |
| 8337 | $SCH_2CH_3$ | $SCH_2CH_3$ | F | Br | Het3 |
| 8338 | $N(CH_3)_2$ | $N(CH_3)_2$ | F | Br | Het3 |
| 8339 | $N(CH_2CH_3)_2$ | $N(CH_2CH_3)_2$ | F | Br | Het3 |
| 8340 | $N(CH_3)(CH_2CH_3)$ | $N(CH_3)(CH_2CH_3)$ | F | Br | Het3 |
| 8341 | $O—(CH_2CH_2)—O$ | | F | Br | Het3 |
| 8342 | $O—(CH_2CH_2CH_2)—O$ | | F | Br | Het3 |
| 8343 | $S—(CH_2CH_2)—S$ | | F | Br | Het3 |
| 8344 | $S—(CH_2CH_2CH_2)—S$ | | F | Br | Het3 |
| 8345 | $—(CH_2)_4—$ | | F | Br | Het3 |
| 8346 | $—(CH_2)_5—$ | | F | Br | Het3 |
| 8347 | H | H | Cl | Br | Het3 |
| 8348 | $CH_3$ | $CH_3$ | Cl | Br | Het3 |
| 8349 | $CH_2CH_3$ | $CH_2CH_3$ | Cl | Br | Het3 |
| 8350 | $CH_2CH_2CH_3$ | $CH_2CH_2CH_3$ | Cl | Br | Het3 |
| 8351 | $OCH_3$ | $OCH_3$ | Cl | Br | Het3 |
| 8352 | $OCH_2CH_3$ | $OCH_2CH_3$ | Cl | Br | Het3 |
| 8353 | $OCH_2CH_2CH_3$ | $OCH_2CH_2CH_3$ | Cl | Br | Het3 |
| 8354 | $SCH_3$ | $SCH_3$ | Cl | Br | Het3 |
| 8355 | $SCH_2CH_3$ | $SCH_2CH_3$ | Cl | Br | Het3 |
| 8356 | $N(CH_3)_2$ | $N(CH_3)_2$ | Cl | Br | Het3 |
| 8357 | $N(CH_2CH_3)_2$ | $N(CH_2CH_3)_2$ | Cl | Br | Het3 |
| 8358 | $N(CH_3)(CH_2CH_3)$ | $N(CH_3)(CH_2CH_3)$ | Cl | Br | Het3 |
| 8359 | $O—(CH_2CH_2)—O$ | | Cl | Br | Het3 |
| 8360 | $O—(CH_2CH_2CH_2)—O$ | | Cl | Br | Het3 |
| 8361 | $S—(CH_2CH_2)—S$ | | Cl | Br | Het3 |
| 8362 | $S—(CH_2CH_2CH_2)—S$ | | Cl | Br | Het3 |
| 8363 | $—(CH_2)_4—$ | | Cl | Br | Het3 |
| 8364 | $—(CH_2)_5—$ | | Cl | Br | Het3 |
| 8365 | H | H | Br | Br | Het3 |
| 8366 | $CH_3$ | $CH_3$ | Br | Br | Het3 |
| 8367 | $CH_2CH_3$ | $CH_2CH_3$ | Br | Br | Het3 |
| 8368 | $CH_2CH_2CH_3$ | $CH_2CH_2CH_3$ | Br | Br | Het3 |
| 8369 | $OCH_3$ | $OCH_3$ | Br | Br | Het3 |
| 8370 | $OCH_2CH_3$ | $OCH_2CH_3$ | Br | Br | Het3 |
| 8371 | $OCH_2CH_2CH_3$ | $OCH_2CH_2CH_3$ | Br | Br | Het3 |
| 8372 | $SCH_3$ | $SCH_3$ | Br | Br | Het3 |
| 8373 | $SCH_2CH_3$ | $SCH_2CH_3$ | Br | Br | Het3 |
| 8374 | $N(CH_3)_2$ | $N(CH_3)_2$ | Br | Br | Het3 |
| 8375 | $N(CH_2CH_3)_2$ | $N(CH_2CH_3)_2$ | Br | Br | Het3 |
| 8376 | $N(CH_3)(CH_2CH_3)$ | $N(CH_3)(CH_2CH_3)$ | Br | Br | Het3 |
| 8377 | $O—(CH_2CH_2)—O$ | | Br | Br | Het3 |
| 8378 | $O—(CH_2CH_2CH_2)—O$ | | Br | Br | Het3 |
| 8379 | $S—(CH_2CH_2)—S$ | | Br | Br | Het3 |
| 8380 | $S—(CH_2CH_2CH_2)—S$ | | Br | Br | Het3 |
| 8381 | $—(CH_2)_4—$ | | Br | Br | Het3 |
| 8382 | $—(CH_2)_5—$ | | Br | Br | Het3 |
| 8383 | H | H | $CH_3$ | Br | Het3 |
| 8384 | $CH_3$ | $CH_3$ | $CH_3$ | Br | Het3 |
| 8385 | $CH_2CH_3$ | $CH_2CH_3$ | $CH_3$ | Br | Het3 |
| 8386 | $CH_2CH_2CH_3$ | $CH_2CH_2CH_3$ | $CH_3$ | Br | Het3 |
| 8387 | $OCH_3$ | $OCH_3$ | $CH_3$ | Br | Het3 |
| 8388 | $OCH_2CH_3$ | $OCH_2CH_3$ | $CH_3$ | Br | Het3 |
| 8389 | $OCH_2CH_2CH_3$ | $OCH_2CH_2CH_3$ | $CH_3$ | Br | Het3 |
| 8390 | $SCH_3$ | $SCH_3$ | $CH_3$ | Br | Het3 |
| 8391 | $SCH_2CH_3$ | $SCH_2CH_3$ | $CH_3$ | Br | Het3 |
| 8392 | $N(CH_3)_2$ | $N(CH_3)_2$ | $CH_3$ | Br | Het3 |
| 8393 | $N(CH_2CH_3)_2$ | $N(CH_2CH_3)_2$ | $CH_3$ | Br | Het3 |
| 8394 | $N(CH_3)(CH_2CH_3)$ | $N(CH_3)(CH_2CH_3)$ | $CH_3$ | Br | Het3 |
| 8395 | $O—(CH_2CH_2)—O$ | | $CH_3$ | Br | Het3 |
| 8396 | $O—(CH_2CH_2CH_2)—O$ | | $CH_3$ | Br | Het3 |
| 8397 | $S—(CH_2CH_2)—S$ | | $CH_3$ | Br | Het3 |
| 8398 | $S—(CH_2CH_2CH_2)—S$ | | $CH_3$ | Br | Het3 |

TABLE 1-continued

I1a1

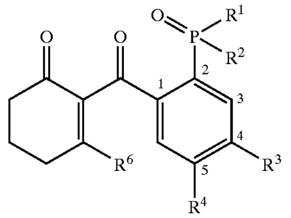

| n | $R^1$ | $R^2$ | $R^3$ | $R^4$ | $R^6$ |
|---|---|---|---|---|---|
| 8399 | $-(CH_2)_4-$ | | $CH_3$ | Br | Het3 |
| 8400 | $-(CH_2)_5-$ | | $CH_3$ | Br | Het3 |
| 8401 | H | H | $CH_2CH_3$ | Br | Het3 |
| 8402 | $CH_3$ | $CH_3$ | $CH_2CH_3$ | Br | Het3 |
| 8403 | $CH_2CH_3$ | $CH_2CH_3$ | $CH_2CH_3$ | Br | Het3 |
| 8404 | $CH_2CH_2CH_3$ | $CH_2CH_2CH_3$ | $CH_2CH_3$ | Br | Het3 |
| 8405 | $OCH_3$ | $OCH_3$ | $CH_2CH_3$ | Br | Het3 |
| 8406 | $OCH_2CH_3$ | $OCH_2CH_3$ | $CH_2CH_3$ | Br | Het3 |
| 8407 | $OCH_2CH_2CH_3$ | $OCH_2CH_2CH_3$ | $CH_2CH_3$ | Br | Het3 |
| 8408 | $SCH_3$ | $SCH_3$ | $CH_2CH_3$ | Br | Het3 |
| 8409 | $SCH_2CH_3$ | $SCH_2CH_3$ | $CH_2CH_3$ | Br | Het3 |
| 8410 | $N(CH_3)_2$ | $N(CH_3)_2$ | $CH_2CH_3$ | Br | Het3 |
| 8411 | $N(CH_2CH_3)_2$ | $N(CH_2CH_3)_2$ | $CH_2CH_3$ | Br | Het3 |
| 8412 | $N(CH_3)(CH_2CH_3)$ | $N(CH_3)(CH_2CH_3)$ | $CH_2CH_3$ | Br | Het3 |
| 8413 | $O-(CH_2CH_2)-O$ | | $CH_2CH_3$ | Br | Het3 |
| 8414 | $O-(CH_2CH_2CH_2)-O$ | | $CH_2CH_3$ | Br | Het3 |
| 8415 | $S-(CH_2CH_2)-S$ | | $CH_2CH_3$ | Br | Het3 |
| 8416 | $S-(CH_2CH_2CH_2)-S$ | | $CH_2CH_3$ | Br | Het3 |
| 8417 | $-(CH_2)_4-$ | | $CH_2CH_3$ | Br | Het3 |
| 8418 | $-(CH_2)_5-$ | | $CH_2CH_3$ | Br | Het3 |
| 8419 | H | H | $CF_3$ | Br | Het3 |
| 8420 | $CH_3$ | $CH_3$ | $CF_3$ | Br | Het3 |
| 8421 | $CH_2CH_3$ | $CH_2CH_3$ | $CF_3$ | Br | Het3 |
| 8422 | $CH_2CH_2CH_3$ | $CH_2CH_2CH_3$ | $CF_3$ | Br | Het3 |
| 8423 | $OCH_3$ | $OCH_3$ | $CF_3$ | Br | Het3 |
| 8424 | $OCH_2CH_3$ | $OCH_2CH_3$ | $CF_3$ | Br | Het3 |
| 8425 | $OCH_2CH_2CH_3$ | $OCH_2CH_2CH_3$ | $CF_3$ | Br | Het3 |
| 8426 | $SCH_3$ | $SCH_3$ | $CF_3$ | Br | Het3 |
| 8427 | $SCH_2CH_3$ | $SCH_2CH_3$ | $CF_3$ | Br | Het3 |
| 8428 | $N(CH_3)_2$ | $N(CH_3)_2$ | $CF_3$ | Br | Het3 |
| 8429 | $N(CH_2CH_3)_2$ | $N(CH_2CH_3)_2$ | $CF_3$ | Br | Het3 |
| 8430 | $N(CH_3)(CH_2CH_3)$ | $N(CH_3)(CH_2CH_3)$ | $CF_3$ | Br | Het3 |
| 8431 | $O-(CH_2CH_2)-O$ | | $CF_3$ | Br | Het3 |
| 8432 | $O-(CH_2CH_2CH_2)-O$ | | $CF_3$ | Br | Het3 |
| 8433 | $S-(CH_2CH_2)-S$ | | $CF_3$ | Br | Het3 |
| 8434 | $S-(CH_2CH_2CH_2)-S$ | | $CF_3$ | Br | Het3 |
| 8435 | $-(CH_2)_4-$ | | $CF_3$ | Br | Het3 |
| 8436 | $-(CH_2)_5-$ | | $CF_3$ | Br | Het3 |
| 8437 | H | H | $OCH_3$ | Br | Het3 |
| 8438 | $CH_3$ | $CH_3$ | $OCH_3$ | Br | Het3 |
| 8439 | $CH_2CH_3$ | $CH_2CH_3$ | $OCH_3$ | Br | Het3 |
| 8440 | $CH_2CH_2CH_3$ | $CH_2CH_2CH_3$ | $OCH_3$ | Br | Het3 |
| 8441 | $OCH_3$ | $OCH_3$ | $OCH_3$ | Br | Het3 |
| 8442 | $OCH_2CH_3$ | $OCH_2CH_3$ | $OCH_3$ | Br | Het3 |
| 8443 | $OCH_2CH_2CH_3$ | $OCH_2CH_2CH_3$ | $OCH_3$ | Br | Het3 |
| 8444 | $SCH_3$ | $SCH_3$ | $OCH_3$ | Br | Het3 |
| 8445 | $SCH_2CH_3$ | $SCH_2CH_3$ | $OCH_3$ | Br | Het3 |
| 8446 | $N(CH_3)_2$ | $N(CH_3)_2$ | $OCH_3$ | Br | Het3 |
| 8447 | $N(CH_2CH_3)_2$ | $N(CH_2CH_3)_2$ | $OCH_3$ | Br | Het3 |
| 8448 | $N(CH_3)(CH_2CH_3)$ | $N(CH_3)(CH_2CH_3)$ | $OCH_3$ | Br | Het3 |
| 8449 | $O-(CH_2CH_2)-O$ | | $OCH_3$ | Br | Het3 |
| 8450 | $O-(CH_2CH_2CH_2)-O$ | | $OCH_3$ | Br | Het3 |
| 8451 | $S-(CH_2CH_2)-S$ | | $OCH_3$ | Br | Het3 |
| 8452 | $S-(CH_2CH_2CH_2)-S$ | | $OCH_3$ | Br | Het3 |
| 8453 | $-(CH_2)_4-$ | | $OCH_3$ | Br | Het3 |
| 8454 | $-(CH_2)_5-$ | | $OCH_3$ | Br | Het3 |
| 8455 | H | H | $OCH_2CH_3$ | Br | Het3 |
| 8456 | $CH_3$ | $CH_3$ | $OCH_2CH_3$ | Br | Het3 |
| 8457 | $CH_2CH_3$ | $CH_2CH_3$ | $OCH_2CH_3$ | Br | Het3 |
| 8458 | $CH_2CH_2CH_3$ | $CH_2CH_2CH_3$ | $OCH_2CH_3$ | Br | Het3 |
| 8459 | $OCH_3$ | $OCH_3$ | $OCH_2CH_3$ | Br | Het3 |
| 8460 | $OCH_2CH_3$ | $OCH_2CH_3$ | $OCH_2CH_3$ | Br | Het3 |
| 8461 | $OCH_2CH_2CH_3$ | $OCH_2CH_2CH_3$ | $OCH_2CH_3$ | Br | Het3 |
| 8462 | $SCH_3$ | $SCH_3$ | $OCH_2CH_3$ | Br | Het3 |

TABLE 1-continued

I1a1

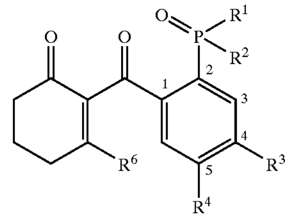

| n | $R^1$ | $R^2$ | $R^3$ | $R^4$ | $R^6$ |
|---|---|---|---|---|---|
| 8463 | $SCH_2CH_3$ | $SCH_2CH_3$ | $OCH_2CH_3$ | Br | Het3 |
| 8464 | $N(CH_3)_2$ | $N(CH_3)_2$ | $OCH_2CH_3$ | Br | Het3 |
| 8465 | $N(CH_2CH_3)_2$ | $N(CH_2CH_3)_2$ | $OCH_2CH_3$ | Br | Het3 |
| 8466 | $N(CH_3)(CH_2CH_3)$ | $N(CH_3)(CH_2CH_3)$ | $OCH_2CH_3$ | Br | Het3 |
| 8467 | $O—(CH_2CH_2)—O$ | | $OCH_2CH_3$ | Br | Het3 |
| 8468 | $O—(CH_2CH_2CH_2)—O$ | | $OCH_2CH_3$ | Br | Het3 |
| 8469 | $S—(CH_2CH_2)—S$ | | $OCH_2CH_3$ | Br | Het3 |
| 8470 | $S—(CH_2CH_2CH_2)—S$ | | $OCH_2CH_3$ | Br | Het3 |
| 8471 | $—(CH_2)_4—$ | | $OCH_2CH_3$ | Br | Het3 |
| 8472 | $—(CH_2)_5—$ | | $OCH_2CH_3$ | Br | Het3 |
| 8473 | H | H | $SCH_3$ | Br | Het3 |
| 8474 | $CH_3$ | $CH_3$ | $SCH_3$ | Br | Het3 |
| 8475 | $CH_2CH_3$ | $CH_2CH_3$ | $SCH_3$ | Br | Het3 |
| 8476 | $CH_2CH_2CH_3$ | $CH_2CH_2CH_3$ | $SCH_3$ | Br | Het3 |
| 8477 | $OCH_3$ | $OCH_3$ | $SCH_3$ | Br | Het3 |
| 8478 | $OCH_2CH_3$ | $OCH_2CH_3$ | $SCH_3$ | Br | Het3 |
| 8479 | $OCH_2CH_2CH_3$ | $OCH_2CH_2CH_3$ | $SCH_3$ | Br | Het3 |
| 8480 | $SCH_3$ | $SCH_3$ | $SCH_3$ | Br | Het3 |
| 8481 | $SCH_2CH_3$ | $SCH_2CH_3$ | $SCH_3$ | Br | Het3 |
| 8482 | $N(CH_3)_2$ | $N(CH_3)_2$ | $SCH_3$ | Br | Het3 |
| 8483 | $N(CH_2CH_3)_2$ | $N(CH_2CH_3)_2$ | $SCH_3$ | Br | Het3 |
| 8484 | $N(CH_3)(CH_2CH_3)$ | $N(CH_3)(CH_2CH_3)$ | $SCH_3$ | Br | Het3 |
| 8485 | $O—(CH_2CH_2)—O$ | | $SCH_3$ | Br | Het3 |
| 8486 | $O—(CH_2CH_2CH_2)—O$ | | $SCH_3$ | Br | Het3 |
| 8487 | $S—(CH_2CH_2)—S$ | | $SCH_3$ | Br | Het3 |
| 8488 | $S—(CH_2CH_2CH_2)—S$ | | $SCH_3$ | Br | Het3 |
| 8489 | $—(CH_2)_4—$ | | $SCH_3$ | Br | Het3 |
| 8490 | $—(CH_2)_5—$ | | $SCH_3$ | Br | Het3 |
| 8491 | H | H | $SO_2CH_3$ | Br | Het3 |
| 8492 | $CH_3$ | $CH_3$ | $SO_2CH_3$ | Br | Het3 |
| 8493 | $CH_2CH_3$ | $CH_2CH_3$ | $SO_2CH_3$ | Br | Het3 |
| 8494 | $CH_2CH_2CH_3$ | $CH_2CH_2CH_3$ | $SO_2CH_3$ | Br | Het3 |
| 8495 | $OCH_3$ | $OCH_3$ | $SO_2CH_3$ | Br | Het3 |
| 8496 | $OCH_2CH_3$ | $OCH_2CH_3$ | $SO_2CH_3$ | Br | Het3 |
| 8497 | $OCH_2CH_2CH_3$ | $OCH_2CH_2CH_3$ | $SO_2CH_3$ | Br | Het3 |
| 8498 | $SCH_3$ | $SCH_3$ | $SO_2CH_3$ | Br | Het3 |
| 8499 | $SCH_2CH_3$ | $SCH_2CH_3$ | $SO_2CH_3$ | Br | Het3 |
| 8500 | $N(CH_3)_2$ | $N(CH_3)_2$ | $SO_2CH_3$ | Br | Het3 |
| 8501 | $N(CH_2CH_3)_2$ | $N(CH_2CH_3)_2$ | $SO_2CH_3$ | Br | Het3 |
| 8502 | $N(CH_3)(CH_2CH_3)$ | $N(CH_3)(CH_2CH_3)$ | $SO_2CH_3$ | Br | Het3 |
| 8503 | $O—(CH_2CH_2)—O$ | | $SO_2CH_3$ | Br | Het3 |
| 8504 | $O—(CH_2CH_2CH_2)—O$ | | $SO_2CH_3$ | Br | Het3 |
| 8505 | $S—(CH_2CH_2)—S$ | | $SO_2CH_3$ | Br | Het3 |
| 8506 | $S—(CH_2CH_2CH_2)—S$ | | $SO_2CH_3$ | Br | Het3 |
| 8507 | $—(CH_2)_4—$ | | $SO_2CH_3$ | Br | Het3 |
| 8508 | $—(CH_2)_5—$ | | $SO_2CH_3$ | Br | Het3 |
| 8509 | H | H | $PO(OCH_3)_2$ | Br | Het3 |
| 8510 | $CH_3$ | $CH_3$ | $PO(OCH_3)_2$ | Br | Het3 |
| 8511 | $CH_2CH_3$ | $CH_2CH_3$ | $PO(OCH_3)_2$ | Br | Het3 |
| 8512 | $CH_2CH_2CH_3$ | $CH_2CH_2CH_3$ | $PO(OCH_3)_2$ | Br | Het3 |
| 8513 | $OCH_3$ | $OCH_3$ | $PO(OCH_3)_2$ | Br | Het3 |
| 8514 | $OCH_2CH_3$ | $OCH_2CH_3$ | $PO(OCH_3)_2$ | Br | Het3 |
| 8515 | $OCH_2CH_2CH_3$ | $OCH_2CH_2CH_3$ | $PO(OCH_3)_2$ | Br | Het3 |
| 8516 | $SCH_3$ | $SCH_3$ | $PO(OCH_3)_2$ | Br | Het3 |
| 8517 | $SCH_2CH_3$ | $SCH_2CH_3$ | $PO(OCH_3)_2$ | Br | Het3 |
| 8518 | $N(CH_3)_2$ | $N(CH_3)_2$ | $PO(OCH_3)_2$ | Br | Het3 |
| 8519 | $N(CH_2CH_3)_2$ | $N(CH_2CH_3)_2$ | $PO(OCH_3)_2$ | Br | Het3 |
| 8520 | $N(CH_3)(CH_2CH_3)$ | $N(CH_3)(CH_2CH_3)$ | $PO(OCH_3)_2$ | Br | Het3 |
| 8521 | $O—(CH_2CH_2)—O$ | | $PO(OCH_3)_2$ | Br | Het3 |
| 8522 | $O—(CH_2CH_2CH_2)—O$ | | $PO(OCH_3)_2$ | Br | Het3 |
| 8523 | $S—(CH_2CH_2)—S$ | | $PO(OCH_3)_2$ | Br | Het3 |
| 8524 | $S—(CH_2CH_2CH_2)—S$ | | $PO(OCH_3)_2$ | Br | Het3 |
| 8525 | $—(CH_2)_4—$ | | $PO(OCH_3)_2$ | Br | Het3 |
| 8526 | $—(CH_2)_5—$ | | $PO(OCH_3)_2$ | Br | Het3 |

TABLE 1-continued

I1a1

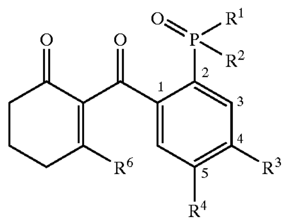

| n | $R^1$ | $R^2$ | $R^3$ | $R^4$ | $R^6$ |
|---|---|---|---|---|---|
| 8527 | H | H | $PO(OCH_2CH_3)_2$ | Br | Het3 |
| 8528 | $CH_3$ | $CH_3$ | $PO(OCH_2CH_3)_2$ | Br | Het3 |
| 8529 | $CH_2CH_3$ | $CH_2CH_3$ | $PO(OCH_2CH_3)_2$ | Br | Het3 |
| 8530 | $CH_2CH_2CH_3$ | $CH_2CH_2CH_3$ | $PO(OCH_2CH_3)_2$ | Br | Het3 |
| 8531 | $OCH_3$ | $OCH_3$ | $PO(OCH_2CH_3)_2$ | Br | Het3 |
| 8532 | $OCH_2CH_3$ | $OCH_2CH_3$ | $PO(OCH_2CH_3)_2$ | Br | Het3 |
| 8533 | $OCH_2CH_2CH_3$ | $OCH_2CH_2CH_3$ | $PO(OCH_2CH_3)_2$ | Br | Het3 |
| 8534 | $SCH_3$ | $SCH_3$ | $PO(OCH_2CH_3)_2$ | Br | Het3 |
| 8535 | $SCH_2CH_3$ | $SCH_2CH_3$ | $PO(OCH_2CH_3)_2$ | Br | Het3 |
| 8536 | $N(CH_3)_2$ | $N(CH_3)_2$ | $PO(OCH_2CH_3)_2$ | Br | Het3 |
| 8537 | $N(CH_2CH_3)_2$ | $N(CH_2CH_3)_2$ | $PO(OCH_2CH_3)_2$ | Br | Het3 |
| 8538 | $N(CH_3)(CH_2CH_3)$ | $N(CH_3)(CH_2CH_3)$ | $PO(OCH_2CH_3)_2$ | Br | Het3 |
| 8539 | $O—(CH_2CH_2)—O$ | | $PO(OCH_2CH_3)_2$ | Br | Het3 |
| 8540 | $O—(CH_2CH_2CH_2)—O$ | | $PO(OCH_2CH_3)_2$ | Br | Het3 |
| 8541 | $S—(CH_2CH_2)—S$ | | $PO(OCH_2CH_3)_2$ | Br | Het3 |
| 8542 | $S—(CH_2CH_2CH_2)—S$ | | $PO(OCH_2CH_3)_2$ | Br | Het3 |
| 8543 | $—(CH_2)_4—$ | | $PO(OCH_2CH_3)_2$ | Br | Het3 |
| 8544 | $—(CH_2)_5—$ | | $PO(OCH_2CH_3)_2$ | Br | Het3 |
| 8545 | H | H | $PO(CH_3)_2$ | Br | Het3 |
| 8546 | $CH_3$ | $CH_3$ | $PO(CH_3)_2$ | Br | Het3 |
| 8547 | $CH_2CH_3$ | $CH_2CH_3$ | $PO(CH_3)_2$ | Br | Het3 |
| 8548 | $CH_2CH_2CH_3$ | $CH_2CH_2CH_3$ | $PO(CH_3)_2$ | Br | Het3 |
| 8549 | $OCH_3$ | $OCH_3$ | $PO(CH_3)_2$ | Br | Het3 |
| 8550 | $OCH_2CH_3$ | $OCH_2CH_3$ | $PO(CH_3)_2$ | Br | Het3 |
| 8551 | $OCH_2CH_2CH_3$ | $OCH_2CH_2CH_3$ | $PO(CH_3)_2$ | Br | Het3 |
| 8552 | $SCH_3$ | $SCH_3$ | $PO(CH_3)_2$ | Br | Het3 |
| 8553 | $SCH_2CH_3$ | $SCH_2CH_3$ | $PO(CH_3)_2$ | Br | Het3 |
| 8554 | $N(CH_3)_2$ | $N(CH_3)_2$ | $PO(CH_3)_2$ | Br | Het3 |
| 8555 | $N(CH_2CH_3)_2$ | $N(CH_2CH_3)_2$ | $PO(CH_3)_2$ | Br | Het3 |
| 8556 | $N(CH_3)(CH_2CH_3)$ | $N(CH_3)(CH_2CH_3)$ | $PO(CH_3)_2$ | Br | Het3 |
| 8557 | $O—(CH_2CH_2)—O$ | | $PO(CH_3)_2$ | Br | Het3 |
| 8558 | $O—(CH_2CH_2CH_2)—O$ | | $PO(CH_3)_2$ | Br | Het3 |
| 8559 | $S—(CH_2CH_2)—S$ | | $PO(CH_3)_2$ | Br | Het3 |
| 8560 | $S—(CH_2CH_2CH_2)—S$ | | $PO(CH_3)_2$ | Br | Het3 |
| 8561 | $—(CH_2)_4—$ | | $PO(CH_3)_2$ | Br | Het3 |
| 8562 | $—(CH_2)_5—$ | | $PO(CH_3)_2$ | Br | Het3 |
| 8563 | H | H | $PC(CH_2CH_3)_2$ | Br | Het3 |
| 8564 | $CH_3$ | $CH_3$ | $PC(CH_2CH_3)_2$ | Br | Het3 |
| 8565 | $CH_2CH_3$ | $CH_2CH_3$ | $PC(CH_2CH_3)_2$ | Br | Het3 |
| 8566 | $CH_2CH_2CH_3$ | $CH_2CH_2CH_3$ | $PC(CH_2CH_3)_2$ | Br | Het3 |
| 8567 | $OCH_3$ | $OCH_3$ | $PC(CH_2CH_3)_2$ | Br | Het3 |
| 8568 | $OCH_2CH_3$ | $OCH_2CH_3$ | $PC(CH_2CH_3)_2$ | Br | Het3 |
| 8569 | $OCH_2CH_2CH_3$ | $OCH_2CH_2CH_3$ | $PC(CH_2CH_3)_2$ | Br | Het3 |
| 8570 | $SCH_3$ | $SCH_3$ | $PC(CH_2CH_3)_2$ | Br | Het3 |
| 8571 | $SCH_2CH_3$ | $SCH_2CH_3$ | $PC(CH_2CH_3)_2$ | Br | Het3 |
| 8572 | $N(CH_3)_2$ | $N(CH_3)_2$ | $PC(CH_2CH_3)_2$ | Br | Het3 |
| 8573 | $N(CH_2CH_3)_2$ | $N(CH_2CH_3)_2$ | $PC(CH_2CH_3)_2$ | Br | Het3 |
| 8574 | $N(CH_3)(CH_2CH_3)$ | $N(CH_3)(CH_2CH_3)$ | $PC(CH_2CH_3)_2$ | Br | Het3 |
| 8575 | $O—(CH_2CH_2)—O$ | | $PC(CH_2CH_3)_2$ | Br | Het3 |
| 8576 | $O—(CH_2CH_2CH_2)—O$ | | $PC(CH_2CH_3)_2$ | Br | Het3 |
| 8577 | $S—(CH_2CH_2)—S$ | | $PC(CH_2CH_3)_2$ | Br | Het3 |
| 8578 | $S—(CH_2CH_2CH_2)—S$ | | $PC(CH_2CH_3)_2$ | Br | Het3 |
| 8579 | $—(CH_2)_4—$ | | $PC(CH_2CH_3)_2$ | Br | Het3 |
| 8580 | $—(CH_2)_5—$ | | $PC(CH_2CH_3)_2$ | Br | Het3 |

where:

Het1 is 1-methoxy-N-methylamino;

Het2 is 1-tetrahydropyrrolyl;

Het3 is 1-tetrahydroisoxazolyl.

Extraordinary preference is also given to the compounds I1a2 (≡I where X=O; $R^3$ is attached in the 4-position, $R^4$ is attached in the 5-position and "$P(=X)R^1R^2$" is attached in the 2-position; $Q=Q^1$; $R^7$, $R^8$, $R^9$, $R^{11}$, $R^{12}$=H and $R^{10}=CH_3$), in particular to the compounds I1a2.n, where the variables $R^1$ to $R^4$ and $R^6$ are as defined in Table 1.

I1a2

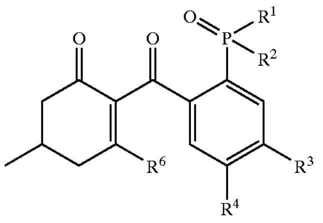

Extraordinary preference is also given to the compounds I1a3 (≡I where X=O; $R^3$ is attached in the 4-position, $R^4$ is attached in the 5-position and "$P(=X)R^1R^2$" is attached in the 2-position; $Q=Q^1$; $R^8$, $R^9$, $R^{10}$, $R^{11}$, $R^{12}$=H and $R^7=CH_3$), in particular to the compounds I1a3.n, where the variables $R^1$ to $R^4$ and $R^6$ are as defined in Table 1.

I1a3

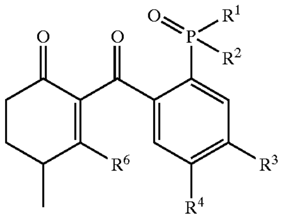

Extraordinary preference is also given to the compounds I1a4 (≡I where X=O; $R^3$ is attached in the 4-position, $R^4$ is attached in the 5-position and "$P(=X)R^1R^2$" is attached in the 2-position; $Q=Q^1$; $R^7$, $R^8$, $R^{11}$, $R^{12}$=H and $R^9$, $R^{10}=CH_3$), in particular to the compounds I1a4.n, where the variables $R^1$ to $R^4$ and $R^6$ are as defined in Table 1.

I1a4

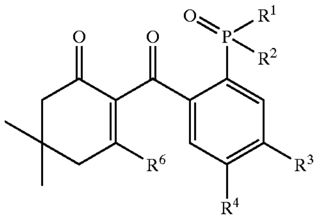

Extraordinary preference is also given to the compounds I1a5 (≡I where X=O; $R^3$ is attached in the 4-position, $R^4$ is attached in the 5-position and "$P(=X)R^1R^2$" is attached in the 2-position; $Q=Q^1$; $R^7$, $R^8=CH_3$ and $R^9$, $R^{10}$, $R^{11}$, $R^{12}$= H), in particular to the compounds I1a5.n, where the variables $R^1$ to $R^4$ and $R^6$ are as defined in Table 1.

I1a5

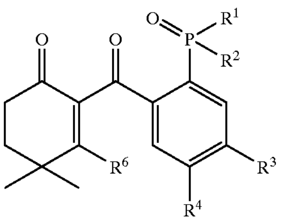

Extraordinary preference is also given to the compounds I1a6 (≡I where X=O; $R^3$ is attached in the 4-position, $R^4$ is attached in the 5-position and "$P(=X)R^1R^2$" is attached in the 2-position; $Q=Q^1$; $R^7$, $R^8$, $R^9$, $R^{10}$=H and $R^{11}$, $R^{12}=CH_3$), in particular to the compounds I1a6.n, where the variables $R^1$ to $R^4$ and $R^6$ are as defined in Table 1.

I1a6

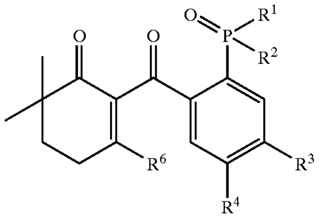

Extraordinary preference is also given to the compounds I1a7 (≡I where X=O; $R^3$ is attached in the 4-position, $R^4$ is attached in the 5-position and "$P(=X)R^1R^2$" is attached in the 2-position; $Q=Q^1$; $R^7$, $R^8$, $R^{11}$, $R^{12}$=H and $R^9$ and $R^{10}$ together with the carbon to which they are attached form a carbonyl group), in particular to the compounds I1a7.n, where the variables $R^1$ to $R^4$ and $R^6$ are as defined in Table 1.

I1a7

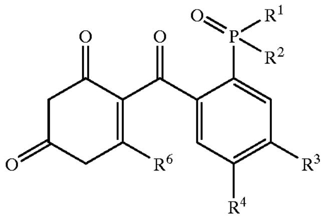

Extraordinary preference is also given to the compounds I1a8 (≡I where X=O; $R^3$ is attached in the 4-position, $R^4$ is attached in the 5-position and "$P(=X)R^1R^2$" is attached in the 2-position; $Q=Q^1$; $R^7$, $R^8$, $R^{11}$, $R^{12}=CH_3$ and $R^9$ and $R^{10}$ together with the carbon to which they are attached form a carbonyl group), in particular to the compounds I1a8.n, where the variables $R^1$ to $R^4$ and $R^6$ are as defined in Table 1.

I1a8

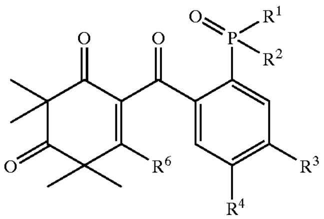

Extraordinary preference is also given to the compounds I1a9 (≡I where X=O; $R^3$ is attached in the 4-position, $R^4$ is attached in the 5-position and "P(═X)$R^1R^2$" is attached in the 2-position; Q=$Q^1$; $R^7$ and $R^{11}$ together form a —$CH_2$—$CH_2$— chain and $R^8$, $R^9$, $R^{10}$, $R^{12}$=H), in particular to the compounds I1a9.n, where the variables $R^1$ to $R^4$ and $R^6$ are as defined in Table 1.

I1a9

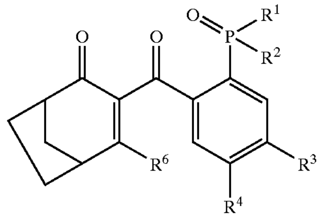

Extraordinary preference is also given to the compounds I2a1 (≡I where X=O; $R^3$ is attached in the 2-position, $R^4$ is attached in the 5-position and "P(═X)$R^1R^2$" is attached in the 4-position; Q=$Q^1$; $R^7$, $R^8$, $R^9$, $R^{10}$, $R^{11}$, $R^{12}$=H), in particular to the compounds I2a1.n, where the variables $R^1$ to $R^4$ and $R^6$ are as defined in Table 1.

I2a1

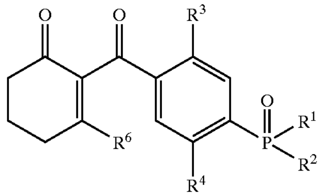

Extraordinary preference is also given to the compounds I2a2 (≡I where X=O; $R^3$ is attached in the 2-position, $R^4$ is attached in the 5-position and "P(═X)$R^1R^2$" is attached in the 4-position; Q=$Q^1$; $R^7$, $R^8$, $R^9$, $R^{11}$, $R^{12}$=H and $R^{10}$=$CH_3$), in particular to the compounds I2a2.n, where the variables $R^1$ to $R^4$ and $R^6$ are as defined in Table 1.

I2a2

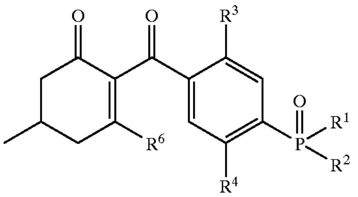

Extraordinary preference is also given to the compounds I2a3 (≡I where X=O; $R^3$ is attached in the 2-position, $R^4$ is attached in the 5-position and "P(═X)$R^1R^2$" is attached in the 4-position; Q=$Q^1$; $R^8$, $R^9$, $R^{10}$, $R^{11}$, $R^{12}$=H and $R^7$=$CH_3$), in particular to the compounds I2a3.n, where the variables $R^1$ to $R^4$ and $R^6$ are as defined in Table 1.

I2a3

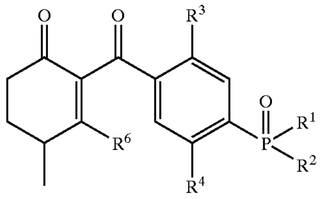

Extraordinary preference is also given to the compounds I2a4 (≡I where X=O; $R^3$ is attached in the 2-position, $R^4$ is attached in the 5-position and "P(═X)$R^1R^2$" is attached in the 4-position; Q=$Q^1$; $R^7$, $R^8$, $R^{11}$, $R^{12}$=H and $R^9$, $R^{10}$=$CH_3$), in particular to the compounds I2a4.n, where the variables $R^1$ to $R^4$ and $R^6$ are as defined in Table 1.

I2a4

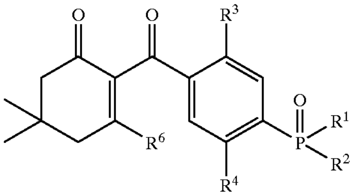

Extraordinary preference is also given to the compounds I2a5 (≡I where X=O; $R^3$ is attached in the 2-position, $R^4$ is attached in the 5-position and "P(═X)$R^1R^2$" is attached in the 4-position; Q=$Q^1$; $R^7$, $R^8$=$CH_3$, $R^9$, $R^{10}$, $R^{11}$, $R^{12}$=H), in particular to the compounds I2a5.n, where the variables $R^1$ to $R^4$ and $R^6$ are as defined in Table 1.

I2a5

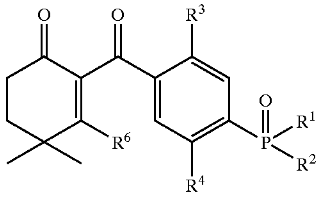

Extraordinary preference is also given to the compounds I2a6 (≡I where X=O; $R^3$ is attached in the 2-position, $R^4$ is attached in the 5-position and "P(═X)$R^1R^2$" is attached in the 4-position; Q=$Q^1$; $R^7$, $R^8$, $R^9$, $R^{10}$=H and $R^{11}$, $R^{12}$=$CH_3$), in particular to the compounds I2a6.n, where the variables $R^1$ to $R^4$ and $R^6$ are as defined in Table 1.

I2a6

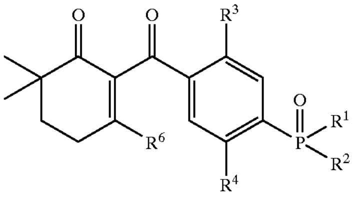

Extraordinary preference is also given to the compounds I2a7 (≡I where X=O; $R^3$ is attached in the 2-position, $R^4$ is attached in the 5-position and "P(=X)$R^1R^2$" is attached in the 4-position; Q=$Q^1$; $R^7$, $R^8$, $R^{11}$, $R^{12}$=H and $R^9$ and $R^{10}$ together with the carbon to which they are attached form a carbonyl group), in particular to the compounds I2a7.n, where the variables $R^1$ to $R^4$ and $R^6$ are as defined in Table 1.

I2a7

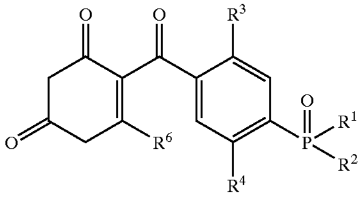

Extraordinary preference is also given to the compounds I2a8 (≡I where X=O; $R^3$ is attached in the 2-position, $R^4$ is attached in the 5-position and "P(=X)$R^1R^2$" is attached in the 4-position; Q=$Q^1$; $R^7$, $R^8$, $R^{11}$, $R^{12}$=$CH_3$ and $R^9$ and $R^{10}$ together with the carbon to which they are attached form a carbonyl group), in particular to the compounds I2a8.n, where the variables $R^1$ to $R^4$ and $R^6$ are as defined in Table 1.

I2a8

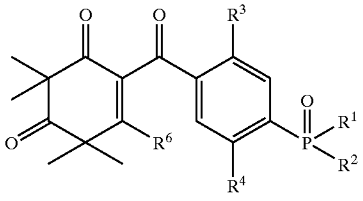

Extraordinary preference is also given to the compounds I2a9 (≡I where X=O; $R^3$ is attached in the 2-position, $R^4$ is attached in the 5-position and "P(=X)$R^1R^2$" is attached in the 4-position; Q=$Q^1$; $R^7$ and $R^{11}$ together form a $—CH_2—CH_2—$ chain and $R^8$, $R^9$, $R^{10}$, $R^{12}$=H), in particular to the compounds I2a9.n, where the variables $R^1$ to $R^4$ and $R^6$ are as defined in Table 1.

I2a9

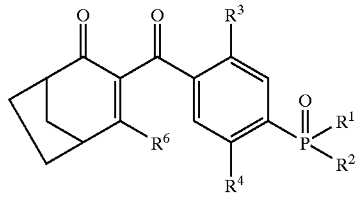

Extraordinary preference is also given to the compounds I1b1 (≡I where X=O; $R^3$ is attached in the 4-position, $R^4$ is attached in the 5-position and "P(=X)$R^1R^2$" is attached in the 2-position; Q=$Q^2$; $R^{21}$=$CH_3$ and $R^{22}$=H), in particular to the compounds I1b1.n, where the variables $R^1$ to $R^4$ and $R^{20}$ (which in this case corresponds to $R^6$) are as defined in Table 1.

I1b1

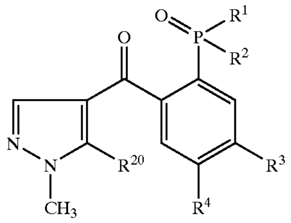

Extraordinary preference is also given to the compounds I1b2 (≡I where X=O; $R^3$ is attached in the 4-position, $R^4$ is attached in the 5-position and "P(=X)$R^1R^2$" is attached in the 2-position; Q=$Q^2$; $R^{21}$=$CH_2CH_3$ and $R^{22}$=H), in particular to the compounds I1b2.n, where the variables $R^1$ to $R^4$ and $R^{20}$ (which in this case corresponds to $R^6$) are as defined in Table 1.

I1b2

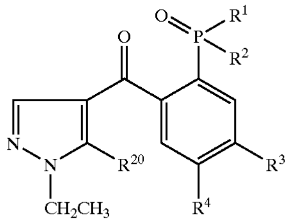

Extraordinary preference is also given to the compounds I1b3 (≡I where X=O; $R^3$ is attached in the 4-position, $R^4$ is attached in the 5-position and "P(=X)$R^1R^2$" is attached in the 2-position; Q=$Q^2$; $R^{21}$=$CH(CH_3)_2$ and $R^{22}$=H), in particular to the compounds I1b3.n, where the variables $R^1$ to $R^4$ and $R^{20}$ (which in this case corresponds to $R^6$) are as defined in Table 1.

I1b3

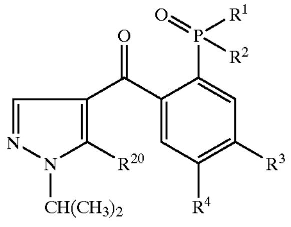

Extraordinary preference is also given to the compounds I1b4 (≡I where X=O; $R^3$ is attached in the 4-position, $R^4$ is attached in the 5-position and "P(=X)$R^1R^2$" is attached in the 2-position; Q=$Q^2$; $R^{21}$=$C(CH_3)_3$ and $R^{22}$=H), in particular to the compounds I1b4.n, where the variables $R^1$ to $R^4$ and $R^{20}$ (which in this case corresponds to $R^6$) are as defined in Table 1.

I1b4

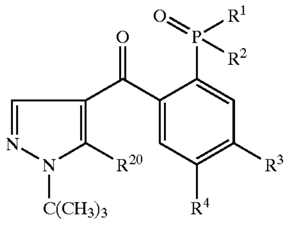

Extraordinary preference is also given to the compounds I1b5 (≡I where X=O; $R^3$ is attached in the 4-position, $R^4$ is attached in the 5-position and "P(=X)$R^1R^2$" is attached in the 2-position; Q=$Q^2$; $R^{21}$=$CH_2CF_3$ and $R^{22}$=H), in particular to the compounds I1b5.n, where the variables $R^1$ to $R^4$ and $R^{20}$ (which in this case corresponds to $R^6$) are as defined in Table 1.

I1b5

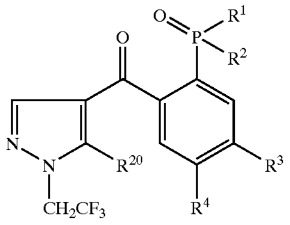

Extraordinary preference is also given to the compounds I1b6 (≡where X=O; $R^3$ is attached in the 4-position, $R^4$ is attached in the 5-position and "P(=X)$R^1R^2$" is attached in the 2-position; Q=$Q^2$; $R^{21}$=$CH_3$ and $R^{22}$=$CH_3$), in particular to the compounds I1b6.n, where the variables $R^1$ to $R^4$ and $R^{20}$ (which in this case corresponds to $R^6$) are as defined in Table 1.

I1b6

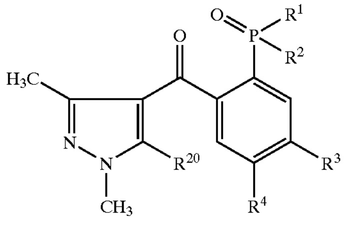

Extraordinary preference is also given to the compounds I1b7 (≡I where X=O; $R^3$ is attached in the 4-position, $R^4$ is attached in the 5-position and "P(=X)$R^1R^7$" is attached in the 2-position; Q=$Q^2$; $R^{21}$=$CH_2CH_3$ and $R^{22}$=$CH_3$), in particular to the compounds I1b7.n, where the variables $R^1$ to $R^4$ and $R^{20}$ (which in this case corresponds to $R^6$) are as defined in Table 1.

I1b7

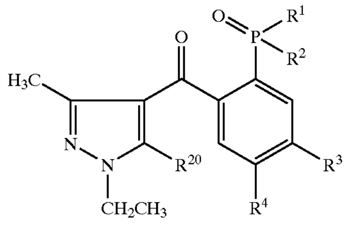

Extraordinary preference is also given to the compounds I1b8 (≡I where X=O; $R^3$ is attached in the 4-position, $R^4$ is attached in the 5-position and "P(=X)$R^1R^2$" is attached in the 2-position; Q=$Q^2$; $R^{21}$=$CH(CH_3)_2$ and $R^{22}$=$CH_3$), in particular to the compounds I1b8.n, where the variables $R^1$ to $R^4$ and $R^{20}$ (which in this case corresponds to $R^6$) are as defined in Table 1.

I1b8

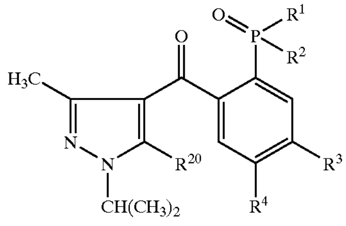

Extraordinary preference is also given to the compounds I1b9 (≡I where X=O; $R^3$ is attached in the 4-position, $R^4$ is attached in the 5-position and "P(=X)$R^1R^2$" is attached in the 2-position; Q=$Q^2$; $R^{21}$=$C(CH_3)_3$ and $R^{22}$=$CH_3$), in particular to the compounds I1b9.n, where the variables $R^1$ to $R^4$ and $R^{20}$ (which in this case corresponds to $R^6$) are as defined in Table 1.

I1b9

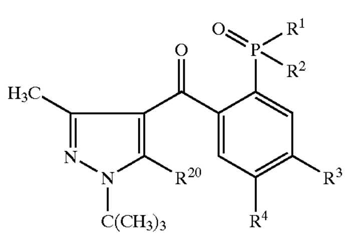

Extraordinary preference is also given to the compounds I1b10 (≡I where X=O; $R^3$ is attached in the 4-position, $R^4$ is attached in the 5-position and "P(=X)$R^1R^2$" is attached in the 2-position; Q=$Q^2$; $R^{21}$=$CH_2CH_3$ and $R^{22}$=$CH_3$), in particular to the compounds I1b10.n, where the variables $R^1$ to $R^4$ and $R^{20}$ (which in this case corresponds to $R^6$) are as defined in Table 1.

I1b10

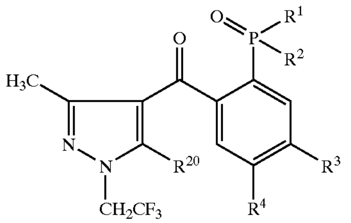

Extraordinary preference is also given to the compounds I1b11 (≡I where X=O; $R^3$ is attached in the 4-position, $R^4$ is attached in the 5-position and "P(═X)$R^1R^2$" is attached in the 2-position; Q=$Q^2$; $R^{21}$=$CH_3$ and $R^{22}$=$CH_3$), in particular to the compounds I1b11.n, where the variables $R^1$ to $R^4$ and $R^{20}$ (which in this case corresponds to $R^6$) are as defined in Table 1.

I1b11

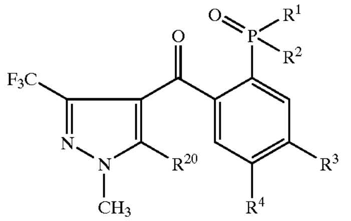

Extraordinary preference is also given to the compounds I1b12 (≡I where X=O; $R^3$ is attached in the 4-position, $R^4$ is attached in the 5-position and "P(═X)$R^1R^2$" is attached in the 2-position; Q=$Q^2$; $R^{21}$=$CH_2CH_3$ and $R^{22}$=$CF_3$), in particular to the compounds I1b12.n, where the variables $R^1$ to $R^4$ and $R^{20}$ (which in this case corresponds to $R^6$) are as defined in Table 1.

I1b12

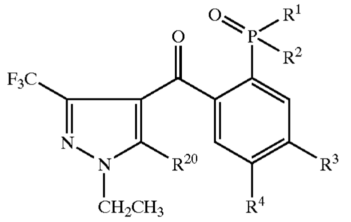

Extraordinary preference is also given to the compounds I1b13 (≡I where X=O; $R^3$ is attached in the 4-position, $R^4$ is attached in the 5-position and "P(═X)$R^1R^2$" is attached in the 2-position; Q=$Q^2$; $R^{21}$=$CH(CH_3)_2$ and $R^{22}$=$CF_3$), in particular to the compounds I1b13.n, where the variables $R^1$ to $R^4$ and $R^{20}$ (which in this case corresponds to $R^6$) are as defined in Table 1.

I1b13

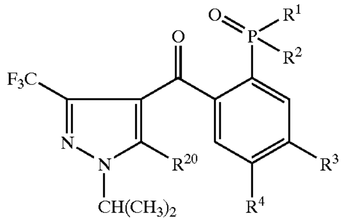

Extraordinary preference is also given to the compounds I1b14 (≡I where X=O; $R^3$ is attached in the 4-position, $R^4$ is attached in the 5-position and "P(═X)$R^1R^2$" is attached in the 2-position; Q=$Q^2$; $R^{21}$=$C(CH_3)_3$ and $R^{22}$=$CF_3$), in particular to the compounds I1b14.n, where the variables $R^1$ to $R^4$ and $R^{20}$ (which in this case corresponds to $R^6$) are as defined in Table 1.

I1b14

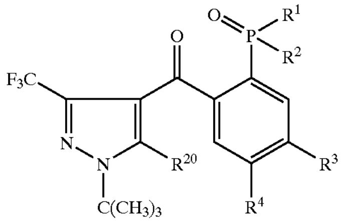

Extraordinary preference is also given to the compounds I1b15 (≡I where X=O; $R^3$ is attached in the 4-position, $R^4$ is attached in the 5-position and "P(═X)$R^1R^2$" is attached in the 2-position; Q=$Q^2$; $R^{21}$=$CH_2CF_3$ and $R^{22}$=$CF_3$), in particular to the compounds I1b15.n, where the variables $R^1$ to $R^4$ and $R^{20}$ (which in this case corresponds to $R^6$) are as defined in Table 1.

I1b15

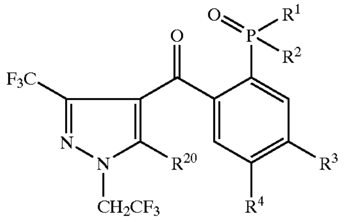

Extraordinary preference is also given to the compounds I2b1 (≡I where X=O; $R^3$ is attached in the 2-position, $R^4$ is attached in the 5-position and "P(═X)$R^1R^2$" is attached in the 4-position; Q=$Q^2$; $R^{21}$=$CH_3$ and $R^{22}$=H), in particular to the compounds I2b1.n, where the variables $R^1$ to $R^4$ and $R^{20}$ (which in this case corresponds to $R^6$) are as defined in Table 1.

I2b1

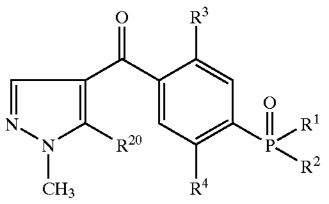

Extraordinary preference is also given to the compounds I2b2 (≡I where X=O; $R^3$ is attached in the 2-position, $R^4$ is attached in the 5-position and "P(═X)$R^1R^2$" is attached in the 4-position; Q=$Q^2$; $R^{21}$=$CH_2CH_3$ and $R^{22}$=H), in particular to the compounds I2b2.n, where the variables $R^1$ to $R^4$ and $R^{20}$ (which in this case corresponds to $R^6$) are as defined in Table 1.

I2b2

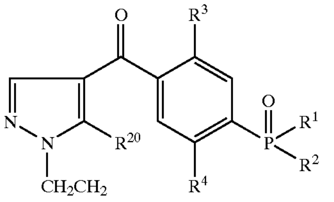

Extraordinary preference is also given to the compounds I2b3 ($\equiv$I where X=O; $R^3$ is attached in the 2-position, $R^4$ is attached in the 5-position and "P(=X)$R^1R^2$" is attached in the 4-position; Q=$Q^2$; $R^{21}$=$CH(CH_3)_2$ and $R^{22}$=H), in particular to the compounds I2b3.n, where the variables $R^1$ to $R^4$ and $R^{20}$ (which in this case corresponds to $R^6$) are as defined in Table 1.

I2b3

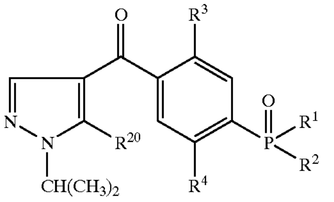

Extraordinary preference is also given to the compounds I2b4 ($\equiv$I where X=O; $R^3$ is attached in the 2-position, $R^4$ is attached in the 5-position and "P(=X)$R^1R^2$" is attached in the 4-position; Q=$Q^2$; $R^{21}$=$C(CH_3)_3$ and $R^{22}$=H), in particular to the compounds I2b4.n, where the variables $R^1$ to $R^4$ and $R^{20}$ (which in this case corresponds to $R^6$) are as defined in Table 1.

I2b4

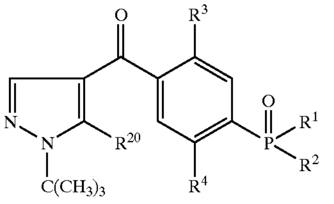

Extraordinary preference is also given to the compounds I2b5 ($\equiv$I where X=O; $R^3$ is attached in the 2-position, $R^4$ is attached in the 5-position and "P(=X)$R^1R^2$" is attached in the 4-position; Q=$Q^2$; $R^{21}$=$CH_2CF_3$ and $R^{22}$=H), in particular to the compounds I2b5.n, where the variables $R^1$ to $R^4$ and $R^{20}$ (which in this case corresponds to $R^6$) are as defined in Table 1.

I2b5

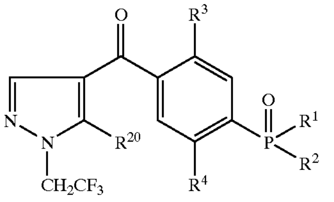

Extraordinary preference is also given to the compounds I2b6 ($\equiv$I where X=O; $R^3$ is attached in the 2-position, $R^4$ is attached in the 5-position and "P(=X)$R^1R^2$" is attached in the 4-position; Q=$Q^2$; $R^{21}$=$CH_3$ and $R^{22}$=$CH_3$), in particular to the compounds I2b6.n, where the variables $R^1$ to $R^4$ and $R^{20}$ (which in this case corresponds to $R^6$) are as defined in Table 1.

I2b6

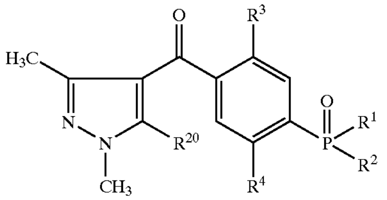

Extraordinary preference is also given to the compounds I2b7 ($\equiv$I where X=O; $R^3$ is attached in the 2-position, $R^4$ is attached in the 5-position and "P(=X)$R^1R^7$" is attached in the 24-position; Q=$Q^2$; $R^{21}$=$CH_2CH_3$ and $R^{22}$=$CH_3$), in particular to the compounds I2b7.n, where the variables $R^1$ to $R^4$ and $R^{20}$ (which in this case corresponds to $R^6$) are as defined in Table 1.

I2b7

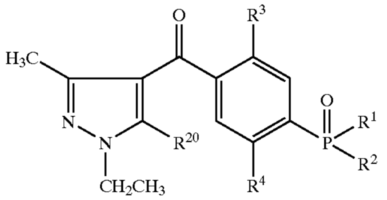

Extraordinary preference is also given to the compounds I2b8 ($\equiv$I where X=O; $R^3$ is attached in the 2-position, $R^4$ is attached in the 5-position and "P(=X)$R^1R^2$" is attached in the 4-position; Q=$Q^2$; $R^{21}$=$CH(CH_3)_2$ and $R^{22}$=$CH_3$), in particular to the compounds I2b8.n, where the variables $R^1$ to $R^4$ and $R^{20}$ (which in this case corresponds to $R^6$) are as defined in Table 1.

I2b8

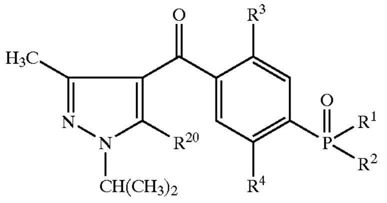

Extraordinary preference is also given to the compounds I1b9 ($\equiv$I where X=O; $R^3$ is attached in the 2-position, $R^4$ is attached in the 5-position and "P(=X)$R^1R^2$" is attached in the 4-position; Q=$Q^2$; $R^{21}$=$C(CH_3)_3$ and $R^{22}$=$CH_3$), in particular to the compounds I2b9.n, where the variables $R^1$ to $R^4$ and $R^{20}$ (which in this case corresponds to $R^6$) are as defined in Table 1.

I2b9

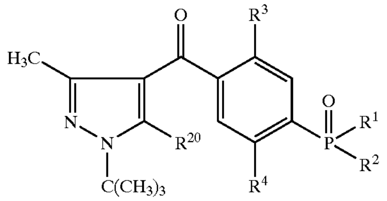

Extraordinary preference is also given to the compounds I2b10 (≡I where X=O; $R^3$ is attached in the 2-position, $R^4$ is attached in the 5-position and "P(=X)$R^1R^2$" is attached in the 4-position; Q=$Q^2$; $R^{21}$=$CH_2CF_3$ and $R^{22}$=$CH_3$), in particular to the compounds I2b10.n, where the variables $R^1$ to $R^4$ and $R^{20}$ (which in this case corresponds to $R^6$) are as defined in Table 1.

I2b10

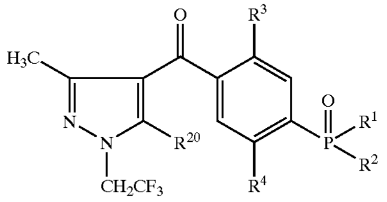

Extraordinary preference is also given to the compounds I2b11 (≡I where X=O; $R^3$ is attached in the 2-position, $R^4$ is attached in the 5-position and "P(=X)$R^1R^2$" is attached in the 4-position; Q=$Q^2$; $R^{21}$=$CH_3$ and $R^{22}$=$CF_3$), in particular to the compounds I2b11.n, where the variables $R^1$ to $R^4$ and $R^{20}$ (which in this case corresponds to $R^6$) are as defined in Table 1.

I2b11

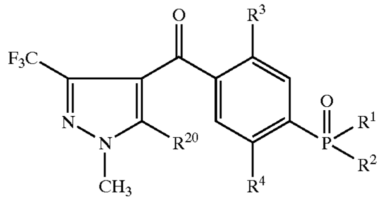

Extraordinary preference is also given to the compounds I2b12 (≡I where X=O; $R^3$ is attached in the 2-position, $R^4$ is attached in the 5-position and "P(=X)$R^1R^2$" is attached in the 4-position; Q=$Q^2$; $R^{21}$=$CH_2CH_3$ and $R^{22}$=$CF_3$), in particular to the compounds I2b12.n, where the variables $R^1$ to $R^4$ and $R^{20}$ (which in this case corresponds to $R^6$) are as defined in Table 1.

I2b12

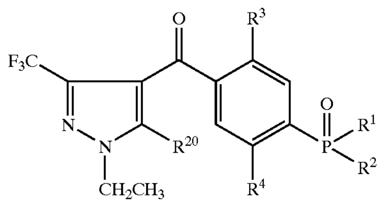

Extraordinary preference is also given to the compounds I2b13(≡I where X=O; $R^3$ is attached in the 2-position, $R^4$ is attached in the 5-position and "P(=X)$R^1R^2$" is attached in the 4-position; Q=$Q^2$; $R^{21}$=$CH(CH_3)_2$ and $R^{22}$=$CF_3$), in particular to the compounds I2b13.n, where the variables $R^1$ to $R^4$ and $R^{20}$ (which in this case corresponds to $R^6$) are as defined in Table 1.

I2b13

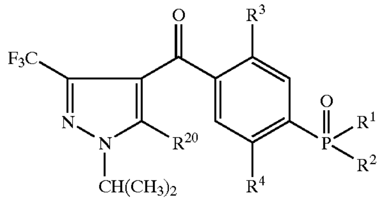

Extraordinary preference is also given to the compounds I1b14 (≡I where X=O; $R^3$ is attached in the 2-position, $R^4$ is attached in the 5-position and "P(=X)$R^1R^2$" is attached in the 4-position; Q=$Q^2$; $R^{21}$=$C(CH_3)_3$ and $R^{22}$=$CF_3$), in particular to the compounds I2b14.n, where the variables $R^1$ to $R^4$ and $R^{20}$ (which in this case corresponds to $R^6$) are as defined in Table 1.

I2b14

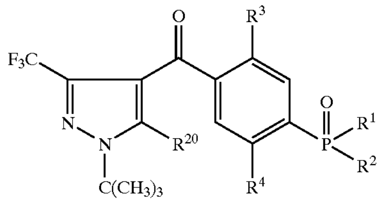

Extraordinary preference is also given to the compounds I2b15 (≡I where X=O; $R^3$ is attached in the 2-position, $R^4$ is attached in the 5-position and "P(=X)$R^1R^2$" is attached in the 4-position; Q=$Q^2$; $R^{21}$=$CH_2CF_3$ and $R^{22}$=$CF_3$), in particular to the compounds I2b15.n, where the variables $R^1$ to $R^4$ and $R^{20}$ (which in this case corresponds to $R^6$) are as defined in Table 1.

I2b15

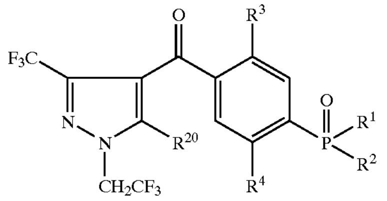

Extraordinary preference is also given to the compounds I1c1 (≡I where X=O; $R^3$ is attached in the 4-position and "P(=X)$R^1R^2$" is attached in the 2-position; Q=$Q^3$; 1=0, $R^{23}$=cyclopropyl and $R^{24}$=H), in particular to the compounds Ic1.n, where the variables $R^1$ to $R^3$ are as defined in Table 2.

I1c1

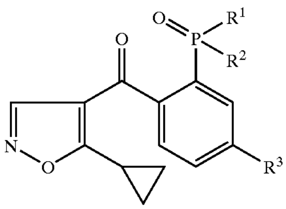

TABLE 2

| n | $R^1$ | $R^2$ | $R^3$ |
|---|---|---|---|
| 1 | H | H | H |
| 2 | $CH_3$ | $CH_3$ | H |
| 3 | $CH_2CH_3$ | $CH_2CH_3$ | H |
| 4 | $CH_2CH_2CH_3$ | $CH_2CH_2CH_3$ | H |
| 5 | $OCH_3$ | $OCH_3$ | H |
| 6 | $OCH_2CH_3$ | $OCH_2CH_3$ | H |
| 7 | $OCH_2CH_2CH_3$ | $OCH_2CH_2CH_3$ | H |
| 8 | $SCH_3$ | $SCH_3$ | H |
| 9 | $SCH_2CH_3$ | $SCH_2CH_3$ | H |
| 10 | $N(CH_3)_2$ | $N(CH_3)_2$ | H |
| 11 | $N(CH_2CH_3)_2$ | $N(CH_2CH_3)_2$ | H |
| 12 | $N(CH_3)(CH_2CH_3)$ | $N(CH_3)(CH_2CH_3)$ | H |
| 13 | $O-(CH_2CH_2)-O$ | | H |
| 14 | $O-(CH_2CH_2CH_2)-O$ | | H |
| 15 | $S-(CH_2CH_2)-S$ | | H |
| 16 | $S-(CH_2CH_2CH_2)-S$ | | H |
| 17 | $-(CH_2)_4-$ | | H |
| 18 | $-(CH_2)_5-$ | | H |
| 19 | H | H | $NO_2$ |
| 20 | $CH_3$ | $CH_3$ | $NO_2$ |
| 21 | $CH_2CH_3$ | $CH_2CH_3$ | $NO_2$ |
| 22 | $CH_2CH_2CH_3$ | $CH_2CH_2CH_3$ | $NO_2$ |
| 23 | $OCH_3$ | $OCH_3$ | $NO_2$ |
| 24 | $OCH_2CH_3$ | $OCH_2CH_3$ | $NO_2$ |
| 25 | $OCH_2CH_2CH_3$ | $OCH_2CH_2CH_3$ | $NO_2$ |
| 26 | $SCH_3$ | $SCH_3$ | $NO_2$ |
| 27 | $SCH_2CH_3$ | $SCH_2CH_3$ | $NO_2$ |
| 28 | $N(CH_3)_2$ | $N(CH_3)_2$ | $NO_2$ |
| 29 | $N(CH_2CH_3)_2$ | $N(CH_2CH_3)_2$ | $NO_2$ |
| 30 | $N(CH_3)(CH_2CH_3)$ | $N(CH_3)(CH_2CH_3)$ | $NO_2$ |
| 31 | $O-(CH_2CH_2)-O$ | | $NO_2$ |
| 32 | $O-(CH_2CH_2CH_2)-O$ | | $NO_2$ |
| 33 | $S-(CH_2CH_2)-S$ | | $NO_2$ |
| 34 | $S-(CH_2CH_2CH_2)-S$ | | $NO_2$ |
| 35 | $-(CH_2)_4-$ | | $NO_2$ |
| 36 | $-(CH_2)_5-$ | | $NO_2$ |
| 37 | H | H | CN |
| 38 | $CH_3$ | $CH_3$ | CN |
| 39 | $CH_2CH_3$ | $CH_2CH_3$ | CN |
| 40 | $CH_2CH_2CH_3$ | $CH_2CH_2CH_3$ | CN |
| 41 | $OCH_3$ | $OCH_3$ | CN |
| 42 | $OCH_2CH_3$ | $OCH_2CH_3$ | CN |
| 43 | $OCH_2CH_2CH_3$ | $OCH_2CH_2CH_3$ | CN |
| 44 | $SCH_3$ | $SCH_3$ | CN |
| 45 | $SCH_2CH_3$ | $SCH_2CH_3$ | CN |
| 46 | $N(CH_3)_2$ | $N(CH_3)_2$ | CN |
| 47 | $N(CH_2CH_3)_2$ | $N(CH_2CH_3)_2$ | CN |
| 48 | $N(CH_3)(CH_2CH_3)$ | $N(CH_3)(CH_2CH_3)$ | CN |
| 49 | $O-(CH_2CH_2)-O$ | | CN |
| 50 | $O-(CH_2CH_2CH_2)-O$ | | CN |
| 51 | $S-(CH_2CH_2)-S$ | | CN |
| 52 | $S-(CH_2CH_2CH_2)-S$ | | CN |
| 53 | $-(CH_2)_4-$ | | CN |
| 54 | $-(CH_2)_5-$ | | CN |
| 55 | H | H | F |
| 56 | $CH_3$ | $CH_3$ | F |
| 57 | $CH_2CH_3$ | $CH_2CH_3$ | F |
| 58 | $CH_2CH_2CH_3$ | $CH_2CH_2CH_3$ | F |
| 59 | $OCH_3$ | $OCH_3$ | F |
| 60 | $OCH_2CH_3$ | $OCH_2CH_3$ | F |
| 61 | $OCH_2CH_2CH_3$ | $OCH_2CH_2CH_3$ | F |
| 62 | $SCH_3$ | $SCH_3$ | F |
| 63 | $SCH_2CH_3$ | $SCH_2CH_3$ | F |
| 64 | $N(CH_3)_2$ | $N(CH_3)_2$ | F |
| 65 | $N(CH_2CH_3)_2$ | $N(CH_2CH_3)_2$ | F |
| 66 | $N(CH_3)(CH_2CH_3)$ | $N(CH_3)(CH_2CH_3)$ | F |
| 67 | $O-(CH_2CH_2)-O$ | | F |
| 68 | $O-(CH_2CH_2CH_2)-O$ | | F |
| 69 | $S-(CH_2CH_2)-S$ | | F |
| 70 | $S-(CH_2CH_2CH_2)-S$ | | F |
| 71 | $-(CH_2)_4-$ | | F |
| 72 | $-(CH_2)_5-$ | | F |
| 73 | H | H | Cl |
| 74 | $CH_3$ | $CH_3$ | Cl |
| 75 | $CH_2CH_3$ | $CH_2CH_3$ | Cl |
| 76 | $CH_2CH_2CH_3$ | $CH_2CH_2CH_3$ | Cl |
| 77 | $OCH_3$ | $OCH_3$ | Cl |

TABLE 2-continued

| n | $R^1$ | $R^2$ | $R^3$ |
|---|---|---|---|
| 78 | $OCH_2CH_3$ | $OCH_2CH_3$ | Cl |
| 79 | $OCH_2CH_2CH_3$ | $OCH_2CH_2CH_3$ | Cl |
| 80 | $SCH_3$ | $SCH_3$ | Cl |
| 81 | $SCH_2CH_3$ | $SCH_2CH_3$ | Cl |
| 82 | $N(CH_3)_2$ | $N(CH_3)_2$ | Cl |
| 83 | $N(CH_2CH_3)_2$ | $N(CH_2CH_3)_2$ | Cl |
| 84 | $N(CH_3)(CH_2CH_3)$ | $N(CH_3)(CH_2CH_3)$ | Cl |
| 85 | $O-(CH_2CH_2)-O$ | | Cl |
| 86 | $O-(CH_2CH_2CH_2)-O$ | | Cl |
| 87 | $S-(CH_2CH_2)-S$ | | Cl |
| 88 | $S-(CH_2CH_2CH_2)-S$ | | Cl |
| 89 | $-(CH_2)_4-$ | | Cl |
| 90 | $-(CH_2)_5-$ | | Cl |
| 91 | H | H | Br |
| 92 | $CH_3$ | $CH_3$ | Br |
| 93 | $CH_2CH_3$ | $CH_2CH_3$ | Br |
| 94 | $CH_2CH_2CH_3$ | $CH_2CH_2CH_3$ | Br |
| 95 | $OCH_3$ | $OCH_3$ | Br |
| 96 | $OCH_2CH_3$ | $OCH_2CH_3$ | Br |
| 97 | $OCH_2CH_2CH_3$ | $OCH_2CH_2CH_3$ | Br |
| 98 | $SCH_3$ | $SCH_3$ | Br |
| 99 | $SCH_2CH_3$ | $SCH_2CH_3$ | Br |
| 100 | $N(CH_3)_2$ | $N(CH_3)_2$ | Br |
| 101 | $N(CH_2CH_3)_2$ | $N(CH_2CH_3)_2$ | Br |
| 102 | $N(CH_3)(CH_2CH_3)$ | $N(CH_3)(CH_2CH_3)$ | Br |
| 103 | $O-(CH_2CH_2)-O$ | | Br |
| 104 | $O-(CH_2CH_2CH_2)-O$ | | Br |
| 105 | $S-(CH_2CH_2)-S$ | | Br |
| 106 | $S-(CH_2CH_2CH_2)-S$ | | Br |
| 107 | $-(CH_2)_4-$ | | Br |
| 108 | $-(CH_2)_5-$ | | Br |
| 109 | H | H | $CH_3$ |
| 110 | $CH_3$ | $CH_3$ | $CH_3$ |
| 111 | $CH_2CH_3$ | $CH_2CH_3$ | $CH_3$ |
| 112 | $CH_2CH_2CH_3$ | $CH_2CH_2CH_3$ | $CH_3$ |
| 113 | $OCH_3$ | $OCH_3$ | $CH_3$ |
| 114 | $OCH_2CH_3$ | $OCH_2CH_3$ | $CH_3$ |
| 115 | $OCH_2CH_2CH_3$ | $OCH_2CH_2CH_3$ | $CH_3$ |
| 116 | $SCH_3$ | $SCH_3$ | $CH_3$ |
| 117 | $SCH_2CH_3$ | $SCH_2CH_3$ | $CH_3$ |
| 118 | $N(CH_3)_2$ | $N(CH_3)_2$ | $CH_3$ |
| 119 | $N(CH_2CH_3)_2$ | $N(CH_2CH_3)_2$ | $CH_3$ |
| 120 | $N(CH_3)(CH_2CH_3)$ | $N(CH_3)(CH_2CH_3)$ | $CH_3$ |
| 121 | $O-(CH_2CH_2)-O$ | | $CH_3$ |
| 122 | $O-(CH_2CH_2CH_2)-O$ | | $CH_3$ |
| 123 | $S-(CH_2CH_2)-S$ | | $CH_3$ |
| 124 | $S-(CH_2CH_2CH_2)-S$ | | $CH_3$ |
| 125 | $-(CH_2)_4-$ | | $CH_3$ |
| 126 | $-(CH_2)_5-$ | | $CH_3$ |
| 127 | H | H | $CH_2CH_3$ |
| 128 | $CH_3$ | $CH_3$ | $CH_2CH_3$ |
| 129 | $CH_2CH_3$ | $CH_2CH_3$ | $CH_2CH_3$ |
| 130 | $CH_2CH_2CH_3$ | $CH_2CH_2CH_3$ | $CH_2CH_3$ |
| 131 | $OCH_3$ | $OCH_3$ | $CH_2CH_3$ |
| 132 | $OCH_2CH_3$ | $OCH_2CH_3$ | $CH_2CH_3$ |
| 133 | $OCH_2CH_2CH_3$ | $OCH_2CH_2CH_3$ | $CH_2CH_3$ |
| 134 | $SCH_3$ | $SCH_3$ | $CH_2CH_3$ |
| 135 | $SCH_2CH_3$ | $SCH_2CH_3$ | $CH_2CH_3$ |
| 136 | $N(CH_3)_2$ | $N(CH_3)_2$ | $CH_2CH_3$ |
| 137 | $N(CH_2CH_3)_2$ | $N(CH_2CH_3)_2$ | $CH_2CH_3$ |
| 138 | $N(CH_3)(CH_2CH_3)$ | $N(CH_3)(CH_2CH_3)$ | $CH_2CH_3$ |
| 139 | $O-(CH_2CH_2)-O$ | | $CH_2CH_3$ |
| 140 | $O-(CH_2CH_2CH_2)-O$ | | $CH_2CH_3$ |
| 141 | $S-(CH_2CH_2)-S$ | | $CH_2CH_3$ |
| 142 | $S-(CH_2CH_2CH_2)-S$ | | $CH_2CH_3$ |
| 143 | $-(CH_2)_4-$ | | $CH_2CH_3$ |
| 144 | $-(CH_2)_5-$ | | $CH_2CH_3$ |
| 145 | H | H | $CF_3$ |
| 146 | $CH_3$ | $CH_3$ | $CF_3$ |
| 147 | $CH_2CH_3$ | $CH_2CH_3$ | $CF_3$ |
| 148 | $CH_2CH_2CH_3$ | $CH_2CH_2CH_3$ | $CF_3$ |
| 149 | $OCH_3$ | $OCH_3$ | $CF_3$ |
| 150 | $OCH_2CH_3$ | $OCH_2CH_3$ | $CF_3$ |
| 151 | $OCH_2CH_2CH_3$ | $OCH_2CH_2CH_3$ | $CF_3$ |
| 152 | $SCH_3$ | $SCH_3$ | $CF_3$ |
| 153 | $SCH_2CH_3$ | $SCH_2CH_3$ | $CF_3$ |
| 154 | $N(CH_3)_2$ | $N(CH_3)_2$ | $CF_3$ |

TABLE 2-continued

| n | $R^1$ | $R^2$ | $R^3$ |
|---|---|---|---|
| 155 | $N(CH_2CH_3)_2$ | $N(CH_2CH_3)_2$ | $CF_3$ |
| 156 | $N(CH_3)(CH_2CH_3)$ | $N(CH_3)(CH_2CH_3)$ | $CF_3$ |
| 157 | $O—(CH_2CH_2)—O$ | | $CF_3$ |
| 158 | $O—(CH_2CH_2CH_2)—O$ | | $CF_3$ |
| 159 | $S—(CH_2CH_2)—S$ | | $CF_3$ |
| 160 | $S—(CH_2CH_2CH_2)—S$ | | $CF_3$ |
| 161 | $—(CH_2)_4—$ | | $CF_3$ |
| 162 | $—(CH_2)_5—$ | | $CF_3$ |
| 163 | H | H | $OCH_3$ |
| 164 | $CH_3$ | $CH_3$ | $OCH_3$ |
| 165 | $CH_2CH_3$ | $CH_2CH_3$ | $OCH_3$ |
| 166 | $CH_2CH_2CH_3$ | $CH_2CH_2CH_3$ | $OCH_3$ |
| 167 | $OCH_3$ | $OCH_3$ | $OCH_3$ |
| 168 | $OCH_2CH_3$ | $OCH_2CH_3$ | $OCH_3$ |
| 169 | $OCH_2CH_2CH_3$ | $OCH_2CH_2CH_3$ | $OCH_3$ |
| 170 | $SCH_3$ | $SCH_3$ | $OCH_3$ |
| 171 | $SCH_2CH_3$ | $SCH_2CH_3$ | $OCH_3$ |
| 172 | $N(CH_3)_2$ | $N(CH_3)_2$ | $OCH_3$ |
| 173 | $N(CH_2CH_3)_2$ | $N(CH_2CH_3)_2$ | $OCH_3$ |
| 174 | $N(CH_3)(CH_2CH_3)$ | $N(CH_3)(CH_2CH_3)$ | $OCH_3$ |
| 175 | $O—(CH_2CH_2)—O$ | | $OCH_3$ |
| 176 | $O—(CH_2CH_2CH_2)—O$ | | $OCH_3$ |
| 177 | $S—(CH_2CH_2)—S$ | | $OCH_3$ |
| 178 | $S—(CH_2CH_2CH_2)—S$ | | $OCH_3$ |
| 179 | $—(CH_2)_4—$ | | $OCH_3$ |
| 180 | $—(CH_2)_5—$ | | $OCH_3$ |
| 181 | H | H | $OCH_2CH_3$ |
| 182 | $CH_3$ | $CH_3$ | $OCH_2CH_3$ |
| 183 | $CH_2CH_3$ | $CH_2CH_3$ | $OCH_2CH_3$ |
| 184 | $CH_2CH_2CH_3$ | $CH_2CH_2CH_3$ | $OCH_2CH_3$ |
| 185 | $OCH_3$ | $OCH_3$ | $OCH_2CH_3$ |
| 186 | $OCH_2CH_3$ | $OCH_2CH_3$ | $OCH_2CH_3$ |
| 187 | $OCH_2CH_2CH_3$ | $OCH_2CH_2CH_3$ | $OCH_2CH_3$ |
| 188 | $SCH_3$ | $SCH_3$ | $OCH_2CH_3$ |
| 189 | $SCH_2CH_3$ | $SCH_2CH_3$ | $OCH_2CH_3$ |
| 190 | $N(CH_3)_2$ | $N(CH_3)_2$ | $OCH_2CH_3$ |
| 191 | $N(CH_2CH_3)_2$ | $N(CH_2CH_3)_2$ | $OCH_2CH_3$ |
| 192 | $N(CH_3)(CH_2CH_3)$ | $N(CH_3)(CH_2CH_3)$ | $OCH_2CH_3$ |
| 193 | $O—(CH_2CH_2)—O$ | | $OCH_2CH_3$ |
| 194 | $O—(CH_2CH_2CH_2)—O$ | | $OCH_2CH_3$ |
| 195 | $S—(CH_2CH_2)—S$ | | $OCH_2CH_3$ |
| 196 | $S—(CH_2CH_2CH_2)—S$ | | $OCH_2CH_3$ |
| 197 | $—(CH_2)_4—$ | | $OCH_2CH_3$ |
| 198 | $—(CH_2)_5—$ | | $OCH_2CH_3$ |
| 199 | H | H | $SCH_3$ |
| 200 | $CH_3$ | $CH_3$ | $SCH_3$ |
| 201 | $CH_2CH_3$ | $CH_2CH_3$ | $SCH_3$ |
| 202 | $CH_2CH_2CH_3$ | $CH_2CH_2CH_3$ | $SCH_3$ |
| 203 | $OCH_3$ | $OCH_3$ | $SCH_3$ |
| 204 | $OCH_2CH_3$ | $OCH_2CH_3$ | $SCH_3$ |
| 205 | $OCH_2CH_2CH_3$ | $OCH_2CH_2CH_3$ | $SCH_3$ |
| 206 | $SCH_3$ | $SCH_3$ | $SCH_3$ |
| 207 | $SCH_2CH_3$ | $SCH_2CH_3$ | $SCH_3$ |
| 208 | $N(CH_3)_2$ | $N(CH_3)_2$ | $SCH_3$ |
| 209 | $N(CH_2CH_3)_2$ | $N(CH_2CH_3)_2$ | $SCH_3$ |
| 210 | $N(CH_3)(CH_2CH_3)$ | $N(CH_3)(CH_2CH_3)$ | $SCH_3$ |
| 211 | $O—(CH_2CH_2)—O$ | | $SCH_3$ |
| 212 | $O—(CH_2CH_2CH_2)—O$ | | $SCH_3$ |
| 213 | $S—(CH_2CH_2)—S$ | | $SCH_3$ |
| 214 | $S—(CH_2CH_2CH_2)—S$ | | $SCH_3$ |
| 215 | $—(CH_2)_4—$ | | $SCH_3$ |
| 216 | $—(CH_2)_5—$ | | $SCH_3$ |
| 217 | H | H | $SO_2CH_3$ |
| 218 | $CH_3$ | $CH_3$ | $SO_2CH_3$ |
| 219 | $CH_2CH_3$ | $CH_2CH_3$ | $SO_2CH_3$ |
| 220 | $CH_2CH_2CH_3$ | $CH_2CH_2CH_3$ | $SO_2CH_3$ |
| 221 | $OCH_3$ | $OCH_3$ | $SO_2CH_3$ |
| 222 | $OCH_2CH_3$ | $OCH_2CH_3$ | $SO_2CH_3$ |
| 223 | $OCH_2CH_2CH_3$ | $OCH_2CH_2CH_3$ | $SO_2CH_3$ |
| 224 | $SCH_3$ | $SCH_3$ | $SO_2CH_3$ |
| 225 | $SCH_2CH_3$ | $SCH_2CH_3$ | $SO_2CH_3$ |
| 226 | $N(CH_3)_2$ | $N(CH_3)_2$ | $SO_2CH_3$ |
| 227 | $N(CH_2CH_3)_2$ | $N(CH_2CH_3)_2$ | $SO_2CH_3$ |
| 228 | $N(CH_3)(CH_2CH_3)$ | $N(CH_3)(CH_2CH_3)$ | $SO_2CH_3$ |
| 229 | $O—(CH_2CH_2)—O$ | | $SO_2CH_3$ |
| 230 | $O—(CH_2CH_2CH_2)—O$ | | $SO_2CH_3$ |
| 231 | $S—(CH_2CH_2)—S$ | | $SO_2CH_3$ |

TABLE 2-continued

| n | $R^1$ | $R^2$ | $R^3$ |
|---|---|---|---|
| 232 | $S—(CH_2CH_2CH_2)—S$ | | $SO_2CH_3$ |
| 233 | $—(CH_2)_4—$ | | $SO_2CH_3$ |
| 234 | $—(CH_2)_5—$ | | $SO_2CH_3$ |
| 235 | H | H | $PO(OCH_3)_2$ |
| 236 | $CH_3$ | $CH_3$ | $PO(OCH_3)_2$ |
| 237 | $CH_2CH_3$ | $CH_2CH_3$ | $PO(OCH_3)_2$ |
| 238 | $CH_2CH_2CH_3$ | $CH_2CH_2CH_3$ | $PO(OCH_3)_2$ |
| 239 | $OCH_3$ | $OCH_3$ | $PO(OCH_3)_2$ |
| 240 | $OCH_2CH_3$ | $OCH_2CH_3$ | $PO(OCH_3)_2$ |
| 241 | $OCH_2CH_2CH_3$ | $OCH_2CH_2CH_3$ | $PO(OCH_3)_2$ |
| 242 | $SCH_3$ | $SCH_3$ | $PO(OCH_3)_2$ |
| 243 | $SCH_2CH_3$ | $SCH_2CH_3$ | $PO(OCH_3)_2$ |
| 244 | $N(CH_3)_2$ | $N(CH_3)_2$ | $PO(OCH_3)_2$ |
| 245 | $N(CH_2CH_3)_2$ | $N(CH_2CH_3)_2$ | $PO(OCH_3)_2$ |
| 246 | $N(CH_3)(CH_2CH_3)$ | $N(CH_3)(CH_2CH_3)$ | $PO(OCH_3)_2$ |
| 247 | $O—(CH_2CH_2)—O$ | | $PO(OCH_3)_2$ |
| 248 | $O—(CH_2CH_2CH_2)—O$ | | $PO(OCH_3)_2$ |
| 249 | $S—(CH_2CH_2)—S$ | | $PO(OCH_3)_2$ |
| 250 | $S—(CH_2CH_2CH_2)—S$ | | $PO(OCH_3)_2$ |
| 251 | $—(CH_2)_4—$ | | $PO(OCH_3)_2$ |
| 252 | $—(CH_2)_5—$ | | $PO(OCH_3)_2$ |
| 253 | H | H | $PO(OCH_2CH_3)_2$ |
| 254 | $CH_3$ | $CH_3$ | $PO(OCH_2CH_3)_2$ |
| 255 | $CH_2CH_3$ | $CH_2CH_3$ | $PO(OCH_2CH_3)_2$ |
| 256 | $CH_2CH_2CH_3$ | $CH_2CH_2CH_3$ | $PO(OCH_2CH_3)_2$ |
| 257 | $OCH_3$ | $OCH_3$ | $PO(OCH_2CH_3)_2$ |
| 258 | $OCH_2CH_3$ | $OCH_2CH_3$ | $PO(OCH_2CH_3)_2$ |
| 259 | $OCH_2CH_2CH_3$ | $OCH_2CH_2CH_3$ | $PO(OCH_2CH_3)_2$ |
| 260 | $SCH_3$ | $SCH_3$ | $PO(OCH_2CH_3)_2$ |
| 261 | $SCH_2CH_3$ | $SCH_2CH_3$ | $PO(OCH_2CH_3)_2$ |
| 262 | $N(CH_3)_2$ | $N(CH_3)_2$ | $PO(OCH_2CH_3)_2$ |
| 263 | $N(CH_2CH_3)_2$ | $N(CH_2CH_3)_2$ | $PO(OCH_2CH_3)_2$ |
| 264 | $N(CH_3)(CH_2CH_3)$ | $N(CH_3)(CH_2CH_3)$ | $PO(OCH_2CH_3)_2$ |
| 265 | $O—(CH_2CH_2)—O$ | | $PO(OCH_2CH_3)_2$ |
| 266 | $O—(CH_2CH_2CH_2)—O$ | | $PO(OCH_2CH_3)_2$ |
| 267 | $S—(CH_2CH_2)—S$ | | $PO(OCH_2CH_3)_2$ |
| 268 | $S—(CH_2CH_2CH_2)—S$ | | $PO(OCH_2CH_3)_2$ |
| 269 | $—(CH_2)_4—$ | | $PO(OCH_2CH_3)_2$ |
| 270 | $—(CH_2)_5—$ | | $PO(OCH_2CH_3)_2$ |
| 271 | H | H | $PO(CH_3)_2$ |
| 272 | $CH_3$ | $CH_3$ | $PO(CH_3)_2$ |
| 273 | $CH_2CH_3$ | $CH_2CH_3$ | $PO(CH_3)_2$ |
| 274 | $CH_2CH_2CH_3$ | $CH_2CH_2CH_3$ | $PO(CH_3)_2$ |
| 275 | $OCH_3$ | $OCH_3$ | $PO(CH_3)_2$ |
| 276 | $OCH_2CH_3$ | $OCH_2CH_3$ | $PO(CH_3)_2$ |
| 277 | $OCH_2CH_2CH_3$ | $OCH_2CH_2CH_3$ | $PO(CH_3)_2$ |
| 278 | $SCH_3$ | $SCH_3$ | $PO(CH_3)_2$ |
| 279 | $SCH_2CH_3$ | $SCH_2CH_3$ | $PO(CH_3)_2$ |
| 280 | $N(CH_3)_2$ | $N(CH_3)_2$ | $PO(CH_3)_2$ |
| 281 | $N(CH_2CH_3)_2$ | $N(CH_2CH_3)_2$ | $PO(CH_3)_2$ |
| 282 | $N(CH_3)(CH_2CH_3)$ | $N(CH_3)(CH_2CH_3)$ | $PO(CH_3)_2$ |
| 283 | $O—(CH_2CH_2)—O$ | | $PO(CH_3)_2$ |
| 284 | $O—(CH_2CH_2CH_2)—O$ | | $PO(CH_3)_2$ |
| 285 | $S—(CH_2CH_2)—S$ | | $PO(CH_3)_2$ |
| 286 | $S—(CH_2CH_2CH_2)—S$ | | $PO(CH_3)_2$ |
| 287 | $—(CH_2)_4—$ | | $PO(CH_3)_2$ |
| 288 | $—(CH_2)_5—$ | | $PO(CH_3)_2$ |
| 289 | H | H | $PO(CH_2CH_3)_2$ |
| 290 | $CH_3$ | $CH_3$ | $PO(CH_2CH_3)_2$ |
| 291 | $CH_2CH_3$ | $CH_2CH_3$ | $PO(CH_2CH_3)_2$ |
| 292 | $CH_2CH_2CH_3$ | $CH_2CH_2CH_3$ | $PO(CH_2CH_3)_2$ |
| 293 | $OCH_3$ | $OCH_3$ | $PO(CH_2CH_3)_2$ |
| 294 | $OCH_2CH_3$ | $OCH_2CH_3$ | $PO(CH_2CH_3)_2$ |
| 295 | $OCH_2CH_2CH_3$ | $OCH_2CH_2CH_3$ | $PO(CH_2CH_3)_2$ |
| 296 | $SCH_3$ | $SCH_3$ | $PO(CH_2CH_3)_2$ |
| 297 | $SCH_2CH_3$ | $SCH_2CH_3$ | $PO(CH_2CH_3)_2$ |
| 298 | $N(CH_3)_2$ | $N(CH_3)_2$ | $PO(CH_2CH_3)_2$ |
| 299 | $N(CH_2CH_3)_2$ | $N(CH_2CH_3)_2$ | $PO(CH_2CH_3)_2$ |
| 300 | $N(CH_3)(CH_2CH_3)$ | $N(CH_3)(CH_2CH_3)$ | $PO(CH_2CH_3)_2$ |
| 301 | $O—(CH_2CH_2)—O$ | | $PO(CH_2CH_3)_2$ |
| 302 | $O—(CH_2CH_2CH_2)—O$ | | $PO(CH_2CH_3)_2$ |
| 303 | $S—(CH_2CH_2)—S$ | | $PO(CH_2CH_3)_2$ |
| 304 | $S—(CH_2CH_2CH_2)—S$ | | $PO(CH_2CH_3)_2$ |
| 305 | $—(CH_2)_4—$ | | $PO(CH_2CH_3)_2$ |
| 306 | $—(CH_2)_5—$ | | $PO(CH_2CH_3)_2$ |

Extraordinary preference is also given to the compounds I1c2 (≡I where X=O; $R^3$ is attached in the 4-position, $R^4$ in the 5-position and "P(=X)$R^1R^2$" in the 2-position; Q=$Q^3$; $R^4$=$CH_3$, $R^{23}$=cyclopropyl and $R^{24}$=H), in particular to the compounds I1c2.n, where the variables $R^1$ to $R^3$ are as defined in Table 2.

I1c2

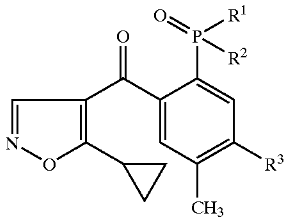

Extraordinary preference is also given to the compounds I1c3 (≡I where X=O; $R^3$ is attached in the 4-position, $R^4$ in the 5-position and "P(=X)$R^1R^2$" in the 2-position; Q=$Q^3$; $R^4$=Cl, $R^{23}$=cyclopropyl and $R^{24}$=H), in particular to the compounds I1c3.n, where the variables $R^1$ to $R^3$ are as defined in Table 2.

I1c3

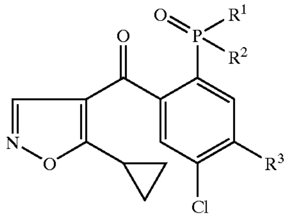

Extraordinary preference is also given to the compounds I1c4 (≡I where X=O; $R^3$ is attached in the 4-position, $R^4$ in the 5-position and "P(=X)$R^1R^2$" in the 2-position; Q=$Q^3$; $R^4$=Br, $R^{23}$=cyclopropyl and $R^{24}$=H), in particular to the compounds I1c4, where the variables $R^1$ to $R^3$ are as defined in Table 2.

I1c4

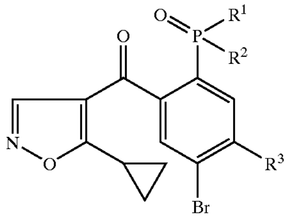

Extraordinary preference is also given to the compounds I2c1 (≡I where X=O; $R^3$ is attached in the 2-position and "P(=X)$R^1R^2$" is attached in the 4-position; Q=$Q^3$; 1=0; $R^{23}$=cyclopropyl and $R^{24}$=H), in particular to the compounds I2c1.n, where the variables $R^1$ to $R^3$ are as defined in Table 2.

I2c1

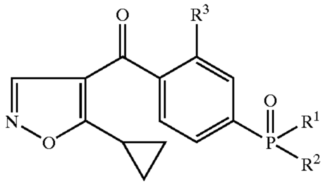

Extraordinary preference is also given to the compounds I2c2 (≡I where X=O; $R^3$ is attached in the 2-position, $R^4$ in the 5-position and "P(=X)$R^1R^2$" in the 4-position; Q=$Q^3$; $R^4$=$CH_3$, $R^{23}$=cyclopropyl and $R^{24}$=H), in particular to the compounds I2c2.n, where the variables $R^1$ to $R^3$ are as defined in Table 2.

I2c2

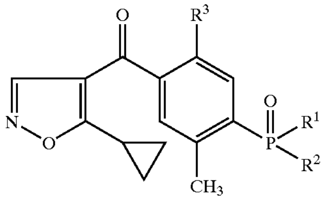

Extraordinary preference is also given to the compounds I2c3 (≡I where X=O; $R^3$ is attached in the 2-position, $R^4$ in the 5-position and "P(=X)$R^1R^2$" in the 2-position; Q=$Q^3$; $R^4$=Cl, $R^{23}$=cyclopropyl and $R^{24}$=H), in particular to the compounds I2c3.n, where the variables $R^1$ to $R^3$ are as defined in Table 2.

I2c3

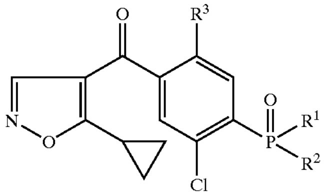

Extraordinary preference is also given to the compounds I2c4 (≡I where X=O; $R^3$ is attached in the 2-position, $R^4$ in the 5-position and "P(=X)$R^1R^2$" in the 4-position; Q=$Q^3$; $R^4$=Br, $R^{23}$=cyclopropyl and $R^{24}$=H), in particular to the compounds I2c4, where the variables $R^1$ to $R^3$ are as defined in Table 2.

I2c4

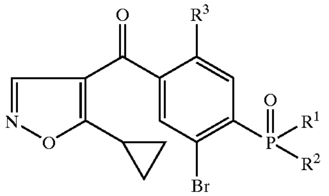

Extraordinary preference is also given to the compounds I1d1 (≡I where X=O; $R^3$ is attached in the 4-position and "P(=X)$R^1R^2$" is attached in the 2-position; Q=$Q^4$; 1=0; $R^{25}$=cyclopropyl), in particular to the compounds I1d1.n, where the variables $R^1$ to $R^3$ are as defined in Table 2.

I1d1

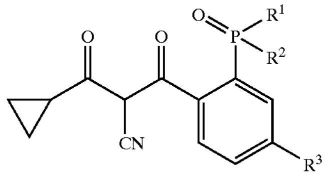

Extraordinary preference is also given to the compounds I1d2 (≡I where X=O; $R^3$ is attached in the 4-position, $R^4$ is attached in the 5-position and "P(=X)$R^1R^2$" is attached in the 2-position; Q=$Q^4$; $R^4$=$CH_3$, $R^{25}$=cyclopropyl), in particular to the compounds I1d2.n, where the variables $R^1$ to $R^3$ are as defined in Table 2.

I1d2

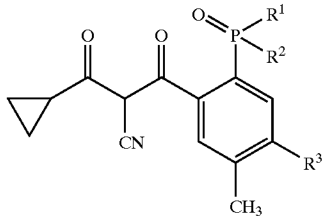

Extraordinary preference is also given to the compounds I1d3 (≡I where X=O; $R^3$ is attached in the 4-position, $R^4$ is attached in the 5-position and "P(=X)$R^1R^2$" is attached in the 2-position; Q=$Q^4$; $R^4$=Cl, $R^{25}$=cyclopropyl), in particular to the compounds I1d3.n, where the variables $R^1$ to $R^3$ are as defined in Table 2.

I1d3

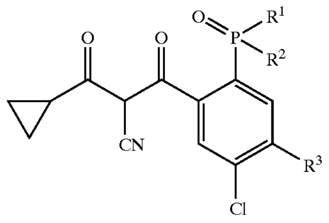

Extraordinary preference is also given to the compounds I1d4 (≡I where X=O; $R^3$ is attached in the 4-position, $R^4$ is attached in the 5-position and "P(=X)$R^1R^2$" is attached in the 2-position; Q=$Q^4$; $R^4$=Br, $R^{25}$=cyclopropyl), in particular to the compounds I1d4, where the variables $R^1$ to $R^3$ are as defined in Table 2.

I1d4

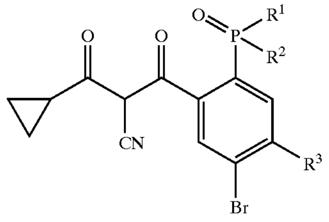

Extraordinary preference is also given to the compounds I2d1 (≡I where X=O; $R^3$ is attached in the 2-position and "P(=X)$R^1R^2$" is attached in the 4-position; Q=$Q^4$; 1=0; $R^{25}$=cyclopropyl), in particular to the compounds I2d1.n, where the variables $R^1$ to $R^3$ are as defined in Table 2.

I2d1

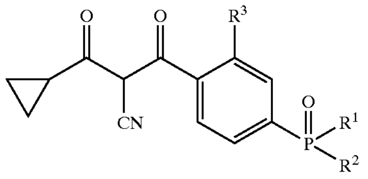

Extraordinary preference is also given to the compounds I2d2 (≡I where X=O; $R^3$ is attached in the 4-position, $R^4$ is attached in the 5-position and "P(=X)$R^1R^2$" is attached in the 2-position; Q=$Q^4$; $R^4$=$CH_3$, $R^{25}$=cyclopropyl), in particular to the compounds I2a2.n, where the variables $R^1$ to $R^3$ are as defined in Table 2.

I2d2

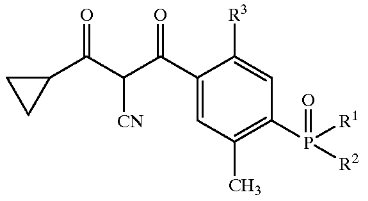

Extraordinary preference is also given to the compounds I2d3 (≡I where X=O; $R^3$ is attached in the 2-position, $R^4$ is attached in the 5-position and "P(=X)$R^1R^2$" is attached in the 2-position; Q=$Q^4$; $R^4$=Cl, $R^{25}$=cyclopropyl), in particular to the compounds I2d3.n, where the variables $R^1$ to $R^3$ are as defined in Table 2.

I2d3

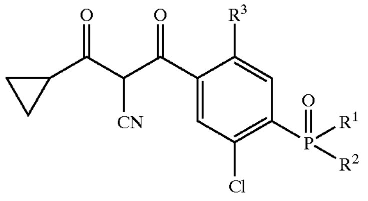

Extraordinary preference is also given to the compounds I2d4 (≡I where X=O; $R^3$ is attached in the 4-position, $R^4$ is attached in the 5-position and "P(=X)$R^1R^2$" is attached in the 2-position; Q=$Q^4$; $R^4$=Br, $R^{25}$=cyclopropyl), in particular to the compounds I2d4, where the variables $R^1$ to $R^3$ are as defined in Table 2.

I2d4

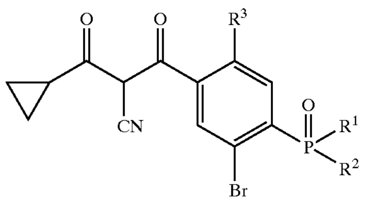

The phosphorus-containing benzoyl derivatives of the formula I can be obtained by different routes, for example by the following processes:

A. Preparation of compounds of the formula Ia where $R^6$=halogen by reaction of compounds of the formula Ia (≡I where $Q=Q^1$) where $R^6$=hydroxyl with halogenating agents:

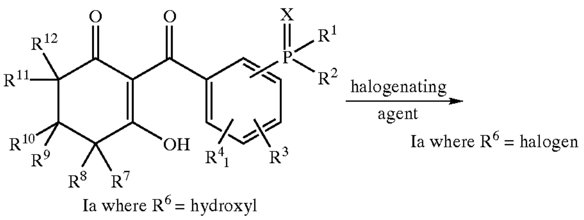

Suitable halogenating agents are, for example, phosgene, diphosgene, triphosgene, thionyl chloride, oxalyl chloride, phosphorus oxychloride, phosphorus pentachloride, mesyl chloride, chloromethylene-N,N-dimethylammonium chloride, oxalyl bromide, phosphorus oxybromide, etc.

The starting materials are generally employed in equimolar amounts. However, it may also be advantageous to employ an excess of one or the other component.

Suitable solvents are, for example, chlorinated hydrocarbons, such as methylene chloride or 1,2-dichloroethane, aromatic hydrocarbons, for example toluene, xylene or chlorobenzene, polar aprotic solvents, such as acetonitrile, dimethylformamide or dimethyl sulfoxide, or mixtures of these. However, it is also possible to carry out the reaction without a solvent.

In general, the reaction temperature is in the range from 0° C. to the boiling point of the reaction mixture.

Work-up can be carried out in a manner known per se to afford the product.

B. Preparation of compounds of the formula Ia (≡I where $Q=Q^1$) where $R^6=OR^{13}$, $OSO_2R^{14}$, $OPR^{15}R^{16}$, $OPOR^{15}R^{16}$ or $OPSR^{15}R^{16}$ by reaction of compounds of the formula Ia (≡I where $Q=Q^1$) where $R^6$=hydroxyl with alkylating, sulfonylating or phosphonylating agents IIα, IIβ, IIγ, IIδ or IIε.

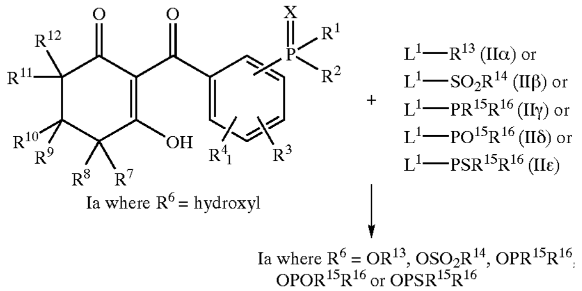

$L^1$ is a nucleophilically replaceable leaving group, such as halogen, for example chlorine or bromine, hetaryl, for example imidazolyl, carboxylate, for example acetate, or sulfonate, for example mesylate or triflate, etc.

The compounds of the formula IIα, IIβ, IIγ, IIδ or IIε can be employed directly, such as in the case of the carbonyl halides, or generated in situ, for example activated carboxylic acids (using carboxylic acid and dicyclohexylcarbodiimide, etc.).

The starting materials are generally employed in equimolar amounts. However, it may also be advantageous to employ an excess of one or the other component.

If appropriate, it may also be advantageous to carry out the reaction in the presence of a base. The reactants and the base are advantageously employed in equimolar amounts. In certain cases, an excess of base of, for example, 1.5 to 3 molar equivalents may be advantageous.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

The reaction temperature is generally in the range from 0° C. to the boiling point of the reaction mixture.

Work-up can be carried out in a manner known per se to afford the product.

C. Preparation of compounds of the formula Ia (≡I where $Q=Q^1$) where $R^6=OR^{13}$, $SR^{13}$, $POR^{15}R^{16}$, $NR^{17}R^{18}$, $ONR^{18}R^{19}$, N-bonded heterocyclyl or O-(N-bonded heterocyclyl) by reaction of compounds of the formula Ia (≡I where $Q=Q^1$) where $R^6$=halogen, $OSO_2R^{14}$ with compounds of the formula IIIα, IIIβ, IIIγ, IIIδ, IIIε, IIIη or IIIΘ, if appropriate in the presence of a base or with prior salt formation.

Ia where $R^6$ = halogen, $OSO_2R^{14}$ +
$HOR^{13}$ (IIIα) or
$HSR^{13}$ (IIIβ) or
$HPOR^{15}R^{16}$ (IIIγ) or
$HNR^{17}R^{18}$(IIIδ) or
$HONR^{18}R^{19}$ (IIIε) or
H(N-bonded heterocylyl (IIIη) or
H(ON-bonded heterocyclyl) (IIIϑ)

Ia where $R^6 = OR^{13}$, $SR^{13}$, $POR^{15}R^{16}$, $NR^{17}R^{18}$, $ONR^{17}R^{18}$, N-bonded heterocyclyl or ON-bonded heterocyclyl The starting materials are employed in equimolar amounts. However, it may also be advantageous to employ an excess of one or the other component.

If appropriate, it may also be advantageous to carry out the reaction in the presence of a base. The reactants and the base are advantageously employed in equimolar amounts. An excess of base of, for example, from 1.5 to 3 molar equivalents, based on Ia (≡I where $Q=Q^1$) where $R^6$=halogen, $OSO_2R^{14}$, may be advantageous in certain cases.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using sodium hydride or potassium tert-butoxide.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or mixtures of these.

In general, the reaction temperature is in the range from 0° C. to the boiling point of the reaction mixture.

Work-up can be carried out in a manner known per se to afford the product.

D. Preparation of compounds of the formula Ia (≡I where Q=$Q^1$) where $R^6$=$SOR^{14}$, $SO_2R^{14}$ by reaction of compounds of the formula Ia (≡I where Q=$Q^1$) where $R^6$=$SR^{14}$ with an oxidizing agent.

$$\text{Ia where } R^6 = SR^{14} \xrightarrow{\text{oxidizing agent}} \text{Ia where } R^6 = SOR^{14} \text{ or } SO_2R^{14}$$

Suitable oxidizing agents are, for example, m-chloroperbenzoic acid, peroxyacetic acid, trifluoroperoxyacetic acid, hydrogen peroxide, if appropriate in the presence of a catalyst, such as tungstate.

The starting materials are generally employed in equimolar amounts. However, it may also be advantageous to employ an excess of one or the other component.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile or dimethylformamide, or esters, such as ethyl acetate, or mixtures of these.

In general, the reaction temperature is in the range from 0° C. to the boiling point of the reaction mixture.

Work-up can be carried out in a manner known per se to afford the product.

E. Preparation of compounds of the formula Ia (≡I where Q=$Q^1$) where $R^6$=OH by reaction of an activated phosphorus-containing benzoic acid of the formula IVα or a phosphorus-containing benzoic acid IVβ, which is preferably activated in situ, with a cyclohexanedione of the formula V to give the acylation product, followed by rearrangement.

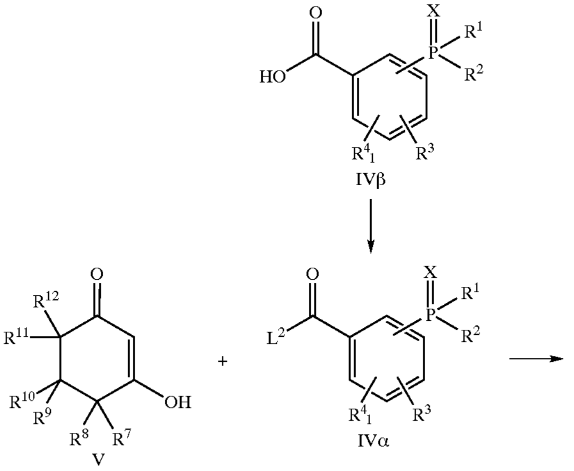

IVβ

V

IVα

-continued

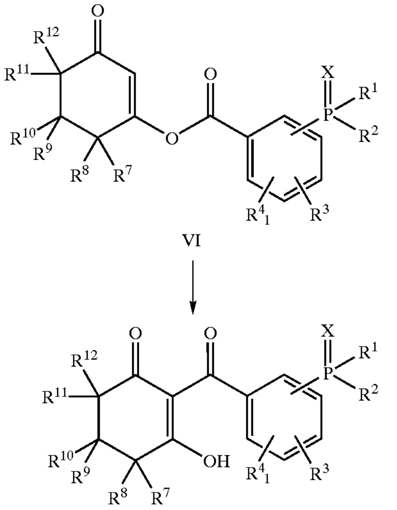

VI

Ia where $R^6$ = OH $L^2$ is a nucleophilically replaceable leaving group, such as halogen, for example bromine or chlorine, hetaryl, for example imidazolyl or pyridyl, carboxylate, for example acetate or trifluoroacetate, etc.

The activated benzoic acid IV can be employed directly, such as in the case of the benzoyl halides, or generated in situ, for example using dicyclohexylcarbodiimide, triphenylphosphine/azodicarboxylic acid ester, 2-pyridine disulfide/triphenylphosphine, carbonyldiimidazole, etc.

If appropriate, it may be advantageous to carry out the acylation reaction in the presence of a base. The reactants and the auxiliary base are advantageously employed in equimolar amounts. A slight excess of auxiliary base, for example from 1. to 1.5 molar equivalents, based on IVα or IVβ, may be advantageous in certain cases.

Suitable auxiliary bases are tertiary alkylamines, pyridine or alkali metal carbonates. Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

If the activated carboxylic acid component used is a phosphorus-containing benzoyl halide, it may be advantageous to cool the reaction mixture to 0–10° C. when adding this reaction partner. The mixture is subsequently stirred at 20–100° C., preferably at 25–50° C., until the reaction has gone to completion. Work-up is carried out in a customary manner, for example by pouring the reaction mixture into water and extracting the product of value. Solvents which are suitable for this purpose are, in particular, methylene chloride, diethyl ether and ethyl acetate. The organic phase is dried and the solvent is removed, and the crude ester can then be employed for the rearrangement without further purification.

The rearrangement of the esters VI to the compounds of the formula Ia is advantageously carried out at 20–100° C. in a solvent and in the presence of a base and, if appropriate, using a cyano compound as catalyst.

Suitable solvents are, for example, acetonitrile, methylene chloride, 1,2-dichloroethane, dioxane, ethyl acetate, toluene or mixtures of these. Preferred solvents are acetonitrile and dioxane.

Suitable bases are tertiary amines, such as triethylamine, aromatic amines, such as pyridine, or alkali metal carbonates, such as sodium carbonate or potassium carbonate, which are preferably employed in equimolar amounts or in up to four-fold excess, based on the ester. Preference is given to using triethylamine or alkali metal carbonate, preferably in twice the equimolar amount, based on the ester.

Suitable cyano compounds are inorganic cyanides, such as sodium cyanide or potassium cyanide, and organic cyano compounds, such as acetone cyanohydrin or trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent, based on the ester.

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or the mixture is extracted with methylene chloride or ethyl acetate and the extract is dried and concentrated.

F. Preparation of compounds of the formula Ib (≡I where $Q=Q^2$) where $R^{20}$=halogen by reaction of compounds of the formula Ib (≡I where $Q=Q^2$) where $R^{20}$=hydroxyl with halogenating agents:

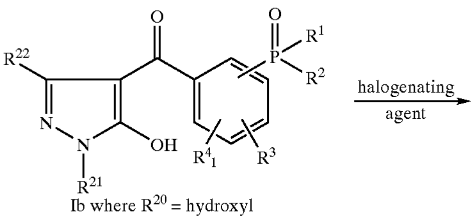

Ib where $R^{20}$ = hydroxyl

Ib where $R^{20}$ = halogen

What has been said in section A applies analogously.

G. Preparation of compounds of the formula Ib (≡I where $Q=Q^2$) where $R^{20}=OR^{13}$, $OSO_2R^{14}$, $OPR^{15}R^{16}$, $OPOR^{15}R^{16}$ or $OPSR^{15}R^{16}$ by reaction of compounds of the formula Ib (≡I where $Q=Q^2$) where $R^6$=hydroxyl with alkylating, sulfonylating or phosphonylating agents IIα, IIβ, IIγ, IIδ or IIε.

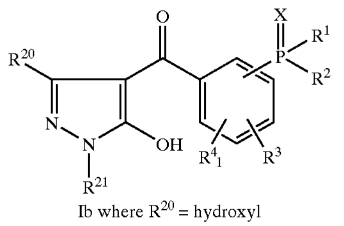

Ib where $R^{20}$ = hydroxyl

\+

$L^1$—$R^{13}$ (IIα) or
$L^1$—$SO_2R^{14}$ (IIβ) or
$L^1$—$PR^{15}R^{16}$ (IIγ) or
$L^1$—$PO^{15}R^{16}$ (IIδ) or
$L^1$—$PSR^{15}R^{16}$ (IIε)

Ib where $R^{20} = OR^{13}$, $OSO_2R^{14}$, $OPR^{15}R^{16}$, $OPOR^{15}R^{16}$ or $OPSR^{15}R^{16}$ What has been said in section B applies analogously.

H. Preparation of compounds of the formula Ib (≡I where $Q=Q^2$) where $R^6=OR^{13}$, $SR^{13}$, $POR^{15}R^{16}$, $NR^{17}R^{18}$, $ONR^{18}R^{19}$, N-bonded heterocyclyl or O—(N-bonded heterocyclyl) by reaction of compounds of the formula Ib (≡I where $Q=Q^2$) where $R^{20}$=halogen, $OSO_2R^{14}$ with compounds of the formula IIIα, IIIβ, IIIγ, IIIδ, IIIε, IIIη or IIIΘ, if appropriate in the presence of a base or with prior salt formation.

Ib where $R^6$ = halogen, $OSO_2R^{14}$ +

$HOR^{13}$ (IIIα) or
$HSR^{13}$ (IIIβ) or
$HPOR^{15}R^{16}$ (IIIγ) or
$HNR^{17}R^{18}$(IIIδ) or
$HONR^{18}R^{19}$ (IIIε) or
H(N-bonded heterocylyl (IIIη) or
H(ON-bonded heterocyclyl) (IIIϑ)

Ib where $R^{20} = OR^{13}$, $SR^{13}$, $POR^{15}R^{16}$, $NR^{17}R^{18}$, $ONR^{17}R^{18}$, N-bonded heterocyclyl or ON-bonded heterocyclyl What has been said in section C applies analogously.

I. Preparation of compounds of the formula Ib (≡I where $Q=Q^2$) where $R^{20}=SOR^{14}$, $SO_2R^{14}$ by reaction of compounds of the formula Ib (≡I where $Q=Q^2$) where $R^{20}=SR^{14}$ with an oxidizing agent.

Ib where $R^6 = SR^8$ oxidizing agent Ib where $R^6 = SOR^8$ or $SO_2R^8$

What has been said in section D applies analogously.

K. Preparation of compounds of the formula Ib (≡I where $Q=Q^2$) where $R^{20}$≠hydroxyl by reaction of a metallated pyrazole derivative of the formula VII with a phosphorus-containing benzoic acid derivative of the formula VIγ:

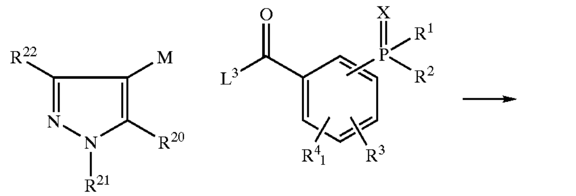

VII where $R^{20}$ ≠ hydroxyl IVγ

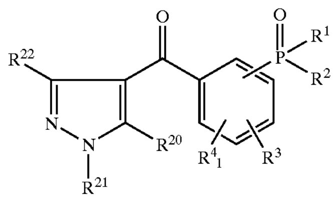

Ib where $R^{20}$ ≠ hydroxyl

M is a metal, in particular an alkali metal, such as lithium or sodium, an alkaline earth metal, such as magnesium, or a transition metal, such as palladium, nickel, etc., and $L^3$ is a nucleophilically replaceable leaving group, such as halogen, for example chlorine or bromine, alkylsulfonate, such as mesylate, haloalkylsulfonate, such as triflate, or cyanide.

The reaction is generally carried out at temperatures from −100° C. to the reflux temperature of the reaction mixture. Suitable solvents are inert aprotic solvents, such as ethers, such as diethyl ether, tetrahydrofuran. The compounds of the formula Ivγ are generally employed in excess; however, it may also be advantageous to employ them in equimolar amounts or substoichiometric amounts. Work-up is carried out to afford the product.

The metallated pyrazole derivatives of the formula VII can be generated in a manner known per se by reacting pyrazoles halogenated in the 4-position with metals such as lithium, sodium, magnesium etc., or with organometallic compounds, for example butyllithium. However, it is also possible to metallate pyrazoles which are linked to hydrogen in the 4-position directly, for example using the abovementioned metals or organometallic compounds. The reactions are generally carried out in an inert aprotic solvent, preferably in ether, such as diethyl ether, tetrahydrofuran, etc. The reaction temperature is in the range from −100° C. to the boiling point of the reaction mixture. The compounds of the formula VII are generally directly reacted further or generated in situ.

L. Preparation of compounds of the formula Ib (≡I where $Q=Q^2$) where $R^{20}$=hydroxyl by reaction of an activated phosphorus-containing benzoic acid of the formula IVα or a phosphorus-containing benzoic acid IVβ, which is preferably activated in situ, with a pyrazole of the formula VIII to give the acylating product, followed by rearrangement.

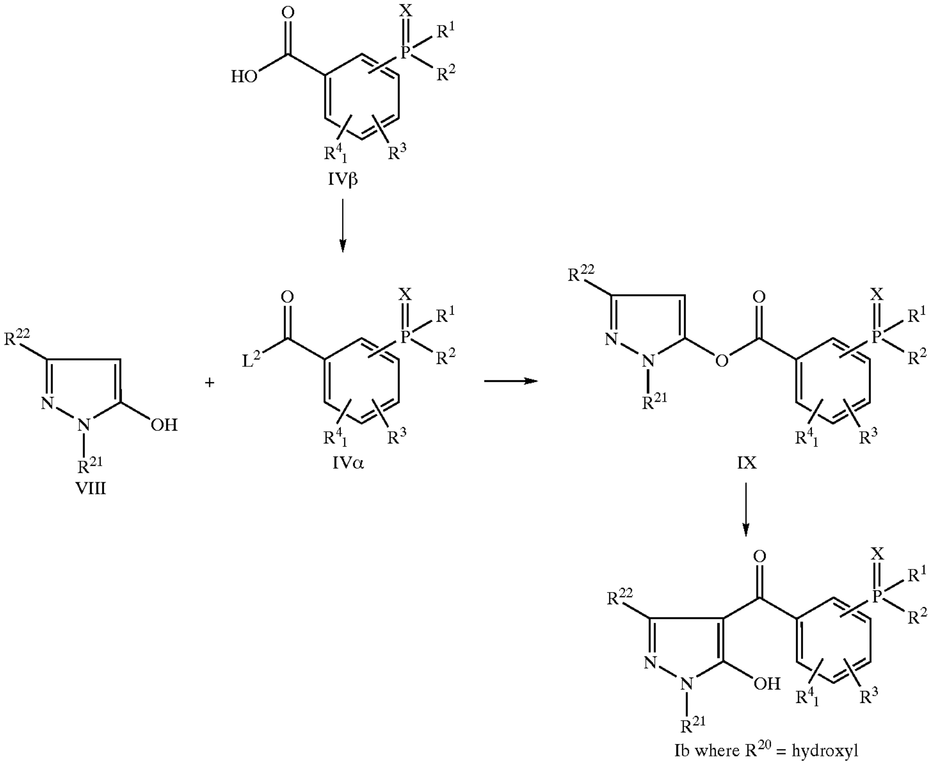
IVβ
VIII
IVα
IX
Ib where $R^{20}$ = hydroxyl

What has been said in section E applies analogously.

However, it is also possible to generate the ester IX in situ by reacting a pyrazole of the formula VIII, or an alkali metal salt thereof, with a phosphorus-containing benzene derivative of the formula X in the presence of carbon monoxide, a catalyst and a base.

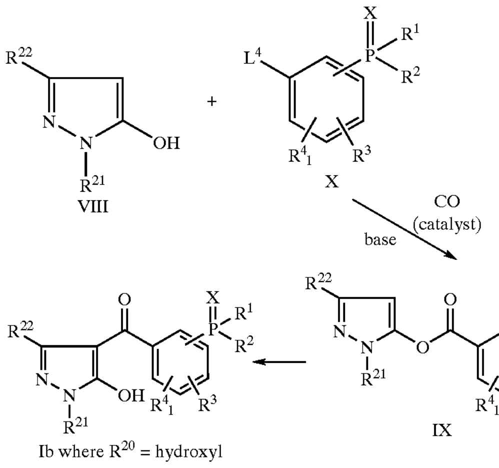

VIII
X
IX
Ib where $R^{20}$ = hydroxyl $L^4$ is a leaving group, such as halogen, for example chlorine, bromine or iodine, or sulfonate, such as mesylate or triflate; preference is given to bromine or triflate.

If appropriate, the ester IX reacts directly to give the phosphorus-containing benzoyl derivative of the formula Ib.

Suitable catalysts are palladium-ligand complexes in which the palladium is present in oxidation state 0, metallic palladium, which has optionally been absorbed on a carrier, and preferably palladium(II) salts. The reaction with palladium(II) salts and metallic palladium is preferably carried out in the presence of complex ligands.

An example of a suitable palladium(0)-ligand complex is tetrakis(triphenylphosphine)palladium.

Metallic palladium is preferably absorbed on an inert carrier such as, for example, active carbon, silica, alumina, barium sulfate or calcium carbonate. The reaction is preferably carried out in the presence of complex ligands such as, for example, triphenylphosphine.

Examples of suitable palladium(II) salts are palladium acetate and palladium chloride. The presence of complex ligands such as, for example, triphenylphosphine is preferred.

Suitable complex ligands for the palladium-ligand complexes, or in whose presence the reaction is preferably carried out with metallic palladium or palladium(II) salts, are tertiary phosphines whose structure is represented by the following formulae:

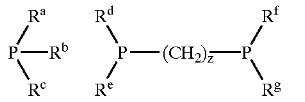

where z is from 1 to 4 and the radicals $R^a$ to $R^g$ are $C_1$–$C_6$-alkyl, aryl-$C_1$–$C_2$-alkyl or preferably aryl. Aryl is, for example, naphthyl and unsubstituted or substituted phenyl, such as, for example, 2-tolyl and, in particular, unsubstituted phenyl.

The complex palladium salts can be prepared in a manner known per se starting from commercially obtainable palladium salts such as palladium chloride or palladium acetate and the appropriate phosphines, such as, for example, triphenylphosphine or 1,2-bis(diphenylphosphino)ethane. Many of the complex palladium salts are commercially available. Preferred palladium salts are [(R)(+)-2,2'-bis(diphenylphosphino)-1,1'-binaphthyl]palladium(II) chloride, bis(triphenylphosphine)palladium(II) acetate and, in particular, bis(triphenylphosphine)palladium(II) chloride.

The palladium catalyst is generally employed in a concentration of from 0.05 to 5 mol %, and preferably 1–3 mol %.

Suitable bases are tertiary amines, such as, for example, N-methylpiperidine, ethyldiisopropylamine, 1,8-bisdimethylaminonaphthalene or, in particular, triethylamine. Also suitable are alkali metal carbonates, such as sodium carbonate or potassium carbonate. However, mixtures of potassium carbonate and triethylamine are also suitable.

In general, from 2 to 4 molar equivalents, in particular 2 molar equivalents, of the alkali metal carbonate and from 1 to 4 molar equivalents, in particular 2 molar equivalents, of the tertiary amine are employed, based on the phosphorus-containing benzene derivative of the formula X.

Suitable solvents are nitrites, such as benzonitrile and acetonitrile, amides, such as dimethylformamide, dimethylacetamide, tetra-$C_1$–$C_4$-alkylureas or N-methylpyrrolidone and, preferably, ethers such as tetrahydrofuran, methyl tert-butyl ether. Particularly preferred solvents are ethers such as 1,4-dioxane and dimethoxyethane.

M. Preparation of compounds of the formula Ic (≡I where Q=$Q^3$) where $R^{24}$=H by reaction of a 1,3-dicarbonyl compound of the formula XI with hydroxylamine.

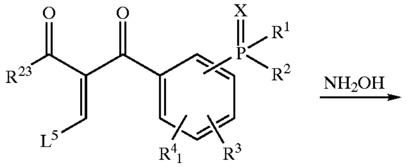

XI

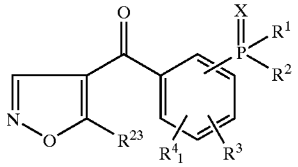

Ic where $R^{24}$ = H $L^5$ is an O—$C_1$–$C_6$-alkyl or N($C_1$–$C_6$-alkyl$)_2$ group. The 1,3-dicarbonyl compound of the formula XI is reacted with hydroxylamine which is generated in situ, for example from hydroxylamine salt using a base or an acid acceptor, such as triethylamine or sodium acetate.

The starting material of the formula XI is obtained by reacting the β-keto esters of the formula XII, which are known per se, with an activated phosphorus-containing benzoic acid IVα. The acylation product XIII is subsequently converted into the 1,3-diketone XIV using, for example, p-toluenesulfonic acid as catalyst in an inert solvent, such as toluene. The 1,3-diketone XIV is subsequently reacted with an orthoester or dimethylformamide dialkyl acetal to give the 1,3-dicarbonyl compound of the formula XI.

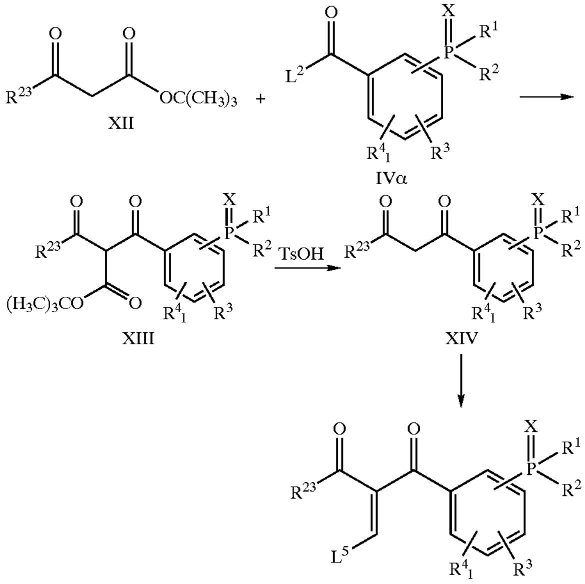

XII IVα XIII XIV XI

N. Preparation of compounds of the formula Ic (≡I where Q=$Q^3$) by cycloaddition of the α,β-unsaturated benzoyl derivative XV with a nitrile oxide of the formula XVI

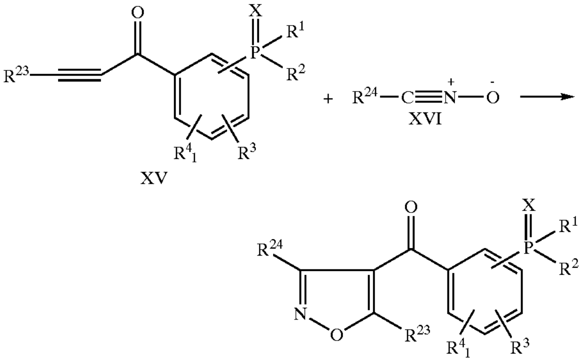

XV XVI Ic

The α,β-unsaturated benzoyl derivative XV is obtained by ethynylation of the activated phosphorus-containing benzoic acid of the formula IVα.

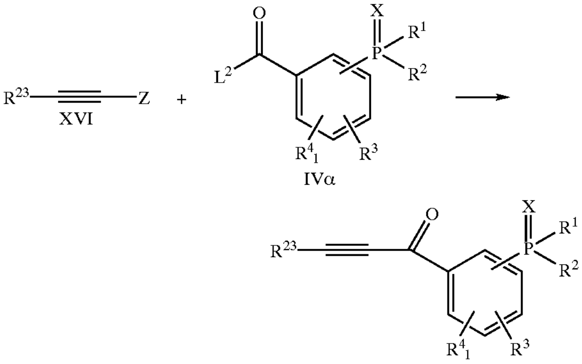

XVI IVα XV

Z is a metal such as lithium, an organotin radical such as $Sn(C_4H_9)_3$ or a zinc radical such as ZnCl or ZnBr.

O. Preparation of compounds of the formula Id (≡I where $Q=Q^4$) by reaction of the cyanoketone XVII with an activated phosphorus-containing benzoic acid of the formula IVα in the presence of a base such as triethylamine, sodium carbonate, sodium hydride or magnesium ethoxide in an inert organic solvent such as diethyl ether, tetrahydrofuran, N,N-diethylformamide, dichloromethane or acetonitrile.

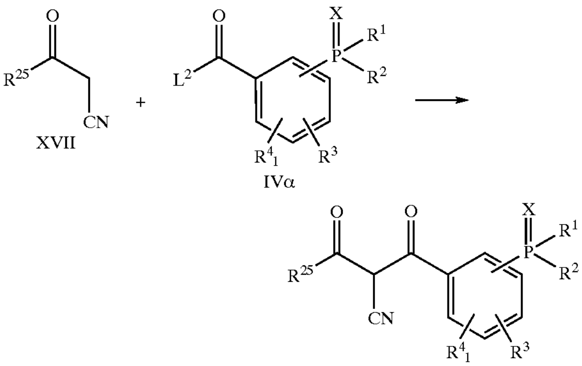

XVII IVα Id

The phosphorus-containing benzoyl halides of the formula IVα where $L^2$=halogen can be prepared in a manner known per se by reacting the benzoic acids of the formula IVβ with halogenating agents such as thionyl chloride, thionyl bromide, phosgene, diphosgene, triphosgene, oxalyl chloride, oxalyl bromide.

The phosphorus-containing benzoic acids of the formula IVβ can be prepared in a manner known per se by acidic or basic hydrolysis from the corresponding phosphorus-containing benzoic esters IVδ (cf. J. March, "Advanced Organic Chemistry", $4^{th}$ edition, Wiley, New York, p. 378 ff.)

IVδ

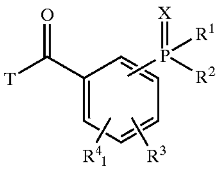

where T is $C_1$–$C_6$-alkoxy.

The phosphorus-containing benzoic esters IVδ are obtainable by different routes:

They can be obtained by electrophilic or nucleophilic aromatic substitution of benzoic esters of the formula XVIII and, if appropriate, further functionalization of the group thus introduced.

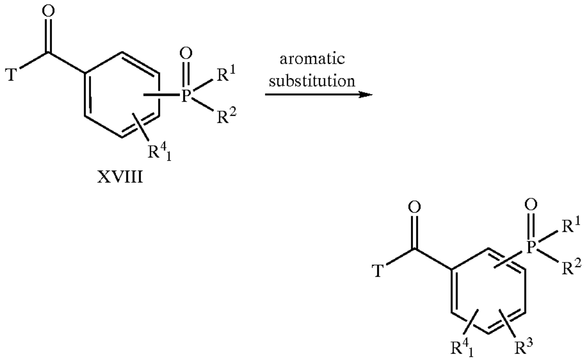

XVIII

IVδ where $R^3 \neq H$

For example, the ester of the formula XVIII can be nitrated analogously to known methods ($R^3=NO_2$; cf. J. March, "Advanced Organic Chemistry", $4^{th}$ edition, p. 522 ff.), brominated or chlorinated ($R^3$=Cl, Br; cf. J. March, "Advanced Organic Chemistry", $4^{th}$ edition, p. 531 ff.).

The abovementioned electrophilic aromatic substitution reaction may result in mixtures of isomers, which can be separated or purified by distillation, crystallization or chromatographic methods.

Phosphorus-containing benzoic esters of the formula IVδ where $R^3=NH_2$ can be obtained by reduction of the corresponding nitro compounds of the formula IVδ where $R^3=NO_2$.

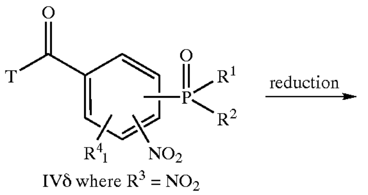

IVδ where $R^3 = NO_2$

-continued

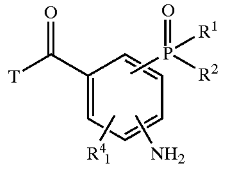

IVδ where $R^3 = NH_2$

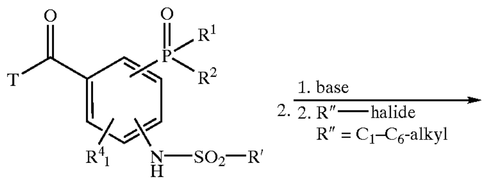

IVδ where $R^3 = NHSO_2R'$

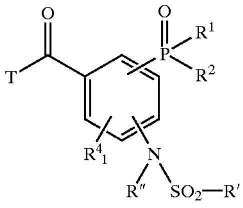

IVδ where $R^3 = N''SO_2R'$

Suitable reducing agents are, inter alia, metals such as iron or zinc in the presence of hydrochloric acid and catalytically activated hydrogen (cf. J. March, "Advanced Organic Chemistry", 4th edition, p. 1216 ff.)

Phosphorus-containing benzoic esters of the formula IVδ where $R^3$=($C_1$–$C_6$-alkylsulfonyl)amino, ($C_1$–$C_6$-haloalkylsulfonyl)amino can be obtained by reaction of the corresponding amino compounds with appropriately substituted sulfonyl chlorides in the presence of a base (cf.

T. W. Green et al., "Protective Groups in Organic Synthesis", p. 379 f.)

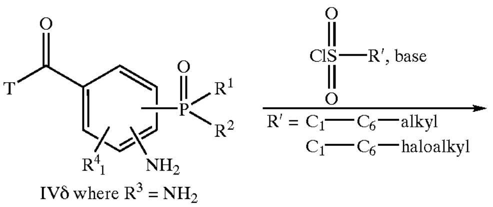

IVδ where $R^3 = NH_2$

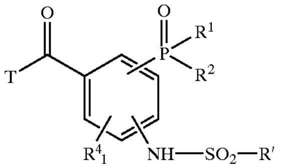

IVδ where $R^3 = NHSO_2R'$

The latter can be converted into the corresponding N-alkyl derivatives by alkylation in the presence of a base.

Suitable bases are, inter alia, sodium hydride, potassium hydride, potassium tert-butoxide, and suitable alkyl halides are alkyl bromides and alkyl iodides (cf. J. P. Dunn et al., J. Med. Chem. 1981, 24, p. 1097).

Phosphorus-containing benzoic esters of the formula IVδ where $R^3$=halogen, cyano, $C_1$–$C_6$-alkyl, $C_1$–$C_6$-alkylthio or $C_1$–$C_6$-haloalkylthio can be obtained from the corresponding amino compounds by Sandmeyer reaction or related reactions (cf. J. March, "Advanced Organic Chemistry", 4th edition, pp. 723–724, pp. 669–671)

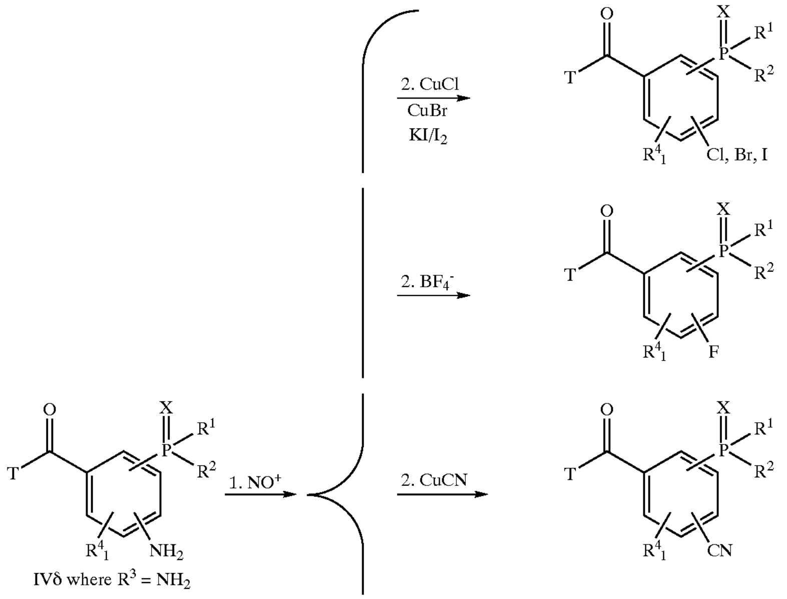

IVδ where $R^3 = NH_2$

-continued

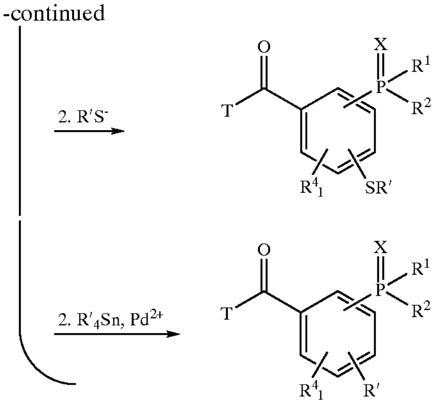

R' = $C_1$–$C_6$-alkyl
$C_1$–$C_6$-haloalkyl

If appropriate, it may be advantageous to carry out the reactions in the presence of metal catalysts such as, for example, copper(I) or palladium(II) (cf., for example, Kikukawa et al., J. Org. Chem. 1983, 48, 1333).

Phosphorus-containing benzoic esters of the formula IVδ where $R^3$=$S(O)_{1,2}$—$C_1$–$C_6$-alkyl or $S(O)_{1,2}$—$C_1$–$C_6$-haloalkyl can be obtained by reaction of the corresponding sulfur compounds with an oxidizing agent such as bromine, peroxyacetic acid, m-chloroperbenzoic acid and hydrogen peroxide, if appropriate in the presence of a catalyst such as tungstate.

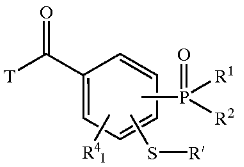

IVδ where $R^3$ = $NH_2$

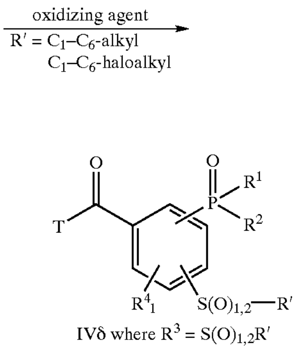

IVδ where $R^3$ = $S(O)_{1,2}R'$

Phosphorus-containing benzoic esters of the formula IVδ here $R^3$=aminosulfonyl, $C_1$–$C_6$-alkylaminosulfonyl or di($C_1$–$C_6$-alkyl)aminosulfonyl can be obtained by reaction of the corresponding sulfonyl chloride with ammonia or suitable amines. If appropriate, it may be useful to operate in the presence of a base such as triethylamine, sodium carbonate, potassium carbonate, sodium bicarbonate, potassium bicarbonate or pyridine (cf. J. March, "Advanced Organic Chemistry", $4^{th}$ edition, p. 499). The sulfonyl chloride is obtained by sulfochlorination of the corresponding diazonium salt.

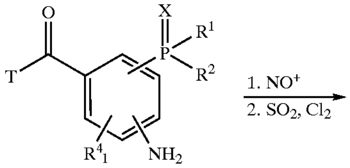

IVδ where $R^3$ = $NH_2$

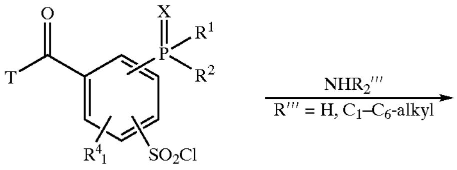

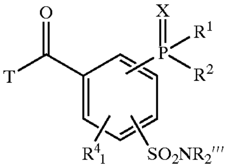

IVδ where $R^3$ = $SO_2NR_2'''$

Phosphorus-containing benzoic esters of the formula IVδ where $R^3$=$C_1$–$C_6$-alkoxy or $C_1$–$C_6$-haloalkoxy can be obtained by alkylation of the corresponding phenols in the presence of a base. Suitable bases are, in addition to the customary bases, in particular sodium carbonate, potassium carbonate, sodium hydride or potassium tert-butoxide. Preferred alkylating agents are appropriate halogenated or non-halogenated alkyl bromides or chlorides (cf., for example, H. Fener et al., "The Chemistry of the Ether Linkage", Wiley, New York, 1967, pp. 445–498.)

The phenols can be obtained by boiling down of corresponding diazonium compounds.

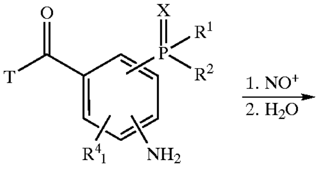

IVδ where $R^3$ = $NH_2$

-continued

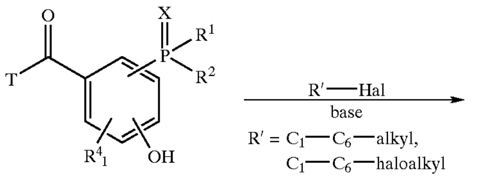

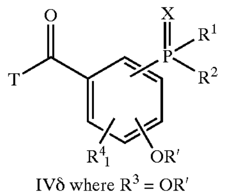

IVδ where $R^3$ = OR′

Phosphorus-containing benzoic esters of the formula IVδ where $R^3$=$PXR^1R^2$ can be obtained by reaction of compounds of the formula IVδ where $R^3$=Br, I, $OSO_2CF_3$ etc., with suitable phosphonous acids or phosphorous acids in the presence of a transition metal catalyst such as nickel or palladium and, if appropriate, of a base (cf., for example, T. Hirao et al., Synthesis 1981, 56).

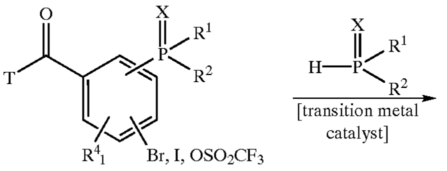

IVδ where $R^3$ = Br, I, $OSO_2CF_3$

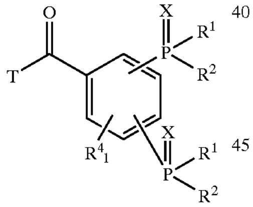

Phosphorus-containing benzoic esters of the formula IVδ where $R^3$=phenyl can be prepared by reaction of a corresponding bromide or iodide of the formula IVδ where $R^3$=Br or I with a phenyl bromide or phenyl iodide, which may be substituted, in the presence of copper (cf. Ranta et al., Synthesis 1974, 9; Goshaer et al., Russ. Chem. Rev. 1972, 41, 1046)

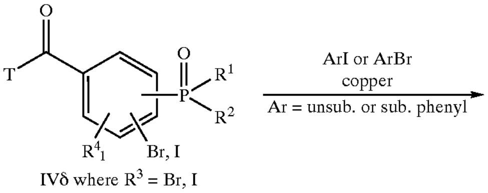

IVδ where $R^3$ = Br, I

-continued

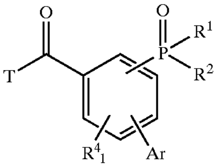

IVδ where $R^3$ = Ar

Phosphorus-containing benzoic esters of the formula IVδ where $R^3$=unsub. or sub. phenyl, unsub. or sub. heterocyclyl can be obtained by reaction of compounds of the formula IVδ where $R^3$=a leaving group such as bromine, iodine, triflate, fluorosulfonyloxy, etc., with an unsub. or sub. phenyl or heterocyclyl stannane (Stille coupling), an unsub. or sub. phenyl or heterocyclyl boron compound (Suzuki coupling) or an unsub. or sub. phenyl or heterocyclyl zinc compound (Negishi coupling) in a manner known per se (cf. Tetrahedron Lett. 1986, 27, 5265) in the presence of a palladium or nickel catalyst and, if appropriate, a base.

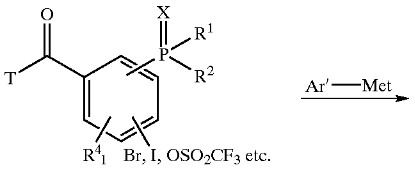

IVδ where $R^3$ = Br, I, $OSO_2CF_3$ etc.

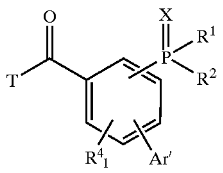

IVδ where $R^3$ = Ar′

Ar'=unsub. or sub. phenyl or heterocyclyl

Met=$Sn(C_1\text{-}C_4\text{-alkyl})_3$, $B(OH)_2$, ZnBr, ZnCl

Phosphorus-containing benzoic esters of the formula IVδ where $R^3$=unsub. or sub. heterocyclyl can also be obtained by constructing the heterocycle from suitable precursors.

1,2,4-Oxadiazoline derivatives, for example, can be prepared from aldoximes of the formula XIX by condensation with aldehydes of the ketones (cf., for example, Arch. Pharm. 1993, 326, 383–389).

The thioamides of the formula XX are suitable precursors for 2-thiazolinyl derivatives (cf., for example, Tetrahedron 1986, 42, 1449–1460) and for 2-thiazolyl derivatives (cf., for example, Houben-Weyl, "Methoden der organischen Chemie"[Methods of Organic Chemistry], $4^{th}$ edition, Vol. E5, p. 1268 ff. (1985)).

2-Oxazolinyl, 2-thiazolinyl and 2-imidazolinyl derivatives are obtainable from the carboxylic acids of the formula XXI (cf., for example, Tetrahedron Lett. 1981, 22, 4471–4474).

According to processes known from the literature, it is possible to prepare 1,3-thiazole-5(4H)-thion-2-yl or 5-oxo-2-imidazolin-2-yl derivatives from carbonyl halides of the formula XXII where Hal is halogen, in particular from carbonyl chlorides (cf., for example, Helv. Chim. Acta, 1986, 69, 374–388; Heterocycles 1989, 29, 1185–1189).

Furthermore, it is possible to prepare 2-oxazolyl derivatives from the carboxylic acids of the formula XXI or the carbonyl halides of the formula XXII (cf., for example, Heterocyclic Chem. 1991, 28, 17–28).

The conversion of oximes of the formula XXIV into 4,5-dihydroisoxazol-3-yl or isoxazol-3-yl derivatives can be carried out in a manner known per se via the intermediate of the hydroxamoyl chlorides or bromides. Using the latter, nitrile oxides are generated in situ which react with alkenes or alkynes to give the desired products (cf., for example, Chem. Ber. 1973, 106, 3258–3274). 1,3-Dipolar cycloaddition with chlorosulfonyl isocyanate to the nitrile oxide formed in situ affords 1,2,4-oxadiazolin-5-on-3-yl derivatives (cf., for example, Heterocycles 1988, 27, 683–685).

The aldehydes of the formula XXV can be converted into 2,4-dihydro-1,2,4-triazol-3-on-5-yl derivatives via the intermediate of the semicarbazones (cf., for example, J. Heterocyclic Chem. 1986, 23, 881–883).

2-Imidazolinyl derivatives are preparable from benzonitriles of the formula XXVI by known methods (cf., for example, J. Org. Chem. 1987, 52, 1017–1021).

It is also possible to prepare 1,2,4-triazol-3-yl derivatives by known processes from the benzonitriles of the formula XXVI (cf., for example, J. Chem. Soc. 1954, 3461–3464).

The aldehydes XXV can be reacted in a manner known per se by Wittig reaction with phosphonium salts $(Ph)_3P^+ CH_2COR^*X^-$ (J. March, "Advanced Organic Chemistry", 3rd edition, p. 864 ff., Wiley-Interscience Publication, 1985) to give α,β-unsaturated ketones XXVII. By reaction with hydroxylamine, these give the corresponding oximes which can be converted into the 5-isoxazolyl derivatives by oxidative cyclization (J. Am. Chem. Soc. 1972, 94, 9128) (the meaning of R* thus corresponds to the meaning of a radical by which the heterocyclyl may be substituted).

It is also possible to convert the aldehydes XXV with alkoxymethylphosphonium salts in a manner known per se (J. March, "Advanced Organic Chemistry", 3rd edition, p. 864 ff., Wiley-Interscience Publication, 1985) into the corresponding enol ethers. Cleavage of these enol ethers analogously to processes known from the literature yield the acetaldehyde derivatives XXVIII. By bromination in the α-position these can be converted into the α-bromoacetaldehyde derivatives (Tetrahedron Lett. 1988, 29, 5893), which afford, by cyclization with amides, thioamides and amidines, oxazoles, thiazoles and imidazoles. Furthermore, the acetaldehyde derivatives XXVIII can be converted with dimethylformamide dimethyl acetal into corresponding enamines which can then be converted into isoxazoles or pyrazoles using hydroxylamines and hydrazines, respectively.

Furthermore, the aldehydes XXV can be converted into hydroxyketone derivatives by Aldol reaction with ketones. Subsequent oxidation leads to 1,3-diketones which can be converted into isoxazoles, pyrazoles or pyrimidines using hydroxylamine, hydrazines or amidines.

The aldehydes XXV can also be converted by methods known from the literature (Houben-Weyl, "Methoden der organischen Chemie"[Methods of Organic Chemistry], 4th edition, Vol. E14b) into the corresponding diazo compounds XXIX. 1,3-dipolar cycloaddition to alkenes or alkynes and subsequent isomerization leads to pyrazolines or pyrazoles.

The aldehyde XXV can be prepared analogously to processes known from the literature, for example from the corresponding methyl compound XXX, by bromination, for example with N-bromosuccinimide or 1,3-dibromo-5,5-dimethylhydantoin, and subsequent oxidation (cf. Synth. Commun. 1992, 22, 1967–1971).

The oximes of the formula XXIV are advantageously obtained by reacting, in a manner known per se, aldehydes of the formula XXV with hydroxylamine (cf. J. March, "Advanced Organic Chemistry", 3rd edition, pp. 805–806, Wiley, New York, 1985).

The conversion of the oximes XXIV into the nitrites XXVI can also be carried out by processes known per se (cf. J. March, "Advanced Organic Chemistry", 3rd edition, pp. 931–932, Wiley, New York, 1985).

The nitrites of the formula XXVI can be converted in a manner known per se with hydroxylamine into the corresponding aldoximes XIX, converted with hydrogen sulfide into the thioamides XX or hydrolyzed to give the carboxylic acids XXI. The latter can also be obtained from the aldehydes XXV by oxidation (cf. J. March, "Advanced Organic Chemistry", 3rd edition, p. 629 ff., Wiley, New York, 1985).

The acyl halides XXII can be obtained analogously to standard processes from the corresponding carboxylic acids of the formula XXI.

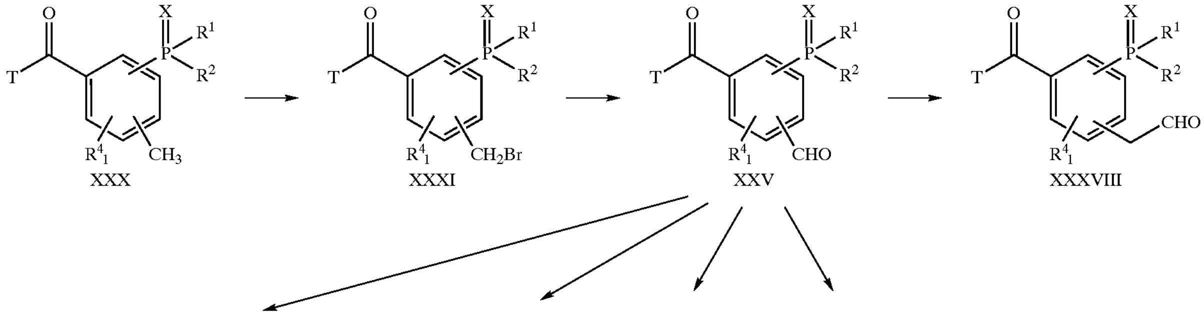

XXX XXXI XXV XXXVIII

-continued

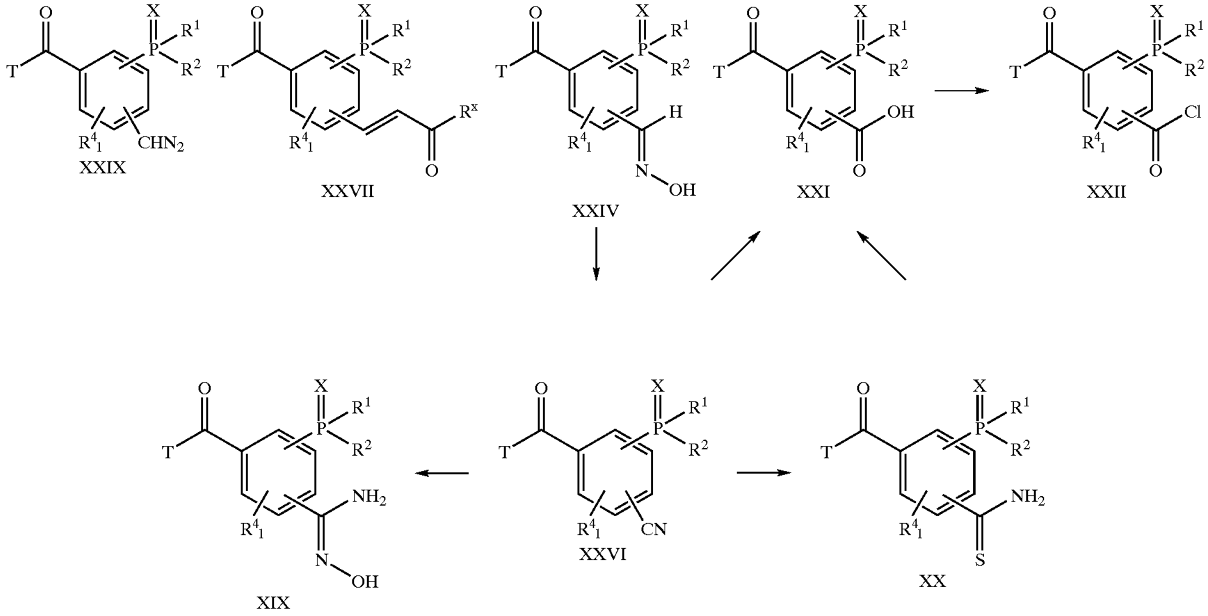

XXIX XXVII XXIV XXI XXII

XIX XXVI XX

The phosphorus-containing compounds of the formula IVδ are obtainable by reaction of compounds of the formula XXXII where $L^5$=bromine, iodine, triflate and a corresponding substituted phosphorous acid or phosphonous acid in the presence of a transition metal catalyst, such as nickel or palladium, and, if appropriate, a base (cf., for example, T. Hirao et al., Synthesis 1981, 56.)

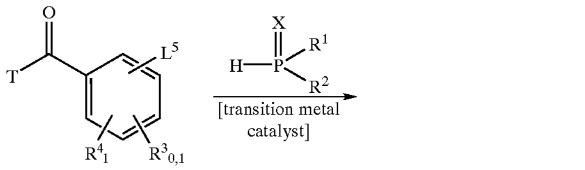

$L^5 = Br, I, OSO_2CF_3$
XXXII

IVδ

The compounds of the formula XXXII where $L^5$=Br, I are obtained from the corresponding nitro compounds by reaction of the nitro group and subsequent Sandmeyer reaction. The compounds of the formula XXXII where $L^5$=$OSO_2CF_3$ can be obtained by reacting the corresponding phenol with trifluoromethylsulfonyl chloride or trifluoromethylsulfonic anhydride.

The compounds of the formula IVδ where $R^1$, $R^2$=$C_1$–$C_6$-alkoxy, $C_1$–$C_6$-alkylthio, $C_1$–$C_6$-alkylamino etc., can also be obtained by reaction of nucleophilically substitutable phosphorus compounds of the formula IVδ where L', L"=a leaving group, such as halogen, $C_1$–$C_6$-alkoxy, etc., with suitable alcohols, amines or mercaptans, if appropriate in the presence of a base, (cf., for example, L. J. Kaplan, J.Org. Chem. 1979, 44, 2226; Houben-Weyl, "Methoden der organischen Chemie"[Methods of Organic Chemistry], Vol. XII/1, p. 423 ff.; R. Z. Greenley et al., J. Org. Chem. 1964, 29, 1009).

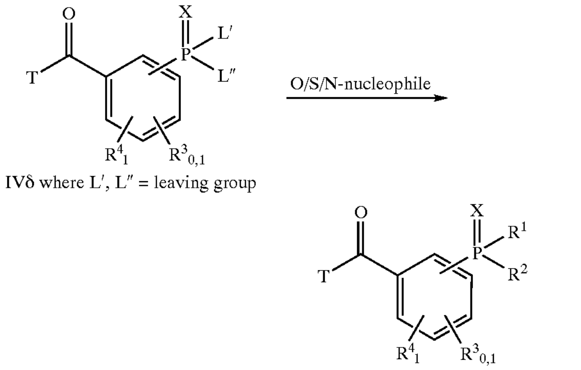

IVδ where L', L" = leaving group

IVδ where
$R^1$, $R^2$ = $C_1$—$C_6$—alkoxy, $C_1$—$C_6$—alkylthio, $C_1$—$C_6$—alkylamino Compounds of the formula IVδ where L', L"=halogen can be obtained by reaction of compounds of the formula IVδ where $R^1$, $R^2$=$OCH_3$ with halogenating agents (cf. z. B. W. Althoff et al., Chem. Ber. 1978, 111, 1845).

Suitable halogenating agents are, inter alia, phosgene, thionyl chloride and thionyl bromide.

Compounds of the formula IVβ are furthermore obtainable by oxidation of compounds of the formula XXXIII.

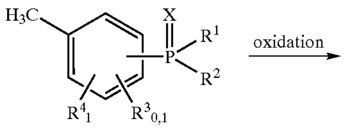

XXXIII

-continued

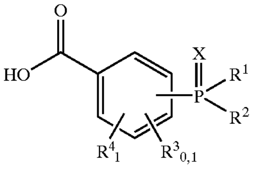

IVβ

Suitable oxidizing agents are, for example, potassium permanganate (cf., for example, Houben Weyl, "Methoden der Organischen Chemie"[Methods of Organic Chemistry], Vol. IV/1a, 1981, and Vol. VIII, 1952; E. I. Bengtsson, Acta Chem. Scand. 1953, 7, 774), chromium(VI) compounds (cf., for example, A. W. Singer et al., Org. Synth. Coll. Vol. III 1955, 740) or atmospheric oxygen in the presence of a catalyst such as, for example, cobalt or manganese (cf., for example, A. S. Hay et al., Can. J. Chem. 1965, 43, 1306).

The compounds of the formula XXXIII are obtainable by reaction of organometallic compounds of the formula XXXIV (where Met'=Li, Mg) with phosphorus compounds carrying nucleophilically replaceable groups (L=halogen, such as Cl, Br, alkoxy, etc.) (cf., for example, A. Berger et al., J. Org. Chem. 1951, 16, 1250; M. Sander, Chem. Ber. 1960, 93, 1220).

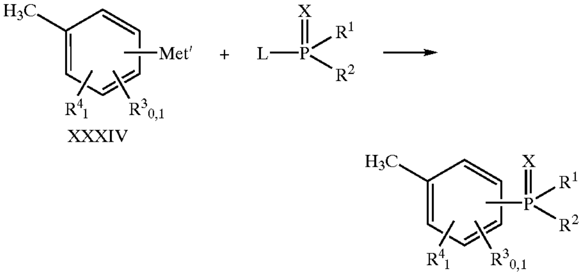

XXXIV

XXXIII

These compounds can also be obtained by oxidation of the corresponding phosphorus(III) compounds, which can be prepared analogously to the reaction shown above.

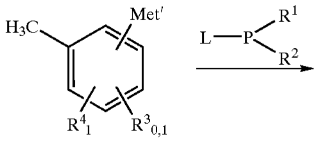

XXXIV

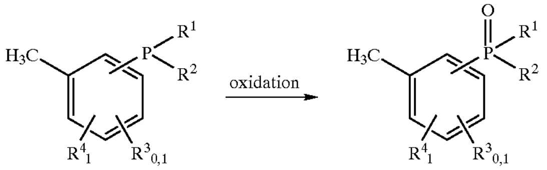

XXXIII where X = O

Suitable oxidizing agents are, for example, hydrogen peroxide, peroxyacetic acid, etc.

The compounds of the formula XXXIII (where $R^2$=$C_1$–$C_6$-alkoxy, $C_1$–$C_6$-alkyl, $C_2$–$C_6$-alkenyl, $C_2$–$C_6$-alkynyl, etc.) can furthermore be obtained by reacting a phosphorus compound of the formula XXXV with an alkyl halide (Arbuzov reaction).

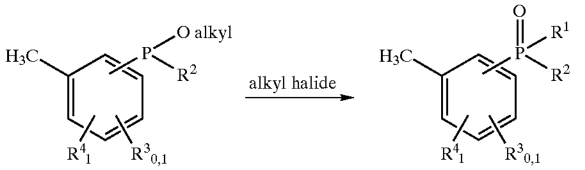

XXXV

XXXIII
where $R^2$ = $C_1$–$C_6$-alkoxy, $C_1$–$C_6$-alkyl, $C_2$–$C_6$-alkenyl, $C_2$–$C_6$-alkynyl etc.

Preferred alkyl halides are the corresponding bromides and iodides (cf., for example, B. A. Arbuzov, Pure Appl. Chem. 1964, 9, 307; G. M. Kosolapoff, Org. React. 1951, 6, 273).

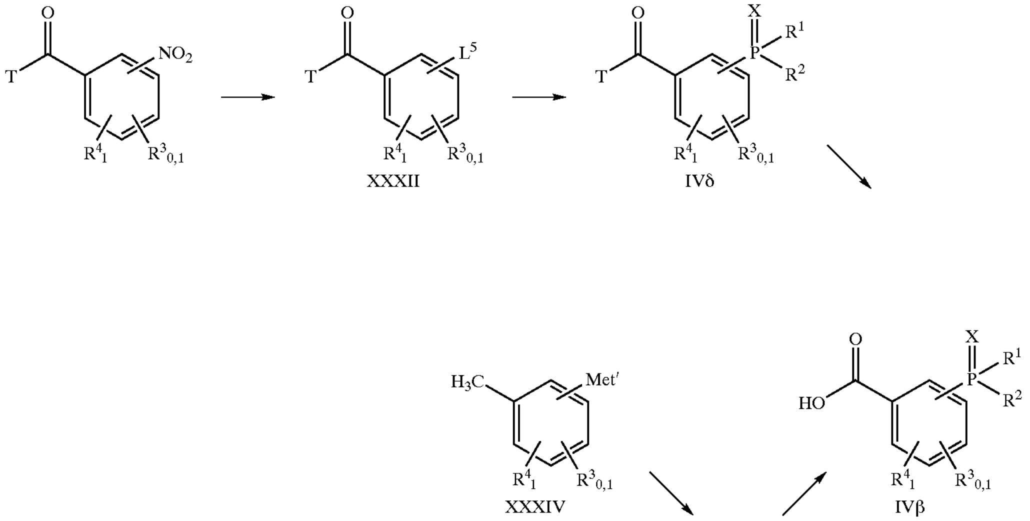

XXXII

IVδ

XXXIV

IVβ

-continued

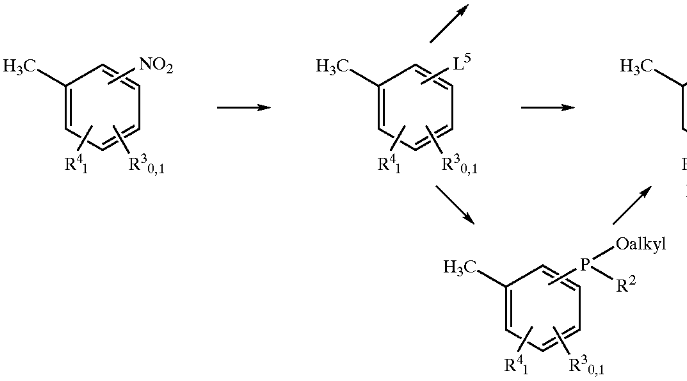

XXXIII

XXXV

In general, it is possible to introduce or synthesize the radical $R^3$ at a suitable stage of the reaction sequence of the preparation of compounds of the formula I, where these reactions are described above or can be prepared analogously to known processes.

It may also be feasible to change the order of the reaction steps.

Furthermore, it is possible to modify the substituents $R^1$ and $R^2$ at a suitable stage of the reaction sequence. For example, the radicals $R^1$, $R^2$=$C_1$–$C_6$-alkoxy can be converted by reaction with organometallic compounds into $R^1$, $R^2$=$C_1$–$C_6$-alkyl, $C_2$–$C_6$-alkenyl, $C_2$–$C_6$-alkynyl etc. Organometallic reagents which are suitable for this purpose are appropriate organolithium or organomagnesium compounds (cf., for example, Houben-Weyl, "Methoden der Organischen Chemie"[Methods of Organic Chemistry], Vol. E. 2, p. 38 ff., Wiley, New York).

Novel are the phosphorus-containing benzoic acid derivatives of the formula IV

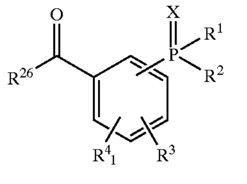

IV where:

X is oxygen or sulfur;

$R^1$,$R^2$ are hydrogen, $C_1$–$C_6$-alkyl, $C_2$–$C_6$-alkenyl, $C_2$–$C_6$-alkynyl, $C_1$–$C_6$-alkoxy, $C_3$–$C_6$-alkenyloxy, $C_3$–$C_6$-alkynyloxy, mercapto, $C_1$–$C_6$-alkylthio, $C_3$–$C_6$-alkenylthio, $C_3$–$C_6$-alkynylthio, amino, $C_1$–$C_6$-alkylamino, di($C_1$–$C_6$-alkyl)amino, ($C_1$–$C_6$-alkoxy)($C_1$–$C_6$-alkyl)amino, ($C_3$–$C_6$-alkenyl)($C_1$–$C_6$-alkyl)amino, ($C_3$–$C_6$-alkynyl)($C_1$–$C_6$-alkyl)amino, di($C_3$–$C_6$-alkenyl)amino or di($C_3$–$C_6$-alkynyl)amino, where the abovementioned alkyl, alkenyl or alkynyl radicals may be partially or fully halogenated and/or may carry one to three of the following groups:

nitro, cyano, $C_1$–$C_4$-alkoxy, $C_1$–$C_4$-alkylthio, $C_1$–$C_4$-alkylsulfinyl, $C_1$–$C_4$-alkylsulfonyl, di($C_1$–$C_4$-alkyl)amino, $C_1$–$C_4$-alkylcarbonyl, $C_1$–$C_4$-alkoxycarbonyl, are phenyl or heterocyclyl, where the two last-mentioned radicals for their part may be partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

are phenoxy which may by partially or fully halogenated and/or may carry one to three of the following groups: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl; or $R^1$ and $R^2$ together form a —O—$(CH_2)_m$—O—, —O—$(CH_2)_m$—S—, —S—$(CH_2)_m$—S—, —$NR^5$—$(CH_2)_m$—$NR^5$—, —O—$(CH_2)_m$—$NR^5$—, —S—$(CH_2)_m$—$NR^5$—, —$(CH_2)_n$—O—, —$(CH_2)_n$—S— or —$(CH_2)_n$—$NR^5$ chain which may carry one to three radicals from the following group:

halogen, cyano, $C_1$–$C_4$-alkyl, $C_1$–$C_4$-haloalkyl, $C_1$–$C_4$-alkoxy, $C_1$–$C_4$-alkoxycarbonyl or phenyl which is unsubstituted or partially or fully halogenated and/or may carry one to three of the following groups: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl; or $R^1$ and $R^2$ together form —$(CH_2)_p$ chain which may be interrupted by oxygen, sulfur or $NR^5$ and/or may carry one to three radicals from the following group:

halogen, cyano, $C_1$–$C_4$-alkyl, $C_1$–$C_4$-haloalkyl, $C_1$–$C_4$-alkoxy, $C_1$–$C_4$-alkoxycarbonyl or phenyl which is unsubstituted or partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^3$ is cyano, halogen, $C_1$–$C_6$-alkyl, $C_1$–$C_6$-haloalkyl, $C_1$–$C_6$-alkoxy-$C_1$–$C_6$-alkyl, $C_1$–$C_6$-haloalkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylcarbonyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, $C_1$–$C_6$-alkylaminosulfonyl, di($C_1$–$C_6$-alkyl)aminosulfonyl, ($C_1$–$C_6$-alkylsulfonyl)amino, ($C_1$–$C_6$-haloalkylsulfonyl)amino, N—($C_1$–$C_6$-alkyl)—N—($C_1$–$C_6$-alkylsulfonyl)amino, N—($C_1$–$C_6$-alkyl)—N—($C_1$–$C_6$-haloalkylsulfonyl)amino, —P(=X)$R^1R^2$, phenyl or heterocyclyl, where the two last-mentioned radicals may be partially or fully halogenated and/or may carry one to three of the following groups:

nitro, cyano, $C_1$–$C_4$-alkyl, $C_1$–$C_4$-haloalkyl, $C_1$–$C_4$–alkoxy, $C_1$–$C_4$-haloalkoxy or $C_1$–$C_4$-alkoxycarbonyl;

$R^4$ is nitro, cyano, halogen, $C_1$–$C_6$-alkyl, $C_1$–$C_6$-alkoxy, $C_1$–$C_6$-alkylthio, $C_1$–$C_6$-alkylsulfinyl or $C_1$–$C_6$-alkylsulfonyl;

$R^5$ is hydrogen, $C_1$–$C_6$-alkyl, $C_1$–$C_6$-haloalkyl or $C_1$–$C_6$-alkoxy;

l is 0, 1 or 2;

m is 2, 3 or 4;

n is 3, 4 or 5;

p is 4, 5 or 6;

$R^{26}$ is a radical which can be removed by hydrolysis.

Examples of radicals which can be removed by hydrolysis are alkoxy, phenoxy, alkylthio and phenylthio radicals, which may be unsubstituted or substituted; halides, heteroaryl radicals attached via nitrogen; amino and imino radicals which may be unsubstituted or substituted, etc.

Preference is given to phosphorus-containing benzoic acid derivatives of the formula IVα where $L^2$=halogen (≡IV where $R^{26}$=halogen),

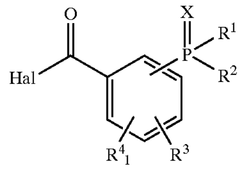

IVα where $L^2$ = halogen where the variables X, $R^1$ to $R^4$ and l are as defined under the compounds of the formula IV. Hal is halogen, in particular chlorine or bromine.

Preference is also given to the phosphorus-containing benzoic derivatives of the formula IVβ (≡IV where $R^{26}$= hydroxyl),

IVβ

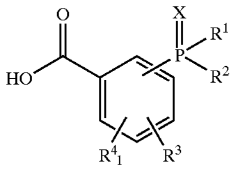

where the variables X, $R^1$ to $R^4$ and l are as defined under the compounds of the formula IV.

Preference is also given to the phosphorus-containing benzoic acid derivatives of the formula IVδ (≡IV where $R^{26}$=$C_1$–$C_6$-alkoxy),

IVδ

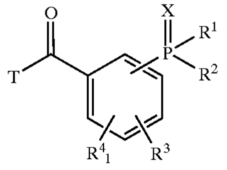

where the variables X, $R^1$ to $R^4$ and l are as defined under the compounds of the formula IV and T is $C_1$–$C_6$-alkoxy.

The particularly preferred embodiments of the phosphorus-containing benzoic acid derivatives of the formulae IV, IVα where $L^2$=halogen, IVβ and IVδ with respect to the variables X, $R^1$ to $R^4$ and 1 correspond to those of the phosphorus-containing benzoyl derivatives of the formula I.

Particular preference is also given to the compounds of the formula IV where the variables have the following meanings:

$R^1$,$R^2$ are hydrogen, $C_1$–$C_6$-alkyl, $C_2$–$C_6$-alkenyl, $C_2$–$C_6$-alkynyl, $C_1$–$C_6$-alkoxy, $C_3$–$C_6$-alkenyloxy, $C_3$–$C_6$-alkynyloxy, mercapto, $C_1$–$C_6$-alkylthio, $C_3$–$C_6$-alkenylthio, $C_3$–$C_6$-alkynylthio, amino, $C_1$–$C_6$-alkylamino or di-($C_1$–$C_6$-alkyl)amino, where the alkyl, alkenyl or alkynyl radicals mentioned may be partially or fully halogenated and/or may carry one to three of the following groups:

nitro, cyano, $C_1$–$C_4$-alkoxy, $C_1$–$C_4$-alkylthio, $C_1$–$C_4$-alkylsulfonyl, di($C_1$–$C_4$-alkyl)-amino, $C_1$–$C_4$-alkylcarbonyl, $C_1$–$C_4$-alkoxycarbonyl, phenyl or heterocyclyl, where the two lastmentioned radicals for their part may be partially or fully halogenated and/or may carry one to three of the following groups:

nitro, cyano, $C_1$—$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

are phenoxy which may be partially or fully halogenated and/or may carry one to three of the following groups: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl; or $R^1$ and $R^2$ together form a —O—$(CH_2)_m$—O—, —O—$(CH_2)_m$—S—, —S—$(CH_2)_m$—S—, —$NR^5$—$(CH_2)_m$—$NR^5$—, —O—$(CH_2)_m$—$NR^5$— or —S—$(CH_2)_m$—$NR^5$— chain which may carry one to three radicals from the following group:

halogen, cyano, $C_1$–$C_4$-alkyl, $C_1$–$C_4$-haloalkyl, $C_1$–$C_4$-alkoxy, $C_1$–$C_4$-alkoxycarbonyl or phenyl, which is unsubstituted or partially or fully halogenated and/or may carry one to three of the following groups:

nitro, cyano, $C_1$—$C_4$-alkyl, $C_1$—$C_4$-haloalkyl, $C_1$—$C_4$-alkoxy, $C_1$—$C_4$-haloalkoxy or $C_1$–$C_4$-alkoxycarbonyl;

$R_3$ is cyano, halogen, $C_1$–$C_6$-alkyl, $C_1$–$C_6$-haloalkyl, $C_1$–$C_6$-alkylcarbonyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, —P(═X)$R^1R^2$, phenyl or heterocyclyl, where the two lastmentioned radicals may be partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^4$ is nitro, cyano, halogen, $C_1$–$C_6$-alkyl, $C_1$–$C_6$-alkoxy, $C_1$–$C_6$-alkylthio, $C_1$–$C_6$-alkylsulfinyl or $C_1$–$C_6$-alkylsulfonyl;

$R^5$ is hydrogen, $C_1$–$C_6$-alkyl, $C_1$–$C_6$-haloalkyl or $C_1$–$C_6$-alkoxy;

l is 0, 1 or 2;

m is 2, 3 or 4;

$R^{26}$ is a radical which can be removed by hydrolysis.

Especially preferred are the compounds of the formula IV where the variables have the following meanings:

$R^1$, $R^2$ are hydrogen, $C_1$–$C_6$-alkyl, $C_1$–$C_6$-alkoxy or $C_1$–$C_6$-alkylthio, where the alkyl radicals mentioned may be partially or fully halogenated and/or may carry one to three of the following groups: nitro, cyano, $C_1$–$C_4$-alkoxy, $C_1$–$C_4$-alkylthio, di-($C_1$–$C_4$-alkyl) amino, $C_1$–$C_4$-alkylcarbonyl or $C_1$–$C_4$-alkoxycarbonyl;

$R^3$ is cyano, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

l is 0.

PREPARATION EXAMPLES

1. Synthesis of diethyl{3-chloro-4-[(2-hydroxy-4,4-dimethyl-6-oxocyclohex-1-en-1-yl)carbonyl]phenyl}phosphonate (Compound 3.1)

Step a) Diethyl(3-chloro-4-methylphenyl)phosphonate

A mixture of 32.0 g (0.127 mol) of 2-chloro-4-iodotoluene, 17.5 g (0.127 mol) of diethyl phosphite, 12.8 g (0.127 mol) of triethylamine and 14.7 g (0.0127 mol) of tetrakis(triphenylphosphine)palladium (0) in 200 ml of acetonitrile was refluxed for 5 hours. After cooling, the mixture was stirred into water and extracted with ethyl acetate. The organic phase was dried and concentrated and the residue was then distilled.

Yield: 23.4 g (70%); colorless oil $^1$H NMR ($CDCl_3$): δ=7.88 (m,1H); 7.60 (m,1H); 7,52 (m,1H); 4.10 (m,4H); 2.40 (s,3H); 1.34 (t, 6H)

Step b) Diethyl(3-chloro-4-hydroxycarbonylphenyl) phosphonate (Compound 6.1)

At 80° C., a solution of 1.76 g (11 mmol) of potassium permanganate in 10 ml of water was added a little at a time to a solution of 1.0 g (3.81 mmol) of the product from step a) in 5 ml of pyridine. The mixture was stirred at room temperature for 6 hours, sodium carbonate solution was added and the precipitate was filtered off. The filtrate was acidified using hydrochloric acid and extracted with ethyl acetate.

Yield: 0.75 g (67%); colorless solid $^1$H NMR ($d^6$-DMSO) δ=13.8 (brd s, 1H); 7.90 (m,1H); 7.75 (m,2H); 4.06 (m,4H); 1.25 (t,6H)

Step c) Diethyl {3-chloro-4-[(2-hydroxy-4,4-dimethyl-6-oxo-cyclohex-1-en-1-yl)carbonyl]phenyl}phosphonate A mixture of 0.65 g (2.2 mmol) of the product from step b), 0.45 g (2.2 mmol) of N,N-dicyclohexylcarbodiimide and 0.31 g of dimedone in 30 ml of acetonitrile was stirred at room temperature overnight. 0.45 g (4.4 mmol) of triethylamine and 0.2 ml of trimethylsilyl cyanide were then added, and the mixture was stirred at room temperature for a further 18 hours. The reaction mixture was poured into 50 ml each of ethyl acetate and 2% strength sodium carbonate solution and filtered. The aqueous phase was washed with diethyl ether and subsequently adjusted to a pH of 4–5 using hydrochloric acid. The mixture was extracted with ethyl acetate, the organic phase was dried and the solvent was removed.

Yield: 0.36 g (39%); red oil $^1$H NMR ($CDCl_3$): δ=7.78 (m,2H); 7.28 (m,1H); 4.12 (m,4H); 2.65 (m,2H); 2.32 (m,2H); 1.32 (t,6H); 1.14 (s,6H).

2. Synthesis of diethyl {3-chloro-4-[(1-ethyl-5-hydroxy-1H-pyrazol-4-ylcarbonyl]phenyl}phosphonate (Compound 5.1)

At room temperature, a mixture of 1.0 g (3.4 mmol) of the product from Synthesis 1 step b), 0.71 g (3.4 mmol) of N,N-dicyclohexylcarbodiimide and 0.38 g (3.4 mmol) of 5-hydroxy-1-ethylpyrazole was stirred for 36 hours. The reaction mixture was poured into 50 ml each of ethyl acetate and 2% strength sodium carbonate solution, the organic phase was dried and the solvent was removed. The residue was chromatographed over silica gel using cyclohexane/ethyl acetate. The resulting O-acylated product (0.36 g) in 1,4-dioxane was then admixed with potassium carbonate and refluxed for 4 hours. The reaction mixture was poured into water and extracted with ethyl acetate. The aqueous phase was washed once with diethyl ether, adjusted to pH 4 using hydrochloric acid and extracted with ethyl acetate. The organic phase was dried and the solvent was removed.

Yield: 0.17 g; red oil $^1$H NMR ($CDCl_3$): δ=7.95 (m,1H); 7.78 (m,1H); 7.55 (m,1H); 7.38 (s,1H); 4.40 (m,2H); 4.13 (m,4H); 1.44 (t,3H); 1.36 (t,6H)

In addition to the compounds of the formula I or IV described above, Tables 3 to 7 list other compounds which were prepared or are preparable in a similar manner:

TABLE 3

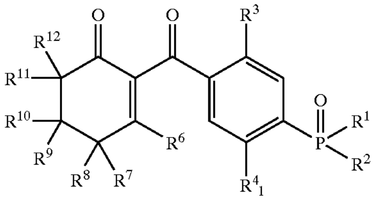

I2a where X = O

| No. | $R^1$ | $R^2$ | $R^3$ | $R^4_1$ | $R^6$ | $R^7$ | $R^8$ | $R^9$ | $R^{10}$ | $R^{11}$ | $R^{12}$ | physical data mp [° C.]. $^1$H NMR [δppm] |
|---|---|---|---|---|---|---|---|---|---|---|---|---|
| 3.1 | $OCH_2CH_3$ | $OCH_2CH_3$ | Cl | H(1 = O) | OH | H | H | $CH_3$ | $CH_3$ | H | H | 7.78(m.2H); 7.28(m.1H); 4.12(m.4H); 2.65(m.2H); 2.32(m.2H); 1.32(t.6H); 1.14(s.6H) |
| 3.2 | $OCH_2CH_3$ | $OCH_2CH_3$ | Cl | H(1 = O) | OH | H | H | H | H | H | H | 97–98 |
| 3.3 | $CH_3$ | $CH_3$ | Cl | H(1 = O) | OH | H | H | $CH_3$ | $CH_3$ | H | H | 7.70(m.2H); 7.35(m.1H); 2.68(s.2H); 2.35(s.2H); 1.78(d.6H); 1.12(s.6H) |
| 3.4 | $CH_3$ | $CH_3$ | Cl | H(1 = O) | OH | H | H | H | H | H | H | 60–62 |

TABLE 3-continued

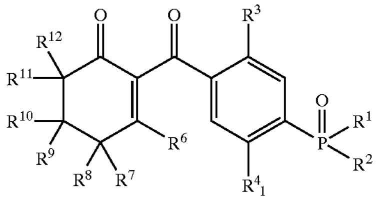

I2a where X = O

| No. | $R^1$ | $R^2$ | $R^3$ | $R^4_1$ | $R^6$ | $R^7$ | $R^8$ | $R^9$ | $R^{10}$ | $R^{11}$ | $R^{12}$ | physical data mp [° C.]. $^1H$ NMR [δppm] |
|---|---|---|---|---|---|---|---|---|---|---|---|---|
| 3.5 | $CH_3$ | $CH_3$ | Cl | H(1 = O) | OH | $CH_3$ | $CH_3$ | | =O | $CH_3$ | $CH_3$ | 99–100 |
| 3.6 | $OCH_2CH_3$ | $OCH_2CH_3$ | Cl | H(1 = O) | OH | $CH_3$ | $CH_3$ | | =O | $CH_3$ | $CH_3$ | 121–122 |

TABLE 4

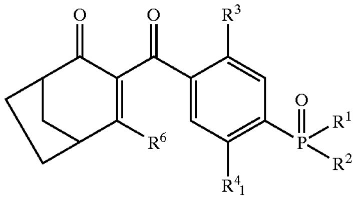

I2a where X = O; $R^8.R^9.R^{10}.R^{12}$ =H;
$R^7+R^{11}$ = $-CH_2-CH_2-$

| No. | $R^1$ | $R^2$ | $R^3$ | $R^4_1$ | $R^6$ | physical data mp [° C.], $^1H$ NMR [δppm] |
|---|---|---|---|---|---|---|
| 4.1 | $OCH_2CH_3$ | $OCH_2CH_3$ | Cl | H(1 = O) | $SC_6H_5$ | 7.78(m.2H); 7.52(m.6H); 4.10(m.4H); 3.07(t.1H); 2.90(t.1H); 2.05(m.2H); 1.84(m.2H); 1.55(m.2H); 1.38(t.6H) |
| 4.2 | $OCH_2CH_3$ | $OCH_2CH_3$ | Cl | H(1 = O) | OH | 150 |
| 4.3 | $CH_3$ | $CH_3$ | Cl | H(1 = O) | OH | 178–179 |

TABLE 5

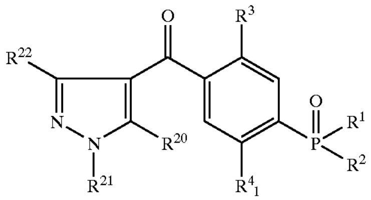

I2b where X = O

| No. | $R^1$ | $R^2$ | $R^3$ | $R^4_1$ | $R^{20}$ | $R^{21}$ | $R^{22}$ | physical data mp [° C.], $^1H$ NMR [δppm] |
|---|---|---|---|---|---|---|---|---|
| 5.1 | $OCH_2CH_3$ | $OCH_2CH_3$ | Cl | H(1 = O) | OH | $CH_2CH_3$ | H | 7.95(m.1H); 7.78(m.1H); 7.55(m.1H); 7.38(s.1H); 4.40(m.2H); 4.13(m.4H); 1.44(t.3H); 1.36(t.6H) |
| 5.2 | $OCH_2CH_3$ | $OCH_2CH_3$ | Cl | H(1 = O) | OH | $CH_3$ | H | 7.90(d.1H); 7.80(m.1H); 7.54(m.1H); 7.38(s.1H); 4.16(m.4H); 3.70(s.3H); 1.38(t.6H) |

TABLE 6

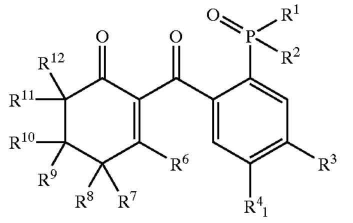

I1a where X = O

| No. | $R^1$ | $R^2$ | $R^3$ | $R^4_1$ | $R^6$ | $R^7$ | $R^8$ | $R^9$ | $R^{10}$ | $R^{11}$ | $R^{12}$ | physical data mp [° C.], $^1H$ NMR [δppm] |
|---|---|---|---|---|---|---|---|---|---|---|---|---|
| 6.1 | $CH_3$ | $CH_3$ | Cl | H(1 = O) | OH | H | H | H | H | H | H | 200–201 |
| 6.2 | $CH_3$ | $CH_3$ | Cl | H(1 = O) | OH | H | H | $CH_3$ | $CH_3$ | H | H | 161–162 |

TABLE 7

IV2

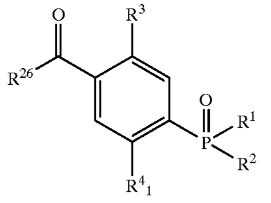

where X = O

| No. | $R^1$ | $R^2$ | $R^3$ | $R^4_1$ | $R^{26}$ | physical data mp [° C.], $^1H$ NMR [δ ppm] |
|---|---|---|---|---|---|---|
| 7.1 | $OCH_2CH_3$ | $OCH_2CH_3$ | Cl | H(l═O) | OH | 13.8 (bs. 1H); 7.90 (m.1H);7.75 (m.2H); 4.06 (m.4H); 1.25 (t.6H) |
| 7.2 | $CH_3$ | $CH_3$ | Cl | H(l═O) | OH | 7.84 (m.3H); 1.68 (d.6H) |

The compounds of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa*, Musa spec., *Nicotiana tabacum* (*N.rustica*), *Olea europaea, Oryza sativa, Phaseolus lunatus, Phaseolus vulgaris, Picea abies*, Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds of the formula I may also be used in crops which tolerate the action of herbicides owing to breeding, including genetic engineering methods.

The compounds of the formula I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, spreading or watering. The use forms depend on the intended purpose; in any case, they should guarantee the finest possible distribution of the active ingredients according to the invention.

The herbicidal compositions comprise a herbicidally effective amount of at least one compound of the formula I or an agriculturally useful salt of I, and auxiliaries which are customary for the formulation of crop protection agents.

Suitable as inert auxiliaries are essentially the following:

mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, Asuspensions, pastes, wettable powders or water-dispersible granules by adding water. To prepare emulsions, pastes or oil dispersions, the phosphorus-containing benzoyl derivatives of the formula I, either as such or dissolved in an oil or solvent, can be homogenized in water by means of a wetting agent, tackifier, dispersant or emulsifier. Alternatively, it is also possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for scattering and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

The formulation examples below illustrate the preparation of such compositions:

I. 20 parts by weight of the compound No. 3.3 are dissolved in a mixture composed of 80 parts by weight of alkylated benzene, 10 parts by weight of the adduct of from 8 to 10 mol of ethylene oxide to 1 mol of oleic acid N-monoethanol-amide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

iii. 20 parts by weight of the compound No. 3.3 are dissolved in a mixture composed of 40 parts by weight of cyclohexanone, 30 parts by weight of isobutanol, 20 parts by weight of the adduct of 7 mol of ethylene oxide to 1 mol of isooctyl-phenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. 3.3 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the compound No. 3.3 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the compound No. 3.3 are mixed with 97 parts by weight of finely divided kaolin. This gives a dust which comprises 3% by weight of the active ingredient.

VI. 20 parts by weight of the compound No. 3.3 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 3.3 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 3.3 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be appled pre- or post-emergence. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

The rates of application of the compound of the formula I are from 0.001 to 3.0, preferably 0.01 to 1.0, kg/ha of active substance (a.s.), depending on the control target, the season, the target plants and the growth stage.

To widen the spectrum of action and to achieve synergistic effects, the phosphorus-containing benzoyl derivatives of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, amino-phosphoric acid and its derivatives, aminotriazoles, anilides, aryloxy-/heteroaryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies.

Non-phytotoxic oils and oil concentrates may also be added.

USE EXAMPLES

The herbicidal activity of the phosphorus-containing benzoyl derivatives of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover causes uniform germination of the test plants, unless this was adversely affected by the active ingredients.

For the post-emergence treatment, the test plants were first grown to a height of 3 to 15 cm, depending on the plant habit, and only then treated with the active compounds which had been suspended or emulsified in water. For this purpose, the test plants were either sown directly and grown in the same containers, or they were first grown separately as seedlings and transplanted into the test containers a few days prior to treatment. The rate of application for the post-emergence treatment was 0.5 or 0.25 kg/ha of a.s. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

338

| Scientific name | English name |
|---|---|
| *Chenopodium album* | lambsquarters (goosefoot) |
| *Echinochloa crus-galli* | barnyardgrass |
| *Setaria faberi* | giant foxtail |
| *Setaria viridis* | green foxtail |
| *Solanum nigrum* | black nightshade |

The compounds 3.4, applied post-emergence, showed very good activity against the abovementioned harmful plants at rates of application of 0.5 and 0.25 kg/ha, respectively.

We claim:

1. Phosphorus-containing benzoyl derivatives of the formula I

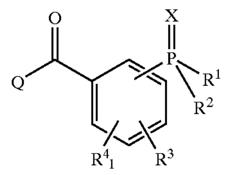

I in which:

X is oxygen or sulfur;

$R^1$, $R^2$ are hydrogen, $C_1$–$C_6$-alkyl, $C_2$–$C_6$-alkenyl, $C_2$–$C_6$-alkynyl, hydroxyl, $C_1$–$C_6$-alkoxy, $C_3$–$C_6$-alkenyloxy, $C_3$–$C_6$-alkynyloxy, mercapto, $C_1$–$C_6$-alkylthio, $C_3$–$C_6$-alkenylthio, $C_3$–$C_6$-alkynylthio, amino, $C_1$–$C_6$-alkylamino, di($C_1$–$C_6$-alkyl)amino, ($C_1$–$C_6$-alkoxy)($C_1$–$C_6$-alkyl)amino, ($C_3$–$C_6$-alkenyl)($C_1$–$C_6$-alkyl)amino, ($C_3$–$C_6$-alkynyl)($C_1$–$C_6$-alkyl)amino, di($C_3$–$C_6$-alkenyl)amino or di($C_3$–$C_6$-alkynyl)amino, where the abovementioned alkyl, alkenyl or alkynyl radicals may be partially or fully halogenated and/or may carry one to three of the following groups:

nitro, cyano, $C_1$–$C_4$-alkoxy, $C_1$–$C_4$-alkylthio, $C_1$–$C_4$-alkylsulfinyl, $C_1$–$C_4$-alkylsulfonyl, di($C_1$–$C_4$-alkyl)amino, $C_1$–$C_4$-alkylcarbonyl, $C_1$–$C_4$-alkoxycarbonyl, phenyl or heterocyclyl, where the two last-mentioned radicals for their part may be partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

are phenyl or phenoxy which may by partially or fully halogenated and/or may carry one to three of the following groups: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl; or $R^1$ and $R^2$ together form an $—O—(CH_2)_m—O—$, $—O—(CH_2)_m—S—$, $—S—(CH_2)_m—S—$, $—NR^5—(CH_2)_m—NR^5—$, $—O—(CH_2)_m—NR^5—$, $—S—(CH_2)_m—$ $NR^5$—, —$(CH_2)_n$—O—, —$(CH_2)_n$—S— or —$(CH_2)_n$—$NR^5$ chain which may carry one to three radicals from the following group:

halogen, cyano, $C_1$–$C_4$-alkyl, $C_1$–$C_4$-haloalkyl, $C_1$–$C_4$-alkoxy, $C_1$–$C_4$-alkoxycarbonyl or phenyl which is unsubstituted or partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl; or $R^1$ and $R^2$ together form a —$(CH_2)_p$ chain which may be interrupted by oxygen, sulfur or $NR^5$ and/or may carry one to three radicals from the following group:

halogen, cyano, $C_1$–$C_4$-alkyl, $C_1$–$C_4$-haloalkyl, $C_1$–$C_4$-alkoxy, $C_1$–$C_4$-alkoxycarbonyl or phenyl which is unsubstituted or partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^3$ is hydrogen, nitro, cyano, halogen, $C_1$–$C_6$-alkyl, $C_1$–$C_6$-haloalkyl, $C_1$–$C_6$-alkoxy-$C_1$–$C_6$-alkyl, $C_1$–$C_6$-haloalkoxy-$C_1$–$C_6$alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylcarbonyl, $C_1$–$C_6$-alkoxycarbonyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, $C_1$–$C_6$-alkylaminosulfonyl, di($C_1$–$C_6$-alkyl)aminosulfonyl, ($C_1$–$C_6$-alkylsulfonyl)amino, ($C_1$–$C_6$-haloalkylsulfonyl)amino, N—($C_1$–$C_6$-alkyl)—N—($C_1$–$C_6$-alkylsulfonyl)amino, N—($C_1$–$C_6$-alkyl)-N—($C_1$–$C_6$-haloalkylsulfonyl)amino, —P(=X)$R^1R^2$, phenyl or heterocyclyl, where the two last-mentioned radicals may be partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^4$ is nitro, cyano, halogen, $C_1$–$C_6$-alkyl, $C_1$–$C_6$-alkoxy, $C_1$–$C_6$-alkylthio, $C_1$–$C_6$-alkylsulfinyl or $C_1$–$C_6$-alkylsulfonyl;

$R^5$ is hydrogen, $C_1$–$C_6$-alkyl, $C_1$–$C_6$-haloalkyl or $C_1$–$C_6$-alkoxy;

l is 0, 1 or 2;

m is 2, 3 or 4;

n is 3, 4 or 5;

p is 4, 5 or 6;

Q is a radical of the formula $Q^1$ $Q^1$

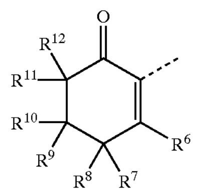

$R^6$ is hydroxyl, mercapto, halogen, $OR^{13}$, $SR^{13}$, $SOR^{14}$, $SO_2R^{14}$, $OSO_2R^{14}$, $POR^{15}R^{16}$, $OPR^{15}R^{16}$, $OPOR^{15}R^{16}$, $OPSR^{15}R^{16}$, $NR^{17}R^{18}$, $ONR^{18}R^{19}$, N-bonded heterocyclyl or O—(N-bonded heterocyclyl), where the heterocyclyl radical of the two last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^7$, $R^9$, $R^{11}$ are hydrogen, nitro, halogen, cyano, $C_1$–$C_6$-alkyl, $C_1$–$C_6$-haloalky, di($C_1$–$C_6$-alkoxy)methyl, di($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl;

$R^8$, $R^{10}$, $R^{12}$ are hydrogen, $C_1$–$C_6$-alkyl, $C_1$–$C_6$-alkoxy, $C_1$-$C_6$-alkylthio or $C_1$–$C_6$-alkoxycarbonyl; or $R^7$ and $R^8$ or $R^9$ and $R^{10}$ or $R^{11}$ and $R^{12}$ together form an —O—$(CH_2)_u$—O—, —O—$(CH_2)_u$—S—, —S—$(CH_2)_u$—S—, —O—$(CH_2)_v$— or —S—$(CH_2)_v$ chain which may be substituted by one to three radicals from the following group:

halogen, cyano, $C_1$–$C_4$-alkyl, $C_1$–$C_4$-haloalkyl or $C_1$–$C_4$-alkoxycarbonyl; or $R^7$ and $R^8$ or $R^9$ and $R^{10}$ or $R^{11}$ and $R^{12}$ together form a —$(CH_2)_w$ chain which may be interrupted by oxygen or sulfur and/or may be substituted by one to four radicals from the following group: halogen, cyano, $C_1$–$C_4$-alkyl, $C_1$–$C_4$-haloalkyl or $C_1$–$C_4$-alkoxycarbonyl; or $R^7$ and $R^8$ or $R^9$ and $R^{10}$ or $R^{11}$ and $R^{12}$ together form a methylidene group which may be substituted by one to two radicals from the following group:

halogen, hydroxyl, formyl, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl; or $R^7$ and $R^8$ or $R^9$ and $R^{10}$ or $R^{11}$ and $R^{12}$ together with the carbon to which they are attached form a carbonyl group; or $R^7$ and $R^9$ or $R^9$ and $R^{11}$ or $R^7$ and $R^{11}$ together form a —$(CH_2)_v$ chain which may be substituted by one to three radicals from the following group:

halogen, $C_1$–$C_6$-alkyl, $C_1$–$C_6$-alkoxy, hydroxyl or $C_1$–$C_6$-alkoxycarbonyl;

$R^{13}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$cycloalkyl, $C_1$–$C_{20}$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkylaminocarbonyl, $C_1$–$C_6$-alkylcarbonyl-$C_1$–$C_6$-alkyl or $C_1$–$C_6$-alkoxyimino-$C_1$–$C_6$-alkyl, where the abovementioned alkyl and cycloalkyl radicals may be partially or fully halogenated and/or may carry one to three of the following groups:

cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)-aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl, heterocyclylcarbonyl, phenylaminocarbonyl or heterocyclylaminocarbonyl, where the phenyl and the heterocyclyl radical of the 8 last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$, $R^{15}$, $R^{16}$ are $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, amino, $C_1$–$C_6$-alkylamino, $C_1$–$C_6$-haloalkylamino, di($C_1$–$C_6$-alkyl)amino or di($C_1$–$C_6$-haloalkyl)amino, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, di($C_1$–$C_4$-alkyl)amino, $C_1$–$C_4$-alkylcarbonyl or $C_1$–$C_4$-alkoxycarbonyl;

are phenyl, heterocyclyl, phenoxy or heterocyclyloxy, where the phenyl and the heterocyclyl radical of the last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{17}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, $C_3$–$C_6$-alkenyloxy or $C_3$–$C_6$-alkynyloxy, where the abovementioned alkyl, cycloalkyl and alkoxy radicals may be partially or fully halogenated and/or may carry one to three radicals from the following group:

cyano, $C_1$–$C_4$-alkoxy, $C_1$–$C_4$-alkylthio or di($C_1$–$C_4$-alkyl)amino; is phenyl, heterocyclyl, phenyl-$C_1$–$C_6$-alkyl or heterocyclyl-$C_1$–$C_6$-alkyl, where the phenyl or heterocyclyl radical of the four last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{18}$, $R^{19}$ are $C_1$–$C_6$-alkyl, $C_3$–$C_6$-alkenyl, $C_3$–$C_6$-alkynyl or $C_1$–$C_6$-alkylcarbonyl;

u is from 2 to 4;

v is from 1 to 5;

w is from 2 to 5;

or an agriculturally useful salt thereof.

2. A phosphorus-containing benzoyl derivative of the formula I as claimed in claim 1 where X═O and $R^3$ is attached in position 4, $R^4{}_l$ is attached in position 5 and "P(═X)$R^1R^2$" is attached in position 2 (I1).

I1

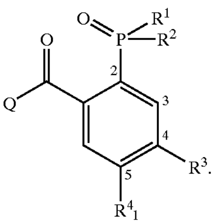

3. A phosphorus-containing benzoyl derivative of the formula I as claimed in claim 1 where X═O and $R^3$ is attached in position 2, $R^4{}_l$ is attached in position 5 and "P(═X)$R^1R^2$" is attached in position 4 (I2).

I2

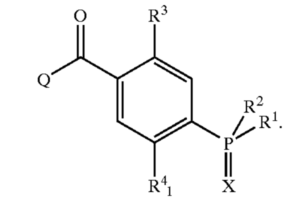

4. A phosphorus-containing benzoyl derivtive of the formula I as claimed in claim 1 where $R^1$, $R^2$ are hydrogen, hydroxyl, $C_1$–$C_6$-alkyl, $C_1$–$C_6$-alkoxy, $C_1$–$C_6$-alkylthio, di-($C_1$–$C_6$-alkyl)amino, where the alkyl radicals of the four lastmentioned substituents may be partially or fully halogenated and/ or may carry one to three of the following groups:

nitro, cyano, $C_1$–$C_4$-alkoxy, $C_1$–$C_4$-alkylsulfonyl or $C_1$–$C_4$-alkoxycarbonyl; or $R^1$ and $R^2$ together form a —O—$(CH_2)_m$—O—, —O—$(CH_2)_m$—S—, —S—$(CH_2)_m$—S—, —$NR^5$—$(CH_2)_m$—$NR^5$—, —O—$(CH_2)_m$—$NR^5$—, —S—$(CH_2)_m$—$NR^5$— or —$(CH_2)_p$— chain which may carry one to three radicals from the following group:

halogen, cyano, $C_1$–$C_4$-alkyl or $C_1$–$C_4$-alkoxycarbonyl.

5. A phosphorus-containing benzoyl derivative of the formula I as claimed in claim 1 where $R^3$ is nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylsulfonyl, $C_1$–$C_4$-haloalkylsulfonyl, —P(═O)$(CH_3)_2$, —P(═O)$(CH_2CH_3)_2$, —P(═O)$(OCH_3)_2$ or —P(═O)$(OCH_2CH_3)_2$.

6. A process for preparing, compounds of the formula Ia (≡I where Q=$Q^1$) where $R^6$=halogen as claimed in claim 1, which comprises reacting a corresponding phosphorus-containing benzoyl derivative of the formula Ia (≡I where Q=$Q^1$) where $R^6$=hydroxyl

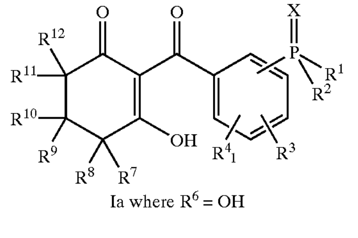

Ia where $R^6$ = OH with a halogenating agent.

7. A process for preparing compounds of the formula Ia (≡I where Q=$Q^1$) where $R^6$=$OR^{13}$, $OSO_2R^{14}$, $OPR^{15}R^{16}$, $OPOR^{15}R^{16}$ or $OPSR^{15}R^{16}$ as claimed in claim 1, which comprises reacting a corresponding phosphorus-containing benzoyl derivative of the formula Ia (≡I where Q=$Q^1$) where $R^6$=hydroxyl

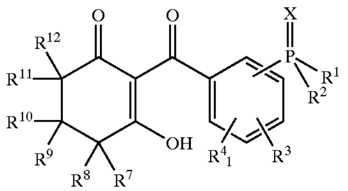

Ia where $R^6$ = OH with a compound of the formula IIα, IIβ, IIγ, IIδ or IIε, $L^1—R^{13}$ (IIα)

$L^1—SO_2R^{14}$ (IIβ)

$L^1—PR^{15}R^{16}$ (IIγ)

$L^1POR^{15}R^{16}$ (IIδ)

$L^1—PSR^{15}R^{16}$ (IIε)

where the variables $R^{13}$ to $R^{16}$ are as defined in claim 1 and $L^1$ is a nucleophilically replaceable leaving group.

8. A process for preparing compounds of the formula Ia (≡I where $Q=Q^1$) where $R=OR^{13}$, $SR^{13}$, $POR^{15}R^{16}$, $NR^{17}R^{18}$, $ONR^{18}R^{19}$, N-bonded heterocyclyl or O—N-bonded heterocyclyl as claimed in claim 1, which comprises reacting a corresponding phosphorus-containing benzoyl derivative of the formula Ia (≡I where $Q=Q^1$) where $R^6$=halogen or $OSO_2R^{14}$

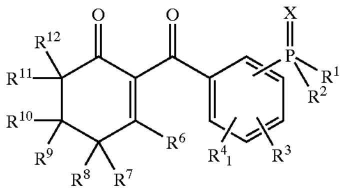

Ia where $R^6$ = halogen or $OSO_2R^{14}$ with a compound of the formula IIIα, IIIβ, IIIγ, IIIδ or IIIε, IIIη or IIIΘ

$HOR^{13}$ (IIIα)

$HSR^{13}$ (IIIβ)

$HPOR^{15}R^{16}$ (IIIγ)

$HNR^{17}R^{18}$ (IIIδ)

$HONR^{18}R^{19}$ (IIε)

H(N-bonded heterocyclyl) (IIIη)

H(ON-bonded heterocyclyl) (IIIϑ)

where the variables $R^{13}$ to $R^{19}$ are as defined in claim 1, if appropriate in the presence of a base.

9. A process for preparing compounds of the formula Ia (≡I where $Q=Q^1$) where $R^6=SOR^{14}$, $SO_2R^{14}$ as claimed in claim 1, which comprises reacting a corresponding phosphorus-containing benzoyl derivative of the formula Ia (≡I where $Q=Q^1$) where $R^6=SR^{14}$

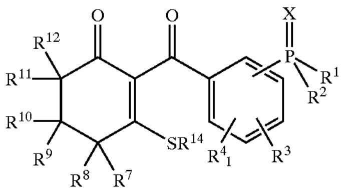

Ia where $R^6$ = $SR^{14}$ with an oxidizing agent.

10. A process for preparing compounds of the formula Ia (≡I where $Q=Q^1$) where $R^6$=hydroxyl as claimed in claim 1, which comprises acylating a cyclohexanedione of the formula V

V

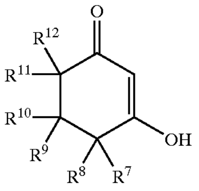

where the variables $R^7$ to $R^{12}$ are as defined in claim 1 with an activated phosphorus-containing benzoic acid of the formula IVα or a phosphorus-containing benzoic acid of the formula IVβ

IVα

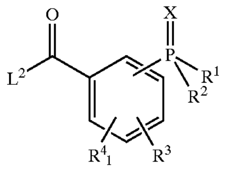

IVβ

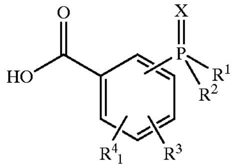

where the variables X, $R^1$ to $R^4$ and l are as defined in claim 1 and $L^2$ is a nucleophilically displaceable leaving group, and rearranging the acylation product, if appropriate in the presence of a catalyst.

11. A composition, comprising a herbicidally effective amount of at least one phosphorus-containing benzoyl derivative of the formula I or an agriculturally useful salt of I as claimed in claim 1 and auxiliaries which are customarily used for formulating crop protection agents.

12. A process for preparing compositions as claimed in claim 11, which comprises mixing a herbicidally effective amount of at least one phosphoris-containing benzoyl derivative of the formula I or of an agriculturally useful salt of I as claimed in claim 1 and auxiliaries which are customarily used for formulating crop protection agents.

13. A method for controlling undesirable vegetation, which comprises allowing a herbicidally effective amount of at least one phosphorus-containing benzoyl derivative of the formula I or an agriculturally useful salt of I as claimed in claim 1 to act on plants, their habitat and/or on seed.

* * * * *